US012440209B2

(12) United States Patent
Harris et al.

(10) Patent No.: US 12,440,209 B2
(45) Date of Patent: Oct. 14, 2025

(54) SURGICAL INSTRUMENT WITH MULTIPLE PROGRAM RESPONSES DURING A FIRING MOTION

(71) Applicant: Cilag GmbH International, Zug (CH)

(72) Inventors: Jason L. Harris, Lebanon, OH (US); Frederick E. Shelton, IV, Hillsboro, OH (US); Mark D. Overmyer, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 17 days.

(21) Appl. No.: 18/195,068

(22) Filed: May 9, 2023

(65) Prior Publication Data

US 2023/0363758 A1 Nov. 16, 2023

Related U.S. Application Data

(63) Continuation of application No. 17/709,576, filed on Mar. 31, 2022, now Pat. No. 11,642,125, which is a (Continued)

(51) Int. Cl.
*A61B 17/068* (2006.01)
*A61B 17/072* (2006.01)
(Continued)

(52) U.S. Cl.
CPC .... *A61B 17/0686* (2013.01); *A61B 17/07207* (2013.01); *A61B 17/320068* (2013.01);
(Continued)

(58) Field of Classification Search
CPC ........ A61B 2090/064; A61B 2090/065; A61B 2017/2927; A61B 2017/00725;
(Continued)

(56) References Cited

U.S. PATENT DOCUMENTS 66,052 A 6/1867 Smith
662,587 A 11/1900 Blake
(Continued)

FOREIGN PATENT DOCUMENTS

AU 2012200594 A1 2/2012
AU 2012203035 A1 6/2012
(Continued)

OTHER PUBLICATIONS

Arjo Loeve et al., Scopes Too Flexible . . . and Too Stiff, 2010, IEEE Pulse, Nov./Dec. 2010 (Year: 2010), 16 pages.
(Continued)

*Primary Examiner* — Thanh K Truong
*Assistant Examiner* — Xavier A Madison
(74) *Attorney, Agent, or Firm* — Barnes & Thornburg LLP

(57) ABSTRACT

A surgical instrument. The surgical instrument includes an elongated channel configured to support a staple cartridge, an anvil pivotably connected to the elongated channel, a knife mechanically coupled to the staple cartridge, an electric motor and a control circuit electrically connected to the electric motor. The control circuit is configured to change a firing motion a first way based on a first value of a projected peak firing force and a second way based on a second value of the projected peak firing force value.

20 Claims, 91 Drawing Sheets

Related U.S. Application Data continuation of application No. 16/919,319, filed on Jul. 2, 2020, now Pat. No. 12,144,500, which is a continuation of application No. 15/130,566, filed on Apr. 15, 2016, now Pat. No. 10,828,028.

(51) Int. Cl.

| | |
|---|---|
| ***A61B 17/32*** | (2006.01) |
| ***G16H 20/40*** | (2018.01) |
| ***G16H 40/63*** | (2018.01) |
| *A61B 17/00* | (2006.01) |
| *A61B 17/29* | (2006.01) |
| *A61B 90/00* | (2016.01) |
| *A61B 90/30* | (2016.01) |

(52) U.S. Cl.

CPC ............ *G16H 20/40* (2018.01); *G16H 40/63* (2018.01); *A61B 2017/00017* (2013.01); *A61B 2017/00022* (2013.01); *A61B 2017/00026* (2013.01); *A61B 2017/00039* (2013.01); *A61B 2017/00075* (2013.01); *A61B 2017/00115* (2013.01); *A61B 2017/00119* (2013.01); *A61B 2017/00123* (2013.01); *A61B 2017/00132* (2013.01); *A61B 2017/00199* (2013.01); *A61B 2017/00398* (2013.01); *A61B 2017/0046* (2013.01); *A61B 2017/00725* (2013.01); *A61B 2017/00734* (2013.01); *A61B 2017/07257* (2013.01); *A61B 2017/07271* (2013.01); *A61B 2017/07285* (2013.01); *A61B 2017/2927* (2013.01); *A61B 2090/061* (2016.02); *A61B 2090/064* (2016.02); *A61B 2090/065* (2016.02); *A61B 2090/0803* (2016.02); *A61B 2090/0807* (2016.02); *A61B 2090/0808* (2016.02); *A61B 2090/0811* (2016.02); *A61B 2090/304* (2016.02); *A61B 2090/309* (2016.02)

(58) Field of Classification Search

CPC ........... A61B 2017/00398; A61B 2017/00199; A61B 2017/00123; A61B 2017/00039

USPC ............................................ 227/175.1–182.1

See application file for complete search history.

(56) References Cited

U.S. PATENT DOCUMENTS

| | | | |
|---|---|---|---|
| 670,748 | A | 3/1901 | Weddeler |
| 719,487 | A | 2/1903 | Minor |
| 804,229 | A | 11/1905 | Hutchinson |
| 903,739 | A | 11/1908 | Lesemann |
| 951,393 | A | 3/1910 | Hahn |
| 1,075,556 | A | 10/1913 | Fenoughty |
| 1,082,105 | A | 12/1913 | Anderson |
| 1,188,721 | A | 6/1916 | Bittner |
| 1,306,107 | A | 6/1919 | Elliott |
| 1,314,601 | A | 9/1919 | McCaskey |
| 1,466,128 | A | 8/1923 | Hallenbeck |
| 1,677,337 | A | 7/1928 | Grove |
| 1,794,907 | A | 3/1931 | Kelly |
| 1,849,427 | A | 3/1932 | Hook |
| 1,912,783 | A | 6/1933 | Meyer |
| 1,944,116 | A | 1/1934 | Stratman |
| 1,954,048 | A | 4/1934 | Jeffrey et al. |
| 2,028,635 | A | 1/1936 | Wappler |
| 2,037,727 | A | 4/1936 | La Chapelle |
| 2,120,951 | A | 6/1938 | Hodgman |
| 2,132,295 | A | 10/1938 | Hawkins |
| 2,161,632 | A | 6/1939 | Nattenheimer |
| D120,434 | S | 5/1940 | Gold |
| 2,211,117 | A | 8/1940 | Hess |
| 2,214,870 | A | 9/1940 | West |
| 2,224,108 | A | 12/1940 | Ridgway |
| 2,224,882 | A | 12/1940 | Peck |
| 2,256,295 | A | 9/1941 | Schmid |
| 2,318,379 | A | 5/1943 | Davis et al. |
| 2,329,440 | A | 9/1943 | La Place |
| 2,377,581 | A | 6/1945 | Shaffrey |
| 2,406,389 | A | 8/1946 | Lee |
| 2,420,552 | A | 5/1947 | Morrill |
| 2,441,096 | A | 5/1948 | Happe |
| 2,448,741 | A | 9/1948 | Scott et al. |
| 2,450,527 | A | 10/1948 | Smith |
| 2,491,872 | A | 12/1949 | Neuman |
| 2,507,872 | A | 5/1950 | Unsinger |
| 2,526,902 | A | 10/1950 | Rublee |
| 2,527,256 | A | 10/1950 | Jackson |
| 2,578,686 | A | 12/1951 | Fish |
| 2,638,901 | A | 5/1953 | Sugarbaker |
| 2,674,149 | A | 4/1954 | Benson |
| 2,701,489 | A | 2/1955 | Osborn |
| 2,711,461 | A | 6/1955 | Happe |
| 2,724,289 | A | 11/1955 | Wight |
| 2,742,955 | A | 4/1956 | Dominguez |
| 2,804,848 | A | 9/1957 | O'Farrell et al. |
| 2,808,482 | A | 10/1957 | Zanichkowsky et al. |
| 2,825,178 | A | 3/1958 | Hawkins |
| 2,853,074 | A | 9/1958 | Olson |
| 2,856,192 | A | 10/1958 | Schuster |
| 2,887,004 | A | 5/1959 | Stewart |
| 2,957,353 | A | 10/1960 | Lewis |
| 2,959,974 | A | 11/1960 | Emrick |
| 3,026,744 | A | 3/1962 | Rouse |
| 3,032,769 | A | 5/1962 | Palmer |
| 3,035,256 | A | 5/1962 | Egbert |
| 3,060,972 | A | 10/1962 | Sheldon |
| 3,075,062 | A | 1/1963 | Iaccarino |
| 3,078,465 | A | 2/1963 | Bobrov |
| 3,079,606 | A | 3/1963 | Bobrov et al. |
| 3,080,564 | A | 3/1963 | Strekopitov et al. |
| 3,166,072 | A | 1/1965 | Sullivan, Jr. |
| 3,180,236 | A | 4/1965 | Beckett |
| 3,196,869 | A | 7/1965 | Scholl |
| 3,204,731 | A | 9/1965 | Bent et al. |
| 3,252,643 | A | 5/1966 | Strekopytov et al. |
| 3,266,494 | A | 8/1966 | Brownrigg et al. |
| 3,269,630 | A | 8/1966 | Fleischer |
| 3,269,631 | A | 8/1966 | Takaro |
| 3,275,211 | A | 9/1966 | Hirsch et al. |
| 3,315,863 | A | 4/1967 | O'Dea |
| 3,317,103 | A | 5/1967 | Cullen et al. |
| 3,317,105 | A | 5/1967 | Astafjev et al. |
| 3,357,296 | A | 12/1967 | Lefever |
| 3,359,978 | A | 12/1967 | Smith, Jr. |
| 3,377,893 | A | 4/1968 | Shorb |
| 3,480,193 | A | 11/1969 | Ralston |
| 3,490,675 | A | 1/1970 | Green et al. |
| 3,494,533 | A | 2/1970 | Green et al. |
| 3,499,591 | A | 3/1970 | Green |
| 3,503,396 | A | 3/1970 | Pierie et al. |
| 3,509,629 | A | 5/1970 | Kidokoro |
| 3,551,987 | A | 1/1971 | Wilkinson |
| 3,568,675 | A | 3/1971 | Harvey |
| 3,572,159 | A | 3/1971 | Tschanz |
| 3,583,393 | A | 6/1971 | Takahashi |
| 3,589,589 | A | 6/1971 | Akopov |
| 3,598,943 | A | 8/1971 | Barrett |
| 3,604,561 | A | 9/1971 | Mallina et al. |
| 3,608,549 | A | 9/1971 | Merrill |
| 3,616,278 | A | 10/1971 | Jansen |
| 3,618,842 | A | 11/1971 | Bryan |
| 3,635,394 | A | 1/1972 | Natelson |
| 3,638,652 | A | 2/1972 | Kelley |
| 3,640,317 | A | 2/1972 | Panfili |
| 3,643,851 | A | 2/1972 | Green et al. |
| 3,650,453 | A | 3/1972 | Smith, Jr. |
| 3,661,339 | A | 5/1972 | Shimizu |
| 3,661,666 | A | 5/1972 | Foster et al. |
| 3,662,939 | A | 5/1972 | Bryan |
| 3,685,250 | A | 8/1972 | Henry et al. |
| 3,688,966 | A | 9/1972 | Perkins et al. |
| 3,692,224 | A | 9/1972 | Astafiev et al. |

(56) References Cited

U.S. PATENT DOCUMENTS 3,695,646 A 10/1972 Mommsen
3,709,221 A 1/1973 Riely
3,717,294 A 2/1973 Green
3,724,237 A 4/1973 Wood
3,726,755 A 4/1973 Shannon
3,727,904 A 4/1973 Gabbey
3,734,207 A 5/1973 Fishbein
3,740,994 A 6/1973 De Carlo, Jr.
3,744,495 A 7/1973 Johnson
3,746,002 A 7/1973 Haller
3,747,603 A 7/1973 Adler
3,747,692 A 7/1973 Davidson
3,751,902 A 8/1973 Kingsbury et al.
3,752,161 A 8/1973 Bent
3,797,494 A 3/1974 Zaffaroni
3,799,151 A 3/1974 Fukaumi et al.
3,808,452 A 4/1974 Hutchinson
3,815,476 A 6/1974 Green et al.
3,819,100 A 6/1974 Noiles et al.
3,821,919 A 7/1974 Knohl
3,822,818 A 7/1974 Strekopytov et al.
3,825,007 A 7/1974 Rand
3,826,978 A 7/1974 Kelly
3,836,171 A 9/1974 Hayashi et al.
3,837,555 A 9/1974 Green
3,841,474 A 10/1974 Maier
3,851,196 A 11/1974 Hinds
3,863,639 A 2/1975 Kleaveland
3,863,940 A 2/1975 Cummings
3,883,624 A 5/1975 McKenzie et al.
3,885,491 A 5/1975 Curtis
3,887,393 A 6/1975 La Rue, Jr.
3,892,228 A 7/1975 Mitsui
3,894,174 A 7/1975 Cartun
3,899,829 A 8/1975 Storm et al.
3,902,247 A 9/1975 Fleer et al.
3,940,844 A 3/1976 Colby et al.
3,944,163 A 3/1976 Hayashi et al.
3,950,686 A 4/1976 Randall
3,952,747 A 4/1976 Kimmell, Jr.
3,955,581 A 5/1976 Spasiano et al.
3,959,879 A 6/1976 Sellers
RE28,932 E 8/1976 Noiles et al.
3,972,734 A 8/1976 King
3,973,179 A 8/1976 Weber et al.
3,981,051 A 9/1976 Brumlik
3,993,072 A 11/1976 Zaffaroni
3,999,110 A 12/1976 Ramstrom et al.
4,025,216 A 5/1977 Hives
4,027,746 A 6/1977 Kine
4,034,143 A 7/1977 Sweet
4,038,987 A 8/1977 Komiya
4,047,654 A 9/1977 Alvarado
4,054,108 A 10/1977 Gill
4,060,089 A 11/1977 Noiles
4,066,133 A 1/1978 Voss
4,085,337 A 4/1978 Moeller
4,100,820 A 7/1978 Evett
4,106,446 A 8/1978 Yamada et al.
4,106,620 A 8/1978 Brimmer et al.
4,108,211 A 8/1978 Tanaka
4,111,206 A 9/1978 Vishnevsky et al.
4,127,227 A 11/1978 Green
4,129,059 A 12/1978 Van Eck
4,132,146 A 1/1979 Uhlig
4,135,517 A 1/1979 Reale
4,149,461 A 4/1979 Simeth
4,154,122 A 5/1979 Severin
4,160,857 A 7/1979 Nardella et al.
4,169,476 A 10/1979 Hiltebrandt
4,169,990 A 10/1979 Lerdman
4,180,285 A 12/1979 Reneau
4,185,701 A 1/1980 Boys
4,190,042 A 2/1980 Sinnreich
4,198,734 A 4/1980 Brumlik
4,198,982 A 4/1980 Fortner et al.
4,203,444 A 5/1980 Bonnell et al.
4,207,898 A 6/1980 Becht
4,213,562 A 7/1980 Garrett et al.
4,226,242 A 10/1980 Jarvik
4,239,431 A 12/1980 Davini
4,241,861 A 12/1980 Fleischer
4,244,372 A 1/1981 Kapitanov et al.
4,250,436 A 2/1981 Weissman
4,250,817 A 2/1981 Michel
4,261,244 A 4/1981 Becht et al.
4,272,002 A 6/1981 Moshofsky
4,272,662 A 6/1981 Simpson
4,274,304 A 6/1981 Curtiss
4,274,398 A 6/1981 Scott, Jr.
4,275,813 A 6/1981 Noiles
4,278,091 A 7/1981 Borzone
4,282,573 A 8/1981 Imai et al.
4,289,131 A 9/1981 Mueller
4,289,133 A 9/1981 Rothfuss
4,290,542 A 9/1981 Fedotov et al.
D261,356 S 10/1981 Robinson
4,293,604 A 10/1981 Campbell
4,296,654 A 10/1981 Mercer
4,296,881 A 10/1981 Lee
4,304,236 A 12/1981 Conta et al.
4,305,539 A 12/1981 Korolkov et al.
4,312,363 A 1/1982 Rothfuss et al.
4,312,685 A 1/1982 Riedl
4,317,451 A 3/1982 Cerwin et al.
4,319,576 A 3/1982 Rothfuss
4,321,002 A 3/1982 Froehlich
4,321,746 A 3/1982 Grinage
4,328,839 A 5/1982 Lyons et al.
4,331,277 A 5/1982 Green
4,340,331 A 7/1982 Savino
4,347,450 A 8/1982 Colligan
4,348,603 A 9/1982 Huber
4,349,028 A 9/1982 Green
4,350,151 A 9/1982 Scott
4,353,371 A 10/1982 Cosman
4,357,940 A 11/1982 Muller
4,361,057 A 11/1982 Kochera
4,366,544 A 12/1982 Shima et al.
4,369,013 A 1/1983 Abildgaard et al.
4,373,147 A 2/1983 Carlson, Jr.
4,376,380 A 3/1983 Burgess
4,379,457 A 4/1983 Gravener et al.
4,380,312 A 4/1983 Landrus
4,382,326 A 5/1983 Rabuse
4,383,634 A 5/1983 Green
4,389,963 A 6/1983 Pearson
4,393,728 A 7/1983 Larson et al.
4,394,613 A 7/1983 Cole
4,396,139 A 8/1983 Hall et al.
4,397,311 A 8/1983 Kanshin et al.
4,402,445 A 9/1983 Green
4,406,621 A 9/1983 Bailey
4,408,692 A 10/1983 Sigel et al.
4,409,057 A 10/1983 Molenda et al.
4,415,112 A 11/1983 Green
4,416,276 A 11/1983 Newton et al.
4,417,890 A 11/1983 Dennehey et al.
4,421,264 A 12/1983 Arter et al.
4,423,456 A 12/1983 Zaidenweber
4,425,915 A 1/1984 Ivanov
4,428,376 A 1/1984 Mericle
4,429,695 A 2/1984 Green
4,430,997 A 2/1984 DiGiovanni et al.
4,434,796 A 3/1984 Karapetian et al.
4,438,659 A 3/1984 Desplats
4,442,964 A 4/1984 Becht
4,448,194 A 5/1984 DiGiovanni et al.
4,451,743 A 5/1984 Suzuki et al.
4,452,376 A 6/1984 Klieman et al.
4,454,887 A 6/1984 Kruger
4,459,519 A 7/1984 Erdman
4,461,305 A 7/1984 Cibley
4,467,805 A 8/1984 Fukuda

(56) References Cited

U.S. PATENT DOCUMENTS 4,468,597 A 8/1984 Baumard et al.
4,469,481 A 9/1984 Kobayashi
4,470,414 A 9/1984 Imagawa et al.
4,471,780 A 9/1984 Menges et al.
4,471,781 A 9/1984 Di Giovanni et al.
4,473,077 A 9/1984 Noiles et al.
4,475,679 A 10/1984 Fleury, Jr.
4,476,864 A 10/1984 Tezel
4,478,220 A 10/1984 Di Giovanni et al.
4,480,641 A 11/1984 Failla et al.
4,481,458 A 11/1984 Lane
4,483,562 A 11/1984 Schoolman
4,485,816 A 12/1984 Krumme
4,485,817 A 12/1984 Swiggett
4,486,928 A 12/1984 Tucker et al.
4,488,523 A 12/1984 Shichman
4,489,875 A 12/1984 Crawford et al.
4,493,983 A 1/1985 Taggert
4,494,057 A 1/1985 Hotta
4,499,895 A 2/1985 Takayama
4,500,024 A 2/1985 DiGiovanni et al.
D278,081 S 3/1985 Green
4,503,842 A 3/1985 Takayama
4,505,272 A 3/1985 Utyamyshev et al.
4,505,273 A 3/1985 Braun et al.
4,505,414 A 3/1985 Filipi
4,506,671 A 3/1985 Green
4,512,038 A 4/1985 Alexander et al.
4,514,477 A 4/1985 Kobayashi
4,520,817 A 6/1985 Green
4,522,327 A 6/1985 Korthoff et al.
4,523,707 A 6/1985 Baxter, III et al.
4,526,174 A 7/1985 Froehlich
4,527,724 A 7/1985 Chow et al.
4,530,357 A 7/1985 Pawloski et al.
4,530,453 A 7/1985 Green
4,531,522 A 7/1985 Bedi et al.
4,532,927 A 8/1985 Miksza, Jr.
4,540,202 A 9/1985 Amphoux et al.
4,548,202 A 10/1985 Duncan
4,556,058 A 12/1985 Green
4,560,915 A 12/1985 Soultanian
4,565,109 A 1/1986 Tsay
4,565,189 A 1/1986 Mabuchi
4,566,620 A 1/1986 Green et al.
4,569,346 A 2/1986 Poirier
4,569,469 A 2/1986 Mongeon et al.
4,571,213 A 2/1986 Ishimoto
4,573,468 A 3/1986 Conta et al.
4,573,469 A 3/1986 Golden et al.
4,573,622 A 3/1986 Green et al.
4,576,165 A 3/1986 Green et al.
4,576,167 A 3/1986 Noiles
4,580,712 A 4/1986 Green
4,585,153 A 4/1986 Failla et al.
4,586,501 A 5/1986 Claracq
4,586,502 A 5/1986 Bedi et al.
4,589,416 A 5/1986 Green
4,589,582 A 5/1986 Bilotti
4,589,870 A 5/1986 Citrin et al.
4,591,085 A 5/1986 Di Giovanni
RE32,214 E 7/1986 Schramm
4,597,753 A 7/1986 Turley
4,600,037 A 7/1986 Hatten
4,604,786 A 8/1986 Howie, Jr.
4,605,001 A 8/1986 Rothfuss et al.
4,605,004 A 8/1986 Di Giovanni et al.
4,606,343 A 8/1986 Conta et al.
4,607,636 A 8/1986 Kula et al.
4,607,638 A 8/1986 Crainich
4,608,980 A 9/1986 Aihara
4,608,981 A 9/1986 Rothfuss et al.
4,610,250 A 9/1986 Green
4,610,383 A 9/1986 Rothfuss et al.
4,612,933 A 9/1986 Brinkerhoff et al.
D286,180 S 10/1986 Korthoff
D286,442 S 10/1986 Korthoff et al.
4,617,893 A 10/1986 Donner et al.
4,617,914 A 10/1986 Ueda
4,617,935 A 10/1986 Cartmell et al.
4,619,262 A 10/1986 Taylor
4,619,391 A 10/1986 Sharkany et al.
4,624,401 A 11/1986 Gassner et al.
D287,278 S 12/1986 Spreckelmeier
4,628,459 A 12/1986 Shinohara et al.
4,628,636 A 12/1986 Folger
4,629,107 A 12/1986 Fedotov et al.
4,632,290 A 12/1986 Green et al.
4,633,861 A 1/1987 Chow et al.
4,633,874 A 1/1987 Chow et al.
4,634,419 A 1/1987 Kreizman et al.
4,635,638 A 1/1987 Weintraub et al.
4,641,076 A 2/1987 Linden
4,642,618 A 2/1987 Johnson et al.
4,642,738 A 2/1987 Meller
4,643,173 A 2/1987 Bell et al.
4,643,731 A 2/1987 Eckenhoff
4,646,722 A 3/1987 Silverstein et al.
4,646,745 A 3/1987 Noiles
4,651,734 A 3/1987 Doss et al.
4,652,820 A 3/1987 Maresca
4,654,028 A 3/1987 Suma
4,655,222 A 4/1987 Florez et al.
4,662,555 A 5/1987 Thornton
4,663,874 A 5/1987 Sano et al.
4,664,305 A 5/1987 Blake, III et al.
4,665,916 A 5/1987 Green
4,667,674 A 5/1987 Korthoff et al.
4,669,647 A 6/1987 Storace
4,671,278 A 6/1987 Chin
4,671,280 A 6/1987 Dorband et al.
4,671,445 A 6/1987 Barker et al.
4,672,964 A 6/1987 Dee et al.
4,675,944 A 6/1987 Wells
4,676,245 A 6/1987 Fukuda
4,679,460 A 7/1987 Yoshigai
4,679,719 A 7/1987 Kramer
4,684,051 A 8/1987 Akopov et al.
4,688,555 A 8/1987 Wardle
4,691,703 A 9/1987 Auth et al.
4,693,248 A 9/1987 Failla
4,698,579 A 10/1987 Richter et al.
4,700,703 A 10/1987 Resnick et al.
4,705,038 A 11/1987 Sjostrom et al.
4,708,141 A 11/1987 Inoue et al.
4,709,120 A 11/1987 Pearson
4,715,520 A 12/1987 Roehr, Jr. et al.
4,719,917 A 1/1988 Barrows et al.
4,721,099 A 1/1988 Chikama
4,722,340 A 2/1988 Takayama et al.
4,724,840 A 2/1988 McVay et al.
4,726,247 A 2/1988 Hormann
4,727,308 A 2/1988 Huljak et al.
4,728,020 A 3/1988 Green et al.
4,728,876 A 3/1988 Mongeon et al.
4,729,260 A 3/1988 Dudden
4,730,726 A 3/1988 Holzwarth
4,741,336 A 5/1988 Failla et al.
4,743,214 A 5/1988 Tai-Cheng
4,744,363 A 5/1988 Hasson
4,747,820 A 5/1988 Hornlein et al.
4,750,902 A 6/1988 Wuchinich et al.
4,752,024 A 6/1988 Green et al.
4,754,909 A 7/1988 Barker et al.
4,755,070 A 7/1988 Cerutti
4,761,326 A 8/1988 Barnes et al.
4,763,669 A 8/1988 Jaeger
4,767,044 A 8/1988 Green
D297,764 S 9/1988 Hunt et al.
4,773,420 A 9/1988 Green
4,777,780 A 10/1988 Holzwarth
4,781,186 A 11/1988 Simpson et al.
4,784,137 A 11/1988 Kulik et al.
4,787,387 A 11/1988 Burbank, III et al.

(56) References Cited

U.S. PATENT DOCUMENTS 4,788,485 A 11/1988 Kawagishi et al.
D298,967 S 12/1988 Hunt
4,788,978 A 12/1988 Strekopytov et al.
4,790,225 A 12/1988 Moody et al.
4,790,314 A 12/1988 Weaver
4,805,617 A 2/1989 Bedi et al.
4,805,823 A 2/1989 Rothfuss
4,807,628 A 2/1989 Peters et al.
4,809,695 A 3/1989 Gwathmey et al.
4,815,460 A 3/1989 Porat et al.
4,817,643 A 4/1989 Olson
4,817,847 A 4/1989 Redtenbacher et al.
4,819,495 A 4/1989 Hormann
4,819,853 A 4/1989 Green
4,821,939 A 4/1989 Green
4,827,552 A 5/1989 Bojar et al.
4,827,911 A 5/1989 Broadwin et al.
4,828,542 A 5/1989 Hermann
4,828,944 A 5/1989 Yabe et al.
4,830,855 A 5/1989 Stewart
4,832,158 A 5/1989 Farrar et al.
4,833,937 A 5/1989 Nagano
4,834,096 A 5/1989 Oh et al.
4,834,720 A 5/1989 Blinkhorn
4,838,859 A 6/1989 Strassmann
4,844,068 A 7/1989 Arata et al.
4,848,637 A 7/1989 Pruitt
4,856,078 A 8/1989 Konopka
4,860,644 A 8/1989 Kohl et al.
4,862,891 A 9/1989 Smith
4,863,423 A 9/1989 Wallace
4,865,030 A 9/1989 Polyak
4,868,530 A 9/1989 Ahs
4,868,958 A 9/1989 Suzuki et al.
4,869,414 A 9/1989 Green et al.
4,869,415 A 9/1989 Fox
4,873,977 A 10/1989 Avant et al.
4,875,486 A 10/1989 Rapoport et al.
4,880,015 A 11/1989 Nierman
4,890,613 A 1/1990 Golden et al.
4,892,244 A 1/1990 Fox et al.
4,893,622 A 1/1990 Green et al.
4,894,051 A 1/1990 Shiber
4,896,584 A 1/1990 Stoll et al.
4,896,678 A 1/1990 Ogawa
4,900,303 A 2/1990 Lemelson
4,903,697 A 2/1990 Resnick et al.
4,909,789 A 3/1990 Taguchi et al.
4,915,100 A 4/1990 Green
4,919,679 A 4/1990 Averill et al.
4,921,479 A 5/1990 Grayzel
4,925,082 A 5/1990 Kim
4,928,699 A 5/1990 Sasai
4,930,503 A 6/1990 Pruitt
4,930,674 A 6/1990 Barak
4,931,047 A 6/1990 Broadwin et al.
4,931,737 A 6/1990 Hishiki
4,932,960 A 6/1990 Green et al.
4,933,800 A 6/1990 Yang
4,933,843 A 6/1990 Scheller et al.
D309,350 S 7/1990 Sutherland et al.
4,938,408 A 7/1990 Bedi et al.
4,941,623 A 7/1990 Pruitt
4,943,182 A 7/1990 Hoblingre
4,944,443 A 7/1990 Oddsen et al.
4,946,067 A 8/1990 Kelsall
4,948,327 A 8/1990 Crupi, Jr.
4,949,707 A 8/1990 LeVahn et al.
4,949,927 A 8/1990 Madocks et al.
4,950,268 A 8/1990 Rink
4,951,860 A 8/1990 Peters et al.
4,951,861 A 8/1990 Schulze et al.
4,954,960 A 9/1990 Lo et al.
4,955,959 A 9/1990 Tompkins et al.
4,957,212 A 9/1990 Duck et al.
4,962,681 A 10/1990 Yang
4,962,877 A 10/1990 Hervas
4,964,559 A 10/1990 Deniega et al.
4,964,863 A 10/1990 Kanshin et al.
4,965,709 A 10/1990 Ngo
4,970,656 A 11/1990 Lo et al.
4,973,274 A 11/1990 Hirukawa
4,973,302 A 11/1990 Armour et al.
4,976,173 A 12/1990 Yang
4,978,049 A 12/1990 Green
4,978,333 A 12/1990 Broadwin et al.
4,979,952 A 12/1990 Kubota et al.
4,984,564 A 1/1991 Yuen
4,986,808 A 1/1991 Broadwin et al.
4,987,049 A 1/1991 Komamura et al.
4,988,334 A 1/1991 Hornlein et al.
4,995,877 A 2/1991 Ams et al.
4,995,959 A 2/1991 Metzner
4,996,975 A 3/1991 Nakamura
5,001,649 A 3/1991 Lo et al.
5,002,543 A 3/1991 Bradshaw et al.
5,002,553 A 3/1991 Shiber
5,005,754 A 4/1991 Van Overloop
5,009,222 A 4/1991 Her
5,009,661 A 4/1991 Michelson
5,012,411 A 4/1991 Policastro et al.
5,014,898 A 5/1991 Heidrich
5,014,899 A 5/1991 Presty et al.
5,015,227 A 5/1991 Broadwin et al.
5,018,515 A 5/1991 Gilman
5,018,657 A 5/1991 Pedlick et al.
5,019,077 A 5/1991 De Bastiani et al.
5,024,652 A 6/1991 Dumenek et al.
5,024,671 A 6/1991 Tu et al.
5,025,559 A 6/1991 McCullough
5,027,834 A 7/1991 Pruitt
5,030,226 A 7/1991 Green et al.
5,031,814 A 7/1991 Tompkins et al.
5,033,552 A 7/1991 Hu
5,035,040 A 7/1991 Kerrigan et al.
5,037,018 A 8/1991 Matsuda et al.
5,038,109 A 8/1991 Goble et al.
5,038,247 A 8/1991 Kelley et al.
5,040,715 A 8/1991 Green et al.
5,042,707 A 8/1991 Taheri
5,056,953 A 10/1991 Marot et al.
5,060,658 A 10/1991 Dejter, Jr. et al.
5,061,269 A 10/1991 Muller
5,062,491 A 11/1991 Takeshima et al.
5,062,563 A 11/1991 Green et al.
5,065,929 A 11/1991 Schulze et al.
5,071,052 A 12/1991 Rodak et al.
5,071,430 A 12/1991 de Salis et al.
5,074,454 A 12/1991 Peters
5,077,506 A 12/1991 Krause
5,079,006 A 1/1992 Urquhart
5,080,556 A 1/1992 Carreno
5,083,695 A 1/1992 Foslien et al.
5,084,057 A 1/1992 Green et al.
5,088,979 A 2/1992 Filipi et al.
5,088,997 A 2/1992 Delahuerga et al.
5,089,606 A 2/1992 Cole et al.
5,094,247 A 3/1992 Hernandez et al.
5,098,004 A 3/1992 Kerrigan
5,098,360 A 3/1992 Hirota
5,100,042 A 3/1992 Gravener et al.
5,100,420 A 3/1992 Green et al.
5,100,422 A 3/1992 Berguer et al.
5,104,025 A 4/1992 Main et al.
5,104,397 A 4/1992 Vasconcelos et al.
5,104,400 A 4/1992 Berguer et al.
5,106,008 A 4/1992 Tompkins et al.
5,108,368 A 4/1992 Hammerslag et al.
5,109,722 A 5/1992 Hufnagle et al.
5,111,987 A 5/1992 Moeinzadeh et al.
5,116,349 A 5/1992 Aranyi
D327,323 S 6/1992 Hunt
5,119,009 A 6/1992 McCaleb et al.
5,122,156 A 6/1992 Granger et al.

(56) References Cited

U.S. PATENT DOCUMENTS

| | | | |
|---|---|---|---|
| 5,124,990 | A | 6/1992 | Williamson |
| 5,129,570 | A | 7/1992 | Schulze et al. |
| 5,137,198 | A | 8/1992 | Nobis et al. |
| 5,139,513 | A | 8/1992 | Segato |
| 5,141,144 | A | 8/1992 | Foslien et al. |
| 5,142,932 | A | 9/1992 | Moya et al. |
| 5,151,102 | A | 9/1992 | Kamiyama et al. |
| 5,155,941 | A | 10/1992 | Takahashi et al. |
| 5,156,151 | A | 10/1992 | Imran |
| 5,156,315 | A | 10/1992 | Green et al. |
| 5,156,609 | A | 10/1992 | Nakao et al. |
| 5,156,614 | A | 10/1992 | Green et al. |
| 5,158,222 | A | 10/1992 | Green et al. |
| 5,158,567 | A | 10/1992 | Green |
| D330,699 | S | 11/1992 | Gill |
| 5,163,598 | A | 11/1992 | Peters et al. |
| 5,163,842 | A | 11/1992 | Nonomura |
| 5,164,652 | A | 11/1992 | Johnson et al. |
| 5,168,605 | A | 12/1992 | Bartlett |
| 5,170,925 | A | 12/1992 | Madden et al. |
| 5,171,247 | A | 12/1992 | Hughett et al. |
| 5,171,249 | A | 12/1992 | Stefanchik et al. |
| 5,171,253 | A | 12/1992 | Klieman |
| 5,173,053 | A | 12/1992 | Swanson et al. |
| 5,173,133 | A | 12/1992 | Morin et al. |
| 5,176,677 | A | 1/1993 | Wuchinich |
| 5,176,688 | A | 1/1993 | Narayan et al. |
| 5,181,514 | A | 1/1993 | Solomon et al. |
| 5,187,422 | A | 2/1993 | Izenbaard et al. |
| 5,188,102 | A | 2/1993 | Idemoto et al. |
| 5,188,111 | A | 2/1993 | Yates et al. |
| 5,188,126 | A | 2/1993 | Fabian et al. |
| 5,190,517 | A | 3/1993 | Zieve et al. |
| 5,190,544 | A | 3/1993 | Chapman et al. |
| 5,190,560 | A | 3/1993 | Woods et al. |
| 5,190,657 | A | 3/1993 | Heagle et al. |
| 5,192,288 | A | 3/1993 | Thompson et al. |
| 5,193,731 | A | 3/1993 | Aranyi |
| 5,195,505 | A | 3/1993 | Josefsen |
| 5,195,968 | A | 3/1993 | Lundquist et al. |
| 5,197,648 | A | 3/1993 | Gingold |
| 5,197,649 | A | 3/1993 | Bessler et al. |
| 5,197,966 | A | 3/1993 | Sommerkamp |
| 5,197,970 | A | 3/1993 | Green et al. |
| 5,200,280 | A | 4/1993 | Karasa |
| 5,201,750 | A | 4/1993 | Hocherl et al. |
| 5,205,459 | A | 4/1993 | Brinkerhoff et al. |
| 5,207,672 | A | 5/1993 | Roth et al. |
| 5,207,697 | A | 5/1993 | Carusillo et al. |
| 5,209,747 | A | 5/1993 | Knoepfler |
| 5,209,756 | A | 5/1993 | Seedhom et al. |
| 5,211,649 | A | 5/1993 | Kohler et al. |
| 5,211,655 | A | 5/1993 | Hasson |
| 5,217,457 | A | 6/1993 | Delahuerga et al. |
| 5,217,478 | A | 6/1993 | Rexroth |
| 5,219,111 | A | 6/1993 | Bilotti et al. |
| 5,220,269 | A | 6/1993 | Chen et al. |
| 5,221,036 | A | 6/1993 | Takase |
| 5,221,281 | A | 6/1993 | Klicek |
| 5,222,945 | A | 6/1993 | Basnight |
| 5,222,963 | A | 6/1993 | Brinkerhoff et al. |
| 5,222,975 | A | 6/1993 | Crainich |
| 5,222,976 | A | 6/1993 | Yoon |
| 5,223,675 | A | 6/1993 | Taft |
| D338,729 | S | 8/1993 | Sprecklemeier et al. |
| 5,234,447 | A | 8/1993 | Kaster et al. |
| 5,236,269 | A | 8/1993 | Handy |
| 5,236,424 | A | 8/1993 | Imran |
| 5,236,440 | A | 8/1993 | Hlavacek |
| 5,236,629 | A | 8/1993 | Mahabadi et al. |
| 5,239,981 | A | 8/1993 | Anapliotis |
| 5,240,163 | A | 8/1993 | Stein et al. |
| 5,242,456 | A | 9/1993 | Nash et al. |
| 5,242,457 | A | 9/1993 | Akopov et al. |
| 5,244,462 | A | 9/1993 | Delahuerga et al. |

| | | | |
|---|---|---|---|
| 5,246,156 | A | 9/1993 | Rothfuss et al. |
| 5,246,443 | A | 9/1993 | Mai |
| 5,251,801 | A | 10/1993 | Ruckdeschel et al. |
| 5,253,793 | A | 10/1993 | Green et al. |
| 5,258,007 | A | 11/1993 | Spetzler et al. |
| 5,258,008 | A | 11/1993 | Wilk |
| 5,258,009 | A | 11/1993 | Conners |
| 5,258,010 | A | 11/1993 | Green et al. |
| 5,258,012 | A | 11/1993 | Luscombe et al. |
| 5,259,366 | A | 11/1993 | Reydel et al. |
| 5,259,835 | A | 11/1993 | Clark et al. |
| 5,260,637 | A | 11/1993 | Pizzi |
| 5,261,135 | A | 11/1993 | Mitchell |
| 5,261,877 | A | 11/1993 | Fine et al. |
| 5,261,922 | A | 11/1993 | Hood |
| 5,263,629 | A | 11/1993 | Trumbull et al. |
| 5,263,937 | A | 11/1993 | Shipp |
| 5,263,973 | A | 11/1993 | Cook |
| 5,264,218 | A | 11/1993 | Rogozinski |
| 5,268,622 | A | 12/1993 | Philipp |
| 5,269,794 | A | 12/1993 | Rexroth |
| 5,271,543 | A | 12/1993 | Grant et al. |
| 5,271,544 | A | 12/1993 | Fox et al. |
| RE34,519 | E | 1/1994 | Fox et al. |
| 5,275,322 | A | 1/1994 | Brinkerhoff et al. |
| 5,275,323 | A | 1/1994 | Schulze et al. |
| 5,275,608 | A | 1/1994 | Forman et al. |
| 5,279,416 | A | 1/1994 | Malec et al. |
| 5,281,216 | A | 1/1994 | Klicek |
| 5,281,400 | A | 1/1994 | Berry, Jr. |
| 5,282,806 | A | 2/1994 | Haber et al. |
| 5,282,826 | A | 2/1994 | Quadri |
| 5,282,829 | A | 2/1994 | Hermes |
| 5,284,128 | A | 2/1994 | Hart |
| 5,285,381 | A | 2/1994 | Iskarous et al. |
| 5,285,945 | A | 2/1994 | Brinkerhoff et al. |
| 5,286,253 | A | 2/1994 | Fucci |
| 5,289,963 | A | 3/1994 | McGarry et al. |
| 5,290,271 | A | 3/1994 | Jernberg |
| 5,290,310 | A | 3/1994 | Makower et al. |
| 5,291,133 | A | 3/1994 | Gokhale et al. |
| 5,292,053 | A | 3/1994 | Bilotti et al. |
| 5,293,024 | A | 3/1994 | Sugahara et al. |
| 5,297,714 | A | 3/1994 | Kramer |
| 5,300,087 | A | 4/1994 | Knoepfler |
| 5,302,148 | A | 4/1994 | Heinz |
| 5,303,606 | A | 4/1994 | Kokinda |
| 5,304,204 | A | 4/1994 | Bregen |
| D347,474 | S | 5/1994 | Olson |
| 5,307,976 | A | 5/1994 | Olson et al. |
| 5,308,353 | A | 5/1994 | Beurrier |
| 5,308,358 | A | 5/1994 | Bond et al. |
| 5,308,576 | A | 5/1994 | Green et al. |
| 5,309,387 | A | 5/1994 | Mori et al. |
| 5,309,927 | A | 5/1994 | Welch |
| 5,312,023 | A | 5/1994 | Green et al. |
| 5,312,024 | A | 5/1994 | Grant et al. |
| 5,312,329 | A | 5/1994 | Beaty et al. |
| 5,313,935 | A | 5/1994 | Kortenbach et al. |
| 5,313,967 | A | 5/1994 | Lieber et al. |
| 5,314,424 | A | 5/1994 | Nicholas |
| 5,314,445 | A | 5/1994 | Heidmueller nee Degwitz et al. |
| 5,314,466 | A | 5/1994 | Stern et al. |
| 5,318,221 | A | 6/1994 | Green et al. |
| 5,318,589 | A | 6/1994 | Lichtman |
| 5,320,627 | A | 6/1994 | Sorensen et al. |
| D348,930 | S | 7/1994 | Olson |
| 5,326,013 | A | 7/1994 | Green et al. |
| 5,329,923 | A | 7/1994 | Lundquist |
| 5,330,486 | A | 7/1994 | Wilk |
| 5,330,487 | A | 7/1994 | Thornton et al. |
| 5,330,502 | A | 7/1994 | Hassler et al. |
| 5,331,971 | A | 7/1994 | Bales et al. |
| 5,332,142 | A | 7/1994 | Robinson et al. |
| 5,333,422 | A | 8/1994 | Warren et al. |
| 5,333,772 | A | 8/1994 | Rothfuss et al. |
| 5,333,773 | A | 8/1994 | Main et al. |
| 5,334,183 | A | 8/1994 | Wuchinich |
| 5,336,130 | A | 8/1994 | Ray |

(56) References Cited

U.S. PATENT DOCUMENTS 5,336,229 A 8/1994 Noda
5,336,232 A 8/1994 Green et al.
5,338,317 A 8/1994 Hasson et al.
5,339,799 A 8/1994 Kami et al.
5,341,724 A 8/1994 Vatel
5,341,807 A 8/1994 Nardella
5,341,810 A 8/1994 Dardel
5,342,380 A 8/1994 Hood
5,342,381 A 8/1994 Tidemand
5,342,385 A 8/1994 Norelli et al.
5,342,395 A 8/1994 Jarrett et al.
5,342,396 A 8/1994 Cook
5,343,382 A 8/1994 Hale et al.
5,343,391 A 8/1994 Mushabac
5,344,059 A 9/1994 Green et al.
5,344,060 A 9/1994 Gravener et al.
5,344,454 A 9/1994 Clarke et al.
5,346,504 A 9/1994 Ortiz et al.
5,348,259 A 9/1994 Blanco et al.
5,350,104 A 9/1994 Main et al.
5,350,355 A 9/1994 Sklar
5,350,388 A 9/1994 Epstein
5,350,391 A 9/1994 Iacovelli
5,350,400 A 9/1994 Esposito et al.
5,352,229 A 10/1994 Goble et al.
5,352,235 A 10/1994 Koros et al.
5,352,238 A 10/1994 Green et al.
5,353,798 A 10/1994 Sieben
5,354,215 A 10/1994 Viracola
5,354,250 A 10/1994 Christensen
5,354,303 A 10/1994 Spaeth et al.
5,355,897 A 10/1994 Pietrafitta et al.
5,356,006 A 10/1994 Alpern et al.
5,356,064 A 10/1994 Green et al.
5,358,506 A 10/1994 Green et al.
5,358,510 A 10/1994 Luscombe et al.
5,359,231 A 10/1994 Flowers et al.
D352,780 S 11/1994 Glaeser et al.
5,359,993 A 11/1994 Slater et al.
5,360,305 A 11/1994 Kerrigan
5,360,428 A 11/1994 Hutchinson, Jr.
5,361,902 A 11/1994 Abidin et al.
5,364,001 A 11/1994 Bryan
5,364,002 A 11/1994 Green et al.
5,364,003 A 11/1994 Williamson, IV
5,366,133 A 11/1994 Geiste
5,366,134 A 11/1994 Green et al.
5,366,479 A 11/1994 McGarry et al.
5,368,015 A 11/1994 Wilk
5,368,592 A 11/1994 Stern et al.
5,368,599 A 11/1994 Hirsch et al.
5,369,565 A 11/1994 Chen et al.
5,370,645 A 12/1994 Klicek et al.
5,372,124 A 12/1994 Takayama et al.
5,372,596 A 12/1994 Klicek et al.
5,372,602 A 12/1994 Burke
5,374,277 A 12/1994 Hassler
5,375,588 A 12/1994 Yoon
5,376,095 A 12/1994 Ortiz
5,379,933 A 1/1995 Green et al.
5,381,649 A 1/1995 Webb
5,381,782 A 1/1995 DeLaRama et al.
5,381,943 A 1/1995 Allen et al.
5,382,247 A 1/1995 Cimino et al.
5,383,460 A 1/1995 Jang et al.
5,383,738 A 1/1995 Herbermann
5,383,874 A 1/1995 Jackson et al.
5,383,880 A 1/1995 Hooven
5,383,881 A 1/1995 Green et al.
5,383,882 A 1/1995 Buess et al.
5,383,888 A 1/1995 Zvenyatsky et al.
5,383,895 A 1/1995 Holmes et al.
5,388,568 A 2/1995 van der Heide
5,389,072 A 2/1995 Imran
5,389,098 A 2/1995 Tsuruta et al.
5,389,102 A 2/1995 Green et al.
5,389,104 A 2/1995 Hahnen et al.
5,391,180 A 2/1995 Tovey et al.
5,392,979 A 2/1995 Green et al.
5,395,030 A 3/1995 Kuramoto et al.
5,395,033 A 3/1995 Byrne et al.
5,395,034 A 3/1995 Allen et al.
5,395,312 A 3/1995 Desai
5,395,384 A 3/1995 Duthoit et al.
5,397,046 A 3/1995 Savage et al.
5,397,324 A 3/1995 Carroll et al.
5,400,267 A 3/1995 Denen et al.
5,403,276 A 4/1995 Schechter et al.
5,403,312 A 4/1995 Yates et al.
5,404,106 A 4/1995 Matsuda
5,404,870 A 4/1995 Brinkerhoff et al.
5,404,960 A 4/1995 Wada et al.
5,405,072 A 4/1995 Zlock et al.
5,405,073 A 4/1995 Porter
5,405,344 A 4/1995 Williamson et al.
5,405,360 A 4/1995 Tovey
5,407,293 A 4/1995 Crainich
5,408,409 A 4/1995 Glassman et al.
5,409,498 A 4/1995 Braddock et al.
5,409,703 A 4/1995 McAnalley et al.
D357,981 S 5/1995 Green et al.
5,411,481 A 5/1995 Allen et al.
5,411,508 A 5/1995 Bessler et al.
5,413,107 A 5/1995 Oakley et al.
5,413,267 A 5/1995 Solyntjes et al.
5,413,268 A 5/1995 Green et al.
5,413,272 A 5/1995 Green et al.
5,413,573 A 5/1995 Koivukangas
5,415,334 A 5/1995 Williamson et al.
5,415,335 A 5/1995 Knodell, Jr.
5,417,203 A 5/1995 Tovey et al.
5,417,361 A 5/1995 Williamson, IV
5,419,766 A 5/1995 Chang et al.
5,421,829 A 6/1995 Olichney et al.
5,422,567 A 6/1995 Matsunaga
5,423,471 A 6/1995 Mastri et al.
5,423,809 A 6/1995 Klicek
5,423,835 A 6/1995 Green et al.
5,425,355 A 6/1995 Kulick
5,425,745 A 6/1995 Green et al.
5,427,298 A 6/1995 Tegtmeier
5,431,322 A 7/1995 Green et al.
5,431,323 A 7/1995 Smith et al.
5,431,645 A 7/1995 Smith et al.
5,431,654 A 7/1995 Nic
5,431,666 A 7/1995 Sauer et al.
5,431,668 A 7/1995 Burbank, III et al.
5,433,721 A 7/1995 Hooven et al.
5,437,681 A 8/1995 Meade et al.
5,438,302 A 8/1995 Goble
5,438,997 A 8/1995 Sieben et al.
5,439,155 A 8/1995 Viola
5,439,156 A 8/1995 Grant et al.
5,439,479 A 8/1995 Shichman et al.
5,441,191 A 8/1995 Linden
5,441,193 A 8/1995 Gravener
5,441,483 A 8/1995 Avitall
5,441,494 A 8/1995 Ortiz
5,441,499 A 8/1995 Fritzsch
5,443,197 A 8/1995 Malis et al.
5,443,198 A 8/1995 Viola et al.
5,443,463 A 8/1995 Stern et al.
5,444,113 A 8/1995 Sinclair et al.
5,445,155 A 8/1995 Sieben
5,445,304 A 8/1995 Plyley et al.
5,445,604 A 8/1995 Lang
5,445,644 A 8/1995 Pietrafitta et al.
5,446,646 A 8/1995 Miyazaki
5,447,265 A 9/1995 Vidal et al.
5,447,417 A 9/1995 Kuhl et al.
5,447,513 A 9/1995 Davison et al.
5,449,355 A 9/1995 Rhum et al.
5,449,365 A 9/1995 Green et al.
5,449,370 A 9/1995 Vaitekunas

(56) References Cited

U.S. PATENT DOCUMENTS 5,452,836 A 9/1995 Huitema et al.
5,452,837 A 9/1995 Williamson, IV et al.
5,454,378 A 10/1995 Palmer et al.
5,454,822 A 10/1995 Schob et al.
5,454,824 A 10/1995 Fontayne et al.
5,454,827 A 10/1995 Aust et al.
5,456,401 A 10/1995 Green et al.
5,456,917 A 10/1995 Wise et al.
5,458,279 A 10/1995 Plyley
5,458,579 A 10/1995 Chodorow et al.
5,462,215 A 10/1995 Viola et al.
5,464,013 A 11/1995 Lemelson
5,464,144 A 11/1995 Guy et al.
5,464,300 A 11/1995 Crainich
5,465,819 A 11/1995 Weilant et al.
5,465,894 A 11/1995 Clark et al.
5,465,895 A 11/1995 Knodel et al.
5,465,896 A 11/1995 Allen et al.
5,466,020 A 11/1995 Page et al.
5,467,911 A 11/1995 Tsuruta et al.
5,468,253 A 11/1995 Bezwada et al.
5,470,006 A 11/1995 Rodak
5,470,007 A 11/1995 Plyley et al.
5,470,008 A 11/1995 Rodak
5,470,009 A 11/1995 Rodak
5,470,010 A 11/1995 Rothfuss et al.
5,471,129 A 11/1995 Mann
5,472,132 A 12/1995 Savage et al.
5,472,442 A 12/1995 Klicek
5,473,204 A 12/1995 Temple
5,474,057 A 12/1995 Makower et al.
5,474,223 A 12/1995 Viola et al.
5,474,566 A 12/1995 Alesi et al.
5,474,570 A 12/1995 Kockerling et al.
5,474,738 A 12/1995 Nichols et al.
5,476,206 A 12/1995 Green et al.
5,476,479 A 12/1995 Green et al.
5,476,481 A 12/1995 Schondorf
5,478,003 A 12/1995 Green et al.
5,478,308 A 12/1995 Cartmell et al.
5,478,354 A 12/1995 Tovey et al.
5,480,089 A 1/1996 Blewett
5,480,409 A 1/1996 Riza
5,482,197 A 1/1996 Green et al.
5,483,952 A 1/1996 Aranyi
5,484,095 A 1/1996 Green et al.
5,484,398 A 1/1996 Stoddard
5,484,451 A 1/1996 Akopov et al.
5,485,947 A 1/1996 Olson et al.
5,485,952 A 1/1996 Fontayne
5,487,377 A 1/1996 Smith et al.
5,487,499 A 1/1996 Sorrentino et al.
5,487,500 A 1/1996 Knodel et al.
5,489,058 A 2/1996 Plyley et al.
5,489,256 A 2/1996 Adair
5,489,290 A 2/1996 Furnish
5,490,819 A 2/1996 Nicholas et al.
5,492,671 A 2/1996 Krafft
5,496,312 A 3/1996 Klicek
5,496,317 A 3/1996 Goble et al.
5,497,933 A 3/1996 DeFonzo et al.
5,498,164 A 3/1996 Ward et al.
5,498,838 A 3/1996 Furman
5,501,654 A 3/1996 Failla et al.
5,503,320 A 4/1996 Webster et al.
5,503,635 A 4/1996 Sauer et al.
5,503,638 A 4/1996 Cooper et al.
5,505,363 A 4/1996 Green et al.
5,507,425 A 4/1996 Ziglioli
5,507,426 A 4/1996 Young et al.
5,507,773 A 4/1996 Huitema et al.
5,509,596 A 4/1996 Green et al.
5,509,916 A 4/1996 Taylor
5,509,918 A 4/1996 Romano
5,511,564 A 4/1996 Wilk
5,514,129 A 5/1996 Smith
5,514,149 A 5/1996 Green et al.
5,514,157 A 5/1996 Nicholas et al.
5,518,163 A 5/1996 Hooven
5,518,164 A 5/1996 Hooven
5,520,609 A 5/1996 Moll et al.
5,520,634 A 5/1996 Fox et al.
5,520,678 A 5/1996 Heckele et al.
5,520,700 A 5/1996 Beyar et al.
5,522,817 A 6/1996 Sander et al.
5,522,831 A 6/1996 Sleister et al.
5,527,264 A 6/1996 Moll et al.
5,527,320 A 6/1996 Carruthers et al.
5,529,235 A 6/1996 Boiarski et al.
D372,086 S 7/1996 Grasso et al.
5,531,305 A 7/1996 Roberts et al.
5,531,744 A 7/1996 Nardella et al.
5,531,856 A 7/1996 Moll et al.
5,533,521 A 7/1996 Granger
5,533,581 A 7/1996 Barth et al.
5,533,661 A 7/1996 Main et al.
5,535,934 A 7/1996 Boiarski et al.
5,535,935 A 7/1996 Vidal et al.
5,535,937 A 7/1996 Boiarski et al.
5,540,375 A 7/1996 Bolanos et al.
5,540,705 A 7/1996 Meade et al.
5,541,376 A 7/1996 Ladtkow et al.
5,541,489 A 7/1996 Dunstan
5,542,594 A 8/1996 McKean et al.
5,542,945 A 8/1996 Fritzsch
5,542,949 A 8/1996 Yoon
5,543,119 A 8/1996 Sutter et al.
5,543,695 A 8/1996 Culp et al.
5,544,802 A 8/1996 Crainich
5,547,117 A 8/1996 Hamblin et al.
5,549,583 A 8/1996 Sanford et al.
5,549,621 A 8/1996 Bessler et al.
5,549,627 A 8/1996 Kieturakis
5,549,628 A 8/1996 Cooper et al.
5,549,637 A 8/1996 Crainich
5,551,622 A 9/1996 Yoon
5,553,624 A 9/1996 Francese et al.
5,553,675 A 9/1996 Pitzen et al.
5,553,765 A 9/1996 Knodel et al.
5,554,148 A 9/1996 Aebischer et al.
5,554,169 A 9/1996 Green et al.
5,556,020 A 9/1996 Hou
5,556,416 A 9/1996 Clark et al.
5,558,533 A 9/1996 Hashizawa et al.
5,558,665 A 9/1996 Kieturakis
5,558,671 A 9/1996 Yates
5,560,530 A 10/1996 Bolanos et al.
5,560,532 A 10/1996 DeFonzo et al.
5,561,881 A 10/1996 Klinger et al.
5,562,239 A 10/1996 Boiarski et al.
5,562,241 A 10/1996 Knodel et al.
5,562,682 A 10/1996 Oberlin et al.
5,562,690 A 10/1996 Green et al.
5,562,694 A 10/1996 Sauer et al.
5,562,701 A 10/1996 Huitema et al.
5,562,702 A 10/1996 Huitema et al.
5,563,481 A 10/1996 Krause
5,564,615 A 10/1996 Bishop et al.
5,569,161 A 10/1996 Ebling et al.
5,569,270 A 10/1996 Weng
5,569,284 A 10/1996 Young et al.
5,571,090 A 11/1996 Sherts
5,571,100 A 11/1996 Goble et al.
5,571,116 A 11/1996 Bolanos et al.
5,571,285 A 11/1996 Chow et al.
5,571,488 A 11/1996 Beerstecher et al.
5,573,169 A 11/1996 Green et al.
5,573,543 A 11/1996 Akopov et al.
5,574,431 A 11/1996 McKeown et al.
5,575,054 A 11/1996 Klinzing et al.
5,575,789 A 11/1996 Bell et al.
5,575,799 A 11/1996 Bolanos et al.
5,575,803 A 11/1996 Cooper et al.
5,575,805 A 11/1996 Li

(56) References Cited

U.S. PATENT DOCUMENTS 5,577,654 A 11/1996 Bishop
5,578,052 A 11/1996 Koros et al.
5,579,978 A 12/1996 Green et al.
5,580,067 A 12/1996 Hamblin et al.
5,582,611 A 12/1996 Tsuruta et al.
5,582,617 A 12/1996 Klieman et al.
5,582,907 A 12/1996 Pall
5,583,114 A 12/1996 Barrows et al.
5,584,425 A 12/1996 Savage et al.
5,586,711 A 12/1996 Plyley et al.
5,588,579 A 12/1996 Schnut et al.
5,588,580 A 12/1996 Paul et al.
5,588,581 A 12/1996 Conlon et al.
5,591,170 A 1/1997 Spievack et al.
5,591,187 A 1/1997 Dekel
5,597,107 A 1/1997 Knodel et al.
5,599,151 A 2/1997 Daum et al.
5,599,279 A 2/1997 Slotman et al.
5,599,344 A 2/1997 Paterson
5,599,350 A 2/1997 Schulze et al.
5,599,852 A 2/1997 Scopelianos et al.
5,601,224 A 2/1997 Bishop et al.
5,601,573 A 2/1997 Fogelberg et al.
5,601,604 A 2/1997 Vincent
5,602,449 A 2/1997 Krause et al.
5,603,443 A 2/1997 Clark et al.
5,605,272 A 2/1997 Witt et al.
5,605,273 A 2/1997 Hamblin et al.
5,607,094 A 3/1997 Clark et al.
5,607,095 A 3/1997 Smith et al.
5,607,303 A 3/1997 Nakamura
5,607,433 A 3/1997 Polla et al.
5,607,436 A 3/1997 Pratt et al.
5,607,450 A 3/1997 Zvenyatsky et al.
5,607,474 A 3/1997 Athanasiou et al.
5,609,285 A 3/1997 Grant et al.
5,609,601 A 3/1997 Kolesa et al.
5,611,709 A 3/1997 McAnulty
5,611,813 A 3/1997 Lichtman
5,613,499 A 3/1997 Palmer et al.
5,613,937 A 3/1997 Garrison et al.
5,613,966 A 3/1997 Makower et al.
5,614,887 A 3/1997 Buchbinder
5,615,820 A 4/1997 Viola
5,618,294 A 4/1997 Aust et al.
5,618,303 A 4/1997 Marlow et al.
5,618,307 A 4/1997 Donlon et al.
5,619,992 A 4/1997 Guthrie et al.
5,620,289 A 4/1997 Curry
5,620,326 A 4/1997 Younker
5,620,452 A 4/1997 Yoon
5,624,398 A 4/1997 Smith et al.
5,624,452 A 4/1997 Yates
5,626,587 A 5/1997 Bishop et al.
5,626,595 A 5/1997 Sklar et al.
5,626,979 A 5/1997 Mitsui et al.
5,628,446 A 5/1997 Geiste et al.
5,628,743 A 5/1997 Cimino
5,628,745 A 5/1997 Bek
5,630,539 A 5/1997 Plyley et al.
5,630,540 A 5/1997 Blewett
5,630,541 A 5/1997 Williamson, IV et al.
5,630,782 A 5/1997 Adair
5,631,973 A 5/1997 Green
5,632,432 A 5/1997 Schulze et al.
5,632,433 A 5/1997 Grant et al.
5,633,374 A 5/1997 Humphrey et al.
5,634,584 A 6/1997 Okorocha et al.
5,636,779 A 6/1997 Palmer
5,636,780 A 6/1997 Green et al.
5,637,110 A 6/1997 Pennybacker et al.
5,638,582 A 6/1997 Klatt et al.
5,639,008 A 6/1997 Gallagher et al.
D381,077 S 7/1997 Hunt
5,643,291 A 7/1997 Pier et al.
5,643,293 A 7/1997 Kogasaka et al.
5,643,294 A 7/1997 Tovey et al.
5,643,319 A 7/1997 Green et al.
5,645,209 A 7/1997 Green et al.
5,647,526 A 7/1997 Green et al.
5,647,869 A 7/1997 Goble et al.
5,649,937 A 7/1997 Bito et al.
5,649,956 A 7/1997 Jensen et al.
5,651,491 A 7/1997 Heaton et al.
5,651,762 A 7/1997 Bridges
5,651,821 A 7/1997 Uchida
5,653,373 A 8/1997 Green et al.
5,653,374 A 8/1997 Young et al.
5,653,677 A 8/1997 Okada et al.
5,653,721 A 8/1997 Knodel et al.
5,653,748 A 8/1997 Strecker
5,655,698 A 8/1997 Yoon
5,656,917 A 8/1997 Theobald
5,657,417 A 8/1997 Di Troia
5,657,429 A 8/1997 Wang et al.
5,657,921 A 8/1997 Young et al.
5,658,238 A 8/1997 Suzuki et al.
5,658,281 A 8/1997 Heard
5,658,298 A 8/1997 Vincent et al.
5,658,300 A 8/1997 Bito et al.
5,658,307 A 8/1997 Exconde
5,662,258 A 9/1997 Knodel et al.
5,662,260 A 9/1997 Yoon
5,662,662 A 9/1997 Bishop et al.
5,662,667 A 9/1997 Knodel
5,664,404 A 9/1997 Ivanov et al.
5,665,085 A 9/1997 Nardella
5,667,517 A 9/1997 Hooven
5,667,526 A 9/1997 Levin
5,667,527 A 9/1997 Cook
5,667,864 A 9/1997 Landoll
5,669,544 A 9/1997 Schulze et al.
5,669,904 A 9/1997 Platt, Jr. et al.
5,669,907 A 9/1997 Platt, Jr. et al.
5,669,918 A 9/1997 Balazs et al.
5,672,945 A 9/1997 Krause
5,673,840 A 10/1997 Schulze et al.
5,673,841 A 10/1997 Schulze et al.
5,673,842 A 10/1997 Bittner et al.
5,674,184 A 10/1997 Hassler, Jr.
5,674,286 A 10/1997 D'Alessio et al.
5,678,748 A 10/1997 Plyley et al.
5,680,981 A 10/1997 Mililli et al.
5,680,982 A 10/1997 Schulze et al.
5,680,983 A 10/1997 Plyley et al.
5,681,341 A 10/1997 Lunsford et al.
5,683,349 A 11/1997 Makower et al.
5,683,432 A 11/1997 Goedeke et al.
5,685,474 A 11/1997 Seeber
5,686,090 A 11/1997 Schilder et al.
5,688,270 A 11/1997 Yates et al.
5,690,269 A 11/1997 Bolanos et al.
5,690,675 A 11/1997 Sawyer et al.
5,692,668 A 12/1997 Schulze et al.
5,693,020 A 12/1997 Rauh
5,693,042 A 12/1997 Boiarski et al.
5,693,051 A 12/1997 Schulze et al.
5,695,494 A 12/1997 Becker
5,695,502 A 12/1997 Pier et al.
5,695,504 A 12/1997 Gifford, III et al.
5,695,524 A 12/1997 Kelley et al.
5,697,542 A 12/1997 Knodel et al.
5,697,543 A 12/1997 Burdorff
5,697,909 A 12/1997 Eggers et al.
5,697,943 A 12/1997 Sauer et al.
5,700,265 A 12/1997 Romano
5,700,270 A 12/1997 Peyser et al.
5,700,276 A 12/1997 Benecke
5,702,387 A 12/1997 Arts et al.
5,702,408 A 12/1997 Wales et al.
5,702,409 A 12/1997 Rayburn et al.
5,704,087 A 1/1998 Strub
5,704,534 A 1/1998 Huitema et al.
5,704,792 A 1/1998 Sobhani

(56) References Cited

U.S. PATENT DOCUMENTS

| | | | |
|---|---|---|---|
| 5,706,997 | A | 1/1998 | Green et al. |
| 5,706,998 | A | 1/1998 | Plyley et al. |
| 5,707,392 | A | 1/1998 | Kortenbach |
| 5,709,334 | A | 1/1998 | Sorrentino et al. |
| 5,709,335 | A | 1/1998 | Heck |
| 5,709,680 | A | 1/1998 | Yates et al. |
| 5,709,706 | A | 1/1998 | Kienzle et al. |
| 5,711,472 | A | 1/1998 | Bryan |
| 5,711,960 | A | 1/1998 | Shikinami |
| 5,712,460 | A | 1/1998 | Carr et al. |
| 5,713,128 | A | 2/1998 | Schrenk et al. |
| 5,713,505 | A | 2/1998 | Huitema |
| 5,713,895 | A | 2/1998 | Lontine et al. |
| 5,713,896 | A | 2/1998 | Nardella |
| 5,713,920 | A | 2/1998 | Bezwada et al. |
| 5,715,604 | A | 2/1998 | Lanzoni |
| 5,715,836 | A | 2/1998 | Kliegis et al. |
| 5,715,987 | A | 2/1998 | Kelley et al. |
| 5,715,988 | A | 2/1998 | Palmer |
| 5,716,352 | A | 2/1998 | Viola et al. |
| 5,716,366 | A | 2/1998 | Yates |
| 5,718,359 | A | 2/1998 | Palmer et al. |
| 5,718,360 | A | 2/1998 | Green et al. |
| 5,718,548 | A | 2/1998 | Cotellessa |
| 5,718,714 | A | 2/1998 | Livneh |
| 5,720,744 | A | 2/1998 | Eggleston et al. |
| D393,067 | S | 3/1998 | Geary et al. |
| 5,724,025 | A | 3/1998 | Tavori |
| 5,725,536 | A | 3/1998 | Oberlin et al. |
| 5,725,554 | A | 3/1998 | Simon et al. |
| 5,728,110 | A | 3/1998 | Vidal et al. |
| 5,728,113 | A | 3/1998 | Sherts |
| 5,728,121 | A | 3/1998 | Bimbo et al. |
| 5,730,758 | A | 3/1998 | Allgeyer |
| 5,732,712 | A | 3/1998 | Adair |
| 5,732,821 | A | 3/1998 | Stone et al. |
| 5,732,871 | A | 3/1998 | Clark et al. |
| 5,732,872 | A | 3/1998 | Bolduc et al. |
| 5,733,308 | A | 3/1998 | Daugherty et al. |
| 5,735,445 | A | 4/1998 | Vidal et al. |
| 5,735,848 | A | 4/1998 | Yates et al. |
| 5,735,874 | A | 4/1998 | Measamer et al. |
| 5,736,271 | A | 4/1998 | Cisar et al. |
| 5,738,474 | A | 4/1998 | Blewett |
| 5,738,629 | A | 4/1998 | Moll et al. |
| 5,738,648 | A | 4/1998 | Lands et al. |
| 5,741,271 | A | 4/1998 | Nakao et al. |
| 5,743,456 | A | 4/1998 | Jones et al. |
| 5,746,770 | A | 5/1998 | Zeitels et al. |
| 5,747,953 | A | 5/1998 | Philipp |
| 5,749,889 | A | 5/1998 | Bacich et al. |
| 5,749,893 | A | 5/1998 | Vidal et al. |
| 5,749,896 | A | 5/1998 | Cook |
| 5,749,968 | A | 5/1998 | Melanson et al. |
| 5,752,644 | A | 5/1998 | Bolanos et al. |
| 5,752,965 | A | 5/1998 | Francis et al. |
| 5,752,970 | A | 5/1998 | Yoon |
| 5,752,973 | A | 5/1998 | Kieturakis |
| 5,755,717 | A | 5/1998 | Yates et al. |
| 5,755,726 | A | 5/1998 | Pratt et al. |
| 5,758,814 | A | 6/1998 | Gallagher et al. |
| 5,762,255 | A | 6/1998 | Chrisman et al. |
| 5,762,256 | A | 6/1998 | Mastri et al. |
| 5,762,458 | A | 6/1998 | Wang et al. |
| 5,765,565 | A | 6/1998 | Adair |
| 5,766,186 | A | 6/1998 | Faraz et al. |
| 5,766,188 | A | 6/1998 | Igaki |
| 5,766,205 | A | 6/1998 | Zvenyatsky et al. |
| 5,769,303 | A | 6/1998 | Knodel et al. |
| 5,769,640 | A | 6/1998 | Jacobus et al. |
| 5,769,748 | A | 6/1998 | Eyerly et al. |
| 5,769,791 | A | 6/1998 | Benaron et al. |
| 5,769,892 | A | 6/1998 | Kingwell |
| 5,772,099 | A | 6/1998 | Gravener |
| 5,772,379 | A | 6/1998 | Evensen |
| 5,772,578 | A | 6/1998 | Heimberger et al. |
| 5,772,659 | A | 6/1998 | Becker et al. |
| 5,773,991 | A | 6/1998 | Chen |
| 5,776,130 | A | 7/1998 | Buysse et al. |
| 5,778,939 | A | 7/1998 | Hok-Yin |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,782,748 | A | 7/1998 | Palmer et al. |
| 5,782,749 | A | 7/1998 | Riza |
| 5,782,859 | A | 7/1998 | Nicholas et al. |
| 5,784,934 | A | 7/1998 | Izumisawa |
| 5,785,232 | A | 7/1998 | Vidal et al. |
| 5,785,647 | A | 7/1998 | Tompkins et al. |
| 5,787,897 | A | 8/1998 | Kieturakis |
| 5,791,231 | A | 8/1998 | Cohn et al. |
| 5,792,135 | A | 8/1998 | Madhani et al. |
| 5,792,162 | A | 8/1998 | Jolly et al. |
| 5,792,165 | A | 8/1998 | Klieman et al. |
| 5,792,573 | A | 8/1998 | Pitzen et al. |
| 5,794,834 | A | 8/1998 | Hamblin et al. |
| 5,796,188 | A | 8/1998 | Bays |
| 5,797,536 | A | 8/1998 | Smith et al. |
| 5,797,537 | A | 8/1998 | Oberlin et al. |
| 5,797,538 | A | 8/1998 | Heaton et al. |
| 5,797,637 | A | 8/1998 | Ervin |
| 5,797,900 | A | 8/1998 | Madhani et al. |
| 5,797,906 | A | 8/1998 | Rhum et al. |
| 5,797,927 | A | 8/1998 | Yoon |
| 5,797,941 | A | 8/1998 | Schulze et al. |
| 5,797,959 | A | 8/1998 | Castro et al. |
| 5,798,752 | A | 8/1998 | Buxton et al. |
| 5,799,857 | A | 9/1998 | Robertson et al. |
| 5,800,379 | A | 9/1998 | Edwards |
| 5,800,423 | A | 9/1998 | Jensen |
| 5,804,726 | A | 9/1998 | Geib et al. |
| 5,804,936 | A | 9/1998 | Brodsky et al. |
| 5,806,676 | A | 9/1998 | Wasgien |
| 5,807,241 | A | 9/1998 | Heimberger |
| 5,807,376 | A | 9/1998 | Viola et al. |
| 5,807,378 | A | 9/1998 | Jensen et al. |
| 5,807,393 | A | 9/1998 | Williamson, IV et al. |
| 5,809,441 | A | 9/1998 | McKee |
| 5,810,240 | A | 9/1998 | Robertson |
| 5,810,721 | A | 9/1998 | Mueller et al. |
| 5,810,811 | A | 9/1998 | Yates et al. |
| 5,810,846 | A | 9/1998 | Virnich et al. |
| 5,810,855 | A | 9/1998 | Rayburn et al. |
| 5,812,188 | A | 9/1998 | Adair |
| 5,813,813 | A | 9/1998 | Daum et al. |
| 5,814,055 | A | 9/1998 | Knodel et al. |
| 5,814,057 | A | 9/1998 | Oi et al. |
| 5,816,471 | A | 10/1998 | Plyley et al. |
| 5,817,084 | A | 10/1998 | Jensen |
| 5,817,091 | A | 10/1998 | Nardella et al. |
| 5,817,093 | A | 10/1998 | Williamson, IV et al. |
| 5,817,109 | A | 10/1998 | McGarry et al. |
| 5,817,119 | A | 10/1998 | Klieman et al. |
| 5,820,009 | A | 10/1998 | Melling et al. |
| 5,823,066 | A | 10/1998 | Huitema et al. |
| 5,824,333 | A | 10/1998 | Scopelianos et al. |
| 5,826,776 | A | 10/1998 | Schulze et al. |
| 5,827,271 | A | 10/1998 | Buysse et al. |
| 5,827,298 | A | 10/1998 | Hart et al. |
| 5,827,323 | A | 10/1998 | Klieman et al. |
| 5,829,662 | A | 11/1998 | Allen et al. |
| 5,830,598 | A | 11/1998 | Patterson |
| 5,833,690 | A | 11/1998 | Yates et al. |
| 5,833,695 | A | 11/1998 | Yoon |
| 5,833,696 | A | 11/1998 | Whitfield et al. |
| 5,836,503 | A | 11/1998 | Ehrenfels et al. |
| 5,836,960 | A | 11/1998 | Kolesa et al. |
| 5,839,369 | A | 11/1998 | Chatterjee et al. |
| 5,839,639 | A | 11/1998 | Sauer et al. |
| 5,841,284 | A | 11/1998 | Takahashi |
| 5,843,021 | A | 12/1998 | Edwards et al. |
| 5,843,096 | A | 12/1998 | Igaki et al. |

(56) References Cited

U.S. PATENT DOCUMENTS 5,843,097 A 12/1998 Mayenberger et al.
5,843,122 A 12/1998 Riza
5,843,132 A 12/1998 Ilvento
5,843,169 A 12/1998 Taheri
5,846,254 A 12/1998 Schulze et al.
5,847,566 A 12/1998 Marritt et al.
5,849,011 A 12/1998 Jones et al.
5,849,020 A 12/1998 Long et al.
5,849,023 A 12/1998 Mericle
5,851,179 A 12/1998 Ritson et al.
5,851,212 A 12/1998 Zirps et al.
5,853,366 A 12/1998 Dowlatshahi
5,855,311 A 1/1999 Hamblin et al.
5,855,583 A 1/1999 Wang et al.
5,860,581 A 1/1999 Robertson et al.
5,860,975 A 1/1999 Goble et al.
5,865,361 A 2/1999 Milliman et al.
5,865,638 A 2/1999 Trafton
5,868,361 A 2/1999 Rinderer
5,868,664 A 2/1999 Speier et al.
5,868,760 A 2/1999 McGuckin, Jr.
5,868,790 A 2/1999 Vincent et al.
5,871,135 A 2/1999 Williamson IV et al.
5,873,885 A 2/1999 Weidenbenner
5,876,401 A 3/1999 Schulze et al.
5,878,193 A 3/1999 Wang et al.
5,878,607 A 3/1999 Nunes et al.
5,878,937 A 3/1999 Green et al.
5,878,938 A 3/1999 Bittner et al.
5,881,777 A 3/1999 Bassi et al.
5,881,943 A 3/1999 Heck et al.
5,891,094 A 4/1999 Masterson et al.
5,891,160 A 4/1999 Williamson, IV et al.
5,891,558 A 4/1999 Bell et al.
5,893,506 A 4/1999 Powell
5,893,835 A 4/1999 Witt et al.
5,893,855 A 4/1999 Jacobs
5,893,863 A 4/1999 Yoon
5,893,878 A 4/1999 Pierce
5,894,979 A 4/1999 Powell
5,897,552 A 4/1999 Edwards et al.
5,897,562 A 4/1999 Bolanos et al.
5,899,824 A 5/1999 Kurtz et al.
5,899,914 A 5/1999 Zirps et al.
5,901,895 A 5/1999 Heaton et al.
5,902,312 A 5/1999 Frater et al.
5,903,117 A 5/1999 Gregory
5,904,647 A 5/1999 Ouchi
5,904,693 A 5/1999 Dicesare et al.
5,904,702 A 5/1999 Ek et al.
5,906,577 A 5/1999 Beane et al.
5,906,625 A 5/1999 Bito et al.
5,907,211 A 5/1999 Hall et al.
5,907,664 A 5/1999 Wang et al.
5,908,149 A 6/1999 Welch et al.
5,908,402 A 6/1999 Blythe
5,908,427 A 6/1999 Mckean et al.
5,909,062 A 6/1999 Krietzman
5,911,353 A 6/1999 Bolanos et al.
5,915,616 A 6/1999 Viola et al.
5,916,225 A 6/1999 Kugel
5,918,791 A 7/1999 Sorrentino et al.
5,919,198 A 7/1999 Graves, Jr. et al.
5,921,956 A 7/1999 Grinberg et al.
5,922,001 A 7/1999 Yoon
5,922,003 A 7/1999 Anctil et al.
5,924,864 A 7/1999 Loge et al.
5,928,137 A 7/1999 Green
5,928,256 A 7/1999 Riza
5,931,847 A 8/1999 Bittner et al.
5,931,853 A 8/1999 McEwen et al.
5,937,951 A 8/1999 Izuchukwu et al.
5,938,667 A 8/1999 Peyser et al.
5,941,442 A 8/1999 Geiste et al.
5,941,890 A 8/1999 Voegele et al.
5,944,172 A 8/1999 Hannula
5,944,715 A 8/1999 Goble et al.
5,946,978 A 9/1999 Yamashita
5,947,984 A 9/1999 Whipple
5,947,996 A 9/1999 Logeman
5,948,030 A 9/1999 Miller et al.
5,948,429 A 9/1999 Bell et al.
5,951,301 A 9/1999 Younker
5,951,516 A 9/1999 Bunyan
5,951,552 A 9/1999 Long et al.
5,951,574 A 9/1999 Stefanchik et al.
5,951,575 A 9/1999 Bolduc et al.
5,951,581 A 9/1999 Saadat et al.
5,954,259 A 9/1999 Viola et al.
5,957,831 A 9/1999 Adair
5,964,394 A 10/1999 Robertson
5,964,774 A 10/1999 McKean et al.
5,966,126 A 10/1999 Szabo
5,971,916 A 10/1999 Koren
5,973,221 A 10/1999 Collyer et al.
D416,089 S 11/1999 Barton et al.
5,976,122 A 11/1999 Madhani et al.
5,977,746 A 11/1999 Hershberger et al.
5,980,248 A 11/1999 Kusakabe et al.
5,980,569 A 11/1999 Scirica
5,984,949 A 11/1999 Levin
5,988,479 A 11/1999 Palmer
5,990,379 A 11/1999 Gregory
5,993,466 A 11/1999 Yoon
5,997,528 A 12/1999 Bisch et al.
5,997,552 A 12/1999 Person et al.
6,001,108 A 12/1999 Wang et al.
6,003,517 A 12/1999 Sheffield et al.
6,004,319 A 12/1999 Goble et al.
6,004,335 A 12/1999 Vaitekunas et al.
6,007,521 A 12/1999 Bidwell et al.
6,010,054 A 1/2000 Johnson et al.
6,010,513 A 1/2000 Tormala et al.
6,010,520 A 1/2000 Pattison
6,012,494 A 1/2000 Balazs
6,013,076 A 1/2000 Goble et al.
6,013,991 A 1/2000 Philipp
6,015,406 A 1/2000 Goble et al.
6,015,417 A 1/2000 Reynolds, Jr.
6,017,322 A 1/2000 Snoke et al.
6,017,354 A 1/2000 Culp et al.
6,017,356 A 1/2000 Frederick et al.
6,018,227 A 1/2000 Kumar et al.
6,019,745 A 2/2000 Gray
6,019,780 A 2/2000 Lombardo et al.
6,022,352 A 2/2000 Vandewalle
6,023,275 A 2/2000 Horvitz et al.
6,023,641 A 2/2000 Thompson
6,024,708 A 2/2000 Bales et al.
6,024,741 A 2/2000 Williamson, IV et al.
6,024,748 A 2/2000 Manzo et al.
6,024,750 A 2/2000 Mastri et al.
6,024,764 A 2/2000 Schroeppel
6,027,501 A 2/2000 Goble et al.
6,030,384 A 2/2000 Nezhat
6,032,849 A 3/2000 Mastri et al.
6,033,105 A 3/2000 Barker et al.
6,033,378 A 3/2000 Lundquist et al.
6,033,399 A 3/2000 Gines
6,033,427 A 3/2000 Lee
6,036,641 A 3/2000 Taylor et al.
6,036,667 A 3/2000 Manna et al.
6,037,724 A 3/2000 Buss et al.
6,037,927 A 3/2000 Rosenberg
6,039,126 A 3/2000 Hsieh
6,039,733 A 3/2000 Buysse et al.
6,039,734 A 3/2000 Goble
6,042,601 A 3/2000 Smith
6,042,607 A 3/2000 Williamson, IV et al.
6,043,626 A 3/2000 Snyder et al.
6,045,560 A 4/2000 McKean et al.
6,047,861 A 4/2000 Vidal et al.
6,049,145 A 4/2000 Austin et al.
6,050,172 A 4/2000 Corves et al.

(56) References Cited

U.S. PATENT DOCUMENTS

| | | | |
|---|---|---|---|
| 6,050,472 | A | 4/2000 | Shibata |
| 6,050,989 | A | 4/2000 | Fox et al. |
| 6,050,990 | A | 4/2000 | Tankovich et al. |
| 6,050,996 | A | 4/2000 | Schmaltz et al. |
| 6,053,390 | A | 4/2000 | Green et al. |
| 6,053,899 | A | 4/2000 | Slanda et al. |
| 6,053,922 | A | 4/2000 | Krause et al. |
| 6,054,142 | A | 4/2000 | Li et al. |
| 6,055,062 | A | 4/2000 | Dina et al. |
| RE36,720 | E | 5/2000 | Green et al. |
| 6,056,735 | A | 5/2000 | Okada et al. |
| 6,056,746 | A | 5/2000 | Goble et al. |
| 6,059,806 | A | 5/2000 | Hoegerle |
| 6,062,360 | A | 5/2000 | Shields |
| 6,063,020 | A | 5/2000 | Jones et al. |
| 6,063,025 | A | 5/2000 | Bridges et al. |
| 6,063,050 | A | 5/2000 | Manna et al. |
| 6,063,095 | A | 5/2000 | Wang et al. |
| 6,063,097 | A | 5/2000 | Oi et al. |
| 6,063,098 | A | 5/2000 | Houser et al. |
| 6,065,679 | A | 5/2000 | Levie et al. |
| 6,065,919 | A | 5/2000 | Peck |
| 6,066,132 | A | 5/2000 | Chen et al. |
| 6,066,151 | A | 5/2000 | Miyawaki et al. |
| 6,068,627 | A | 5/2000 | Orszulak et al. |
| 6,071,233 | A | 6/2000 | Ishikawa et al. |
| 6,072,299 | A | 6/2000 | Kurle et al. |
| 6,074,386 | A | 6/2000 | Goble et al. |
| 6,074,401 | A | 6/2000 | Gardiner et al. |
| 6,075,441 | A | 6/2000 | Maloney |
| 6,077,280 | A | 6/2000 | Fossum |
| 6,077,286 | A | 6/2000 | Cuschieri et al. |
| 6,077,290 | A | 6/2000 | Marini |
| 6,079,606 | A | 6/2000 | Milliman et al. |
| 6,080,181 | A | 6/2000 | Jensen et al. |
| 6,082,577 | A | 7/2000 | Coates et al. |
| 6,083,191 | A | 7/2000 | Rose |
| 6,083,223 | A | 7/2000 | Baker |
| 6,083,234 | A | 7/2000 | Nicholas et al. |
| 6,083,242 | A | 7/2000 | Cook |
| 6,086,544 | A | 7/2000 | Hibner et al. |
| 6,086,600 | A | 7/2000 | Kortenbach |
| 6,090,106 | A | 7/2000 | Goble et al. |
| 6,090,123 | A | 7/2000 | Culp et al. |
| 6,093,186 | A | 7/2000 | Goble |
| 6,094,021 | A | 7/2000 | Noro et al. |
| D429,252 | S | 8/2000 | Haitani et al. |
| 6,099,537 | A | 8/2000 | Sugai et al. |
| 6,099,551 | A | 8/2000 | Gabbay |
| 6,102,271 | A | 8/2000 | Longo et al. |
| 6,102,926 | A | 8/2000 | Tartaglia et al. |
| 6,104,162 | A | 8/2000 | Sainsbury et al. |
| 6,104,304 | A | 8/2000 | Clark et al. |
| 6,106,511 | A | 8/2000 | Jensen |
| 6,109,500 | A | 8/2000 | Alli et al. |
| 6,110,187 | A | 8/2000 | Donlon |
| 6,113,618 | A | 9/2000 | Nic |
| 6,117,148 | A | 9/2000 | Ravo et al. |
| 6,117,158 | A | 9/2000 | Measamer et al. |
| 6,119,913 | A | 9/2000 | Adams et al. |
| 6,120,433 | A | 9/2000 | Mizuno et al. |
| 6,120,462 | A | 9/2000 | Hibner et al. |
| 6,123,241 | A | 9/2000 | Walter et al. |
| 6,123,701 | A | 9/2000 | Nezhat |
| H1904 | H | 10/2000 | Yates et al. |
| RE36,923 | E | 10/2000 | Hiroi et al. |
| 6,126,058 | A | 10/2000 | Adams et al. |
| 6,126,359 | A | 10/2000 | Dittrich et al. |
| 6,126,670 | A | 10/2000 | Walker et al. |
| 6,131,789 | A | 10/2000 | Schulze et al. |
| 6,131,790 | A | 10/2000 | Piraka |
| 6,132,368 | A | 10/2000 | Cooper |
| 6,134,962 | A | 10/2000 | Sugitani |
| 6,139,546 | A | 10/2000 | Koenig et al. |
| 6,142,149 | A | 11/2000 | Steen |
| 6,142,933 | A | 11/2000 | Longo et al. |
| 6,147,135 | A | 11/2000 | Yuan et al. |
| 6,149,660 | A | 11/2000 | Laufer et al. |
| 6,151,323 | A | 11/2000 | O'Connell et al. |
| 6,152,935 | A | 11/2000 | Kammerer et al. |
| 6,155,473 | A | 12/2000 | Tompkins et al. |
| 6,156,056 | A | 12/2000 | Kearns et al. |
| 6,157,169 | A | 12/2000 | Lee |
| 6,159,146 | A | 12/2000 | El Gazayerli |
| 6,159,200 | A | 12/2000 | Verdura et al. |
| 6,159,224 | A | 12/2000 | Yoon |
| 6,162,208 | A | 12/2000 | Hipps |
| 6,162,220 | A | 12/2000 | Nezhat |
| 6,162,537 | A | 12/2000 | Martin et al. |
| 6,165,175 | A | 12/2000 | Wampler et al. |
| 6,165,184 | A | 12/2000 | Verdura et al. |
| 6,165,188 | A | 12/2000 | Saadat et al. |
| 6,167,185 | A | 12/2000 | Smiley et al. |
| 6,168,605 | B1 | 1/2001 | Measamer et al. |
| 6,171,305 | B1 | 1/2001 | Sherman |
| 6,171,316 | B1 | 1/2001 | Kovac et al. |
| 6,171,330 | B1 | 1/2001 | Benchetrit |
| 6,173,074 | B1 | 1/2001 | Russo |
| 6,174,308 | B1 | 1/2001 | Goble et al. |
| 6,174,309 | B1 | 1/2001 | Wrublewski et al. |
| 6,174,318 | B1 | 1/2001 | Bates et al. |
| 6,175,290 | B1 | 1/2001 | Forsythe et al. |
| 6,179,195 | B1 | 1/2001 | Adams et al. |
| 6,179,776 | B1 | 1/2001 | Adams et al. |
| 6,181,105 | B1 | 1/2001 | Cutolo et al. |
| 6,182,673 | B1 | 2/2001 | Kindermann et al. |
| 6,185,356 | B1 | 2/2001 | Parker et al. |
| 6,186,142 | B1 | 2/2001 | Schmidt et al. |
| 6,186,957 | B1 | 2/2001 | Milam |
| 6,187,003 | B1 | 2/2001 | Buysse et al. |
| 6,190,386 | B1 | 2/2001 | Rydell |
| 6,193,129 | B1 | 2/2001 | Bittner et al. |
| 6,197,042 | B1 | 3/2001 | Ginn et al. |
| 6,200,311 | B1 | 3/2001 | Danek et al. |
| 6,200,330 | B1 | 3/2001 | Benderev et al. |
| 6,202,914 | B1 | 3/2001 | Geiste et al. |
| 6,206,894 | B1 | 3/2001 | Thompson et al. |
| 6,206,897 | B1 | 3/2001 | Jamiolkowski et al. |
| 6,206,903 | B1 | 3/2001 | Ramans |
| 6,206,904 | B1 | 3/2001 | Ouchi |
| 6,209,414 | B1 | 4/2001 | Uneme |
| 6,210,403 | B1 | 4/2001 | Klicek |
| 6,211,626 | B1 | 4/2001 | Lys et al. |
| 6,213,999 | B1 | 4/2001 | Platt, Jr. et al. |
| 6,214,028 | B1 | 4/2001 | Yoon et al. |
| 6,220,368 | B1 | 4/2001 | Ark et al. |
| 6,221,007 | B1 | 4/2001 | Green |
| 6,221,023 | B1 | 4/2001 | Matsuba et al. |
| 6,223,100 | B1 | 4/2001 | Green |
| 6,223,835 | B1 | 5/2001 | Habedank et al. |
| 6,224,617 | B1 | 5/2001 | Saadat et al. |
| 6,228,080 | B1 | 5/2001 | Gines |
| 6,228,081 | B1 | 5/2001 | Goble |
| 6,228,083 | B1 | 5/2001 | Lands et al. |
| 6,228,084 | B1 | 5/2001 | Kirwan, Jr. |
| 6,228,089 | B1 | 5/2001 | Wahrburg |
| 6,228,098 | B1 | 5/2001 | Kayan et al. |
| 6,231,565 | B1 | 5/2001 | Tovey et al. |
| 6,234,178 | B1 | 5/2001 | Goble et al. |
| 6,235,036 | B1 | 5/2001 | Gardner et al. |
| 6,237,604 | B1 | 5/2001 | Burnside et al. |
| 6,238,384 | B1 | 5/2001 | Peer |
| 6,241,139 | B1 | 6/2001 | Milliman et al. |
| 6,241,140 | B1 | 6/2001 | Adams et al. |
| 6,241,723 | B1 | 6/2001 | Heim et al. |
| 6,245,084 | B1 | 6/2001 | Mark et al. |
| 6,248,116 | B1 | 6/2001 | Chevillon et al. |
| 6,248,117 | B1 | 6/2001 | Blatter |
| 6,249,076 | B1 | 6/2001 | Madden et al. |
| 6,249,105 | B1 | 6/2001 | Andrews et al. |
| 6,250,532 | B1 | 6/2001 | Green et al. |
| 6,251,485 | B1 | 6/2001 | Harris et al. |
| D445,745 | S | 7/2001 | Norman |
| 6,254,534 | B1 | 7/2001 | Butler et al. |

(56) References Cited

U.S. PATENT DOCUMENTS 6,254,619 B1 7/2001 Garabet et al.
6,254,642 B1 7/2001 Taylor
6,258,107 B1 7/2001 Balazs et al.
6,261,246 B1 7/2001 Pantages et al.
6,261,286 B1 7/2001 Goble et al.
6,261,679 B1 7/2001 Chen et al.
6,264,086 B1 7/2001 McGuckin, Jr.
6,264,087 B1 7/2001 Whitman
6,264,617 B1 7/2001 Bales et al.
6,269,997 B1 8/2001 Balazs et al.
6,270,508 B1 8/2001 Klieman et al.
6,270,916 B1 8/2001 Sink et al.
6,273,252 B1 8/2001 Mitchell
6,273,876 B1 8/2001 Klima et al.
6,273,897 B1 8/2001 Dalessandro et al.
6,277,114 B1 8/2001 Bullivant et al.
6,280,407 B1 8/2001 Manna et al.
6,283,981 B1 9/2001 Beaupre
6,293,927 B1 9/2001 McGuckin, Jr.
6,293,942 B1 9/2001 Goble et al.
6,296,640 B1 10/2001 Wampler et al.
6,302,311 B1 10/2001 Adams et al.
6,302,743 B1 10/2001 Chiu et al.
6,305,891 B1 10/2001 Burlingame
6,306,134 B1 10/2001 Goble et al.
6,306,149 B1 10/2001 Meade
6,306,424 B1 10/2001 Vyakarnam et al.
6,309,397 B1 10/2001 Julian et al.
6,309,400 B2 10/2001 Beaupre
6,309,403 B1 10/2001 Minor et al.
6,312,435 B1 11/2001 Wallace et al.
6,315,184 B1 11/2001 Whitman
6,317,616 B1 11/2001 Glossop
6,319,510 B1 11/2001 Yates
6,320,123 B1 11/2001 Reimers
6,322,494 B1 11/2001 Bullivant et al.
6,324,339 B1 11/2001 Hudson et al.
6,325,799 B1 12/2001 Goble
6,325,805 B1 12/2001 Ogilvie et al.
6,325,810 B1 12/2001 Hamilton et al.
6,328,498 B1 12/2001 Mersch
6,330,965 B1 12/2001 Milliman et al.
6,331,181 B1 12/2001 Tierney et al.
6,331,761 B1 12/2001 Kumar et al.
6,333,029 B1 12/2001 Vyakarnam et al.
6,334,860 B1 1/2002 Dorn
6,334,861 B1 1/2002 Chandler et al.
6,336,926 B1 1/2002 Goble
6,338,737 B1 1/2002 Toledano
6,338,738 B1 1/2002 Bellotti et al.
6,343,731 B1 2/2002 Adams et al.
6,346,077 B1 2/2002 Taylor et al.
6,348,061 B1 2/2002 Whitman
6,349,868 B1 2/2002 Mattingly et al.
D454,951 S 3/2002 Bon
6,352,503 B1 3/2002 Matsui et al.
6,352,532 B1 3/2002 Kramer et al.
6,355,699 B1 3/2002 Vyakarnam et al.
6,356,072 B1 3/2002 Chass
6,358,224 B1 3/2002 Tims et al.
6,358,263 B2 3/2002 Mark et al.
6,358,459 B1 3/2002 Ziegler et al.
6,361,542 B1 3/2002 Dimitriu et al.
6,364,828 B1 4/2002 Yeung et al.
6,364,877 B1 4/2002 Goble et al.
6,364,888 B1 4/2002 Niemeyer et al.
6,366,441 B1 4/2002 Ozawa et al.
6,370,981 B2 4/2002 Watarai
6,371,114 B1 4/2002 Schmidt et al.
6,373,152 B1 4/2002 Wang et al.
6,377,011 B1 4/2002 Ben-Ur
6,383,201 B1 5/2002 Dong
6,387,092 B1 5/2002 Burnside et al.
6,387,113 B1 5/2002 Hawkins et al.
6,387,114 B2 5/2002 Adams
6,391,038 B2 5/2002 Vargas et al.
6,392,854 B1 5/2002 O'Gorman
6,394,998 B1 5/2002 Wallace et al.
6,398,779 B1 6/2002 Buysse et al.
6,398,781 B1 6/2002 Goble et al.
6,398,797 B2 6/2002 Bombard et al.
6,402,766 B2 6/2002 Bowman et al.
6,402,780 B2 6/2002 Williamson, IV et al.
6,406,440 B1 6/2002 Stefanchik
6,406,472 B1 6/2002 Jensen
6,409,724 B1 6/2002 Penny et al.
H2037 H 7/2002 Yates et al.
6,412,639 B1 7/2002 Hickey
6,413,274 B1 7/2002 Pedros
6,415,542 B1 7/2002 Bates et al.
6,416,486 B1 7/2002 Wampler
6,416,509 B1 7/2002 Goble et al.
6,419,695 B1 7/2002 Gabbay
6,423,079 B1 7/2002 Blake, III
6,424,885 B1 7/2002 Niemeyer et al.
RE37,814 E 8/2002 Allgeyer
6,428,070 B1 8/2002 Takanashi et al.
6,428,487 B1 8/2002 Burdorff et al.
6,429,611 B1 8/2002 Li
6,430,298 B1 8/2002 Kettl et al.
6,432,065 B1 8/2002 Burdorff et al.
6,436,097 B1 8/2002 Nardella
6,436,107 B1 8/2002 Wang et al.
6,436,110 B2 8/2002 Bowman et al.
6,436,115 B1 8/2002 Beaupre
6,436,122 B1 8/2002 Frank et al.
6,439,439 B1 8/2002 Rickard et al.
6,439,446 B1 8/2002 Perry et al.
6,440,146 B2 8/2002 Nicholas et al.
6,441,577 B2 8/2002 Blumenkranz et al.
D462,758 S 9/2002 Epstein et al.
6,443,973 B1 9/2002 Whitman
6,445,530 B1 9/2002 Baker
6,447,518 B1 9/2002 Krause et al.
6,447,523 B1 9/2002 Middleman et al.
6,447,799 B1 9/2002 Ullman
6,447,864 B2 9/2002 Johnson et al.
6,450,391 B1 9/2002 Kayan et al.
6,450,989 B2 9/2002 Dubrul et al.
6,454,656 B2 9/2002 Brissette et al.
6,454,781 B1 9/2002 Witt et al.
6,457,338 B1 10/2002 Frenken
6,457,625 B1 10/2002 Tormala et al.
6,458,077 B1 10/2002 Boebel et al.
6,458,142 B1 10/2002 Faller et al.
6,458,147 B1 10/2002 Cruise et al.
6,460,627 B1 10/2002 Below et al.
6,463,824 B1 10/2002 Prell et al.
6,468,275 B1 10/2002 Wampler et al.
6,468,286 B2 10/2002 Mastri et al.
6,471,106 B1 10/2002 Reining
6,471,659 B2 10/2002 Eggers et al.
6,478,210 B2 11/2002 Adams et al.
6,482,063 B1 11/2002 Frigard
6,482,200 B2 11/2002 Shippert
6,482,217 B1 11/2002 Pintor et al.
6,485,490 B2 11/2002 Wampler et al.
6,485,503 B2 11/2002 Jacobs et al.
6,485,667 B1 11/2002 Tan
6,486,286 B1 11/2002 McGall et al.
6,488,196 B1 12/2002 Fenton, Jr.
6,488,197 B1 12/2002 Whitman
6,488,659 B1 12/2002 Rosenman
6,491,201 B1 12/2002 Whitman
6,491,690 B1 12/2002 Goble et al.
6,491,701 B2 12/2002 Tierney et al.
6,491,702 B2 12/2002 Heilbrun et al.
6,492,785 B1 12/2002 Kasten et al.
6,494,882 B1 12/2002 Lebouitz et al.
6,494,885 B1 12/2002 Dhindsa
6,494,888 B1 12/2002 Laufer et al.
6,494,896 B1 12/2002 D'Alessio et al.
6,498,480 B1 12/2002 Manara
6,500,176 B1 12/2002 Truckai et al.

(56) References Cited

U.S. PATENT DOCUMENTS

| | | | |
|---|---|---|---|
| 6,500,189 | B1 | 12/2002 | Lang et al. |
| 6,500,194 | B2 | 12/2002 | Benderev et al. |
| D468,749 | S | 1/2003 | Friedman |
| 6,503,139 | B2 | 1/2003 | Coral |
| 6,503,257 | B2 | 1/2003 | Grant et al. |
| 6,503,259 | B2 | 1/2003 | Huxel et al. |
| 6,505,768 | B2 | 1/2003 | Whitman |
| 6,506,197 | B1 | 1/2003 | Rollero et al. |
| 6,506,399 | B2 | 1/2003 | Donovan |
| 6,510,854 | B2 | 1/2003 | Goble |
| 6,511,468 | B1 | 1/2003 | Cragg et al. |
| 6,512,360 | B1 | 1/2003 | Goto et al. |
| 6,514,252 | B2 | 2/2003 | Nezhat et al. |
| 6,516,073 | B1 | 2/2003 | Schulz et al. |
| 6,517,528 | B1 | 2/2003 | Pantages et al. |
| 6,517,535 | B2 | 2/2003 | Edwards |
| 6,517,565 | B1 | 2/2003 | Whitman et al. |
| 6,517,566 | B1 | 2/2003 | Hovland et al. |
| 6,520,971 | B1 | 2/2003 | Perry et al. |
| 6,520,972 | B2 | 2/2003 | Peters |
| 6,522,101 | B2 | 2/2003 | Malackowski |
| 6,524,180 | B1 | 2/2003 | Simms et al. |
| 6,525,499 | B2 | 2/2003 | Naganuma |
| D471,206 | S | 3/2003 | Buzzard et al. |
| 6,527,782 | B2 | 3/2003 | Hogg et al. |
| 6,527,785 | B2 | 3/2003 | Sancoff et al. |
| 6,530,942 | B2 | 3/2003 | Fogarty et al. |
| 6,532,958 | B1 | 3/2003 | Buan et al. |
| 6,533,157 | B1 | 3/2003 | Whitman |
| 6,533,723 | B1 | 3/2003 | Lockery et al. |
| 6,533,784 | B2 | 3/2003 | Truckai et al. |
| 6,535,764 | B2 | 3/2003 | Imran et al. |
| 6,539,297 | B2 | 3/2003 | Weiberle et al. |
| D473,239 | S | 4/2003 | Cockerill |
| 6,539,816 | B2 | 4/2003 | Kogiso et al. |
| 6,540,737 | B2 | 4/2003 | Bacher et al. |
| 6,543,456 | B1 | 4/2003 | Freeman |
| 6,545,384 | B1 | 4/2003 | Pelrine et al. |
| 6,547,786 | B1 | 4/2003 | Goble |
| 6,550,546 | B2 | 4/2003 | Thurler et al. |
| 6,551,333 | B2 | 4/2003 | Kuhns et al. |
| 6,554,844 | B2 | 4/2003 | Lee et al. |
| 6,554,861 | B2 | 4/2003 | Knox et al. |
| 6,555,770 | B2 | 4/2003 | Kawase |
| 6,558,378 | B2 | 5/2003 | Sherman et al. |
| 6,558,379 | B1 | 5/2003 | Batchelor et al. |
| 6,558,429 | B2 | 5/2003 | Taylor |
| 6,561,187 | B2 | 5/2003 | Schmidt et al. |
| 6,565,560 | B1 | 5/2003 | Goble et al. |
| 6,566,619 | B2 | 5/2003 | Gillman et al. |
| 6,569,085 | B2 | 5/2003 | Kortenbach et al. |
| 6,569,171 | B2 | 5/2003 | DeGuillebon et al. |
| 6,569,173 | B1 | 5/2003 | Blatter et al. |
| 6,572,629 | B2 | 6/2003 | Kalloo et al. |
| 6,575,969 | B1 | 6/2003 | Rittman et al. |
| 6,578,751 | B2 | 6/2003 | Hartwick |
| 6,582,364 | B2 | 6/2003 | Butler et al. |
| 6,582,427 | B1 | 6/2003 | Goble et al. |
| 6,582,441 | B1 | 6/2003 | He et al. |
| 6,583,533 | B2 | 6/2003 | Pelrine et al. |
| 6,585,144 | B2 | 7/2003 | Adams et al. |
| 6,585,664 | B2 | 7/2003 | Burdorff et al. |
| 6,586,898 | B2 | 7/2003 | King et al. |
| 6,587,750 | B2 | 7/2003 | Gerbi et al. |
| 6,588,277 | B2 | 7/2003 | Giordano et al. |
| 6,588,643 | B2 | 7/2003 | Bolduc et al. |
| 6,588,931 | B2 | 7/2003 | Betzner et al. |
| 6,589,118 | B1 | 7/2003 | Soma et al. |
| 6,589,164 | B1 | 7/2003 | Flaherty |
| 6,592,538 | B1 | 7/2003 | Hotchkiss et al. |
| 6,592,572 | B1 | 7/2003 | Suzuta |
| 6,592,597 | B2 | 7/2003 | Grant et al. |
| 6,594,552 | B1 | 7/2003 | Nowlin et al. |
| 6,595,914 | B2 | 7/2003 | Kato |
| 6,596,296 | B1 | 7/2003 | Nelson et al. |
| 6,596,304 | B1 | 7/2003 | Bayon et al. |
| 6,596,432 | B2 | 7/2003 | Kawakami et al. |
| 6,599,295 | B1 | 7/2003 | Tornier et al. |
| 6,599,323 | B2 | 7/2003 | Melican et al. |
| D478,665 | S | 8/2003 | Isaacs et al. |
| D478,986 | S | 8/2003 | Johnston et al. |
| 6,601,749 | B2 | 8/2003 | Sullivan et al. |
| 6,602,252 | B2 | 8/2003 | Mollenauer |
| 6,602,262 | B2 | 8/2003 | Griego et al. |
| 6,603,050 | B2 | 8/2003 | Heaton |
| 6,605,078 | B2 | 8/2003 | Adams |
| 6,605,669 | B2 | 8/2003 | Awokola et al. |
| 6,605,911 | B1 | 8/2003 | Klesing |
| 6,607,475 | B2 | 8/2003 | Doyle et al. |
| 6,611,793 | B1 | 8/2003 | Burnside et al. |
| 6,613,069 | B2 | 9/2003 | Boyd et al. |
| 6,616,686 | B2 | 9/2003 | Coleman et al. |
| 6,619,529 | B2 | 9/2003 | Green et al. |
| 6,620,111 | B2 | 9/2003 | Stephens et al. |
| 6,620,161 | B2 | 9/2003 | Schulze et al. |
| 6,620,166 | B1 | 9/2003 | Wenstrom, Jr. et al. |
| 6,625,517 | B1 | 9/2003 | Bogdanov et al. |
| 6,626,834 | B2 | 9/2003 | Dunne et al. |
| 6,626,901 | B1 | 9/2003 | Treat et al. |
| 6,626,938 | B1 | 9/2003 | Butaric et al. |
| H2086 | H | 10/2003 | Amsler |
| 6,629,630 | B2 | 10/2003 | Adams |
| 6,629,974 | B2 | 10/2003 | Penny et al. |
| 6,629,988 | B2 | 10/2003 | Weadock |
| 6,635,838 | B1 | 10/2003 | Kornelson |
| 6,636,412 | B2 | 10/2003 | Smith |
| 6,638,108 | B2 | 10/2003 | Tachi |
| 6,638,285 | B2 | 10/2003 | Gabbay |
| 6,638,297 | B1 | 10/2003 | Huitema |
| RE38,335 | E | 11/2003 | Aust et al. |
| 6,641,528 | B2 | 11/2003 | Torii |
| 6,644,532 | B2 | 11/2003 | Green et al. |
| 6,645,201 | B1 | 11/2003 | Utley et al. |
| 6,646,307 | B1 | 11/2003 | Yu et al. |
| 6,648,816 | B2 | 11/2003 | Irion et al. |
| 6,648,901 | B2 | 11/2003 | Fleischman et al. |
| 6,652,595 | B1 | 11/2003 | Nicolo |
| D484,243 | S | 12/2003 | Ryan et al. |
| D484,595 | S | 12/2003 | Ryan et al. |
| D484,596 | S | 12/2003 | Ryan et al. |
| 6,656,177 | B2 | 12/2003 | Truckai et al. |
| 6,656,193 | B2 | 12/2003 | Grant et al. |
| 6,659,940 | B2 | 12/2003 | Adler |
| 6,660,008 | B1 | 12/2003 | Foerster et al. |
| 6,663,623 | B1 | 12/2003 | Oyama et al. |
| 6,663,641 | B1 | 12/2003 | Kovac et al. |
| 6,666,854 | B1 | 12/2003 | Lange |
| 6,666,860 | B1 | 12/2003 | Takahashi |
| 6,666,875 | B1 | 12/2003 | Sakurai et al. |
| 6,667,825 | B2 | 12/2003 | Lu et al. |
| 6,669,073 | B2 | 12/2003 | Milliman et al. |
| 6,670,806 | B2 | 12/2003 | Wendt et al. |
| 6,671,185 | B2 | 12/2003 | Duval |
| D484,977 | S | 1/2004 | Ryan et al. |
| 6,676,660 | B2 | 1/2004 | Wampler et al. |
| 6,677,687 | B2 | 1/2004 | Ho et al. |
| 6,679,269 | B2 | 1/2004 | Swanson |
| 6,679,410 | B2 | 1/2004 | Wursch et al. |
| 6,681,978 | B2 | 1/2004 | Geiste et al. |
| 6,681,979 | B2 | 1/2004 | Whitman |
| 6,682,527 | B2 | 1/2004 | Strul |
| 6,682,528 | B2 | 1/2004 | Frazier et al. |
| 6,682,544 | B2 | 1/2004 | Mastri et al. |
| 6,685,698 | B2 | 2/2004 | Morley et al. |
| 6,685,727 | B2 | 2/2004 | Fisher et al. |
| 6,689,153 | B1 | 2/2004 | Skiba |
| 6,692,507 | B2 | 2/2004 | Pugsley et al. |
| 6,692,692 | B2 | 2/2004 | Stetzel |
| 6,695,198 | B2 | 2/2004 | Adams et al. |
| 6,695,199 | B2 | 2/2004 | Whitman |
| 6,695,774 | B2 | 2/2004 | Hale et al. |
| 6,695,849 | B2 | 2/2004 | Michelson |
| 6,696,814 | B2 | 2/2004 | Henderson et al. |
| 6,697,048 | B2 | 2/2004 | Rosenberg et al. |

(56) References Cited

U.S. PATENT DOCUMENTS 6,698,643 B2 3/2004 Whitman
6,699,177 B1 3/2004 Wang et al.
6,699,214 B2 3/2004 Gellman
6,699,235 B2 3/2004 Wallace et al.
6,704,210 B1 3/2004 Myers
6,705,503 B1 3/2004 Pedicini et al.
6,709,445 B2 3/2004 Boebel et al.
6,712,773 B1 3/2004 Viola
6,716,215 B1 4/2004 David et al.
6,716,223 B2 4/2004 Leopold et al.
6,716,232 B1 4/2004 Vidal et al.
6,716,233 B1 4/2004 Whitman
6,720,734 B2 4/2004 Norris
6,722,550 B1 4/2004 Ricordi et al.
6,722,552 B2 4/2004 Fenton, Jr.
6,723,087 B2 4/2004 O'Neill et al.
6,723,091 B2 4/2004 Goble et al.
6,723,106 B1 4/2004 Charles et al.
6,723,109 B2 4/2004 Solingen
6,726,651 B1 4/2004 Robinson et al.
6,726,697 B2 4/2004 Nicholas et al.
6,726,705 B2 4/2004 Peterson et al.
6,726,706 B2 4/2004 Dominguez
6,729,119 B2 5/2004 Schnipke et al.
6,731,976 B2 5/2004 Penn et al.
6,736,810 B2 5/2004 Hoey et al.
6,736,825 B2 5/2004 Blatter et al.
6,736,854 B2 5/2004 Vadurro et al.
6,740,030 B2 5/2004 Martone et al.
6,743,230 B2 6/2004 Lutze et al.
6,744,385 B2 6/2004 Kazuya et al.
6,747,121 B2 6/2004 Gogolewski
6,747,300 B2 6/2004 Nadd et al.
6,749,560 B1 6/2004 Konstorum et al.
6,749,600 B1 6/2004 Levy
6,752,768 B2 6/2004 Burdorff et al.
6,752,816 B2 6/2004 Culp et al.
6,754,959 B1 6/2004 Guiette, III et al.
6,755,195 B1 6/2004 Lemke et al.
6,755,338 B2 6/2004 Hahnen et al.
6,755,825 B2 6/2004 Shoenman et al.
6,755,843 B2 6/2004 Chung et al.
6,756,705 B2 6/2004 Pulford, Jr.
6,758,846 B2 7/2004 Goble et al.
6,761,685 B2 7/2004 Adams et al.
6,762,339 B1 7/2004 Klun et al.
6,763,307 B2 7/2004 Berg et al.
6,764,445 B2 7/2004 Ramans et al.
6,766,957 B2 7/2004 Matsuura et al.
6,767,352 B2 7/2004 Field et al.
6,767,356 B2 7/2004 Kanner et al.
6,769,590 B2 8/2004 Vresh et al.
6,769,594 B2 8/2004 Orban, III
6,770,027 B2 8/2004 Banik et al.
6,770,070 B1 8/2004 Balbierz
6,770,072 B1 8/2004 Truckai et al.
6,770,078 B2 8/2004 Bonutti
6,773,409 B2 8/2004 Truckai et al.
6,773,437 B2 8/2004 Ogilvie et al.
6,773,438 B1 8/2004 Knodel et al.
6,773,458 B1 8/2004 Brauker et al.
6,775,575 B2 8/2004 Bommannan et al.
6,777,838 B2 8/2004 Miekka et al.
6,778,846 B1 8/2004 Martinez et al.
6,780,151 B2 8/2004 Grabover et al.
6,780,180 B1 8/2004 Goble et al.
6,783,524 B2 8/2004 Anderson et al.
6,784,775 B2 8/2004 Mandell et al.
6,786,382 B1 9/2004 Hoffman
6,786,864 B2 9/2004 Matsuura et al.
6,786,896 B1 9/2004 Madhani et al.
6,788,018 B1 9/2004 Blumenkranz
6,790,173 B2 9/2004 Saadat et al.
6,793,652 B1 9/2004 Whitman et al.
6,793,661 B2 9/2004 Hamilton et al.
6,793,663 B2 9/2004 Kneifel et al.
6,793,669 B2 9/2004 Nakamura et al.
6,796,921 B1 9/2004 Buck et al.
6,799,669 B2 10/2004 Fukumura et al.
6,801,009 B2 10/2004 Makaran et al.
6,802,822 B1 10/2004 Dodge
6,802,843 B2 10/2004 Truckai et al.
6,802,844 B2 10/2004 Ferree
6,805,273 B2 10/2004 Bilotti et al.
6,806,808 B1 10/2004 Watters et al.
6,806,867 B1 10/2004 Arruda et al.
6,808,525 B2 10/2004 Latterell et al.
6,810,359 B2 10/2004 Sakaguchi
6,814,154 B2 11/2004 Chou
6,814,741 B2 11/2004 Bowman et al.
6,817,508 B1 11/2004 Racenet et al.
6,817,509 B2 11/2004 Geiste et al.
6,817,974 B2 11/2004 Cooper et al.
6,818,018 B1 11/2004 Sawhney
6,820,791 B2 11/2004 Adams
6,821,273 B2 11/2004 Mollenauer
6,821,282 B2 11/2004 Perry et al.
6,821,284 B2 11/2004 Sturtz et al.
6,827,246 B2 12/2004 Sullivan et al.
6,827,712 B2 12/2004 Tovey et al.
6,827,725 B2 12/2004 Batchelor et al.
6,828,902 B2 12/2004 Casden
6,830,174 B2 12/2004 Hillstead et al.
6,831,629 B2 12/2004 Nishino et al.
6,832,998 B2 12/2004 Goble
6,834,001 B2 12/2004 Myono
6,835,173 B2 12/2004 Couvillon, Jr.
6,835,199 B2 12/2004 McGuckin, Jr. et al.
6,835,336 B2 12/2004 Watt
6,836,611 B2 12/2004 Popovic et al.
6,837,846 B2 1/2005 Jaffe et al.
6,837,883 B2 1/2005 Moll et al.
6,838,493 B2 1/2005 Williams et al.
6,840,423 B2 1/2005 Adams et al.
6,840,938 B1 1/2005 Morley et al.
6,841,967 B2 1/2005 Kim et al.
6,843,403 B2 1/2005 Whitman
6,843,789 B2 1/2005 Goble
6,843,793 B2 1/2005 Brock et al.
6,846,307 B2 1/2005 Whitman et al.
6,846,308 B2 1/2005 Whitman et al.
6,846,309 B2 1/2005 Whitman et al.
6,847,190 B2 1/2005 Schaefer et al.
6,849,071 B2 2/2005 Whitman et al.
6,850,817 B1 2/2005 Green
6,852,122 B2 2/2005 Rush
6,852,330 B2 2/2005 Bowman et al.
6,853,879 B2 2/2005 Sunaoshi
6,858,005 B2 2/2005 Ohline et al.
6,859,882 B2 2/2005 Fung
RE38,708 E 3/2005 Bolanos et al.
D502,994 S 3/2005 Blake, III
6,860,169 B2 3/2005 Shinozaki
6,861,142 B1 3/2005 Wilkie et al.
6,861,954 B2 3/2005 Levin
6,863,668 B2 3/2005 Gillespie et al.
6,863,694 B1 3/2005 Boyce et al.
6,863,924 B2 3/2005 Ranganathan et al.
6,866,178 B2 3/2005 Adams et al.
6,866,668 B2 3/2005 Giannetti et al.
6,866,671 B2 3/2005 Tierney et al.
6,867,248 B1 3/2005 Martin et al.
6,869,430 B2 3/2005 Balbierz et al.
6,869,435 B2 3/2005 Blake, III
6,872,214 B2 3/2005 Sonnenschein et al.
6,874,669 B2 4/2005 Adams et al.
6,876,850 B2 4/2005 Maeshima et al.
6,877,647 B2 4/2005 Green et al.
6,878,106 B1 4/2005 Herrmann
6,882,127 B2 4/2005 Konigbauer
6,883,199 B1 4/2005 Lundell et al.
6,884,392 B2 4/2005 Malkin et al.
6,884,428 B2 4/2005 Binette et al.
6,886,730 B2 5/2005 Fujisawa et al.

(56) References Cited

U.S. PATENT DOCUMENTS

| | | | |
|---|---|---|---|
| 6,887,244 | B1 | 5/2005 | Walker et al. |
| 6,887,710 | B2 | 5/2005 | Call et al. |
| 6,889,116 | B2 | 5/2005 | Jinno |
| 6,893,435 | B2 | 5/2005 | Goble |
| 6,894,140 | B2 | 5/2005 | Roby |
| 6,895,176 | B2 | 5/2005 | Archer et al. |
| 6,899,538 | B2 | 5/2005 | Matoba |
| 6,899,593 | B1 | 5/2005 | Moeller et al. |
| 6,899,705 | B2 | 5/2005 | Niemeyer |
| 6,899,915 | B2 | 5/2005 | Yelick et al. |
| 6,905,057 | B2 | 6/2005 | Swayze et al. |
| 6,905,497 | B2 | 6/2005 | Truckai et al. |
| 6,905,498 | B2 | 6/2005 | Hooven |
| 6,908,472 | B2 | 6/2005 | Wiener et al. |
| 6,911,033 | B2 | 6/2005 | de Guillebon et al. |
| 6,911,916 | B1 | 6/2005 | Wang et al. |
| 6,913,579 | B2 | 7/2005 | Truckai et al. |
| 6,913,608 | B2 | 7/2005 | Liddicoat et al. |
| 6,913,613 | B2 | 7/2005 | Schwarz et al. |
| 6,921,397 | B2 | 7/2005 | Corcoran et al. |
| 6,921,412 | B1 | 7/2005 | Black et al. |
| 6,923,093 | B2 | 8/2005 | Ullah |
| 6,923,803 | B2 | 8/2005 | Goble |
| 6,923,819 | B2 | 8/2005 | Meade et al. |
| 6,925,849 | B2 | 8/2005 | Jairam |
| 6,926,716 | B2 | 8/2005 | Baker et al. |
| 6,927,315 | B1 | 8/2005 | Heinecke et al. |
| 6,928,902 | B1 | 8/2005 | Eyssallenne |
| 6,929,641 | B2 | 8/2005 | Goble et al. |
| 6,929,644 | B2 | 8/2005 | Truckai et al. |
| 6,931,830 | B2 | 8/2005 | Liao |
| 6,932,218 | B2 | 8/2005 | Kosann et al. |
| 6,932,810 | B2 | 8/2005 | Ryan |
| 6,936,042 | B2 | 8/2005 | Wallace et al. |
| 6,936,948 | B2 | 8/2005 | Bell et al. |
| D509,297 | S | 9/2005 | Wells |
| D509,589 | S | 9/2005 | Wells |
| 6,938,706 | B2 | 9/2005 | Ng |
| 6,939,358 | B2 | 9/2005 | Palacios et al. |
| 6,942,662 | B2 | 9/2005 | Goble et al. |
| 6,942,674 | B2 | 9/2005 | Belef et al. |
| 6,945,444 | B2 | 9/2005 | Gresham et al. |
| 6,945,981 | B2 | 9/2005 | Donofrio et al. |
| 6,949,196 | B2 | 9/2005 | Schmitz et al. |
| 6,951,562 | B2 | 10/2005 | Zwirnmann |
| 6,953,138 | B1 | 10/2005 | Dworak et al. |
| 6,953,139 | B2 | 10/2005 | Milliman et al. |
| 6,953,461 | B2 | 10/2005 | McClurken et al. |
| 6,957,758 | B2 | 10/2005 | Aranyi |
| 6,958,035 | B2 | 10/2005 | Friedman et al. |
| D511,525 | S | 11/2005 | Hernandez et al. |
| 6,959,851 | B2 | 11/2005 | Heinrich |
| 6,959,852 | B2 | 11/2005 | Shelton, IV et al. |
| 6,960,107 | B1 | 11/2005 | Schaub et al. |
| 6,960,163 | B2 | 11/2005 | Ewers et al. |
| 6,960,220 | B2 | 11/2005 | Marino et al. |
| 6,962,587 | B2 | 11/2005 | Johnson et al. |
| 6,963,792 | B1 | 11/2005 | Green |
| 6,964,363 | B2 | 11/2005 | Wales et al. |
| 6,966,907 | B2 | 11/2005 | Goble |
| 6,966,909 | B2 | 11/2005 | Marshall et al. |
| 6,968,908 | B2 | 11/2005 | Tokunaga et al. |
| 6,969,385 | B2 | 11/2005 | Moreyra |
| 6,969,395 | B2 | 11/2005 | Eskuri |
| 6,971,988 | B2 | 12/2005 | Orban, III |
| 6,972,199 | B2 | 12/2005 | Lebouitz et al. |
| 6,974,435 | B2 | 12/2005 | Daw et al. |
| 6,974,462 | B2 | 12/2005 | Sater |
| 6,978,921 | B2 | 12/2005 | Shelton, IV et al. |
| 6,978,922 | B2 | 12/2005 | Bilotti et al. |
| 6,981,628 | B2 | 1/2006 | Wales |
| 6,981,941 | B2 | 1/2006 | Whitman et al. |
| 6,981,978 | B2 | 1/2006 | Gannoe |
| 6,984,203 | B2 | 1/2006 | Tartaglia et al. |
| 6,984,231 | B2 | 1/2006 | Goble et al. |
| 6,986,451 | B1 | 1/2006 | Mastri et al. |
| 6,988,649 | B2 | 1/2006 | Shelton, IV et al. |
| 6,988,650 | B2 | 1/2006 | Schwemberger et al. |
| 6,989,034 | B2 | 1/2006 | Hammer et al. |
| 6,990,731 | B2 | 1/2006 | Haytayan |
| 6,990,796 | B2 | 1/2006 | Schnipke et al. |
| 6,991,146 | B2 | 1/2006 | Sinisi et al. |
| 6,993,200 | B2 | 1/2006 | Tastl et al. |
| 6,993,413 | B2 | 1/2006 | Sunaoshi |
| 6,994,708 | B2 | 2/2006 | Manzo |
| 6,995,729 | B2 | 2/2006 | Govari et al. |
| 6,996,433 | B2 | 2/2006 | Burbank et al. |
| 6,997,931 | B2 | 2/2006 | Sauer et al. |
| 6,997,935 | B2 | 2/2006 | Anderson et al. |
| 6,998,736 | B2 | 2/2006 | Lee et al. |
| 6,998,816 | B2 | 2/2006 | Wieck et al. |
| 6,999,821 | B2 | 2/2006 | Jenney et al. |
| 7,000,818 | B2 | 2/2006 | Shelton, IV et al. |
| 7,000,819 | B2 | 2/2006 | Swayze et al. |
| 7,000,911 | B2 | 2/2006 | McCormick et al. |
| 7,001,380 | B2 | 2/2006 | Goble |
| 7,001,408 | B2 | 2/2006 | Knodel et al. |
| 7,004,174 | B2 | 2/2006 | Eggers et al. |
| 7,005,828 | B2 | 2/2006 | Karikomi |
| 7,007,176 | B2 | 2/2006 | Goodfellow et al. |
| 7,008,433 | B2 | 3/2006 | Voellmicke et al. |
| 7,008,435 | B2 | 3/2006 | Cummins |
| 7,009,039 | B2 | 3/2006 | Yayon et al. |
| 7,011,213 | B2 | 3/2006 | Clark et al. |
| 7,011,657 | B2 | 3/2006 | Truckai et al. |
| 7,014,640 | B2 | 3/2006 | Kemppainen et al. |
| 7,018,357 | B2 | 3/2006 | Emmons |
| 7,018,390 | B2 | 3/2006 | Turovskiy et al. |
| 7,021,399 | B2 | 4/2006 | Driessen |
| 7,021,669 | B1 | 4/2006 | Lindermeir et al. |
| 7,022,131 | B1 | 4/2006 | Derowe et al. |
| 7,023,159 | B2 | 4/2006 | Gorti et al. |
| 7,025,064 | B2 | 4/2006 | Wang et al. |
| 7,025,732 | B2 | 4/2006 | Thompson et al. |
| 7,025,743 | B2 | 4/2006 | Mann et al. |
| 7,025,774 | B2 | 4/2006 | Freeman et al. |
| 7,025,775 | B2 | 4/2006 | Gadberry et al. |
| 7,028,570 | B2 | 4/2006 | Ohta et al. |
| 7,029,435 | B2 | 4/2006 | Nakao |
| 7,029,439 | B2 | 4/2006 | Roberts et al. |
| 7,030,904 | B2 | 4/2006 | Adair et al. |
| 7,032,798 | B2 | 4/2006 | Whitman et al. |
| 7,032,799 | B2 | 4/2006 | Viola et al. |
| 7,033,356 | B2 | 4/2006 | Latterell et al. |
| 7,033,378 | B2 | 4/2006 | Smith et al. |
| 7,035,716 | B2 | 4/2006 | Harris et al. |
| 7,035,762 | B2 | 4/2006 | Menard et al. |
| 7,036,680 | B1 | 5/2006 | Flannery |
| 7,037,314 | B2 | 5/2006 | Armstrong |
| 7,037,344 | B2 | 5/2006 | Kagan et al. |
| 7,038,421 | B2 | 5/2006 | Trifilo |
| 7,041,088 | B2 | 5/2006 | Nawrocki et al. |
| 7,041,102 | B2 | 5/2006 | Truckai et al. |
| 7,041,868 | B2 | 5/2006 | Greene et al. |
| 7,043,852 | B2 | 5/2006 | Hayashida et al. |
| 7,044,350 | B2 | 5/2006 | Kameyama et al. |
| 7,044,352 | B2 | 5/2006 | Shelton, IV et al. |
| 7,044,353 | B2 | 5/2006 | Mastri et al. |
| 7,046,082 | B2 | 5/2006 | Komiya et al. |
| 7,048,165 | B2 | 5/2006 | Haramiishi |
| 7,048,687 | B1 | 5/2006 | Reuss et al. |
| 7,048,716 | B1 | 5/2006 | Kucharczyk et al. |
| 7,048,745 | B2 | 5/2006 | Tierney et al. |
| 7,052,454 | B2 | 5/2006 | Taylor |
| 7,052,494 | B2 | 5/2006 | Goble et al. |
| 7,052,499 | B2 | 5/2006 | Steger et al. |
| 7,055,730 | B2 | 6/2006 | Ehrenfels et al. |
| 7,055,731 | B2 | 6/2006 | Shelton, IV et al. |
| 7,056,123 | B2 | 6/2006 | Gregorio et al. |
| 7,056,284 | B2 | 6/2006 | Martone et al. |
| 7,056,330 | B2 | 6/2006 | Gayton |
| 7,059,331 | B2 | 6/2006 | Adams et al. |
| 7,059,508 | B2 | 6/2006 | Shelton, IV et al. |
| 7,063,671 | B2 | 6/2006 | Couvillon, Jr. |

(56) References Cited

U.S. PATENT DOCUMENTS

| | | | |
|---|---|---|---|
| 7,063,712 | B2 | 6/2006 | Vargas et al. |
| 7,064,509 | B1 | 6/2006 | Fu et al. |
| 7,066,879 | B2 | 6/2006 | Fowler et al. |
| 7,066,944 | B2 | 6/2006 | Laufer et al. |
| 7,067,038 | B2 | 6/2006 | Trokhan et al. |
| 7,070,083 | B2 | 7/2006 | Jankowski |
| 7,070,559 | B2 | 7/2006 | Adams et al. |
| 7,070,597 | B2 | 7/2006 | Truckai et al. |
| 7,071,287 | B2 | 7/2006 | Rhine et al. |
| 7,075,412 | B1 | 7/2006 | Reynolds et al. |
| 7,075,770 | B1 | 7/2006 | Smith |
| 7,077,856 | B2 | 7/2006 | Whitman |
| 7,080,769 | B2 | 7/2006 | Vresh et al. |
| 7,081,114 | B2 | 7/2006 | Rashidi |
| 7,081,318 | B2 | 7/2006 | Lee et al. |
| 7,083,073 | B2 | 8/2006 | Yoshie et al. |
| 7,083,075 | B2 | 8/2006 | Swayze et al. |
| 7,083,571 | B2 | 8/2006 | Wang et al. |
| 7,083,615 | B2 | 8/2006 | Peterson et al. |
| 7,083,619 | B2 | 8/2006 | Truckai et al. |
| 7,083,620 | B2 | 8/2006 | Jahns et al. |
| 7,083,626 | B2 | 8/2006 | Hart et al. |
| 7,086,267 | B2 | 8/2006 | Dworak et al. |
| 7,087,049 | B2 | 8/2006 | Nowlin et al. |
| 7,087,054 | B2 | 8/2006 | Truckai et al. |
| 7,087,071 | B2 | 8/2006 | Nicholas et al. |
| 7,090,637 | B2 | 8/2006 | Danitz et al. |
| 7,090,673 | B2 | 8/2006 | Dycus et al. |
| 7,090,683 | B2 | 8/2006 | Brock et al. |
| 7,090,684 | B2 | 8/2006 | McGuckin, Jr. et al. |
| 7,091,191 | B2 | 8/2006 | Laredo et al. |
| 7,091,412 | B2 | 8/2006 | Wang et al. |
| 7,093,492 | B2 | 8/2006 | Treiber et al. |
| 7,094,202 | B2 | 8/2006 | Nobis et al. |
| 7,094,247 | B2 | 8/2006 | Monassevitch et al. |
| 7,094,916 | B2 | 8/2006 | DeLuca et al. |
| 7,096,972 | B2 | 8/2006 | Orozco, Jr. |
| 7,097,089 | B2 | 8/2006 | Marczyk |
| 7,097,644 | B2 | 8/2006 | Long |
| 7,097,650 | B2 | 8/2006 | Weller et al. |
| 7,098,794 | B2 | 8/2006 | Lindsay et al. |
| 7,100,949 | B2 | 9/2006 | Williams et al. |
| 7,101,187 | B1 | 9/2006 | Deconinck et al. |
| 7,101,363 | B2 | 9/2006 | Nishizawa et al. |
| 7,101,371 | B2 | 9/2006 | Dycus et al. |
| 7,101,394 | B2 | 9/2006 | Hamm et al. |
| 7,104,741 | B2 | 9/2006 | Krohn |
| 7,108,695 | B2 | 9/2006 | Witt et al. |
| 7,108,701 | B2 | 9/2006 | Evens et al. |
| 7,108,709 | B2 | 9/2006 | Cummins |
| 7,111,768 | B2 | 9/2006 | Cummins et al. |
| 7,111,769 | B2 | 9/2006 | Wales et al. |
| 7,112,201 | B2 | 9/2006 | Truckai et al. |
| 7,112,214 | B2 | 9/2006 | Peterson et al. |
| RE39,358 | E | 10/2006 | Goble |
| D530,339 | S | 10/2006 | Hernandez et al. |
| 7,114,642 | B2 | 10/2006 | Whitman |
| 7,116,100 | B1 | 10/2006 | Mock et al. |
| 7,118,020 | B2 | 10/2006 | Lee et al. |
| 7,118,528 | B1 | 10/2006 | Piskun |
| 7,118,563 | B2 | 10/2006 | Weckwerth et al. |
| 7,118,582 | B1 | 10/2006 | Wang et al. |
| 7,119,534 | B2 | 10/2006 | Butzmann |
| 7,121,446 | B2 | 10/2006 | Arad et al. |
| 7,121,773 | B2 | 10/2006 | Mikiya et al. |
| 7,122,028 | B2 | 10/2006 | Looper et al. |
| 7,125,403 | B2 | 10/2006 | Julian et al. |
| 7,125,409 | B2 | 10/2006 | Truckai et al. |
| 7,126,303 | B2 | 10/2006 | Farritor et al. |
| 7,126,879 | B2 | 10/2006 | Snyder |
| 7,128,253 | B2 | 10/2006 | Mastri et al. |
| 7,128,254 | B2 | 10/2006 | Shelton, IV et al. |
| 7,128,748 | B2 | 10/2006 | Mooradian et al. |
| 7,131,445 | B2 | 11/2006 | Amoah |
| 7,133,601 | B2 | 11/2006 | Phillips et al. |
| 7,134,364 | B2 | 11/2006 | Kageler et al. |
| 7,134,587 | B2 | 11/2006 | Schwemberger et al. |
| 7,135,027 | B2 | 11/2006 | Delmotte |
| 7,137,980 | B2 | 11/2006 | Buysse et al. |
| 7,137,981 | B2 | 11/2006 | Long |
| 7,139,016 | B2 | 11/2006 | Squilla et al. |
| 7,140,527 | B2 | 11/2006 | Ehrenfels et al. |
| 7,140,528 | B2 | 11/2006 | Shelton, IV |
| 7,141,055 | B2 | 11/2006 | Abrams et al. |
| 7,143,923 | B2 | 12/2006 | Shelton, IV et al. |
| 7,143,924 | B2 | 12/2006 | Scirica et al. |
| 7,143,925 | B2 | 12/2006 | Shelton, IV et al. |
| 7,143,926 | B2 | 12/2006 | Shelton, IV et al. |
| 7,146,191 | B2 | 12/2006 | Kerner et al. |
| 7,147,138 | B2 | 12/2006 | Shelton, IV |
| 7,147,139 | B2 | 12/2006 | Schwemberger et al. |
| 7,147,140 | B2 | 12/2006 | Wukusick et al. |
| 7,147,637 | B2 | 12/2006 | Goble |
| 7,147,648 | B2 | 12/2006 | Lin |
| 7,147,650 | B2 | 12/2006 | Lee |
| 7,150,748 | B2 | 12/2006 | Ebbutt et al. |
| 7,153,300 | B2 | 12/2006 | Goble |
| 7,153,314 | B2 | 12/2006 | Laufer et al. |
| 7,155,316 | B2 | 12/2006 | Sutherland et al. |
| 7,156,846 | B2 | 1/2007 | Dycus et al. |
| 7,156,863 | B2 | 1/2007 | Sonnenschein et al. |
| 7,159,750 | B2 | 1/2007 | Racenet et al. |
| 7,160,296 | B2 | 1/2007 | Pearson et al. |
| 7,160,299 | B2 | 1/2007 | Baily |
| 7,160,311 | B2 | 1/2007 | Blatter et al. |
| 7,161,036 | B2 | 1/2007 | Oikawa et al. |
| 7,161,580 | B2 | 1/2007 | Bailey et al. |
| 7,162,758 | B2 | 1/2007 | Skinner |
| 7,163,563 | B2 | 1/2007 | Schwartz et al. |
| 7,166,117 | B2 | 1/2007 | Hellenkamp |
| 7,166,133 | B2 | 1/2007 | Evans et al. |
| 7,168,604 | B2 | 1/2007 | Milliman et al. |
| 7,169,146 | B2 | 1/2007 | Truckai et al. |
| 7,170,910 | B2 | 1/2007 | Chen et al. |
| 7,171,279 | B2 | 1/2007 | Buckingham et al. |
| 7,172,104 | B2 | 2/2007 | Scirica et al. |
| 7,172,593 | B2 | 2/2007 | Trieu et al. |
| 7,172,615 | B2 | 2/2007 | Morriss et al. |
| 7,174,202 | B2 | 2/2007 | Bladen et al. |
| 7,174,636 | B2 | 2/2007 | Lowe |
| 7,177,533 | B2 | 2/2007 | McFarlin et al. |
| 7,179,223 | B2 | 2/2007 | Motoki et al. |
| 7,179,267 | B2 | 2/2007 | Nolan et al. |
| 7,182,239 | B1 | 2/2007 | Myers |
| 7,182,763 | B2 | 2/2007 | Nardella |
| 7,183,737 | B2 | 2/2007 | Kitagawa |
| 7,187,960 | B2 | 3/2007 | Abreu |
| 7,188,758 | B2 | 3/2007 | Viola et al. |
| 7,189,207 | B2 | 3/2007 | Viola |
| 7,190,147 | B2 | 3/2007 | Gileff et al. |
| 7,193,199 | B2 | 3/2007 | Jang |
| 7,195,627 | B2 | 3/2007 | Amoah et al. |
| 7,196,911 | B2 | 3/2007 | Takano et al. |
| D541,418 | S | 4/2007 | Schechter et al. |
| 7,197,965 | B1 | 4/2007 | Anderson |
| 7,199,537 | B2 | 4/2007 | Okamura et al. |
| 7,199,545 | B2 | 4/2007 | Oleynikov et al. |
| 7,202,576 | B1 | 4/2007 | Dechene et al. |
| 7,202,653 | B2 | 4/2007 | Pai |
| 7,204,404 | B2 | 4/2007 | Nguyen et al. |
| 7,204,835 | B2 | 4/2007 | Latterell et al. |
| 7,205,959 | B2 | 4/2007 | Henriksson |
| 7,206,626 | B2 | 4/2007 | Quaid, III |
| 7,207,233 | B2 | 4/2007 | Wadge |
| 7,207,471 | B2 | 4/2007 | Heinrich et al. |
| 7,207,472 | B2 | 4/2007 | Wukusick et al. |
| 7,207,556 | B2 | 4/2007 | Saitoh et al. |
| 7,208,005 | B2 | 4/2007 | Frecker et al. |
| 7,210,609 | B2 | 5/2007 | Leiboff et al. |
| 7,211,081 | B2 | 5/2007 | Goble |
| 7,211,084 | B2 | 5/2007 | Goble et al. |
| 7,211,092 | B2 | 5/2007 | Hughett |
| 7,211,979 | B2 | 5/2007 | Khatib et al. |
| 7,213,736 | B2 | 5/2007 | Wales et al. |

(56) References Cited

U.S. PATENT DOCUMENTS 7,214,224 B2 5/2007 Goble
7,215,517 B2 5/2007 Takamatsu
7,217,285 B2 5/2007 Vargas et al.
7,220,260 B2 5/2007 Fleming et al.
7,220,272 B2 5/2007 Weadock
7,225,959 B2 6/2007 Patton et al.
7,225,963 B2 6/2007 Scirica
7,225,964 B2 6/2007 Mastri et al.
7,226,450 B2 6/2007 Athanasiou et al.
7,226,467 B2 6/2007 Lucatero et al.
7,228,505 B2 6/2007 Shimazu et al.
7,229,408 B2 6/2007 Douglas et al.
7,234,624 B2 6/2007 Gresham et al.
7,235,072 B2 6/2007 Sartor et al.
7,235,089 B1 6/2007 McGuckin, Jr.
7,235,302 B2 6/2007 Jing et al.
7,237,708 B1 7/2007 Guy et al.
7,238,195 B2 7/2007 Viola
7,238,901 B2 7/2007 Kim et al.
7,239,657 B1 7/2007 Gunnarsson
7,241,288 B2 7/2007 Braun
7,241,289 B2 7/2007 Braun
7,246,734 B2 7/2007 Shelton, IV
7,247,161 B2 7/2007 Johnston et al.
7,249,267 B2 7/2007 Chapuis
7,252,641 B2 8/2007 Thompson et al.
7,252,660 B2 8/2007 Kunz
7,255,012 B2 8/2007 Hedtke
7,255,696 B2 8/2007 Goble et al.
7,256,695 B2 8/2007 Hamel et al.
7,258,262 B2 8/2007 Mastri et al.
7,258,546 B2 8/2007 Beier et al.
7,260,431 B2 8/2007 Libbus et al.
7,265,374 B2 9/2007 Lee et al.
7,267,677 B2 9/2007 Johnson et al.
7,267,679 B2 9/2007 McGuckin, Jr. et al.
7,272,002 B2 9/2007 Drapeau
7,273,483 B2 9/2007 Wiener et al.
7,273,488 B2 9/2007 Nakamura et al.
D552,623 S 10/2007 Vong et al.
7,275,674 B2 10/2007 Racenet et al.
7,276,044 B2 10/2007 Ferry et al.
7,276,068 B2 10/2007 Johnson et al.
7,278,562 B2 10/2007 Mastri et al.
7,278,563 B1 10/2007 Green
7,278,949 B2 10/2007 Bader
7,278,994 B2 10/2007 Goble
7,282,048 B2 10/2007 Goble et al.
7,283,096 B2 10/2007 Geisheimer et al.
7,286,850 B2 10/2007 Frielink et al.
7,287,682 B1 10/2007 Ezzat et al.
7,289,139 B2 10/2007 Amling et al.
7,293,685 B2 11/2007 Ehrenfels et al.
7,295,893 B2 11/2007 Sunaoshi
7,295,907 B2 11/2007 Lu et al.
7,296,722 B2 11/2007 Ivanko
7,296,724 B2 11/2007 Green et al.
7,297,149 B2 11/2007 Vitali et al.
7,300,373 B2 11/2007 Jinno et al.
7,300,431 B2 11/2007 Dubrovsky
7,300,450 B2 11/2007 Vleugels et al.
7,303,106 B2 12/2007 Milliman et al.
7,303,107 B2 12/2007 Milliman et al.
7,303,108 B2 12/2007 Shelton, IV
7,303,502 B2 12/2007 Thompson
7,303,556 B2 12/2007 Metzger
7,306,597 B2 12/2007 Manzo
7,308,998 B2 12/2007 Mastri et al.
7,311,238 B2 12/2007 Liu
7,311,709 B2 12/2007 Truckal et al.
7,313,430 B2 12/2007 Urquhart et al.
7,314,473 B2 1/2008 Jinno et al.
7,317,955 B2 1/2008 McGreevy
7,320,704 B2 1/2008 Lashinski et al.
7,322,859 B2 1/2008 Evans
7,322,975 B2 1/2008 Goble et al.
7,322,994 B2 1/2008 Nicholas et al.
7,324,572 B2 1/2008 Chang
7,326,203 B2 2/2008 Papineau et al.
7,326,213 B2 2/2008 Benderev et al.
7,328,828 B2 2/2008 Ortiz et al.
7,328,829 B2 2/2008 Arad et al.
7,330,004 B2 2/2008 DeJonge et al.
7,331,340 B2 2/2008 Barney
7,331,343 B2 2/2008 Schmidt et al.
7,331,403 B2 2/2008 Berry et al.
7,331,406 B2 2/2008 Wottreng, Jr. et al.
7,331,969 B1 2/2008 Inganas et al.
7,334,717 B2 2/2008 Rethy et al.
7,334,718 B2 2/2008 McAlister et al.
7,335,199 B2 2/2008 Goble et al.
7,335,401 B2 2/2008 Finke et al.
7,336,045 B2 2/2008 Clermonts
7,336,048 B2 2/2008 Lohr
7,336,183 B2 2/2008 Reddy et al.
7,336,184 B2 2/2008 Smith et al.
7,337,774 B2 3/2008 Webb
7,338,505 B2 3/2008 Belson
7,338,513 B2 3/2008 Lee et al.
7,341,554 B2 3/2008 Sekine et al.
7,341,555 B2 3/2008 Ootawara et al.
7,341,591 B2 3/2008 Grinberg
7,343,920 B2 3/2008 Toby et al.
7,344,532 B2 3/2008 Goble et al.
7,344,533 B2 3/2008 Pearson et al.
7,346,344 B2 3/2008 Fontaine
7,346,406 B2 3/2008 Brotto et al.
7,348,763 B1 3/2008 Reinhart et al.
7,348,875 B2 3/2008 Hughes et al.
RE40,237 E 4/2008 Bilotti et al.
7,351,258 B2 4/2008 Ricotta et al.
7,354,398 B2 4/2008 Kanazawa
7,354,440 B2 4/2008 Truckal et al.
7,354,447 B2 4/2008 Shelton, IV et al.
7,354,502 B2 4/2008 Polat et al.
7,357,287 B2 4/2008 Shelton, IV et al.
7,357,806 B2 4/2008 Rivera et al.
7,361,168 B2 4/2008 Makower et al.
7,361,195 B2 4/2008 Schwartz et al.
7,362,062 B2 4/2008 Schneider et al.
7,364,060 B2 4/2008 Milliman
7,364,061 B2 4/2008 Swayze et al.
7,367,485 B2 5/2008 Shelton, IV et al.
7,367,973 B2 5/2008 Manzo et al.
7,368,124 B2 5/2008 Chun et al.
7,371,210 B2 5/2008 Brock et al.
7,371,403 B2 5/2008 McCarthy et al.
7,375,493 B2 5/2008 Calhoon et al.
7,377,918 B2 5/2008 Amoah
7,377,928 B2 5/2008 Zubik et al.
7,378,817 B2 5/2008 Calhoon et al.
RE40,388 E 6/2008 Gines
D570,868 S 6/2008 Hosokawa et al.
7,380,695 B2 6/2008 Doll et al.
7,380,696 B2 6/2008 Shelton, IV et al.
7,384,403 B2 6/2008 Sherman
7,384,417 B2 6/2008 Cucin
7,386,365 B2 6/2008 Nixon
7,386,730 B2 6/2008 Uchikubo
7,388,217 B2 6/2008 Buschbeck et al.
7,388,484 B2 6/2008 Hsu
7,391,173 B2 6/2008 Schena
7,394,190 B2 7/2008 Huang
7,396,356 B2 7/2008 Mollenauer
7,397,364 B2 7/2008 Govari
7,398,707 B2 7/2008 Morley et al.
7,398,907 B2 7/2008 Racenet et al.
7,398,908 B2 7/2008 Holsten et al.
7,400,107 B2 7/2008 Schneider et al.
7,400,752 B2 7/2008 Zacharias
7,401,000 B2 7/2008 Nakamura
7,401,721 B2 7/2008 Holsten et al.
7,404,449 B2 7/2008 Bermingham et al.
7,404,508 B2 7/2008 Smith et al.

(56) References Cited

U.S. PATENT DOCUMENTS

| | | | |
|---|---|---|---|
| 7,404,509 | B2 | 7/2008 | Ortiz et al. |
| 7,404,822 | B2 | 7/2008 | Viart et al. |
| D575,793 | S | 8/2008 | Ording |
| 7,407,074 | B2 | 8/2008 | Ortiz et al. |
| 7,407,075 | B2 | 8/2008 | Holsten et al. |
| 7,407,076 | B2 | 8/2008 | Racenet et al. |
| 7,407,077 | B2 | 8/2008 | Ortiz et al. |
| 7,407,078 | B2 | 8/2008 | Shelton, IV et al. |
| 7,408,310 | B2 | 8/2008 | Hong et al. |
| 7,410,085 | B2 | 8/2008 | Wolf et al. |
| 7,410,086 | B2 | 8/2008 | Ortiz et al. |
| 7,410,483 | B2 | 8/2008 | Danitz et al. |
| 7,413,563 | B2 | 8/2008 | Corcoran et al. |
| 7,416,101 | B2 | 8/2008 | Shelton, IV et al. |
| 7,418,078 | B2 | 8/2008 | Blanz et al. |
| RE40,514 | E | 9/2008 | Mastri et al. |
| 7,419,080 | B2 | 9/2008 | Smith et al. |
| 7,419,081 | B2 | 9/2008 | Ehrenfels et al. |
| 7,419,321 | B2 | 9/2008 | Tereschouk |
| 7,419,495 | B2 | 9/2008 | Menn et al. |
| 7,422,136 | B1 | 9/2008 | Marczyk |
| 7,422,138 | B2 | 9/2008 | Bilotti et al. |
| 7,422,139 | B2 | 9/2008 | Shelton, IV et al. |
| 7,424,965 | B2 | 9/2008 | Racenet et al. |
| 7,427,607 | B2 | 9/2008 | Suzuki |
| D578,644 | S | 10/2008 | Shumer et al. |
| 7,430,772 | B2 | 10/2008 | Van Es |
| 7,430,849 | B1 | 10/2008 | Coutts et al. |
| 7,431,188 | B1 | 10/2008 | Marczyk |
| 7,431,189 | B2 | 10/2008 | Shelton, IV et al. |
| 7,431,230 | B2 | 10/2008 | McPherson et al. |
| 7,431,694 | B2 | 10/2008 | Stefanchik et al. |
| 7,431,730 | B2 | 10/2008 | Viola |
| 7,434,715 | B2 | 10/2008 | Shelton, IV et al. |
| 7,434,717 | B2 | 10/2008 | Shelton, IV et al. |
| 7,435,249 | B2 | 10/2008 | Buysse et al. |
| 7,438,209 | B1 | 10/2008 | Hess et al. |
| 7,438,718 | B2 | 10/2008 | Milliman et al. |
| 7,439,354 | B2 | 10/2008 | Lenges et al. |
| 7,441,684 | B2 | 10/2008 | Shelton, IV et al. |
| 7,441,685 | B1 | 10/2008 | Boudreaux |
| 7,442,201 | B2 | 10/2008 | Pugsley et al. |
| 7,443,547 | B2 | 10/2008 | Moreno et al. |
| D580,942 | S | 11/2008 | Oshiro et al. |
| 7,446,131 | B1 | 11/2008 | Liu et al. |
| 7,448,525 | B2 | 11/2008 | Shelton, IV et al. |
| 7,450,010 | B1 | 11/2008 | Gravelle et al. |
| 7,450,991 | B2 | 11/2008 | Smith et al. |
| 7,451,904 | B2 | 11/2008 | Shelton, IV |
| 7,455,208 | B2 | 11/2008 | Wales et al. |
| 7,455,676 | B2 | 11/2008 | Holsten et al. |
| 7,455,682 | B2 | 11/2008 | Viola |
| 7,455,687 | B2 | 11/2008 | Saunders et al. |
| D582,934 | S | 12/2008 | Byeon |
| 7,461,767 | B2 | 12/2008 | Viola et al. |
| 7,462,187 | B2 | 12/2008 | Johnston et al. |
| 7,464,845 | B2 | 12/2008 | Chou |
| 7,464,846 | B2 | 12/2008 | Shelton, IV et al. |
| 7,464,847 | B2 | 12/2008 | Viola et al. |
| 7,464,848 | B2 | 12/2008 | Green et al. |
| 7,464,849 | B2 | 12/2008 | Shelton, IV et al. |
| 7,467,740 | B2 | 12/2008 | Shelton, IV et al. |
| 7,467,849 | B2 | 12/2008 | Silverbrook et al. |
| 7,472,814 | B2 | 1/2009 | Mastri et al. |
| 7,472,815 | B2 | 1/2009 | Shelton, IV et al. |
| 7,472,816 | B2 | 1/2009 | Holsten et al. |
| 7,473,221 | B2 | 1/2009 | Ewers et al. |
| 7,473,253 | B2 | 1/2009 | Dycus et al. |
| 7,473,263 | B2 | 1/2009 | Johnston et al. |
| 7,476,237 | B2 | 1/2009 | Taniguchi et al. |
| 7,479,147 | B2 | 1/2009 | Honeycutt et al. |
| 7,479,608 | B2 | 1/2009 | Smith |
| 7,481,347 | B2 | 1/2009 | Roy |
| 7,481,348 | B2 | 1/2009 | Marczyk |
| 7,481,349 | B2 | 1/2009 | Holsten et al. |
| 7,481,824 | B2 | 1/2009 | Boudreaux et al. |
| 7,485,124 | B2 | 2/2009 | Kuhns et al. |
| 7,485,133 | B2 | 2/2009 | Cannon et al. |
| 7,485,142 | B2 | 2/2009 | Milo |
| 7,487,899 | B2 | 2/2009 | Shelton, IV et al. |
| 7,489,055 | B2 | 2/2009 | Jeong et al. |
| 7,490,749 | B2 | 2/2009 | Schall et al. |
| 7,491,232 | B2 | 2/2009 | Bolduc et al. |
| 7,492,261 | B2 | 2/2009 | Cambre et al. |
| 7,494,039 | B2 | 2/2009 | Racenet et al. |
| 7,494,460 | B2 | 2/2009 | Haarstad et al. |
| 7,494,499 | B2 | 2/2009 | Nagase et al. |
| 7,494,501 | B2 | 2/2009 | Ahlberg et al. |
| 7,497,137 | B2 | 3/2009 | Tellenbach et al. |
| 7,500,979 | B2 | 3/2009 | Hueil et al. |
| 7,501,198 | B2 | 3/2009 | Barlev et al. |
| 7,503,474 | B2 | 3/2009 | Hillstead et al. |
| 7,506,790 | B2 | 3/2009 | Shelton, IV |
| 7,506,791 | B2 | 3/2009 | Omaits et al. |
| 7,507,202 | B2 | 3/2009 | Schoellhorn |
| 7,510,107 | B2 | 3/2009 | Timm et al. |
| 7,510,534 | B2 | 3/2009 | Burdorff et al. |
| 7,510,566 | B2 | 3/2009 | Jacobs et al. |
| 7,513,407 | B1 | 4/2009 | Chang |
| 7,513,408 | B2 | 4/2009 | Shelton, IV et al. |
| 7,517,356 | B2 | 4/2009 | Heinrich |
| 7,524,320 | B2 | 4/2009 | Tierney et al. |
| 7,527,632 | B2 | 5/2009 | Houghton et al. |
| 7,530,984 | B2 | 5/2009 | Sonnenschein et al. |
| 7,530,985 | B2 | 5/2009 | Takemoto et al. |
| 7,533,790 | B1 | 5/2009 | Knodel et al. |
| 7,533,906 | B2 | 5/2009 | Luettgen et al. |
| 7,534,259 | B2 | 5/2009 | Lashinski et al. |
| 7,540,867 | B2 | 6/2009 | Jinno et al. |
| 7,540,872 | B2 | 6/2009 | Schechter et al. |
| 7,542,807 | B2 | 6/2009 | Bertolero et al. |
| 7,543,730 | B1 | 6/2009 | Marczyk |
| 7,544,197 | B2 | 6/2009 | Kelsch et al. |
| 7,546,939 | B2 | 6/2009 | Adams et al. |
| 7,546,940 | B2 | 6/2009 | Milliman et al. |
| 7,547,287 | B2 | 6/2009 | Boecker et al. |
| 7,547,312 | B2 | 6/2009 | Bauman et al. |
| 7,549,563 | B2 | 6/2009 | Mather et al. |
| 7,549,564 | B2 | 6/2009 | Boudreaux |
| 7,549,998 | B2 | 6/2009 | Braun |
| 7,552,854 | B2 | 6/2009 | Wixey et al. |
| 7,553,173 | B2 | 6/2009 | Kowalick |
| 7,553,275 | B2 | 6/2009 | Padget et al. |
| 7,554,343 | B2 | 6/2009 | Bromfield |
| 7,556,185 | B2 | 7/2009 | Viola |
| 7,556,186 | B2 | 7/2009 | Milliman |
| 7,556,647 | B2 | 7/2009 | Drews et al. |
| 7,559,449 | B2 | 7/2009 | Viola |
| 7,559,450 | B2 | 7/2009 | Wales et al. |
| 7,559,452 | B2 | 7/2009 | Wales et al. |
| 7,559,937 | B2 | 7/2009 | de la Torre et al. |
| 7,561,637 | B2 | 7/2009 | Jonsson et al. |
| 7,562,910 | B2 | 7/2009 | Kertesz et al. |
| 7,563,269 | B2 | 7/2009 | Hashiguchi |
| 7,563,862 | B2 | 7/2009 | Sieg et al. |
| 7,565,993 | B2 | 7/2009 | Milliman et al. |
| 7,566,300 | B2 | 7/2009 | Devierre et al. |
| 7,567,045 | B2 | 7/2009 | Fristedt |
| 7,568,603 | B2 | 8/2009 | Shelton, IV et al. |
| 7,568,604 | B2 | 8/2009 | Ehrenfels et al. |
| 7,568,619 | B2 | 8/2009 | Todd et al. |
| 7,572,285 | B2 | 8/2009 | Frey et al. |
| 7,572,298 | B2 | 8/2009 | Roller et al. |
| 7,575,144 | B2 | 8/2009 | Ortiz et al. |
| 7,578,825 | B2 | 8/2009 | Huebner |
| D600,712 | S | 9/2009 | LaManna et al. |
| 7,583,063 | B2 | 9/2009 | Dooley |
| 7,584,880 | B2 | 9/2009 | Racenet et al. |
| 7,586,289 | B2 | 9/2009 | Andruk et al. |
| 7,588,174 | B2 | 9/2009 | Holsten et al. |
| 7,588,175 | B2 | 9/2009 | Timm et al. |
| 7,588,176 | B2 | 9/2009 | Timm et al. |
| 7,588,177 | B2 | 9/2009 | Racenet |
| 7,591,783 | B2 | 9/2009 | Boulais et al. |

(56) References Cited

U.S. PATENT DOCUMENTS

| | | | |
|---|---|---|---|
| 7,591,818 | B2 | 9/2009 | Bertolero et al. |
| 7,593,766 | B2 | 9/2009 | Faber et al. |
| 7,595,642 | B2 | 9/2009 | Doyle |
| 7,597,229 | B2 | 10/2009 | Boudreaux et al. |
| 7,597,230 | B2 | 10/2009 | Racenet et al. |
| 7,597,693 | B2 | 10/2009 | Garrison |
| 7,597,699 | B2 | 10/2009 | Rogers |
| 7,598,972 | B2 | 10/2009 | Tomita |
| 7,600,663 | B2 | 10/2009 | Green |
| 7,604,118 | B2 | 10/2009 | Lio et al. |
| 7,604,150 | B2 | 10/2009 | Boudreaux |
| 7,604,151 | B2 | 10/2009 | Hess et al. |
| 7,604,668 | B2 | 10/2009 | Farnsworth et al. |
| 7,605,826 | B2 | 10/2009 | Sauer |
| 7,607,557 | B2 | 10/2009 | Shelton, IV et al. |
| 7,608,091 | B2 | 10/2009 | Goldfarb et al. |
| D604,325 | S | 11/2009 | Ebeling et al. |
| 7,611,038 | B2 | 11/2009 | Racenet et al. |
| 7,611,474 | B2 | 11/2009 | Hibner et al. |
| 7,615,003 | B2 | 11/2009 | Stefanchik et al. |
| 7,615,006 | B2 | 11/2009 | Abe |
| 7,615,067 | B2 | 11/2009 | Lee et al. |
| 7,617,961 | B2 | 11/2009 | Viola |
| 7,618,427 | B2 | 11/2009 | Ortiz et al. |
| D605,201 | S | 12/2009 | Lorenz et al. |
| D606,992 | S | 12/2009 | Liu et al. |
| D607,010 | S | 12/2009 | Kocmick |
| 7,624,902 | B2 | 12/2009 | Marczyk et al. |
| 7,624,903 | B2 | 12/2009 | Green et al. |
| 7,625,370 | B2 | 12/2009 | Hart et al. |
| 7,625,388 | B2 | 12/2009 | Boukhny et al. |
| 7,625,662 | B2 | 12/2009 | Vaisnys et al. |
| 7,630,841 | B2 | 12/2009 | Comisky et al. |
| 7,631,793 | B2 | 12/2009 | Rethy et al. |
| 7,631,794 | B2 | 12/2009 | Rethy et al. |
| 7,635,074 | B2 | 12/2009 | Olson et al. |
| 7,635,922 | B2 | 12/2009 | Becker |
| 7,637,409 | B2 | 12/2009 | Marczyk |
| 7,637,410 | B2 | 12/2009 | Marczyk |
| 7,638,958 | B2 | 12/2009 | Philipp et al. |
| 7,641,091 | B2 | 1/2010 | Olson et al. |
| 7,641,092 | B2 | 1/2010 | Kruszynski et al. |
| 7,641,093 | B2 | 1/2010 | Doll et al. |
| 7,641,095 | B2 | 1/2010 | Viola |
| 7,641,671 | B2 | 1/2010 | Crainich |
| 7,644,016 | B2 | 1/2010 | Nycz et al. |
| 7,644,484 | B2 | 1/2010 | Vereschagin |
| 7,644,783 | B2 | 1/2010 | Roberts et al. |
| 7,644,848 | B2 | 1/2010 | Swayze et al. |
| 7,645,230 | B2 | 1/2010 | Mikkaichi et al. |
| 7,648,055 | B2 | 1/2010 | Marczyk |
| 7,648,457 | B2 | 1/2010 | Stefanchik et al. |
| 7,648,519 | B2 | 1/2010 | Lee et al. |
| 7,650,185 | B2 | 1/2010 | Maile et al. |
| 7,651,017 | B2 | 1/2010 | Ortiz et al. |
| 7,651,498 | B2 | 1/2010 | Shifrin et al. |
| 7,654,431 | B2 | 2/2010 | Hueil et al. |
| 7,655,003 | B2 | 2/2010 | Lorang et al. |
| 7,655,004 | B2 | 2/2010 | Long |
| 7,655,288 | B2 | 2/2010 | Bauman et al. |
| 7,655,584 | B2 | 2/2010 | Biran et al. |
| 7,656,131 | B2 | 2/2010 | Embrey et al. |
| 7,658,311 | B2 | 2/2010 | Boudreaux |
| 7,658,312 | B2 | 2/2010 | Vidal et al. |
| 7,658,705 | B2 | 2/2010 | Melvin et al. |
| 7,659,219 | B2 | 2/2010 | Biran et al. |
| 7,661,448 | B2 | 2/2010 | Kim et al. |
| 7,662,161 | B2 | 2/2010 | Briganti et al. |
| 7,665,646 | B2 | 2/2010 | Prommersberger |
| 7,665,647 | B2 | 2/2010 | Shelton, IV et al. |
| 7,666,195 | B2 | 2/2010 | Kelleher et al. |
| 7,669,746 | B2 | 3/2010 | Shelton, IV |
| 7,669,747 | B2 | 3/2010 | Weisenburgh, II et al. |
| 7,670,334 | B2 | 3/2010 | Hueil et al. |
| 7,670,337 | B2 | 3/2010 | Young |
| 7,673,780 | B2 | 3/2010 | Shelton, IV et al. |
| 7,673,781 | B2 | 3/2010 | Swayze et al. |
| 7,673,782 | B2 | 3/2010 | Hess et al. |
| 7,673,783 | B2 | 3/2010 | Morgan et al. |
| 7,674,253 | B2 | 3/2010 | Fisher et al. |
| 7,674,255 | B2 | 3/2010 | Braun |
| 7,674,263 | B2 | 3/2010 | Ryan |
| 7,674,270 | B2 | 3/2010 | Layer |
| 7,678,121 | B1 | 3/2010 | Knodel |
| 7,682,307 | B2 | 3/2010 | Danitz et al. |
| 7,682,367 | B2 | 3/2010 | Shah et al. |
| 7,682,686 | B2 | 3/2010 | Curro et al. |
| 7,686,201 | B2 | 3/2010 | Csiky |
| 7,686,804 | B2 | 3/2010 | Johnson et al. |
| 7,686,826 | B2 | 3/2010 | Lee et al. |
| 7,688,028 | B2 | 3/2010 | Phillips et al. |
| 7,690,547 | B2 | 4/2010 | Racenet et al. |
| 7,691,098 | B2 | 4/2010 | Wallace et al. |
| 7,691,103 | B2 | 4/2010 | Fernandez et al. |
| 7,691,106 | B2 | 4/2010 | Schenberger et al. |
| 7,694,864 | B2 | 4/2010 | Okada et al. |
| 7,694,865 | B2 | 4/2010 | Scirica |
| 7,695,485 | B2 | 4/2010 | Whitman et al. |
| 7,695,493 | B2 | 4/2010 | Saadat et al. |
| 7,699,204 | B2 | 4/2010 | Viola |
| 7,699,835 | B2 | 4/2010 | Lee et al. |
| 7,699,844 | B2 | 4/2010 | Utley et al. |
| 7,699,846 | B2 | 4/2010 | Ryan |
| 7,699,856 | B2 | 4/2010 | Van Wyk et al. |
| 7,699,859 | B2 | 4/2010 | Bombard et al. |
| 7,699,860 | B2 | 4/2010 | Huitema et al. |
| 7,699,868 | B2 | 4/2010 | Frank et al. |
| 7,703,653 | B2 | 4/2010 | Shah et al. |
| 7,705,559 | B2 | 4/2010 | Powell et al. |
| 7,706,853 | B2 | 4/2010 | Hacker et al. |
| 7,708,180 | B2 | 5/2010 | Murray et al. |
| 7,708,181 | B2 | 5/2010 | Cole et al. |
| 7,708,182 | B2 | 5/2010 | Viola |
| 7,708,758 | B2 | 5/2010 | Lee et al. |
| 7,708,768 | B2 | 5/2010 | Danek et al. |
| 7,709,136 | B2 | 5/2010 | Touchton et al. |
| 7,712,182 | B2 | 5/2010 | Zeiler et al. |
| 7,713,190 | B2 | 5/2010 | Brock et al. |
| 7,713,542 | B2 | 5/2010 | Xu et al. |
| 7,714,239 | B2 | 5/2010 | Smith |
| 7,714,334 | B2 | 5/2010 | Lin |
| 7,717,312 | B2 | 5/2010 | Beetel |
| 7,717,313 | B2 | 5/2010 | Criscuolo et al. |
| 7,717,846 | B2 | 5/2010 | Zirps et al. |
| 7,717,873 | B2 | 5/2010 | Swick |
| 7,717,915 | B2 | 5/2010 | Miyazawa |
| 7,717,926 | B2 | 5/2010 | Whitfield et al. |
| 7,718,180 | B2 | 5/2010 | Karp |
| 7,718,556 | B2 | 5/2010 | Matsuda et al. |
| 7,721,930 | B2 | 5/2010 | McKenna et al. |
| 7,721,931 | B2 | 5/2010 | Shelton, IV et al. |
| 7,721,932 | B2 | 5/2010 | Cole et al. |
| 7,721,933 | B2 | 5/2010 | Ehrenfels et al. |
| 7,721,934 | B2 | 5/2010 | Shelton, IV et al. |
| 7,721,936 | B2 | 5/2010 | Shalton, IV et al. |
| 7,722,527 | B2 | 5/2010 | Bouchier et al. |
| 7,722,607 | B2 | 5/2010 | Dumbauld et al. |
| 7,722,610 | B2 | 5/2010 | Viola et al. |
| 7,725,214 | B2 | 5/2010 | Diolaiti |
| 7,726,171 | B2 | 6/2010 | Langlotz et al. |
| 7,726,537 | B2 | 6/2010 | Olson et al. |
| 7,726,538 | B2 | 6/2010 | Holsten et al. |
| 7,726,539 | B2 | 6/2010 | Holsten et al. |
| 7,727,954 | B2 | 6/2010 | McKay |
| 7,728,553 | B2 | 6/2010 | Carrier et al. |
| 7,729,742 | B2 | 6/2010 | Govari |
| 7,731,072 | B2 | 6/2010 | Timm et al. |
| 7,731,073 | B2 | 6/2010 | Wixey et al. |
| 7,731,724 | B2 | 6/2010 | Huitema et al. |
| 7,735,703 | B2 | 6/2010 | Morgan et al. |
| 7,735,704 | B2 | 6/2010 | Bilotti |
| 7,736,254 | B2 | 6/2010 | Schena |
| 7,736,306 | B2 | 6/2010 | Brustad et al. |
| 7,736,356 | B2 | 6/2010 | Cooper et al. |

(56) References Cited

U.S. PATENT DOCUMENTS 7,736,374 B2 6/2010 Vaughan et al.
7,738,971 B2 6/2010 Swayze et al.
7,740,159 B2 6/2010 Shelton, IV et al.
7,742,036 B2 6/2010 Grant et al.
7,743,960 B2 6/2010 Whitman et al.
7,744,624 B2 6/2010 Bettuchi
7,744,627 B2 6/2010 Orban, III et al.
7,744,628 B2 6/2010 Viola
7,747,146 B2 6/2010 Milano et al.
7,748,587 B2 7/2010 Haramiishi et al.
7,748,632 B2 7/2010 Coleman et al.
7,749,204 B2 7/2010 Dhanaraj et al.
7,749,240 B2 7/2010 Takahashi et al.
7,751,870 B2 7/2010 Whitman
7,753,245 B2 7/2010 Boudreaux et al.
7,753,246 B2 7/2010 Scirica
7,753,904 B2 7/2010 Shelton, IV et al.
7,757,924 B2 7/2010 Gerbi et al.
7,758,594 B2 7/2010 Lamson et al.
7,758,612 B2 7/2010 Shipp
7,758,613 B2 7/2010 Whitman
7,762,462 B2 7/2010 Gelbman
7,762,998 B2 7/2010 Birk et al.
D622,286 S 8/2010 Umezawa
7,766,207 B2 8/2010 Mather et al.
7,766,209 B2 8/2010 Baxter. III et al.
7,766,210 B2 8/2010 Shelton, IV et al.
7,766,821 B2 8/2010 Brunnen et al.
7,766,894 B2 8/2010 Weitzner et al.
7,770,658 B2 8/2010 Ito et al.
7,770,773 B2 8/2010 Whitman et al.
7,770,774 B2 8/2010 Mastri et al.
7,770,775 B2 8/2010 Shelton, IV et al.
7,770,776 B2 8/2010 Chen et al.
7,771,396 B2 8/2010 Stefanchik et al.
7,772,720 B2 8/2010 McGee et al.
7,772,725 B2 8/2010 Siman-Tov
7,775,972 B2 8/2010 Brock et al.
7,776,037 B2 8/2010 Odom
7,776,060 B2 8/2010 Mooradian et al.
7,776,065 B2 8/2010 Griffiths et al.
7,778,004 B2 8/2010 Nerheim et al.
7,779,614 B1 8/2010 McGonagle et al.
7,779,737 B2 8/2010 Newman, Jr. et al.
7,780,054 B2 8/2010 Wales
7,780,055 B2 8/2010 Scirica et al.
7,780,309 B2 8/2010 McMillan et al.
7,780,651 B2 8/2010 Madhani et al.
7,780,663 B2 8/2010 Yates et al.
7,780,685 B2 8/2010 Hunt et al.
7,782,382 B2 8/2010 Fujimura
7,784,662 B2 8/2010 Wales et al.
7,784,663 B2 8/2010 Shelton, IV
7,787,256 B2 8/2010 Chan et al.
7,789,283 B2 9/2010 Shah
7,789,875 B2 9/2010 Brock et al.
7,789,883 B2 9/2010 Takashino et al.
7,789,889 B2 9/2010 Zubik et al.
7,793,812 B2 9/2010 Moore et al.
7,794,475 B2 9/2010 Hess et al.
7,798,386 B2 9/2010 Schall et al.
7,799,039 B2 9/2010 Shelton, IV et al.
7,799,044 B2 9/2010 Johnston et al.
7,799,965 B2 9/2010 Patel et al.
7,803,151 B2 9/2010 Whitman
7,806,871 B2 10/2010 Li et al.
7,806,891 B2 10/2010 Nowlin et al.
7,810,690 B2 10/2010 Bilotti et al.
7,810,691 B2 10/2010 Boyden et al.
7,810,692 B2 10/2010 Hall et al.
7,810,693 B2 10/2010 Broehl et al.
7,811,275 B2 10/2010 Birk et al.
7,814,816 B2 10/2010 Alberti et al.
7,815,092 B2 10/2010 Whitman et al.
7,815,565 B2 10/2010 Stefanchik et al.
7,815,662 B2 10/2010 Spivey et al.
7,819,296 B2 10/2010 Hueil et al.
7,819,297 B2 10/2010 Doll et al.
7,819,298 B2 10/2010 Hall et al.
7,819,299 B2 10/2010 Shelton, IV et al.
7,819,799 B2 10/2010 Merril et al.
7,819,884 B2 10/2010 Lee et al.
7,819,885 B2 10/2010 Cooper
7,819,886 B2 10/2010 Whitfield et al.
7,819,894 B2 10/2010 Mitsuishi et al.
7,823,076 B2 10/2010 Borovsky et al.
7,823,592 B2 11/2010 Bettuchi et al.
7,823,760 B2 11/2010 Zemlok et al.
7,824,401 B2 11/2010 Manzo et al.
7,824,422 B2 11/2010 Benchetrit
7,824,426 B2 11/2010 Racenet et al.
7,828,189 B2 11/2010 Holsten et al.
7,828,794 B2 11/2010 Sartor
7,828,808 B2 11/2010 Hinman et al.
7,829,416 B2 11/2010 Kudou et al.
7,831,292 B2 11/2010 Quaid et al.
7,832,408 B2 11/2010 Shelton, IV et al.
7,832,611 B2 11/2010 Boyden et al.
7,832,612 B2 11/2010 Baxter, III et al.
7,833,234 B2 11/2010 Bailly et al.
7,835,823 B2 11/2010 Sillman et al.
7,836,400 B2 11/2010 May et al.
7,837,079 B2 11/2010 Holsten et al.
7,837,080 B2 11/2010 Schwemberger
7,837,081 B2 11/2010 Holsten et al.
7,837,425 B2 11/2010 Saeki et al.
7,837,685 B2 11/2010 Weinberg et al.
7,837,687 B2 11/2010 Harp
7,837,694 B2 11/2010 Tethrake et al.
7,838,789 B2 11/2010 Stoffers et al.
7,839,109 B2 11/2010 Carmen, Jr. et al.
7,840,253 B2 11/2010 Tremblay et al.
7,841,503 B2 11/2010 Sonnenschein et al.
7,842,025 B2 11/2010 Coleman et al.
7,842,028 B2 11/2010 Lee
7,843,158 B2 11/2010 Prisco
7,845,533 B2 12/2010 Marczyk et al.
7,845,534 B2 12/2010 Viola et al.
7,845,535 B2 12/2010 Scircia
7,845,536 B2 12/2010 Viola et al.
7,845,537 B2 12/2010 Shelton, IV et al.
7,845,538 B2 12/2010 Whitman
7,845,912 B2 12/2010 Sung et al.
7,846,085 B2 12/2010 Silverman et al.
7,846,149 B2 12/2010 Jankowski
7,846,161 B2 12/2010 Dumbauld et al.
7,848,066 B2 12/2010 Yanagishima
7,850,623 B2 12/2010 Griffin et al.
7,850,642 B2 12/2010 Moll et al.
7,850,982 B2 12/2010 Stopek et al.
7,853,813 B2 12/2010 Lee
7,854,735 B2 12/2010 Houser et al.
7,854,736 B2 12/2010 Ryan
7,857,183 B2 12/2010 Shelton, IV
7,857,184 B2 12/2010 Viola
7,857,185 B2 12/2010 Swayze et al.
7,857,186 B2 12/2010 Baxter, III et al.
7,857,813 B2 12/2010 Schmitz et al.
7,861,906 B2 1/2011 Doll et al.
7,862,502 B2 1/2011 Pool et al.
7,862,546 B2 1/2011 Conlon et al.
7,862,579 B2 1/2011 Ortiz et al.
7,866,525 B2 1/2011 Scirica
7,866,527 B2 1/2011 Hall et al.
7,866,528 B2 1/2011 Olson et al.
7,870,989 B2 1/2011 Viola et al.
7,871,418 B2 1/2011 Thompson et al.
7,871,440 B2 1/2011 Schwartz et al.
7,875,055 B2 1/2011 Cichocki, Jr.
7,877,869 B2 2/2011 Mehdizadeh et al.
7,879,063 B2 2/2011 Khosravi
7,879,070 B2 2/2011 Ortiz et al.
7,879,367 B2 2/2011 Heublein et al.
7,883,461 B2 2/2011 Albrecht et al.

(56) References Cited

U.S. PATENT DOCUMENTS 7,883,465 B2 2/2011 Donofrio et al.
7,883,540 B2 2/2011 Niwa et al.
7,886,951 B2 2/2011 Hessler
7,886,952 B2 2/2011 Scirica et al.
7,887,530 B2 2/2011 Zemlok et al.
7,887,535 B2 2/2011 Lands et al.
7,887,536 B2 2/2011 Johnson et al.
7,887,563 B2 2/2011 Cummins
7,887,755 B2 2/2011 Mingerink et al.
7,891,531 B1 2/2011 Ward
7,891,532 B2 2/2011 Mastri et al.
7,892,200 B2 2/2011 Birk et al.
7,892,245 B2 2/2011 Liddicoat et al.
7,893,586 B2 2/2011 West et al.
7,896,214 B2 3/2011 Farascioni
7,896,215 B2 3/2011 Adams et al.
7,896,671 B2 3/2011 Kim et al.
7,896,869 B2 3/2011 DiSilvestro et al.
7,896,877 B2 3/2011 Hall et al.
7,896,895 B2 3/2011 Boudreaux et al.
7,896,897 B2 3/2011 Gresham et al.
7,896,900 B2 3/2011 Frank et al.
7,898,198 B2 3/2011 Murphree
7,900,805 B2 3/2011 Shelton, IV et al.
7,900,806 B2 3/2011 Chen et al.
7,901,381 B2 3/2011 Birk et al.
7,905,380 B2 3/2011 Shelton, IV et al.
7,905,381 B2 3/2011 Baxter et al.
7,905,881 B2 3/2011 Masuda et al.
7,905,889 B2 3/2011 Catanese, III et al.
7,905,890 B2 3/2011 Whitfield et al.
7,905,902 B2 3/2011 Huitema et al.
7,909,039 B2 3/2011 Hur
7,909,191 B2 3/2011 Baker et al.
7,909,220 B2 3/2011 Viola
7,909,221 B2 3/2011 Viola et al.
7,909,224 B2 3/2011 Prommersberger
7,913,891 B2 3/2011 Doll et al.
7,913,893 B2 3/2011 Mastri et al.
7,914,521 B2 3/2011 Wang et al.
7,914,543 B2 3/2011 Roth et al.
7,914,551 B2 3/2011 Ortiz et al.
7,918,230 B2 4/2011 Whitman et al.
7,918,376 B1 4/2011 Knodel et al.
7,918,377 B2 4/2011 Measamer et al.
7,918,845 B2 4/2011 Saadat et al.
7,918,848 B2 4/2011 Lau et al.
7,918,861 B2 4/2011 Brock et al.
7,918,867 B2 4/2011 Dana et al.
7,922,061 B2 4/2011 Shelton, IV et al.
7,922,063 B2 4/2011 Zemlok et al.
7,922,743 B2 4/2011 Heinrich et al.
7,923,144 B2 4/2011 Kohn et al.
7,926,691 B2 4/2011 Viola et al.
7,926,692 B2 4/2011 Racenet et al.
7,927,328 B2 4/2011 Orszulak et al.
7,928,281 B2 4/2011 Augustine
7,930,040 B1 4/2011 Kelsch et al.
7,930,065 B2 4/2011 Larkin et al.
7,931,660 B2 4/2011 Aranyi et al.
7,931,695 B2 4/2011 Ringeisen
7,931,877 B2 4/2011 Steffens et al.
7,934,630 B2 5/2011 Shelton, IV et al.
7,934,631 B2 5/2011 Balbierz et al.
7,934,896 B2 5/2011 Schnier
7,935,130 B2 5/2011 Williams
7,935,773 B2 5/2011 Hadba et al.
7,936,142 B2 5/2011 Otsuka et al.
7,938,307 B2 5/2011 Bettuchi
7,939,152 B2 5/2011 Haskin et al.
7,941,865 B2 5/2011 Seman, Jr. et al.
7,942,300 B2 5/2011 Rethy et al.
7,942,303 B2 5/2011 Shah
7,942,890 B2 5/2011 D'Agostino et al.
7,944,175 B2 5/2011 Mori et al.
7,945,792 B2 5/2011 Cherpantier
7,945,798 B2 5/2011 Carlson et al.
7,946,453 B2 5/2011 Voegele et al.
7,947,011 B2 5/2011 Birk et al.
7,948,381 B2 5/2011 Lindsay et al.
7,950,560 B2 5/2011 Zemlok et al.
7,950,561 B2 5/2011 Aranyi
7,950,562 B2 5/2011 Beardsley et al.
7,951,071 B2 5/2011 Whitman et al.
7,951,166 B2 5/2011 Orban, III et al.
7,952,464 B2 5/2011 Nikitin et al.
7,954,682 B2 6/2011 Giordano et al.
7,954,684 B2 6/2011 Boudreaux
7,954,685 B2 6/2011 Viola
7,954,686 B2 6/2011 Baxter, III et al.
7,954,687 B2 6/2011 Zemlok et al.
7,954,688 B2 6/2011 Argentine et al.
7,955,253 B2 6/2011 Ewers et al.
7,955,257 B2 6/2011 Frasier et al.
7,955,322 B2 6/2011 Devengenzo et al.
7,955,327 B2 6/2011 Sartor et al.
7,955,380 B2 6/2011 Chu et al.
7,959,050 B2 6/2011 Smith et al.
7,959,051 B2 6/2011 Smith et al.
7,959,052 B2 6/2011 Sonnenschein et al.
7,963,432 B2 6/2011 Knodel et al.
7,963,433 B2 6/2011 Whitman et al.
7,963,913 B2 6/2011 Devengenzo et al.
7,963,963 B2 6/2011 Francischelli et al.
7,963,964 B2 6/2011 Santilli et al.
7,964,206 B2 6/2011 Suokas et al.
7,966,236 B2 6/2011 Noriega et al.
7,966,269 B2 6/2011 Bauer et al.
7,966,799 B2 6/2011 Morgan et al.
7,967,178 B2 6/2011 Scirica et al.
7,967,179 B2 6/2011 Olson et al.
7,967,180 B2 6/2011 Scirica
7,967,181 B2 6/2011 Viola et al.
7,967,791 B2 6/2011 Franer et al.
7,967,839 B2 6/2011 Flock et al.
7,972,298 B2 7/2011 Wallace et al.
7,972,315 B2 7/2011 Birk et al.
7,976,213 B2 7/2011 Bertolotti et al.
7,976,508 B2 7/2011 Hoag
7,976,563 B2 7/2011 Summerer
7,979,137 B2 7/2011 Tracey et al.
7,980,443 B2 7/2011 Scheib et al.
7,981,025 B2 7/2011 Pool et al.
7,981,102 B2 7/2011 Patel et al.
7,981,132 B2 7/2011 Dubrul et al.
7,987,405 B2 7/2011 Turner et al.
7,988,015 B2 8/2011 Mason et al.
7,988,026 B2 8/2011 Knodel et al.
7,988,027 B2 8/2011 Olson et al.
7,988,028 B2 8/2011 Farascioni et al.
7,988,779 B2 8/2011 Disalvo et al.
7,992,757 B2 8/2011 Wheeler et al.
7,993,360 B2 8/2011 Hacker et al.
7,994,670 B2 8/2011 Ji
7,997,054 B2 8/2011 Bertsch et al.
7,997,468 B2 8/2011 Farascioni
7,997,469 B2 8/2011 Olson et al.
8,002,696 B2 8/2011 Suzuki
8,002,784 B2 8/2011 Jinno et al.
8,002,785 B2 8/2011 Weiss et al.
8,002,795 B2 8/2011 Beetel
8,006,365 B2 8/2011 Levin et al.
8,006,885 B2 8/2011 Marczyk
8,006,889 B2 8/2011 Adams et al.
8,007,370 B2 8/2011 Hirsch et al.
8,007,465 B2 8/2011 Birk et al.
8,007,479 B2 8/2011 Birk et al.
8,007,511 B2 8/2011 Brock et al.
8,007,513 B2 8/2011 Nalagatla et al.
8,008,598 B2 8/2011 Whitman et al.
8,010,180 B2 8/2011 Quaid et al.
8,011,550 B2 9/2011 Aranyi et al.
8,011,551 B2 9/2011 Marczyk et al.
8,011,553 B2 9/2011 Mastri et al.

(56) References Cited

U.S. PATENT DOCUMENTS

| | | | |
|---|---|---|---|
| 8,011,555 | B2 | 9/2011 | Tarinelli et al. |
| 8,012,170 | B2 | 9/2011 | Whitman et al. |
| 8,016,176 | B2 | 9/2011 | Kasvikis et al. |
| 8,016,177 | B2 | 9/2011 | Bettuchi et al. |
| 8,016,178 | B2 | 9/2011 | Olson et al. |
| 8,016,849 | B2 | 9/2011 | Wenchell |
| 8,016,855 | B2 | 9/2011 | Whitman et al. |
| 8,016,858 | B2 | 9/2011 | Whitman |
| 8,016,881 | B2 | 9/2011 | Furst |
| 8,020,741 | B2 | 9/2011 | Cole et al. |
| 8,020,742 | B2 | 9/2011 | Marczyk |
| 8,020,743 | B2 | 9/2011 | Shelton, IV |
| 8,021,375 | B2 | 9/2011 | Aldrich et al. |
| 8,025,199 | B2 | 9/2011 | Whitman et al. |
| 8,025,896 | B2 | 9/2011 | Malaviya et al. |
| 8,028,835 | B2 | 10/2011 | Yasuda et al. |
| 8,028,882 | B2 | 10/2011 | Viola |
| 8,028,883 | B2 | 10/2011 | Stopek |
| 8,028,884 | B2 | 10/2011 | Sniffin et al. |
| 8,028,885 | B2 | 10/2011 | Smith et al. |
| 8,029,510 | B2 | 10/2011 | Hoegerle |
| 8,031,069 | B2 | 10/2011 | Cohn et al. |
| 8,033,438 | B2 | 10/2011 | Scirica |
| 8,033,439 | B2 | 10/2011 | Racenet et al. |
| 8,033,440 | B2 | 10/2011 | Wenchell et al. |
| 8,033,442 | B2 | 10/2011 | Racenet et al. |
| 8,034,077 | B2 | 10/2011 | Smith et al. |
| 8,034,337 | B2 | 10/2011 | Simard |
| 8,034,363 | B2 | 10/2011 | Li et al. |
| 8,035,487 | B2 | 10/2011 | Malackowski |
| 8,037,591 | B2 | 10/2011 | Spivey et al. |
| 8,038,044 | B2 | 10/2011 | Viola |
| 8,038,045 | B2 | 10/2011 | Bettuchi et al. |
| 8,038,046 | B2 | 10/2011 | Smith et al. |
| 8,038,686 | B2 | 10/2011 | Huitema et al. |
| 8,043,207 | B2 | 10/2011 | Adams |
| 8,043,328 | B2 | 10/2011 | Hahnen et al. |
| 8,044,536 | B2 | 10/2011 | Nguyen et al. |
| 8,044,604 | B2 | 10/2011 | Hagino et al. |
| 8,047,236 | B2 | 11/2011 | Perry |
| 8,048,503 | B2 | 11/2011 | Farnsworth et al. |
| 8,052,636 | B2 | 11/2011 | Moll et al. |
| 8,052,697 | B2 | 11/2011 | Phillips |
| 8,056,787 | B2 | 11/2011 | Boudreaux et al. |
| 8,056,788 | B2 | 11/2011 | Mastri et al. |
| 8,056,789 | B1 | 11/2011 | White et al. |
| 8,057,508 | B2 | 11/2011 | Shelton, IV |
| 8,058,771 | B2 | 11/2011 | Giordano et al. |
| 8,060,250 | B2 | 11/2011 | Reiland et al. |
| 8,061,014 | B2 | 11/2011 | Smith et al. |
| 8,061,576 | B2 | 11/2011 | Cappola |
| 8,062,236 | B2 | 11/2011 | Soltz |
| 8,062,306 | B2 | 11/2011 | Nobis et al. |
| 8,062,330 | B2 | 11/2011 | Prommersberger et al. |
| 8,063,619 | B2 | 11/2011 | Zhu et al. |
| 8,066,158 | B2 | 11/2011 | Vogel et al. |
| 8,066,166 | B2 | 11/2011 | Demmy et al. |
| 8,066,167 | B2 | 11/2011 | Measamer et al. |
| 8,066,168 | B2 | 11/2011 | Vidal et al. |
| 8,066,720 | B2 | 11/2011 | Knodel et al. |
| D650,074 | S | 12/2011 | Hunt et al. |
| D650,789 | S | 12/2011 | Arnold |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,070,743 | B2 | 12/2011 | Kagan et al. |
| 8,074,858 | B2 | 12/2011 | Marczyk |
| 8,074,859 | B2 | 12/2011 | Kostrzewski |
| 8,074,861 | B2 | 12/2011 | Ehrenfels et al. |
| 8,075,476 | B2 | 12/2011 | Vargas |
| 8,075,571 | B2 | 12/2011 | Vitali et al. |
| 8,079,950 | B2 | 12/2011 | Stern et al. |
| 8,079,989 | B2 | 12/2011 | Birk et al. |
| 8,080,004 | B2 | 12/2011 | Downey et al. |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,084,001 | B2 | 12/2011 | Burns et al. |
| 8,084,969 | B2 | 12/2011 | David et al. |
| 8,085,013 | B2 | 12/2011 | Wei et al. |
| 8,087,562 | B1 | 1/2012 | Manoux et al. |
| 8,087,563 | B2 | 1/2012 | Milliman et al. |
| 8,089,509 | B2 | 1/2012 | Chatenever et al. |
| 8,091,753 | B2 | 1/2012 | Viola |
| 8,091,756 | B2 | 1/2012 | Viola |
| 8,092,443 | B2 | 1/2012 | Bischoff |
| 8,092,932 | B2 | 1/2012 | Phillips et al. |
| 8,093,572 | B2 | 1/2012 | Kuduvalli |
| 8,096,458 | B2 | 1/2012 | Hessler |
| 8,096,459 | B2 | 1/2012 | Ortiz et al. |
| 8,097,017 | B2 | 1/2012 | Viola |
| 8,100,310 | B2 | 1/2012 | Zemlok |
| 8,100,824 | B2 | 1/2012 | Hegeman et al. |
| 8,100,872 | B2 | 1/2012 | Patel |
| 8,102,138 | B2 | 1/2012 | Sekine et al. |
| 8,102,278 | B2 | 1/2012 | Deck et al. |
| 8,105,320 | B2 | 1/2012 | Manzo |
| 8,105,350 | B2 | 1/2012 | Lee et al. |
| 8,107,925 | B2 | 1/2012 | Natsuno et al. |
| 8,108,033 | B2 | 1/2012 | Drew et al. |
| 8,108,072 | B2 | 1/2012 | Zhao et al. |
| 8,109,426 | B2 | 2/2012 | Milliman et al. |
| 8,110,208 | B1 | 2/2012 | Hen |
| 8,113,405 | B2 | 2/2012 | Milliman |
| 8,113,407 | B2 | 2/2012 | Holsten et al. |
| 8,113,408 | B2 | 2/2012 | Wenchell et al. |
| 8,113,410 | B2 | 2/2012 | Hall et al. |
| 8,114,017 | B2 | 2/2012 | Bacher |
| 8,114,100 | B2 | 2/2012 | Smith et al. |
| 8,114,345 | B2 | 2/2012 | Dlugos, Jr. et al. |
| 8,118,206 | B2 | 2/2012 | Zand et al. |
| 8,118,207 | B2 | 2/2012 | Racenet et al. |
| 8,120,301 | B2 | 2/2012 | Goldberg et al. |
| 8,122,128 | B2 | 2/2012 | Burke, II et al. |
| 8,123,103 | B2 | 2/2012 | Milliman |
| 8,123,523 | B2 | 2/2012 | Carron et al. |
| 8,123,766 | B2 | 2/2012 | Bauman et al. |
| 8,123,767 | B2 | 2/2012 | Bauman et al. |
| 8,125,168 | B2 | 2/2012 | Johnson et al. |
| 8,127,975 | B2 | 3/2012 | Olson et al. |
| 8,127,976 | B2 | 3/2012 | Scirica et al. |
| 8,128,624 | B2 | 3/2012 | Couture et al. |
| 8,128,643 | B2 | 3/2012 | Aranyi et al. |
| 8,128,645 | B2 | 3/2012 | Sonnenschein et al. |
| 8,128,662 | B2 | 3/2012 | Altarac et al. |
| 8,132,703 | B2 | 3/2012 | Milliman et al. |
| 8,132,705 | B2 | 3/2012 | Viola et al. |
| 8,132,706 | B2 | 3/2012 | Marczyk et al. |
| 8,133,500 | B2 | 3/2012 | Ringeisen et al. |
| 8,134,306 | B2 | 3/2012 | Drader et al. |
| 8,136,711 | B2 | 3/2012 | Beardsley et al. |
| 8,136,712 | B2 | 3/2012 | Zingman |
| 8,136,713 | B2 | 3/2012 | Hathaway et al. |
| 8,137,339 | B2 | 3/2012 | Jinno et al. |
| 8,140,417 | B2 | 3/2012 | Shibata |
| 8,141,762 | B2 | 3/2012 | Bedi et al. |
| 8,141,763 | B2 | 3/2012 | Milliman |
| 8,142,200 | B2 | 3/2012 | Crunkilton et al. |
| 8,142,425 | B2 | 3/2012 | Eggers |
| 8,142,461 | B2 | 3/2012 | Houser et al. |
| 8,142,515 | B2 | 3/2012 | Therin et al. |
| 8,143,520 | B2 | 3/2012 | Cutler |
| 8,146,790 | B2 | 4/2012 | Milliman |
| 8,147,421 | B2 | 4/2012 | Farquhar et al. |
| 8,147,456 | B2 | 4/2012 | Fisher et al. |
| 8,147,485 | B2 | 4/2012 | Wham et al. |
| 8,152,041 | B2 | 4/2012 | Kostrzewski |
| 8,152,756 | B2 | 4/2012 | Webster et al. |
| 8,154,239 | B2 | 4/2012 | Katsuki et al. |
| 8,157,145 | B2 | 4/2012 | Shelton, IV et al. |
| 8,157,148 | B2 | 4/2012 | Scirica |
| 8,157,151 | B2 | 4/2012 | Ingmanson et al. |
| 8,157,152 | B2 | 4/2012 | Holsten et al. |
| 8,157,153 | B2 | 4/2012 | Shelton, IV et al. |

(56) References Cited

U.S. PATENT DOCUMENTS

| | | | |
|---|---|---|---|
| 8,157,793 | B2 | 4/2012 | Omori et al. |
| 8,157,834 | B2 | 4/2012 | Conlon |
| 8,161,977 | B2 | 4/2012 | Shelton, IV et al. |
| 8,162,138 | B2 | 4/2012 | Bettenhausen et al. |
| 8,162,197 | B2 | 4/2012 | Mastri et al. |
| 8,162,668 | B2 | 4/2012 | Toly |
| 8,162,933 | B2 | 4/2012 | Francischelli et al. |
| 8,162,965 | B2 | 4/2012 | Reschke et al. |
| 8,167,185 | B2 | 5/2012 | Shelton, IV et al. |
| 8,167,622 | B2 | 5/2012 | Zhou |
| 8,167,895 | B2 | 5/2012 | D'Agostino et al. |
| 8,167,898 | B1 | 5/2012 | Schaller et al. |
| 8,170,241 | B2 | 5/2012 | Roe et al. |
| 8,172,004 | B2 | 5/2012 | Ho |
| 8,172,120 | B2 | 5/2012 | Boyden et al. |
| 8,172,122 | B2 | 5/2012 | Kasvikis et al. |
| 8,172,124 | B2 | 5/2012 | Shelton, IV et al. |
| 8,177,776 | B2 | 5/2012 | Humayun et al. |
| 8,177,797 | B2 | 5/2012 | Shimoji et al. |
| 8,179,705 | B2 | 5/2012 | Chapuis |
| 8,180,458 | B2 | 5/2012 | Kane et al. |
| 8,181,839 | B2 | 5/2012 | Beetel |
| 8,181,840 | B2 | 5/2012 | Milliman |
| 8,182,422 | B2 | 5/2012 | Bayer et al. |
| 8,182,444 | B2 | 5/2012 | Uber, III et al. |
| 8,183,807 | B2 | 5/2012 | Tsai et al. |
| 8,186,555 | B2 | 5/2012 | Shelton, IV et al. |
| 8,186,556 | B2 | 5/2012 | Viola |
| 8,186,558 | B2 | 5/2012 | Sapienza |
| 8,186,560 | B2 | 5/2012 | Hess et al. |
| 8,190,238 | B2 | 5/2012 | Moll et al. |
| 8,191,752 | B2 | 6/2012 | Scirica |
| 8,192,350 | B2 | 6/2012 | Ortiz et al. |
| 8,192,460 | B2 | 6/2012 | Orban, III et al. |
| 8,192,651 | B2 | 6/2012 | Young et al. |
| 8,193,129 | B2 | 6/2012 | Tagawa et al. |
| 8,196,795 | B2 | 6/2012 | Moore et al. |
| 8,196,796 | B2 | 6/2012 | Shelton, IV et al. |
| 8,197,501 | B2 | 6/2012 | Shadeck et al. |
| 8,197,502 | B2 | 6/2012 | Smith et al. |
| 8,197,837 | B2 | 6/2012 | Jamiolkowski et al. |
| 8,201,720 | B2 | 6/2012 | Hessler |
| 8,201,721 | B2 | 6/2012 | Zemlok et al. |
| 8,202,549 | B2 | 6/2012 | Stucky et al. |
| 8,205,779 | B2 | 6/2012 | Ma et al. |
| 8,205,780 | B2 | 6/2012 | Sorrentino et al. |
| 8,205,781 | B2 | 6/2012 | Baxter, III et al. |
| 8,207,863 | B2 | 6/2012 | Neubauer et al. |
| 8,210,411 | B2 | 7/2012 | Yates et al. |
| 8,210,414 | B2 | 7/2012 | Bettuchi et al. |
| 8,210,415 | B2 | 7/2012 | Ward |
| 8,210,416 | B2 | 7/2012 | Milliman et al. |
| 8,210,721 | B2 | 7/2012 | Chen et al. |
| 8,211,125 | B2 | 7/2012 | Spivey |
| 8,214,019 | B2 | 7/2012 | Govari et al. |
| 8,215,531 | B2 | 7/2012 | Shelton, IV et al. |
| 8,215,532 | B2 | 7/2012 | Marczyk |
| 8,215,533 | B2 | 7/2012 | Viola et al. |
| 8,220,468 | B2 | 7/2012 | Cooper et al. |
| 8,220,688 | B2 | 7/2012 | Laurent et al. |
| 8,220,690 | B2 | 7/2012 | Hess et al. |
| 8,221,402 | B2 | 7/2012 | Francischelli et al. |
| 8,221,424 | B2 | 7/2012 | Cha |
| 8,221,433 | B2 | 7/2012 | Lozier et al. |
| 8,225,799 | B2 | 7/2012 | Bettuchi |
| 8,225,979 | B2 | 7/2012 | Farascioni et al. |
| 8,226,553 | B2 | 7/2012 | Shelton, IV et al. |
| 8,226,635 | B2 | 7/2012 | Petrie et al. |
| 8,226,675 | B2 | 7/2012 | Houser et al. |
| 8,226,715 | B2 | 7/2012 | Hwang et al. |
| 8,227,946 | B2 | 7/2012 | Kim |
| 8,228,020 | B2 | 7/2012 | Shin et al. |
| 8,228,048 | B2 | 7/2012 | Spencer |
| 8,229,549 | B2 | 7/2012 | Whitman et al. |
| 8,230,235 | B2 | 7/2012 | Goodman et al. |
| 8,231,040 | B2 | 7/2012 | Zemlok et al. |
| 8,231,042 | B2 | 7/2012 | Hessler et al. |
| 8,231,043 | B2 | 7/2012 | Tarinelli et al. |
| 8,235,272 | B2 | 8/2012 | Nicholas et al. |
| 8,235,274 | B2 | 8/2012 | Cappola |
| 8,236,010 | B2 | 8/2012 | Ortiz et al. |
| 8,236,011 | B2 | 8/2012 | Harris et al. |
| 8,236,020 | B2 | 8/2012 | Smith et al. |
| 8,237,388 | B2 | 8/2012 | Jinno et al. |
| 8,240,537 | B2 | 8/2012 | Marczyk |
| 8,241,271 | B2 | 8/2012 | Millman et al. |
| 8,241,284 | B2 | 8/2012 | Dycus et al. |
| 8,241,308 | B2 | 8/2012 | Kortenbach et al. |
| 8,241,322 | B2 | 8/2012 | Whitman et al. |
| 8,245,594 | B2 | 8/2012 | Rogers et al. |
| 8,245,898 | B2 | 8/2012 | Smith et al. |
| 8,245,899 | B2 | 8/2012 | Swensgard et al. |
| 8,245,900 | B2 | 8/2012 | Scirica |
| 8,245,901 | B2 | 8/2012 | Stopek |
| 8,246,608 | B2 | 8/2012 | Omori et al. |
| 8,246,637 | B2 | 8/2012 | Viola et al. |
| 8,252,009 | B2 | 8/2012 | Weller et al. |
| 8,256,654 | B2 | 9/2012 | Bettuchi et al. |
| 8,256,655 | B2 | 9/2012 | Sniffin et al. |
| 8,256,656 | B2 | 9/2012 | Milliman et al. |
| 8,257,251 | B2 | 9/2012 | Shelton, IV et al. |
| 8,257,356 | B2 | 9/2012 | Bleich et al. |
| 8,257,386 | B2 | 9/2012 | Lee et al. |
| 8,257,391 | B2 | 9/2012 | Orban, III et al. |
| 8,257,634 | B2 | 9/2012 | Scirica |
| 8,258,745 | B2 | 9/2012 | Smith et al. |
| 8,261,958 | B1 | 9/2012 | Knodel |
| 8,262,560 | B2 | 9/2012 | Whitman |
| 8,262,655 | B2 | 9/2012 | Ghabrial et al. |
| 8,266,232 | B2 | 9/2012 | Piper et al. |
| 8,267,300 | B2 | 9/2012 | Boudreaux |
| 8,267,849 | B2 | 9/2012 | Wazer et al. |
| 8,267,924 | B2 | 9/2012 | Zemlok et al. |
| 8,267,946 | B2 | 9/2012 | Whitfield et al. |
| 8,267,951 | B2 | 9/2012 | Whayne et al. |
| 8,268,344 | B2 | 9/2012 | Ma et al. |
| 8,269,121 | B2 | 9/2012 | Smith |
| 8,272,553 | B2 | 9/2012 | Mastri et al. |
| 8,272,554 | B2 | 9/2012 | Whitman et al. |
| 8,272,918 | B2 | 9/2012 | Lam |
| 8,273,404 | B2 | 9/2012 | Dave et al. |
| 8,276,594 | B2 | 10/2012 | Shah |
| 8,276,801 | B2 | 10/2012 | Zemlok et al. |
| 8,276,802 | B2 | 10/2012 | Kostrzewski |
| 8,277,473 | B2 | 10/2012 | Sunaoshi et al. |
| 8,281,446 | B2 | 10/2012 | Moskovich |
| 8,281,973 | B2 | 10/2012 | Wenchell et al. |
| 8,281,974 | B2 | 10/2012 | Hessler et al. |
| 8,282,654 | B2 | 10/2012 | Ferrari et al. |
| 8,285,367 | B2 | 10/2012 | Hyde et al. |
| 8,286,723 | B2 | 10/2012 | Puzio et al. |
| 8,286,845 | B2 | 10/2012 | Perry et al. |
| 8,286,846 | B2 | 10/2012 | Smith et al. |
| 8,286,847 | B2 | 10/2012 | Taylor |
| 8,287,487 | B2 | 10/2012 | Estes |
| 8,287,522 | B2 | 10/2012 | Moses et al. |
| 8,287,561 | B2 | 10/2012 | Nunez et al. |
| 8,288,984 | B2 | 10/2012 | Yang |
| 8,289,403 | B2 | 10/2012 | Dobashi et al. |
| 8,290,883 | B2 | 10/2012 | Takeuchi et al. |
| 8,292,147 | B2 | 10/2012 | Viola |
| 8,292,148 | B2 | 10/2012 | Viola |
| 8,292,150 | B2 | 10/2012 | Bryant |
| 8,292,151 | B2 | 10/2012 | Viola |
| 8,292,152 | B2 | 10/2012 | Milliman et al. |
| 8,292,155 | B2 | 10/2012 | Shelton, IV et al. |
| 8,292,157 | B2 | 10/2012 | Smith et al. |
| 8,292,158 | B2 | 10/2012 | Sapienza |
| 8,292,801 | B2 | 10/2012 | Dejima et al. |
| 8,292,888 | B2 | 10/2012 | Whitman |
| 8,292,906 | B2 | 10/2012 | Taylor et al. |
| 8,294,399 | B2 | 10/2012 | Suzuki et al. |
| 8,298,161 | B2 | 10/2012 | Vargas |
| 8,298,189 | B2 | 10/2012 | Fisher et al. |

(56) References Cited

U.S. PATENT DOCUMENTS

| | | | |
|---|---|---|---|
| 8,298,233 | B2 | 10/2012 | Mueller |
| 8,298,677 | B2 | 10/2012 | Wiesner et al. |
| 8,302,323 | B2 | 11/2012 | Fortier et al. |
| 8,303,621 | B2 | 11/2012 | Miyamoto et al. |
| 8,308,040 | B2 | 11/2012 | Huang et al. |
| 8,308,041 | B2 | 11/2012 | Kostrzewski |
| 8,308,042 | B2 | 11/2012 | Aranyi |
| 8,308,043 | B2 | 11/2012 | Bindra et al. |
| 8,308,046 | B2 | 11/2012 | Prommersberger |
| 8,308,659 | B2 | 11/2012 | Scheibe et al. |
| 8,308,725 | B2 | 11/2012 | Bell et al. |
| 8,310,188 | B2 | 11/2012 | Nakai |
| 8,313,496 | B2 | 11/2012 | Sauer et al. |
| 8,313,499 | B2 | 11/2012 | Magnusson et al. |
| 8,313,509 | B2 | 11/2012 | Kostrzewski |
| 8,317,070 | B2 | 11/2012 | Hueil et al. |
| 8,317,071 | B1 | 11/2012 | Knodel |
| 8,317,074 | B2 | 11/2012 | Ortiz et al. |
| 8,317,437 | B2 | 11/2012 | Merkley et al. |
| 8,317,744 | B2 | 11/2012 | Kirschenman |
| 8,317,790 | B2 | 11/2012 | Bell et al. |
| 8,319,002 | B2 | 11/2012 | Daniels et al. |
| D672,784 | S | 12/2012 | Clanton et al. |
| 8,322,455 | B2 | 12/2012 | Shelton, IV et al. |
| 8,322,589 | B2 | 12/2012 | Boudreaux |
| 8,322,590 | B2 | 12/2012 | Patel et al. |
| 8,322,901 | B2 | 12/2012 | Michelotti |
| 8,323,271 | B2 | 12/2012 | Humayun et al. |
| 8,323,789 | B2 | 12/2012 | Rozhin et al. |
| 8,324,585 | B2 | 12/2012 | McBroom et al. |
| 8,327,514 | B2 | 12/2012 | Kim |
| 8,328,061 | B2 | 12/2012 | Kasvikis |
| 8,328,062 | B2 | 12/2012 | Viola |
| 8,328,063 | B2 | 12/2012 | Milliman et al. |
| 8,328,064 | B2 | 12/2012 | Racenet et al. |
| 8,328,065 | B2 | 12/2012 | Shah |
| 8,328,802 | B2 | 12/2012 | Deville et al. |
| 8,328,823 | B2 | 12/2012 | Aranyi et al. |
| 8,333,313 | B2 | 12/2012 | Boudreaux et al. |
| 8,333,691 | B2 | 12/2012 | Schaaf |
| 8,333,764 | B2 | 12/2012 | Francischelli et al. |
| 8,333,779 | B2 | 12/2012 | Smith et al. |
| 8,334,468 | B2 | 12/2012 | Palmer et al. |
| 8,336,753 | B2 | 12/2012 | Olson et al. |
| 8,336,754 | B2 | 12/2012 | Cappola et al. |
| 8,342,377 | B2 | 1/2013 | Milliman et al. |
| 8,342,378 | B2 | 1/2013 | Marczyk et al. |
| 8,342,379 | B2 | 1/2013 | Whitman et al. |
| 8,342,380 | B2 | 1/2013 | Viola |
| 8,343,150 | B2 | 1/2013 | Artale |
| 8,347,978 | B2 | 1/2013 | Forster et al. |
| 8,348,118 | B2 | 1/2013 | Segura |
| 8,348,123 | B2 | 1/2013 | Scirica et al. |
| 8,348,124 | B2 | 1/2013 | Scirica |
| 8,348,125 | B2 | 1/2013 | Viola et al. |
| 8,348,126 | B2 | 1/2013 | Olson et al. |
| 8,348,127 | B2 | 1/2013 | Marczyk |
| 8,348,129 | B2 | 1/2013 | Bedi et al. |
| 8,348,130 | B2 | 1/2013 | Shah et al. |
| 8,348,131 | B2 | 1/2013 | Omaits et al. |
| 8,348,837 | B2 | 1/2013 | Wenchell |
| 8,348,948 | B2 | 1/2013 | Bahney |
| 8,348,959 | B2 | 1/2013 | Wolford et al. |
| 8,348,972 | B2 | 1/2013 | Soltz et al. |
| 8,349,987 | B2 | 1/2013 | Kapiamba et al. |
| 8,352,004 | B2 | 1/2013 | Mannheimer et al. |
| 8,353,437 | B2 | 1/2013 | Boudreaux |
| 8,353,438 | B2 | 1/2013 | Baxter, III et al. |
| 8,353,439 | B2 | 1/2013 | Baxter et al. |
| 8,356,740 | B1 | 1/2013 | Knodel |
| 8,357,144 | B2 | 1/2013 | Whitman et al. |
| 8,357,158 | B2 | 1/2013 | Mckenna et al. |
| 8,357,161 | B2 | 1/2013 | Mueller |
| 8,359,174 | B2 | 1/2013 | Nakashima et al. |
| 8,360,296 | B2 | 1/2013 | Zingman |
| 8,360,297 | B2 | 1/2013 | Shelton, IV et al. |
| 8,360,298 | B2 | 1/2013 | Farascioni et al. |
| 8,360,299 | B2 | 1/2013 | Zemlok et al. |
| 8,361,501 | B2 | 1/2013 | DiTizio et al. |
| D676,866 | S | 2/2013 | Chaudhri |
| 8,365,972 | B2 | 2/2013 | Aranyi et al. |
| 8,365,973 | B1 | 2/2013 | White et al. |
| 8,365,975 | B1 | 2/2013 | Manoux et al. |
| 8,365,976 | B2 | 2/2013 | Hess et al. |
| 8,366,559 | B2 | 2/2013 | Papenfuss et al. |
| 8,366,719 | B2 | 2/2013 | Markey et al. |
| 8,366,787 | B2 | 2/2013 | Brown et al. |
| 8,368,327 | B2 | 2/2013 | Benning et al. |
| 8,369,056 | B2 | 2/2013 | Senriuchi et al. |
| 8,371,393 | B2 | 2/2013 | Higuchi et al. |
| 8,371,491 | B2 | 2/2013 | Huitema et al. |
| 8,371,492 | B2 | 2/2013 | Aranyi et al. |
| 8,371,493 | B2 | 2/2013 | Aranyi et al. |
| 8,371,494 | B2 | 2/2013 | Racenet et al. |
| 8,372,094 | B2 | 2/2013 | Bettuchi et al. |
| 8,374,723 | B2 | 2/2013 | Zhao et al. |
| 8,376,865 | B2 | 2/2013 | Forster et al. |
| 8,377,029 | B2 | 2/2013 | Nagao et al. |
| 8,377,044 | B2 | 2/2013 | Coe et al. |
| 8,377,059 | B2 | 2/2013 | Deville et al. |
| 8,381,828 | B2 | 2/2013 | Whitman et al. |
| 8,381,834 | B2 | 2/2013 | Barhitte et al. |
| 8,382,773 | B2 | 2/2013 | Whitfield et al. |
| 8,382,790 | B2 | 2/2013 | Uenohara et al. |
| D677,273 | S | 3/2013 | Randall et al. |
| 8,387,848 | B2 | 3/2013 | Johnson et al. |
| 8,388,633 | B2 | 3/2013 | Rousseau et al. |
| 8,389,588 | B2 | 3/2013 | Ringeisen et al. |
| 8,393,513 | B2 | 3/2013 | Jankowski |
| 8,393,514 | B2 | 3/2013 | Shelton, IV et al. |
| 8,393,516 | B2 | 3/2013 | Kostrzewski |
| 8,397,832 | B2 | 3/2013 | Blickle et al. |
| 8,397,971 | B2 | 3/2013 | Yates et al. |
| 8,397,972 | B2 | 3/2013 | Kostrzewski |
| 8,397,973 | B1 | 3/2013 | Hausen |
| 8,398,633 | B2 | 3/2013 | Mueller |
| 8,398,669 | B2 | 3/2013 | Kim |
| 8,398,673 | B2 | 3/2013 | Hinchliffe et al. |
| 8,398,674 | B2 | 3/2013 | Prestel |
| 8,400,108 | B2 | 3/2013 | Powell et al. |
| 8,400,851 | B2 | 3/2013 | Byun |
| 8,403,138 | B2 | 3/2013 | Weisshaupt et al. |
| 8,403,195 | B2 | 3/2013 | Beardsley et al. |
| 8,403,196 | B2 | 3/2013 | Beardsley et al. |
| 8,403,198 | B2 | 3/2013 | Sorrentino et al. |
| 8,403,832 | B2 | 3/2013 | Cunningham et al. |
| 8,403,926 | B2 | 3/2013 | Nobis et al. |
| 8,403,945 | B2 | 3/2013 | Whitfield et al. |
| 8,403,946 | B2 | 3/2013 | Whitfield et al. |
| 8,403,950 | B2 | 3/2013 | Palmer et al. |
| D680,646 | S | 4/2013 | Hunt et al. |
| 8,408,439 | B2 | 4/2013 | Huang et al. |
| 8,408,442 | B2 | 4/2013 | Racenet et al. |
| 8,409,079 | B2 | 4/2013 | Okamoto et al. |
| 8,409,174 | B2 | 4/2013 | Omori |
| 8,409,175 | B2 | 4/2013 | Lee et al. |
| 8,409,211 | B2 | 4/2013 | Baroud |
| 8,409,222 | B2 | 4/2013 | Whitfield et al. |
| 8,409,223 | B2 | 4/2013 | Sorrentino et al. |
| 8,409,234 | B2 | 4/2013 | Stahler et al. |
| 8,411,500 | B2 | 4/2013 | Gapihan et al. |
| 8,413,661 | B2 | 4/2013 | Rousseau et al. |
| 8,413,870 | B2 | 4/2013 | Pastorelli et al. |
| 8,413,871 | B2 | 4/2013 | Racenet et al. |
| 8,413,872 | B2 | 4/2013 | Patel |
| 8,414,469 | B2 | 4/2013 | Diolaiti |
| 8,414,577 | B2 | 4/2013 | Boudreaux et al. |
| 8,414,598 | B2 | 4/2013 | Brock et al. |
| 8,418,073 | B2 | 4/2013 | Mohr et al. |
| 8,418,906 | B2 | 4/2013 | Farascioni et al. |
| 8,418,907 | B2 | 4/2013 | Johnson et al. |
| 8,418,908 | B1 | 4/2013 | Beardsley |
| 8,418,909 | B2 | 4/2013 | Kostrzewski |
| 8,419,635 | B2 | 4/2013 | Shelton, IV et al. |

(56) References Cited

U.S. PATENT DOCUMENTS

| | | | |
|---|---|---|---|
| 8,419,717 | B2 | 4/2013 | Diolaiti et al. |
| 8,419,747 | B2 | 4/2013 | Hinman et al. |
| 8,419,754 | B2 | 4/2013 | Laby et al. |
| 8,419,755 | B2 | 4/2013 | Deem et al. |
| 8,423,182 | B2 | 4/2013 | Robinson et al. |
| 8,424,737 | B2 | 4/2013 | Scirica |
| 8,424,739 | B2 | 4/2013 | Racenet et al. |
| 8,424,740 | B2 | 4/2013 | Shelton, IV et al. |
| 8,424,741 | B2 | 4/2013 | McGuckin, Jr. et al. |
| 8,425,600 | B2 | 4/2013 | Maxwell |
| 8,427,430 | B2 | 4/2013 | Lee et al. |
| 8,430,292 | B2 | 4/2013 | Patel et al. |
| 8,430,892 | B2 | 4/2013 | Bindra et al. |
| 8,430,898 | B2 | 4/2013 | Wiener et al. |
| 8,435,257 | B2 | 5/2013 | Smith et al. |
| 8,439,246 | B1 | 5/2013 | Knodel |
| 8,439,830 | B2 | 5/2013 | McKinley et al. |
| 8,444,036 | B2 | 5/2013 | Shelton, IV |
| 8,444,037 | B2 | 5/2013 | Nicholas et al. |
| 8,444,549 | B2 | 5/2013 | Viola et al. |
| 8,449,536 | B2 | 5/2013 | Selig |
| 8,449,560 | B2 | 5/2013 | Roth et al. |
| 8,453,904 | B2 | 6/2013 | Eskaros et al. |
| 8,453,906 | B2 | 6/2013 | Huang et al. |
| 8,453,907 | B2 | 6/2013 | Laurent et al. |
| 8,453,908 | B2 | 6/2013 | Bedi et al. |
| 8,453,912 | B2 | 6/2013 | Mastri et al. |
| 8,453,914 | B2 | 6/2013 | Laurent et al. |
| 8,454,495 | B2 | 6/2013 | Kawano et al. |
| 8,454,551 | B2 | 6/2013 | Allen et al. |
| 8,454,628 | B2 | 6/2013 | Smith et al. |
| 8,454,640 | B2 | 6/2013 | Johnston et al. |
| 8,457,757 | B2 | 6/2013 | Cauller et al. |
| 8,459,520 | B2 | 6/2013 | Giordano et al. |
| 8,459,521 | B2 | 6/2013 | Zemlok et al. |
| 8,459,524 | B2 | 6/2013 | Pribanic et al. |
| 8,459,525 | B2 | 6/2013 | Yates et al. |
| 8,464,922 | B2 | 6/2013 | Marczyk |
| 8,464,923 | B2 | 6/2013 | Shelton, IV |
| 8,464,924 | B2 | 6/2013 | Gresham et al. |
| 8,464,925 | B2 | 6/2013 | Hull et al. |
| 8,465,475 | B2 | 6/2013 | Isbell, Jr. |
| 8,465,502 | B2 | 6/2013 | Zergiebel |
| 8,465,515 | B2 | 6/2013 | Drew et al. |
| 8,469,254 | B2 | 6/2013 | Czernik et al. |
| 8,469,946 | B2 | 6/2013 | Sugita |
| 8,469,973 | B2 | 6/2013 | Meade et al. |
| 8,470,355 | B2 | 6/2013 | Skalla et al. |
| D686,240 | S | 7/2013 | Lin |
| D686,244 | S | 7/2013 | Moriya et al. |
| 8,474,677 | B2 | 7/2013 | Woodard, Jr. et al. |
| 8,475,453 | B2 | 7/2013 | Marczyk et al. |
| 8,475,454 | B1 | 7/2013 | Alshemari |
| 8,475,474 | B2 | 7/2013 | Bombard et al. |
| 8,479,968 | B2 | 7/2013 | Hodgkinson et al. |
| 8,479,969 | B2 | 7/2013 | Shelton, IV |
| 8,480,703 | B2 | 7/2013 | Nicholas et al. |
| 8,483,509 | B2 | 7/2013 | Matsuzaka |
| 8,485,412 | B2 | 7/2013 | Shelton, IV et al. |
| 8,485,413 | B2 | 7/2013 | Scheib et al. |
| 8,485,970 | B2 | 7/2013 | Widenhouse et al. |
| 8,486,047 | B2 | 7/2013 | Stopek |
| 8,487,199 | B2 | 7/2013 | Palmer et al. |
| 8,487,487 | B2 | 7/2013 | Dietz et al. |
| 8,490,851 | B2 | 7/2013 | Blier et al. |
| 8,490,852 | B2 | 7/2013 | Viola |
| 8,490,853 | B2 | 7/2013 | Criscuolo et al. |
| 8,491,581 | B2 | 7/2013 | Deville et al. |
| 8,491,603 | B2 | 7/2013 | Yeung et al. |
| 8,496,153 | B2 | 7/2013 | Demmy et al. |
| 8,496,154 | B2 | 7/2013 | Marczyk et al. |
| 8,496,156 | B2 | 7/2013 | Sniffin et al. |
| 8,496,683 | B2 | 7/2013 | Prommersberger et al. |
| 8,498,691 | B2 | 7/2013 | Moll et al. |
| 8,499,673 | B2 | 8/2013 | Keller |
| 8,499,966 | B2 | 8/2013 | Palmer et al. |
| 8,499,992 | B2 | 8/2013 | Whitman et al. |
| 8,499,993 | B2 | 8/2013 | Shelton, IV et al. |
| 8,499,994 | B2 | 8/2013 | D'Arcangelo |
| 8,500,721 | B2 | 8/2013 | Jinno |
| 8,500,762 | B2 | 8/2013 | Sholev et al. |
| 8,502,091 | B2 | 8/2013 | Palmer et al. |
| 8,505,799 | B2 | 8/2013 | Viola et al. |
| 8,505,801 | B2 | 8/2013 | Ehrenfels et al. |
| 8,506,555 | B2 | 8/2013 | Ruiz Morales |
| 8,506,557 | B2 | 8/2013 | Zemlok et al. |
| 8,506,580 | B2 | 8/2013 | Zergiebel et al. |
| 8,506,581 | B2 | 8/2013 | Wingardner, III et al. |
| 8,511,308 | B2 | 8/2013 | Hecox et al. |
| 8,512,359 | B2 | 8/2013 | Whitman et al. |
| 8,512,402 | B2 | 8/2013 | Marczyk et al. |
| 8,517,239 | B2 | 8/2013 | Scheib et al. |
| 8,517,241 | B2 | 8/2013 | Nicholas et al. |
| 8,517,243 | B2 | 8/2013 | Giordano et al. |
| 8,517,244 | B2 | 8/2013 | Shelton, IV et al. |
| 8,517,938 | B2 | 8/2013 | Eisenhardt et al. |
| 8,518,024 | B2 | 8/2013 | Williams et al. |
| 8,521,273 | B2 | 8/2013 | Kliman |
| 8,523,042 | B2 | 9/2013 | Masiakos et al. |
| 8,523,043 | B2 | 9/2013 | Ullrich et al. |
| 8,523,787 | B2 | 9/2013 | Ludwin et al. |
| 8,523,881 | B2 | 9/2013 | Cabiri et al. |
| 8,523,882 | B2 | 9/2013 | Huitema et al. |
| 8,523,900 | B2 | 9/2013 | Jinno et al. |
| 8,529,588 | B2 | 9/2013 | Ahlberg et al. |
| 8,529,599 | B2 | 9/2013 | Holsten |
| 8,529,600 | B2 | 9/2013 | Woodard, Jr. et al. |
| 8,529,819 | B2 | 9/2013 | Ostapoff et al. |
| 8,531,153 | B2 | 9/2013 | Baarman et al. |
| 8,532,747 | B2 | 9/2013 | Nock et al. |
| 8,534,527 | B2 | 9/2013 | Brendel et al. |
| 8,534,528 | B2 | 9/2013 | Shelton, IV |
| 8,535,304 | B2 | 9/2013 | Sklar et al. |
| 8,535,340 | B2 | 9/2013 | Allen |
| 8,539,866 | B2 | 9/2013 | Nayak et al. |
| 8,540,128 | B2 | 9/2013 | Shelton, IV et al. |
| 8,540,129 | B2 | 9/2013 | Baxter, III et al. |
| 8,540,130 | B2 | 9/2013 | Moore et al. |
| 8,540,131 | B2 | 9/2013 | Swayze |
| 8,540,133 | B2 | 9/2013 | Bedi et al. |
| 8,540,646 | B2 | 9/2013 | Mendez-Coll |
| 8,540,733 | B2 | 9/2013 | Whitman et al. |
| 8,540,735 | B2 | 9/2013 | Mitelberg et al. |
| 8,550,984 | B2 | 10/2013 | Takemoto |
| 8,551,076 | B2 | 10/2013 | Duval et al. |
| 8,555,660 | B2 | 10/2013 | Takenaka et al. |
| 8,556,151 | B2 | 10/2013 | Viola |
| 8,556,918 | B2 | 10/2013 | Bauman et al. |
| 8,556,935 | B1 | 10/2013 | Knodel et al. |
| 8,560,147 | B2 | 10/2013 | Taylor et al. |
| 8,561,617 | B2 | 10/2013 | Lindh et al. |
| 8,561,870 | B2 | 10/2013 | Baxter, III et al. |
| 8,561,871 | B2 | 10/2013 | Rajappa et al. |
| 8,561,873 | B2 | 10/2013 | Ingmanson et al. |
| 8,562,592 | B2 | 10/2013 | Conlon et al. |
| 8,562,598 | B2 | 10/2013 | Falkenstein et al. |
| 8,567,656 | B2 | 10/2013 | Shelton, IV et al. |
| 8,568,416 | B2 | 10/2013 | Schmitz et al. |
| 8,568,425 | B2 | 10/2013 | Ross et al. |
| D692,916 | S | 11/2013 | Granchi et al. |
| 8,573,459 | B2 | 11/2013 | Smith et al. |
| 8,573,461 | B2 | 11/2013 | Shelton, IV et al. |
| 8,573,462 | B2 | 11/2013 | Smith et al. |
| 8,573,465 | B2 | 11/2013 | Shelton, IV |
| 8,574,199 | B2 | 11/2013 | Bulow et al. |
| 8,574,263 | B2 | 11/2013 | Mueller |
| 8,575,880 | B2 | 11/2013 | Grantz |
| 8,575,895 | B2 | 11/2013 | Garrastacho et al. |
| 8,579,176 | B2 | 11/2013 | Smith et al. |
| 8,579,178 | B2 | 11/2013 | Holsten et al. |
| 8,579,897 | B2 | 11/2013 | Vakharia et al. |
| 8,579,937 | B2 | 11/2013 | Gresham |
| 8,584,919 | B2 | 11/2013 | Hueil et al. |
| 8,584,920 | B2 | 11/2013 | Hodgkinson |

(56) References Cited

U.S. PATENT DOCUMENTS

| | | | |
|---|---|---|---|
| 8,584,921 | B2 | 11/2013 | Scirica |
| 8,585,583 | B2 | 11/2013 | Sakaguchi et al. |
| 8,585,598 | B2 | 11/2013 | Razzaque et al. |
| 8,585,721 | B2 | 11/2013 | Kirsch |
| 8,590,760 | B2 | 11/2013 | Cummins et al. |
| 8,590,762 | B2 | 11/2013 | Hess et al. |
| 8,590,764 | B2 | 11/2013 | Hartwick et al. |
| 8,591,400 | B2 | 11/2013 | Sugiyama |
| 8,596,515 | B2 | 12/2013 | Okoniewski |
| 8,597,745 | B2 | 12/2013 | Farnsworth et al. |
| 8,599,450 | B2 | 12/2013 | Kubo et al. |
| 8,602,125 | B2 | 12/2013 | King |
| 8,602,287 | B2 | 12/2013 | Yates et al. |
| 8,602,288 | B2 | 12/2013 | Shelton, IV et al. |
| 8,603,077 | B2 | 12/2013 | Cooper et al. |
| 8,603,089 | B2 | 12/2013 | Viola |
| 8,603,110 | B2 | 12/2013 | Maruyama et al. |
| 8,603,135 | B2 | 12/2013 | Mueller |
| 8,608,043 | B2 | 12/2013 | Scirica |
| 8,608,044 | B2 | 12/2013 | Hueil et al. |
| 8,608,045 | B2 | 12/2013 | Smith et al. |
| 8,608,046 | B2 | 12/2013 | Laurent et al. |
| 8,608,745 | B2 | 12/2013 | Guzman et al. |
| 8,613,383 | B2 | 12/2013 | Beckman et al. |
| 8,613,384 | B2 | 12/2013 | Pastorelli et al. |
| 8,616,427 | B2 | 12/2013 | Viola |
| 8,616,431 | B2 | 12/2013 | Timm et al. |
| 8,617,155 | B2 | 12/2013 | Johnson et al. |
| 8,620,473 | B2 | 12/2013 | Diolaiti et al. |
| 8,622,274 | B2 | 1/2014 | Yates et al. |
| 8,622,275 | B2 | 1/2014 | Baxter, III et al. |
| 8,627,993 | B2 | 1/2014 | Smith et al. |
| 8,627,994 | B2 | 1/2014 | Zemlok et al. |
| 8,627,995 | B2 | 1/2014 | Smith et al. |
| 8,628,467 | B2 | 1/2014 | Whitman et al. |
| 8,628,518 | B2 | 1/2014 | Blumenkranz et al. |
| 8,628,544 | B2 | 1/2014 | Farascioni |
| 8,628,545 | B2 | 1/2014 | Cabrera et al. |
| 8,631,987 | B2 | 1/2014 | Shelton, IV et al. |
| 8,631,992 | B1 | 1/2014 | Hausen et al. |
| 8,631,993 | B2 | 1/2014 | Kostrzewski |
| 8,632,462 | B2 | 1/2014 | Yoo et al. |
| 8,632,525 | B2 | 1/2014 | Kerr et al. |
| 8,632,535 | B2 | 1/2014 | Shelton, IV et al. |
| 8,632,539 | B2 | 1/2014 | Twomey et al. |
| 8,632,563 | B2 | 1/2014 | Nagase et al. |
| 8,636,187 | B2 | 1/2014 | Hueil et al. |
| 8,636,190 | B2 | 1/2014 | Zemlok et al. |
| 8,636,191 | B2 | 1/2014 | Meagher |
| 8,636,193 | B2 | 1/2014 | Whitman et al. |
| 8,636,736 | B2 | 1/2014 | Yates et al. |
| 8,636,766 | B2 | 1/2014 | Milliman et al. |
| 8,639,936 | B2 | 1/2014 | Hu et al. |
| 8,640,788 | B2 | 2/2014 | Dachs, II et al. |
| 8,646,674 | B2 | 2/2014 | Schulte et al. |
| 8,647,258 | B2 | 2/2014 | Aranyi et al. |
| 8,652,120 | B2 | 2/2014 | Giordano et al. |
| 8,652,151 | B2 | 2/2014 | Lehman et al. |
| 8,652,155 | B2 | 2/2014 | Houser et al. |
| 8,656,929 | B2 | 2/2014 | Miller et al. |
| 8,657,174 | B2 | 2/2014 | Yates et al. |
| 8,657,175 | B2 | 2/2014 | Sonnenschein et al. |
| 8,657,176 | B2 | 2/2014 | Shelton, IV et al. |
| 8,657,177 | B2 | 2/2014 | Scirica et al. |
| 8,657,178 | B2 | 2/2014 | Hueil et al. |
| 8,657,482 | B2 | 2/2014 | Malackowski et al. |
| 8,657,808 | B2 | 2/2014 | McPherson et al. |
| 8,657,814 | B2 | 2/2014 | Werneth et al. |
| 8,657,821 | B2 | 2/2014 | Palermo |
| D701,238 | S | 3/2014 | Lai et al. |
| 8,662,370 | B2 | 3/2014 | Takei |
| 8,663,106 | B2 | 3/2014 | Stivoric et al. |
| 8,663,192 | B2 | 3/2014 | Hester et al. |
| 8,663,245 | B2 | 3/2014 | Francischelli et al. |
| 8,663,262 | B2 | 3/2014 | Smith et al. |
| 8,663,270 | B2 | 3/2014 | Donnigan et al. |
| 8,664,792 | B2 | 3/2014 | Rebsdorf |
| 8,668,129 | B2 | 3/2014 | Olson |
| 8,668,130 | B2 | 3/2014 | Hess et al. |
| 8,672,206 | B2 | 3/2014 | Aranyi et al. |
| 8,672,207 | B2 | 3/2014 | Shelton, IV et al. |
| 8,672,208 | B2 | 3/2014 | Hess et al. |
| 8,672,209 | B2 | 3/2014 | Crainich |
| 8,672,922 | B2 | 3/2014 | Loh et al. |
| 8,672,935 | B2 | 3/2014 | Okada et al. |
| 8,672,951 | B2 | 3/2014 | Smith et al. |
| 8,673,210 | B2 | 3/2014 | Deshays |
| 8,675,820 | B2 | 3/2014 | Baic et al. |
| 8,678,263 | B2 | 3/2014 | Viola |
| 8,678,994 | B2 | 3/2014 | Sonnenschein et al. |
| 8,679,093 | B2 | 3/2014 | Farra |
| 8,679,098 | B2 | 3/2014 | Hart |
| 8,679,137 | B2 | 3/2014 | Bauman et al. |
| 8,679,154 | B2 | 3/2014 | Smith et al. |
| 8,679,156 | B2 | 3/2014 | Smith et al. |
| 8,679,454 | B2 | 3/2014 | Guire et al. |
| 8,684,248 | B2 | 4/2014 | Milliman |
| 8,684,249 | B2 | 4/2014 | Racenet et al. |
| 8,684,250 | B2 | 4/2014 | Bettuchi et al. |
| 8,684,253 | B2 | 4/2014 | Giordano et al. |
| 8,684,962 | B2 | 4/2014 | Kirschenman et al. |
| 8,685,004 | B2 | 4/2014 | Zemlock et al. |
| 8,685,020 | B2 | 4/2014 | Weizman et al. |
| 8,690,893 | B2 | 4/2014 | Deitch et al. |
| 8,695,866 | B2 | 4/2014 | Leimbach et al. |
| 8,696,665 | B2 | 4/2014 | Hunt et al. |
| 8,701,958 | B2 | 4/2014 | Shelton, IV et al. |
| 8,701,959 | B2 | 4/2014 | Shah |
| 8,706,316 | B1 | 4/2014 | Hoevenaar |
| 8,708,210 | B2 | 4/2014 | Zemlok et al. |
| 8,708,211 | B2 | 4/2014 | Zemlok et al. |
| 8,708,212 | B2 | 4/2014 | Williams |
| 8,708,213 | B2 | 4/2014 | Shelton, IV et al. |
| 8,709,012 | B2 | 4/2014 | Muller |
| 8,714,352 | B2 | 5/2014 | Farascioni et al. |
| 8,714,429 | B2 | 5/2014 | Demmy |
| 8,714,430 | B2 | 5/2014 | Natarajan et al. |
| 8,715,256 | B2 | 5/2014 | Greener |
| 8,715,302 | B2 | 5/2014 | Ibrahim et al. |
| 8,720,766 | B2 | 5/2014 | Hess et al. |
| 8,721,630 | B2 | 5/2014 | Ortiz et al. |
| 8,721,666 | B2 | 5/2014 | Schroeder et al. |
| 8,727,197 | B2 | 5/2014 | Hess et al. |
| 8,727,199 | B2 | 5/2014 | Wenchell |
| 8,727,200 | B2 | 5/2014 | Roy |
| 8,727,961 | B2 | 5/2014 | Ziv |
| 8,728,099 | B2 | 5/2014 | Cohn et al. |
| 8,728,119 | B2 | 5/2014 | Cummins |
| 8,733,470 | B2 | 5/2014 | Matthias et al. |
| 8,733,611 | B2 | 5/2014 | Milliman |
| 8,733,612 | B2 | 5/2014 | Ma |
| 8,733,613 | B2 | 5/2014 | Huitema et al. |
| 8,733,614 | B2 | 5/2014 | Ross et al. |
| 8,734,336 | B2 | 5/2014 | Bonadio et al. |
| 8,734,359 | B2 | 5/2014 | Ibanez et al. |
| 8,734,478 | B2 | 5/2014 | Widenhouse et al. |
| 8,734,831 | B2 | 5/2014 | Kim et al. |
| 8,739,033 | B2 | 5/2014 | Rosenberg |
| 8,739,417 | B2 | 6/2014 | Tokunaga et al. |
| 8,740,034 | B2 | 6/2014 | Morgan et al. |
| 8,740,037 | B2 | 6/2014 | Shelton, IV et al. |
| 8,740,038 | B2 | 6/2014 | Shelton, IV et al. |
| 8,740,987 | B2 | 6/2014 | Geremakis et al. |
| 8,746,529 | B2 | 6/2014 | Shelton, IV et al. |
| 8,746,530 | B2 | 6/2014 | Giordano et al. |
| 8,746,533 | B2 | 6/2014 | Whitman et al. |
| 8,746,535 | B2 | 6/2014 | Shelton, IV et al. |
| 8,747,238 | B2 | 6/2014 | Shelton, IV et al. |
| 8,747,441 | B2 | 6/2014 | Konieczynski et al. |
| 8,752,264 | B2 | 6/2014 | Ackley et al. |
| 8,752,699 | B2 | 6/2014 | Morgan et al. |
| 8,752,747 | B2 | 6/2014 | Shelton, IV et al. |
| 8,752,748 | B2 | 6/2014 | Whitman et al. |
| 8,752,749 | B2 | 6/2014 | Moore et al. |

(56) References Cited

U.S. PATENT DOCUMENTS 8,753,664 B2 6/2014 Dao et al.
8,757,287 B2 6/2014 Mak et al.
8,757,465 B2 6/2014 Woodard, Jr. et al.
8,758,235 B2 6/2014 Jaworek
8,758,366 B2 6/2014 McLean et al.
8,758,391 B2 6/2014 Swayze et al.
8,758,438 B2 6/2014 Boyce et al.
8,763,875 B2 7/2014 Morgan et al.
8,763,876 B2 7/2014 Kostrzewski
8,763,877 B2 7/2014 Schall et al.
8,763,879 B2 7/2014 Shelton, IV et al.
8,764,732 B2 7/2014 Hartwell
8,765,942 B2 7/2014 Feraud et al.
8,770,458 B2 7/2014 Scirica
8,770,459 B2 7/2014 Racenet et al.
8,770,460 B2 7/2014 Belzer
8,771,169 B2 7/2014 Whitman et al.
8,771,260 B2 7/2014 Conlon et al.
8,777,004 B2 7/2014 Shelton, IV et al.
8,777,082 B2 7/2014 Scirica
8,777,083 B2 7/2014 Racenet et al.
8,777,898 B2 7/2014 Suon et al.
8,783,541 B2 7/2014 Shelton, IV et al.
8,783,542 B2 7/2014 Riestenberg et al.
8,783,543 B2 7/2014 Shelton, IV et al.
8,784,304 B2 7/2014 Mikkaichi et al.
8,784,404 B2 7/2014 Doyle et al.
8,784,415 B2 7/2014 Malackowski et al.
8,789,737 B2 7/2014 Hodgkinson et al.
8,789,739 B2 7/2014 Swensgard
8,789,740 B2 7/2014 Baxter, III et al.
8,789,741 B2 7/2014 Baxter, III et al.
8,790,658 B2 7/2014 Cigarini et al.
8,790,684 B2 7/2014 Dave et al.
D711,905 S 8/2014 Morrison et al.
8,794,496 B2 8/2014 Scirica
8,794,497 B2 8/2014 Zingman
8,795,159 B2 8/2014 Moriyama
8,795,276 B2 8/2014 Dietz et al.
8,795,308 B2 8/2014 Valin
8,795,324 B2 8/2014 Kawai et al.
8,796,995 B2 8/2014 Cunanan et al.
8,800,681 B2 8/2014 Rousson et al.
8,800,837 B2 8/2014 Zemlok
8,800,838 B2 8/2014 Shelton, IV
8,800,839 B2 8/2014 Beetel
8,800,840 B2 8/2014 Jankowski
8,800,841 B2 8/2014 Ellerhorst et al.
8,801,710 B2 8/2014 Ullrich et al.
8,801,734 B2 8/2014 Shelton, IV et al.
8,801,735 B2 8/2014 Shelton, IV et al.
8,801,752 B2 8/2014 Fortier et al.
8,801,801 B2 8/2014 Datta et al.
8,806,973 B2 8/2014 Ross et al.
8,807,414 B2 8/2014 Ross et al.
8,808,161 B2 8/2014 Gregg et al.
8,808,164 B2 8/2014 Hoffman et al.
8,808,274 B2 8/2014 Hartwell
8,808,294 B2 8/2014 Fox et al.
8,808,308 B2 8/2014 Boukhny et al.
8,808,311 B2 8/2014 Heinrich et al.
8,808,325 B2 8/2014 Hess et al.
8,810,197 B2 8/2014 Juergens
8,811,017 B2 8/2014 Fujii et al.
8,813,866 B2 8/2014 Suzuki
8,814,024 B2 8/2014 Woodard, Jr. et al.
8,814,025 B2 8/2014 Miller et al.
8,814,836 B2 8/2014 Ignon et al.
8,815,594 B2 8/2014 Harris et al.
8,818,523 B2 8/2014 Olson et al.
8,820,603 B2 9/2014 Shelton, IV et al.
8,820,605 B2 9/2014 Shelton, IV
8,820,606 B2 9/2014 Hodgkinson
8,820,607 B2 9/2014 Marczyk
8,820,608 B2 9/2014 Miyamoto
8,821,514 B2 9/2014 Aranyi
8,822,934 B2 9/2014 Sayeh et al.
8,825,164 B2 9/2014 Tweden et al.
8,827,133 B2 9/2014 Shelton, IV et al.
8,827,134 B2 9/2014 Viola et al.
8,827,903 B2 9/2014 Shelton, IV et al.
8,828,046 B2 9/2014 Stefanchik et al.
8,831,779 B2 9/2014 Ortmaier et al.
8,833,219 B2 9/2014 Pierce
8,833,630 B2 9/2014 Milliman
8,833,632 B2 9/2014 Swensgard
8,834,353 B2 9/2014 Dejima et al.
8,834,465 B2 9/2014 Ramstein et al.
8,834,498 B2 9/2014 Byrum et al.
8,834,518 B2 9/2014 Faller et al.
8,840,003 B2 9/2014 Morgan et al.
8,840,004 B2 9/2014 Holsten et al.
8,840,603 B2 9/2014 Shelton, IV et al.
8,840,609 B2 9/2014 Stuebe
8,840,876 B2 9/2014 Eemeta et al.
8,844,789 B2 9/2014 Shelton, IV et al.
8,844,790 B2 9/2014 Demmy et al.
8,845,622 B2 9/2014 Paik et al.
8,851,215 B2 10/2014 Goto
8,851,354 B2 10/2014 Swensgard et al.
8,851,355 B2 10/2014 Aranyi et al.
8,852,174 B2 10/2014 Burbank
8,852,185 B2 10/2014 Twomey
8,852,199 B2 10/2014 Deslauriers et al.
8,852,218 B2 10/2014 Hughett, Sr. et al.
8,855,822 B2 10/2014 Bartol et al.
8,857,693 B2 10/2014 Schuckmann et al.
8,857,694 B2 10/2014 Shelton, IV et al.
8,858,538 B2 10/2014 Belson et al.
8,858,547 B2 10/2014 Brogna
8,858,571 B2 10/2014 Shelton, IV et al.
8,858,590 B2 10/2014 Shelton, IV et al.
8,864,007 B2 10/2014 Widenhouse et al.
8,864,009 B2 10/2014 Shelton, IV et al.
8,864,010 B2 10/2014 Williams
8,864,750 B2 10/2014 Ross et al.
8,869,912 B2 10/2014 Ro et al.
8,869,913 B2 10/2014 Matthias et al.
8,870,049 B2 10/2014 Amid et al.
8,870,050 B2 10/2014 Hodgkinson
8,870,867 B2 10/2014 Walberg et al.
8,870,912 B2 10/2014 Brisson et al.
8,871,829 B2 10/2014 Gerold et al.
8,875,971 B2 11/2014 Hall et al.
8,875,972 B2 11/2014 Weisenburgh, II et al.
8,876,698 B2 11/2014 Sakamoto et al.
8,876,857 B2 11/2014 Burbank
8,876,858 B2 11/2014 Braun
8,882,660 B2 11/2014 Phee et al.
8,882,792 B2 11/2014 Dietz et al.
8,884,560 B2 11/2014 Ito
8,887,979 B2 11/2014 Mastri et al.
8,888,688 B2 11/2014 Julian et al.
8,888,695 B2 11/2014 Piskun et al.
8,888,792 B2 11/2014 Harris et al.
8,888,809 B2 11/2014 Davison et al.
8,893,946 B2 11/2014 Boudreaux et al.
8,893,949 B2 11/2014 Shelton, IV et al.
8,894,647 B2 11/2014 Beardsley et al.
8,894,654 B2 11/2014 Anderson
8,899,460 B2 12/2014 Wojcicki
8,899,461 B2 12/2014 Farascioni
8,899,462 B2 12/2014 Kostrzewski et al.
8,899,463 B2 12/2014 Schall et al.
8,899,464 B2 12/2014 Hueil et al.
8,899,465 B2 12/2014 Shelton, IV et al.
8,899,466 B2 12/2014 Baxter, III et al.
8,900,267 B2 12/2014 Woolfson et al.
8,905,287 B2 12/2014 Racenet et al.
8,905,977 B2 12/2014 Shelton et al.
8,910,846 B2 12/2014 Viola
8,910,847 B2 12/2014 Nalagatla et al.
8,911,426 B2 12/2014 Coppeta et al.
8,911,448 B2 12/2014 Stein

(56) References Cited

U.S. PATENT DOCUMENTS

| | | | |
|---|---|---|---|
| 8,911,460 | B2 | 12/2014 | Neurohr et al. |
| 8,911,471 | B2 | 12/2014 | Spivey et al. |
| 8,912,746 | B2 | 12/2014 | Reid et al. |
| 8,915,842 | B2 | 12/2014 | Weisenburgh et al. |
| 8,920,368 | B2 | 12/2014 | Sandhu et al. |
| 8,920,433 | B2 | 12/2014 | Barrier et al. |
| 8,920,435 | B2 | 12/2014 | Smith et al. |
| 8,920,438 | B2 | 12/2014 | Aranyi et al. |
| 8,920,443 | B2 | 12/2014 | Hiles et al. |
| 8,920,444 | B2 | 12/2014 | Hiles et al. |
| 8,922,163 | B2 | 12/2014 | Macdonald |
| 8,925,782 | B2 | 1/2015 | Shelton, IV |
| 8,925,783 | B2 | 1/2015 | Zemlok et al. |
| 8,925,788 | B2 | 1/2015 | Hess et al. |
| 8,926,506 | B2 | 1/2015 | Widenhouse et al. |
| 8,926,598 | B2 | 1/2015 | Mollere et al. |
| 8,931,576 | B2 | 1/2015 | Iwata |
| 8,931,679 | B2 | 1/2015 | Kostrzewski |
| 8,931,680 | B2 | 1/2015 | Milliman |
| 8,931,682 | B2 | 1/2015 | Timm et al. |
| 8,931,692 | B2 | 1/2015 | Sancak |
| 8,936,614 | B2 | 1/2015 | Allen, IV |
| 8,937,408 | B2 | 1/2015 | Ganem et al. |
| 8,939,343 | B2 | 1/2015 | Milliman et al. |
| 8,939,344 | B2 | 1/2015 | Olson et al. |
| 8,939,898 | B2 | 1/2015 | Omoto |
| 8,944,069 | B2 | 2/2015 | Miller et al. |
| 8,945,095 | B2 | 2/2015 | Blumenkranz et al. |
| 8,945,098 | B2 | 2/2015 | Seibold et al. |
| 8,945,163 | B2 | 2/2015 | Voegele et al. |
| 8,955,732 | B2 | 2/2015 | Zemlok et al. |
| 8,956,342 | B1 | 2/2015 | Russo et al. |
| 8,956,390 | B2 | 2/2015 | Shah et al. |
| 8,958,860 | B2 | 2/2015 | Banerjee et al. |
| 8,960,519 | B2 | 2/2015 | Whitman et al. |
| 8,960,520 | B2 | 2/2015 | McCuen |
| 8,960,521 | B2 | 2/2015 | Kostrzewski |
| 8,961,191 | B2 | 2/2015 | Hanshew |
| 8,961,504 | B2 | 2/2015 | Hoarau et al. |
| 8,961,542 | B2 | 2/2015 | Whitfield et al. |
| 8,963,714 | B2 | 2/2015 | Medhal et al. |
| D725,674 | S | 3/2015 | Jung et al. |
| 8,967,443 | B2 | 3/2015 | McCuen |
| 8,967,444 | B2 | 3/2015 | Beetel |
| 8,967,446 | B2 | 3/2015 | Beardsley et al. |
| 8,967,448 | B2 | 3/2015 | Carter et al. |
| 8,968,276 | B2 | 3/2015 | Zemlok et al. |
| 8,968,308 | B2 | 3/2015 | Horner et al. |
| 8,968,312 | B2 | 3/2015 | Marczyk et al. |
| 8,968,337 | B2 | 3/2015 | Whitfield et al. |
| 8,968,340 | B2 | 3/2015 | Chowaniec et al. |
| 8,968,355 | B2 | 3/2015 | Malkowski et al. |
| 8,968,358 | B2 | 3/2015 | Reschke |
| 8,970,507 | B2 | 3/2015 | Holbein et al. |
| 8,973,803 | B2 | 3/2015 | Hall et al. |
| 8,973,804 | B2 | 3/2015 | Hess et al. |
| 8,973,805 | B2 | 3/2015 | Scirica et al. |
| 8,974,440 | B2 | 3/2015 | Farritor et al. |
| 8,974,542 | B2 | 3/2015 | Fujimoto et al. |
| 8,974,932 | B2 | 3/2015 | McGahan et al. |
| 8,978,954 | B2 | 3/2015 | Shelton, IV et al. |
| 8,978,955 | B2 | 3/2015 | Aronhalt et al. |
| 8,978,956 | B2 | 3/2015 | Schall et al. |
| 8,979,843 | B2 | 3/2015 | Timm et al. |
| 8,979,890 | B2 | 3/2015 | Boudreaux |
| 8,982,195 | B2 | 3/2015 | Claus et al. |
| 8,984,711 | B2 | 3/2015 | Ota et al. |
| 8,985,240 | B2 | 3/2015 | Winnard |
| 8,985,429 | B2 | 3/2015 | Balek et al. |
| 8,986,302 | B2 | 3/2015 | Aldridge et al. |
| 8,989,903 | B2 | 3/2015 | Weir et al. |
| 8,991,676 | B2 | 3/2015 | Hess et al. |
| 8,991,677 | B2 | 3/2015 | Moore et al. |
| 8,991,678 | B2 | 3/2015 | Wellman et al. |
| 8,992,042 | B2 | 3/2015 | Eichenholz |
| 8,992,422 | B2 | 3/2015 | Spivey et al. |
| 8,992,565 | B2 | 3/2015 | Brisson et al. |
| 8,996,165 | B2 | 3/2015 | Wang et al. |
| 8,998,058 | B2 | 4/2015 | Moore et al. |
| 8,998,059 | B2 | 4/2015 | Smith et al. |
| 8,998,060 | B2 | 4/2015 | Bruewer et al. |
| 8,998,061 | B2 | 4/2015 | Williams et al. |
| 8,998,939 | B2 | 4/2015 | Price et al. |
| 9,000,720 | B2 | 4/2015 | Stulen et al. |
| 9,002,518 | B2 | 4/2015 | Manzo et al. |
| 9,004,339 | B1 | 4/2015 | Park |
| 9,004,799 | B1 | 4/2015 | Tibbits |
| 9,005,230 | B2 | 4/2015 | Yates et al. |
| 9,005,238 | B2 | 4/2015 | DeSantis et al. |
| 9,005,243 | B2 | 4/2015 | Stopek et al. |
| 9,010,606 | B2 | 4/2015 | Aranyi et al. |
| 9,010,608 | B2 | 4/2015 | Casasanta, Jr. et al. |
| 9,010,611 | B2 | 4/2015 | Ross et al. |
| 9,011,437 | B2 | 4/2015 | Woodruff et al. |
| 9,011,439 | B2 | 4/2015 | Shalaby et al. |
| 9,011,471 | B2 | 4/2015 | Timm et al. |
| 9,014,856 | B2 | 4/2015 | Manzo et al. |
| 9,016,539 | B2 | 4/2015 | Kostrzewski et al. |
| 9,016,540 | B2 | 4/2015 | Whitman et al. |
| 9,016,541 | B2 | 4/2015 | Viola et al. |
| 9,016,542 | B2 | 4/2015 | Shelton, IV et al. |
| 9,016,545 | B2 | 4/2015 | Aranyi et al. |
| 9,017,331 | B2 | 4/2015 | Fox |
| 9,017,355 | B2 | 4/2015 | Smith et al. |
| 9,017,369 | B2 | 4/2015 | Renger et al. |
| 9,017,371 | B2 | 4/2015 | Whitman et al. |
| 9,017,849 | B2 | 4/2015 | Stulen et al. |
| 9,017,851 | B2 | 4/2015 | Felder et al. |
| D729,274 | S | 5/2015 | Clement et al. |
| 9,021,684 | B2 | 5/2015 | Lenker et al. |
| 9,023,014 | B2 | 5/2015 | Chowaniec et al. |
| 9,023,069 | B2 | 5/2015 | Kasvikis et al. |
| 9,023,071 | B2 | 5/2015 | Miller et al. |
| 9,026,347 | B2 | 5/2015 | Gadh et al. |
| 9,027,817 | B2 | 5/2015 | Milliman et al. |
| 9,028,468 | B2 | 5/2015 | Scarfogliero et al. |
| 9,028,494 | B2 | 5/2015 | Shelton, IV et al. |
| 9,028,495 | B2 | 5/2015 | Mueller et al. |
| 9,028,510 | B2 | 5/2015 | Miyamoto et al. |
| 9,028,511 | B2 | 5/2015 | Weller et al. |
| 9,028,519 | B2 | 5/2015 | Yates et al. |
| 9,028,529 | B2 | 5/2015 | Fox et al. |
| 9,030,166 | B2 | 5/2015 | Kano |
| 9,030,169 | B2 | 5/2015 | Christensen et al. |
| 9,033,203 | B2 | 5/2015 | Woodard, Jr. et al. |
| 9,033,204 | B2 | 5/2015 | Shelton, IV et al. |
| 9,034,505 | B2 | 5/2015 | Detry et al. |
| 9,038,881 | B1 | 5/2015 | Schaller et al. |
| 9,039,690 | B2 | 5/2015 | Kersten et al. |
| 9,039,694 | B2 | 5/2015 | Ross et al. |
| 9,039,720 | B2 | 5/2015 | Madan |
| 9,039,736 | B2 | 5/2015 | Scirica et al. |
| 9,040,062 | B2 | 5/2015 | Maeda et al. |
| 9,043,027 | B2 | 5/2015 | Durant et al. |
| 9,044,227 | B2 | 6/2015 | Shelton, IV et al. |
| 9,044,228 | B2 | 6/2015 | Woodard, Jr. et al. |
| 9,044,229 | B2 | 6/2015 | Scheib et al. |
| 9,044,230 | B2 | 6/2015 | Morgan et al. |
| 9,044,238 | B2 | 6/2015 | Orszulak |
| 9,044,241 | B2 | 6/2015 | Barner et al. |
| 9,044,261 | B2 | 6/2015 | Houser |
| 9,044,281 | B2 | 6/2015 | Pool et al. |
| 9,050,083 | B2 | 6/2015 | Yates et al. |
| 9,050,084 | B2 | 6/2015 | Schmid et al. |
| 9,050,089 | B2 | 6/2015 | Orszulak |
| 9,050,100 | B2 | 6/2015 | Yates et al. |
| 9,050,120 | B2 | 6/2015 | Swarup et al. |
| 9,050,123 | B2 | 6/2015 | Krause et al. |
| 9,050,176 | B2 | 6/2015 | Datta et al. |
| 9,050,192 | B2 | 6/2015 | Mansmann |
| 9,055,941 | B2 | 6/2015 | Schmid et al. |
| 9,055,942 | B2 | 6/2015 | Balbierz et al. |
| 9,055,943 | B2 | 6/2015 | Zemlok et al. |
| 9,055,944 | B2 | 6/2015 | Hodgkinson et al. |

(56) References Cited

U.S. PATENT DOCUMENTS 9,055,961 B2 6/2015 Manzo et al.
9,060,770 B2 6/2015 Shelton, IV et al.
9,060,776 B2 6/2015 Yates et al.
9,060,794 B2 6/2015 Kang et al.
9,060,894 B2 6/2015 Wubbeling
9,061,392 B2 6/2015 Forgues et al.
9,070,068 B2 6/2015 Coveley et al.
9,072,515 B2 7/2015 Hall et al.
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,654 B2 7/2015 Whitman et al.
9,084,586 B2 7/2015 Hafner et al.
9,084,601 B2 7/2015 Moore et al.
9,084,602 B2 7/2015 Gleiman
9,086,875 B2 7/2015 Harrat et al.
9,089,326 B2 7/2015 Krumanaker et al.
9,089,330 B2 7/2015 Widenhouse et al.
9,089,338 B2 7/2015 Smith et al.
9,089,352 B2 7/2015 Jeong
9,089,360 B2 7/2015 Messerly et al.
9,091,588 B2 7/2015 Lefler
D736,792 S 8/2015 Brinda et al.
9,095,339 B2 8/2015 Moore et al.
9,095,346 B2 8/2015 Houser et al.
9,095,362 B2 8/2015 Dachs et al.
9,095,367 B2 8/2015 Olson et al.
9,095,642 B2 8/2015 Harder et al.
9,096,033 B2 8/2015 Holop et al.
9,098,153 B2 8/2015 Shen et al.
9,099,863 B2 8/2015 Smith et al.
9,099,877 B2 8/2015 Banos et al.
9,099,922 B2 8/2015 Toosky et al.
9,101,358 B2 8/2015 Kerr et al.
9,101,359 B2 8/2015 Smith et al.
9,101,385 B2 8/2015 Shelton, IV et al.
9,101,475 B2 8/2015 Wei et al.
9,101,621 B2 8/2015 Zeldis
9,107,663 B2 8/2015 Swensgard
9,107,667 B2 8/2015 Hodgkinson
9,107,690 B2 8/2015 Bales, Jr. et al.
9,110,587 B2 8/2015 Kim et al.
9,113,862 B2 8/2015 Morgan et al.
9,113,864 B2 8/2015 Morgan et al.
9,113,865 B2 8/2015 Shelton, IV et al.
9,113,866 B2 8/2015 Felder et al.
9,113,868 B2 8/2015 Felder et al.
9,113,873 B2 8/2015 Marczyk et al.
9,113,874 B2 8/2015 Shelton, IV et al.
9,113,875 B2 8/2015 Viola et al.
9,113,876 B2 8/2015 Zemlok et al.
9,113,879 B2 8/2015 Felder et al.
9,113,880 B2 8/2015 Zemlok et al.
9,113,881 B2 8/2015 Scirica
9,113,883 B2 8/2015 Aronhalt et al.
9,113,884 B2 8/2015 Shelton, IV et al.
9,113,887 B2 8/2015 Behnke, II et al.
9,119,615 B2 9/2015 Felder et al.
9,119,657 B2 9/2015 Shelton, IV et al.
9,119,898 B2 9/2015 Bayon et al.
9,119,957 B2 9/2015 Gantz et al.
9,123,286 B2 9/2015 Park
9,124,097 B2 9/2015 Cruz
9,125,651 B2 9/2015 Mandakolathur Vasudevan et al.
9,125,654 B2 9/2015 Aronhalt et al.
9,125,662 B2 9/2015 Shelton, IV
9,126,317 B2 9/2015 Lawton et al.
9,131,835 B2 9/2015 Widenhouse et al.
9,131,940 B2 9/2015 Huitema et al.
9,131,950 B2 9/2015 Matthew
9,131,957 B2 9/2015 Skarbnik et al.
9,138,225 B2 9/2015 Huang et al.
9,138,226 B2 9/2015 Racenet et al.
9,144,455 B2 9/2015 Kennedy et al.
D740,414 S 10/2015 Katsura
D741,882 S 10/2015 Shmilov et al.
9,149,274 B2 10/2015 Spivey et al.
9,149,324 B2 10/2015 Huang et al.
9,149,325 B2 10/2015 Worrell et al.
9,153,994 B2 10/2015 Wood et al.
9,154,189 B2 10/2015 Von Novak et al.
9,161,753 B2 10/2015 Prior
9,161,769 B2 10/2015 Stoddard et al.
9,161,803 B2 10/2015 Yates et al.
9,161,807 B2 10/2015 Garrison
9,161,855 B2 10/2015 Rousseau et al.
9,164,271 B2 10/2015 Ebata et al.
9,167,960 B2 10/2015 Yamaguchi et al.
9,168,038 B2 10/2015 Shelton, IV et al.
9,168,039 B1 10/2015 Knodel
9,168,042 B2 10/2015 Milliman
9,168,054 B2 10/2015 Turner et al.
9,168,144 B2 10/2015 Rivin et al.
9,171,244 B2 10/2015 Endou et al.
9,179,832 B2 11/2015 Diolaiti
9,179,911 B2 11/2015 Morgan et al.
9,179,912 B2 11/2015 Yates et al.
9,180,223 B2 11/2015 Yu et al.
9,182,244 B2 11/2015 Luke et al.
9,186,046 B2 11/2015 Ramamurthy et al.
9,186,137 B2 11/2015 Farascioni et al.
9,186,140 B2 11/2015 Hiles et al.
9,186,142 B2 11/2015 Fanelli et al.
9,186,143 B2 11/2015 Timm et al.
9,186,148 B2 11/2015 Felder et al.
9,186,221 B2 11/2015 Burbank
9,192,376 B2 11/2015 Almodovar
9,192,380 B2 11/2015 (Tarinelli) Racenet et al.
9,192,384 B2 11/2015 Bettuchi
9,192,430 B2 11/2015 Rachlin et al.
9,192,434 B2 11/2015 Twomey et al.
9,193,045 B2 11/2015 Saur et al.
9,197,079 B2 11/2015 Yip et al.
D744,528 S 12/2015 Agrawal
D746,459 S 12/2015 Kaercher et al.
9,198,642 B2 12/2015 Storz
9,198,644 B2 12/2015 Balek et al.
9,198,661 B2 12/2015 Swensgard
9,198,662 B2 12/2015 Barton et al.
9,198,683 B2 12/2015 Friedman et al.
9,204,830 B2 12/2015 Zand et al.
9,204,877 B2 12/2015 Whitman et al.
9,204,878 B2 12/2015 Hall et al.
9,204,879 B2 12/2015 Shelton, IV
9,204,880 B2 12/2015 Baxter, III et al.
9,204,881 B2 12/2015 Penna
9,204,923 B2 12/2015 Manzo et al.
9,204,924 B2 12/2015 Marczyk et al.
9,211,120 B2 12/2015 Scheib et al.
9,211,121 B2 12/2015 Hall et al.
9,211,122 B2 12/2015 Hagerty et al.
9,216,013 B2 12/2015 Scirica et al.
9,216,019 B2 12/2015 Schmid et al.
9,216,020 B2 12/2015 Zhang et al.
9,216,030 B2 12/2015 Fan et al.
9,216,062 B2 12/2015 Duque et al.
9,220,500 B2 12/2015 Swayze et al.
9,220,501 B2 12/2015 Baxter, III et al.
9,220,502 B2 12/2015 Zemlok et al.
9,220,504 B2 12/2015 Viola et al.
9,220,508 B2 12/2015 Dannaher
9,220,559 B2 12/2015 Worrell et al.
9,220,570 B2 12/2015 Kim et al.
D746,854 S 1/2016 Shardlow et al.
9,226,686 B2 1/2016 Blair
9,226,750 B2 1/2016 Weir et al.
9,226,751 B2 1/2016 Shelton, IV et al.
9,226,754 B2 1/2016 D'Agostino et al.
9,226,760 B2 1/2016 Shelton, IV
9,226,761 B2 1/2016 Burbank
9,226,767 B2 1/2016 Stulen et al.
9,226,799 B2 1/2016 Lightcap et al.
9,232,941 B2 1/2016 Mandakolathur Vasudevan et al.

(56) References Cited

U.S. PATENT DOCUMENTS 9,232,945 B2 1/2016 Zingman
9,232,979 B2 1/2016 Parihar et al.
9,233,610 B2 1/2016 Kim et al.
9,237,891 B2 1/2016 Shelton, IV
9,237,892 B2 1/2016 Hodgkinson
9,237,895 B2 1/2016 McCarthy et al.
9,237,900 B2 1/2016 Boudreaux et al.
9,237,921 B2 1/2016 Messerly et al.
9,239,064 B2 1/2016 Helbig et al.
9,240,740 B2 1/2016 Zeng et al.
9,241,711 B2 1/2016 Ivanko
9,241,712 B2 1/2016 Zemlok et al.
9,241,714 B2 1/2016 Timm et al.
9,241,716 B2 1/2016 Whitman
9,241,731 B2 1/2016 Boudreaux et al.
9,241,758 B2 1/2016 Franer et al.
9,244,524 B2 1/2016 Inoue et al.
D748,668 S 2/2016 Kim et al.
D749,128 S 2/2016 Perez et al.
D749,623 S 2/2016 Gray et al.
D750,122 S 2/2016 Shardlow et al.
D750,129 S 2/2016 Kwon
9,254,131 B2 2/2016 Soltz et al.
9,254,170 B2 2/2016 Parihar et al.
9,259,265 B2 2/2016 Harris et al.
9,259,268 B2 2/2016 Behnke, II et al.
9,259,274 B2 2/2016 Prisco
9,259,275 B2 2/2016 Burbank
9,261,172 B2 2/2016 Solomon et al.
9,265,500 B2 2/2016 Sorrentino et al.
9,265,510 B2 2/2016 Dietzel et al.
9,265,516 B2 2/2016 Casey et al.
9,265,585 B2 2/2016 Wingardner et al.
9,271,718 B2 3/2016 Milad et al.
9,271,727 B2 3/2016 McGuckin, Jr. et al.
9,271,753 B2 3/2016 Butler et al.
9,271,799 B2 3/2016 Shelton, IV et al.
9,272,406 B2 3/2016 Aronhalt et al.
9,274,095 B2 3/2016 Humayun et al.
9,277,919 B2 3/2016 Timmer et al.
9,277,922 B2 3/2016 Carter et al.
9,277,969 B2 3/2016 Brannan et al.
9,282,962 B2 3/2016 Schmid et al.
9,282,963 B2 3/2016 Bryant
9,282,966 B2 3/2016 Shelton, IV et al.
9,282,974 B2 3/2016 Shelton, IV
9,283,028 B2 3/2016 Johnson
9,283,045 B2 3/2016 Rhee et al.
9,283,054 B2 3/2016 Morgan et al.
9,283,334 B2 3/2016 Mantell et al.
9,289,206 B2 3/2016 Hess et al.
9,289,207 B2 3/2016 Shelton, IV
9,289,210 B2 3/2016 Baxter, III et al.
9,289,211 B2 3/2016 Williams et al.
9,289,212 B2 3/2016 Shelton, IV et al.
9,289,225 B2 3/2016 Shelton, IV et al.
9,289,256 B2 3/2016 Shelton, IV et al.
9,293,757 B2 3/2016 Toussaint et al.
9,295,464 B2 3/2016 Shelton, IV et al.
9,295,465 B2 3/2016 Farascioni
9,295,466 B2 3/2016 Hodgkinson et al.
9,295,467 B2 3/2016 Scirica
9,295,468 B2 3/2016 Heinrich et al.
9,295,514 B2 3/2016 Shelton, IV et al.
9,295,522 B2 3/2016 Kostrzewski
9,295,565 B2 3/2016 McLean
9,295,784 B2 3/2016 Eggert et al.
D753,167 S 4/2016 Yu et al.
9,301,691 B2 4/2016 Hufnagel et al.
9,301,752 B2 4/2016 Mandakolathur Vasudevan et al.
9,301,753 B2 4/2016 Aldridge et al.
9,301,755 B2 4/2016 Shelton, IV et al.
9,301,759 B2 4/2016 Spivey et al.
9,301,811 B2 4/2016 Goldberg et al.
9,307,965 B2 4/2016 Ming et al.
9,307,986 B2 4/2016 Hall et al.
9,307,987 B2 4/2016 Swensgard et al.
9,307,988 B2 4/2016 Shelton, IV
9,307,989 B2 4/2016 Shelton, IV et al.
9,307,994 B2 4/2016 Gresham et al.
9,308,009 B2 4/2016 Madan et al.
9,308,011 B2 4/2016 Chao et al.
9,308,646 B2 4/2016 Lim et al.
9,313,915 B2 4/2016 Niu et al.
9,314,246 B2 4/2016 Shelton, IV et al.
9,314,247 B2 4/2016 Shelton, IV et al.
9,314,261 B2 4/2016 Bales, Jr. et al.
9,314,291 B2 4/2016 Schall et al.
9,314,339 B2 4/2016 Mansmann
9,314,908 B2 4/2016 Tanimoto et al.
9,320,518 B2 4/2016 Henderson et al.
9,320,520 B2 4/2016 Shelton, IV et al.
9,320,521 B2 4/2016 Shelton, IV et al.
9,320,523 B2 4/2016 Shelton, IV et al.
9,325,516 B2 4/2016 Pera et al.
D755,196 S 5/2016 Meyers et al.
D756,373 S 5/2016 Raskin et al.
D756,377 S 5/2016 Connolly et al.
D757,028 S 5/2016 Goldenberg et al.
9,326,767 B2 5/2016 Koch et al.
9,326,768 B2 5/2016 Shelton, IV
9,326,769 B2 5/2016 Shelton, IV et al.
9,326,770 B2 5/2016 Shelton, IV et al.
9,326,771 B2 5/2016 Baxter, III et al.
9,326,788 B2 5/2016 Batross et al.
9,326,812 B2 5/2016 Waaler et al.
9,326,824 B2 5/2016 Inoue et al.
9,327,061 B2 5/2016 Govil et al.
9,331,721 B2 5/2016 Martinez Nuevo et al.
9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,040 B2 5/2016 Shellenberger et al.
9,333,082 B2 5/2016 Wei et al.
9,337,668 B2 5/2016 Yip
9,339,226 B2 5/2016 Van Der Walt et al.
9,339,342 B2 5/2016 Prisco et al.
9,345,477 B2 5/2016 Anim et al.
9,345,479 B2 5/2016 (Tarinelli) Racenet et al.
9,345,480 B2 5/2016 Hessler et al.
9,345,481 B2 5/2016 Hall et al.
9,345,503 B2 5/2016 Ishida et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
9,352,071 B2 5/2016 Landgrebe et al.
D758,433 S 6/2016 Lee et al.
D759,063 S 6/2016 Chen
9,358,003 B2 6/2016 Hall et al.
9,358,004 B2 6/2016 Sniffin et al.
9,358,005 B2 6/2016 Shelton, IV et al.
9,358,015 B2 6/2016 Sorrentino et al.
9,358,031 B2 6/2016 Manzo
9,358,065 B2 6/2016 Ladtkow et al.
9,364,217 B2 6/2016 Kostrzewski et al.
9,364,219 B2 6/2016 Olson et al.
9,364,220 B2 6/2016 Williams
9,364,223 B2 6/2016 Scirica
9,364,226 B2 6/2016 Zemlok et al.
9,364,228 B2 6/2016 Straehnz et al.
9,364,229 B2 6/2016 D'Agostino et al.
9,364,230 B2 6/2016 Shelton, IV et al.
9,364,231 B2 6/2016 Wenchell
9,364,233 B2 6/2016 Alexander, III et al.
9,364,279 B2 6/2016 Houser et al.
9,368,991 B2 6/2016 Qahouq
9,370,341 B2 6/2016 Ceniccola et al.
9,370,358 B2 6/2016 Shelton, IV et al.
9,370,361 B2 6/2016 Viola et al.
9,370,362 B2 6/2016 Petty et al.

(56) References Cited

U.S. PATENT DOCUMENTS 9,370,364 B2 6/2016 Smith et al.
9,370,400 B2 6/2016 Parihar
9,375,206 B2 6/2016 Vidal et al.
9,375,218 B2 6/2016 Wheeler et al.
9,375,230 B2 6/2016 Ross et al.
9,375,232 B2 6/2016 Hunt et al.
9,375,255 B2 6/2016 Houser et al.
D761,309 S 7/2016 Lee et al.
9,381,058 B2 7/2016 Houser et al.
9,383,881 B2 7/2016 Day et al.
9,385,640 B2 7/2016 Sun et al.
9,386,983 B2 7/2016 Swensgard et al.
9,386,984 B2 7/2016 Aronhalt et al.
9,386,985 B2 7/2016 Koch, Jr. et al.
9,386,988 B2 7/2016 Baxter, III et al.
9,387,003 B2 7/2016 Kaercher et al.
9,392,885 B2 7/2016 Vogler et al.
9,393,015 B2 7/2016 Laurent et al.
9,393,017 B2 7/2016 Flanagan et al.
9,393,018 B2 7/2016 Wang et al.
9,393,354 B2 7/2016 Freedman et al.
9,396,369 B1 7/2016 Whitehurst et al.
9,396,669 B2 7/2016 Karkanias et al.
9,398,905 B2 7/2016 Martin
9,398,911 B2 7/2016 Auld
D763,277 S 8/2016 Ahmed et al.
D764,498 S 8/2016 Capela et al.
9,402,604 B2 8/2016 Williams et al.
9,402,625 B2 8/2016 Coleman et al.
9,402,626 B2 8/2016 Ortiz et al.
9,402,627 B2 8/2016 Stevenson et al.
9,402,629 B2 8/2016 Ehrenfels et al.
9,402,679 B2 8/2016 Ginnebaugh et al.
9,402,682 B2 8/2016 Worrell et al.
9,402,688 B2 8/2016 Min et al.
9,408,604 B2 8/2016 Shelton, IV et al.
9,408,605 B1 8/2016 Knodel et al.
9,408,606 B2 8/2016 Shelton, IV
9,408,622 B2 8/2016 Stulen et al.
9,411,370 B2 8/2016 Benni et al.
9,413,128 B2 8/2016 Tien et al.
9,414,838 B2 8/2016 Shelton, IV et al.
9,414,849 B2 8/2016 Nagashimada
9,414,880 B2 8/2016 Monson et al.
9,420,967 B2 8/2016 Zand et al.
9,421,003 B2 8/2016 Williams et al.
9,421,014 B2 8/2016 Ingmanson et al.
9,421,030 B2 8/2016 Cole et al.
9,421,060 B2 8/2016 Monson et al.
9,421,062 B2 8/2016 Houser et al.
9,421,682 B2 8/2016 McClaskey et al.
9,427,223 B2 8/2016 Park et al.
9,427,231 B2 8/2016 Racenet et al.
9,429,204 B2 8/2016 Stefan et al.
D767,624 S 9/2016 Lee et al.
9,433,411 B2 9/2016 Racenet et al.
9,433,414 B2 9/2016 Chen et al.
9,433,419 B2 9/2016 Gonzalez et al.
9,433,420 B2 9/2016 Hodgkinson
9,439,649 B2 9/2016 Shelton, IV et al.
9,439,650 B2 9/2016 McGuckin, Jr. et al.
9,439,651 B2 9/2016 Smith et al.
9,439,668 B2 9/2016 Timm et al.
9,445,808 B2 9/2016 Woodard, Jr. et al.
9,445,813 B2 9/2016 Shelton, IV et al.
9,445,816 B2 9/2016 Swayze et al.
9,445,817 B2 9/2016 Bettuchi
9,446,226 B2 9/2016 Zilberman
9,451,938 B2 9/2016 Overes et al.
9,451,958 B2 9/2016 Shelton, IV et al.
9,452,020 B2 9/2016 Griffiths et al.
D768,152 S 10/2016 Gutierrez et al.
D768,156 S 10/2016 Frincke
D768,167 S 10/2016 Jones et al.
D769,315 S 10/2016 Scotti
D769,930 S 10/2016 Agrawal
9,461,340 B2 10/2016 Li et al.
9,463,012 B2 10/2016 Bonutti et al.
9,463,040 B2 10/2016 Jeong et al.
9,463,260 B2 10/2016 Stopek
9,468,438 B2 10/2016 Baber et al.
9,468,447 B2 10/2016 Aman et al.
9,470,297 B2 10/2016 Aranyi et al.
9,471,969 B2 10/2016 Zeng et al.
9,474,506 B2 10/2016 Magnin et al.
9,474,513 B2 10/2016 Ishida et al.
9,474,523 B2 10/2016 Meade et al.
9,474,540 B2 10/2016 Stokes et al.
9,475,180 B2 10/2016 Eshleman et al.
9,477,649 B1 10/2016 Davidson et al.
D770,476 S 11/2016 Jitkoff et al.
D770,515 S 11/2016 Cho et al.
D771,116 S 11/2016 Dellinger et al.
D772,905 S 11/2016 Ingenlath
9,480,476 B2 11/2016 Aldridge et al.
9,480,492 B2 11/2016 Aranyi et al.
9,483,095 B2 11/2016 Tran et al.
9,486,186 B2 11/2016 Fiebig et al.
9,486,213 B2 11/2016 Altman et al.
9,486,214 B2 11/2016 Shelton, IV
9,486,215 B2 11/2016 Olson et al.
9,486,302 B2 11/2016 Boey et al.
9,488,197 B2 11/2016 Wi
9,492,146 B2 11/2016 Kostrzewski et al.
9,492,167 B2 11/2016 Shelton, IV et al.
9,492,170 B2 11/2016 Bear et al.
9,492,172 B2 11/2016 Weisshaupt et al.
9,492,189 B2 11/2016 Williams et al.
9,492,192 B2 11/2016 To et al.
9,492,237 B2 11/2016 Kang et al.
9,498,213 B2 11/2016 Marczyk et al.
9,498,219 B2 11/2016 Moore et al.
9,498,231 B2 11/2016 Haider et al.
9,504,455 B2 11/2016 Whitman et al.
9,504,483 B2 11/2016 Houser et al.
9,504,520 B2 11/2016 Worrell et al.
9,504,521 B2 11/2016 Deutmeyer et al.
9,504,528 B2 11/2016 Ivinson et al.
9,507,399 B2 11/2016 Chien
D774,547 S 12/2016 Capela et al.
D775,336 S 12/2016 Shelton, IV et al.
9,510,827 B2 12/2016 Kostrzewski
9,510,828 B2 12/2016 Yates et al.
9,510,830 B2 12/2016 Shelton, IV et al.
9,510,846 B2 12/2016 Sholev et al.
9,510,895 B2 12/2016 Houser et al.
9,510,925 B2 12/2016 Hotter et al.
9,515,366 B2 12/2016 Herbsommer et al.
9,517,063 B2 12/2016 Swayze et al.
9,517,065 B2 12/2016 Simms et al.
9,517,068 B2 12/2016 Shelton, IV et al.
9,517,326 B2 12/2016 Hinman et al.
9,521,996 B2 12/2016 Armstrong
9,522,003 B2 12/2016 Weir et al.
9,522,005 B2 12/2016 Williams et al.
9,522,014 B2 12/2016 Nishizawa et al.
9,522,029 B2 12/2016 Yates et al.
9,526,481 B2 12/2016 Storz et al.
9,526,499 B2 12/2016 Kostrzewski et al.
9,526,563 B2 12/2016 Twomey
9,526,564 B2 12/2016 Rusin
9,526,921 B2 12/2016 Kimball et al.
D776,683 S 1/2017 Gobinski et al.
D777,773 S 1/2017 Shi
9,532,783 B2 1/2017 Swayze et al.
9,539,060 B2 1/2017 Lightcap et al.
9,539,726 B2 1/2017 Simaan et al.
9,545,253 B2 1/2017 Worrell et al.
9,545,258 B2 1/2017 Smith et al.
9,549,732 B2 1/2017 Yates et al.
9,549,733 B2 1/2017 Knodel
9,549,735 B2 1/2017 Shelton, IV et al.
9,549,750 B2 1/2017 Shelton, IV et al.
9,554,794 B2 1/2017 Baber et al.

(56) References Cited

U.S. PATENT DOCUMENTS

| | | | |
|---|---|---|---|
| 9,554,796 | B2 | 1/2017 | Kostrzewski |
| 9,554,803 | B2 | 1/2017 | Smith et al. |
| 9,554,812 | B2 | 1/2017 | Inkpen et al. |
| 9,554,854 | B2 | 1/2017 | Yates et al. |
| 9,559,624 | B2 | 1/2017 | Philipp |
| 9,561,013 | B2 | 2/2017 | Tsuchiya |
| 9,561,029 | B2 | 2/2017 | Scheib et al. |
| 9,561,030 | B2 | 2/2017 | Zhang et al. |
| 9,561,031 | B2 | 2/2017 | Heinrich et al. |
| 9,561,032 | B2 | 2/2017 | Shelton, IV et al. |
| 9,561,038 | B2 | 2/2017 | Shelton, IV et al. |
| 9,561,045 | B2 | 2/2017 | Hinman et al. |
| 9,561,072 | B2 | 2/2017 | Ko |
| 9,561,082 | B2 | 2/2017 | Yen et al. |
| 9,566,061 | B2 | 2/2017 | Aronhalt et al. |
| 9,566,062 | B2 | 2/2017 | Boudreaux |
| 9,566,064 | B2 | 2/2017 | Williams et al. |
| 9,566,065 | B2 | 2/2017 | Knodel |
| 9,566,067 | B2 | 2/2017 | Milliman et al. |
| 9,572,552 | B1 | 2/2017 | Bodor et al. |
| 9,572,574 | B2 | 2/2017 | Shelton, IV et al. |
| 9,572,576 | B2 | 2/2017 | Hodgkinson et al. |
| 9,572,577 | B2 | 2/2017 | Lloyd et al. |
| 9,572,592 | B2 | 2/2017 | Price et al. |
| 9,574,644 | B2 | 2/2017 | Parihar |
| 9,579,088 | B2 | 2/2017 | Farritor et al. |
| 9,579,143 | B2 | 2/2017 | Ullrich et al. |
| 9,579,158 | B2 | 2/2017 | Brianza et al. |
| D780,803 | S | 3/2017 | Gill et al. |
| D781,879 | S | 3/2017 | Butcher et al. |
| D782,530 | S | 3/2017 | Paek et al. |
| 9,585,550 | B2 | 3/2017 | Abel et al. |
| 9,585,657 | B2 | 3/2017 | Shelton, IV et al. |
| 9,585,658 | B2 | 3/2017 | Shelton, IV |
| 9,585,659 | B2 | 3/2017 | Viola et al. |
| 9,585,660 | B2 | 3/2017 | Laurent et al. |
| 9,585,662 | B2 | 3/2017 | Shelton, IV et al. |
| 9,585,663 | B2 | 3/2017 | Shelton, IV et al. |
| 9,585,672 | B2 | 3/2017 | Bastia |
| 9,590,433 | B2 | 3/2017 | Li |
| 9,592,050 | B2 | 3/2017 | Schmid et al. |
| 9,592,052 | B2 | 3/2017 | Shelton, IV |
| 9,592,053 | B2 | 3/2017 | Shelton, IV et al. |
| 9,592,054 | B2 | 3/2017 | Schmid et al. |
| 9,597,073 | B2 | 3/2017 | Sorrentino et al. |
| 9,597,075 | B2 | 3/2017 | Shelton, IV et al. |
| 9,597,078 | B2 | 3/2017 | Scirica et al. |
| 9,597,080 | B2 | 3/2017 | Milliman et al. |
| 9,597,104 | B2 | 3/2017 | Nicholas et al. |
| 9,597,143 | B2 | 3/2017 | Madan et al. |
| 9,603,595 | B2 | 3/2017 | Shelton, IV et al. |
| 9,603,598 | B2 | 3/2017 | Shelton, IV et al. |
| 9,603,599 | B2 | 3/2017 | Miller et al. |
| 9,603,991 | B2 | 3/2017 | Shelton, IV et al. |
| D783,658 | S | 4/2017 | Hurst et al. |
| 9,610,068 | B2 | 4/2017 | Kappel et al. |
| 9,610,079 | B2 | 4/2017 | Kamei et al. |
| 9,610,080 | B2 | 4/2017 | Whitfield et al. |
| 9,610,412 | B2 | 4/2017 | Zemlok et al. |
| 9,614,258 | B2 | 4/2017 | Takahashi et al. |
| 9,615,826 | B2 | 4/2017 | Shelton, IV et al. |
| 9,622,745 | B2 | 4/2017 | Ingmanson et al. |
| 9,622,746 | B2 | 4/2017 | Simms et al. |
| 9,629,623 | B2 | 4/2017 | Lytle, IV et al. |
| 9,629,626 | B2 | 4/2017 | Soltz et al. |
| 9,629,627 | B2 | 4/2017 | Kostrzewski et al. |
| 9,629,628 | B2 | 4/2017 | Aranyi |
| 9,629,629 | B2 | 4/2017 | Leimbach et al. |
| 9,629,631 | B2 | 4/2017 | Nicholas et al. |
| 9,629,632 | B2 | 4/2017 | Linder et al. |
| 9,629,652 | B2 | 4/2017 | Mumaw et al. |
| 9,629,814 | B2 | 4/2017 | Widenhouse et al. |
| D785,794 | S | 5/2017 | Magno, Jr. |
| D786,280 | S | 5/2017 | Ma |
| D786,896 | S | 5/2017 | Kim et al. |
| D787,547 | S | 5/2017 | Basargin et al. |
| D788,123 | S | 5/2017 | Shan et al. |
| D788,140 | S | 5/2017 | Hemsley et al. |
| 9,636,091 | B2 | 5/2017 | Beardsley et al. |
| 9,636,111 | B2 | 5/2017 | Wenchell |
| 9,636,112 | B2 | 5/2017 | Penna et al. |
| 9,636,113 | B2 | 5/2017 | Wenchell |
| 9,636,850 | B2 | 5/2017 | Stopek et al. |
| 9,641,122 | B2 | 5/2017 | Romanowich et al. |
| 9,642,620 | B2 | 5/2017 | Baxter, III et al. |
| 9,642,642 | B2 | 5/2017 | Lim |
| 9,649,096 | B2 | 5/2017 | Sholev |
| 9,649,110 | B2 | 5/2017 | Parihar et al. |
| 9,649,111 | B2 | 5/2017 | Shelton, IV et al. |
| 9,649,190 | B2 | 5/2017 | Mathies |
| 9,651,032 | B2 | 5/2017 | Weaver et al. |
| 9,655,613 | B2 | 5/2017 | Schaller |
| 9,655,614 | B2 | 5/2017 | Swensgard et al. |
| 9,655,615 | B2 | 5/2017 | Knodel et al. |
| 9,655,616 | B2 | 5/2017 | Aranyi |
| 9,655,624 | B2 | 5/2017 | Shelton, IV et al. |
| 9,661,991 | B2 | 5/2017 | Glossop |
| 9,662,108 | B2 | 5/2017 | Williams |
| 9,662,110 | B2 | 5/2017 | Huang et al. |
| 9,662,111 | B2 | 5/2017 | Holsten et al. |
| 9,662,116 | B2 | 5/2017 | Smith et al. |
| 9,662,130 | B2 | 5/2017 | Bartels et al. |
| 9,662,131 | B2 | 5/2017 | Omori et al. |
| D788,792 | S | 6/2017 | Alessandri et al. |
| D789,384 | S | 6/2017 | Lin et al. |
| D790,570 | S | 6/2017 | Butcher et al. |
| 9,668,728 | B2 | 6/2017 | Williams et al. |
| 9,668,729 | B2 | 6/2017 | Williams et al. |
| 9,668,732 | B2 | 6/2017 | Patel et al. |
| 9,668,733 | B2 | 6/2017 | Williams |
| 9,668,734 | B2 | 6/2017 | Kostrzewski et al. |
| 9,668,735 | B2 | 6/2017 | Beetel |
| 9,675,344 | B2 | 6/2017 | Combrowski et al. |
| 9,675,348 | B2 | 6/2017 | Smith et al. |
| 9,675,351 | B2 | 6/2017 | Hodgkinson et al. |
| 9,675,354 | B2 | 6/2017 | Weir et al. |
| 9,675,355 | B2 | 6/2017 | Shelton, IV et al. |
| 9,675,368 | B2 | 6/2017 | Guo et al. |
| 9,675,372 | B2 | 6/2017 | Laurent et al. |
| 9,675,375 | B2 | 6/2017 | Houser et al. |
| 9,675,405 | B2 | 6/2017 | Trees et al. |
| 9,675,819 | B2 | 6/2017 | Dunbar et al. |
| 9,681,870 | B2 | 6/2017 | Baxter, III et al. |
| 9,681,873 | B2 | 6/2017 | Smith et al. |
| 9,681,884 | B2 | 6/2017 | Clem et al. |
| 9,687,230 | B2 | 6/2017 | Leimbach et al. |
| 9,687,231 | B2 | 6/2017 | Baxter et al. |
| 9,687,232 | B2 | 6/2017 | Shelton, IV et al. |
| 9,687,233 | B2 | 6/2017 | Fernandez et al. |
| 9,687,236 | B2 | 6/2017 | Leimbach et al. |
| 9,687,237 | B2 | 6/2017 | Schmid et al. |
| 9,687,253 | B2 | 6/2017 | Detry et al. |
| 9,689,466 | B2 | 6/2017 | Kanai et al. |
| 9,690,362 | B2 | 6/2017 | Leimbach et al. |
| 9,693,772 | B2 | 7/2017 | Ingmanson et al. |
| 9,693,774 | B2 | 7/2017 | Gettinger et al. |
| 9,693,775 | B2 | 7/2017 | Agarwal et al. |
| 9,693,777 | B2 | 7/2017 | Schellin et al. |
| 9,700,309 | B2 | 7/2017 | Jaworek et al. |
| 9,700,310 | B2 | 7/2017 | Morgan et al. |
| 9,700,312 | B2 | 7/2017 | Kostrzewski et al. |
| 9,700,314 | B2 | 7/2017 | Marczyk |
| 9,700,315 | B2 | 7/2017 | Chen et al. |
| 9,700,317 | B2 | 7/2017 | Aronhalt et al. |
| 9,700,318 | B2 | 7/2017 | Scirica et al. |
| 9,700,319 | B2 | 7/2017 | Motooka et al. |
| 9,700,320 | B2 | 7/2017 | Dinardo et al. |
| 9,700,321 | B2 | 7/2017 | Shelton, IV et al. |
| 9,700,334 | B2 | 7/2017 | Hinman et al. |
| 9,700,381 | B2 | 7/2017 | Amat Girbau |
| 9,702,823 | B2 | 7/2017 | Maher et al. |
| 9,706,674 | B2 | 7/2017 | Collins et al. |
| 9,706,981 | B2 | 7/2017 | Nicholas et al. |
| 9,706,991 | B2 | 7/2017 | Hess et al. |

(56) References Cited

U.S. PATENT DOCUMENTS 9,706,993 B2 7/2017 Hessler et al.
9,707,003 B2 7/2017 Hoell, Jr. et al.
9,707,005 B2 7/2017 Strobl et al.
9,707,026 B2 7/2017 Malackowski et al.
9,707,033 B2 7/2017 Parihar et al.
9,707,043 B2 7/2017 Bozung
9,707,684 B2 7/2017 Ruiz Morales et al.
9,713,466 B2 7/2017 Kostrzewski
9,713,468 B2 7/2017 Harris et al.
9,713,470 B2 7/2017 Scirica et al.
9,713,474 B2 7/2017 Lorenz
D795,919 S 8/2017 Bischoff et al.
9,717,497 B2 8/2017 Zerkle et al.
9,717,498 B2 8/2017 Aranyi et al.
9,718,190 B2 8/2017 Larkin et al.
9,722,236 B2 8/2017 Sathrum
9,724,091 B2 8/2017 Shelton, IV et al.
9,724,092 B2 8/2017 Baxter, III et al.
9,724,094 B2 8/2017 Baber et al.
9,724,095 B2 8/2017 Gupta et al.
9,724,096 B2 8/2017 Thompson et al.
9,724,098 B2 8/2017 Baxter, III et al.
9,724,118 B2 8/2017 Schulte et al.
9,724,163 B2 8/2017 Orban
9,730,692 B2 8/2017 Shelton, IV et al.
9,730,695 B2 8/2017 Leimbach et al.
9,730,697 B2 8/2017 Morgan et al.
9,730,717 B2 8/2017 Katsuki et al.
9,730,757 B2 8/2017 Brudniok
9,731,410 B2 8/2017 Hirabayashi et al.
9,733,663 B2 8/2017 Leimbach et al.
9,737,297 B2 8/2017 Racenet et al.
9,737,298 B2 8/2017 Isbell, Jr.
9,737,299 B2 8/2017 Yan
9,737,301 B2 8/2017 Baber et al.
9,737,302 B2 8/2017 Shelton, IV et al.
9,737,303 B2 8/2017 Shelton, IV et al.
9,737,323 B2 8/2017 Thapliyal et al.
9,737,365 B2 8/2017 Hegeman et al.
9,743,927 B2 8/2017 Whitman
9,743,928 B2 8/2017 Shelton, IV et al.
9,743,929 B2 8/2017 Leimbach et al.
D798,319 S 9/2017 Bergstrand et al.
9,750,498 B2 9/2017 Timm et al.
9,750,499 B2 9/2017 Leimbach et al.
9,750,501 B2 9/2017 Shelton, IV et al.
9,750,502 B2 9/2017 Scirica et al.
9,750,503 B2 9/2017 Milliman
9,750,639 B2 9/2017 Barnes et al.
9,751,176 B2 9/2017 McRoberts et al.
9,757,123 B2 9/2017 Giordano et al.
9,757,124 B2 9/2017 Schellin et al.
9,757,126 B2 9/2017 Cappola
9,757,128 B2 9/2017 Baber et al.
9,757,129 B2 9/2017 Williams
9,757,130 B2 9/2017 Shelton, IV
9,763,662 B2 9/2017 Shelton, IV et al.
9,763,668 B2 9/2017 Whitfield et al.
9,770,245 B2 9/2017 Swayze et al.
9,770,274 B2 9/2017 Pool et al.
D798,886 S 10/2017 Prophete et al.
D800,742 S 10/2017 Rhodes
D800,744 S 10/2017 Jitkoff et al.
D800,766 S 10/2017 Park et al.
D800,904 S 10/2017 Leimbach et al.
9,775,608 B2 10/2017 Aronhalt et al.
9,775,609 B2 10/2017 Shelton, IV et al.
9,775,610 B2 10/2017 Nicholas et al.
9,775,611 B2 10/2017 Kostrzewski
9,775,613 B2 10/2017 Shelton, IV et al.
9,775,614 B2 10/2017 Shelton, IV et al.
9,775,618 B2 10/2017 Bettuchi et al.
9,775,635 B2 10/2017 Takei
9,775,678 B2 10/2017 Lohmeier
9,782,169 B2 10/2017 Kimsey et al.
9,782,170 B2 10/2017 Zemlok et al.
9,782,180 B2 10/2017 Smith et al.
9,782,187 B2 10/2017 Zergiebel et al.
9,782,193 B2 10/2017 Thistle
9,782,214 B2 10/2017 Houser et al.
9,788,834 B2 10/2017 Schmid et al.
9,788,835 B2 10/2017 Morgan et al.
9,788,836 B2 10/2017 Overmyer et al.
9,788,847 B2 10/2017 Jinno
9,788,851 B2 10/2017 Dannaher et al.
9,788,902 B2 10/2017 Inoue et al.
9,795,379 B2 10/2017 Leimbach et al.
9,795,380 B2 10/2017 Shelton, IV et al.
9,795,381 B2 10/2017 Shelton, IV
9,795,382 B2 10/2017 Shelton, IV
9,795,383 B2 10/2017 Aldridge et al.
9,795,384 B2 10/2017 Weaner et al.
9,797,486 B2 10/2017 Zergiebel et al.
9,801,626 B2 10/2017 Parihar et al.
9,801,627 B2 10/2017 Harris et al.
9,801,628 B2 10/2017 Harris et al.
9,801,634 B2 10/2017 Shelton, IV et al.
9,801,679 B2 10/2017 Trees et al.
9,802,033 B2 10/2017 Hibner et al.
9,804,618 B2 10/2017 Leimbach et al.
D803,234 S 11/2017 Day et al.
D803,235 S 11/2017 Markson et al.
D803,850 S 11/2017 Chang et al.
9,808,244 B2 11/2017 Leimbach et al.
9,808,246 B2 11/2017 Shelton, IV et al.
9,808,247 B2 11/2017 Shelton, IV et al.
9,808,248 B2 11/2017 Hoffman
9,808,249 B2 11/2017 Shelton, IV
9,814,460 B2 11/2017 Kimsey et al.
9,814,462 B2 11/2017 Woodard, Jr. et al.
9,814,463 B2 11/2017 Williams et al.
9,814,530 B2 11/2017 Weir et al.
9,814,561 B2 11/2017 Forsell
9,815,118 B1 11/2017 Schmitt et al.
9,820,445 B2 11/2017 Simpson et al.
9,820,737 B2 11/2017 Beardsley et al.
9,820,738 B2 11/2017 Lytle, IV et al.
9,820,741 B2 11/2017 Kostrzewski
9,820,768 B2 11/2017 Gee et al.
9,825,455 B2 11/2017 Sandhu et al.
9,826,976 B2 11/2017 Parihar et al.
9,826,977 B2 11/2017 Leimbach et al.
9,826,978 B2 11/2017 Shelton, IV et al.
9,829,698 B2 11/2017 Haraguchi et al.
D806,108 S 12/2017 Day
9,833,235 B2 12/2017 Penna et al.
9,833,236 B2 12/2017 Shelton, IV et al.
9,833,238 B2 12/2017 Baxter, III et al.
9,833,239 B2 12/2017 Yates et al.
9,833,241 B2 12/2017 Huitema et al.
9,833,242 B2 12/2017 Baxter, III et al.
9,839,420 B2 12/2017 Shelton, IV et al.
9,839,421 B2 12/2017 Zerkle et al.
9,839,422 B2 12/2017 Schellin et al.
9,839,423 B2 12/2017 Vendely et al.
9,839,427 B2 12/2017 Swayze et al.
9,839,428 B2 12/2017 Baxter, III et al.
9,839,429 B2 12/2017 Weisenburgh, II et al.
9,839,480 B2 12/2017 Pribanic et al.
9,839,481 B2 12/2017 Blumenkranz et al.
9,844,368 B2 12/2017 Boudreaux et al.
9,844,369 B2 12/2017 Huitema et al.
9,844,372 B2 12/2017 Shelton, IV et al.
9,844,373 B2 12/2017 Swayze et al.
9,844,374 B2 12/2017 Lytle, IV et al.
9,844,375 B2 12/2017 Overmyer et al.
9,844,376 B2 12/2017 Baxter, III et al.
9,844,379 B2 12/2017 Shelton, IV et al.
9,848,871 B2 12/2017 Harris et al.
9,848,873 B2 12/2017 Shelton, IV
9,848,875 B2 12/2017 Aronhalt et al.
9,848,877 B2 12/2017 Shelton, IV et al.
9,850,994 B2 12/2017 Schena
D808,989 S 1/2018 Ayvazian et al.

(56) References Cited

U.S. PATENT DOCUMENTS

| | | | |
|---|---|---|---|
| 9,855,039 | B2 | 1/2018 | Racenet et al. |
| 9,855,040 | B2 | 1/2018 | Kostrzewski |
| 9,855,662 | B2 | 1/2018 | Ruiz Morales et al. |
| 9,861,261 | B2 | 1/2018 | Shahinian |
| 9,861,359 | B2 | 1/2018 | Shelton, IV et al. |
| 9,861,361 | B2 | 1/2018 | Aronhalt et al. |
| 9,861,362 | B2 | 1/2018 | Whitman et al. |
| 9,861,366 | B2 | 1/2018 | Aranyi |
| 9,861,382 | B2 | 1/2018 | Smith et al. |
| 9,861,446 | B2 | 1/2018 | Lang |
| 9,867,612 | B2 | 1/2018 | Parihar et al. |
| 9,867,613 | B2 | 1/2018 | Marczyk et al. |
| 9,867,615 | B2 | 1/2018 | Fanelli et al. |
| 9,867,617 | B2 | 1/2018 | Ma |
| 9,867,618 | B2 | 1/2018 | Hall et al. |
| 9,867,620 | B2 | 1/2018 | Fischvogt et al. |
| 9,868,198 | B2 | 1/2018 | Nicholas et al. |
| 9,872,682 | B2 | 1/2018 | Hess et al. |
| 9,872,683 | B2 | 1/2018 | Hopkins et al. |
| 9,872,684 | B2 | 1/2018 | Hall et al. |
| 9,872,722 | B2 | 1/2018 | Lech |
| 9,877,721 | B2 | 1/2018 | Schellin et al. |
| 9,877,722 | B2 | 1/2018 | Schellin et al. |
| 9,877,723 | B2 | 1/2018 | Hall et al. |
| 9,877,776 | B2 | 1/2018 | Boudreaux |
| D810,099 | S | 2/2018 | Riedel |
| 9,883,843 | B2 | 2/2018 | Garlow |
| 9,883,860 | B2 | 2/2018 | Leimbach |
| 9,883,861 | B2 | 2/2018 | Shelton, IV et al. |
| 9,884,456 | B2 | 2/2018 | Schellin et al. |
| 9,888,914 | B2 | 2/2018 | Martin et al. |
| 9,888,919 | B2 | 2/2018 | Leimbach et al. |
| 9,888,921 | B2 | 2/2018 | Williams et al. |
| 9,888,924 | B2 | 2/2018 | Ebersole et al. |
| 9,889,230 | B2 | 2/2018 | Bennett et al. |
| 9,895,147 | B2 | 2/2018 | Shelton, IV |
| 9,895,148 | B2 | 2/2018 | Shelton, IV et al. |
| 9,895,813 | B2 | 2/2018 | Blumenkranz et al. |
| 9,901,339 | B2 | 2/2018 | Farascioni |
| 9,901,341 | B2 | 2/2018 | Kostrzewski |
| 9,901,342 | B2 | 2/2018 | Shelton, IV et al. |
| 9,901,344 | B2 | 2/2018 | Moore et al. |
| 9,901,345 | B2 | 2/2018 | Moore et al. |
| 9,901,346 | B2 | 2/2018 | Moore et al. |
| 9,901,358 | B2 | 2/2018 | Faller et al. |
| 9,901,406 | B2 | 2/2018 | State et al. |
| 9,901,412 | B2 | 2/2018 | Lathrop et al. |
| D813,899 | S | 3/2018 | Erant et al. |
| 9,907,456 | B2 | 3/2018 | Miyoshi |
| 9,907,552 | B2 | 3/2018 | Measamer et al. |
| 9,907,553 | B2 | 3/2018 | Cole et al. |
| 9,907,600 | B2 | 3/2018 | Stulen et al. |
| 9,907,620 | B2 | 3/2018 | Shelton, IV et al. |
| 9,913,641 | B2 | 3/2018 | Takemoto et al. |
| 9,913,642 | B2 | 3/2018 | Leimbach et al. |
| 9,913,644 | B2 | 3/2018 | McCuen |
| 9,913,646 | B2 | 3/2018 | Shelton, IV |
| 9,913,647 | B2 | 3/2018 | Weisenburgh, II et al. |
| 9,913,648 | B2 | 3/2018 | Shelton, IV et al. |
| 9,913,694 | B2 | 3/2018 | Brisson |
| 9,913,733 | B2 | 3/2018 | Piron et al. |
| 9,918,704 | B2 | 3/2018 | Shelton, IV et al. |
| 9,918,714 | B2 | 3/2018 | Gibbons, Jr. |
| 9,918,715 | B2 | 3/2018 | Menn |
| 9,918,716 | B2 | 3/2018 | Baxter, III et al. |
| 9,918,717 | B2 | 3/2018 | Czernik |
| 9,918,730 | B2 | 3/2018 | Trees et al. |
| 9,924,941 | B2 | 3/2018 | Burbank |
| 9,924,942 | B2 | 3/2018 | Swayze et al. |
| 9,924,943 | B2 | 3/2018 | Mohan Pinjala et al. |
| 9,924,944 | B2 | 3/2018 | Shelton, IV et al. |
| 9,924,945 | B2 | 3/2018 | Zheng et al. |
| 9,924,946 | B2 | 3/2018 | Vendely et al. |
| 9,924,947 | B2 | 3/2018 | Shelton, IV et al. |
| 9,924,961 | B2 | 3/2018 | Shelton, IV et al. |
| 9,931,106 | B2 | 4/2018 | Au et al. |
| 9,931,116 | B2 | 4/2018 | Racenet et al. |
| 9,931,117 | B2 | 4/2018 | Hathaway et al. |
| 9,931,118 | B2 | 4/2018 | Shelton, IV et al. |
| 9,931,120 | B2 | 4/2018 | Chen et al. |
| 9,936,949 | B2 | 4/2018 | Measamer et al. |
| 9,936,950 | B2 | 4/2018 | Shelton, IV et al. |
| 9,936,951 | B2 | 4/2018 | Hufnagel et al. |
| 9,936,952 | B2 | 4/2018 | Demmy |
| 9,936,954 | B2 | 4/2018 | Shelton, IV et al. |
| 9,937,626 | B2 | 4/2018 | Rockrohr |
| 9,943,309 | B2 | 4/2018 | Shelton, IV et al. |
| 9,943,310 | B2 | 4/2018 | Harris et al. |
| 9,943,312 | B2 | 4/2018 | Posada et al. |
| 9,949,754 | B2 | 4/2018 | Newhauser et al. |
| 9,953,193 | B2 | 4/2018 | Butler et al. |
| D819,072 | S | 5/2018 | Clediere |
| 9,955,954 | B2 | 5/2018 | Destoumieux et al. |
| 9,955,965 | B2 | 5/2018 | Chen et al. |
| 9,955,966 | B2 | 5/2018 | Zergiebel |
| 9,956,677 | B2 | 5/2018 | Baskar et al. |
| 9,962,129 | B2 | 5/2018 | Jerebko et al. |
| 9,962,157 | B2 | 5/2018 | Sapre |
| 9,962,158 | B2 | 5/2018 | Hall et al. |
| 9,962,159 | B2 | 5/2018 | Heinrich et al. |
| 9,962,161 | B2 | 5/2018 | Scheib et al. |
| 9,968,354 | B2 | 5/2018 | Shelton, IV et al. |
| 9,968,355 | B2 | 5/2018 | Shelton, IV et al. |
| 9,968,356 | B2 | 5/2018 | Shelton, IV et al. |
| 9,968,397 | B2 | 5/2018 | Taylor et al. |
| 9,974,529 | B2 | 5/2018 | Shelton, IV et al. |
| 9,974,538 | B2 | 5/2018 | Baxter, III et al. |
| 9,974,539 | B2 | 5/2018 | Yates et al. |
| 9,974,541 | B2 | 5/2018 | Calderoni |
| 9,974,542 | B2 | 5/2018 | Hodgkinson |
| 9,980,713 | B2 | 5/2018 | Aronhalt et al. |
| 9,980,724 | B2 | 5/2018 | Farascioni et al. |
| 9,980,729 | B2 | 5/2018 | Moore et al. |
| 9,980,740 | B2 | 5/2018 | Krause et al. |
| 9,980,769 | B2 | 5/2018 | Trees et al. |
| D819,680 | S | 6/2018 | Nguyen |
| D819,682 | S | 6/2018 | Howard et al. |
| D819,684 | S | 6/2018 | Dart |
| D820,307 | S | 6/2018 | Jian et al. |
| D820,867 | S | 6/2018 | Dickens et al. |
| 9,987,000 | B2 | 6/2018 | Shelton, IV et al. |
| 9,987,003 | B2 | 6/2018 | Timm et al. |
| 9,987,006 | B2 | 6/2018 | Morgan et al. |
| 9,987,008 | B2 | 6/2018 | Scirica et al. |
| 9,987,095 | B2 | 6/2018 | Chowaniec et al. |
| 9,987,097 | B2 | 6/2018 | Van Der Weide et al. |
| 9,987,099 | B2 | 6/2018 | Chen et al. |
| 9,993,248 | B2 | 6/2018 | Shelton, IV et al. |
| 9,993,258 | B2 | 6/2018 | Shelton, IV et al. |
| 9,993,284 | B2 | 6/2018 | Boudreaux |
| 9,999,408 | B2 | 6/2018 | Boudreaux et al. |
| 9,999,423 | B2 | 6/2018 | Schuckmann et al. |
| 9,999,426 | B2 | 6/2018 | Moore et al. |
| 9,999,431 | B2 | 6/2018 | Shelton, IV et al. |
| 9,999,472 | B2 | 6/2018 | Weir et al. |
| 10,004,497 | B2 | 6/2018 | Overmyer et al. |
| 10,004,498 | B2 | 6/2018 | Morgan et al. |
| 10,004,500 | B2 | 6/2018 | Shelton, IV et al. |
| 10,004,501 | B2 | 6/2018 | Shelton, IV et al. |
| 10,004,505 | B2 | 6/2018 | Moore et al. |
| 10,004,506 | B2 | 6/2018 | Shelton, IV et al. |
| 10,004,552 | B1 | 6/2018 | Kleyman et al. |
| D822,206 | S | 7/2018 | Shelton, IV et al. |
| 10,010,322 | B2 | 7/2018 | Shelton, IV et al. |
| 10,010,324 | B2 | 7/2018 | Huitema et al. |
| 10,010,395 | B2 | 7/2018 | Puckett et al. |
| 10,013,049 | B2 | 7/2018 | Leimbach et al. |
| 10,016,199 | B2 | 7/2018 | Baber et al. |
| 10,016,656 | B2 | 7/2018 | Devor et al. |
| 10,022,120 | B2 | 7/2018 | Martin et al. |
| 10,022,123 | B2 | 7/2018 | Williams et al. |
| 10,022,125 | B2 | 7/2018 | Stopek et al. |
| 10,024,407 | B2 | 7/2018 | Aranyi et al. |
| 10,028,742 | B2 | 7/2018 | Shelton, IV et al. |

(56) References Cited

U.S. PATENT DOCUMENTS 10,028,743 B2 7/2018 Shelton, IV et al.
10,028,744 B2 7/2018 Shelton, IV et al.
10,028,761 B2 7/2018 Leimbach et al.
10,029,108 B2 7/2018 Powers et al.
10,029,125 B2 7/2018 Shapiro et al.
10,034,344 B2 7/2018 Yoshida
10,034,668 B2 7/2018 Ebner
D826,405 S 8/2018 Shelton, IV et al.
10,039,440 B2 8/2018 Fenech et al.
10,039,529 B2 8/2018 Kerr et al.
10,039,532 B2 8/2018 Srinivas et al.
10,039,545 B2 8/2018 Sadowski et al.
10,041,822 B2 8/2018 Zemlok
10,045,769 B2 8/2018 Aronhalt et al.
10,045,776 B2 8/2018 Shelton, IV et al.
10,045,778 B2 8/2018 Yates et al.
10,045,779 B2 8/2018 Savage et al.
10,045,781 B2 8/2018 Cropper et al.
10,045,782 B2 8/2018 Murthy Aravalli
10,045,869 B2 8/2018 Forsell
10,046,904 B2 8/2018 Evans et al.
10,052,044 B2 8/2018 Shelton, IV et al.
10,052,099 B2 8/2018 Morgan et al.
10,052,100 B2 8/2018 Morgan et al.
10,052,102 B2 8/2018 Baxter, III et al.
10,052,104 B2 8/2018 Shelton, IV et al.
10,052,164 B2 8/2018 Overmyer
10,058,317 B2 8/2018 Fan et al.
10,058,327 B2 8/2018 Weisenburgh, II et al.
10,058,373 B2 8/2018 Takashino et al.
10,058,395 B2 8/2018 Devengenzo et al.
10,058,963 B2 8/2018 Shelton, IV et al.
10,064,620 B2 9/2018 Gettinger et al.
10,064,621 B2 9/2018 Kerr et al.
10,064,622 B2 9/2018 Murthy Aravalli
10,064,624 B2 9/2018 Shelton, IV et al.
10,064,639 B2 9/2018 Ishida et al.
10,064,642 B2 9/2018 Marczyk et al.
10,064,649 B2 9/2018 Golebieski et al.
10,064,688 B2 9/2018 Shelton, IV et al.
10,070,861 B2 9/2018 Spivey et al.
10,070,863 B2 9/2018 Swayze et al.
10,071,452 B2 9/2018 Shelton, IV et al.
10,076,325 B2 9/2018 Huang et al.
10,076,326 B2 9/2018 Yates et al.
10,076,340 B2 9/2018 Belagali et al.
10,080,552 B2 9/2018 Nicholas et al.
D830,550 S 10/2018 Miller et al.
D831,209 S 10/2018 Huitema et al.
D831,676 S 10/2018 Park et al.
D832,301 S 10/2018 Smith
10,085,624 B2 10/2018 Isoda et al.
10,085,643 B2 10/2018 Bandic et al.
10,085,728 B2 10/2018 Jogasaki et al.
10,085,746 B2 10/2018 Fischvogt
10,085,748 B2 10/2018 Morgan et al.
10,085,749 B2 10/2018 Cappola et al.
10,085,750 B2 10/2018 Zergiebel et al.
10,085,751 B2 10/2018 Overmyer et al.
10,085,754 B2 10/2018 Sniffin et al.
10,085,806 B2 10/2018 Hagn et al.
10,092,290 B2 10/2018 Yigit et al.
10,092,292 B2 10/2018 Boudreaux et al.
10,098,635 B2 10/2018 Burbank
10,098,636 B2 10/2018 Shelton, IV et al.
10,098,640 B2 10/2018 Bertolero et al.
10,098,642 B2 10/2018 Baxter, III et al.
10,099,303 B2 10/2018 Yoshida et al.
10,101,861 B2 10/2018 Kiyoto
10,105,126 B2 10/2018 Sauer
10,105,128 B2 10/2018 Cooper et al.
10,105,136 B2 10/2018 Yates et al.
10,105,139 B2 10/2018 Yates et al.
10,105,140 B2 10/2018 Malinouskas et al.
10,105,142 B2 10/2018 Baxter, III et al.
10,105,149 B2 10/2018 Haider et al.
10,106,932 B2 10/2018 Anderson et al.
10,111,657 B2 10/2018 McCuen
10,111,658 B2 10/2018 Chowaniec et al.
10,111,660 B2 10/2018 Hemmann
10,111,665 B2 10/2018 Aranyi et al.
10,111,679 B2 10/2018 Baber et al.
10,111,698 B2 10/2018 Scheib et al.
10,111,702 B2 10/2018 Kostrzewski
D833,608 S 11/2018 Miller et al.
10,117,649 B2 11/2018 Baxter et al.
10,117,650 B2 11/2018 Nicholas et al.
10,117,652 B2 11/2018 Schmid et al.
10,117,653 B2 11/2018 Leimbach et al.
10,117,654 B2 11/2018 Ingmanson et al.
10,123,798 B2 11/2018 Baxter, III et al.
10,123,845 B2 11/2018 Yeung
10,124,493 B2 11/2018 Rothfuss et al.
10,130,352 B2 11/2018 Widenhouse et al.
10,130,359 B2 11/2018 Hess et al.
10,130,360 B2 11/2018 Olson et al.
10,130,361 B2 11/2018 Yates et al.
10,130,363 B2 11/2018 Huitema et al.
10,130,366 B2 11/2018 Shelton, IV et al.
10,130,367 B2 11/2018 Cappola et al.
10,130,382 B2 11/2018 Gladstone
10,130,738 B2 11/2018 Shelton, IV et al.
10,130,830 B2 11/2018 Miret Carceller et al.
10,133,248 B2 11/2018 Fitzsimmons et al.
10,135,242 B2 11/2018 Baber et al.
10,136,879 B2 11/2018 Ross et al.
10,136,887 B2 11/2018 Shelton, IV et al.
10,136,889 B2 11/2018 Shelton, IV et al.
10,136,890 B2 11/2018 Shelton, IV et al.
10,136,891 B2 11/2018 Shelton, IV et al.
10,136,949 B2 11/2018 Felder et al.
D835,659 S 12/2018 Anzures et al.
D836,124 S 12/2018 Fan
10,143,474 B2 12/2018 Bucciaglia et al.
10,146,423 B1 12/2018 Reed et al.
10,149,679 B2 12/2018 Shelton, IV et al.
10,149,680 B2 12/2018 Parihar et al.
10,149,682 B2 12/2018 Shelton, IV et al.
10,149,683 B2 12/2018 Smith et al.
10,149,712 B2 12/2018 Manwaring et al.
10,152,789 B2 12/2018 Carnes et al.
10,154,841 B2 12/2018 Weaner et al.
10,159,481 B2 12/2018 Whitman et al.
10,159,482 B2 12/2018 Swayze et al.
10,159,483 B2 12/2018 Beckman et al.
10,159,506 B2 12/2018 Boudreaux et al.
10,161,816 B2 12/2018 Jackson et al.
10,163,065 B1 12/2018 Koski et al.
10,163,589 B2 12/2018 Zergiebel et al.
10,164,466 B2 12/2018 Calderoni
D837,244 S 1/2019 Kuo et al.
D837,245 S 1/2019 Kuo et al.
10,166,023 B2 1/2019 Vendely et al.
10,166,025 B2 1/2019 Leimbach et al.
10,166,026 B2 1/2019 Shelton, IV et al.
10,172,611 B2 1/2019 Shelton, IV et al.
10,172,615 B2 1/2019 Marczyk et al.
10,172,616 B2 1/2019 Murray et al.
10,172,617 B2 1/2019 Shelton, IV et al.
10,172,618 B2 1/2019 Shelton, IV et al.
10,172,619 B2 1/2019 Harris et al.
10,172,620 B2 1/2019 Harris et al.
10,172,636 B2 1/2019 Stulen et al.
10,172,669 B2 1/2019 Felder et al.
10,175,127 B2 1/2019 Collins et al.
10,178,992 B2 1/2019 Wise et al.
10,180,463 B2 1/2019 Beckman et al.
10,182,813 B2 1/2019 Leimbach et al.
10,182,815 B2 1/2019 Williams et al.
10,182,816 B2 1/2019 Shelton, IV et al.
10,182,818 B2 1/2019 Hensel et al.
10,182,819 B2 1/2019 Shelton, IV
10,182,868 B2 1/2019 Meier et al.
10,188,385 B2 1/2019 Kerr et al.

(56) References Cited

U.S. PATENT DOCUMENTS

| | | | |
|---|---|---|---|
| 10,188,389 | B2 | 1/2019 | Vendely et al. |
| 10,188,393 | B2 | 1/2019 | Smith et al. |
| 10,188,394 | B2 | 1/2019 | Shelton, IV et al. |
| 10,190,888 | B2 | 1/2019 | Hryb et al. |
| D839,900 | S | 2/2019 | Gan |
| D841,667 | S | 2/2019 | Coren |
| 10,194,801 | B2 | 2/2019 | Elhawary et al. |
| 10,194,904 | B2 | 2/2019 | Viola et al. |
| 10,194,907 | B2 | 2/2019 | Marczyk et al. |
| 10,194,908 | B2 | 2/2019 | Duque et al. |
| 10,194,910 | B2 | 2/2019 | Shelton, IV et al. |
| 10,194,911 | B2 | 2/2019 | Miller et al. |
| 10,194,912 | B2 | 2/2019 | Scheib et al. |
| 10,194,913 | B2 | 2/2019 | Nalagatla et al. |
| 10,194,976 | B2 | 2/2019 | Boudreaux |
| 10,194,992 | B2 | 2/2019 | Robinson |
| 10,201,348 | B2 | 2/2019 | Scheib et al. |
| 10,201,349 | B2 | 2/2019 | Leimbach et al. |
| 10,201,363 | B2 | 2/2019 | Shelton, IV |
| 10,201,364 | B2 | 2/2019 | Leimbach et al. |
| 10,201,365 | B2 | 2/2019 | Boudreaux et al. |
| 10,201,381 | B2 | 2/2019 | Zergiebel et al. |
| 10,206,605 | B2 | 2/2019 | Shelton, IV et al. |
| 10,206,676 | B2 | 2/2019 | Shelton, IV |
| 10,206,677 | B2 | 2/2019 | Harris et al. |
| 10,206,678 | B2 | 2/2019 | Shelton, IV et al. |
| 10,206,748 | B2 | 2/2019 | Burbank |
| 10,210,244 | B1 | 2/2019 | Branavan et al. |
| 10,211,586 | B2 | 2/2019 | Adams et al. |
| 10,213,198 | B2 | 2/2019 | Aronhalt et al. |
| 10,213,201 | B2 | 2/2019 | Shelton, IV et al. |
| 10,213,202 | B2 | 2/2019 | Flanagan et al. |
| 10,213,203 | B2 | 2/2019 | Swayze et al. |
| 10,213,204 | B2 | 2/2019 | Aranyi et al. |
| 10,213,262 | B2 | 2/2019 | Shelton, IV et al. |
| D842,328 | S | 3/2019 | Jian et al. |
| 10,219,811 | B2 | 3/2019 | Haider et al. |
| 10,219,832 | B2 | 3/2019 | Bagwell et al. |
| 10,220,522 | B2 | 3/2019 | Rockrohr |
| 10,226,239 | B2 | 3/2019 | Nicholas et al. |
| 10,226,249 | B2 | 3/2019 | Jaworek et al. |
| 10,226,250 | B2 | 3/2019 | Beckman et al. |
| 10,226,251 | B2 | 3/2019 | Scheib et al. |
| 10,226,274 | B2 | 3/2019 | Worrell et al. |
| 10,231,634 | B2 | 3/2019 | Zand et al. |
| 10,231,653 | B2 | 3/2019 | Bohm et al. |
| 10,231,734 | B2 | 3/2019 | Thompson et al. |
| 10,231,794 | B2 | 3/2019 | Shelton, IV et al. |
| 10,238,385 | B2 | 3/2019 | Yates et al. |
| 10,238,386 | B2 | 3/2019 | Overmyer et al. |
| 10,238,387 | B2 | 3/2019 | Yates et al. |
| 10,238,389 | B2 | 3/2019 | Yates et al. |
| 10,238,390 | B2 | 3/2019 | Harris et al. |
| 10,238,391 | B2 | 3/2019 | Leimbach et al. |
| D844,666 | S | 4/2019 | Espeleta et al. |
| D844,667 | S | 4/2019 | Espeleta et al. |
| D845,342 | S | 4/2019 | Espeleta et al. |
| D847,199 | S | 4/2019 | Whitmore |
| 10,244,991 | B2 | 4/2019 | Shademan et al. |
| 10,245,027 | B2 | 4/2019 | Shelton, IV et al. |
| 10,245,028 | B2 | 4/2019 | Shelton, IV et al. |
| 10,245,029 | B2 | 4/2019 | Hunter et al. |
| 10,245,030 | B2 | 4/2019 | Hunter et al. |
| 10,245,032 | B2 | 4/2019 | Shelton, IV |
| 10,245,033 | B2 | 4/2019 | Overmyer et al. |
| 10,245,034 | B2 | 4/2019 | Shelton, IV et al. |
| 10,245,035 | B2 | 4/2019 | Swayze et al. |
| 10,245,038 | B2 | 4/2019 | Hopkins et al. |
| 10,245,058 | B2 | 4/2019 | Omori et al. |
| 10,251,645 | B2 | 4/2019 | Kostrzewski |
| 10,251,648 | B2 | 4/2019 | Harris et al. |
| 10,251,649 | B2 | 4/2019 | Schellin et al. |
| 10,251,725 | B2 | 4/2019 | Valentine et al. |
| 10,258,322 | B2 | 4/2019 | Fanton et al. |
| 10,258,330 | B2 | 4/2019 | Shelton, IV et al. |
| 10,258,331 | B2 | 4/2019 | Shelton, IV et al. |
| 10,258,332 | B2 | 4/2019 | Schmid et al. |
| 10,258,333 | B2 | 4/2019 | Shelton, IV et al. |
| 10,258,336 | B2 | 4/2019 | Baxter, III et al. |
| 10,258,363 | B2 | 4/2019 | Worrell et al. |
| 10,258,418 | B2 | 4/2019 | Shelton, IV et al. |
| 10,264,797 | B2 | 4/2019 | Zhang et al. |
| 10,265,065 | B2 | 4/2019 | Shelton, IV et al. |
| 10,265,067 | B2 | 4/2019 | Yates et al. |
| 10,265,068 | B2 | 4/2019 | Harris et al. |
| 10,265,072 | B2 | 4/2019 | Shelton, IV et al. |
| 10,265,073 | B2 | 4/2019 | Scheib et al. |
| 10,265,074 | B2 | 4/2019 | Shelton, IV et al. |
| 10,265,090 | B2 | 4/2019 | Ingmanson et al. |
| 10,271,840 | B2 | 4/2019 | Sapre |
| 10,271,844 | B2 | 4/2019 | Valentine et al. |
| 10,271,845 | B2 | 4/2019 | Shelton, IV |
| 10,271,846 | B2 | 4/2019 | Shelton, IV et al. |
| 10,271,847 | B2 | 4/2019 | Racenet et al. |
| 10,271,849 | B2 | 4/2019 | Vendely et al. |
| 10,271,851 | B2 | 4/2019 | Shelton, IV et al. |
| D847,989 | S | 5/2019 | Shelton, IV et al. |
| D848,473 | S | 5/2019 | Zhu et al. |
| D849,046 | S | 5/2019 | Kuo et al. |
| 10,278,696 | B2 | 5/2019 | Gurumurthy et al. |
| 10,278,697 | B2 | 5/2019 | Shelton, IV et al. |
| 10,278,702 | B2 | 5/2019 | Shelton, IV et al. |
| 10,278,703 | B2 | 5/2019 | Nativ et al. |
| 10,278,707 | B2 | 5/2019 | Thompson et al. |
| 10,278,722 | B2 | 5/2019 | Shelton, IV et al. |
| 10,278,780 | B2 | 5/2019 | Shelton, IV |
| 10,285,694 | B2 | 5/2019 | Viola et al. |
| 10,285,695 | B2 | 5/2019 | Jaworek et al. |
| 10,285,699 | B2 | 5/2019 | Vendely et al. |
| 10,285,700 | B2 | 5/2019 | Scheib |
| 10,285,705 | B2 | 5/2019 | Shelton, IV et al. |
| 10,285,724 | B2 | 5/2019 | Faller et al. |
| 10,285,750 | B2 | 5/2019 | Coulson et al. |
| 10,292,701 | B2 | 5/2019 | Scheib et al. |
| 10,292,704 | B2 | 5/2019 | Harris et al. |
| 10,292,707 | B2 | 5/2019 | Shelton, IV et al. |
| 10,293,100 | B2 | 5/2019 | Shelton, IV et al. |
| 10,293,553 | B2 | 5/2019 | Racenet et al. |
| 10,299,787 | B2 | 5/2019 | Shelton, IV |
| 10,299,788 | B2 | 5/2019 | Heinrich et al. |
| 10,299,789 | B2 | 5/2019 | Marczyk et al. |
| 10,299,790 | B2 | 5/2019 | Beardsley |
| 10,299,792 | B2 | 5/2019 | Huitema et al. |
| 10,299,817 | B2 | 5/2019 | Shelton, IV et al. |
| 10,299,818 | B2 | 5/2019 | Riva |
| 10,299,878 | B2 | 5/2019 | Shelton, IV et al. |
| 10,303,851 | B2 | 5/2019 | Nguyen et al. |
| D850,617 | S | 6/2019 | Shelton, IV et al. |
| D851,676 | S | 6/2019 | Foss et al. |
| D851,762 | S | 6/2019 | Shelton, IV et al. |
| 10,307,159 | B2 | 6/2019 | Harris et al. |
| 10,307,160 | B2 | 6/2019 | Vendely et al. |
| 10,307,161 | B2 | 6/2019 | Jankowski |
| 10,307,163 | B2 | 6/2019 | Moore et al. |
| 10,307,170 | B2 | 6/2019 | Parfett et al. |
| 10,307,202 | B2 | 6/2019 | Smith et al. |
| 10,314,559 | B2 | 6/2019 | Razzaque et al. |
| 10,314,577 | B2 | 6/2019 | Laurent et al. |
| 10,314,578 | B2 | 6/2019 | Leimbach et al. |
| 10,314,579 | B2 | 6/2019 | Chowaniec et al. |
| 10,314,580 | B2 | 6/2019 | Scheib et al. |
| 10,314,582 | B2 | 6/2019 | Shelton, IV et al. |
| 10,314,584 | B2 | 6/2019 | Scirica et al. |
| 10,314,587 | B2 | 6/2019 | Harris et al. |
| 10,314,588 | B2 | 6/2019 | Turner et al. |
| 10,314,589 | B2 | 6/2019 | Shelton, IV et al. |
| 10,314,590 | B2 | 6/2019 | Shelton, IV et al. |
| 10,315,566 | B2 | 6/2019 | Choi et al. |
| 10,321,907 | B2 | 6/2019 | Shelton, IV et al. |
| 10,321,909 | B2 | 6/2019 | Shelton, IV et al. |
| 10,321,927 | B2 | 6/2019 | Hinman |
| 10,327,743 | B2 | 6/2019 | St. Goar et al. |
| 10,327,764 | B2 | 6/2019 | Harris et al. |
| 10,327,765 | B2 | 6/2019 | Timm et al. |

(56) References Cited

U.S. PATENT DOCUMENTS

| | | | |
|---|---|---|---|
| 10,327,767 | B2 | 6/2019 | Shelton, IV et al. |
| 10,327,769 | B2 | 6/2019 | Overmyer et al. |
| 10,327,776 | B2 | 6/2019 | Harris et al. |
| 10,327,777 | B2 | 6/2019 | Harris et al. |
| D854,032 | S | 7/2019 | Jones et al. |
| D854,151 | S | 7/2019 | Shelton, IV et al. |
| 10,335,144 | B2 | 7/2019 | Shelton, IV et al. |
| 10,335,145 | B2 | 7/2019 | Harris et al. |
| 10,335,147 | B2 | 7/2019 | Rector et al. |
| 10,335,148 | B2 | 7/2019 | Shelton, IV et al. |
| 10,335,149 | B2 | 7/2019 | Baxter, III et al. |
| 10,335,150 | B2 | 7/2019 | Shelton, IV |
| 10,335,151 | B2 | 7/2019 | Shelton, IV et al. |
| 10,337,148 | B2 | 7/2019 | Rouse et al. |
| 10,342,533 | B2 | 7/2019 | Shelton, IV et al. |
| 10,342,535 | B2 | 7/2019 | Scheib et al. |
| 10,342,541 | B2 | 7/2019 | Shelton, IV et al. |
| 10,342,543 | B2 | 7/2019 | Shelton, IV et al. |
| 10,342,623 | B2 | 7/2019 | Huelman et al. |
| 10,349,937 | B2 | 7/2019 | Williams |
| 10,349,939 | B2 | 7/2019 | Shelton, IV et al. |
| 10,349,941 | B2 | 7/2019 | Marczyk et al. |
| 10,349,963 | B2 | 7/2019 | Fiksen et al. |
| 10,350,016 | B2 | 7/2019 | Burbank et al. |
| 10,357,246 | B2 | 7/2019 | Shelton, IV et al. |
| 10,357,247 | B2 | 7/2019 | Shelton, IV et al. |
| 10,357,248 | B2 | 7/2019 | Dalessandro et al. |
| 10,357,252 | B2 | 7/2019 | Harris et al. |
| 10,363,031 | B2 | 7/2019 | Alexander, III et al. |
| 10,363,033 | B2 | 7/2019 | Timm et al. |
| 10,363,036 | B2 | 7/2019 | Yates et al. |
| 10,363,037 | B2 | 7/2019 | Aronhalt et al. |
| D855,634 | S | 8/2019 | Kim |
| D856,359 | S | 8/2019 | Huang et al. |
| 10,368,838 | B2 | 8/2019 | Williams et al. |
| 10,368,861 | B2 | 8/2019 | Baxter, III et al. |
| 10,368,863 | B2 | 8/2019 | Timm et al. |
| 10,368,864 | B2 | 8/2019 | Harris et al. |
| 10,368,865 | B2 | 8/2019 | Harris et al. |
| 10,368,866 | B2 | 8/2019 | Wang et al. |
| 10,368,867 | B2 | 8/2019 | Harris et al. |
| 10,368,892 | B2 | 8/2019 | Stulen et al. |
| 10,374,544 | B2 | 8/2019 | Yokoyama et al. |
| 10,376,263 | B2 | 8/2019 | Morgan et al. |
| 10,383,626 | B2 | 8/2019 | Soltz |
| 10,383,628 | B2 | 8/2019 | Kang et al. |
| 10,383,629 | B2 | 8/2019 | Ross et al. |
| 10,383,630 | B2 | 8/2019 | Shelton, IV et al. |
| 10,383,631 | B2 | 8/2019 | Collings et al. |
| 10,383,633 | B2 | 8/2019 | Shelton, IV et al. |
| 10,383,634 | B2 | 8/2019 | Shelton, IV et al. |
| 10,390,823 | B2 | 8/2019 | Shelton, IV et al. |
| 10,390,825 | B2 | 8/2019 | Shelton, IV et al. |
| 10,390,828 | B2 | 8/2019 | Vendely et al. |
| 10,390,829 | B2 | 8/2019 | Eckert et al. |
| 10,390,830 | B2 | 8/2019 | Schulz |
| 10,390,841 | B2 | 8/2019 | Shelton, IV et al. |
| 10,390,897 | B2 | 8/2019 | Kostrzewski |
| D859,466 | S | 9/2019 | Okada et al. |
| D860,219 | S | 9/2019 | Rasmussen et al. |
| D861,035 | S | 9/2019 | Park et al. |
| 10,398,433 | B2 | 9/2019 | Boudreaux et al. |
| 10,398,434 | B2 | 9/2019 | Shelton, IV et al. |
| 10,398,436 | B2 | 9/2019 | Shelton, IV et al. |
| 10,398,460 | B2 | 9/2019 | Overmyer |
| 10,404,136 | B2 | 9/2019 | Oktavec et al. |
| 10,405,854 | B2 | 9/2019 | Schmid et al. |
| 10,405,857 | B2 | 9/2019 | Shelton, IV et al. |
| 10,405,859 | B2 | 9/2019 | Harris et al. |
| 10,405,863 | B2 | 9/2019 | Wise et al. |
| 10,405,914 | B2 | 9/2019 | Manwaring et al. |
| 10,405,932 | B2 | 9/2019 | Overmyer |
| 10,405,937 | B2 | 9/2019 | Black et al. |
| 10,413,155 | B2 | 9/2019 | Inoue |
| 10,413,291 | B2 | 9/2019 | Worthington et al. |
| 10,413,293 | B2 | 9/2019 | Shelton, IV et al. |
| 10,413,294 | B2 | 9/2019 | Shelton, IV et al. |
| 10,413,297 | B2 | 9/2019 | Harris et al. |
| 10,413,370 | B2 | 9/2019 | Yates et al. |
| 10,413,373 | B2 | 9/2019 | Yates et al. |
| 10,420,548 | B2 | 9/2019 | Whitman et al. |
| 10,420,549 | B2 | 9/2019 | Yates et al. |
| 10,420,550 | B2 | 9/2019 | Shelton, IV |
| 10,420,551 | B2 | 9/2019 | Calderoni |
| 10,420,552 | B2 | 9/2019 | Shelton, IV et al. |
| 10,420,553 | B2 | 9/2019 | Shelton, IV et al. |
| 10,420,554 | B2 | 9/2019 | Collings et al. |
| 10,420,555 | B2 | 9/2019 | Shelton, IV et al. |
| 10,420,558 | B2 | 9/2019 | Nalagatla et al. |
| 10,420,559 | B2 | 9/2019 | Marczyk et al. |
| 10,420,560 | B2 | 9/2019 | Shelton, IV et al. |
| 10,420,561 | B2 | 9/2019 | Shelton, IV et al. |
| 10,420,577 | B2 | 9/2019 | Chowaniec et al. |
| D861,707 | S | 10/2019 | Yang |
| D862,518 | S | 10/2019 | Niven et al. |
| D863,343 | S | 10/2019 | Mazlish et al. |
| D864,388 | S | 10/2019 | Barber |
| D865,174 | S | 10/2019 | Auld et al. |
| D865,175 | S | 10/2019 | Widenhouse et al. |
| 10,426,463 | B2 | 10/2019 | Shelton, IV et al. |
| 10,426,466 | B2 | 10/2019 | Contini et al. |
| 10,426,467 | B2 | 10/2019 | Miller et al. |
| 10,426,468 | B2 | 10/2019 | Contini et al. |
| 10,426,469 | B2 | 10/2019 | Shelton, IV et al. |
| 10,426,471 | B2 | 10/2019 | Shelton, IV et al. |
| 10,426,476 | B2 | 10/2019 | Harris et al. |
| 10,426,477 | B2 | 10/2019 | Harris et al. |
| 10,426,478 | B2 | 10/2019 | Shelton, IV et al. |
| 10,426,481 | B2 | 10/2019 | Aronhalt et al. |
| 10,426,555 | B2 | 10/2019 | Crowley et al. |
| 10,433,837 | B2 | 10/2019 | Worthington et al. |
| 10,433,839 | B2 | 10/2019 | Scheib et al. |
| 10,433,840 | B2 | 10/2019 | Shelton, IV et al. |
| 10,433,842 | B2 | 10/2019 | Amariglio et al. |
| 10,433,844 | B2 | 10/2019 | Shelton, IV et al. |
| 10,433,845 | B2 | 10/2019 | Baxter, III et al. |
| 10,433,846 | B2 | 10/2019 | Vendely et al. |
| 10,433,849 | B2 | 10/2019 | Shelton, IV et al. |
| 10,433,918 | B2 | 10/2019 | Shelton, IV et al. |
| 10,441,279 | B2 | 10/2019 | Shelton, IV et al. |
| 10,441,280 | B2 | 10/2019 | Timm et al. |
| 10,441,281 | B2 | 10/2019 | Shelton, IV et al. |
| 10,441,285 | B2 | 10/2019 | Shelton, IV et al. |
| 10,441,286 | B2 | 10/2019 | Shelton, IV et al. |
| 10,441,345 | B2 | 10/2019 | Aldridge et al. |
| 10,441,369 | B2 | 10/2019 | Shelton, IV et al. |
| 10,448,948 | B2 | 10/2019 | Shelton, IV et al. |
| 10,448,950 | B2 | 10/2019 | Shelton, IV et al. |
| 10,448,952 | B2 | 10/2019 | Shelton, IV et al. |
| 10,456,122 | B2 | 10/2019 | Koltz et al. |
| 10,456,132 | B2 | 10/2019 | Gettinger et al. |
| 10,456,133 | B2 | 10/2019 | Yates et al. |
| 10,456,137 | B2 | 10/2019 | Vendely et al. |
| 10,456,140 | B2 | 10/2019 | Shelton, IV et al. |
| D865,796 | S | 11/2019 | Xu et al. |
| 10,463,367 | B2 | 11/2019 | Kostrzewski et al. |
| 10,463,369 | B2 | 11/2019 | Shelton, IV et al. |
| 10,463,370 | B2 | 11/2019 | Yates et al. |
| 10,463,371 | B2 | 11/2019 | Kostrzewski |
| 10,463,372 | B2 | 11/2019 | Shelton, IV et al. |
| 10,463,373 | B2 | 11/2019 | Mozdzierz et al. |
| 10,463,382 | B2 | 11/2019 | Ingmanson et al. |
| 10,463,383 | B2 | 11/2019 | Shelton, IV et al. |
| 10,463,384 | B2 | 11/2019 | Shelton, IV et al. |
| 10,470,762 | B2 | 11/2019 | Leimbach et al. |
| 10,470,763 | B2 | 11/2019 | Yates et al. |
| 10,470,764 | B2 | 11/2019 | Baxter, III et al. |
| 10,470,767 | B2 | 11/2019 | Gleiman et al. |
| 10,470,768 | B2 | 11/2019 | Harris et al. |
| 10,470,769 | B2 | 11/2019 | Shelton, IV et al. |
| 10,471,282 | B2 | 11/2019 | Kirk et al. |
| 10,471,576 | B2 | 11/2019 | Totsu |
| 10,471,607 | B2 | 11/2019 | Butt et al. |
| 10,478,181 | B2 | 11/2019 | Shelton, IV et al. |

(56) References Cited

U.S. PATENT DOCUMENTS 10,478,182 B2 11/2019 Taylor
10,478,185 B2 11/2019 Nicholas
10,478,187 B2 11/2019 Shelton, IV et al.
10,478,188 B2 11/2019 Harris et al.
10,478,189 B2 11/2019 Bear et al.
10,478,190 B2 11/2019 Miller et al.
10,478,207 B2 11/2019 Lathrop
10,482,292 B2 11/2019 Clouser et al.
10,485,536 B2 11/2019 Ming et al.
10,485,537 B2 11/2019 Yates et al.
10,485,539 B2 11/2019 Shelton, IV et al.
10,485,541 B2 11/2019 Shelton, IV et al.
10,485,542 B2 11/2019 Shelton, IV et al.
10,485,543 B2 11/2019 Shelton, IV et al.
10,485,546 B2 11/2019 Shelton, IV et al.
10,485,547 B2 11/2019 Shelton, IV et al.
D869,655 S 12/2019 Shelton, IV et al.
D870,742 S 12/2019 Cornell
10,492,783 B2 12/2019 Shelton, IV et al.
10,492,785 B2 12/2019 Overmyer et al.
10,492,787 B2 12/2019 Smith et al.
10,492,814 B2 12/2019 Snow et al.
10,492,847 B2 12/2019 Godara et al.
10,492,851 B2 12/2019 Hughett, Sr. et al.
10,498,269 B2 12/2019 Zemlok et al.
10,499,890 B2 12/2019 Shelton, IV et al.
10,499,914 B2 12/2019 Huang et al.
10,499,917 B2 12/2019 Scheib et al.
10,499,918 B2 12/2019 Schellin et al.
10,500,000 B2 12/2019 Swayze et al.
10,500,004 B2 12/2019 Hanuschik et al.
10,500,309 B2 12/2019 Shah et al.
10,507,034 B2 12/2019 Timm
10,508,720 B2 12/2019 Nicholas
10,512,461 B2 12/2019 Gupta et al.
10,512,462 B2 12/2019 Felder et al.
10,512,464 B2 12/2019 Park et al.
10,517,590 B2 12/2019 Giordano et al.
10,517,592 B2 12/2019 Shelton, IV et al.
10,517,594 B2 12/2019 Shelton, IV et al.
10,517,595 B2 12/2019 Hunter et al.
10,517,596 B2 12/2019 Hunter et al.
10,517,599 B2 12/2019 Baxter, III et al.
10,517,682 B2 12/2019 Giordano et al.
10,524,784 B2 1/2020 Kostrzewski
10,524,787 B2 1/2020 Shelton, IV et al.
10,524,788 B2 1/2020 Vendely et al.
10,524,789 B2 1/2020 Swayze et al.
10,524,790 B2 1/2020 Shelton, IV et al.
10,524,795 B2 1/2020 Nalagatla et al.
10,524,870 B2 1/2020 Saraliev et al.
10,531,874 B2 1/2020 Morgan et al.
10,531,887 B2 1/2020 Shelton, IV et al.
10,537,324 B2 1/2020 Shelton, IV et al.
10,537,325 B2 1/2020 Bakos et al.
10,537,351 B2 1/2020 Shelton, IV et al.
10,542,908 B2 1/2020 Mei et al.
10,542,974 B2 1/2020 Yates et al.
10,542,976 B2 1/2020 Calderoni et al.
10,542,978 B2 1/2020 Chowaniec et al.
10,542,979 B2 1/2020 Shelton, IV et al.
10,542,982 B2 1/2020 Beckman et al.
10,542,985 B2 1/2020 Zhan et al.
10,542,988 B2 1/2020 Schellin et al.
10,542,991 B2 1/2020 Shelton, IV et al.
10,548,504 B2 2/2020 Shelton, IV et al.
10,548,593 B2 2/2020 Shelton, IV et al.
10,548,600 B2 2/2020 Shelton, IV et al.
10,548,673 B2 2/2020 Harris et al.
10,561,412 B2 2/2020 Bookbinder et al.
10,561,418 B2 2/2020 Richard et al.
10,561,419 B2 2/2020 Beardsley
10,561,420 B2 2/2020 Harris et al.
10,561,422 B2 2/2020 Schellin et al.
10,561,432 B2 2/2020 Estrella et al.
10,561,474 B2 2/2020 Adams et al.
10,562,160 B2 2/2020 Iwata et al.
10,568,493 B2 2/2020 Blase et al.
10,568,621 B2 2/2020 Shelton, IV et al.
10,568,624 B2 2/2020 Shelton, IV et al.
10,568,625 B2 2/2020 Harris et al.
10,568,626 B2 2/2020 Shelton, IV et al.
10,568,629 B2 2/2020 Shelton, IV et al.
10,568,632 B2 2/2020 Miller et al.
10,568,652 B2 2/2020 Hess et al.
10,569,071 B2 2/2020 Harris et al.
D879,808 S 3/2020 Harris et al.
D879,809 S 3/2020 Harris et al.
10,575,868 B2 3/2020 Hall et al.
10,580,320 B2 3/2020 Kamiguchi et al.
10,582,928 B2 3/2020 Hunter et al.
10,588,231 B2 3/2020 Sgroi, Jr. et al.
10,588,623 B2 3/2020 Schmid et al.
10,588,625 B2 3/2020 Weaner et al.
10,588,626 B2 3/2020 Overmyer et al.
10,588,629 B2 3/2020 Malinouskas et al.
10,588,630 B2 3/2020 Shelton, IV et al.
10,588,631 B2 3/2020 Shelton, IV et al.
10,588,632 B2 3/2020 Shelton, IV et al.
10,588,633 B2 3/2020 Shelton, IV et al.
10,589,410 B2 3/2020 Aho
10,595,835 B2 3/2020 Kerr et al.
10,595,862 B2 3/2020 Shelton, IV et al.
10,595,882 B2 3/2020 Parfett et al.
10,595,887 B2 3/2020 Shelton, IV et al.
10,595,929 B2 3/2020 Boudreaux et al.
10,603,036 B2 3/2020 Hunter et al.
10,603,039 B2 3/2020 Vendely et al.
10,603,041 B2 3/2020 Miller et al.
10,603,117 B2 3/2020 Schings et al.
10,603,128 B2 3/2020 Zergiebel et al.
D882,783 S 4/2020 Shelton, IV et al.
10,610,224 B2 4/2020 Shelton, IV et al.
10,610,225 B2 4/2020 Reed et al.
10,610,236 B2 4/2020 Baril
10,610,313 B2 4/2020 Bailey et al.
10,610,346 B2 4/2020 Schwartz
10,614,184 B2 4/2020 Solki
10,617,411 B2 4/2020 Williams
10,617,412 B2 4/2020 Shelton, IV et al.
10,617,413 B2 4/2020 Shelton, IV et al.
10,617,414 B2 4/2020 Shelton, IV et al.
10,617,416 B2 4/2020 Leimbach et al.
10,617,417 B2 4/2020 Baxter, III et al.
10,617,418 B2 4/2020 Barton et al.
10,617,420 B2 4/2020 Shelton, IV et al.
10,617,438 B2 4/2020 O'Keefe et al.
10,624,616 B2 4/2020 Mukherjee et al.
10,624,630 B2 4/2020 Deville et al.
10,624,633 B2 4/2020 Shelton, IV et al.
10,624,634 B2 4/2020 Shelton, IV et al.
10,624,635 B2 4/2020 Harris et al.
10,624,709 B2 4/2020 Remm
10,624,861 B2 4/2020 Widenhouse et al.
10,625,062 B2 4/2020 Matlock et al.
10,631,857 B2 4/2020 Kostrzewski
10,631,858 B2 4/2020 Burbank
10,631,859 B2 4/2020 Shelton, IV et al.
10,631,860 B2 4/2020 Bakos et al.
10,636,104 B2 4/2020 Mazar et al.
10,639,018 B2 5/2020 Shelton, IV et al.
10,639,034 B2 5/2020 Harris et al.
10,639,035 B2 5/2020 Shelton, IV et al.
10,639,036 B2 5/2020 Yates et al.
10,639,037 B2 5/2020 Shelton, IV et al.
10,639,089 B2 5/2020 Manwaring et al.
10,639,115 B2 5/2020 Shelton, IV et al.
10,642,633 B1 5/2020 Chopra et al.
10,645,905 B2 5/2020 Gandola et al.
10,646,220 B2 5/2020 Shelton, IV et al.
10,646,292 B2 5/2020 Solomon et al.
10,653,413 B2 5/2020 Worthington et al.
10,653,417 B2 5/2020 Shelton, IV et al.
10,653,435 B2 5/2020 Shelton, IV et al.

(56) References Cited

U.S. PATENT DOCUMENTS 10,660,640 B2 5/2020 Yates et al.
10,667,408 B2 5/2020 Sgroi, Jr. et al.
D888,953 S 6/2020 Baxter, III et al.
10,667,808 B2 6/2020 Baxter, III et al.
10,667,809 B2 6/2020 Bakos et al.
10,667,810 B2 6/2020 Shelton, IV et al.
10,667,811 B2 6/2020 Harris et al.
10,667,818 B2 6/2020 McLain et al.
10,674,895 B2 6/2020 Yeung et al.
10,675,021 B2 6/2020 Harris et al.
10,675,024 B2 6/2020 Shelton, IV et al.
10,675,025 B2 6/2020 Swayze et al.
10,675,026 B2 6/2020 Harris et al.
10,675,028 B2 6/2020 Shelton, IV et al.
10,675,035 B2 6/2020 Zingman
10,675,080 B2 6/2020 Woloszko et al.
10,675,102 B2 6/2020 Forgione et al.
10,677,035 B2 6/2020 Balan et al.
10,682,134 B2 6/2020 Shelton, IV et al.
10,682,136 B2 6/2020 Harris et al.
10,682,137 B2 6/2020 Stokes et al.
10,682,138 B2 6/2020 Shelton, IV et al.
10,682,141 B2 6/2020 Moore et al.
10,682,142 B2 6/2020 Shelton, IV et al.
10,687,806 B2 6/2020 Shelton, IV et al.
10,687,809 B2 6/2020 Shelton, IV et al.
10,687,810 B2 6/2020 Shelton, IV et al.
10,687,812 B2 6/2020 Shelton, IV et al.
10,687,813 B2 6/2020 Shelton, IV et al.
10,687,817 B2 6/2020 Shelton, IV et al.
10,687,819 B2 6/2020 Stokes et al.
10,687,904 B2 6/2020 Harris et al.
10,695,053 B2 6/2020 Hess et al.
10,695,055 B2 6/2020 Shelton, IV et al.
10,695,057 B2 6/2020 Shelton, IV et al.
10,695,058 B2 6/2020 Lytle, IV et al.
10,695,062 B2 6/2020 Leimbach et al.
10,695,063 B2 6/2020 Morgan et al.
10,695,074 B2 6/2020 Carusillo
10,695,081 B2 6/2020 Shelton, IV et al.
10,695,119 B2 6/2020 Smith
10,695,123 B2 6/2020 Allen, IV
10,695,187 B2 6/2020 Moskowitz et al.
D890,784 S 7/2020 Shelton, IV et al.
10,702,266 B2 7/2020 Parihar et al.
10,702,267 B2 7/2020 Hess et al.
10,702,270 B2 7/2020 Shelton, IV et al.
10,702,271 B2 7/2020 Aranyi et al.
10,705,660 B2 7/2020 Xiao
10,709,446 B2 7/2020 Harris et al.
10,709,468 B2 7/2020 Shelton, IV et al.
10,709,469 B2 7/2020 Shelton, IV et al.
10,709,496 B2 7/2020 Moua et al.
10,716,563 B2 7/2020 Shelton, IV et al.
10,716,565 B2 7/2020 Shelton, IV et al.
10,716,568 B2 7/2020 Hall et al.
10,716,614 B2 7/2020 Yates et al.
10,717,179 B2 7/2020 Koenig et al.
10,722,232 B2 7/2020 Yates et al.
10,722,233 B2 7/2020 Wellman
10,722,292 B2 7/2020 Arya et al.
10,722,293 B2 7/2020 Arya et al.
10,722,317 B2 7/2020 Ward et al.
D893,717 S 8/2020 Messerly et al.
10,729,432 B2 8/2020 Shelton, IV et al.
10,729,434 B2 8/2020 Harris et al.
10,729,435 B2 8/2020 Richard
10,729,436 B2 8/2020 Shelton, IV et al.
10,729,443 B2 8/2020 Cabrera et al.
10,729,458 B2 8/2020 Stoddard et al.
10,729,501 B2 8/2020 Leimbach et al.
10,729,509 B2 8/2020 Shelton, IV et al.
10,736,616 B2 8/2020 Scheib et al.
10,736,628 B2 8/2020 Yates et al.
10,736,629 B2 8/2020 Shelton, IV et al.
10,736,630 B2 8/2020 Huang et al.
10,736,633 B2 8/2020 Vendely et al.
10,736,634 B2 8/2020 Shelton, IV et al.
10,736,636 B2 8/2020 Baxter, III et al.
10,736,644 B2 8/2020 Windolf et al.
10,736,702 B2 8/2020 Harris et al.
10,737,398 B2 8/2020 Remirez et al.
10,743,849 B2 8/2020 Shelton, IV et al.
10,743,850 B2 8/2020 Hibner et al.
10,743,851 B2 8/2020 Swayze et al.
10,743,868 B2 8/2020 Shelton, IV et al.
10,743,870 B2 8/2020 Hall et al.
10,743,872 B2 8/2020 Leimbach et al.
10,743,873 B2 8/2020 Overmyer et al.
10,743,874 B2 8/2020 Shelton, IV et al.
10,743,875 B2 8/2020 Shelton, IV et al.
10,743,877 B2 8/2020 Shelton, IV et al.
10,743,930 B2 8/2020 Nagtegaal
10,751,048 B2 8/2020 Whitman et al.
10,751,053 B2 8/2020 Harris et al.
10,751,076 B2 8/2020 Laurent et al.
10,751,138 B2 8/2020 Giordano et al.
10,758,229 B2 9/2020 Shelton, IV et al.
10,758,230 B2 9/2020 Shelton, IV et al.
10,758,232 B2 9/2020 Shelton, IV et al.
10,758,233 B2 9/2020 Scheib et al.
10,758,259 B2 9/2020 Demmy et al.
10,765,425 B2 9/2020 Yates et al.
10,765,427 B2 9/2020 Shelton, IV et al.
10,765,429 B2 9/2020 Leimbach et al.
10,765,430 B2 9/2020 Wixey
10,765,432 B2 9/2020 Moore et al.
10,765,442 B2 9/2020 Strobl
10,772,625 B2 9/2020 Shelton, IV et al.
10,772,628 B2 9/2020 Chen et al.
10,772,629 B2 9/2020 Shelton, IV et al.
10,772,630 B2 9/2020 Wixey
10,772,631 B2 9/2020 Zergiebel et al.
10,772,632 B2 9/2020 Kostrzewski
10,772,651 B2 9/2020 Shelton, IV et al.
10,779,818 B2 9/2020 Zemlok et al.
10,779,820 B2 9/2020 Harris et al.
10,779,821 B2 9/2020 Harris et al.
10,779,822 B2 9/2020 Yates et al.
10,779,823 B2 9/2020 Shelton, IV et al.
10,779,824 B2 9/2020 Shelton, IV et al.
10,779,825 B2 9/2020 Shelton, IV et al.
10,779,826 B2 9/2020 Shelton, IV et al.
10,779,903 B2 9/2020 Wise et al.
10,780,539 B2 9/2020 Shelton, IV et al.
10,786,248 B2 9/2020 Rousseau et al.
10,786,253 B2 9/2020 Shelton, IV et al.
10,786,255 B2 9/2020 Hodgkinson et al.
10,792,038 B2 10/2020 Becerra et al.
10,796,471 B2 10/2020 Leimbach et al.
10,799,240 B2 10/2020 Shelton, IV et al.
10,799,306 B2 10/2020 Robinson et al.
10,806,448 B2 10/2020 Shelton, IV et al.
10,806,449 B2 10/2020 Shelton, IV et al.
10,806,450 B2 10/2020 Yates et al.
10,806,451 B2 10/2020 Harris et al.
10,806,453 B2 10/2020 Chen et al.
10,806,479 B2 10/2020 Shelton, IV et al.
10,813,638 B2 10/2020 Shelton, IV et al.
10,813,639 B2 10/2020 Shelton, IV et al.
10,813,640 B2 10/2020 Adams et al.
10,813,641 B2 10/2020 Setser et al.
10,813,683 B2 10/2020 Baxter, III et al.
10,813,705 B2 10/2020 Hares et al.
10,813,710 B2 10/2020 Grubbs
10,820,939 B2 11/2020 Sartor
10,828,028 B2 11/2020 Harris et al.
10,828,030 B2 11/2020 Weir et al.
10,828,032 B2 11/2020 Leimbach et al.
10,828,033 B2 11/2020 Shelton, IV et al.
10,828,089 B2 11/2020 Clark et al.
10,835,245 B2 11/2020 Swayze et al.
10,835,246 B2 11/2020 Shelton, IV et al.
10,835,247 B2 11/2020 Shelton, IV et al.

(56) References Cited

U.S. PATENT DOCUMENTS 10,835,249 B2 11/2020 Schellin et al.
10,835,251 B2 11/2020 Shelton, IV et al.
10,835,330 B2 11/2020 Shelton, IV et al.
10,842,357 B2 11/2020 Moskowitz et al.
10,842,473 B2 11/2020 Scheib et al.
10,842,488 B2 11/2020 Swayze et al.
10,842,489 B2 11/2020 Shelton, IV
10,842,490 B2 11/2020 DiNardo et al.
10,842,491 B2 11/2020 Shelton, IV et al.
10,842,492 B2 11/2020 Shelton, IV et al.
D904,612 S 12/2020 Wynn et al.
D904,613 S 12/2020 Wynn et al.
D906,355 S 12/2020 Messerly et al.
10,849,621 B2 12/2020 Whitfield et al.
10,849,623 B2 12/2020 Dunki-Jacobs et al.
10,849,697 B2 12/2020 Yates et al.
10,856,866 B2 12/2020 Shelton, IV et al.
10,856,867 B2 12/2020 Shelton, IV et al.
10,856,868 B2 12/2020 Shelton, IV et al.
10,856,869 B2 12/2020 Shelton, IV et al.
10,856,870 B2 12/2020 Harris et al.
10,863,981 B2 12/2020 Overmyer et al.
10,863,984 B2 12/2020 Shelton, IV et al.
10,863,986 B2 12/2020 Yates et al.
10,869,663 B2 12/2020 Shelton, IV et al.
10,869,664 B2 12/2020 Shelton, IV
10,869,665 B2 12/2020 Shelton, IV et al.
10,869,666 B2 12/2020 Shelton, IV et al.
10,869,669 B2 12/2020 Shelton, IV et al.
10,874,290 B2 12/2020 Walen et al.
10,874,391 B2 12/2020 Shelton, IV et al.
10,874,392 B2 12/2020 Scirica et al.
10,874,393 B2 12/2020 Satti, III et al.
10,874,396 B2 12/2020 Moore et al.
10,874,399 B2 12/2020 Zhang
10,879,275 B2 12/2020 Li et al.
D907,647 S 1/2021 Siebel et al.
D907,648 S 1/2021 Siebel et al.
D908,216 S 1/2021 Messerly et al.
10,881,395 B2 1/2021 Merchant et al.
10,881,396 B2 1/2021 Shelton, IV et al.
10,881,399 B2 1/2021 Shelton, IV et al.
10,881,401 B2 1/2021 Baber et al.
10,881,446 B2 1/2021 Strobl
10,888,318 B2 1/2021 Parihar et al.
10,888,321 B2 1/2021 Shelton, IV et al.
10,888,322 B2 1/2021 Morgan et al.
10,888,323 B2 1/2021 Chen et al.
10,888,325 B2 1/2021 Harris et al.
10,888,328 B2 1/2021 Shelton, IV et al.
10,888,329 B2 1/2021 Moore et al.
10,888,330 B2 1/2021 Moore et al.
10,888,369 B2 1/2021 Messerly et al.
10,892,899 B2 1/2021 Shelton, IV et al.
10,893,853 B2 1/2021 Shelton, IV et al.
10,893,863 B2 1/2021 Shelton, IV et al.
10,893,864 B2 1/2021 Harris et al.
10,893,867 B2 1/2021 Leimbach et al.
10,898,183 B2 1/2021 Shelton, IV et al.
10,898,184 B2 1/2021 Yates et al.
10,898,185 B2 1/2021 Overmyer et al.
10,898,186 B2 1/2021 Bakos et al.
10,898,190 B2 1/2021 Yates et al.
10,898,193 B2 1/2021 Shelton, IV et al.
10,898,194 B2 1/2021 Moore et al.
10,898,195 B2 1/2021 Moore et al.
10,903,685 B2 1/2021 Yates et al.
D910,847 S 2/2021 Shelton, IV et al.
10,905,415 B2 2/2021 DiNardo et al.
10,905,418 B2 2/2021 Shelton, IV et al.
10,905,420 B2 2/2021 Jasemian et al.
10,905,422 B2 2/2021 Bakos et al.
10,905,423 B2 2/2021 Baber et al.
10,905,426 B2 2/2021 Moore et al.
10,905,427 B2 2/2021 Moore et al.
10,911,515 B2 2/2021 Biasi et al.
10,912,559 B2 2/2021 Harris et al.
10,912,562 B2 2/2021 Dunki-Jacobs et al.
10,912,575 B2 2/2021 Shelton, IV et al.
10,918,364 B2 2/2021 Applegate et al.
10,918,380 B2 2/2021 Morgan et al.
10,918,385 B2 2/2021 Overmyer et al.
10,918,386 B2 2/2021 Shelton, IV et al.
10,919,156 B2 2/2021 Roberts et al.
10,925,600 B2 2/2021 McCuen
10,925,605 B2 2/2021 Moore et al.
D914,878 S 3/2021 Shelton, IV et al.
10,932,772 B2 3/2021 Shelton, IV et al.
10,932,774 B2 3/2021 Shelton, IV
10,932,775 B2 3/2021 Shelton, IV et al.
10,932,778 B2 3/2021 Smith et al.
10,932,779 B2 3/2021 Vendely et al.
10,932,784 B2 3/2021 Mozdzierz et al.
10,932,804 B2 3/2021 Scheib et al.
10,932,806 B2 3/2021 Shelton, IV et al.
10,932,872 B2 3/2021 Shelton, IV et al.
10,944,728 B2 3/2021 Wiener et al.
10,945,727 B2 3/2021 Shelton, IV et al.
10,945,728 B2 3/2021 Morgan et al.
10,945,729 B2 3/2021 Shelton, IV et al.
10,945,731 B2 3/2021 Baxter, III et al.
10,952,708 B2 3/2021 Scheib et al.
10,952,726 B2 3/2021 Chowaniec
10,952,727 B2 3/2021 Giordano et al.
10,952,728 B2 3/2021 Shelton, IV et al.
10,952,759 B2 3/2021 Messerly et al.
10,952,767 B2 3/2021 Kostrzewski et al.
10,959,722 B2 3/2021 Morgan et al.
10,959,725 B2 3/2021 Kerr et al.
10,959,726 B2 3/2021 Williams et al.
10,959,727 B2 3/2021 Hunter et al.
10,959,731 B2 3/2021 Casasanta, Jr. et al.
10,959,744 B2 3/2021 Shelton, IV et al.
10,959,797 B2 3/2021 Licht et al.
D917,500 S 4/2021 Siebel et al.
10,966,627 B2 4/2021 Shelton, IV et al.
10,966,717 B2 4/2021 Shah et al.
10,966,718 B2 4/2021 Shelton, IV et al.
10,966,791 B2 4/2021 Harris et al.
10,973,515 B2 4/2021 Harris et al.
10,973,516 B2 4/2021 Shelton, IV et al.
10,973,517 B2 4/2021 Wixey
10,973,519 B2 4/2021 Weir et al.
10,973,520 B2 4/2021 Shelton, IV et al.
10,980,534 B2 4/2021 Yates et al.
10,980,535 B2 4/2021 Yates et al.
10,980,536 B2 4/2021 Weaner et al.
10,980,537 B2 4/2021 Shelton, IV et al.
10,980,538 B2 4/2021 Nalagatla et al.
10,980,539 B2 4/2021 Harris et al.
10,980,560 B2 4/2021 Shelton, IV et al.
10,983,646 B2 4/2021 Yoon et al.
10,987,102 B2 4/2021 Gonzalez et al.
10,987,178 B2 4/2021 Shelton, IV et al.
10,993,713 B2 5/2021 Shelton, IV et al.
10,993,715 B2 5/2021 Shelton, IV et al.
10,993,716 B2 5/2021 Shelton, IV et al.
10,993,717 B2 5/2021 Shelton, IV et al.
11,000,274 B2 5/2021 Shelton, IV et al.
11,000,275 B2 5/2021 Shelton, IV et al.
11,000,277 B2 5/2021 Giordano et al.
11,000,278 B2 5/2021 Shelton, IV et al.
11,000,279 B2 5/2021 Shelton, IV et al.
11,005,291 B2 5/2021 Calderoni
11,006,951 B2 5/2021 Giordano et al.
11,006,955 B2 5/2021 Shelton, IV et al.
11,007,004 B2 5/2021 Shelton, IV et al.
11,007,022 B2 5/2021 Shelton, IV et al.
11,013,511 B2 5/2021 Huang et al.
11,013,552 B2 5/2021 Widenhouse et al.
11,013,563 B2 5/2021 Shelton, IV et al.
11,020,016 B2 6/2021 Wallace et al.
11,020,112 B2 6/2021 Shelton, IV et al.
11,020,113 B2 6/2021 Shelton, IV et al.

(56) References Cited

U.S. PATENT DOCUMENTS 11,020,114 B2 6/2021 Shelton, IV et al.
11,020,115 B2 6/2021 Scheib et al.
11,026,678 B2 6/2021 Overmyer et al.
11,026,680 B2 6/2021 Shelton, IV et al.
11,026,684 B2 6/2021 Shelton, IV et al.
11,026,687 B2 6/2021 Shelton, IV et al.
11,026,712 B2 6/2021 Shelton, IV et al.
11,026,713 B2 6/2021 Stokes et al.
11,026,751 B2 6/2021 Shelton, IV et al.
11,033,267 B2 6/2021 Shelton, IV et al.
11,039,834 B2 6/2021 Harris et al.
11,039,836 B2 6/2021 Shelton, IV et al.
11,039,837 B2 6/2021 Shelton, IV et al.
11,039,849 B2 6/2021 Bucciaglia et al.
11,045,189 B2 6/2021 Yates et al.
11,045,191 B2 6/2021 Shelton, IV et al.
11,045,192 B2 6/2021 Harris et al.
11,045,196 B2 6/2021 Olson et al.
11,045,197 B2 6/2021 Shelton, IV et al.
11,045,199 B2 6/2021 Mozdzierz et al.
11,045,270 B2 6/2021 Shelton, IV et al.
11,051,807 B2 7/2021 Shelton, IV et al.
11,051,810 B2 7/2021 Harris et al.
11,051,811 B2 7/2021 Shelton, IV et al.
11,051,813 B2 7/2021 Shelton, IV et al.
11,051,836 B2 7/2021 Shelton, IV et al.
11,051,840 B2 7/2021 Shelton, IV et al.
11,051,873 B2 7/2021 Wiener et al.
11,058,418 B2 7/2021 Shelton, IV et al.
11,058,420 B2 7/2021 Shelton, IV et al.
11,058,422 B2 7/2021 Harris et al.
11,058,423 B2 7/2021 Shelton, IV et al.
11,058,424 B2 7/2021 Shelton, IV et al.
11,058,425 B2 7/2021 Widenhouse et al.
11,058,426 B2 7/2021 Nalagatla et al.
11,058,498 B2 7/2021 Shelton, IV et al.
11,064,997 B2 7/2021 Shelton, IV et al.
11,064,998 B2 7/2021 Shelton, IV
11,065,048 B2 7/2021 Messerly et al.
11,069,012 B2 7/2021 Shelton, IV et al.
11,071,542 B2 7/2021 Chen et al.
11,071,543 B2 7/2021 Shelton, IV et al.
11,071,545 B2 7/2021 Baber et al.
11,071,554 B2 7/2021 Parfett et al.
11,071,560 B2 7/2021 Deck et al.
11,076,853 B2 8/2021 Parfett et al.
11,076,854 B2 8/2021 Baber et al.
11,076,921 B2 8/2021 Shelton, IV et al.
11,076,929 B2 8/2021 Shelton, IV et al.
11,083,452 B2 8/2021 Schmid et al.
11,083,453 B2 8/2021 Shelton, IV et al.
11,083,454 B2 8/2021 Harris et al.
11,083,455 B2 8/2021 Shelton, IV et al.
11,083,456 B2 8/2021 Shelton, IV et al.
11,083,457 B2 8/2021 Shelton, IV et al.
11,083,458 B2 8/2021 Harris et al.
11,090,045 B2 8/2021 Shelton, IV
11,090,046 B2 8/2021 Shelton, IV et al.
11,090,047 B2 8/2021 Shelton, IV et al.
11,090,048 B2 8/2021 Fanelli et al.
11,090,049 B2 8/2021 Bakos et al.
11,090,075 B2 8/2021 Hunter et al.
11,096,688 B2 8/2021 Shelton, IV et al.
11,096,689 B2 8/2021 Overmyer et al.
11,100,631 B2 8/2021 Yates et al.
11,103,241 B2 8/2021 Yates et al.
11,103,248 B2 8/2021 Shelton, IV et al.
11,103,268 B2 8/2021 Shelton, IV et al.
11,103,269 B2 8/2021 Shelton, IV et al.
11,109,858 B2 9/2021 Shelton, IV et al.
11,109,859 B2 9/2021 Overmyer et al.
11,109,860 B2 9/2021 Shelton, IV et al.
11,109,866 B2 9/2021 Shelton, IV et al.
11,109,878 B2 9/2021 Shelton, IV et al.
11,109,925 B2 9/2021 Cooper et al.
11,116,485 B2 9/2021 Scheib et al.
11,116,502 B2 9/2021 Shelton, IV et al.
11,116,594 B2 9/2021 Beardsley
11,123,069 B2 9/2021 Baxter, III et al.
11,123,070 B2 9/2021 Shelton, IV et al.
11,129,611 B2 9/2021 Shelton, IV et al.
11,129,613 B2 9/2021 Harris et al.
11,129,615 B2 9/2021 Scheib et al.
11,129,616 B2 9/2021 Shelton, IV et al.
11,129,634 B2 9/2021 Scheib et al.
11,129,636 B2 9/2021 Shelton, IV et al.
11,129,666 B2 9/2021 Messerly et al.
11,129,680 B2 9/2021 Shelton, IV et al.
11,132,462 B2 9/2021 Shelton, IV et al.
11,133,106 B2 9/2021 Shelton, IV et al.
11,134,938 B2 10/2021 Timm et al.
11,134,940 B2 10/2021 Shelton, IV et al.
11,134,942 B2 10/2021 Harris et al.
11,134,943 B2 10/2021 Giordano et al.
11,134,944 B2 10/2021 Wise et al.
11,134,947 B2 10/2021 Shelton, IV et al.
11,135,352 B2 10/2021 Shelton, IV et al.
11,141,153 B2 10/2021 Shelton, IV et al.
11,141,154 B2 10/2021 Shelton, IV et al.
11,141,155 B2 10/2021 Shelton, IV
11,141,156 B2 10/2021 Shelton, IV
11,141,159 B2 10/2021 Scheib et al.
11,141,160 B2 10/2021 Shelton, IV et al.
11,147,547 B2 10/2021 Shelton, IV et al.
11,147,549 B2 10/2021 Timm et al.
11,147,551 B2 10/2021 Shelton, IV
11,147,553 B2 10/2021 Shelton, IV
11,147,554 B2 10/2021 Aronhalt et al.
11,154,296 B2 10/2021 Aronhalt et al.
11,154,297 B2 10/2021 Swayze et al.
11,154,298 B2 10/2021 Timm et al.
11,154,299 B2 10/2021 Shelton, IV et al.
11,154,300 B2 10/2021 Nalagatla et al.
11,154,301 B2 10/2021 Beckman et al.
11,160,551 B2 11/2021 Shelton, IV et al.
11,160,553 B2 11/2021 Simms et al.
11,160,601 B2 11/2021 Worrell et al.
11,166,716 B2 11/2021 Shelton, IV et al.
11,166,717 B2 11/2021 Shelton, IV et al.
11,166,720 B2 11/2021 Giordano et al.
11,166,772 B2 11/2021 Shelton, IV et al.
11,166,773 B2 11/2021 Ragosta et al.
11,172,580 B2 11/2021 Gaertner, II
11,172,927 B2 11/2021 Shelton, IV
11,172,929 B2 11/2021 Shelton, IV
11,179,150 B2 11/2021 Yates et al.
11,179,151 B2 11/2021 Shelton, IV et al.
11,179,152 B2 11/2021 Morgan et al.
11,179,153 B2 11/2021 Shelton, IV
11,179,155 B2 11/2021 Shelton, IV et al.
11,179,208 B2 11/2021 Yates et al.
11,185,325 B2 11/2021 Shelton, IV et al.
11,185,330 B2 11/2021 Huitema et al.
11,191,539 B2 12/2021 Overmyer et al.
11,191,540 B2 12/2021 Aronhalt et al.
11,191,543 B2 12/2021 Overmyer et al.
11,191,545 B2 12/2021 Vendely et al.
11,197,668 B2 12/2021 Shelton, IV et al.
11,197,670 B2 12/2021 Shelton, IV et al.
11,197,671 B2 12/2021 Shelton, IV et al.
11,197,672 B2 12/2021 Dunki-Jacobs et al.
11,202,570 B2 12/2021 Shelton, IV et al.
11,202,631 B2 12/2021 Shelton, IV et al.
11,202,633 B2 12/2021 Harris et al.
11,207,064 B2 12/2021 Shelton, IV et al.
11,207,065 B2 12/2021 Harris et al.
11,207,067 B2 12/2021 Shelton, IV et al.
11,207,089 B2 12/2021 Kostrzewski et al.
11,207,090 B2 12/2021 Shelton, IV et al.
11,207,146 B2 12/2021 Shelton, IV et al.
11,213,293 B2 1/2022 Worthington et al.
11,213,294 B2 1/2022 Shelton, IV et al.
11,213,302 B2 1/2022 Parfett et al.
11,213,359 B2 1/2022 Shelton, IV et al.

(56) References Cited

U.S. PATENT DOCUMENTS 11,219,453 B2 1/2022 Shelton, IV et al.
11,219,455 B2 1/2022 Shelton, IV et al.
11,224,423 B2 1/2022 Shelton, IV et al.
11,224,426 B2 1/2022 Shelton, IV et al.
11,224,427 B2 1/2022 Shelton, IV et al.
11,224,428 B2 1/2022 Scott et al.
11,224,454 B2 1/2022 Shelton, IV et al.
11,224,497 B2 1/2022 Shelton, IV et al.
11,229,436 B2 1/2022 Shelton, IV et al.
11,229,437 B2 1/2022 Shelton, IV et al.
11,234,698 B2 2/2022 Shelton, IV et al.
11,234,700 B2 2/2022 Ragosta et al.
11,241,229 B2 2/2022 Shelton, IV et al.
11,241,230 B2 2/2022 Shelton, IV et al.
11,241,235 B2 2/2022 Shelton, IV et al.
11,246,590 B2 2/2022 Swayze et al.
11,246,592 B2 2/2022 Shelton, IV et al.
11,246,616 B2 2/2022 Shelton, IV et al.
11,246,618 B2 2/2022 Hall et al.
11,246,678 B2 2/2022 Shelton, IV et al.
11,253,254 B2 2/2022 Kimball et al.
11,253,256 B2 2/2022 Harris et al.
11,259,799 B2 3/2022 Overmyer et al.
11,259,803 B2 3/2022 Shelton, IV et al.
11,259,805 B2 3/2022 Shelton, IV et al.
11,259,806 B2 3/2022 Shelton, IV et al.
11,259,807 B2 3/2022 Shelton, IV et al.
11,266,405 B2 3/2022 Shelton, IV et al.
11,266,406 B2 3/2022 Leimbach et al.
11,266,409 B2 3/2022 Huitema et al.
11,266,410 B2 3/2022 Shelton, IV et al.
11,266,468 B2 3/2022 Shelton, IV et al.
11,272,927 B2 3/2022 Swayze et al.
11,272,928 B2 3/2022 Shelton, IV
11,272,931 B2 3/2022 Boudreaux et al.
11,272,938 B2 3/2022 Shelton, IV et al.
11,278,279 B2 3/2022 Morgan et al.
11,278,280 B2 3/2022 Shelton, IV et al.
11,278,284 B2 3/2022 Shelton, IV et al.
11,284,890 B2 3/2022 Nalagatla et al.
11,284,891 B2 3/2022 Shelton, IV et al.
11,284,898 B2 3/2022 Baxter, III et al.
11,284,953 B2 3/2022 Shelton, IV et al.
11,291,440 B2 4/2022 Harris et al.
11,291,441 B2 4/2022 Giordano et al.
11,291,443 B2 4/2022 Viola et al.
11,291,444 B2 4/2022 Boudreaux et al.
11,291,445 B2 4/2022 Shelton, IV et al.
11,291,447 B2 4/2022 Shelton, IV et al.
11,291,449 B2 4/2022 Swensgard et al.
11,291,451 B2 4/2022 Shelton, IV
11,291,465 B2 4/2022 Parihar et al.
11,291,510 B2 4/2022 Shelton, IV et al.
11,298,125 B2 4/2022 Ming et al.
11,298,127 B2 4/2022 Shelton, IV
11,298,128 B2 4/2022 Messerly et al.
11,298,129 B2 4/2022 Bakos et al.
11,298,130 B2 4/2022 Bakos et al.
11,298,132 B2 4/2022 Shelton, IV et al.
11,298,134 B2 4/2022 Huitema et al.
11,304,695 B2 4/2022 Shelton, IV et al.
11,304,696 B2 4/2022 Shelton, IV et al.
11,304,697 B2 4/2022 Fanelli et al.
11,304,699 B2 4/2022 Shelton, IV et al.
11,304,704 B2 4/2022 Thomas et al.
11,311,295 B2 4/2022 Wingardner et al.
D950,728 S 5/2022 Bakos et al.
D952,144 S 5/2022 Boudreaux
11,317,912 B2 5/2022 Jenkins et al.
11,317,978 B2 5/2022 Cameron et al.
11,376,082 B2 7/2022 Shelton, IV et al.
11,406,442 B2 8/2022 Davison et al.
11,413,041 B2 8/2022 Viola et al.
D964,564 S 9/2022 Boudreaux
11,439,391 B2 9/2022 Bruns et al.
11,452,526 B2 9/2022 Ross et al.
D966,512 S 10/2022 Shelton, IV et al.
D967,421 S 10/2022 Shelton. , IV et al.
D971,232 S 11/2022 Siebel et al.
11,484,309 B2 11/2022 Harris et al.
11,523,859 B2 12/2022 Shelton, IV et al.
D974,560 S 1/2023 Shelton, IV et al.
D975,278 S 1/2023 Shelton, IV et al.
D975,850 S 1/2023 Shelton, IV et al.
D975,851 S 1/2023 Shelton, IV et al.
D976,401 S 1/2023 Shelton, IV et al.
11,553,911 B2 1/2023 Shelton, IV et al.
11,564,682 B2 1/2023 Timm et al.
11,583,279 B2 2/2023 Smith et al.
D980,425 S 3/2023 Baxter, III
2001/0000531 A1 4/2001 Casscells et al.
2001/0025183 A1 9/2001 Shahidi
2001/0025184 A1 9/2001 Messerly
2001/0030219 A1 10/2001 Green et al.
2001/0034530 A1 10/2001 Malackowski et al.
2001/0045442 A1 11/2001 Whitman
2002/0014510 A1 2/2002 Richter et al.
2002/0022810 A1 2/2002 Urich
2002/0022836 A1 2/2002 Goble et al.
2002/0022861 A1 2/2002 Jacobs et al.
2002/0023126 A1 2/2002 Flavin
2002/0029032 A1 3/2002 Arkin
2002/0029036 A1 3/2002 Goble et al.
2002/0042620 A1 4/2002 Julian et al.
2002/0045905 A1 4/2002 Gerbi et al.
2002/0054158 A1 5/2002 Asami
2002/0065535 A1 5/2002 Kneifel et al.
2002/0066764 A1 6/2002 Perry et al.
2002/0077660 A1 6/2002 Kayan et al.
2002/0082612 A1 6/2002 Moll et al.
2002/0087048 A1 7/2002 Brock et al.
2002/0087148 A1 7/2002 Brock et al.
2002/0091374 A1 7/2002 Cooper
2002/0095175 A1 7/2002 Brock et al.
2002/0103494 A1 8/2002 Pacey
2002/0111621 A1 8/2002 Wallace et al.
2002/0111624 A1 8/2002 Witt et al.
2002/0116063 A1 8/2002 Giannetti et al.
2002/0117533 A1 8/2002 Milliman et al.
2002/0117534 A1 8/2002 Green et al.
2002/0127265 A1 9/2002 Bowman et al.
2002/0128633 A1 9/2002 Brock et al.
2002/0133236 A1 9/2002 Rousseau
2002/0134811 A1 9/2002 Napier et al.
2002/0135474 A1 9/2002 Sylliassen
2002/0138086 A1 9/2002 Sixto et al.
2002/0143340 A1 10/2002 Kaneko
2002/0151770 A1 10/2002 Noll et al.
2002/0158593 A1 10/2002 Henderson et al.
2002/0161277 A1 10/2002 Boone et al.
2002/0177848 A1 11/2002 Truckai et al.
2002/0185514 A1 12/2002 Adams et al.
2002/0188170 A1 12/2002 Santamore et al.
2002/0188287 A1 12/2002 Zvuloni et al.
2003/0009193 A1 1/2003 Corsaro
2003/0011245 A1 1/2003 Fiebig
2003/0012805 A1 1/2003 Chen et al.
2003/0018323 A1 1/2003 Wallace et al.
2003/0028236 A1 2/2003 Gillick et al.
2003/0040670 A1 2/2003 Govari
2003/0045835 A1 3/2003 Anderson et al.
2003/0047230 A1 3/2003 Kim
2003/0047582 A1 3/2003 Sonnenschein et al.
2003/0050628 A1 3/2003 Whitman et al.
2003/0050654 A1 3/2003 Whitman et al.
2003/0066858 A1 4/2003 Holgersson
2003/0078647 A1 4/2003 Vallana et al.
2003/0083648 A1 5/2003 Wang et al.
2003/0084983 A1 5/2003 Rangachari et al.
2003/0093103 A1 5/2003 Malackowski et al.
2003/0093160 A1 5/2003 Maksimovic et al.
2003/0094356 A1 5/2003 Waldron
2003/0096158 A1 5/2003 Takano et al.
2003/0105475 A1 6/2003 Sancoff et al.

(56) References Cited

U.S. PATENT DOCUMENTS

2003/0114851 A1 6/2003 Truckai et al.
2003/0121586 A1 7/2003 Mitra et al.
2003/0135204 A1 7/2003 Lee et al.
2003/0135388 A1 7/2003 Martucci et al.
2003/0139741 A1 7/2003 Goble et al.
2003/0144660 A1 7/2003 Mollenauer
2003/0149406 A1 8/2003 Martineau et al.
2003/0153908 A1 8/2003 Goble et al.
2003/0153968 A1 8/2003 Geis et al.
2003/0158463 A1 8/2003 Julian et al.
2003/0163029 A1 8/2003 Sonnenschein et al.
2003/0163085 A1 8/2003 Tanner et al.
2003/0164172 A1 9/2003 Chumas et al.
2003/0181800 A1 9/2003 Bonutti
2003/0181900 A1 9/2003 Long
2003/0190584 A1 10/2003 Heasley
2003/0195387 A1 10/2003 Kortenbach et al.
2003/0205029 A1 11/2003 Chapolini et al.
2003/0212005 A1 11/2003 Petito et al.
2003/0216619 A1 11/2003 Scirica et al.
2003/0216732 A1 11/2003 Truckai et al.
2003/0236505 A1 12/2003 Bonadio et al.
2004/0006335 A1 1/2004 Garrison
2004/0006340 A1 1/2004 Latterell et al.
2004/0007608 A1 1/2004 Ehrenfels et al.
2004/0024457 A1 2/2004 Boyce et al.
2004/0028502 A1 2/2004 Cummins
2004/0030333 A1 2/2004 Goble
2004/0034287 A1 2/2004 Hickle
2004/0034357 A1 2/2004 Beane et al.
2004/0044295 A1 3/2004 Reinert et al.
2004/0044364 A1 3/2004 DeVries et al.
2004/0049121 A1 3/2004 Yaron
2004/0049172 A1 3/2004 Root et al.
2004/0059362 A1 3/2004 Knodel et al.
2004/0068161 A1 4/2004 Couvillon
2004/0068224 A1 4/2004 Couvillon et al.
2004/0068307 A1 4/2004 Goble
2004/0070369 A1 4/2004 Sakakibara
2004/0073222 A1 4/2004 Koseki
2004/0078037 A1 4/2004 Batchelor et al.
2004/0082952 A1 4/2004 Dycus et al.
2004/0085180 A1 5/2004 Juang
2004/0092992 A1 5/2004 Adams et al.
2004/0093020 A1 5/2004 Sinton
2004/0093024 A1 5/2004 Lousararian et al.
2004/0098040 A1 5/2004 Taniguchi et al.
2004/0101822 A1 5/2004 Wiesner et al.
2004/0102783 A1 5/2004 Sutterlin et al.
2004/0108357 A1 6/2004 Milliman et al.
2004/0110439 A1 6/2004 Chaikof et al.
2004/0115022 A1 6/2004 Albertson et al.
2004/0116952 A1 6/2004 Sakurai et al.
2004/0119185 A1 6/2004 Chen
2004/0122419 A1 6/2004 Neuberger
2004/0122423 A1 6/2004 Dycus et al.
2004/0133095 A1 7/2004 Dunki-Jacobs et al.
2004/0133189 A1 7/2004 Sakurai
2004/0143297 A1 7/2004 Ramsey
2004/0147909 A1 7/2004 Johnston et al.
2004/0153100 A1 8/2004 Ahlberg et al.
2004/0158261 A1 8/2004 Vu
2004/0164123 A1 8/2004 Racenet et al.
2004/0166169 A1 8/2004 Malaviya et al.
2004/0167572 A1 8/2004 Roth et al.
2004/0181219 A1 9/2004 Goble et al.
2004/0193189 A1 9/2004 Kortenbach et al.
2004/0197367 A1 10/2004 Rezania et al.
2004/0199181 A1 10/2004 Knodel et al.
2004/0204735 A1 10/2004 Shiroff et al.
2004/0218451 A1 11/2004 Said et al.
2004/0222268 A1 11/2004 Bilotti et al.
2004/0225186 A1 11/2004 Horne et al.
2004/0231870 A1 11/2004 McCormick et al.
2004/0232201 A1 11/2004 Wenchell et al.
2004/0236352 A1 11/2004 Wang et al.
2004/0239582 A1 12/2004 Seymour
2004/0243147 A1 12/2004 Lipow
2004/0243151 A1 12/2004 Demmy et al.
2004/0243163 A1 12/2004 Casiano et al.
2004/0247415 A1 12/2004 Mangone
2004/0249366 A1 12/2004 Kunz
2004/0254455 A1 12/2004 Iddan
2004/0254566 A1 12/2004 Plicchi et al.
2004/0254590 A1 12/2004 Hoffman et al.
2004/0254680 A1 12/2004 Sunaoshi
2004/0260315 A1 12/2004 Dell et al.
2004/0267310 A1 12/2004 Racenet et al.
2005/0010158 A1 1/2005 Brugger et al.
2005/0010213 A1 1/2005 Stad et al.
2005/0021078 A1 1/2005 Vleugels et al.
2005/0023325 A1 2/2005 Gresham et al.
2005/0032511 A1 2/2005 Malone et al.
2005/0033352 A1 2/2005 Zepf et al.
2005/0044489 A1 2/2005 Yamagami et al.
2005/0051163 A1 3/2005 Deem et al.
2005/0054946 A1 3/2005 Krzyzanowski
2005/0057225 A1 3/2005 Marquet
2005/0058890 A1 3/2005 Brazell et al.
2005/0059997 A1 3/2005 Bauman et al.
2005/0067548 A1 3/2005 Inoue
2005/0070929 A1 3/2005 Dalessandro et al.
2005/0075561 A1 4/2005 Golden
2005/0079088 A1 4/2005 Wirth et al.
2005/0080342 A1 4/2005 Gilreath et al.
2005/0085693 A1 4/2005 Belson et al.
2005/0085838 A1 4/2005 Thompson et al.
2005/0090709 A1 4/2005 Okada et al.
2005/0090817 A1 4/2005 Phan
2005/0096683 A1 5/2005 Ellins et al.
2005/0116673 A1 6/2005 Carl et al.
2005/0119524 A1 6/2005 Sekine et al.
2005/0120836 A1 6/2005 Anderson
2005/0124855 A1 6/2005 Jaffe et al.
2005/0125028 A1 6/2005 Looper et al.
2005/0125897 A1 6/2005 Wyslucha et al.
2005/0129735 A1 6/2005 Cook et al.
2005/0130682 A1 6/2005 Takara et al.
2005/0131173 A1 6/2005 McDaniel et al.
2005/0131211 A1 6/2005 Bayley et al.
2005/0131390 A1 6/2005 Heinrich et al.
2005/0131436 A1 6/2005 Johnston et al.
2005/0131457 A1 6/2005 Douglas et al.
2005/0137454 A1 6/2005 Saadat et al.
2005/0137455 A1 6/2005 Ewers et al.
2005/0139636 A1 6/2005 Schwemberger et al.
2005/0143759 A1 6/2005 Kelly
2005/0143769 A1 6/2005 White et al.
2005/0145671 A1 7/2005 Viola
2005/0145672 A1 7/2005 Schwemberger et al.
2005/0150928 A1 7/2005 Kameyama et al.
2005/0154258 A1 7/2005 Tartaglia et al.
2005/0154406 A1 7/2005 Bombard et al.
2005/0159778 A1 7/2005 Heinrich et al.
2005/0165419 A1 7/2005 Sauer et al.
2005/0169974 A1 8/2005 Tenerz et al.
2005/0171522 A1 8/2005 Christopherson
2005/0177176 A1 8/2005 Gerbi et al.
2005/0177181 A1 8/2005 Kagan et al.
2005/0177249 A1 8/2005 Kladakis et al.
2005/0182298 A1 8/2005 Ikeda et al.
2005/0182443 A1 8/2005 Jonn et al.
2005/0184121 A1 8/2005 Heinrich
2005/0186240 A1 8/2005 Ringeisen et al.
2005/0187545 A1 8/2005 Hooven et al.
2005/0191936 A1 9/2005 Marine et al.
2005/0197859 A1 9/2005 Wilson et al.
2005/0203550 A1 9/2005 Laufer et al.
2005/0209614 A1 9/2005 Fenter et al.
2005/0216055 A1 9/2005 Scirica et al.
2005/0222587 A1 10/2005 Jinno et al.
2005/0222611 A1 10/2005 Weitkamp
2005/0222616 A1 10/2005 Rethy et al.
2005/0222665 A1 10/2005 Aranyi

(56) References Cited

U.S. PATENT DOCUMENTS

2005/0228224 A1 10/2005 Okada et al.
2005/0228446 A1 10/2005 Mooradian et al.
2005/0230453 A1 10/2005 Viola
2005/0240178 A1 10/2005 Morley et al.
2005/0242950 A1 11/2005 Lindsay et al.
2005/0245965 A1 11/2005 Orban Iii et al.
2005/0246881 A1 11/2005 Kelly et al.
2005/0251063 A1 11/2005 Basude
2005/0256452 A1 11/2005 DeMarchi et al.
2005/0256546 A1 11/2005 Vaisnys et al.
2005/0258963 A1 11/2005 Rodriguez et al.
2005/0261676 A1 11/2005 Hall et al.
2005/0263563 A1 12/2005 Racenet et al.
2005/0267455 A1 12/2005 Eggers et al.
2005/0267464 A1 12/2005 Truckai et al.
2005/0267529 A1 12/2005 Crockett et al.
2005/0274034 A1 12/2005 Hayashida et al.
2005/0283188 A1 12/2005 Loshakove et al.
2005/0283226 A1 12/2005 Haverkost
2006/0008787 A1 1/2006 Hayman et al.
2006/0011698 A1 1/2006 Okada et al.
2006/0015009 A1 1/2006 Jaffe et al.
2006/0020167 A1 1/2006 Sitzmann
2006/0020258 A1 1/2006 Strauss et al.
2006/0020272 A1 1/2006 Gildenberg
2006/0020336 A1 1/2006 Liddicoat
2006/0025812 A1 2/2006 Shelton
2006/0041188 A1 2/2006 Dirusso et al.
2006/0047275 A1 3/2006 Goble
2006/0049229 A1 3/2006 Milliman et al.
2006/0052824 A1 3/2006 Ransick et al.
2006/0052825 A1 3/2006 Ransick et al.
2006/0064086 A1 3/2006 Odom
2006/0079735 A1 4/2006 Martone et al.
2006/0079874 A1 4/2006 Faller et al.
2006/0079879 A1 4/2006 Faller et al.
2006/0086032 A1 4/2006 Valencic et al.
2006/0087746 A1 4/2006 Lipow
2006/0089535 A1 4/2006 Raz et al.
2006/0097699 A1 5/2006 Kamenoff
2006/0100643 A1 5/2006 Laufer et al.
2006/0100649 A1 5/2006 Hart
2006/0106369 A1 5/2006 Desai et al.
2006/0111711 A1 5/2006 Goble
2006/0111723 A1 5/2006 Chapolini et al.
2006/0116634 A1 6/2006 Shachar
2006/0142656 A1 6/2006 Malackowski et al.
2006/0142772 A1 6/2006 Ralph et al.
2006/0144898 A1 7/2006 Bilotti et al.
2006/0154546 A1 7/2006 Murphy et al.
2006/0161050 A1 7/2006 Butler et al.
2006/0161185 A1 7/2006 Saadat et al.
2006/0167471 A1 7/2006 Phillips
2006/0173290 A1 8/2006 Lavallee et al.
2006/0173470 A1 8/2006 Oray et al.
2006/0176031 A1 8/2006 Forman et al.
2006/0176242 A1 8/2006 Jaramaz et al.
2006/0178556 A1 8/2006 Hasser et al.
2006/0180633 A1 8/2006 Emmons
2006/0180634 A1 8/2006 Shelton et al.
2006/0185682 A1 8/2006 Marczyk
2006/0199999 A1 9/2006 Ikeda et al.
2006/0201989 A1 9/2006 Ojeda
2006/0206100 A1 9/2006 Eskridge et al.
2006/0217729 A1 9/2006 Eskridge et al.
2006/0226196 A1 10/2006 Hueil et al.
2006/0226957 A1 10/2006 Miller et al.
2006/0235368 A1 10/2006 Oz
2006/0241666 A1 10/2006 Briggs et al.
2006/0241691 A1 10/2006 Wilk
2006/0244460 A1 11/2006 Weaver
2006/0247584 A1 11/2006 Sheetz et al.
2006/0252981 A1 11/2006 Matsuda et al.
2006/0252990 A1 11/2006 Kubach
2006/0252993 A1 11/2006 Freed et al.
2006/0258904 A1 11/2006 Stefanchik et al.
2006/0259073 A1 11/2006 Miyamoto et al.
2006/0261763 A1 11/2006 Lott et al.
2006/0263444 A1 11/2006 Ming et al.
2006/0264831 A1 11/2006 Skwarek et al.
2006/0264929 A1 11/2006 Goble et al.
2006/0271042 A1 11/2006 Latterell et al.
2006/0271102 A1 11/2006 Bosshard et al.
2006/0282064 A1 12/2006 Shimizu et al.
2006/0284730 A1 12/2006 Schmid et al.
2006/0287576 A1 12/2006 Tsuji et al.
2006/0289600 A1 12/2006 Wales et al.
2006/0289602 A1 12/2006 Wales et al.
2006/0291981 A1 12/2006 Viola et al.
2007/0005045 A1 1/2007 Mintz et al.
2007/0009570 A1 1/2007 Kim et al.
2007/0010702 A1 1/2007 Wang et al.
2007/0010838 A1 1/2007 Shelton et al.
2007/0016235 A1 1/2007 Tanaka et al.
2007/0018958 A1 1/2007 Tavakoli et al.
2007/0026039 A1 2/2007 Drumheller et al.
2007/0026040 A1 2/2007 Crawley et al.
2007/0027459 A1 2/2007 Horvath et al.
2007/0027468 A1 2/2007 Wales et al.
2007/0027551 A1 2/2007 Farnsworth et al.
2007/0043338 A1 2/2007 Moll et al.
2007/0043384 A1 2/2007 Ortiz et al.
2007/0043387 A1 2/2007 Vargas et al.
2007/0049951 A1 3/2007 Menn
2007/0049966 A1 3/2007 Bonadio et al.
2007/0051375 A1 3/2007 Milliman
2007/0055228 A1 3/2007 Berg et al.
2007/0055305 A1 3/2007 Schnyder et al.
2007/0069851 A1 3/2007 Sung et al.
2007/0073341 A1 3/2007 Smith et al.
2007/0073389 A1 3/2007 Bolduc et al.
2007/0078328 A1 4/2007 Ozaki et al.
2007/0078484 A1 4/2007 Talarico et al.
2007/0084897 A1 4/2007 Shelton et al.
2007/0088376 A1 4/2007 Zacharias
2007/0090788 A1 4/2007 Hansford et al.
2007/0093869 A1 4/2007 Bloom et al.
2007/0102472 A1 5/2007 Shelton
2007/0103437 A1 5/2007 Rosenberg
2007/0106113 A1 5/2007 Ravo
2007/0106317 A1 5/2007 Shelton et al.
2007/0118115 A1 5/2007 Artale et al.
2007/0134251 A1 6/2007 Ashkenazi et al.
2007/0135686 A1 6/2007 Pruitt et al.
2007/0135803 A1 6/2007 Belson
2007/0152612 A1 7/2007 Chen et al.
2007/0152829 A1 7/2007 Lindsay et al.
2007/0155010 A1 7/2007 Farnsworth et al.
2007/0162056 A1 7/2007 Gerbi et al.
2007/0170225 A1 7/2007 Shelton et al.
2007/0173687 A1 7/2007 Shima et al.
2007/0173813 A1 7/2007 Odom
2007/0173872 A1 7/2007 Neuenfeldt
2007/0175950 A1 8/2007 Shelton et al.
2007/0175951 A1 8/2007 Shelton et al.
2007/0175955 A1 8/2007 Shelton et al.
2007/0179476 A1 8/2007 Shelton et al.
2007/0179477 A1 8/2007 Danger
2007/0185545 A1 8/2007 Duke
2007/0187857 A1 8/2007 Riley et al.
2007/0190110 A1 8/2007 Pameijer et al.
2007/0191868 A1 8/2007 Theroux et al.
2007/0191915 A1 8/2007 Strother et al.
2007/0194079 A1 8/2007 Hueil et al.
2007/0194081 A1 8/2007 Hueil et al.
2007/0194082 A1 8/2007 Morgan et al.
2007/0197954 A1 8/2007 Keenan
2007/0198039 A1 8/2007 Jones et al.
2007/0203510 A1 8/2007 Bettuchi
2007/0207010 A1 9/2007 Caspi
2007/0208359 A1 9/2007 Hoffman
2007/0208375 A1 9/2007 Nishizawa et al.
2007/0213750 A1 9/2007 Weadock
2007/0221701 A1 9/2007 Ortiz et al.

(56) References Cited

U.S. PATENT DOCUMENTS

2007/0225562 A1 9/2007 Spivey et al.
2007/0233163 A1 10/2007 Bombard et al.
2007/0243227 A1 10/2007 Gertner
2007/0244471 A1 10/2007 Malackowski
2007/0244496 A1 10/2007 Hellenkamp
2007/0246505 A1 10/2007 Pace-Floridia et al.
2007/0260132 A1 11/2007 Sterling
2007/0260242 A1 11/2007 Dycus et al.
2007/0262592 A1 11/2007 Hwang et al.
2007/0270660 A1 11/2007 Caylor et al.
2007/0275035 A1 11/2007 Herman et al.
2007/0276409 A1 11/2007 Ortiz et al.
2007/0279011 A1 12/2007 Jones et al.
2007/0286892 A1 12/2007 Herzberg et al.
2007/0290027 A1 12/2007 Maatta et al.
2007/0296286 A1 12/2007 Avenell
2008/0000941 A1 1/2008 Sonnenschein et al.
2008/0003196 A1 1/2008 Jonn et al.
2008/0007237 A1 1/2008 Nagashima et al.
2008/0015598 A1 1/2008 Prommersberger
2008/0021486 A1 1/2008 Oyola et al.
2008/0029570 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0030170 A1 2/2008 Dacquay et al.
2008/0039746 A1 2/2008 Hissong et al.
2008/0042861 A1 2/2008 Dacquay et al.
2008/0046000 A1 2/2008 Lee et al.
2008/0051833 A1 2/2008 Gramuglia et al.
2008/0064920 A1 3/2008 Bakos et al.
2008/0064921 A1 3/2008 Larkin et al.
2008/0065153 A1 3/2008 Allard et al.
2008/0069736 A1 3/2008 Mingerink et al.
2008/0071328 A1 3/2008 Haubrich et al.
2008/0077158 A1 3/2008 Haider et al.
2008/0078802 A1 4/2008 Hess et al.
2008/0081948 A1 4/2008 Weisenburgh et al.
2008/0082114 A1 4/2008 Mckenna et al.
2008/0082125 A1 4/2008 Murray et al.
2008/0082126 A1 4/2008 Murray et al.
2008/0083807 A1 4/2008 Beardsley et al.
2008/0083811 A1 4/2008 Marczyk
2008/0085296 A1 4/2008 Powell et al.
2008/0086078 A1 4/2008 Powell et al.
2008/0091072 A1 4/2008 Omori et al.
2008/0094228 A1 4/2008 Welch et al.
2008/0108443 A1 5/2008 Jinno et al.
2008/0114250 A1 5/2008 Urbano et al.
2008/0125634 A1 5/2008 Ryan et al.
2008/0125749 A1 5/2008 Olson
2008/0126984 A1 5/2008 Fleishman et al.
2008/0128469 A1 6/2008 Dalessandro et al.
2008/0129253 A1 6/2008 Shiue et al.
2008/0135600 A1 6/2008 Hiranuma et al.
2008/0140115 A1 6/2008 Stopek
2008/0140159 A1 6/2008 Bornhoft et al.
2008/0149682 A1 6/2008 Uhm
2008/0154299 A1 6/2008 Livneh
2008/0154335 A1 6/2008 Thrope et al.
2008/0169328 A1 7/2008 Shelton
2008/0169332 A1 7/2008 Shelton et al.
2008/0169333 A1 7/2008 Shelton et al.
2008/0172087 A1 7/2008 Fuchs et al.
2008/0177392 A1 7/2008 Williams et al.
2008/0190989 A1 8/2008 Crews et al.
2008/0196253 A1 8/2008 Ezra et al.
2008/0196419 A1 8/2008 Dube
2008/0197167 A1 8/2008 Viola et al.
2008/0200755 A1 8/2008 Bakos
2008/0200762 A1 8/2008 Stokes et al.
2008/0200835 A1 8/2008 Monson et al.
2008/0200911 A1 8/2008 Long
2008/0200933 A1 8/2008 Bakos et al.
2008/0200934 A1 8/2008 Fox
2008/0206186 A1 8/2008 Butler et al.
2008/0208058 A1 8/2008 Sabata et al.
2008/0216704 A1 9/2008 Eisenbeis et al.
2008/0217376 A1 9/2008 Clauson et al.
2008/0234709 A1 9/2008 Houser
2008/0234866 A1 9/2008 Kishi et al.
2008/0242939 A1 10/2008 Johnston
2008/0243088 A1 10/2008 Evans
2008/0243143 A1 10/2008 Kuhns et al.
2008/0249536 A1 10/2008 Stahler et al.
2008/0249608 A1 10/2008 Dave
2008/0255413 A1 10/2008 Zemlok et al.
2008/0255420 A1 10/2008 Lee et al.
2008/0255421 A1 10/2008 Hegeman et al.
2008/0255663 A1 10/2008 Akpek et al.
2008/0262654 A1 10/2008 Omori et al.
2008/0269596 A1 10/2008 Revie et al.
2008/0281171 A1 11/2008 Fennell et al.
2008/0281332 A1 11/2008 Taylor
2008/0287944 A1 11/2008 Pearson et al.
2008/0293910 A1 11/2008 Kapiamba et al.
2008/0294179 A1 11/2008 Balbierz et al.
2008/0296346 A1 12/2008 Shelton, IV et al.
2008/0296347 A1 12/2008 Shelton, IV et al.
2008/0297287 A1 12/2008 Shachar et al.
2008/0298784 A1 12/2008 Kastner
2008/0308504 A1 12/2008 Hallan et al.
2008/0308602 A1 12/2008 Timm et al.
2008/0308603 A1 12/2008 Shelton et al.
2008/0308607 A1 12/2008 Timm et al.
2008/0308807 A1 12/2008 Yamazaki et al.
2008/0312686 A1 12/2008 Ellingwood
2008/0312687 A1 12/2008 Blier
2008/0315829 A1 12/2008 Jones et al.
2009/0001121 A1 1/2009 Hess et al.
2009/0001130 A1 1/2009 Hess et al.
2009/0004455 A1 1/2009 Gravagna et al.
2009/0005809 A1 1/2009 Hess et al.
2009/0007014 A1 1/2009 Coomer et al.
2009/0012534 A1 1/2009 Madhani et al.
2009/0015195 A1 1/2009 Loth-Krausser
2009/0020958 A1 1/2009 Soul
2009/0030437 A1 1/2009 Houser et al.
2009/0043253 A1 2/2009 Podaima
2009/0048583 A1 2/2009 Williams et al.
2009/0048589 A1 2/2009 Takashino et al.
2009/0053288 A1 2/2009 Eskridge, Jr. et al.
2009/0057369 A1 3/2009 Smith et al.
2009/0069806 A1 3/2009 De La Mora Levy et al.
2009/0076506 A1 3/2009 Baker
2009/0078736 A1 3/2009 Van Lue
2009/0081313 A1 3/2009 Aghion et al.
2009/0088659 A1 4/2009 Graham et al.
2009/0090763 A1 4/2009 Zemlok et al.
2009/0099579 A1 4/2009 Nentwick et al.
2009/0099876 A1 4/2009 Whitman
2009/0110533 A1 4/2009 Jinno
2009/0112234 A1 4/2009 Crainich et al.
2009/0114701 A1 5/2009 Zemlok et al.
2009/0118762 A1 5/2009 Crainch et al.
2009/0119011 A1 5/2009 Kondo et al.
2009/0120994 A1 5/2009 Murray et al.
2009/0131819 A1 5/2009 Ritchie et al.
2009/0132400 A1 5/2009 Conway
2009/0135280 A1 5/2009 Johnston et al.
2009/0138003 A1 5/2009 Deville et al.
2009/0143797 A1 6/2009 Smith et al.
2009/0143855 A1 6/2009 Weber et al.
2009/0149871 A9 6/2009 Kagan et al.
2009/0167548 A1 7/2009 Sugahara
2009/0171147 A1 7/2009 Lee et al.
2009/0177218 A1 7/2009 Young et al.
2009/0177226 A1 7/2009 Reinprecht et al.
2009/0181290 A1 7/2009 Baldwin et al.
2009/0188964 A1 7/2009 Orlov
2009/0192534 A1 7/2009 Ortiz et al.
2009/0198272 A1 8/2009 Kerver et al.
2009/0204108 A1 8/2009 Steffen
2009/0204109 A1 8/2009 Grove et al.

(56) References Cited

U.S. PATENT DOCUMENTS

2009/0204126 A1 8/2009 Le
2009/0204925 A1 8/2009 Bhat et al.
2009/0206125 A1 8/2009 Huitema et al.
2009/0206126 A1 8/2009 Huitema et al.
2009/0206131 A1 8/2009 Weisenburgh et al.
2009/0206133 A1 8/2009 Morgan et al.
2009/0206137 A1 8/2009 Hall et al.
2009/0206139 A1 8/2009 Hall et al.
2009/0206141 A1 8/2009 Huitema et al.
2009/0206142 A1 8/2009 Huitema et al.
2009/0206143 A1 8/2009 Huitema et al.
2009/0221993 A1 9/2009 Sohi et al.
2009/0227834 A1 9/2009 Nakamoto et al.
2009/0234273 A1 9/2009 Intoccia et al.
2009/0236401 A1 9/2009 Cole et al.
2009/0242610 A1 10/2009 Shelton, IV et al.
2009/0246873 A1 10/2009 Yamamoto et al.
2009/0247368 A1 10/2009 Chiang
2009/0247901 A1 10/2009 Zimmer
2009/0248100 A1 10/2009 Vaisnys et al.
2009/0253959 A1 10/2009 Yoshie et al.
2009/0255974 A1 10/2009 Viola
2009/0261141 A1 10/2009 Stratton et al.
2009/0262078 A1 10/2009 Pizzi
2009/0264940 A1 10/2009 Beale et al.
2009/0270895 A1 10/2009 Churchill et al.
2009/0273353 A1 11/2009 Kroh et al.
2009/0277288 A1 11/2009 Doepker et al.
2009/0278406 A1 11/2009 Hoffman
2009/0290016 A1 11/2009 Suda
2009/0292283 A1 11/2009 Odom
2009/0306639 A1 12/2009 Nevo et al.
2009/0308907 A1 12/2009 Nalagatla et al.
2009/0318557 A1 12/2009 Stockel
2009/0318936 A1 12/2009 Harris et al.
2009/0325859 A1 12/2009 Ameer et al.
2010/0002013 A1 1/2010 Kagaya
2010/0005035 A1 1/2010 Carpenter et al.
2010/0012703 A1 1/2010 Calabrese et al.
2010/0015104 A1 1/2010 Fraser et al.
2010/0016853 A1 1/2010 Burbank
2010/0016888 A1 1/2010 Calabrese et al.
2010/0017715 A1 1/2010 Balassanian
2010/0023024 A1 1/2010 Zeiner et al.
2010/0030233 A1 2/2010 Whitman et al.
2010/0030239 A1 2/2010 Viola et al.
2010/0032179 A1 2/2010 Hanspers et al.
2010/0036370 A1 2/2010 Mirel et al.
2010/0036441 A1 2/2010 Procter
2010/0051668 A1 3/2010 Milliman et al.
2010/0057118 A1 3/2010 Dietz et al.
2010/0065604 A1 3/2010 Weng
2010/0069833 A1 3/2010 Wenderow et al.
2010/0069942 A1 3/2010 Shelton, IV
2010/0076483 A1 3/2010 Imuta
2010/0076489 A1 3/2010 Stopek et al.
2010/0081883 A1 4/2010 Murray et al.
2010/0094312 A1 4/2010 Ruiz Morales et al.
2010/0094340 A1 4/2010 Stopek et al.
2010/0094400 A1 4/2010 Bolduc et al.
2010/0100123 A1 4/2010 Bennett
2010/0100124 A1 4/2010 Calabrese et al.
2010/0106167 A1 4/2010 Boulnois et al.
2010/0116519 A1 5/2010 Gareis
2010/0122339 A1 5/2010 Boccacci
2010/0125786 A1 5/2010 Ozawa et al.
2010/0133317 A1 6/2010 Shelton, IV et al.
2010/0137990 A1 6/2010 Apatsidis et al.
2010/0138659 A1 6/2010 Carmichael et al.
2010/0145146 A1 6/2010 Melder
2010/0147921 A1 6/2010 Olson
2010/0147922 A1 6/2010 Olson
2010/0159435 A1 6/2010 Mueller et al.
2010/0168741 A1 7/2010 Sanai et al.
2010/0179022 A1 7/2010 Shirokoshi
2010/0180711 A1 7/2010 Kilibarda et al.
2010/0187285 A1 7/2010 Hans et al.
2010/0191255 A1 7/2010 Crainich et al.
2010/0191262 A1 7/2010 Harris et al.
2010/0191292 A1 7/2010 DeMeo et al.
2010/0193566 A1 8/2010 Scheib et al.
2010/0194541 A1 8/2010 Stevenson et al.
2010/0198159 A1 8/2010 Voss et al.
2010/0204717 A1 8/2010 Knodel
2010/0204721 A1 8/2010 Young et al.
2010/0217281 A1 8/2010 Matsuoka et al.
2010/0218019 A1 8/2010 Eckhard
2010/0222901 A1 9/2010 Swayze et al.
2010/0228250 A1 9/2010 Brogna
2010/0234687 A1 9/2010 Azarbarzin et al.
2010/0241115 A1 9/2010 Benamou et al.
2010/0241137 A1 9/2010 Doyle et al.
2010/0245102 A1 9/2010 Yokoi
2010/0249497 A1 9/2010 Peine et al.
2010/0249947 A1 9/2010 Lesh et al.
2010/0256675 A1 10/2010 Romans
2010/0258327 A1 10/2010 Esenwein et al.
2010/0267525 A1 10/2010 Tanner
2010/0267662 A1 10/2010 Fielder et al.
2010/0274160 A1 10/2010 Yachi et al.
2010/0291184 A1 11/2010 Clark et al.
2010/0292540 A1 11/2010 Hess et al.
2010/0298636 A1 11/2010 Castro et al.
2010/0301097 A1 12/2010 Scirica et al.
2010/0310623 A1 12/2010 Laurencin et al.
2010/0312261 A1 12/2010 Suzuki et al.
2010/0318085 A1 12/2010 Austin et al.
2010/0325568 A1 12/2010 Pedersen et al.
2010/0327041 A1 12/2010 Milliman et al.
2010/0331856 A1 12/2010 Carlson et al.
2011/0006101 A1 1/2011 Hall et al.
2011/0009694 A1 1/2011 Schultz et al.
2011/0011916 A1 1/2011 Levine
2011/0016960 A1 1/2011 Debrailly
2011/0021871 A1 1/2011 Berkelaar
2011/0022032 A1 1/2011 Zemlok et al.
2011/0024477 A1 2/2011 Hall
2011/0024478 A1 2/2011 Shelton, IV
2011/0025311 A1 2/2011 Chauvin et al.
2011/0028991 A1 2/2011 Ikeda et al.
2011/0029003 A1 2/2011 Lavigne et al.
2011/0029270 A1 2/2011 Mueglitz
2011/0036891 A1 2/2011 Zemlok et al.
2011/0046667 A1 2/2011 Culligan et al.
2011/0052660 A1 3/2011 Yang et al.
2011/0056717 A1 3/2011 Herisse
2011/0060363 A1 3/2011 Hess et al.
2011/0066156 A1 3/2011 McGahan et al.
2011/0071473 A1 3/2011 Rogers et al.
2011/0082538 A1 4/2011 Dahlgren et al.
2011/0087276 A1 4/2011 Bedi et al.
2011/0088921 A1 4/2011 Forgues et al.
2011/0091515 A1 4/2011 Zilberman et al.
2011/0095064 A1 4/2011 Taylor et al.
2011/0095067 A1 4/2011 Ohdaira
2011/0101069 A1 5/2011 Bombard et al.
2011/0101794 A1 5/2011 Schroeder et al.
2011/0112517 A1 5/2011 Peine et al.
2011/0112530 A1 5/2011 Keller
2011/0114697 A1 5/2011 Baxter et al.
2011/0118708 A1 5/2011 Burbank et al.
2011/0118754 A1 5/2011 Dachs, II et al.
2011/0125149 A1 5/2011 El-Galley et al.
2011/0125176 A1 5/2011 Yates et al.
2011/0127945 A1 6/2011 Yoneda
2011/0129706 A1 6/2011 Takahashi et al.
2011/0139851 A1 6/2011 McCuen
2011/0144764 A1 6/2011 Bagga et al.
2011/0147433 A1 6/2011 Shelton, IV et al.
2011/0160725 A1 6/2011 Kabaya et al.
2011/0163146 A1 7/2011 Ortiz et al.
2011/0172495 A1 7/2011 Armstrong
2011/0174861 A1 7/2011 Shelton, IV et al.
2011/0192882 A1 8/2011 Hess et al.

(56) References Cited

U.S. PATENT DOCUMENTS

2011/0198381 A1 8/2011 McCardle et al.
2011/0199225 A1 8/2011 Touchberry et al.
2011/0204119 A1 8/2011 McCuen
2011/0218400 A1 9/2011 Ma et al.
2011/0218550 A1 9/2011 Ma
2011/0220381 A1 9/2011 Friese et al.
2011/0224543 A1 9/2011 Johnson et al.
2011/0225105 A1 9/2011 Scholer et al.
2011/0230713 A1 9/2011 Kleemann et al.
2011/0235168 A1 9/2011 Sander
2011/0238044 A1 9/2011 Main et al.
2011/0241597 A1 10/2011 Zhu et al.
2011/0251606 A1 10/2011 Kerr
2011/0256266 A1 10/2011 Orme et al.
2011/0271186 A1 11/2011 Owens
2011/0275901 A1 11/2011 Shelton, IV
2011/0276083 A1 11/2011 Shelton, IV et al.
2011/0278035 A1 11/2011 Chen
2011/0278343 A1 11/2011 Knodel et al.
2011/0279268 A1 11/2011 Konishi et al.
2011/0285507 A1 11/2011 Nelson
2011/0290856 A1 12/2011 Shelton, IV et al.
2011/0290858 A1 12/2011 Whitman et al.
2011/0292258 A1 12/2011 Adler et al.
2011/0293690 A1 12/2011 Griffin et al.
2011/0295295 A1 12/2011 Shelton, IV et al.
2011/0295299 A1 12/2011 Braithwaite et al.
2011/0313894 A1 12/2011 Dye et al.
2011/0315413 A1 12/2011 Fisher et al.
2012/0004636 A1 1/2012 Lo
2012/0007442 A1 1/2012 Rhodes et al.
2012/0008880 A1 1/2012 Toth
2012/0010615 A1 1/2012 Cummings et al.
2012/0016239 A1 1/2012 Barthe et al.
2012/0016413 A1 1/2012 Timm et al.
2012/0016467 A1 1/2012 Chen et al.
2012/0029272 A1 2/2012 Shelton, IV et al.
2012/0029550 A1 2/2012 Forsell
2012/0033360 A1 2/2012 Hsu
2012/0059286 A1 3/2012 Hastings et al.
2012/0064483 A1 3/2012 Lint et al.
2012/0074200 A1 3/2012 Schmid et al.
2012/0078243 A1 3/2012 Worrell et al.
2012/0078244 A1 3/2012 Worrell et al.
2012/0080336 A1 4/2012 Shelton, IV et al.
2012/0080344 A1 4/2012 Shelton, IV
2012/0080478 A1 4/2012 Morgan et al.
2012/0080491 A1 4/2012 Shelton, IV et al.
2012/0080498 A1 4/2012 Shelton, IV et al.
2012/0083836 A1 4/2012 Shelton, IV et al.
2012/0086276 A1 4/2012 Sawyers
2012/0095458 A1 4/2012 Cybulski et al.
2012/0101488 A1 4/2012 Aldridge et al.
2012/0109186 A1 5/2012 Parrott et al.
2012/0116261 A1 5/2012 Mumaw et al.
2012/0116262 A1 5/2012 Houser et al.
2012/0116263 A1 5/2012 Houser et al.
2012/0116265 A1 5/2012 Houser et al.
2012/0116266 A1 5/2012 Houser et al.
2012/0116381 A1 5/2012 Houser et al.
2012/0118595 A1 5/2012 Pellenc
2012/0123463 A1 5/2012 Jacobs
2012/0125792 A1 5/2012 Cassivi
2012/0130217 A1 5/2012 Kauphusman et al.
2012/0132286 A1 5/2012 Lim et al.
2012/0132663 A1 5/2012 Kasvikis et al.
2012/0143175 A1 6/2012 Hermann et al.
2012/0171539 A1 7/2012 Rejman et al.
2012/0175398 A1 7/2012 Sandborn et al.
2012/0190964 A1 7/2012 Hyde et al.
2012/0197239 A1 8/2012 Smith et al.
2012/0197272 A1 8/2012 Oray et al.
2012/0203213 A1 8/2012 Kimball et al.
2012/0211542 A1 8/2012 Racenet
2012/0220990 A1 8/2012 Mckenzie et al.
2012/0233298 A1 9/2012 Verbandt et al.
2012/0234895 A1 9/2012 O'Connor et al.
2012/0234897 A1 9/2012 Shelton, IV et al.
2012/0239067 A1 9/2012 Whitman et al.
2012/0239068 A1 9/2012 Morris et al.
2012/0241494 A1 9/2012 Marczyk
2012/0241503 A1 9/2012 Baxter, III et al.
2012/0248169 A1 10/2012 Widenhouse et al.
2012/0251861 A1 10/2012 Liang et al.
2012/0253328 A1 10/2012 Cunningham et al.
2012/0256494 A1 10/2012 Kesler et al.
2012/0271327 A1 10/2012 West et al.
2012/0283707 A1 11/2012 Giordano et al.
2012/0286019 A1 11/2012 Hueil et al.
2012/0289811 A1 11/2012 Viola et al.
2012/0289979 A1 11/2012 Eskaros et al.
2012/0292367 A1 11/2012 Morgan et al.
2012/0296316 A1 11/2012 Imuta
2012/0296342 A1 11/2012 Haglund Wendelschafer
2012/0298722 A1 11/2012 Hess et al.
2012/0301498 A1 11/2012 Altreuter et al.
2012/0310254 A1 12/2012 Manzo et al.
2012/0312861 A1 12/2012 Gurumurthy et al.
2012/0316424 A1 12/2012 Stopek
2012/0330285 A1 12/2012 Hartoumbekis et al.
2012/0330329 A1 12/2012 Harris et al.
2013/0006227 A1 1/2013 Takashino
2013/0008937 A1 1/2013 Viola
2013/0012983 A1 1/2013 Kleyman
2013/0018400 A1 1/2013 Milton et al.
2013/0020375 A1 1/2013 Shelton, IV et al.
2013/0020376 A1 1/2013 Shelton, IV et al.
2013/0023861 A1 1/2013 Shelton, IV et al.
2013/0023910 A1 1/2013 Solomon et al.
2013/0026208 A1 1/2013 Shelton, IV et al.
2013/0026210 A1 1/2013 Shelton, IV et al.
2013/0030462 A1 1/2013 Keating et al.
2013/0041292 A1 2/2013 Cunningham
2013/0056522 A1 3/2013 Swensgard
2013/0057162 A1 3/2013 Pollischansky
2013/0068816 A1 3/2013 Mandakolathur Vasudevan et al.
2013/0069088 A1 3/2013 Speck et al.
2013/0075447 A1 3/2013 Weisenburgh et al.
2013/0087597 A1 4/2013 Shelton, IV et al.
2013/0090534 A1 4/2013 Burns et al.
2013/0096568 A1 4/2013 Justis
2013/0098970 A1 4/2013 Racenet et al.
2013/0106352 A1 5/2013 Nagamine
2013/0112729 A1 5/2013 Beardsley et al.
2013/0116669 A1 5/2013 Shelton, IV et al.
2013/0123816 A1 5/2013 Hodgkinson et al.
2013/0126202 A1 5/2013 Oomori et al.
2013/0131476 A1 5/2013 Siu et al.
2013/0131651 A1 5/2013 Strobl et al.
2013/0136969 A1 5/2013 Yasui et al.
2013/0153639 A1 6/2013 Hodgkinson et al.
2013/0153641 A1 6/2013 Shelton, IV et al.
2013/0158390 A1 6/2013 Tan et al.
2013/0162198 A1 6/2013 Yokota et al.
2013/0165908 A1 6/2013 Purdy et al.
2013/0169217 A1 7/2013 Watanabe et al.
2013/0172713 A1 7/2013 Kirschenman
2013/0172878 A1 7/2013 Smith
2013/0175315 A1 7/2013 Milliman
2013/0175317 A1 7/2013 Yates et al.
2013/0183769 A1 7/2013 Tajima
2013/0211244 A1 8/2013 Nathaniel
2013/0214025 A1 8/2013 Zemlok et al.
2013/0215449 A1 8/2013 Yamasaki
2013/0231681 A1 9/2013 Robinson et al.
2013/0233906 A1 9/2013 Hess et al.
2013/0238021 A1 9/2013 Gross et al.
2013/0248578 A1 9/2013 Arteaga Gonzalez
2013/0253480 A1 9/2013 Kimball et al.
2013/0256373 A1 10/2013 Schmid et al.
2013/0256380 A1 10/2013 Schmid et al.
2013/0267950 A1 10/2013 Rosa et al.
2013/0267978 A1 10/2013 Trissel
2013/0270322 A1 10/2013 Scheib et al.

(56) References Cited

U.S. PATENT DOCUMENTS

2013/0277410 A1 10/2013 Fernandez et al.
2013/0284792 A1 10/2013 Ma
2013/0289565 A1 10/2013 Hassler, Jr.
2013/0293353 A1 11/2013 McPherson et al.
2013/0303845 A1 11/2013 Skula et al.
2013/0304084 A1 11/2013 Beira et al.
2013/0306704 A1 11/2013 Balbierz et al.
2013/0327552 A1 12/2013 Lovelass et al.
2013/0333910 A1 12/2013 Tanimoto et al.
2013/0334280 A1 12/2013 Krehel et al.
2013/0334283 A1 12/2013 Swayze et al.
2013/0334285 A1 12/2013 Swayze et al.
2013/0341374 A1 12/2013 Shelton, IV et al.
2014/0001231 A1 1/2014 Shelton, IV et al.
2014/0001234 A1 1/2014 Shelton, IV et al.
2014/0002322 A1 1/2014 Kanome et al.
2014/0005550 A1 1/2014 Lu et al.
2014/0005640 A1 1/2014 Shelton, IV et al.
2014/0005678 A1 1/2014 Shelton, IV et al.
2014/0005702 A1 1/2014 Timm et al.
2014/0005718 A1 1/2014 Shelton, IV et al.
2014/0008289 A1 1/2014 Williams et al.
2014/0014704 A1 1/2014 Onukuri et al.
2014/0014705 A1 1/2014 Baxter, III
2014/0014707 A1 1/2014 Onukuri et al.
2014/0018832 A1 1/2014 Shelton, IV
2014/0022283 A1 1/2014 Chan et al.
2014/0039549 A1 2/2014 Belsky et al.
2014/0041191 A1 2/2014 Knodel
2014/0048580 A1 2/2014 Merchant et al.
2014/0069240 A1 3/2014 Dauvin et al.
2014/0078715 A1 3/2014 Pickard et al.
2014/0081176 A1 3/2014 Hassan
2014/0088614 A1 3/2014 Blumenkranz
2014/0088639 A1 3/2014 Bartels et al.
2014/0094681 A1 4/2014 Valentine et al.
2014/0100558 A1 4/2014 Schmitz et al.
2014/0107697 A1 4/2014 Patani et al.
2014/0110453 A1 4/2014 Wingardner et al.
2014/0115229 A1 4/2014 Kothamasu et al.
2014/0131418 A1 5/2014 Kostrzewski
2014/0131419 A1 5/2014 Bettuchi
2014/0135832 A1 5/2014 Park et al.
2014/0148803 A1 5/2014 Taylor
2014/0151433 A1 6/2014 Shelton, IV et al.
2014/0155916 A1 6/2014 Hodgkinson et al.
2014/0158747 A1 6/2014 Measamer et al.
2014/0166723 A1 6/2014 Beardsley et al.
2014/0166724 A1 6/2014 Schellin et al.
2014/0166725 A1 6/2014 Schellin et al.
2014/0166726 A1 6/2014 Schellin et al.
2014/0175147 A1 6/2014 Manoux et al.
2014/0175150 A1 6/2014 Shelton, IV et al.
2014/0175152 A1 6/2014 Hess et al.
2014/0181710 A1 6/2014 Baalu et al.
2014/0183244 A1 7/2014 Duque et al.
2014/0188091 A1 7/2014 Vidal et al.
2014/0188101 A1 7/2014 Bales, Jr. et al.
2014/0188159 A1 7/2014 Steege
2014/0207124 A1 7/2014 Aldridge et al.
2014/0209658 A1 7/2014 Skalla et al.
2014/0224857 A1 8/2014 Schmid
2014/0228632 A1 8/2014 Sholev et al.
2014/0228867 A1 8/2014 Thomas et al.
2014/0239047 A1 8/2014 Hodgkinson et al.
2014/0243865 A1 8/2014 Swayze et al.
2014/0246475 A1 9/2014 Hall et al.
2014/0248167 A1 9/2014 Sugimoto et al.
2014/0249557 A1 9/2014 Koch et al.
2014/0249573 A1 9/2014 Arav
2014/0262408 A1 9/2014 Woodard
2014/0263537 A1* 9/2014 Leimbach .............. A61B 17/32
227/175.1
2014/0263541 A1 9/2014 Leimbach et al.
2014/0263543 A1 9/2014 Leimbach et al.
2014/0263552 A1 9/2014 Hall et al.
2014/0263558 A1 9/2014 Hausen et al.
2014/0276720 A1 9/2014 Parihar et al.
2014/0276730 A1 9/2014 Boudreaux et al.
2014/0276776 A1 9/2014 Parihar et al.
2014/0284371 A1 9/2014 Morgan et al.
2014/0287703 A1 9/2014 Herbsommer et al.
2014/0288460 A1 9/2014 Ouyang et al.
2014/0291379 A1 10/2014 Schellin et al.
2014/0291383 A1 10/2014 Spivey et al.
2014/0299648 A1 10/2014 Shelton, IV et al.
2014/0303645 A1 10/2014 Morgan et al.
2014/0303660 A1 10/2014 Boyden et al.
2014/0330161 A1 11/2014 Swayze et al.
2014/0330298 A1 11/2014 Arshonsky et al.
2014/0330579 A1 11/2014 Cashman et al.
2014/0358163 A1 12/2014 Farin et al.
2014/0367445 A1 12/2014 Ingmanson et al.
2014/0371764 A1 12/2014 Oyola et al.
2014/0373003 A1 12/2014 Grez et al.
2014/0374130 A1 12/2014 Nakamura et al.
2014/0378950 A1 12/2014 Chiu
2015/0001272 A1 1/2015 Sniffin et al.
2015/0002089 A1 1/2015 Rejman et al.
2015/0022012 A1 1/2015 Kim et al.
2015/0025549 A1 1/2015 Kilroy et al.
2015/0025571 A1 1/2015 Suzuki et al.
2015/0034697 A1 2/2015 Mastri et al.
2015/0039010 A1 2/2015 Beardsley et al.
2015/0053737 A1 2/2015 Leimbach et al.
2015/0053743 A1 2/2015 Yates et al.
2015/0053746 A1 2/2015 Shelton, IV et al.
2015/0053748 A1 2/2015 Yates et al.
2015/0060516 A1 3/2015 Collings et al.
2015/0060519 A1 3/2015 Shelton, IV et al.
2015/0060520 A1 3/2015 Shelton, IV et al.
2015/0060521 A1 3/2015 Weisenburgh et al.
2015/0066000 A1 3/2015 An et al.
2015/0067582 A1 3/2015 Donnelly et al.
2015/0076208 A1 3/2015 Shelton, IV
2015/0076209 A1 3/2015 Shelton, IV et al.
2015/0076210 A1 3/2015 Shelton, IV et al.
2015/0076211 A1 3/2015 Irka et al.
2015/0080883 A1 3/2015 Haverkost et al.
2015/0082624 A1 3/2015 Craig et al.
2015/0083781 A1 3/2015 Giordano et al.
2015/0087952 A1 3/2015 Albert et al.
2015/0088127 A1 3/2015 Craig et al.
2015/0088547 A1 3/2015 Balram et al.
2015/0090760 A1 4/2015 Giordano et al.
2015/0090762 A1 4/2015 Giordano et al.
2015/0127021 A1 5/2015 Harris et al.
2015/0134077 A1 5/2015 Shelton, IV et al.
2015/0150620 A1 6/2015 Miyamoto et al.
2015/0173749 A1 6/2015 Shelton, IV et al.
2015/0173756 A1 6/2015 Baxter. III et al.
2015/0173789 A1 6/2015 Baxter. III et al.
2015/0196295 A1 7/2015 Shelton, IV et al.
2015/0196299 A1 7/2015 Swayze et al.
2015/0201918 A1 7/2015 Kumar et al.
2015/0201932 A1 7/2015 Swayze et al.
2015/0201936 A1 7/2015 Swayze et al.
2015/0201937 A1 7/2015 Swayze et al.
2015/0201938 A1 7/2015 Swayze et al.
2015/0201939 A1 7/2015 Swayze et al.
2015/0201940 A1 7/2015 Swayze et al.
2015/0201941 A1 7/2015 Swayze et al.
2015/0209035 A1 7/2015 Zemlok
2015/0209045 A1 7/2015 Hodgkinson et al.
2015/0216605 A1 8/2015 Baldwin
2015/0222212 A1 8/2015 Iwata
2015/0223868 A1 8/2015 Brandt et al.
2015/0230697 A1 8/2015 Phee et al.
2015/0230794 A1 8/2015 Wellman et al.
2015/0230861 A1 8/2015 Woloszko et al.
2015/0231409 A1 8/2015 Racenet et al.
2015/0238118 A1 8/2015 Legassey et al.
2015/0272557 A1 10/2015 Overmyer et al.
2015/0272571 A1 10/2015 Leimbach et al.

(56) References Cited

U.S. PATENT DOCUMENTS

2015/0272580 A1 10/2015 Leimbach et al.
2015/0272582 A1 10/2015 Leimbach et al.
2015/0272606 A1 10/2015 Nobis
2015/0297200 A1 10/2015 Fitzsimmons et al.
2015/0297222 A1 10/2015 Huitema et al.
2015/0297223 A1 10/2015 Huitema et al.
2015/0297225 A1 10/2015 Huitema et al.
2015/0297228 A1 10/2015 Huitema et al.
2015/0297824 A1 10/2015 Cabiri et al.
2015/0303417 A1 10/2015 Koeder et al.
2015/0305743 A1 10/2015 Casasanta et al.
2015/0313594 A1 11/2015 Shelton, IV et al.
2015/0324317 A1 11/2015 Collins et al.
2015/0352699 A1 12/2015 Sakai et al.
2015/0366585 A1 12/2015 Lemay et al.
2015/0367497 A1 12/2015 Ito et al.
2015/0372265 A1 12/2015 Morisaku et al.
2015/0374372 A1 12/2015 Zergiebel et al.
2015/0374378 A1 12/2015 Giordano et al.
2016/0000437 A1 1/2016 Giordano et al.
2016/0000452 A1 1/2016 Yates et al.
2016/0000453 A1 1/2016 Yates et al.
2016/0029998 A1 2/2016 Brister et al.
2016/0030042 A1 2/2016 Heinrich et al.
2016/0030043 A1 2/2016 Fanelli et al.
2016/0030076 A1 2/2016 Faller et al.
2016/0051316 A1 2/2016 Boudreaux
2016/0066913 A1 3/2016 Swayze et al.
2016/0069449 A1 3/2016 Kanai et al.
2016/0074035 A1 3/2016 Whitman et al.
2016/0074040 A1 3/2016 Widenhouse et al.
2016/0081678 A1 3/2016 Kappel et al.
2016/0082161 A1 3/2016 Zilberman et al.
2016/0089175 A1 3/2016 Hibner et al.
2016/0099601 A1 4/2016 Leabman et al.
2016/0100838 A1 4/2016 Beaupréet al.
2016/0118201 A1 4/2016 Nicholas et al.
2016/0132026 A1 5/2016 Wingardner et al.
2016/0135835 A1 5/2016 Onuma
2016/0135895 A1 5/2016 Faasse et al.
2016/0139666 A1 5/2016 Rubin et al.
2016/0174969 A1 6/2016 Kerr et al.
2016/0174983 A1 6/2016 Shelton, IV et al.
2016/0175021 A1 6/2016 Hassler, Jr.
2016/0183939 A1 6/2016 Shelton, IV et al.
2016/0183943 A1 6/2016 Shelton, IV
2016/0183944 A1 6/2016 Swensgard et al.
2016/0192927 A1 7/2016 Kostrzewski
2016/0192960 A1 7/2016 Bueno et al.
2016/0199063 A1 7/2016 Mandakolathur Vasudevan et al.
2016/0199956 A1 7/2016 Shelton, IV et al.
2016/0220150 A1 8/2016 Sharonov
2016/0235494 A1 8/2016 Shelton, IV et al.
2016/0242783 A1 8/2016 Shelton, IV et al.
2016/0242855 A1 8/2016 Fichtinger et al.
2016/0249910 A1 9/2016 Shelton, IV et al.
2016/0249922 A1 9/2016 Morgan et al.
2016/0249929 A1 9/2016 Cappola et al.
2016/0256159 A1 9/2016 Pinjala et al.
2016/0256184 A1 9/2016 Shelton, IV et al.
2016/0256221 A1 9/2016 Smith
2016/0256229 A1 9/2016 Morgan et al.
2016/0262745 A1 9/2016 Morgan et al.
2016/0262921 A1 9/2016 Balbierz et al.
2016/0270781 A1 9/2016 Scirica
2016/0287265 A1 10/2016 Macdonald et al.
2016/0287279 A1 10/2016 Bovay et al.
2016/0302820 A1 10/2016 Hibner et al.
2016/0310143 A1 10/2016 Bettuchi
2016/0314716 A1 10/2016 Grubbs
2016/0314717 A1 10/2016 Grubbs
2016/0345972 A1 12/2016 Beardsley et al.
2016/0367122 A1 12/2016 Ichimura et al.
2016/0374669 A1 12/2016 Overmyer et al.
2016/0374716 A1 12/2016 Kessler
2017/0000549 A1 1/2017 Gilbert et al.
2017/0007234 A1 1/2017 Chin et al.
2017/0007244 A1 1/2017 Shelton, IV et al.
2017/0007245 A1 1/2017 Shelton, IV et al.
2017/0007347 A1 1/2017 Jaworek et al.
2017/0020616 A1 1/2017 Vale et al.
2017/0035419 A1 2/2017 Decker et al.
2017/0055819 A1 3/2017 Hansen et al.
2017/0055980 A1 3/2017 Vendely et al.
2017/0056008 A1 3/2017 Shelton, IV et al.
2017/0056016 A1 3/2017 Barton et al.
2017/0056018 A1 3/2017 Zeiner et al.
2017/0066054 A1 3/2017 Birky
2017/0079642 A1 3/2017 Overmyer et al.
2017/0086829 A1 3/2017 Vendely et al.
2017/0086830 A1 3/2017 Yates et al.
2017/0086842 A1 3/2017 Shelton, IV et al.
2017/0086930 A1 3/2017 Thompson et al.
2017/0086932 A1 3/2017 Auld et al.
2017/0095252 A1 4/2017 Smith et al.
2017/0095922 A1 4/2017 Licht et al.
2017/0105727 A1 4/2017 Scheib et al.
2017/0105733 A1 4/2017 Scheib et al.
2017/0105786 A1 4/2017 Scheib et al.
2017/0106302 A1 4/2017 Cummings et al.
2017/0135711 A1 5/2017 Overmyer et al.
2017/0135717 A1 5/2017 Boudreaux et al.
2017/0135747 A1 5/2017 Broderick et al.
2017/0143336 A1 5/2017 Shah et al.
2017/0168187 A1 6/2017 Calderoni et al.
2017/0172382 A1 6/2017 Nir et al.
2017/0172549 A1 6/2017 Smaby et al.
2017/0172662 A1 6/2017 Panescu et al.
2017/0181803 A1 6/2017 Ullmann et al.
2017/0182195 A1 6/2017 Wagner
2017/0182211 A1 6/2017 Raxworthy et al.
2017/0196558 A1 7/2017 Morgan et al.
2017/0196649 A1 7/2017 Yates et al.
2017/0202592 A1 7/2017 Shelton, IV et al.
2017/0202605 A1 7/2017 Shelton, IV et al.
2017/0202607 A1 7/2017 Shelton, IV et al.
2017/0202770 A1 7/2017 Friedrich et al.
2017/0209145 A1 7/2017 Swayze et al.
2017/0224332 A1 8/2017 Hunter et al.
2017/0231628 A1 8/2017 Shelton, IV et al.
2017/0231629 A1 8/2017 Stopek et al.
2017/0238962 A1 8/2017 Hansen et al.
2017/0238991 A1 8/2017 Worrell et al.
2017/0242455 A1 8/2017 Dickens
2017/0245880 A1 8/2017 Honda et al.
2017/0245949 A1 8/2017 Randle
2017/0249431 A1 8/2017 Shelton, IV et al.
2017/0252060 A1 9/2017 Ellingson et al.
2017/0255799 A1 9/2017 Zhao et al.
2017/0258471 A1 9/2017 DiNardo et al.
2017/0262110 A1 9/2017 Polishchuk et al.
2017/0265774 A1 9/2017 Johnson et al.
2017/0281186 A1 10/2017 Shelton, IV et al.
2017/0296173 A1 10/2017 Shelton, IV et al.
2017/0296185 A1 10/2017 Swensgard et al.
2017/0296213 A1 10/2017 Swensgard et al.
2017/0303984 A1 10/2017 Malackowski
2017/0312042 A1 11/2017 Giordano et al.
2017/0319047 A1 11/2017 Poulsen et al.
2017/0319201 A1 11/2017 Morgan et al.
2017/0333034 A1 11/2017 Morgan et al.
2017/0333035 A1 11/2017 Morgan et al.
2017/0348010 A1 12/2017 Chiang
2017/0348043 A1 12/2017 Wang et al.
2017/0354413 A1 12/2017 Chen et al.
2017/0358052 A1 12/2017 Yuan
2017/0360441 A1 12/2017 Sgroi
2018/0008265 A1 1/2018 Hatanaka et al.
2018/0042610 A1 2/2018 Sgroi, Jr.
2018/0042689 A1 2/2018 Mozdzierz et al.
2018/0049738 A1 2/2018 Meloul et al.
2018/0049794 A1 2/2018 Swayze et al.
2018/0051780 A1 2/2018 Shelton, IV et al.
2018/0055501 A1 3/2018 Zemlok et al.

(56) References Cited

U.S. PATENT DOCUMENTS

| | | | |
|---|---|---|---|
| 2018/0067004 A1 | 3/2018 | Sgroi, Jr. | |
| 2018/0085116 A1 | 3/2018 | Yates et al. | |
| 2018/0085117 A1 | 3/2018 | Shelton, IV et al. | |
| 2018/0085120 A1 | 3/2018 | Viola | |
| 2018/0092710 A1 | 4/2018 | Bosisio et al. | |
| 2018/0114591 A1 | 4/2018 | Pribanic et al. | |
| 2018/0116658 A1 | 5/2018 | Aronhalt, IV et al. | |
| 2018/0116662 A1 | 5/2018 | Shelton, IV et al. | |
| 2018/0125481 A1 | 5/2018 | Yates et al. | |
| 2018/0125487 A1 | 5/2018 | Beardsley | |
| 2018/0125488 A1 | 5/2018 | Morgan et al. | |
| 2018/0125594 A1 | 5/2018 | Beardsley | |
| 2018/0132845 A1 | 5/2018 | Schmid et al. | |
| 2018/0132849 A1 | 5/2018 | Miller et al. | |
| 2018/0132850 A1 | 5/2018 | Leimbach et al. | |
| 2018/0132926 A1 | 5/2018 | Asher et al. | |
| 2018/0132952 A1 | 5/2018 | Spivey et al. | |
| 2018/0133521 A1 | 5/2018 | Frushour et al. | |
| 2018/0140299 A1 | 5/2018 | Weaner et al. | |
| 2018/0146960 A1 | 5/2018 | Shelton, IV et al. | |
| 2018/0153542 A1 | 6/2018 | Shelton, IV et al. | |
| 2018/0153634 A1 | 6/2018 | Zemlok et al. | |
| 2018/0161034 A1 | 6/2018 | Scheib et al. | |
| 2018/0168572 A1 | 6/2018 | Burbank | |
| 2018/0168574 A1 | 6/2018 | Robinson et al. | |
| 2018/0168575 A1 | 6/2018 | Simms et al. | |
| 2018/0168577 A1 | 6/2018 | Aronhalt et al. | |
| 2018/0168579 A1 | 6/2018 | Aronhalt et al. | |
| 2018/0168592 A1 | 6/2018 | Overmyer et al. | |
| 2018/0168598 A1 | 6/2018 | Shelton, IV et al. | |
| 2018/0168608 A1 | 6/2018 | Shelton, IV et al. | |
| 2018/0168609 A1 | 6/2018 | Fanelli et al. | |
| 2018/0168610 A1 | 6/2018 | Shelton, IV et al. | |
| 2018/0168615 A1 | 6/2018 | Shelton, IV et al. | |
| 2018/0168618 A1 | 6/2018 | Scott et al. | |
| 2018/0168619 A1 | 6/2018 | Scott et al. | |
| 2018/0168623 A1 | 6/2018 | Simms et al. | |
| 2018/0168625 A1 | 6/2018 | Posada et al. | |
| 2018/0168633 A1 | 6/2018 | Shelton, IV et al. | |
| 2018/0168647 A1 | 6/2018 | Shelton, IV et al. | |
| 2018/0168648 A1 | 6/2018 | Shelton, IV et al. | |
| 2018/0168650 A1 | 6/2018 | Shelton, IV et al. | |
| 2018/0168754 A1 | 6/2018 | Overmyer | |
| 2018/0168756 A1 | 6/2018 | Liao et al. | |
| 2018/0206904 A1 | 7/2018 | Felder et al. | |
| 2018/0228490 A1 | 8/2018 | Richard et al. | |
| 2018/0231111 A1 | 8/2018 | Mika et al. | |
| 2018/0231475 A1 | 8/2018 | Brown et al. | |
| 2018/0235609 A1 | 8/2018 | Harris et al. | |
| 2018/0235617 A1 | 8/2018 | Shelton, IV et al. | |
| 2018/0235618 A1 | 8/2018 | Kostrzewski | |
| 2018/0235626 A1 | 8/2018 | Shelton, IV et al. | |
| 2018/0236181 A1 | 8/2018 | Marlin et al. | |
| 2018/0242970 A1 | 8/2018 | Mozdzierz | |
| 2018/0247711 A1 | 8/2018 | Terry | |
| 2018/0250002 A1 | 9/2018 | Eschbach | |
| 2018/0271520 A1 | 9/2018 | Shelton, IV et al. | |
| 2018/0271553 A1 | 9/2018 | Worrell | |
| 2018/0271604 A1 | 9/2018 | Grout et al. | |
| 2018/0273597 A1 | 9/2018 | Stimson | |
| 2018/0279994 A1 | 10/2018 | Schaer et al. | |
| 2018/0280073 A1 | 10/2018 | Sanai et al. | |
| 2018/0289371 A1 | 10/2018 | Wang et al. | |
| 2018/0296216 A1 | 10/2018 | Shelton, IV et al. | |
| 2018/0296290 A1 | 10/2018 | Namiki et al. | |
| 2018/0317905 A1 | 11/2018 | Olson et al. | |
| 2018/0317915 A1 | 11/2018 | McDonald, II | |
| 2018/0325514 A1 | 11/2018 | Harris et al. | |
| 2018/0333169 A1 | 11/2018 | Leimbach et al. | |
| 2018/0360446 A1 | 12/2018 | Shelton, IV et al. | |
| 2018/0360456 A1 | 12/2018 | Shelton, IV et al. | |
| 2018/0360472 A1 | 12/2018 | Harris et al. | |
| 2018/0360473 A1 | 12/2018 | Shelton, IV et al. | |
| 2018/0368066 A1 | 12/2018 | Howell et al. | |
| 2018/0368833 A1 | 12/2018 | Shelton, IV et al. | |
| 2018/0368843 A1 | 12/2018 | Shelton, IV et al. | |
| 2018/0368844 A1 | 12/2018 | Bakos et al. | |
| 2018/0372806 A1 | 12/2018 | Laughery et al. | |
| 2018/0375165 A1 | 12/2018 | Shelton, IV et al. | |
| 2019/0000459 A1 | 1/2019 | Shelton, IV et al. | |
| 2019/0000461 A1 | 1/2019 | Shelton, IV et al. | |
| 2019/0000462 A1 | 1/2019 | Shelton, IV et al. | |
| 2019/0000470 A1 | 1/2019 | Yates et al. | |
| 2019/0000474 A1 | 1/2019 | Shelton, IV et al. | |
| 2019/0000475 A1 | 1/2019 | Shelton, IV et al. | |
| 2019/0000476 A1 | 1/2019 | Shelton, IV et al. | |
| 2019/0000477 A1 | 1/2019 | Shelton, IV et al. | |
| 2019/0000481 A1 | 1/2019 | Harris et al. | |
| 2019/0000535 A1 | 1/2019 | Messerly et al. | |
| 2019/0000536 A1 | 1/2019 | Yates et al. | |
| 2019/0006047 A1 | 1/2019 | Gorek et al. | |
| 2019/0008515 A1 | 1/2019 | Beardsley et al. | |
| 2019/0015102 A1 | 1/2019 | Baber et al. | |
| 2019/0015165 A1 | 1/2019 | Giordano et al. | |
| 2019/0017311 A1 | 1/2019 | McGettrick et al. | |
| 2019/0021733 A1 | 1/2019 | Burbank | |
| 2019/0029682 A1 | 1/2019 | Huitema et al. | |
| 2019/0029701 A1 | 1/2019 | Shelton, IV et al. | |
| 2019/0033955 A1 | 1/2019 | Leimbach et al. | |
| 2019/0038281 A1 | 2/2019 | Shelton, IV et al. | |
| 2019/0038282 A1 | 2/2019 | Shelton, IV et al. | |
| 2019/0038283 A1 | 2/2019 | Shelton, IV et al. | |
| 2019/0038285 A1 | 2/2019 | Mozdzierz | |
| 2019/0059986 A1 | 2/2019 | Shelton, IV et al. | |
| 2019/0076143 A1 | 3/2019 | Smith | |
| 2019/0090871 A1 | 3/2019 | Shelton, IV et al. | |
| 2019/0091183 A1 | 3/2019 | Tomat et al. | |
| 2019/0099179 A1 | 4/2019 | Leimbach et al. | |
| 2019/0099181 A1 | 4/2019 | Shelton, IV et al. | |
| 2019/0099229 A1 | 4/2019 | Spivey et al. | |
| 2019/0104919 A1 | 4/2019 | Shelton, IV et al. | |
| 2019/0105035 A1 | 4/2019 | Shelton, IV et al. | |
| 2019/0105036 A1 | 4/2019 | Morgan et al. | |
| 2019/0105037 A1 | 4/2019 | Morgan et al. | |
| 2019/0105039 A1 | 4/2019 | Morgan et al. | |
| 2019/0105043 A1 | 4/2019 | Jaworek et al. | |
| 2019/0105044 A1 | 4/2019 | Shelton, IV et al. | |
| 2019/0110779 A1 | 4/2019 | Gardner et al. | |
| 2019/0110791 A1 | 4/2019 | Shelton, IV et al. | |
| 2019/0110792 A1 | 4/2019 | Shelton, IV et al. | |
| 2019/0117224 A1 | 4/2019 | Setser et al. | |
| 2019/0125320 A1 | 5/2019 | Shelton, IV et al. | |
| 2019/0125335 A1 | 5/2019 | Shelton, IV et al. | |
| 2019/0125336 A1 | 5/2019 | Deck et al. | |
| 2019/0125338 A1 | 5/2019 | Shelton, IV et al. | |
| 2019/0125342 A1 | 5/2019 | Beardsley et al. | |
| 2019/0125344 A1 | 5/2019 | DiNardo et al. | |
| 2019/0125357 A1 | 5/2019 | Shelton, IV et al. | |
| 2019/0125358 A1 | 5/2019 | Shelton, IV et al. | |
| 2019/0125361 A1 | 5/2019 | Shelton, IV et al. | |
| 2019/0125377 A1 | 5/2019 | Shelton, IV | |
| 2019/0125378 A1 | 5/2019 | Shelton, IV et al. | |
| 2019/0125388 A1 | 5/2019 | Shelton, IV et al. | |
| 2019/0125430 A1 | 5/2019 | Shelton, IV et al. | |
| 2019/0125431 A1 | 5/2019 | Shelton, IV et al. | |
| 2019/0125432 A1 | 5/2019 | Shelton, IV et al. | |
| 2019/0125454 A1 | 5/2019 | Stokes et al. | |
| 2019/0125455 A1 | 5/2019 | Shelton, IV et al. | |
| 2019/0125457 A1 | 5/2019 | Parihar et al. | |
| 2019/0125458 A1 | 5/2019 | Shelton, IV et al. | |
| 2019/0125459 A1 | 5/2019 | Shelton, IV et al. | |
| 2019/0125476 A1 | 5/2019 | Shelton, IV et al. | |
| 2019/0133422 A1 | 5/2019 | Nakamura | |
| 2019/0133577 A1 | 5/2019 | Weadock et al. | |
| 2019/0138770 A1 | 5/2019 | Compaijen et al. | |
| 2019/0142421 A1 | 5/2019 | Shelton, IV | |
| 2019/0142423 A1 | 5/2019 | Satti, III et al. | |
| 2019/0150925 A1 | 5/2019 | Marczyk et al. | |
| 2019/0151029 A1 | 5/2019 | Robinson | |
| 2019/0159778 A1 | 5/2019 | Shelton, IV et al. | |
| 2019/0175847 A1 | 6/2019 | Pocreva, III et al. | |
| 2019/0183502 A1 | 6/2019 | Shelton, IV et al. | |
| 2019/0192138 A1 | 6/2019 | Shelton, IV et al. | |
| 2019/0192141 A1 | 6/2019 | Shelton, IV et al. | |

(56) References Cited

U.S. PATENT DOCUMENTS

2019/0192146 A1 6/2019 Widenhouse et al.
2019/0192147 A1 6/2019 Shelton, IV et al.
2019/0192148 A1 6/2019 Shelton, IV et al.
2019/0192150 A1 6/2019 Widenhouse et al.
2019/0192151 A1 6/2019 Shelton, IV et al.
2019/0192153 A1 6/2019 Shelton, IV et al.
2019/0192154 A1 6/2019 Shelton, IV et al.
2019/0192155 A1 6/2019 Shelton, IV et al.
2019/0192156 A1 6/2019 Simms et al.
2019/0192157 A1 6/2019 Scott et al.
2019/0192235 A1 6/2019 Harris et al.
2019/0200844 A1 7/2019 Shelton, IV et al.
2019/0200905 A1 7/2019 Shelton, IV et al.
2019/0200906 A1 7/2019 Shelton, IV et al.
2019/0200977 A1 7/2019 Shelton, IV et al.
2019/0200981 A1 7/2019 Harris et al.
2019/0200986 A1 7/2019 Shelton, IV et al.
2019/0200987 A1 7/2019 Shelton, IV et al.
2019/0200988 A1 7/2019 Shelton, IV
2019/0200989 A1 7/2019 Burbank et al.
2019/0200997 A1 7/2019 Shelton, IV et al.
2019/0200998 A1 7/2019 Shelton, IV et al.
2019/0201020 A1 7/2019 Shelton, IV et al.
2019/0201023 A1 7/2019 Shelton, IV et al.
2019/0201024 A1 7/2019 Shelton, IV et al.
2019/0201025 A1 7/2019 Shelton, IV et al.
2019/0201026 A1 7/2019 Shelton, IV et al.
2019/0201027 A1 7/2019 Shelton, IV et al.
2019/0201028 A1 7/2019 Shelton, IV et al.
2019/0201029 A1 7/2019 Shelton, IV et al.
2019/0201030 A1 7/2019 Shelton, IV et al.
2019/0201033 A1 7/2019 Yates et al.
2019/0201034 A1 7/2019 Shelton, IV et al.
2019/0201045 A1 7/2019 Yates et al.
2019/0201046 A1 7/2019 Shelton, IV et al.
2019/0201047 A1 7/2019 Yates et al.
2019/0201079 A1 7/2019 Shelton, IV et al.
2019/0201104 A1 7/2019 Shelton, IV et al.
2019/0201112 A1 7/2019 Wiener et al.
2019/0201113 A1 7/2019 Shelton, IV et al.
2019/0201115 A1 7/2019 Shelton, IV et al.
2019/0201118 A1 7/2019 Shelton, IV et al.
2019/0201120 A1 7/2019 Shelton, IV et al.
2019/0201136 A1 7/2019 Shelton, IV et al.
2019/0201137 A1 7/2019 Shelton, IV et al.
2019/0201139 A1 7/2019 Shelton, IV et al.
2019/0201140 A1 7/2019 Yates et al.
2019/0201142 A1 7/2019 Shelton, IV et al.
2019/0201158 A1 7/2019 Shelton, IV et al.
2019/0201594 A1 7/2019 Shelton, IV et al.
2019/0205001 A1 7/2019 Messerly et al.
2019/0205567 A1 7/2019 Shelton, IV et al.
2019/0206003 A1 7/2019 Harris et al.
2019/0206551 A1 7/2019 Yates et al.
2019/0206555 A1 7/2019 Morgan et al.
2019/0206561 A1 7/2019 Shelton, IV et al.
2019/0206562 A1 7/2019 Shelton, IV et al.
2019/0206564 A1 7/2019 Shelton, IV et al.
2019/0206565 A1 7/2019 Shelton, IV
2019/0206569 A1 7/2019 Shelton, IV et al.
2019/0208641 A1 7/2019 Yates et al.
2019/0209172 A1 7/2019 Shelton, IV et al.
2019/0209247 A1 7/2019 Giordano et al.
2019/0209248 A1 7/2019 Giordano et al.
2019/0209249 A1 7/2019 Giordano et al.
2019/0209250 A1 7/2019 Giordano et al.
2019/0216558 A1 7/2019 Giordano et al.
2019/0239873 A1 8/2019 Laurent et al.
2019/0247048 A1 8/2019 Gasparovich et al.
2019/0261982 A1 8/2019 Holsten
2019/0261983 A1 8/2019 Granger et al.
2019/0261984 A1 8/2019 Nelson et al.
2019/0261987 A1 8/2019 Viola et al.
2019/0262153 A1 8/2019 Tassoni et al.
2019/0269400 A1 9/2019 Mandakolathur Vasudevan et al.
2019/0269402 A1 9/2019 Murray et al.
2019/0269428 A1 9/2019 Allen et al.
2019/0274685 A1 9/2019 Olson et al.
2019/0274716 A1 9/2019 Nott et al.
2019/0282233 A1 9/2019 Burbank et al.
2019/0290264 A1 9/2019 Morgan et al.
2019/0290266 A1 9/2019 Scheib et al.
2019/0290267 A1 9/2019 Baxter, III et al.
2019/0290297 A1 9/2019 Haider et al.
2019/0298340 A1 10/2019 Shelton, IV et al.
2019/0298350 A1 10/2019 Shelton, IV et al.
2019/0298352 A1 10/2019 Shelton, IV et al.
2019/0298353 A1 10/2019 Shelton, IV et al.
2019/0298360 A1 10/2019 Shelton, IV et al.
2019/0298361 A1 10/2019 Shelton, IV et al.
2019/0298362 A1 10/2019 Shelton, IV et al.
2019/0298381 A1 10/2019 Kreidler et al.
2019/0307452 A1 10/2019 Shelton, IV et al.
2019/0307453 A1 10/2019 Shelton, IV et al.
2019/0307454 A1 10/2019 Shelton, IV et al.
2019/0307456 A1 10/2019 Shelton, IV et al.
2019/0307479 A1 10/2019 Shelton, IV et al.
2019/0314015 A1 10/2019 Shelton, IV et al.
2019/0314018 A1 10/2019 Huitema et al.
2019/0321040 A1 10/2019 Shelton, IV
2019/0321062 A1 10/2019 Williams
2019/0328387 A1 10/2019 Overmyer et al.
2019/0328390 A1 10/2019 Harris et al.
2019/0343515 A1 11/2019 Morgan et al.
2019/0343525 A1 11/2019 Shelton, IV et al.
2019/0350581 A1 11/2019 Baxter, III et al.
2019/0350582 A1 11/2019 Shelton, IV et al.
2019/0357909 A1 11/2019 Huitema et al.
2019/0374224 A1 12/2019 Huitema et al.
2019/0388091 A1 12/2019 Eschbach et al.
2020/0000471 A1 1/2020 Shelton, IV et al.
2020/0000531 A1 1/2020 Giordano et al.
2020/0008802 A1 1/2020 Aronhalt et al.
2020/0008809 A1 1/2020 Shelton, IV et al.
2020/0008827 A1 1/2020 Dearden et al.
2020/0015817 A1 1/2020 Harris et al.
2020/0015819 A1 1/2020 Shelton, IV et al.
2020/0015915 A1 1/2020 Swayze et al.
2020/0030020 A1 1/2020 Wang et al.
2020/0037939 A1 2/2020 Castagna et al.
2020/0038016 A1 2/2020 Shelton, IV et al.
2020/0038018 A1 2/2020 Shelton, IV et al.
2020/0038020 A1 2/2020 Yates et al.
2020/0046348 A1 2/2020 Shelton, IV et al.
2020/0046355 A1 2/2020 Harris et al.
2020/0046356 A1 2/2020 Baxter, III et al.
2020/0054320 A1 2/2020 Harris et al.
2020/0054321 A1 2/2020 Harris et al.
2020/0054324 A1 2/2020 Shelton, IV et al.
2020/0054329 A1 2/2020 Shelton, IV et al.
2020/0054332 A1 2/2020 Shelton, IV et al.
2020/0054333 A1 2/2020 Shelton, IV et al.
2020/0054334 A1 2/2020 Shelton, IV et al.
2020/0054355 A1 2/2020 Laurent et al.
2020/0060523 A1 2/2020 Matsuda et al.
2020/0060680 A1 2/2020 Shelton, IV et al.
2020/0060713 A1 2/2020 Leimbach et al.
2020/0061385 A1 2/2020 Schwarz et al.
2020/0077994 A1 3/2020 Shelton, IV et al.
2020/0078015 A1 3/2020 Miller et al.
2020/0085427 A1 3/2020 Giordano et al.
2020/0085431 A1 3/2020 Swayze et al.
2020/0085435 A1 3/2020 Shelton, IV et al.
2020/0085436 A1 3/2020 Beckman et al.
2020/0085518 A1 3/2020 Giordano et al.
2020/0093484 A1 3/2020 Shelton, IV et al.
2020/0093485 A1 3/2020 Shelton, IV et al.
2020/0093506 A1 3/2020 Leimbach et al.
2020/0093550 A1 3/2020 Spivey et al.
2020/0100699 A1 4/2020 Shelton, IV et al.
2020/0100783 A1 4/2020 Yates et al.
2020/0107829 A1 4/2020 Shelton, IV et al.
2020/0114505 A1 4/2020 Kikuchi
2020/0138434 A1 5/2020 Miller et al.

(56) References Cited

U.S. PATENT DOCUMENTS

| | | | |
|---|---|---|---|
| 2020/0138435 | A1 | 5/2020 | Shelton, IV et al. |
| 2020/0138436 | A1 | 5/2020 | Yates et al. |
| 2020/0138507 | A1 | 5/2020 | Davison et al. |
| 2020/0138534 | A1 | 5/2020 | Garcia Kilroy et al. |
| 2020/0146676 | A1 | 5/2020 | Yates et al. |
| 2020/0146741 | A1 | 5/2020 | Long et al. |
| 2020/0187943 | A1 | 6/2020 | Shelton, IV et al. |
| 2020/0197027 | A1 | 6/2020 | Hershberger et al. |
| 2020/0205810 | A1 | 7/2020 | Posey et al. |
| 2020/0205811 | A1 | 7/2020 | Posey et al. |
| 2020/0205823 | A1 | 7/2020 | Vendely et al. |
| 2020/0214706 | A1 | 7/2020 | Vendely et al. |
| 2020/0214731 | A1 | 7/2020 | Shelton, IV et al. |
| 2020/0222047 | A1 | 7/2020 | Shelton, IV et al. |
| 2020/0229812 | A1 | 7/2020 | Parihar et al. |
| 2020/0229814 | A1 | 7/2020 | Amariglio et al. |
| 2020/0229816 | A1 | 7/2020 | Bakos et al. |
| 2020/0237371 | A1 | 7/2020 | Huitema et al. |
| 2020/0253605 | A1 | 8/2020 | Swayze et al. |
| 2020/0261075 | A1 | 8/2020 | Boudreaux et al. |
| 2020/0261078 | A1 | 8/2020 | Bakos et al. |
| 2020/0261081 | A1 | 8/2020 | Boudreaux et al. |
| 2020/0261083 | A1 | 8/2020 | Bakos et al. |
| 2020/0261085 | A1 | 8/2020 | Boudreaux et al. |
| 2020/0261086 | A1 | 8/2020 | Zeiner et al. |
| 2020/0261087 | A1 | 8/2020 | Timm et al. |
| 2020/0261088 | A1 | 8/2020 | Harris et al. |
| 2020/0261106 | A1 | 8/2020 | Hess et al. |
| 2020/0268377 | A1 | 8/2020 | Schmid et al. |
| 2020/0275926 | A1 | 9/2020 | Shelton, IV et al. |
| 2020/0275927 | A1 | 9/2020 | Shelton, IV et al. |
| 2020/0275928 | A1 | 9/2020 | Shelton, IV et al. |
| 2020/0275930 | A1 | 9/2020 | Harris et al. |
| 2020/0280219 | A1 | 9/2020 | Laughery et al. |
| 2020/0281585 | A1 | 9/2020 | Timm et al. |
| 2020/0281587 | A1 | 9/2020 | Schmid et al. |
| 2020/0281590 | A1 | 9/2020 | Shelton, IV et al. |
| 2020/0289112 | A1 | 9/2020 | Whitfield et al. |
| 2020/0297340 | A1 | 9/2020 | Hess et al. |
| 2020/0297341 | A1 | 9/2020 | Yates et al. |
| 2020/0297346 | A1 | 9/2020 | Shelton, IV et al. |
| 2020/0305862 | A1 | 10/2020 | Yates et al. |
| 2020/0305863 | A1 | 10/2020 | Yates et al. |
| 2020/0305864 | A1 | 10/2020 | Yates et al. |
| 2020/0305870 | A1 | 10/2020 | Shelton, IV |
| 2020/0305871 | A1 | 10/2020 | Shelton, IV et al. |
| 2020/0305872 | A1 | 10/2020 | Weidner et al. |
| 2020/0305874 | A1 | 10/2020 | Huitema et al. |
| 2020/0315612 | A1 | 10/2020 | Shelton, IV et al. |
| 2020/0315623 | A1 | 10/2020 | Eisinger et al. |
| 2020/0315625 | A1 | 10/2020 | Hall et al. |
| 2020/0315983 | A1 | 10/2020 | Widenhouse et al. |
| 2020/0323526 | A1 | 10/2020 | Huang et al. |
| 2020/0330092 | A1 | 10/2020 | Shelton, IV et al. |
| 2020/0330093 | A1 | 10/2020 | Shelton, IV et al. |
| 2020/0330094 | A1 | 10/2020 | Baxter, III et al. |
| 2020/0330096 | A1 | 10/2020 | Shelton, IV et al. |
| 2020/0330181 | A1 | 10/2020 | Junger et al. |
| 2020/0337693 | A1 | 10/2020 | Shelton, IV et al. |
| 2020/0337702 | A1 | 10/2020 | Shelton, IV et al. |
| 2020/0337703 | A1 | 10/2020 | Shelton, IV et al. |
| 2020/0337791 | A1 | 10/2020 | Shelton, IV et al. |
| 2020/0345346 | A1 | 11/2020 | Shelton, IV et al. |
| 2020/0345349 | A1 | 11/2020 | Kimball et al. |
| 2020/0345352 | A1 | 11/2020 | Shelton, IV et al. |
| 2020/0345353 | A1 | 11/2020 | Leimbach et al. |
| 2020/0345354 | A1 | 11/2020 | Leimbach et al. |
| 2020/0345355 | A1 | 11/2020 | Baxter, III et al. |
| 2020/0345356 | A1 | 11/2020 | Leimbach et al. |
| 2020/0345357 | A1 | 11/2020 | Leimbach et al. |
| 2020/0345358 | A1 | 11/2020 | Jenkins |
| 2020/0345359 | A1 | 11/2020 | Baxter, III et al. |
| 2020/0345360 | A1 | 11/2020 | Leimbach et al. |
| 2020/0345363 | A1 | 11/2020 | Shelton, IV et al. |
| 2020/0345435 | A1 | 11/2020 | Traina |
| 2020/0345446 | A1 | 11/2020 | Kimball et al. |
| 2020/0352562 | A1 | 11/2020 | Timm et al. |
| 2020/0367885 | A1 | 11/2020 | Yates et al. |
| 2020/0367886 | A1 | 11/2020 | Shelton, IV et al. |
| 2020/0375585 | A1 | 12/2020 | Swayze et al. |
| 2020/0375592 | A1 | 12/2020 | Hall et al. |
| 2020/0375593 | A1 | 12/2020 | Hunter et al. |
| 2020/0375597 | A1 | 12/2020 | Shelton, IV et al. |
| 2020/0390444 | A1 | 12/2020 | Harris et al. |
| 2020/0397430 | A1 | 12/2020 | Patel et al. |
| 2020/0397433 | A1 | 12/2020 | Lytle, IV et al. |
| 2020/0397434 | A1 | 12/2020 | Overmyer et al. |
| 2020/0405290 | A1 | 12/2020 | Shelton, IV et al. |
| 2020/0405292 | A1 | 12/2020 | Shelton, IV et al. |
| 2020/0405293 | A1 | 12/2020 | Shelton, IV et al. |
| 2020/0405294 | A1 | 12/2020 | Shelton, IV |
| 2020/0405295 | A1 | 12/2020 | Shelton, IV et al. |
| 2020/0405296 | A1 | 12/2020 | Shelton, IV et al. |
| 2020/0405302 | A1 | 12/2020 | Shelton, IV et al. |
| 2020/0405304 | A1 | 12/2020 | Mozdzierz et al. |
| 2020/0405306 | A1 | 12/2020 | Shelton, IV et al. |
| 2020/0405307 | A1 | 12/2020 | Shelton, IV et al. |
| 2020/0405308 | A1 | 12/2020 | Shelton, IV |
| 2020/0405312 | A1 | 12/2020 | Shelton, IV et al. |
| 2020/0405314 | A1 | 12/2020 | Shelton, IV et al. |
| 2020/0405316 | A1 | 12/2020 | Shelton, IV et al. |
| 2020/0405341 | A1 | 12/2020 | Hess et al. |
| 2020/0405403 | A1 | 12/2020 | Shelton, IV et al. |
| 2020/0405404 | A1 | 12/2020 | Shelton, IV et al. |
| 2020/0405409 | A1 | 12/2020 | Shelton, IV et al. |
| 2020/0405410 | A1 | 12/2020 | Shelton, IV |
| 2020/0405416 | A1 | 12/2020 | Shelton, IV et al. |
| 2020/0405436 | A1 | 12/2020 | Shelton, IV et al. |
| 2020/0405437 | A1 | 12/2020 | Shelton, IV et al. |
| 2020/0405438 | A1 | 12/2020 | Shelton, IV et al. |
| 2020/0405439 | A1 | 12/2020 | Shelton, IV et al. |
| 2020/0410177 | A1 | 12/2020 | Shelton, IV |
| 2020/0410180 | A1 | 12/2020 | Shelton, IV et al. |
| 2021/0000466 | A1 | 1/2021 | Leimbach et al. |
| 2021/0000467 | A1 | 1/2021 | Shelton, IV et al. |
| 2021/0000470 | A1 | 1/2021 | Leimbach et al. |
| 2021/0007742 | A1 | 1/2021 | Rector et al. |
| 2021/0015480 | A1 | 1/2021 | Shelton, IV et al. |
| 2021/0022741 | A1 | 1/2021 | Baxter, III et al. |
| 2021/0030416 | A1 | 2/2021 | Shelton, IV et al. |
| 2021/0045742 | A1 | 2/2021 | Shelton, IV et al. |
| 2021/0052271 | A1 | 2/2021 | Harris et al. |
| 2021/0059661 | A1 | 3/2021 | Schmid et al. |
| 2021/0059662 | A1 | 3/2021 | Shelton, IV |
| 2021/0059664 | A1 | 3/2021 | Hensel et al. |
| 2021/0059666 | A1 | 3/2021 | Schmid et al. |
| 2021/0059669 | A1 | 3/2021 | Yates et al. |
| 2021/0059670 | A1 | 3/2021 | Overmyer et al. |
| 2021/0059671 | A1 | 3/2021 | Shelton, IV et al. |
| 2021/0059672 | A1 | 3/2021 | Giordano et al. |
| 2021/0059673 | A1 | 3/2021 | Shelton, IV et al. |
| 2021/0068817 | A1 | 3/2021 | Shelton, IV et al. |
| 2021/0068818 | A1 | 3/2021 | Overmyer et al. |
| 2021/0068820 | A1 | 3/2021 | Parihar et al. |
| 2021/0068829 | A1 | 3/2021 | Miller et al. |
| 2021/0068830 | A1 | 3/2021 | Baber et al. |
| 2021/0068831 | A1 | 3/2021 | Baber et al. |
| 2021/0068832 | A1 | 3/2021 | Yates et al. |
| 2021/0068835 | A1 | 3/2021 | Shelton, IV et al. |
| 2021/0077092 | A1 | 3/2021 | Parihar et al. |
| 2021/0077099 | A1 | 3/2021 | Shelton, IV et al. |
| 2021/0077100 | A1 | 3/2021 | Shelton, IV et al. |
| 2021/0077109 | A1 | 3/2021 | Harris et al. |
| 2021/0085313 | A1 | 3/2021 | Morgan et al. |
| 2021/0085314 | A1 | 3/2021 | Schmid et al. |
| 2021/0085315 | A1 | 3/2021 | Aronhalt et al. |
| 2021/0085316 | A1 | 3/2021 | Harris et al. |
| 2021/0085317 | A1 | 3/2021 | Miller et al. |
| 2021/0085318 | A1 | 3/2021 | Swayze et al. |
| 2021/0085319 | A1 | 3/2021 | Swayze et al. |
| 2021/0085320 | A1 | 3/2021 | Leimbach et al. |
| 2021/0085321 | A1 | 3/2021 | Shelton, IV et al. |
| 2021/0085325 | A1 | 3/2021 | Shelton, IV et al. |
| 2021/0085326 | A1 | 3/2021 | Vendely et al. |

(56) References Cited

U.S. PATENT DOCUMENTS

2021/0093321 A1 4/2021 Auld et al.
2021/0093323 A1 4/2021 Scirica et al.
2021/0100541 A1 4/2021 Shelton, IV et al.
2021/0100550 A1 4/2021 Shelton, IV et al.
2021/0100982 A1 4/2021 Laby et al.
2021/0106333 A1 4/2021 Shelton, IV et al.
2021/0107031 A1 4/2021 Bales, Jr. et al.
2021/0121175 A1 4/2021 Yates et al.
2021/0128146 A1 5/2021 Shelton, IV et al.
2021/0128153 A1 5/2021 Sgroi
2021/0137522 A1 5/2021 Shelton, IV et al.
2021/0153866 A1 5/2021 Knapp et al.
2021/0177401 A1 6/2021 Abramek et al.
2021/0177411 A1 6/2021 Williams
2021/0186492 A1 6/2021 Shelton, IV et al.
2021/0186493 A1 6/2021 Shelton, IV et al.
2021/0186494 A1 6/2021 Shelton, IV et al.
2021/0186495 A1 6/2021 Shelton, IV et al.
2021/0186497 A1 6/2021 Shelton, IV et al.
2021/0186498 A1 6/2021 Boudreaux et al.
2021/0186499 A1 6/2021 Shelton, IV et al.
2021/0186500 A1 6/2021 Shelton, IV et al.
2021/0186501 A1 6/2021 Shelton, IV et al.
2021/0186502 A1 6/2021 Shelton, IV et al.
2021/0186504 A1 6/2021 Shelton, IV et al.
2021/0186505 A1 6/2021 Shelton, IV et al.
2021/0186507 A1 6/2021 Shelton, IV et al.
2021/0204941 A1 7/2021 Dewaele et al.
2021/0204951 A1 7/2021 Sgroi et al.
2021/0212671 A1 7/2021 Ramadan et al.
2021/0212691 A1 7/2021 Smith et al.
2021/0212776 A1 7/2021 Schmitt et al.
2021/0219976 A1 7/2021 DiNardo et al.
2021/0228209 A1 7/2021 Shelton, IV et al.
2021/0236117 A1 8/2021 Morgan et al.
2021/0236124 A1 8/2021 Shelton, IV et al.
2021/0244406 A1 8/2021 Kerr et al.
2021/0244407 A1 8/2021 Shelton, IV et al.
2021/0244410 A1 8/2021 Swayze et al.
2021/0244411 A1 8/2021 Smith et al.
2021/0244412 A1 8/2021 Vendely et al.
2021/0259681 A1 8/2021 Shelton, IV et al.
2021/0259687 A1 8/2021 Gonzalez et al.
2021/0259986 A1 8/2021 Widenhouse et al.
2021/0259987 A1 8/2021 Widenhouse et al.
2021/0267589 A1 9/2021 Swayze et al.
2021/0267592 A1 9/2021 Baxter, III et al.
2021/0267594 A1 9/2021 Morgan et al.
2021/0267595 A1 9/2021 Posada et al.
2021/0267596 A1 9/2021 Fanelli et al.
2021/0275053 A1 9/2021 Shelton, IV et al.
2021/0275172 A1 9/2021 Harris et al.
2021/0275173 A1 9/2021 Shelton, IV et al.
2021/0275175 A1 9/2021 Vadali et al.
2021/0275176 A1 9/2021 Beckman et al.
2021/0282767 A1 9/2021 Shelton, IV et al.
2021/0282769 A1 9/2021 Baxter, III et al.
2021/0282774 A1 9/2021 Shelton, IV et al.
2021/0282776 A1 9/2021 Overmyer et al.
2021/0290226 A1 9/2021 Mandakolathur Vasudevan et al.
2021/0290231 A1 9/2021 Baxter, III et al.
2021/0290232 A1 9/2021 Harris et al.
2021/0290233 A1 9/2021 Shelton, IV et al.
2021/0290236 A1 9/2021 Moore et al.
2021/0290322 A1 9/2021 Traina
2021/0298745 A1 9/2021 Leimbach et al.
2021/0298746 A1 9/2021 Leimbach et al.
2021/0307744 A1 10/2021 Walcott et al.
2021/0307748 A1 10/2021 Harris et al.
2021/0307754 A1 10/2021 Shelton, IV et al.
2021/0313975 A1 10/2021 Shan et al.
2021/0315566 A1 10/2021 Yates et al.
2021/0315570 A1 10/2021 Shelton, IV
2021/0315571 A1 10/2021 Swayze et al.
2021/0315573 A1 10/2021 Shelton, IV et al.
2021/0315574 A1 10/2021 Shelton, IV et al.
2021/0315576 A1 10/2021 Shelton, IV et al.
2021/0315577 A1 10/2021 Shelton, IV et al.
2021/0322009 A1 10/2021 Huang et al.
2021/0330321 A1 10/2021 Leimbach et al.
2021/0338233 A1 11/2021 Shelton, IV et al.
2021/0338234 A1 11/2021 Shelton, IV et al.
2021/0338260 A1 11/2021 Le Rolland et al.
2021/0353284 A1 11/2021 Yang et al.
2021/0369271 A1 12/2021 Schings et al.
2021/0369273 A1 12/2021 Yates et al.
2021/0378669 A1 12/2021 Shelton, IV et al.
2021/0393260 A1 12/2021 Shelton, IV et al.
2021/0393261 A1 12/2021 Harris et al.
2021/0393262 A1 12/2021 Shelton, IV et al.
2021/0393268 A1 12/2021 Shelton, IV et al.
2021/0393366 A1 12/2021 Shelton, IV et al.
2022/0000478 A1 1/2022 Shelton, IV et al.
2022/0000479 A1 1/2022 Shelton, IV et al.
2022/0015760 A1 1/2022 Beardsley et al.
2022/0031313 A1 2/2022 Bakos et al.
2022/0031314 A1 2/2022 Bakos et al.
2022/0031315 A1 2/2022 Bakos et al.
2022/0031319 A1 2/2022 Witte et al.
2022/0031320 A1 2/2022 Hall et al.
2022/0031322 A1 2/2022 Parks
2022/0031323 A1 2/2022 Witte
2022/0031324 A1 2/2022 Hall et al.
2022/0031345 A1 2/2022 Witte
2022/0031346 A1 2/2022 Parks
2022/0031350 A1 2/2022 Witte
2022/0031351 A1 2/2022 Moubarak et al.
2022/0049593 A1 2/2022 Groover et al.
2022/0054125 A1 2/2022 Ji et al.
2022/0054130 A1 2/2022 Overmyer et al.
2022/0061642 A1 3/2022 Park et al.
2022/0061836 A1 3/2022 Parihar et al.
2022/0061843 A1 3/2022 Vendely et al.
2022/0061845 A1 3/2022 Shelton, IV et al.
2022/0061862 A1 3/2022 Shelton, IV et al.
2022/0071630 A1 3/2022 Swayze et al.
2022/0071631 A1 3/2022 Harris et al.
2022/0071632 A1 3/2022 Patel et al.
2022/0071635 A1 3/2022 Shelton, IV et al.
2022/0079580 A1 3/2022 Vendely et al.
2022/0079586 A1 3/2022 Shelton, IV et al.
2022/0079588 A1 3/2022 Harris et al.
2022/0079589 A1 3/2022 Harris et al.
2022/0079590 A1 3/2022 Harris et al.
2022/0079595 A1 3/2022 Huitema et al.
2022/0079596 A1 3/2022 Huitema et al.
2022/0087676 A1 3/2022 Shelton, IV et al.
2022/0104816 A1 4/2022 Fernandes et al.
2022/0104820 A1 4/2022 Shelton, IV et al.
2022/0117602 A1 4/2022 Wise et al.
2022/0133299 A1 5/2022 Baxter, III
2022/0133300 A1 5/2022 Leimbach et al.
2022/0133301 A1 5/2022 Leimbach
2022/0133302 A1 5/2022 Zerkle et al.
2022/0133303 A1 5/2022 Huang
2022/0133304 A1 5/2022 Leimbach et al.
2022/0133310 A1 5/2022 Ross
2022/0133311 A1 5/2022 Huang
2022/0133312 A1 5/2022 Huang
2022/0133427 A1 5/2022 Baxter, III
2022/0133428 A1 5/2022 Leimbach et al.
2022/0142643 A1 5/2022 Shelton, IV et al.
2022/0151611 A1 5/2022 Shelton, IV et al.
2022/0151613 A1 5/2022 Vendely et al.
2022/0151614 A1 5/2022 Vendely et al.
2022/0151615 A1 5/2022 Shelton, IV et al.
2022/0151616 A1 5/2022 Shelton, IV et al.
2022/0160358 A1 5/2022 Wixey
2022/0167968 A1 6/2022 Worthington et al.
2022/0167970 A1 6/2022 Aronhalt et al.
2022/0167971 A1 6/2022 Shelton, IV et al.
2022/0167972 A1 6/2022 Shelton, IV et al.
2022/0167973 A1 6/2022 Shelton, IV et al.
2022/0167974 A1 6/2022 Shelton, IV et al.

(56) References Cited

U.S. PATENT DOCUMENTS

| | | | |
|---|---|---|---|
| 2022/0167975 | A1 | 6/2022 | Shelton, IV et al. |
| 2022/0167977 | A1 | 6/2022 | Shelton, IV et al. |
| 2022/0167979 | A1 | 6/2022 | Yates et al. |
| 2022/0167980 | A1 | 6/2022 | Shelton, IV et al. |
| 2022/0167981 | A1 | 6/2022 | Shelton, IV et al. |
| 2022/0167982 | A1 | 6/2022 | Shelton, IV et al. |
| 2022/0167983 | A1 | 6/2022 | Shelton, IV et al. |
| 2022/0167984 | A1 | 6/2022 | Shelton, IV et al. |
| 2022/0167995 | A1 | 6/2022 | Parfett et al. |
| 2022/0168038 | A1 | 6/2022 | Shelton, IV et al. |
| 2022/0175370 | A1 | 6/2022 | Shelton, IV et al. |
| 2022/0175371 | A1 | 6/2022 | Hess et al. |
| 2022/0175372 | A1 | 6/2022 | Shelton, IV et al. |
| 2022/0175375 | A1 | 6/2022 | Harris et al. |
| 2022/0175378 | A1 | 6/2022 | Leimbach et al. |
| 2022/0175381 | A1 | 6/2022 | Scheib et al. |
| 2022/0183685 | A1 | 6/2022 | Shelton, IV et al. |
| 2022/0192667 | A1 | 6/2022 | Shelton, IV et al. |
| 2022/0211367 | A1 | 7/2022 | Schmid et al. |
| 2022/0218332 | A1 | 7/2022 | Shelton, IV et al. |
| 2022/0218333 | A1 | 7/2022 | Parihar et al. |
| 2022/0218334 | A1 | 7/2022 | Parihar et al. |
| 2022/0218336 | A1 | 7/2022 | Timm et al. |
| 2022/0218337 | A1 | 7/2022 | Timm et al. |
| 2022/0218338 | A1 | 7/2022 | Shelton, IV et al. |
| 2022/0218340 | A1 | 7/2022 | Harris et al. |
| 2022/0218342 | A1 | 7/2022 | Harris et al. |
| 2022/0218344 | A1 | 7/2022 | Leimbach et al. |
| 2022/0218345 | A1 | 7/2022 | Shelton, IV et al. |
| 2022/0218346 | A1 | 7/2022 | Shelton, IV et al. |
| 2022/0218347 | A1 | 7/2022 | Shelton, IV et al. |
| 2022/0218348 | A1 | 7/2022 | Swensgard et al. |
| 2022/0218349 | A1 | 7/2022 | Shelton, IV et al. |
| 2022/0218350 | A1 | 7/2022 | Shelton, IV et al. |
| 2022/0218351 | A1 | 7/2022 | Shelton, IV et al. |
| 2022/0218376 | A1 | 7/2022 | Shelton, IV et al. |
| 2022/0218378 | A1 | 7/2022 | Shelton, IV et al. |
| 2022/0218381 | A1 | 7/2022 | Leimbach et al. |
| 2022/0218382 | A1 | 7/2022 | Leimbach et al. |
| 2022/0225980 | A1 | 7/2022 | Shelton, IV et al. |
| 2022/0225981 | A1 | 7/2022 | Shelton, IV et al. |
| 2022/0225982 | A1 | 7/2022 | Yates et al. |
| 2022/0225986 | A1 | 7/2022 | Shelton, IV et al. |
| 2022/0225992 | A1 | 7/2022 | Smith et al. |
| 2022/0225993 | A1 | 7/2022 | Huitema et al. |
| 2022/0225994 | A1 | 7/2022 | Setser et al. |
| 2022/0226012 | A1 | 7/2022 | Shelton, IV et al. |
| 2022/0226013 | A1 | 7/2022 | Hall et al. |
| 2022/0233184 | A1 | 7/2022 | Parihar et al. |
| 2022/0233185 | A1 | 7/2022 | Parihar et al. |
| 2022/0233186 | A1 | 7/2022 | Timm et al. |
| 2022/0233187 | A1 | 7/2022 | Timm et al. |
| 2022/0233188 | A1 | 7/2022 | Timm et al. |
| 2022/0233194 | A1 | 7/2022 | Baxter, III et al. |
| 2022/0233195 | A1 | 7/2022 | Shelton, IV et al. |
| 2022/0233257 | A1 | 7/2022 | Shelton, IV et al. |
| 2022/0240928 | A1 | 8/2022 | Timm et al. |
| 2022/0240929 | A1 | 8/2022 | Timm et al. |
| 2022/0240930 | A1 | 8/2022 | Yates et al. |
| 2022/0240936 | A1 | 8/2022 | Huitema et al. |
| 2022/0240937 | A1 | 8/2022 | Shelton, IV et al. |
| 2022/0249095 | A1 | 8/2022 | Shelton, IV et al. |
| 2022/0265272 | A1 | 8/2022 | Li et al. |
| 2022/0273291 | A1 | 9/2022 | Shelton, IV et al. |
| 2022/0273292 | A1 | 9/2022 | Shelton, IV et al. |
| 2022/0273293 | A1 | 9/2022 | Shelton, IV et al. |
| 2022/0273294 | A1 | 9/2022 | Creamer et al. |
| 2022/0273299 | A1 | 9/2022 | Shelton, IV et al. |
| 2022/0273300 | A1 | 9/2022 | Shelton, IV et al. |
| 2022/0273301 | A1 | 9/2022 | Creamer et al. |
| 2022/0273302 | A1 | 9/2022 | Shelton, IV et al. |
| 2022/0273303 | A1 | 9/2022 | Creamer et al. |
| 2022/0273304 | A1 | 9/2022 | Shelton, IV et al. |
| 2022/0273305 | A1 | 9/2022 | Shelton, IV et al. |
| 2022/0273307 | A1 | 9/2022 | Shelton, IV et al. |
| 2022/0273308 | A1 | 9/2022 | Shelton, IV et al. |
| 2022/0275306 | A1 | 9/2022 | Shelton. , IV et al. |
| 2022/0278438 | A1 | 9/2022 | Shelton. , IV et al. |
| 2022/0287711 | A1 | 9/2022 | Ming et al. |
| 2022/0296230 | A1 | 9/2022 | Adams et al. |
| 2022/0296231 | A1 | 9/2022 | Adams et al. |
| 2022/0296232 | A1 | 9/2022 | Adams et al. |
| 2022/0296233 | A1 | 9/2022 | Morgan et al. |
| 2022/0296234 | A1 | 9/2022 | Shelton, IV et al. |
| 2022/0296235 | A1 | 9/2022 | Morgan et al. |
| 2022/0296236 | A1 | 9/2022 | Bakos et al. |
| 2022/0296237 | A1 | 9/2022 | Bakos et al. |
| 2022/0301685 | A1 | 9/2022 | Bakos et al. |
| 2022/0304679 | A1 | 9/2022 | Bakos et al. |
| 2022/0304680 | A1 | 9/2022 | Shelton, IV et al. |
| 2022/0304681 | A1 | 9/2022 | Shelton, IV et al. |
| 2022/0304682 | A1 | 9/2022 | Shelton, IV et al. |
| 2022/0304683 | A1 | 9/2022 | Shelton, IV et al. |
| 2022/0304684 | A1 | 9/2022 | Bakos et al. |
| 2022/0304685 | A1 | 9/2022 | Bakos et al. |
| 2022/0304686 | A1 | 9/2022 | Shelton, IV et al. |
| 2022/0304687 | A1 | 9/2022 | Shelton, IV et al. |
| 2022/0304688 | A1 | 9/2022 | Shelton, IV et al. |
| 2022/0304689 | A1 | 9/2022 | Shelton, IV |
| 2022/0304690 | A1 | 9/2022 | Baxter. III et al. |
| 2022/0304714 | A1 | 9/2022 | Shelton, IV et al. |
| 2022/0304715 | A1 | 9/2022 | Shelton, IV |
| 2022/0313253 | A1 | 10/2022 | Shelton, IV et al. |
| 2022/0313263 | A1 | 10/2022 | Huitema et al. |
| 2022/0313619 | A1 | 10/2022 | Schmid et al. |
| 2022/0323067 | A1 | 10/2022 | Overmyer et al. |
| 2022/0323070 | A1 | 10/2022 | Ross et al. |
| 2022/0330940 | A1 | 10/2022 | Shelton. , IV et al. |
| 2022/0338870 | A1 | 10/2022 | Swayze et al. |
| 2022/0346774 | A1 | 11/2022 | Hess et al. |
| 2022/0346775 | A1 | 11/2022 | Hess et al. |
| 2022/0354493 | A1 | 11/2022 | Shelton, IV et al. |
| 2022/0354495 | A1 | 11/2022 | Baxter, III et al. |
| 2022/0361879 | A1 | 11/2022 | Baxter, III et al. |
| 2022/0370069 | A1 | 11/2022 | Simms et al. |
| 2022/0378418 | A1 | 12/2022 | Huang et al. |
| 2022/0378420 | A1 | 12/2022 | Leimbach et al. |
| 2022/0378424 | A1 | 12/2022 | Huang et al. |
| 2022/0378425 | A1 | 12/2022 | Huang et al. |
| 2022/0378426 | A1 | 12/2022 | Huang et al. |
| 2022/0378427 | A1 | 12/2022 | Huang et al. |
| 2022/0378428 | A1 | 12/2022 | Shelton, IV et al. |
| 2022/0378435 | A1 | 12/2022 | Dholakia et al. |
| 2022/0387030 | A1 | 12/2022 | Shelton, IV et al. |
| 2022/0387031 | A1 | 12/2022 | Yates et al. |
| 2022/0387032 | A1 | 12/2022 | Huiterna et al. |
| 2022/0387033 | A1 | 12/2022 | Huitema et al. |
| 2022/0387034 | A1 | 12/2022 | Huiterna et al. |
| 2022/0387035 | A1 | 12/2022 | Huitema et al. |
| 2022/0387036 | A1 | 12/2022 | Huitema et al. |
| 2022/0387037 | A1 | 12/2022 | Huitema et al. |
| 2022/0387038 | A1 | 12/2022 | Huitema et al. |
| 2022/0387125 | A1 | 12/2022 | Leimbach et al. |

FOREIGN PATENT DOCUMENTS

| | | | |
|---|---|---|---|
| AU | 2012268848 | A1 | 1/2013 |
| AU | 2011218702 | B2 | 6/2013 |
| AU | 2012200178 | B2 | 7/2013 |
| BR | 112013007744 | A2 | 6/2016 |
| BR | 112013027777 | A2 | 1/2017 |
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |

(56) References Cited

FOREIGN PATENT DOCUMENTS

| | | | |
|---|---|---|---|
| CN | 2738962 | Y | 11/2005 |
| CN | 1777406 | A | 5/2006 |
| CN | 2785249 | Y | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101188900 | A | 5/2008 |
| CN | 101203085 | A | 6/2008 |
| CN | 101273908 | A | 10/2008 |
| CN | 101378791 | A | 3/2009 |
| CN | 101507635 | A | 8/2009 |
| CN | 101522120 | A | 9/2009 |
| CN | 101669833 | A | 3/2010 |
| CN | 101716090 | A | 6/2010 |
| CN | 101721236 | A | 6/2010 |
| CN | 101756727 | A | 6/2010 |
| CN | 101828940 | A | 9/2010 |
| CN | 101856250 | A | 10/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247182 | A | 11/2011 |
| CN | 102247183 | A | 11/2011 |
| CN | 101779977 | B | 12/2011 |
| CN | 102309352 | A | 1/2012 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 102743201 | A | 10/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103635150 | A | 3/2014 |
| CN | 103690212 | A | 4/2014 |
| CN | 103764046 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103860221 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 104027145 | A | 9/2014 |
| CN | 203815517 | U | 9/2014 |
| CN | 102783741 | B | 10/2014 |
| CN | 102973300 | B | 10/2014 |
| CN | 204092074 | U | 1/2015 |
| CN | 104337556 | A | 2/2015 |
| CN | 204158440 | U | 2/2015 |
| CN | 204158441 | U | 2/2015 |
| CN | 102469995 | B | 3/2015 |
| CN | 104422849 | A | 3/2015 |
| CN | 104586463 | A | 5/2015 |
| CN | 204520822 | U | 8/2015 |
| CN | 204636451 | U | 9/2015 |
| CN | 103860225 | B | 3/2016 |
| CN | 103750872 | B | 5/2016 |
| CN | 105682566 | A | 6/2016 |
| CN | 105919642 | A | 9/2016 |
| CN | 103648410 | B | 10/2016 |
| CN | 105997173 | A | 10/2016 |
| CN | 106344091 | A | 1/2017 |
| CN | 104921730 | B | 9/2017 |
| CN | 104349800 | B | 11/2017 |
| CN | 107635483 | A | 1/2018 |
| CN | 208625784 | U | 3/2019 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004041871 | A1 | 3/2006 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0129442 | B1 | 11/1987 |
| EP | 0251444 | A1 | 1/1988 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0516544 | B1 | 3/1996 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1064882 | A1 | 1/2001 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1234587 | A1 | 8/2002 |
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1558161 | A1 | 8/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |

(56) References Cited

FOREIGN PATENT DOCUMENTS

| | | | |
|---|---|---|---|
| EP | 1632191 | A2 | 3/2006 |
| EP | 1082944 | B1 | 5/2006 |
| EP | 1253866 | B1 | 7/2006 |
| EP | 1723914 | A1 | 11/2006 |
| EP | 1285633 | B1 | 12/2006 |
| EP | 1011494 | B1 | 1/2007 |
| EP | 1767163 | A1 | 3/2007 |
| EP | 1837041 | A1 | 9/2007 |
| EP | 0922435 | B1 | 10/2007 |
| EP | 1599146 | B1 | 10/2007 |
| EP | 1330201 | B1 | 6/2008 |
| EP | 2039302 | A2 | 3/2009 |
| EP | 1719461 | B1 | 6/2009 |
| EP | 2116196 | A2 | 11/2009 |
| EP | 2153793 | A2 | 2/2010 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2486868 | A2 | 8/2012 |
| EP | 2517638 | A1 | 10/2012 |
| EP | 2529671 | A2 | 12/2012 |
| EP | 2606812 | A1 | 6/2013 |
| EP | 2649948 | A1 | 10/2013 |
| EP | 2649949 | A1 | 10/2013 |
| EP | 2668910 | A2 | 12/2013 |
| EP | 2687164 | A2 | 1/2014 |
| EP | 2713902 | A1 | 4/2014 |
| EP | 2743042 | A2 | 6/2014 |
| EP | 2764827 | A2 | 8/2014 |
| EP | 2777524 | A2 | 9/2014 |
| EP | 2789299 | A1 | 10/2014 |
| EP | 2842500 | A1 | 3/2015 |
| EP | 2853220 | A1 | 4/2015 |
| EP | 2878274 | A1 | 6/2015 |
| EP | 2298220 | B1 | 6/2016 |
| EP | 2510891 | B1 | 6/2016 |
| EP | 3031404 | A1 | 6/2016 |
| EP | 3047806 | A1 | 7/2016 |
| EP | 3078334 | A1 | 10/2016 |
| EP | 2364651 | B1 | 11/2016 |
| EP | 2747235 | B1 | 11/2016 |
| EP | 3095399 | A2 | 11/2016 |
| EP | 3120781 | A2 | 1/2017 |
| EP | 3135225 | A2 | 3/2017 |
| EP | 2789299 | B1 | 5/2017 |
| EP | 3225190 | A2 | 10/2017 |
| EP | 3235445 | A1 | 10/2017 |
| EP | 3326548 | A1 | 5/2018 |
| EP | 3363378 | A1 | 8/2018 |
| EP | 3409216 | A1 | 12/2018 |
| EP | 3476301 | A1 | 5/2019 |
| EP | 3476334 | A1 | 5/2019 |
| EP | 3275378 | B1 | 7/2019 |
| EP | 3505095 | A1 | 7/2019 |
| EP | 3791810 | A1 | 3/2021 |
| ES | 1070456 | U | 9/2009 |
| FR | 459743 | A | 11/1913 |
| FR | 999646 | A | 2/1952 |
| FR | 1112936 | A | 3/1956 |
| FR | 2598905 | A1 | 11/1987 |
| FR | 2689749 | B1 | 7/1994 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2090534 | B | 6/1984 |
| GB | 2272159 | A | 5/1994 |
| GB | 2336214 | A | 10/1999 |
| GB | 2509523 | A | 7/2014 |
| GR | 930100110 | A | 11/1993 |
| JP | S4711908 | Y1 | 5/1972 |
| JP | S5033988 | U | 4/1975 |
| JP | S5367286 | A | 6/1978 |
| JP | S56112235 | A | 9/1981 |
| JP | S60113007 | A | 6/1985 |
| JP | S62170011 | U | 10/1987 |
| JP | S6333137 | A | 2/1988 |
| JP | S63270040 | A | 11/1988 |
| JP | S63318824 | A | 12/1988 |
| JP | H0129503 | B2 | 6/1989 |
| JP | H02106189 | A | 4/1990 |
| JP | H0378514 | U | 8/1991 |
| JP | H0385009 | U | 8/1991 |
| JP | H0489041 | A | 3/1992 |
| JP | H04215747 | A | 8/1992 |
| JP | H04131860 | U | 12/1992 |
| JP | H0584252 | A | 4/1993 |
| JP | H05123325 | A | 5/1993 |
| JP | H05226945 | A | 9/1993 |
| JP | H0630945 | A | 2/1994 |
| JP | H0636757 | A | 2/1994 |
| JP | H06237937 | A | 8/1994 |
| JP | H06304176 | A | 11/1994 |
| JP | H06327684 | A | 11/1994 |
| JP | H079622 | U | 2/1995 |
| JP | H07124166 | A | 5/1995 |
| JP | H07163573 | A | 6/1995 |
| JP | H07255735 | A | 10/1995 |
| JP | H07285089 | A | 10/1995 |
| JP | H0833642 | A | 2/1996 |
| JP | H08164141 | A | 6/1996 |
| JP | H08182684 | A | 7/1996 |
| JP | H08507708 | A | 8/1996 |
| JP | H08229050 | A | 9/1996 |
| JP | H08289895 | A | 11/1996 |
| JP | H0950795 | A | 2/1997 |
| JP | H09-323068 | A | 12/1997 |
| JP | H10118090 | A | 5/1998 |
| JP | H10-200699 | A | 7/1998 |
| JP | H10296660 | A | 11/1998 |
| JP | 2000014632 | A | 1/2000 |
| JP | 2000033071 | A | 2/2000 |
| JP | 2000112002 | A | 4/2000 |
| JP | 2000166932 | A | 6/2000 |
| JP | 2000171730 | A | 6/2000 |
| JP | 2000210299 | A | 8/2000 |
| JP | 2000271141 | A | 10/2000 |
| JP | 2000287987 | A | 10/2000 |
| JP | 2000325303 | A | 11/2000 |
| JP | 2001-69758 | A | 3/2001 |
| JP | 2001087272 | A | 4/2001 |
| JP | 2001208655 | A | 8/2001 |
| JP | 2001514541 | A | 9/2001 |
| JP | 2001276091 | A | 10/2001 |
| JP | 2002051974 | A | 2/2002 |
| JP | 2002054903 | A | 2/2002 |
| JP | 2002085415 | A | 3/2002 |
| JP | 2002143078 | A | 5/2002 |
| JP | 2002153481 | A | 5/2002 |
| JP | 2002528161 | A | 9/2002 |
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |
| JP | 2004229976 | A | 8/2004 |
| JP | 2005013573 | A | 1/2005 |
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |

(56) References Cited

FOREIGN PATENT DOCUMENTS

| | | | |
|---|---|---|---|
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006187649 | A | 7/2006 |
| JP | 2006218228 | A | 8/2006 |
| JP | 2006281405 | A | 10/2006 |
| JP | 2006291180 | A | 10/2006 |
| JP | 2006346445 | A | 12/2006 |
| JP | 2007-97252 | A | 4/2007 |
| JP | 2007289715 | A | 11/2007 |
| JP | 2007304057 | A | 11/2007 |
| JP | 2007306710 | A | 11/2007 |
| JP | D1322057 | | 2/2008 |
| JP | 2008154804 | A | 7/2008 |
| JP | 2008220032 | A | 9/2008 |
| JP | 2009507526 | A | 2/2009 |
| JP | 2009189838 | A | 8/2009 |
| JP | 2009189846 | A | 8/2009 |
| JP | 2009207260 | A | 9/2009 |
| JP | 2009226028 | A | 10/2009 |
| JP | 2009538684 | A | 11/2009 |
| JP | 2009539420 | A | 11/2009 |
| JP | D1383743 | | 2/2010 |
| JP | 2010065594 | A | 3/2010 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 4728996 | B2 | 7/2011 |
| JP | 2011524199 | A | 9/2011 |
| JP | 2011200665 | A | 10/2011 |
| JP | D1432094 | | 12/2011 |
| JP | 1433631 | S | 2/2012 |
| JP | 2012115542 | A | 6/2012 |
| JP | 2012143283 | A | 8/2012 |
| JP | 5154710 | B1 | 2/2013 |
| JP | 2013099551 | A | 5/2013 |
| JP | 2013126430 | A | 6/2013 |
| JP | D1481426 | | 9/2013 |
| JP | 2013541982 | A | 11/2013 |
| JP | 2013541983 | A | 11/2013 |
| JP | 2013541997 | A | 11/2013 |
| JP | 2014018667 | A | 2/2014 |
| JP | D1492363 | | 2/2014 |
| JP | 2014121599 | A | 7/2014 |
| JP | 2014171879 | A | 9/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015516838 | A | 6/2015 |
| JP | 2015521524 | A | 7/2015 |
| JP | 2015521525 | A | 7/2015 |
| JP | 2016007800 | A | 1/2016 |
| JP | 2016508792 | A | 3/2016 |
| JP | 2016512057 | A | 4/2016 |
| JP | 2016518914 | A | 6/2016 |
| JP | 2016530949 | A | 10/2016 |
| JP | 2017513563 | A | 6/2017 |
| JP | 1601498 | S | 4/2018 |
| JP | 2019513530 | A | 5/2019 |
| JP | 2020501797 | A | 1/2020 |
| JP | D1677030 | S | 1/2021 |
| JP | D1696539 | S | 10/2021 |
| KR | 20100110134 | A | 10/2010 |
| KR | 20110003229 | A | 1/2011 |
| KR | 300631507 | | 3/2012 |
| KR | 300747646 | | 6/2014 |
| KR | 20180053811 | A | 5/2018 |
| RU | 1814161 | C | 5/1993 |
| RU | 2008830 | C1 | 3/1994 |
| RU | 2052979 | C1 | 1/1996 |
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1042742 | A1 | 9/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| SU | 1814161 | A1 | 5/1993 |
| WO | WO-9308754 | A1 | 5/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |
| WO | WO-9827870 | A1 | 7/1998 |
| WO | WO-9903407 | A1 | 1/1999 |
| WO | WO-9903409 | A1 | 1/1999 |
| WO | WO-9948430 | A1 | 9/1999 |
| WO | WO-0024322 | A1 | 5/2000 |
| WO | WO-0024330 | A1 | 5/2000 |
| WO | WO-0036690 | A2 | 6/2000 |
| WO | WO-0053112 | A2 | 9/2000 |
| WO | WO-0024448 | A2 | 10/2000 |
| WO | WO-0057796 | A1 | 10/2000 |
| WO | WO-0105702 | A1 | 1/2001 |
| WO | WO-0154594 | A1 | 8/2001 |
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |

(56) References Cited

FOREIGN PATENT DOCUMENTS

| | | | |
|---|---|---|---|
| WO | WO-2006051252 | A1 | 5/2006 |
| WO | WO-2006059067 | A1 | 6/2006 |
| WO | WO-2006073581 | A2 | 7/2006 |
| WO | WO-2006085389 | A1 | 8/2006 |
| WO | WO-2007015971 | A2 | 2/2007 |
| WO | WO-2007074430 | A1 | 7/2007 |
| WO | WO-2007129121 | A1 | 11/2007 |
| WO | WO-2007137304 | A2 | 11/2007 |
| WO | WO-2007142625 | A2 | 12/2007 |
| WO | WO-2008021969 | A2 | 2/2008 |
| WO | WO-2008061566 | A1 | 5/2008 |
| WO | WO-2008089404 | A2 | 7/2008 |
| WO | WO-2009005969 | A2 | 1/2009 |
| WO | WO-2009067649 | A2 | 5/2009 |
| WO | WO-2009091497 | A2 | 7/2009 |
| WO | WO-2010126129 | A1 | 11/2010 |
| WO | WO-2010134913 | A1 | 11/2010 |
| WO | WO-2011008672 | A2 | 1/2011 |
| WO | WO-2011044343 | A2 | 4/2011 |
| WO | WO-2012006306 | A2 | 1/2012 |
| WO | WO-2012013577 | A1 | 2/2012 |
| WO | WO-2012044606 | A2 | 4/2012 |
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013151888 | A1 | 10/2013 |
| WO | WO-2014004209 | A2 | 1/2014 |
| WO | WO-2014113438 | A1 | 7/2014 |
| WO | WO-2014175894 | A1 | 10/2014 |
| WO | WO-2015032797 | A1 | 3/2015 |
| WO | WO-2015076780 | A1 | 5/2015 |
| WO | WO-2015137040 | A1 | 9/2015 |
| WO | WO-2015138760 | A1 | 9/2015 |
| WO | WO-2015187107 | A1 | 12/2015 |
| WO | WO-2016100682 | A1 | 6/2016 |
| WO | WO-2016107448 | A1 | 7/2016 |
| WO | WO-2017138905 | A1 | 8/2017 |
| WO | WO-2018011664 | A1 | 1/2018 |
| WO | WO-2019036490 | A1 | 2/2019 |
| WO | WO-2019130087 | A1 | 7/2019 |
| WO | WO-2019130089 | A1 | 7/2019 |
| WO | WO-2019208902 | A1 | 10/2019 |
| WO | WO-2021189234 | A1 | 9/2021 |

OTHER PUBLICATIONS

Molina, "Low Level Reader Protocol (LLRP)," Oct. 13, 2010, pp. 1-198.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
Disclosed Anonymously, "Motor-Driven Surgical Stapler Improvements," Research Disclosure Database No. 526041, Published: Feb. 2008.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology, " (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Data Sheet of LM4F230H5QR, 2007.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.

(56) References Cited

OTHER PUBLICATIONS

Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileld=db3a304332d040720132d9395 03e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al., Comparison of the effects of Mg—6Zn and Ti—3Al-2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B-Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec, <http://cdn.mobiusconsulting.com/papers/rfidsystems.pdf>.
Schroeter, John, "Demystifying UHF Gen 2 RFID, HF RFID," *Online Article*, Jun. 2, 2008, pp. 1-3, <https://www.edn.com/design/industrial-control/4019123/Demystifying-UHF-Gen-2-RFID-HF-RFID>.
Adeeb, et al., "*An Inductive Link-Based Wireless Power Transfer System for Biomedical Applications*." Research Article, Nov. 14, 2011, pp. 1-12, vol. 2012, Article ID 879294, Hindawi Publishing Corporation.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry-II: Second Year Diploma in Pharmacy, Nirali Prakashan, p. 339, 2007.
Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHZ) enery on human cardiovascular, reproductive, immune, and other systems: A review of the recent literatured," Int. J. Hyg. Environ. Health 211 (2008) 1-29.

(56) References Cited

OTHER PUBLICATIONS

Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
IEEE Std 802.Mar. 2012 (Revision of IEEE Std 802.Mar. 2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.
Makerbot, 10 Advantages of 3D Printing, 2020 (retrieved via the wayback machine), Makerbot.com (Year: 2020).
U.S. Provisional U.S. Appl. No. 62/798,651, filed Jan. 30, 2019.
U.S. Provisional U.S. Appl. No. 62/840,602, filed Apr. 30, 2019.

* cited by examiner

4342

| TISSUE THICKNESS RANGES (T) | THRESHOLD FORCE (F) |
|---|---|
| T1-T2 | F1 |
| T2-T3 | F2 |
| T3-T4 | F3 |
| . | . |
| . | . |
| . | . |
| Tn-1 - Tn | Fn |

SURGICAL INSTRUMENT WITH MULTIPLE PROGRAM RESPONSES DURING A FIRING MOTION

This application is a continuation application claiming priority under 35 U.S.C. § 120 to U.S. patent application Ser. No. 17/709,576, entitled ROBOTIC SURGICAL SYSTEM INCLUDING A USER INTERFACE AND A CONTROL CIRCUIT, filed Mar. 31, 2022, which issued on May 9, 2023 as U.S. Pat. No. 11,642,125, which is a continuation application claiming priority under 35 U.S.C. § 120 to U.S. patent application Ser. No. 16/919,319, entitled SURGICAL INSTRUMENT WITH MULTIPLE PROGRAM RESPONSES DURING A FIRING MOTION, filed Jul. 2, 2020, now U.S. Patent Application Publication No. 2021/0085316, which is a continuation application claiming priority under 35 U.S.C. § 120 to U.S. patent application Ser. No. 15/130,566, entitled SURGICAL INSTRUMENT WITH MULTIPLE PROGRAM RESPONSES DURING A FIRING MOTION, filed Apr. 15, 2016, which issued on Nov. 10, 2020 as U.S. Pat. No. 10,828,028; the entirety of each of the above-identified applications is hereby incorporated by reference herein.

TECHNICAL FIELD

The present disclosure relates to surgical instruments and, in various circumstances, to surgical stapling and cutting instruments and staple cartridges therefor that are designed to staple and cut tissue.

BACKGROUND

In a motorized surgical stapling and cutting instrument it would be helpful to have variable control program responses (pause, slow down, speed up, backup and re-advance, and stop) depending on how fast the load is increasing or decreasing (slope) as it approaches predefined staged thresholds (load, current, pressure, velocity). While several devices have been made and used, it is believed that no one prior to the inventors has made or used the device described in the appended claims.

SUMMARY

In some aspects, a surgical instrument is provided. The surgical instrument comprises an elongated channel configured to support a staple cartridge; an anvil pivotably connected to the elongated channel; a closure tube mechanically coupled to the anvil; an electric motor; and a control circuit electrically connected to the electric motor, wherein the control circuit is configured to change a closing motion of the surgical instrument at least two different ways based on the closing force.

The foregoing summary is illustrative only and is not intended to be in any way limiting. In addition to the illustrative aspects and features described above, further aspects and features will become apparent by reference to the drawings and the following detailed description.

BRIEF DESCRIPTION

The novel features of the aspects described herein are set forth with particularity in the appended claims. The aspects, however, both as to organization and methods of operation may be better understood by reference to the following description, taken in conjunction with the accompanying drawings as follows.

Figure 23A:
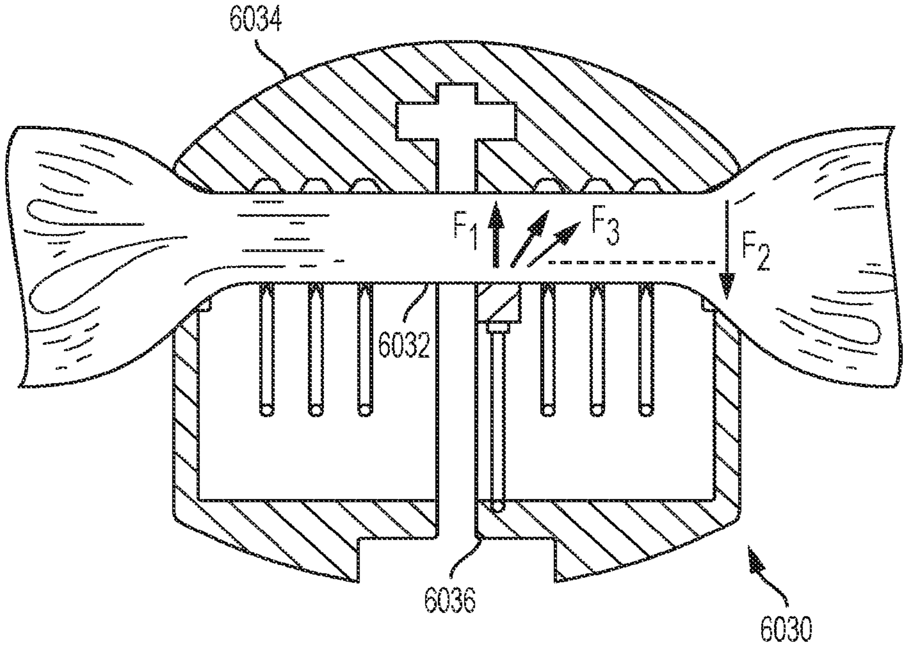
FIG. 23A depicts example forces exerted by an end-effector of a medical device compressing tissue in accordance with one or more aspects of the present disclosure.
Figure 23B:
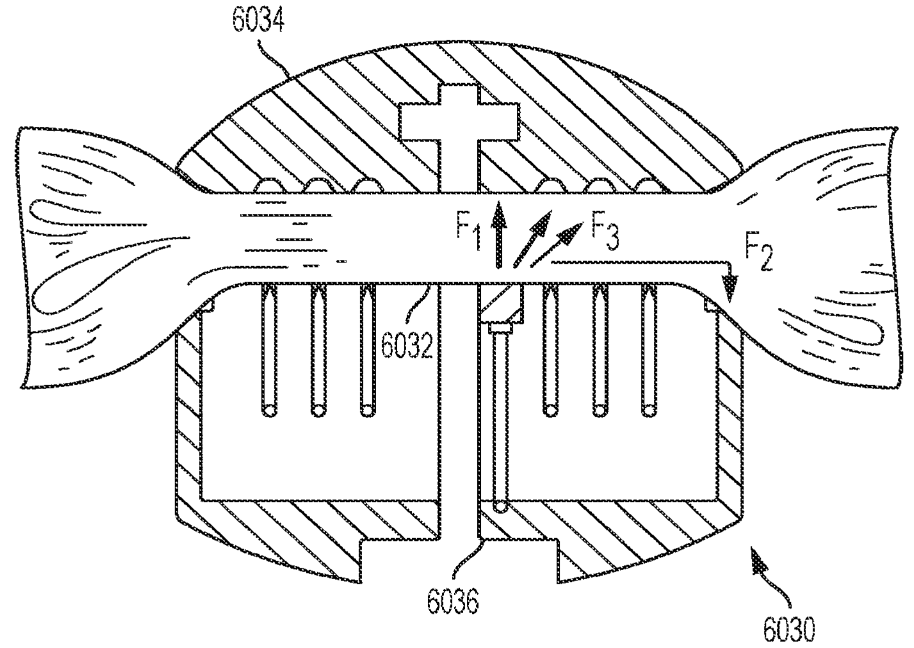

FIG. 23B also depicts example forces exerted by an end-effector of a medical device compressing tissue in accordance with one or more aspects of the present disclosure.

Figure 24:
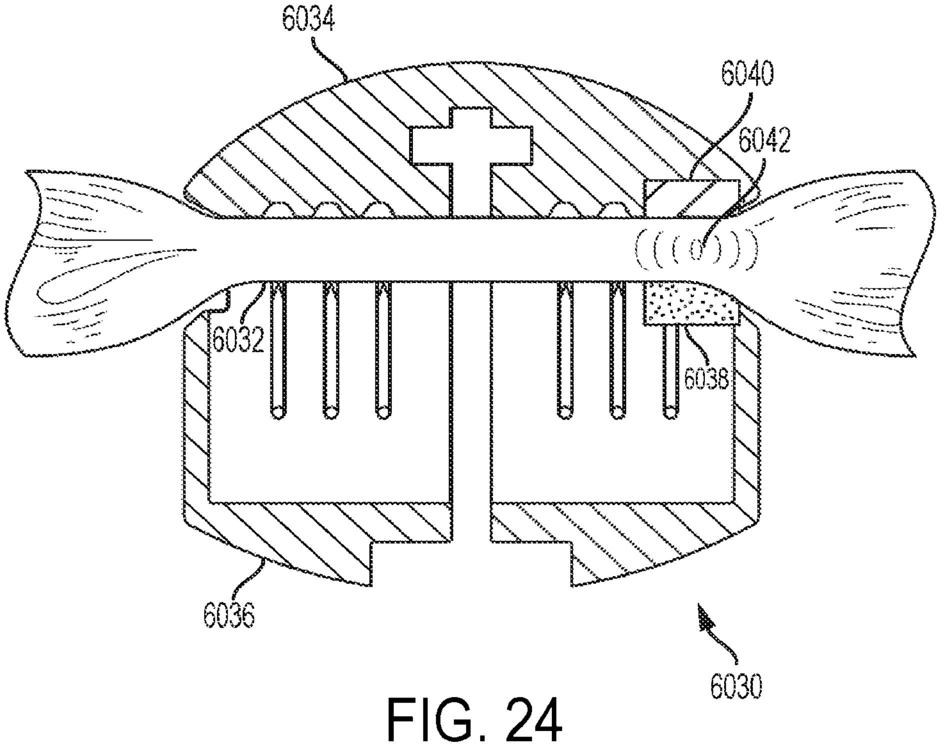

FIG. 24 depicts an example tissue compression sensor system in accordance with one or more aspects of the present disclosure.

Figure 25:
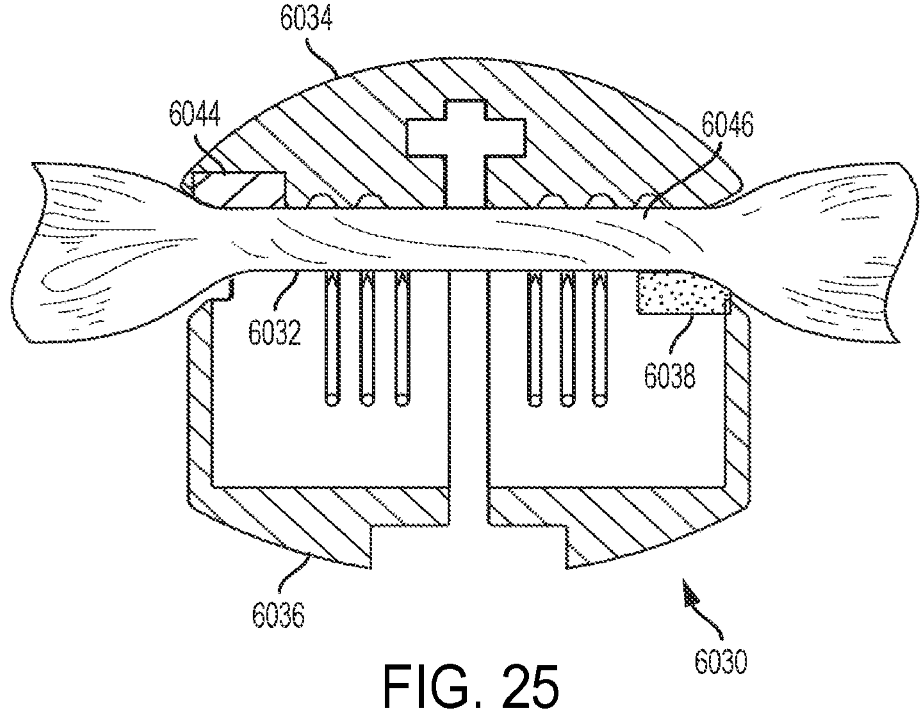

FIG. 25 also depicts an example tissue compression sensor system in accordance with one or more aspects of the present disclosure.

Figure 26:
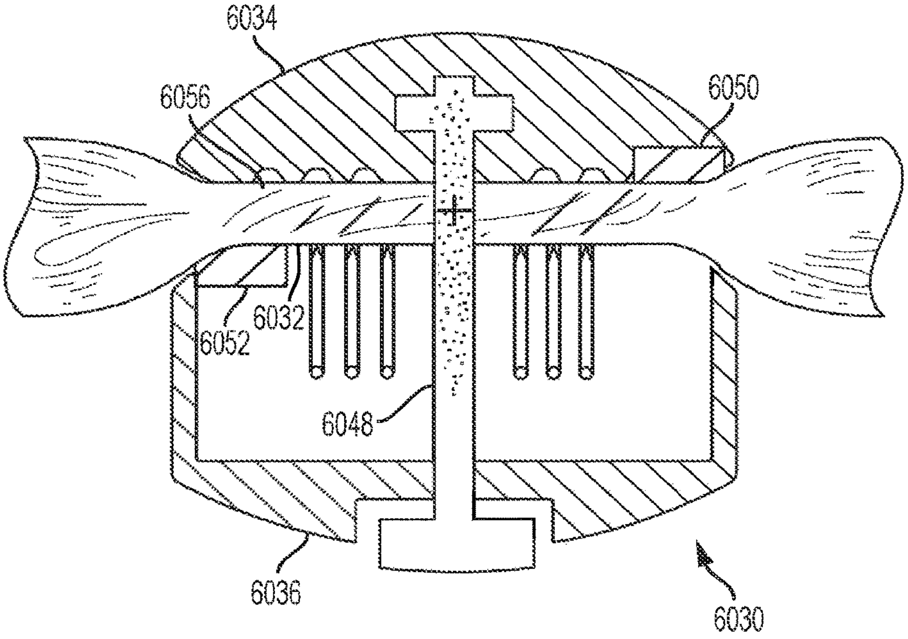

FIG. 26 also depicts an example tissue compression sensor system in accordance with one or more aspects of the present disclosure.

Figure 27:
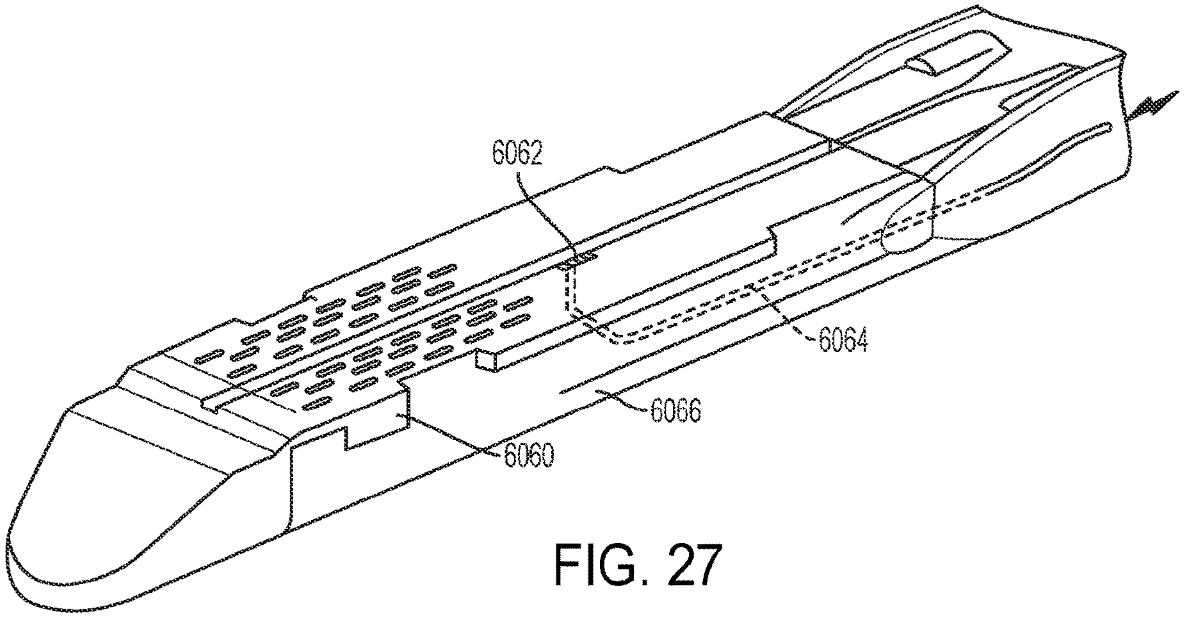

FIG. 27 depicts an example end-effector channel frame in accordance with one or more aspects of the present disclosure.

Figure 28:
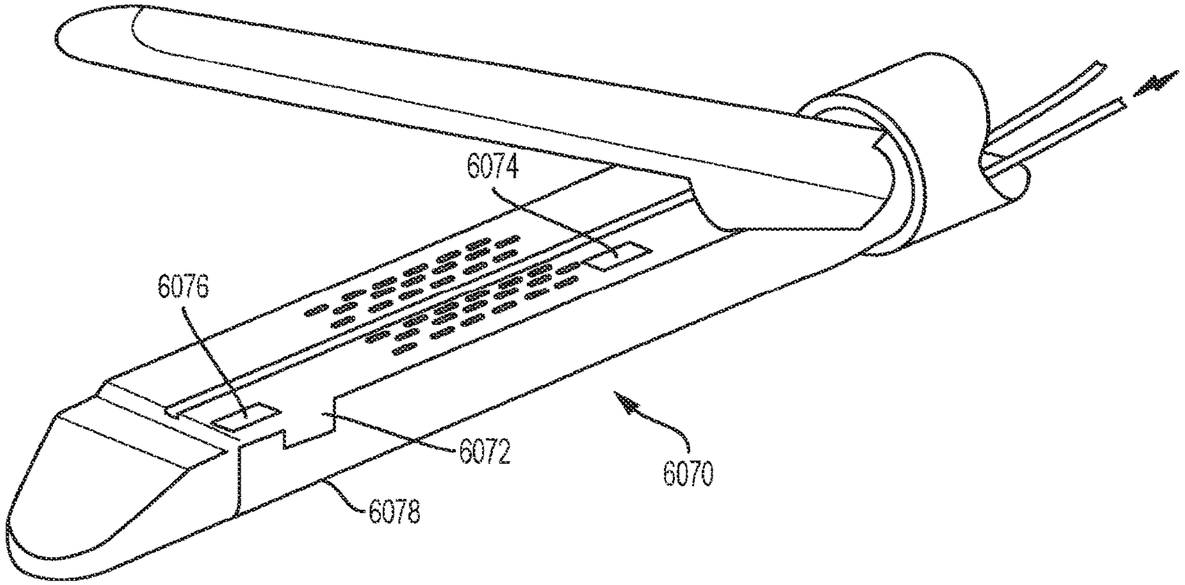

FIG. 28 depicts an example end-effector in accordance with one or more aspects of the present disclosure.

Figure 29:
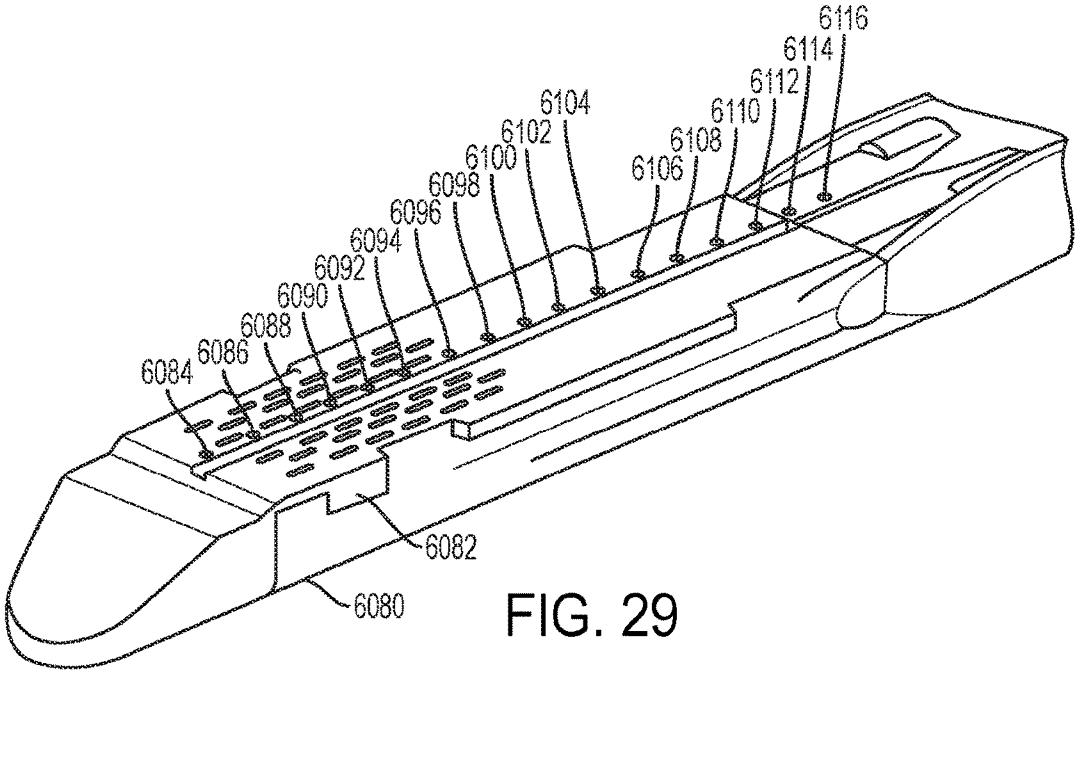

FIG. 29 also depicts an example end-effector channel frame in accordance with one or more aspects of the present disclosure.

Figure 30:
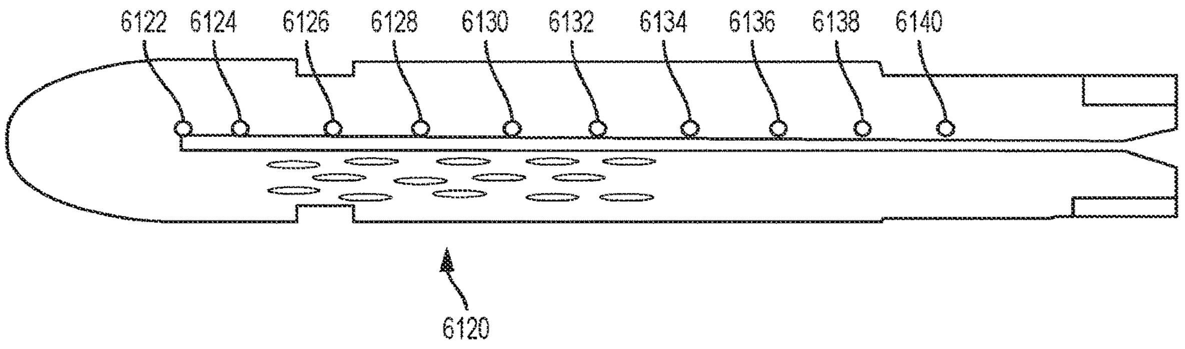

FIG. 30 also depicts an example end-effector channel frame in accordance with one or more aspects of the present disclosure.

Figure 31:
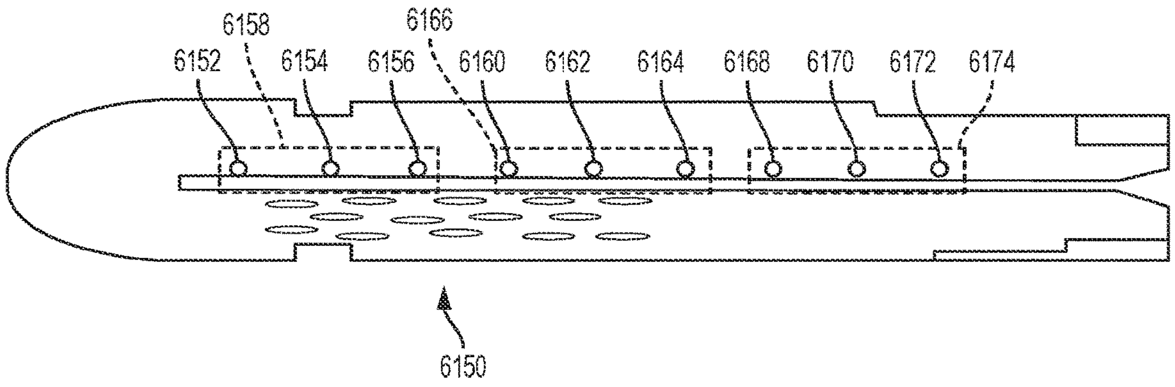

FIG. 31 also depicts an example end-effector channel frame in accordance with one or more aspects of the present disclosure.

Figure 32:
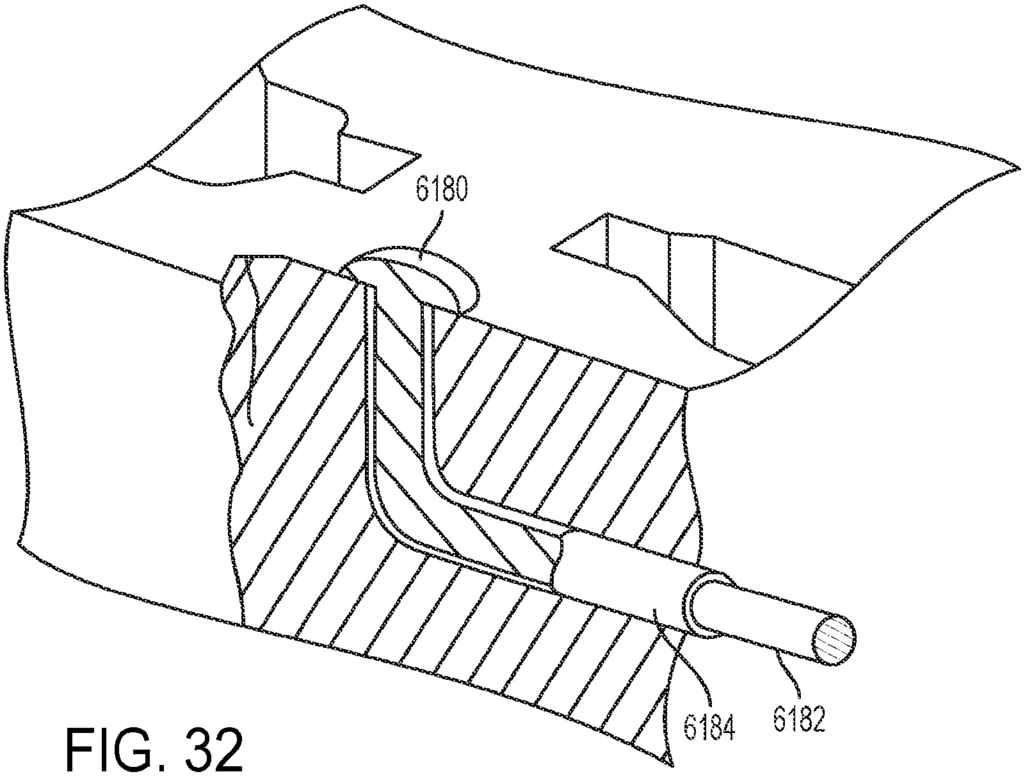

FIG. 32 depicts an example electrode in accordance with one or more aspects of the present disclosure.

Figure 33:
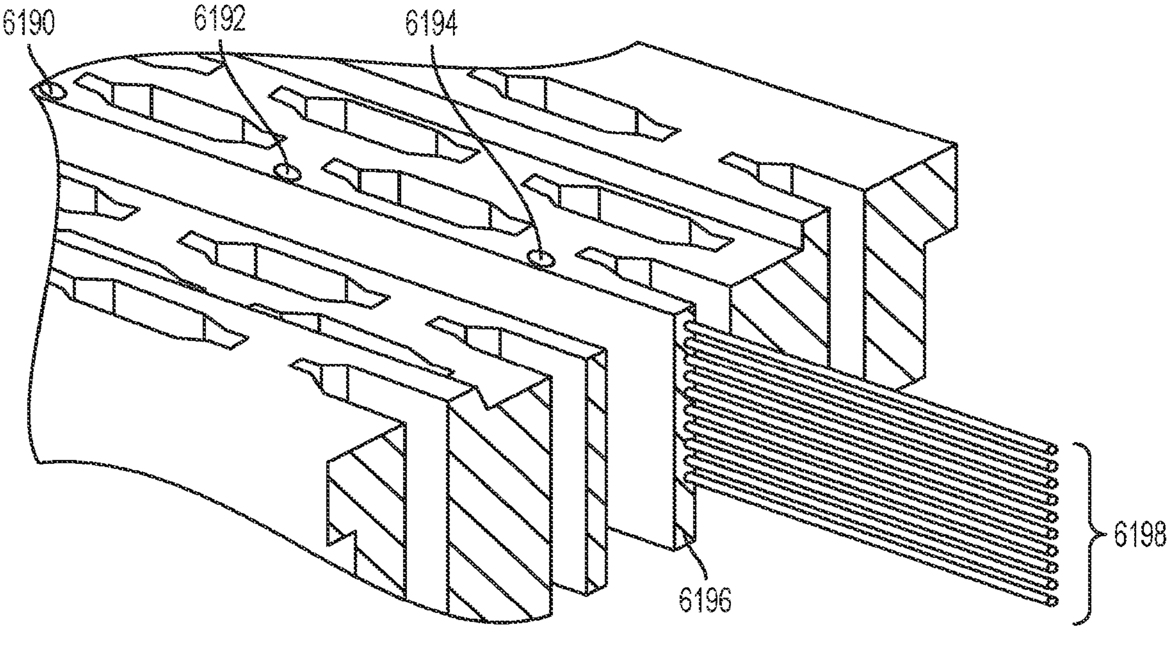

FIG. 33 depicts an example electrode wiring system in accordance with one or more aspects of the present disclosure.

Figure 34:
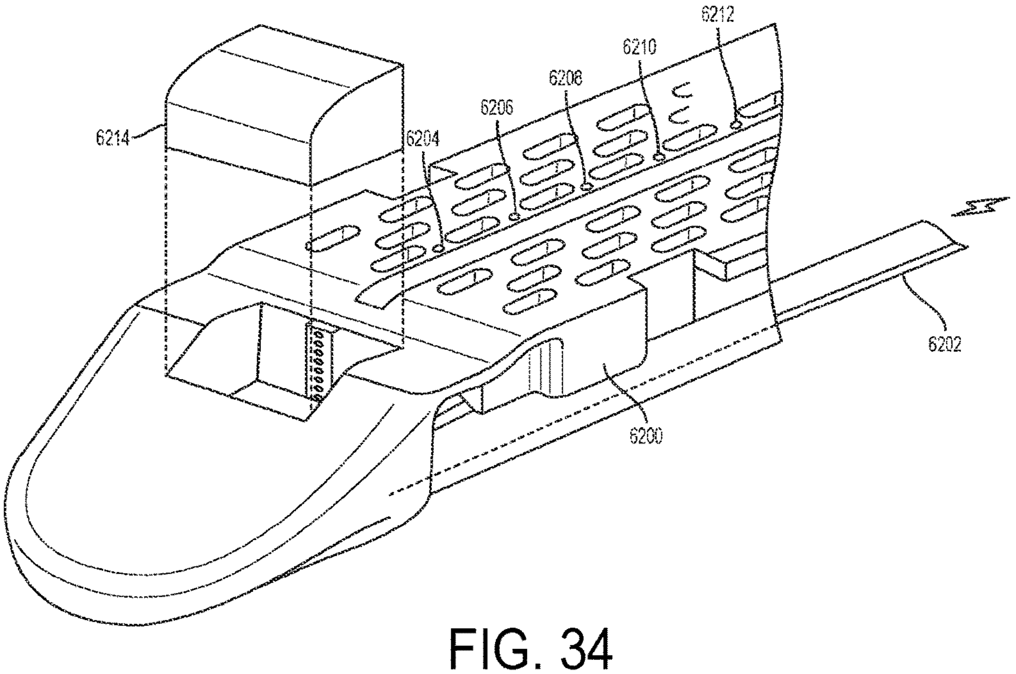

FIG. 34 also depicts an example end-effector channel frame in accordance with one or more aspects of the present disclosure.

Figure 35:
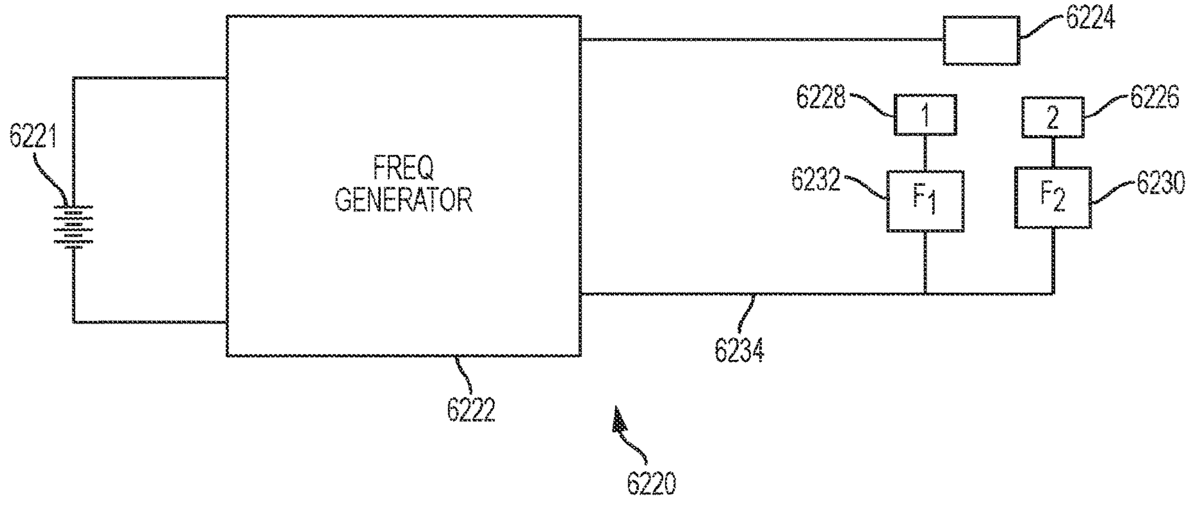

FIG. 35 is an example circuit diagram in accordance with one or more aspects of the present disclosure.

Figure 36:
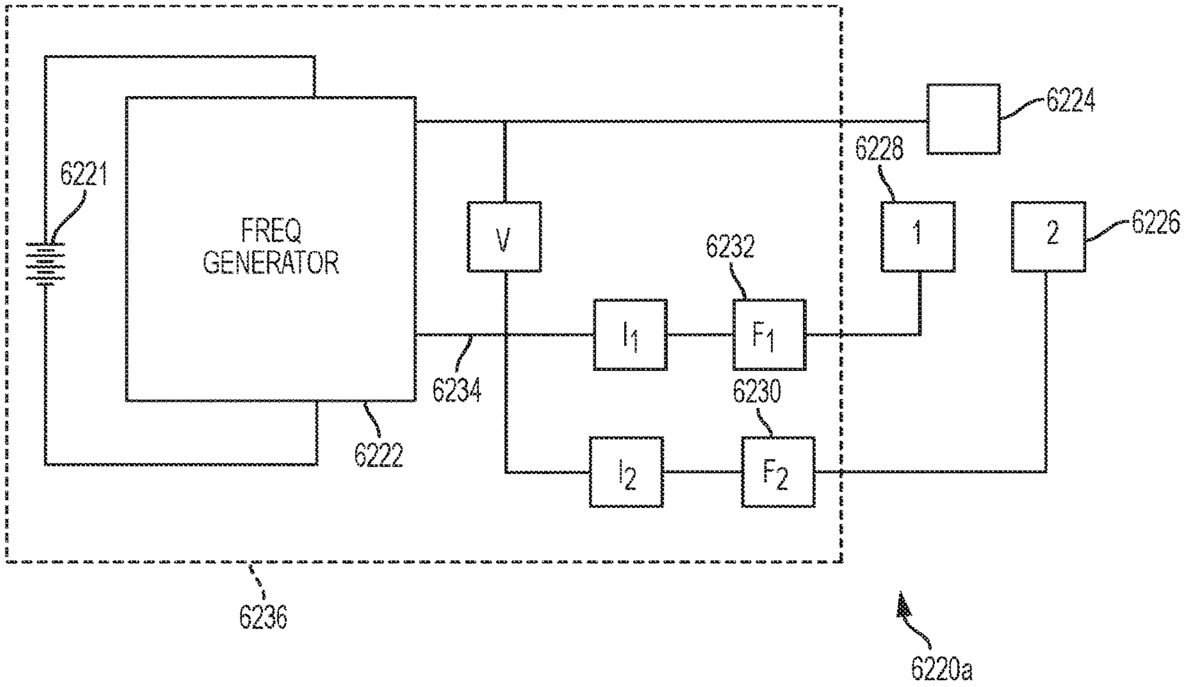

FIG. 36 is also an example circuit diagram in accordance with one or more aspects of the present disclosure.

Figure 37:
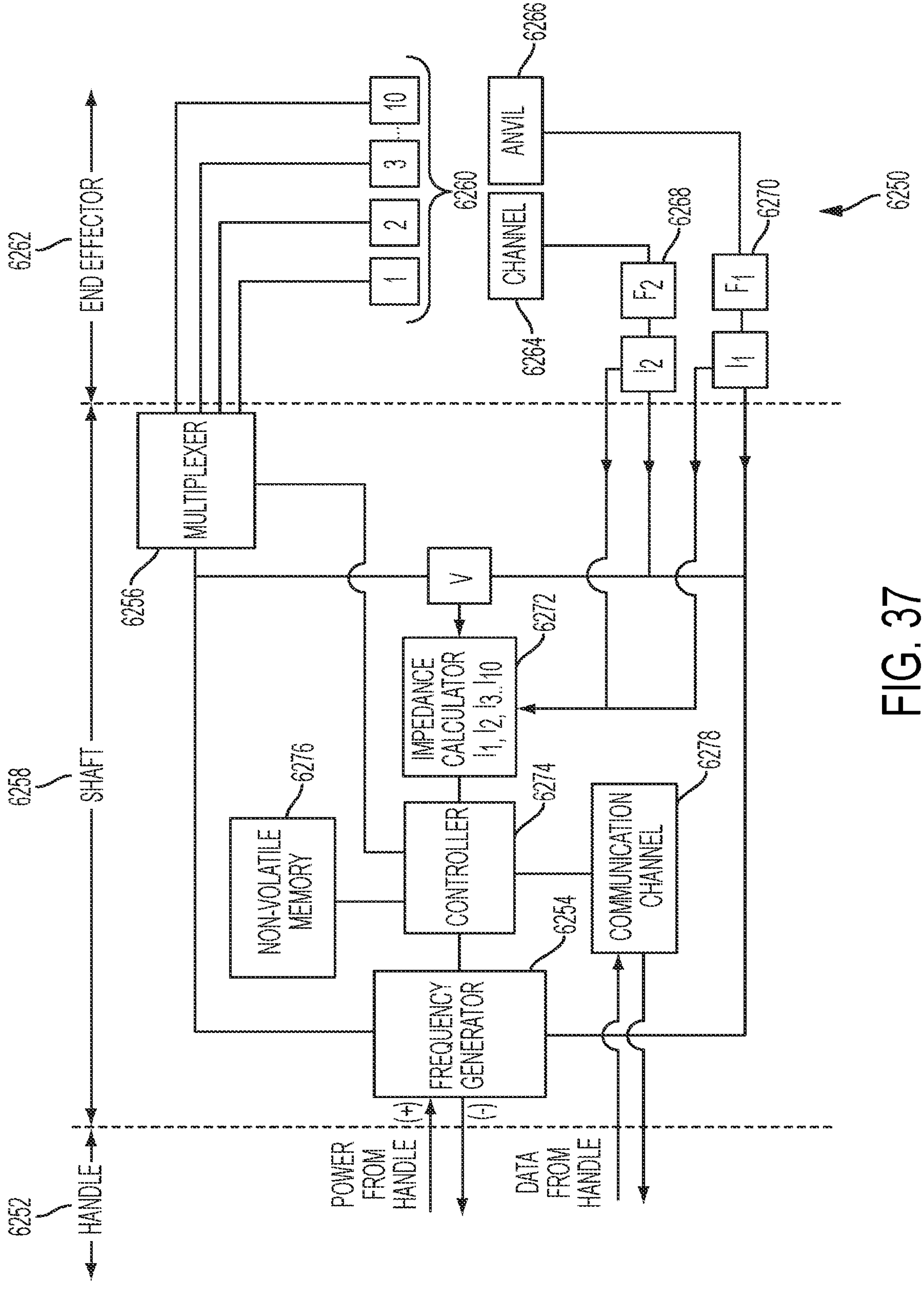

FIG. 37 is also an example circuit diagram in accordance with one or more aspects of the present disclosure.

Figure 38:
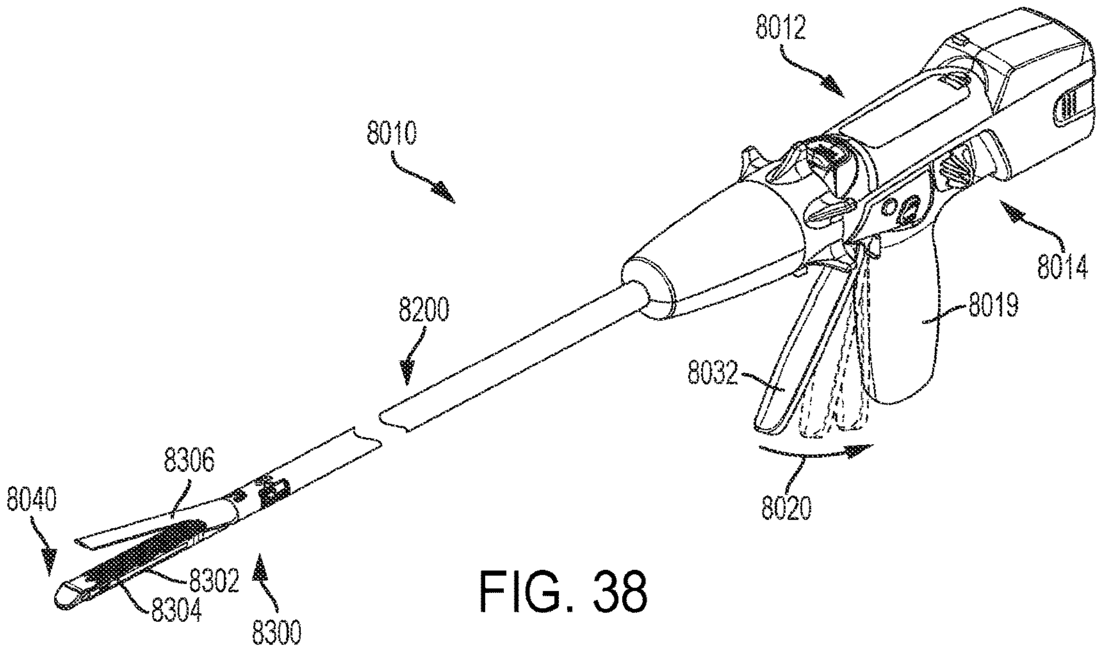

FIG. 38 is a perspective view of a surgical instrument with an articulable, interchangeable shaft in accordance with one or more aspects of the present disclosure.

Figure 39:
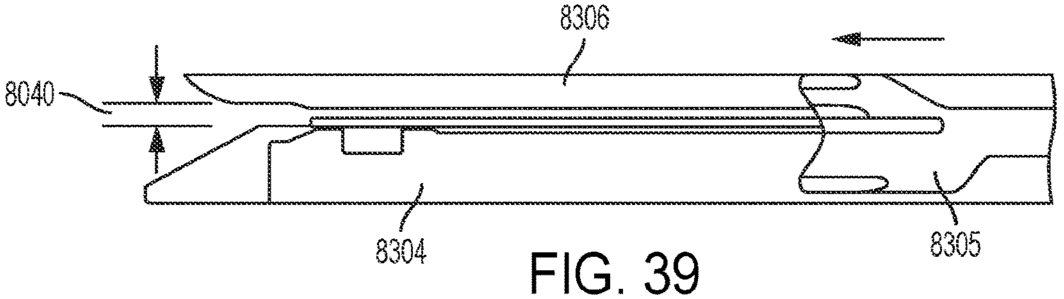

FIG. 39 is a side view of the tip of the surgical instrument shown in FIG. 38 in accordance with one or more aspects of the present disclosure.

Figure 40:
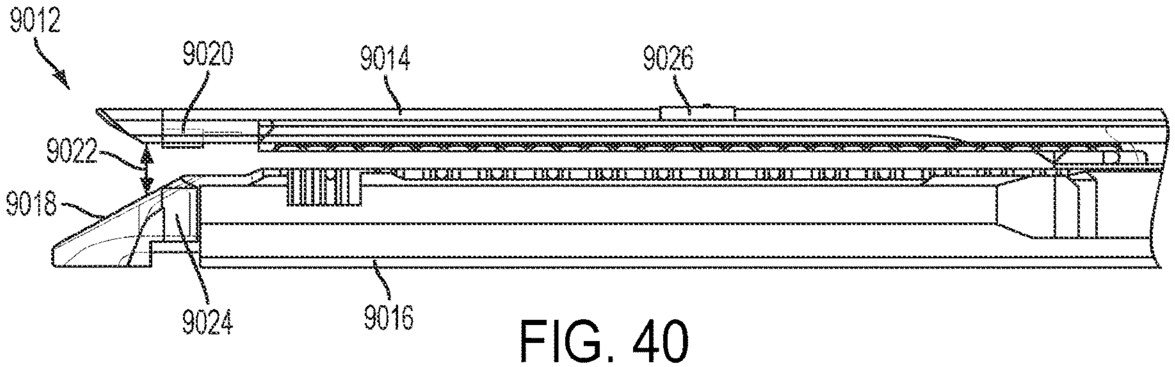

FIG. 40 illustrates a cross-sectional view of an end effector of a surgical instrument in accordance with one or more aspects of the present disclosure.

Figure 41:
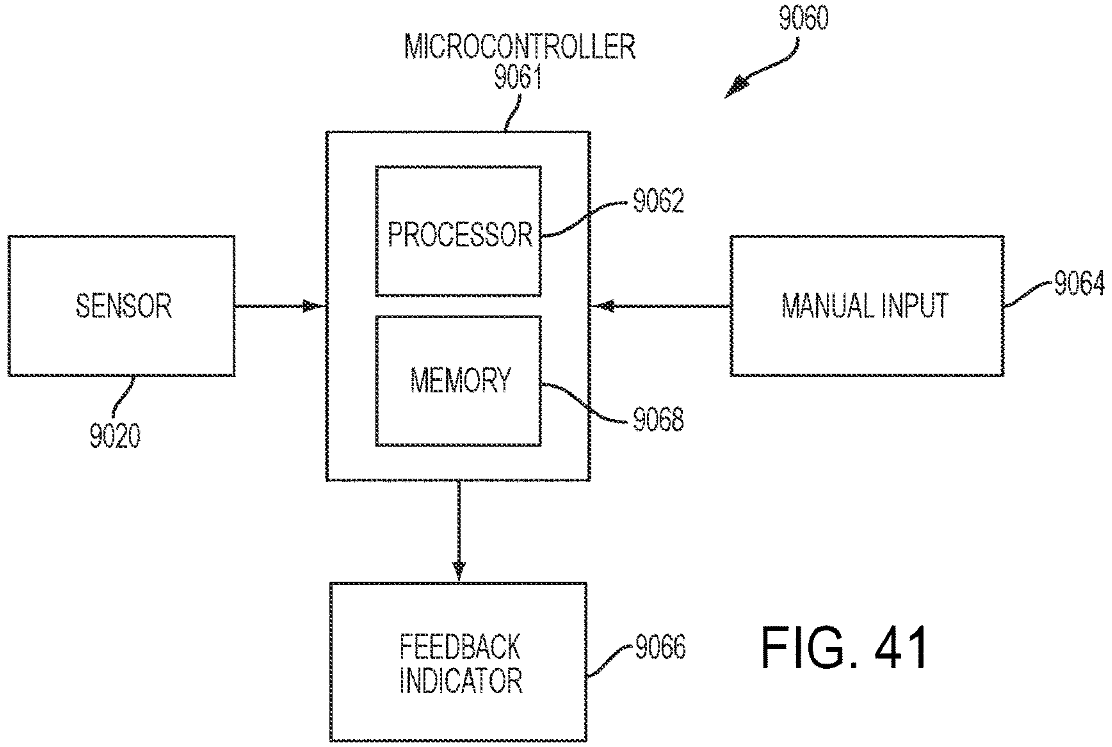

FIG. 41 illustrates a logic diagram of a feedback system in accordance with one or more aspects of the present disclosure.

Figure 42:
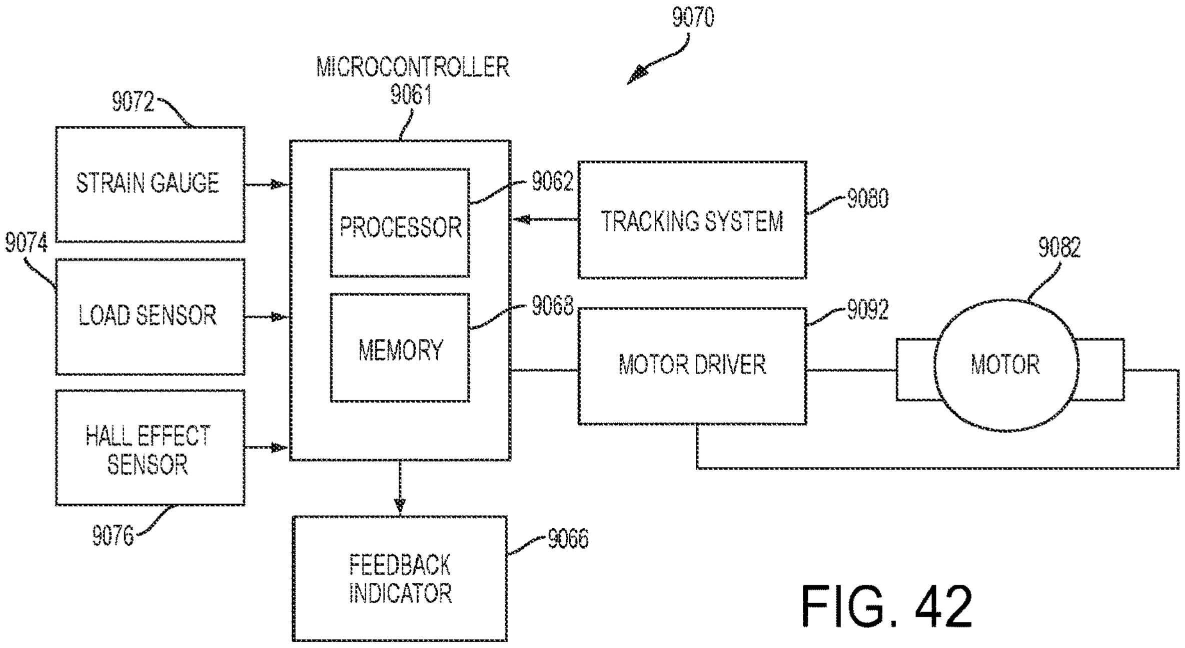

FIG. 42 illustrates a logic diagram of a feedback system in accordance with one or more aspects of the present disclosure.

Figure 43:
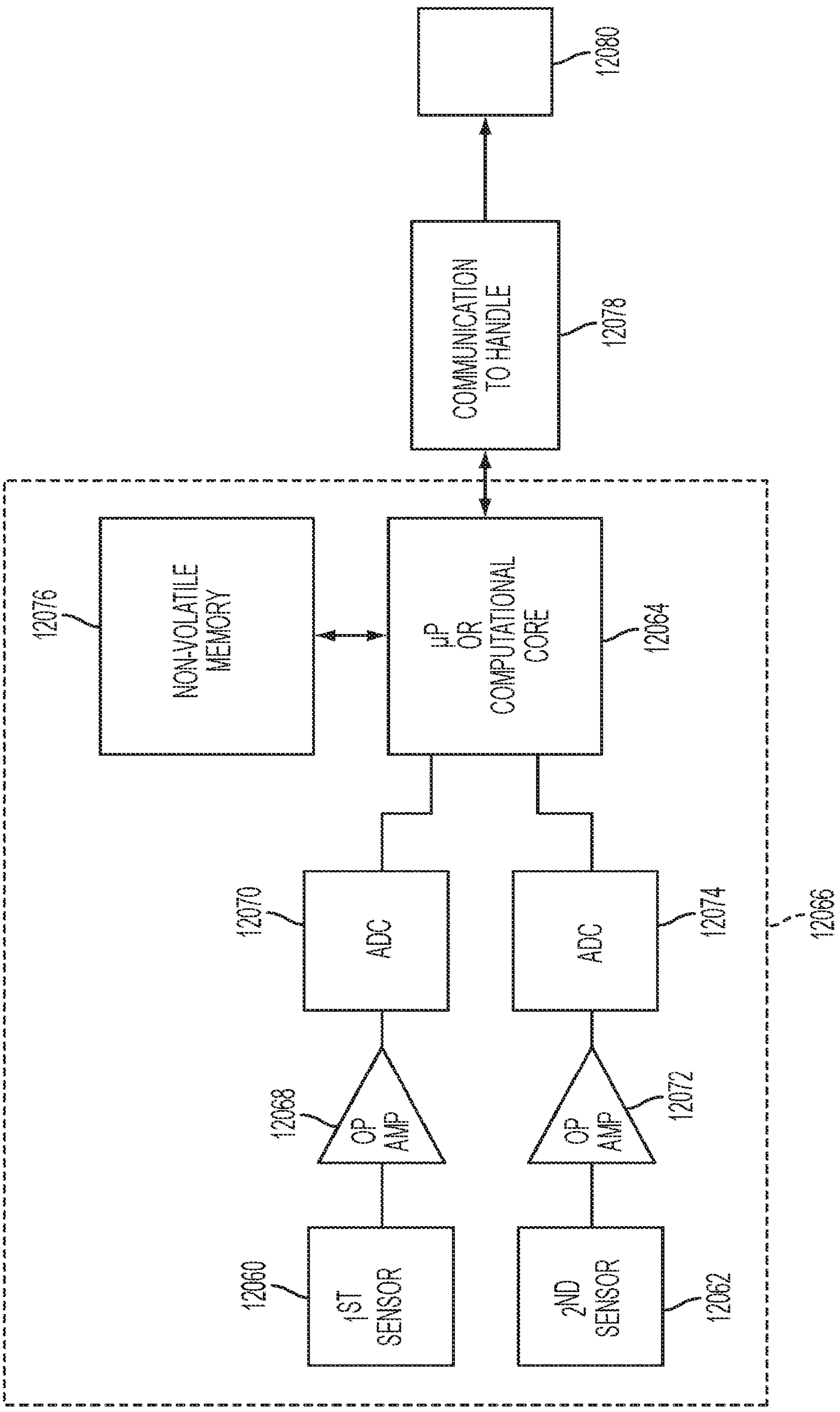

FIG. 43 is a diagram of a smart sensor component in accordance with an aspect the present disclosure.

Figure 44:
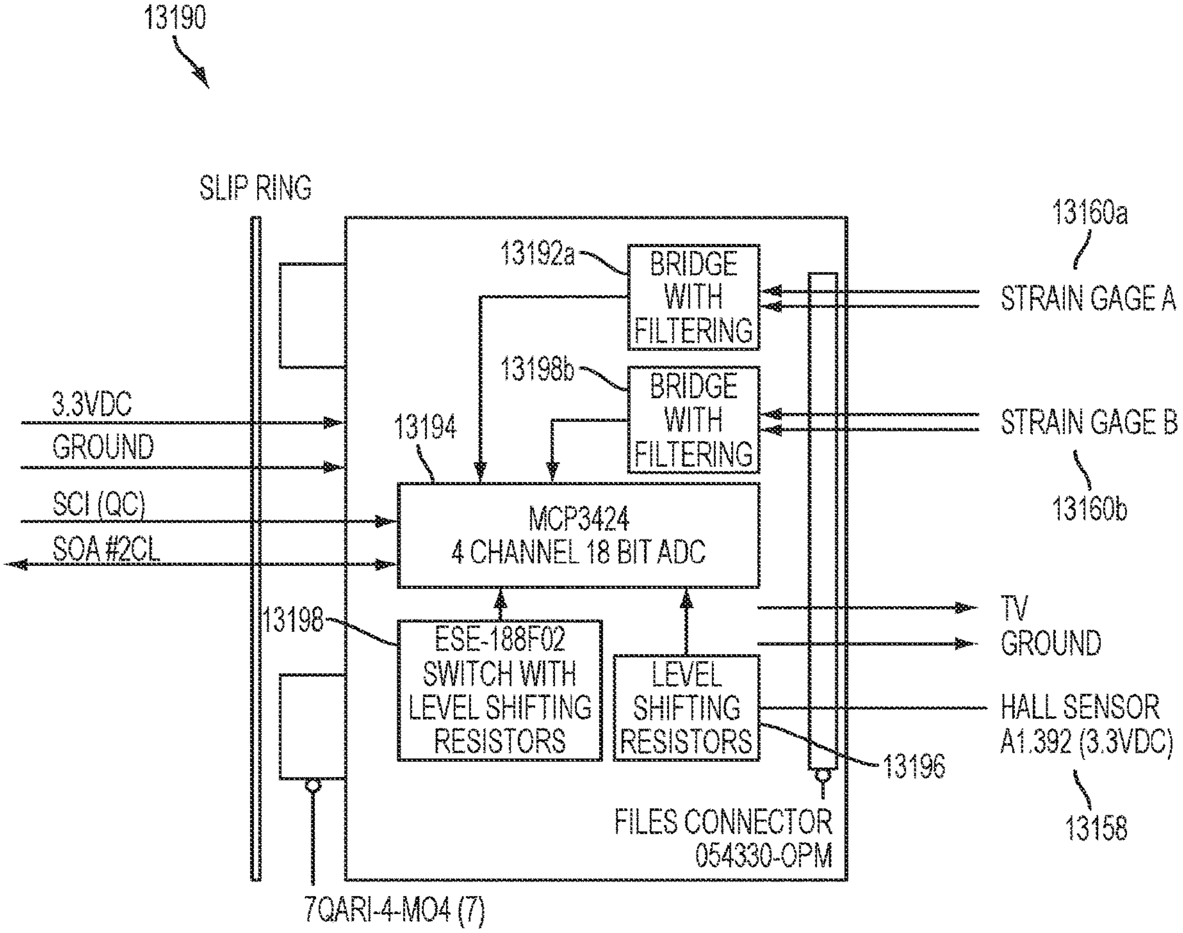

FIG. 44 illustrates one aspect of a circuit configured to convert signals from a first sensor and a plurality of secondary sensors into digital signals receivable by a processor in accordance with one or more aspects of the present disclosure.

Figure 45:
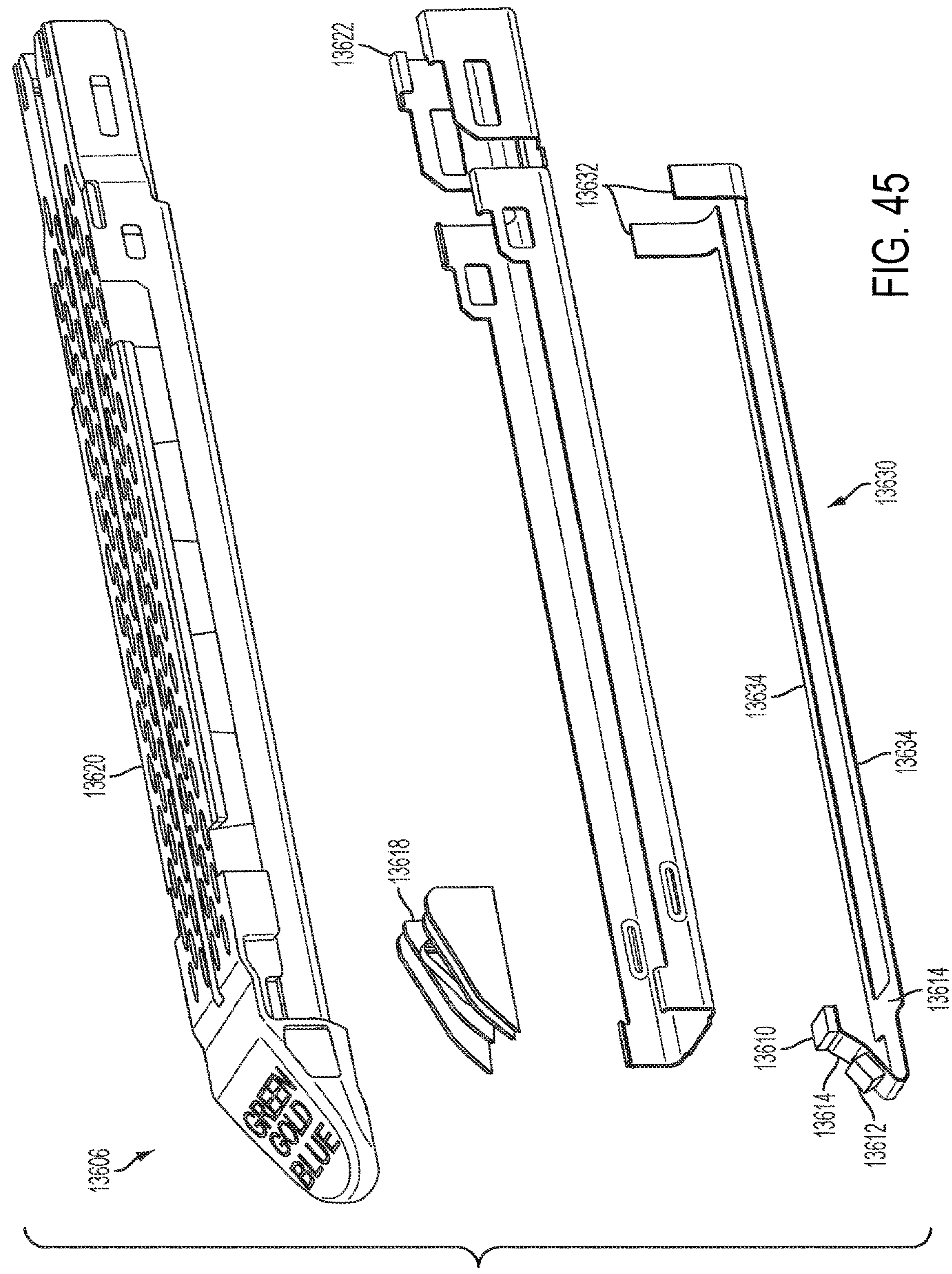

FIG. 45 illustrates one aspect of an exploded view of a staple cartridge that comprises a flex cable connected to a magnetic field sensor and processor in accordance with one or more aspects of the present disclosure.

Figure 46:
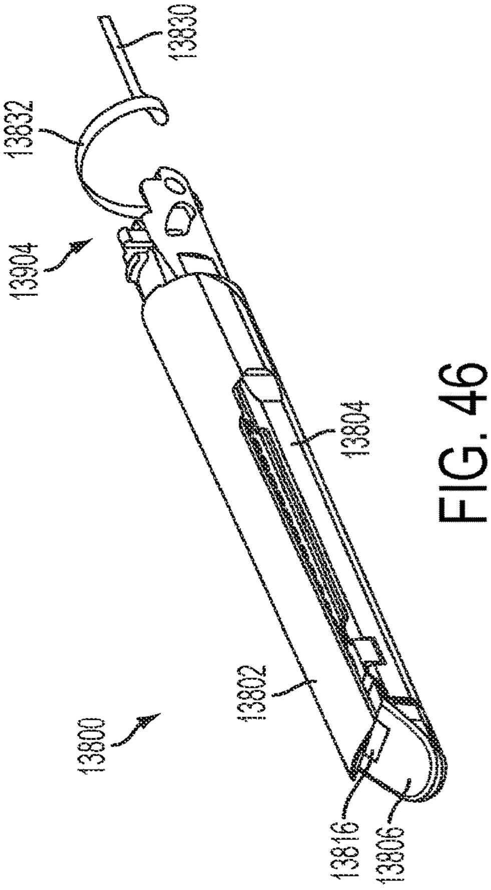

FIG. 46 illustrates the end effector shown in FIG. 46 with a flex cable and without the shaft assembly in accordance with one or more aspects of the present disclosure.

Figure 47:
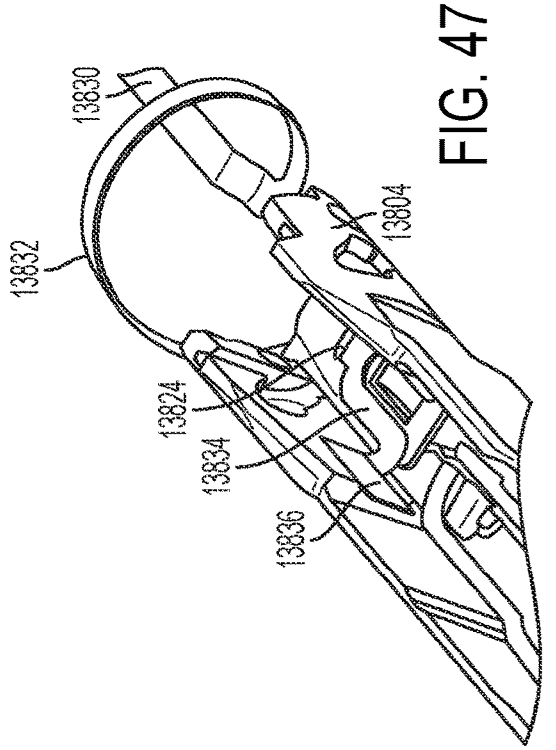
Figure 48:
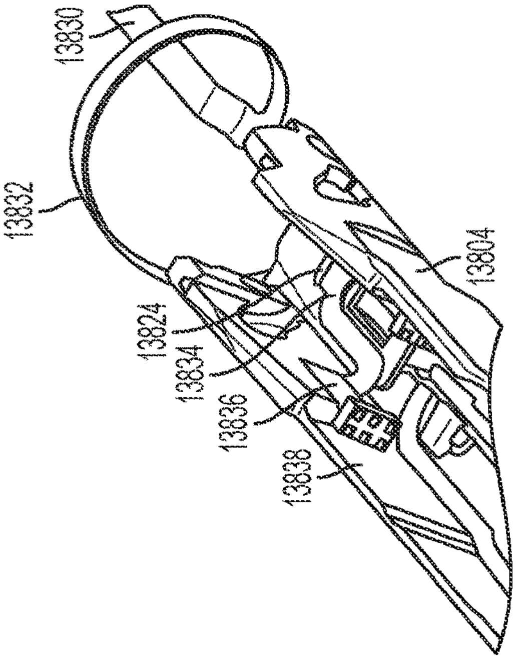

FIGS. 47 and 48 illustrate an elongated channel portion of an end effector without the anvil or the staple cartridge, to illustrate how the flex cable shown in FIG. 46 can be seated within the elongated channel in accordance with one or more aspects of the present disclosure.

Figure 49:
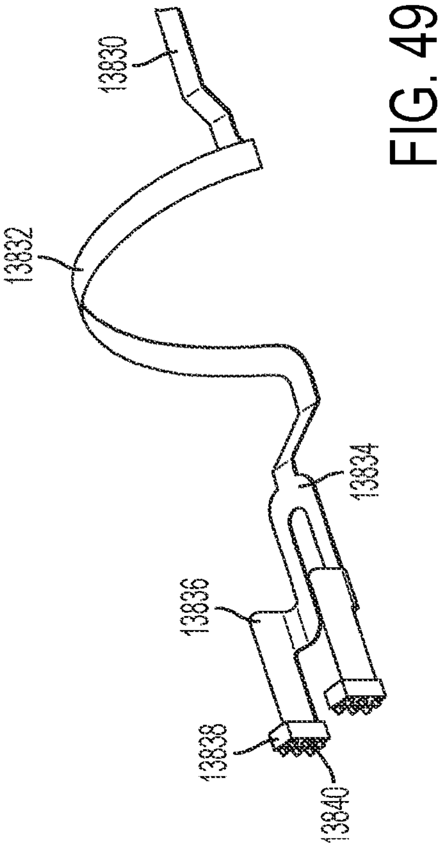

FIG. 49 illustrates a flex cable, shown in FIGS. 46-48, alone in accordance with one or more aspects of the present disclosure.

Figure 50:
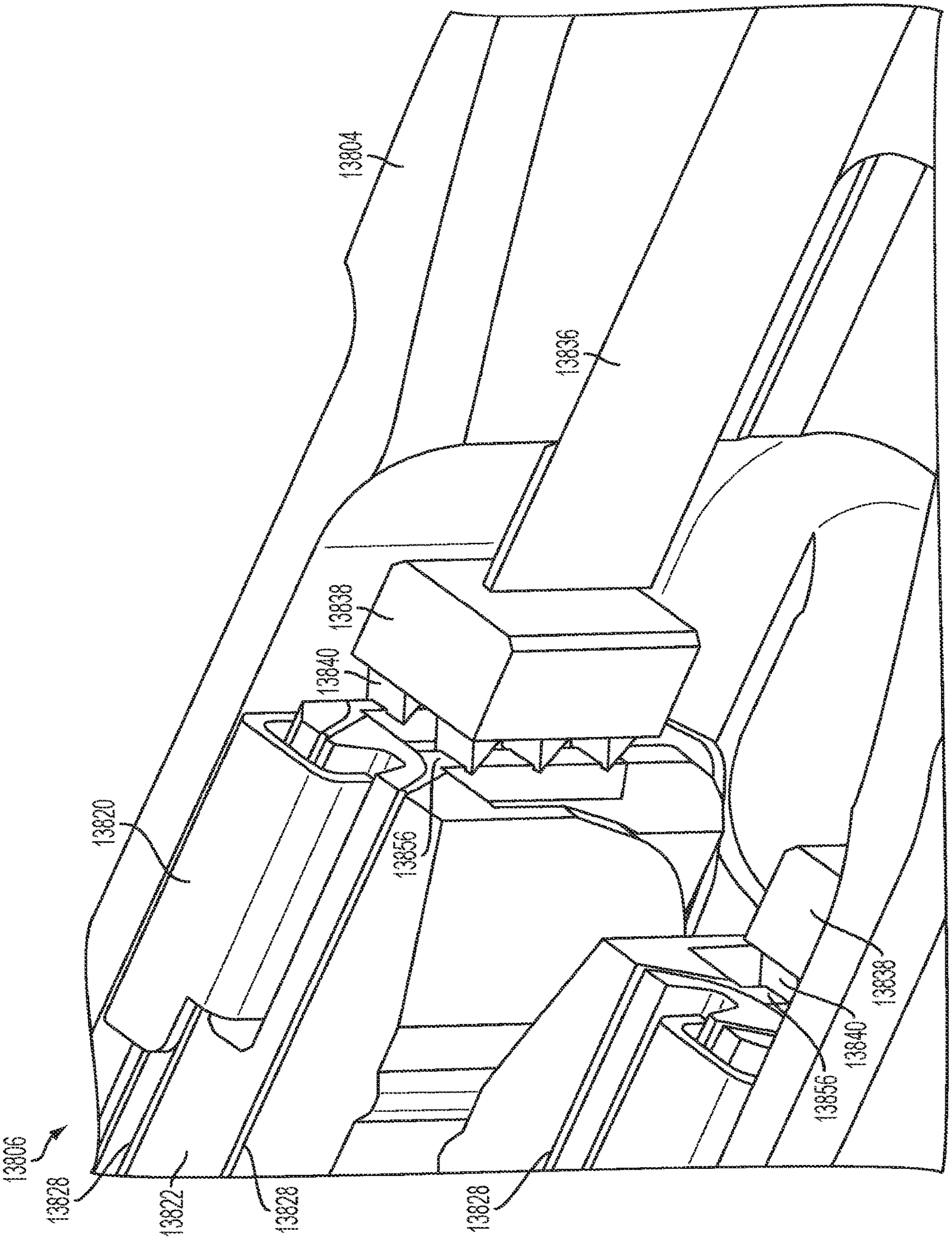
Figure 114:
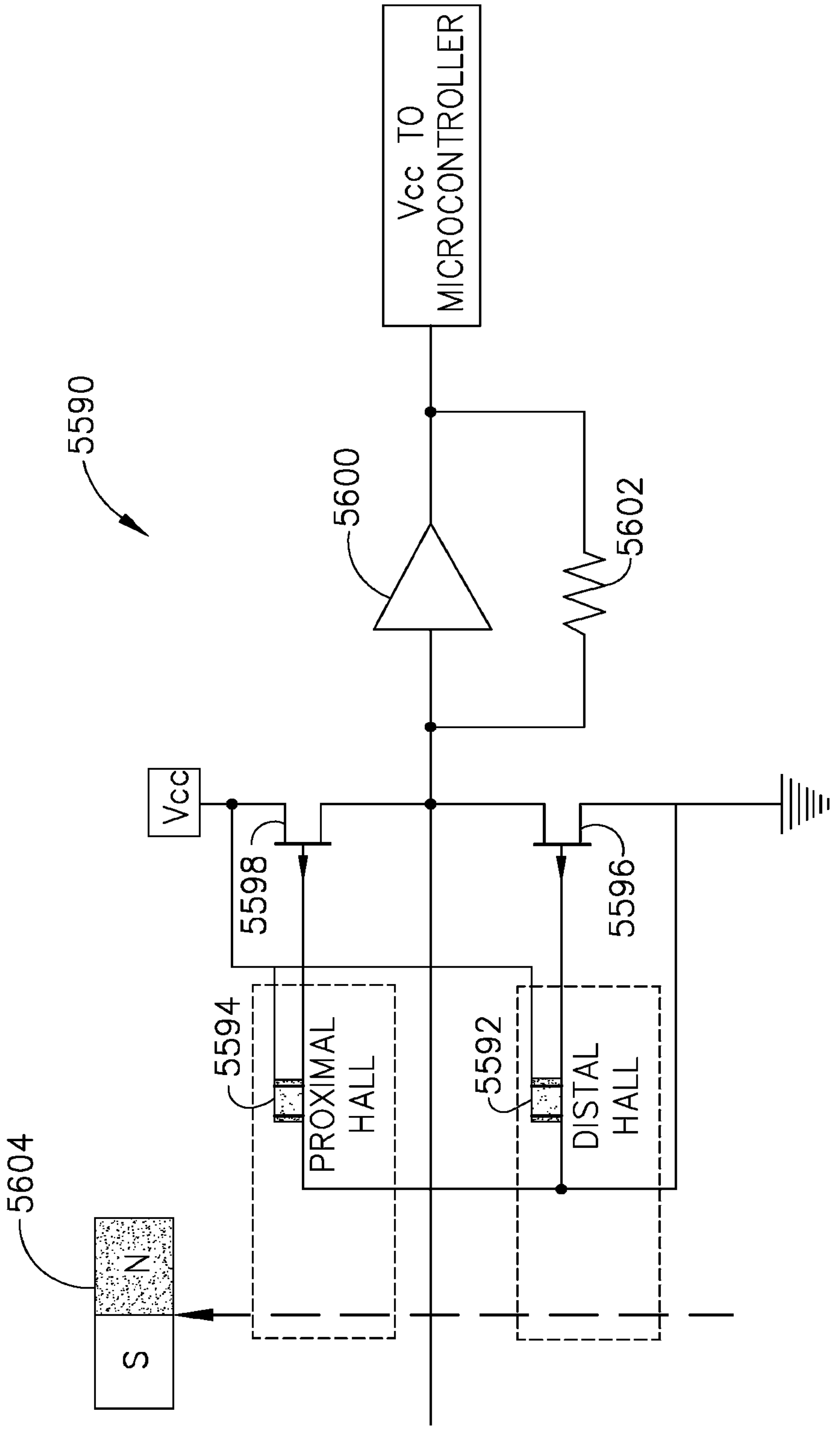
Figure 115:
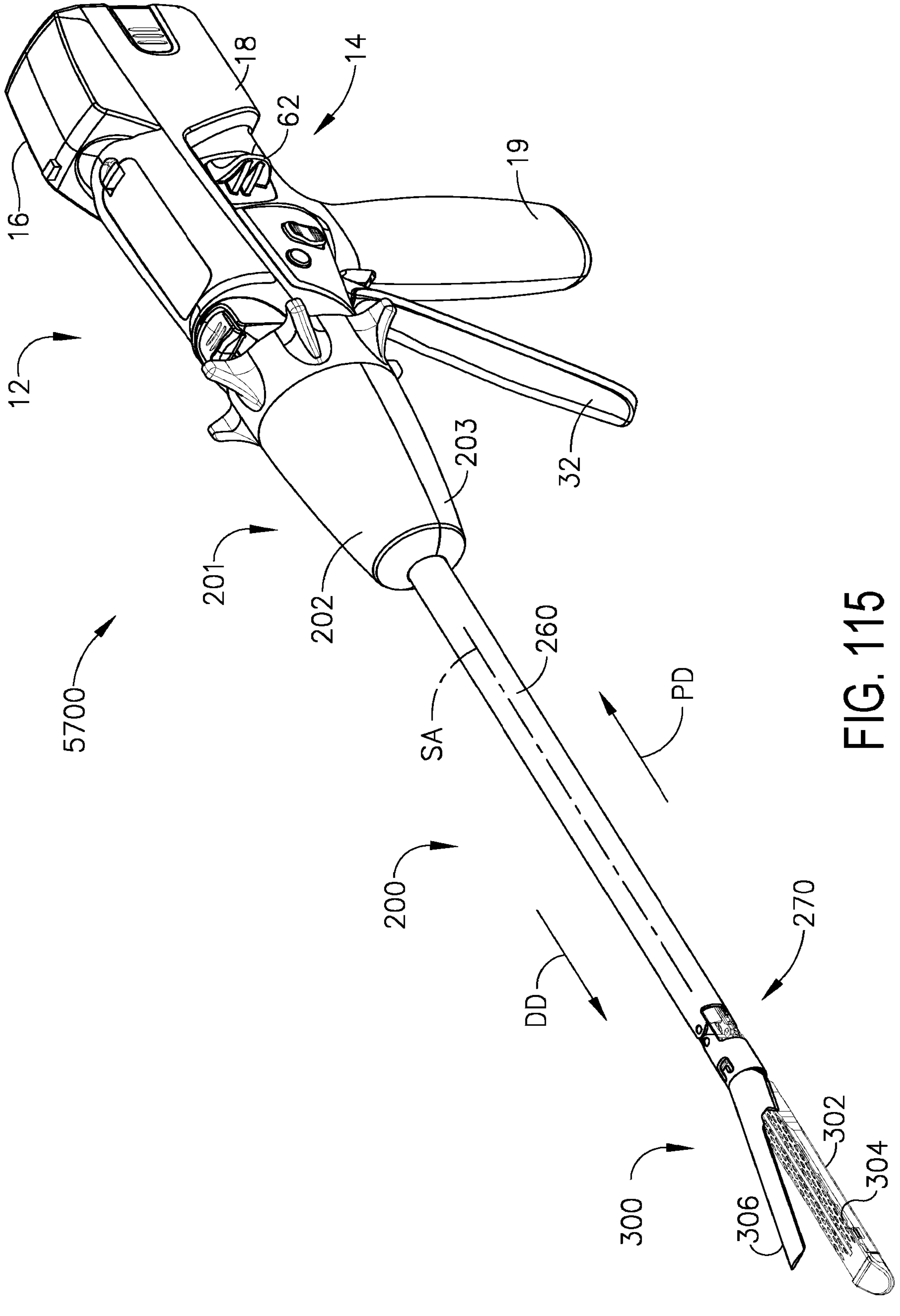

FIG. 50 illustrates a close up view of the elongated channel shown in FIGS. 114 and 115 with a staple cartridge coupled thereto in accordance with one or more aspects of the present disclosure.

Figure 51:
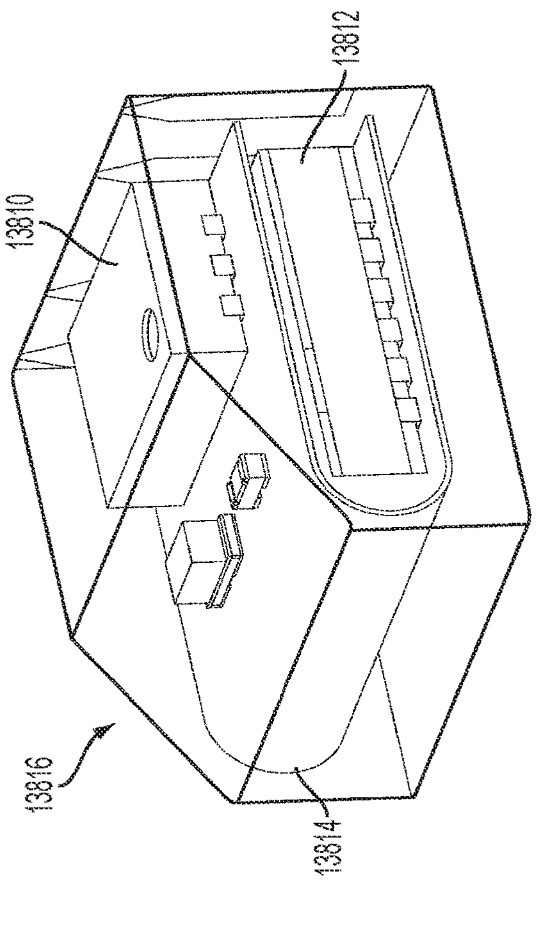
Figure 52:
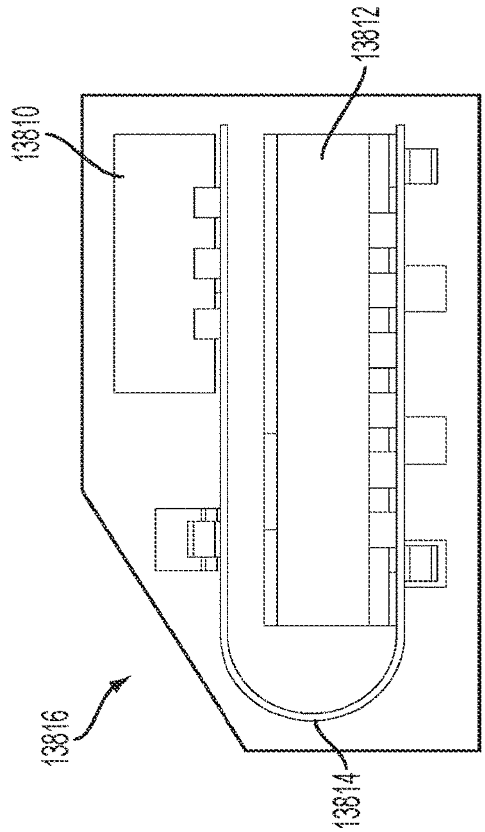

FIGS. 51 and 52 illustrate one aspect of a distal sensor plug where FIG. 51 illustrates a cutaway view of the distal sensor plug and FIG. 52 further illustrates the magnetic field sensor and the processor operatively coupled to the flex board such that they are capable of communicating in accordance with one or more aspects of the present disclosure.

Figure 53:
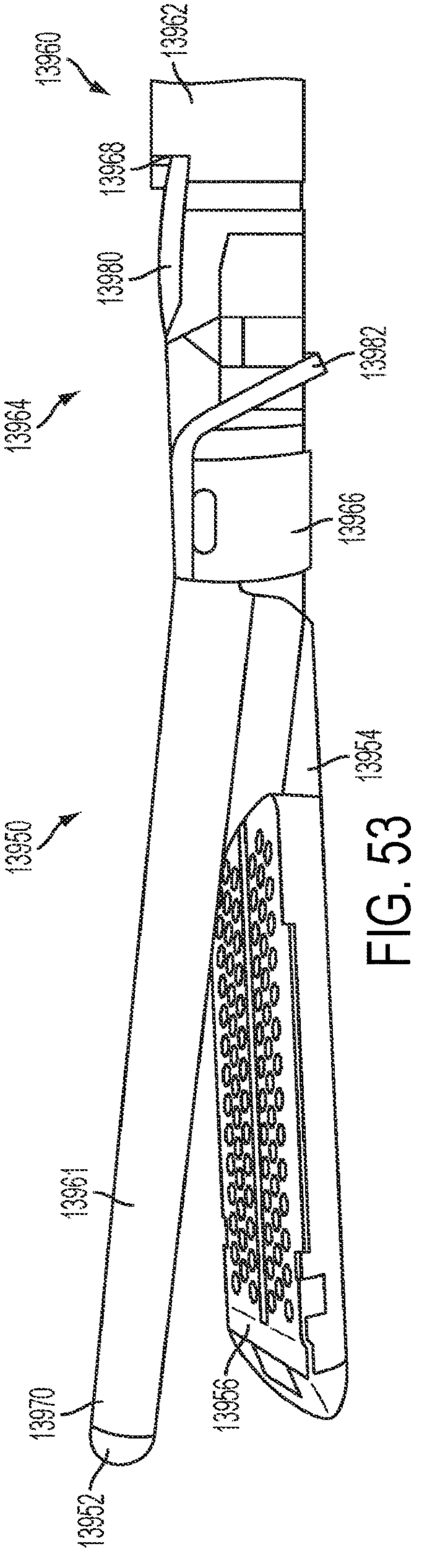

FIG. 53 illustrates an aspect of an end effector with a flex cable operable to provide power to sensors and electronics in the distal tip of the anvil portion in accordance with one or more aspects of the present disclosure.

Figure 54:
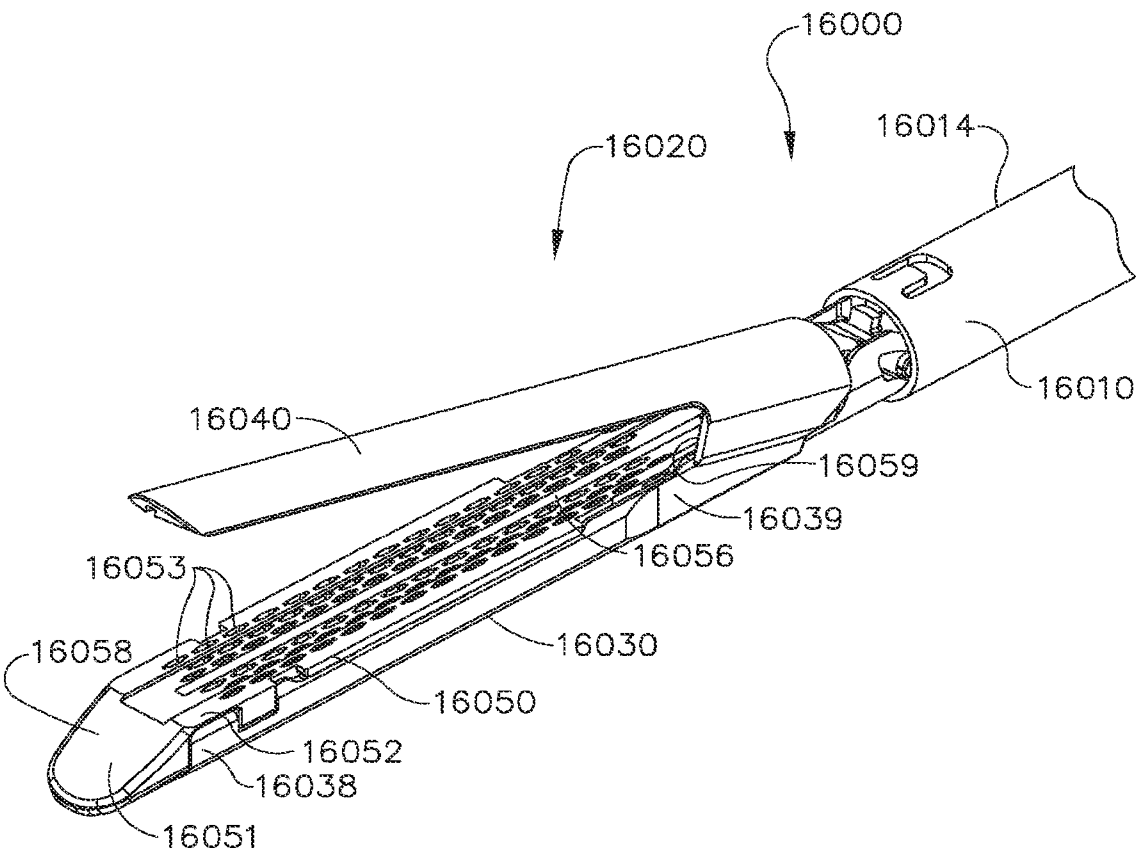

FIG. 54 is a perspective view of an end effector of a surgical stapling instrument including a cartridge channel, a staple cartridge positioned in the cartridge channel, and an anvil in accordance with one or more aspects of the present disclosure.

Figure 55:
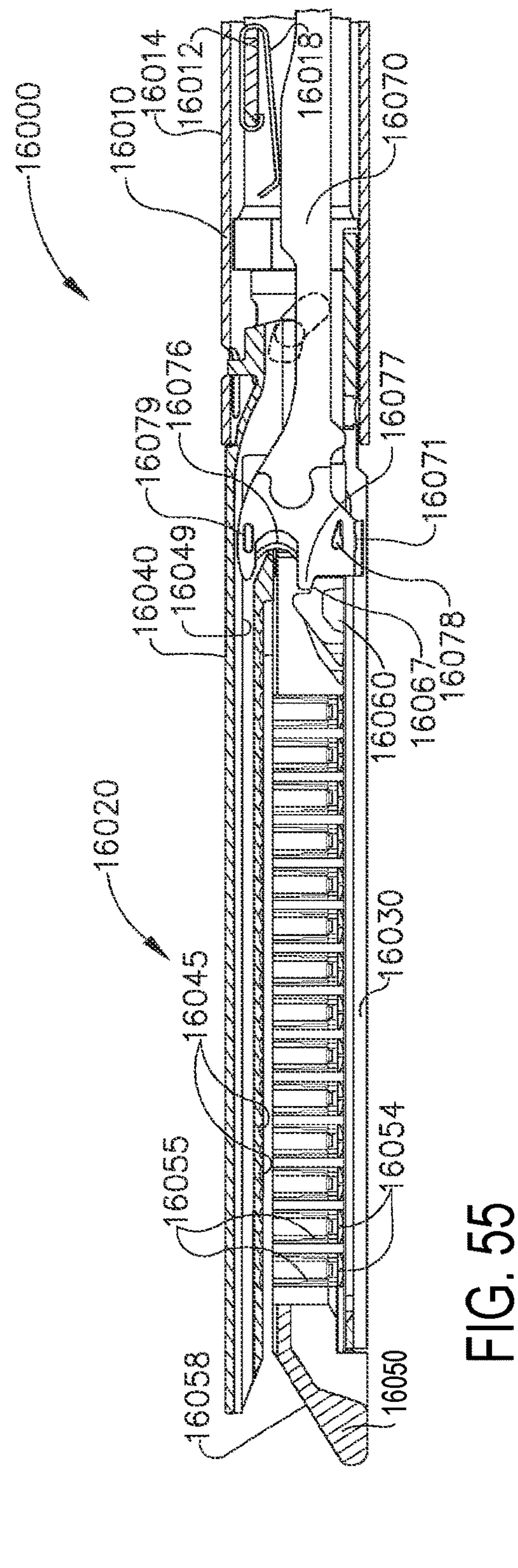

FIG. 55 is a cross-sectional elevational view of the surgical stapling instrument of FIG. 134 illustrating a sled and a firing member in an unfired position in accordance with one or more aspects of the present disclosure.

Figure 56:
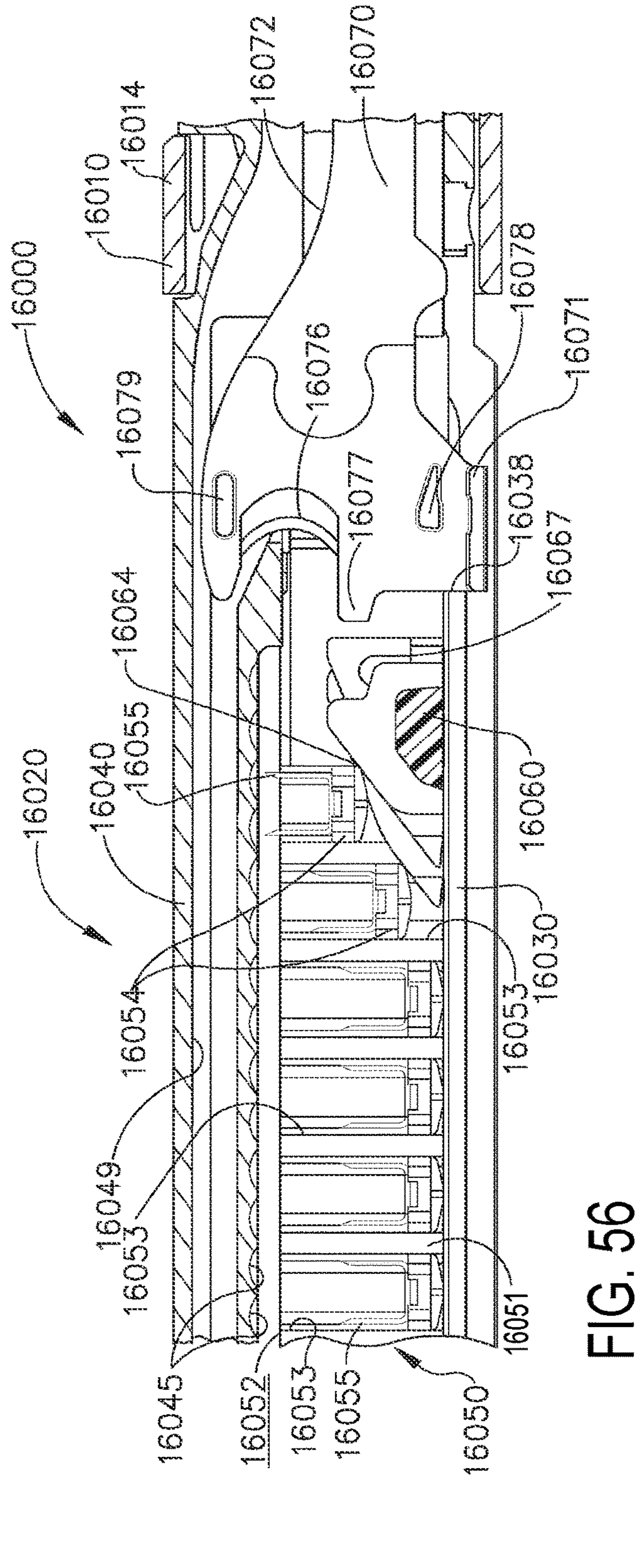

FIG. 56 is a detail view depicting the sled of FIG. 55 in a partially advanced position and the firing member in its unfired position in accordance with one or more aspects of the present disclosure.

Figure 57:
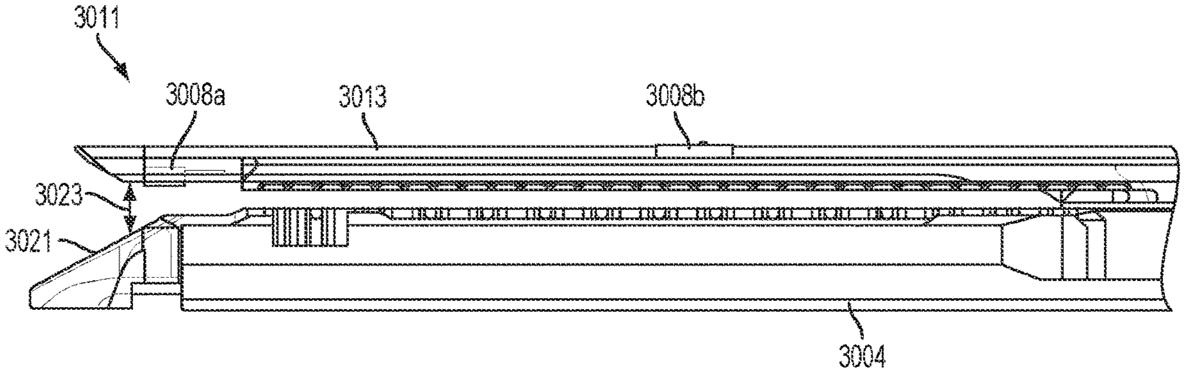

FIG. 57 illustrates one aspect of an end effector comprising a first sensor and a second sensor in accordance with one or more aspects of the present disclosure.

Figure 58:
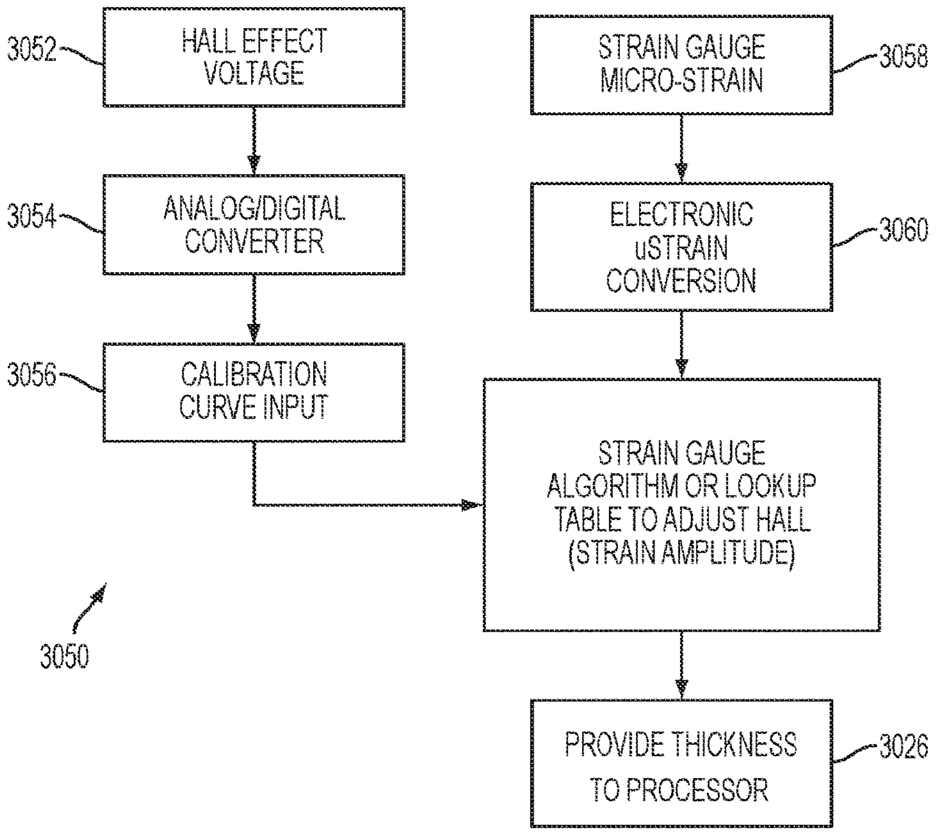

FIG. 58 is a logic diagram illustrating one aspect of a process for determining the thickness of a tissue section clamped between an anvil and a staple cartridge of an end effector in accordance with one or more aspects of the present disclosure.

Figure 59:
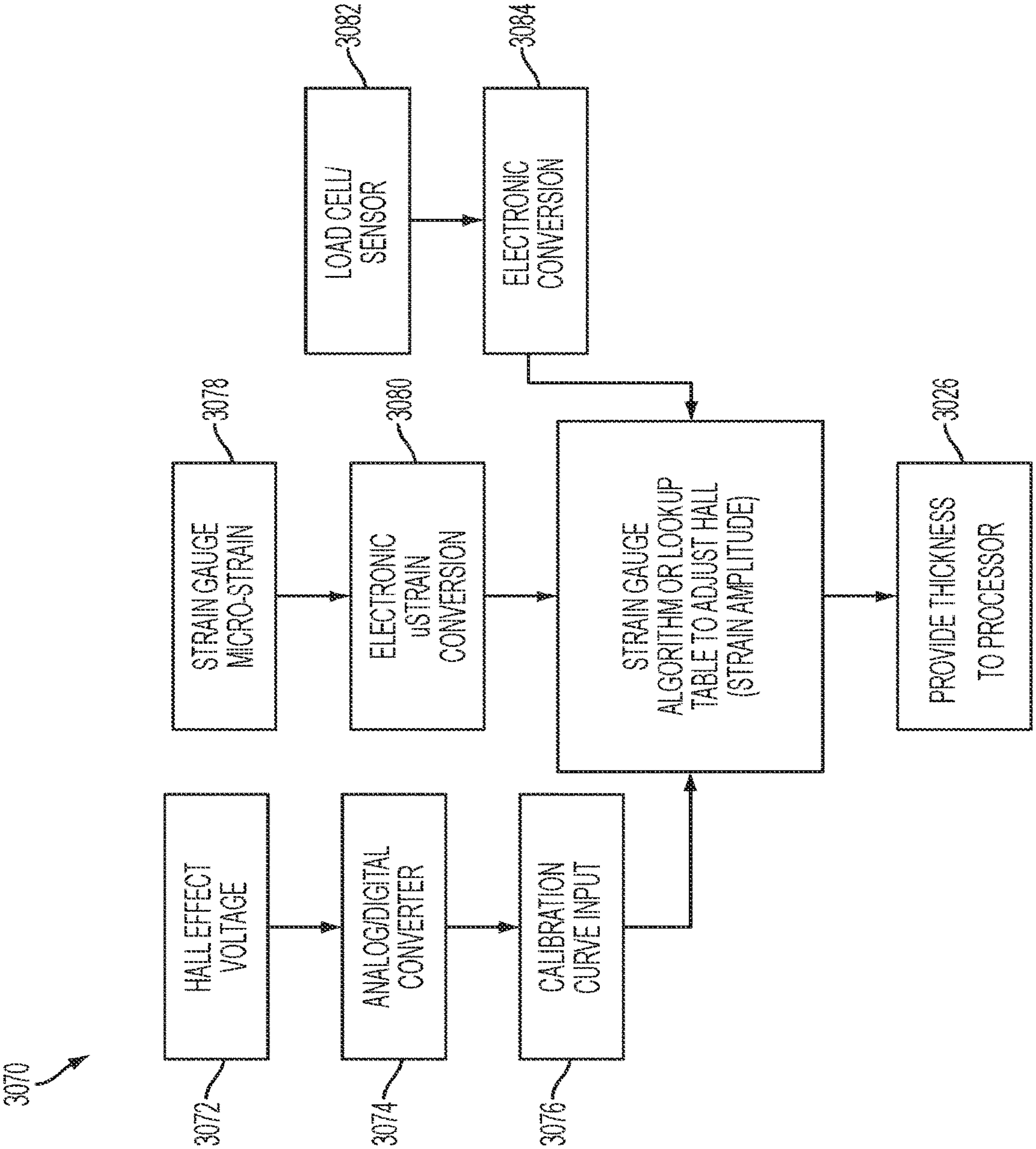

FIG. 59 is a logic diagram illustrating one aspect of a process for determining the thickness of a tissue section clamped between the anvil and the staple cartridge of the end effector in accordance with one or more aspects of the present disclosure.

Figure 60:
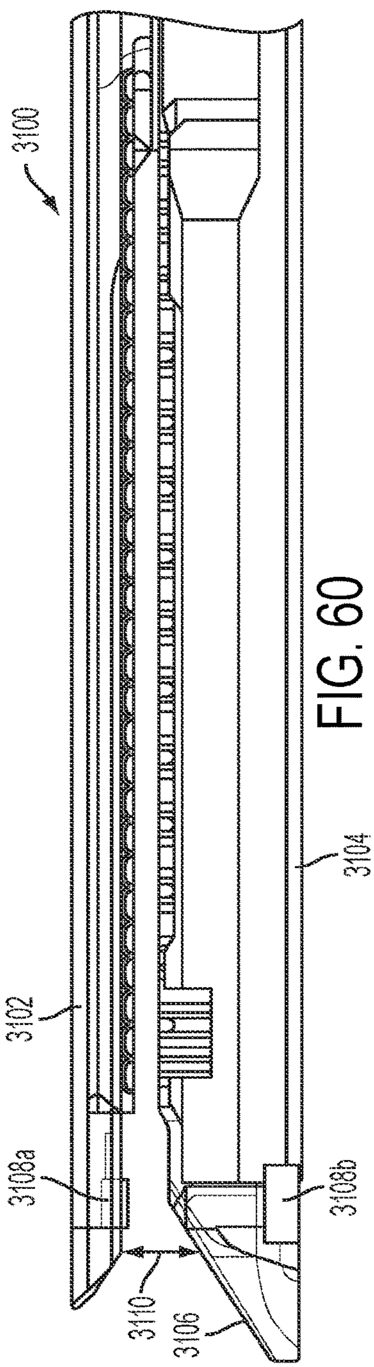

FIG. 60 illustrates one aspect of an end effector comprising a first sensor and a second sensor in accordance with one or more aspects of the present disclosure.

Figure 61:
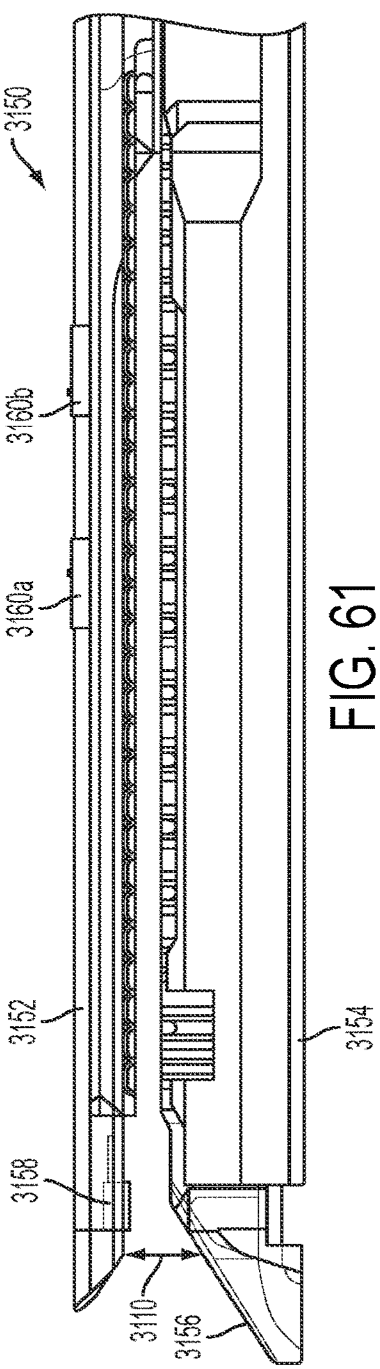

FIG. 61 illustrates one aspect of an end effector comprising a first sensor and a plurality of second sensors in accordance with one or more aspects of the present disclosure.

Figure 62:
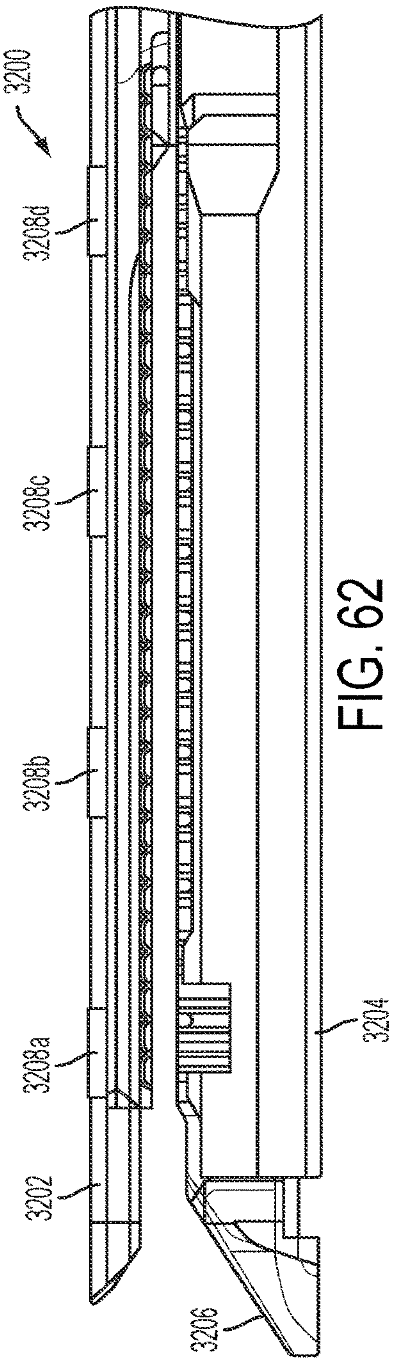

FIG. 62 illustrates one aspect of an end effector comprising a plurality of sensors in accordance with one or more aspects of the present disclosure.

Figure 63:
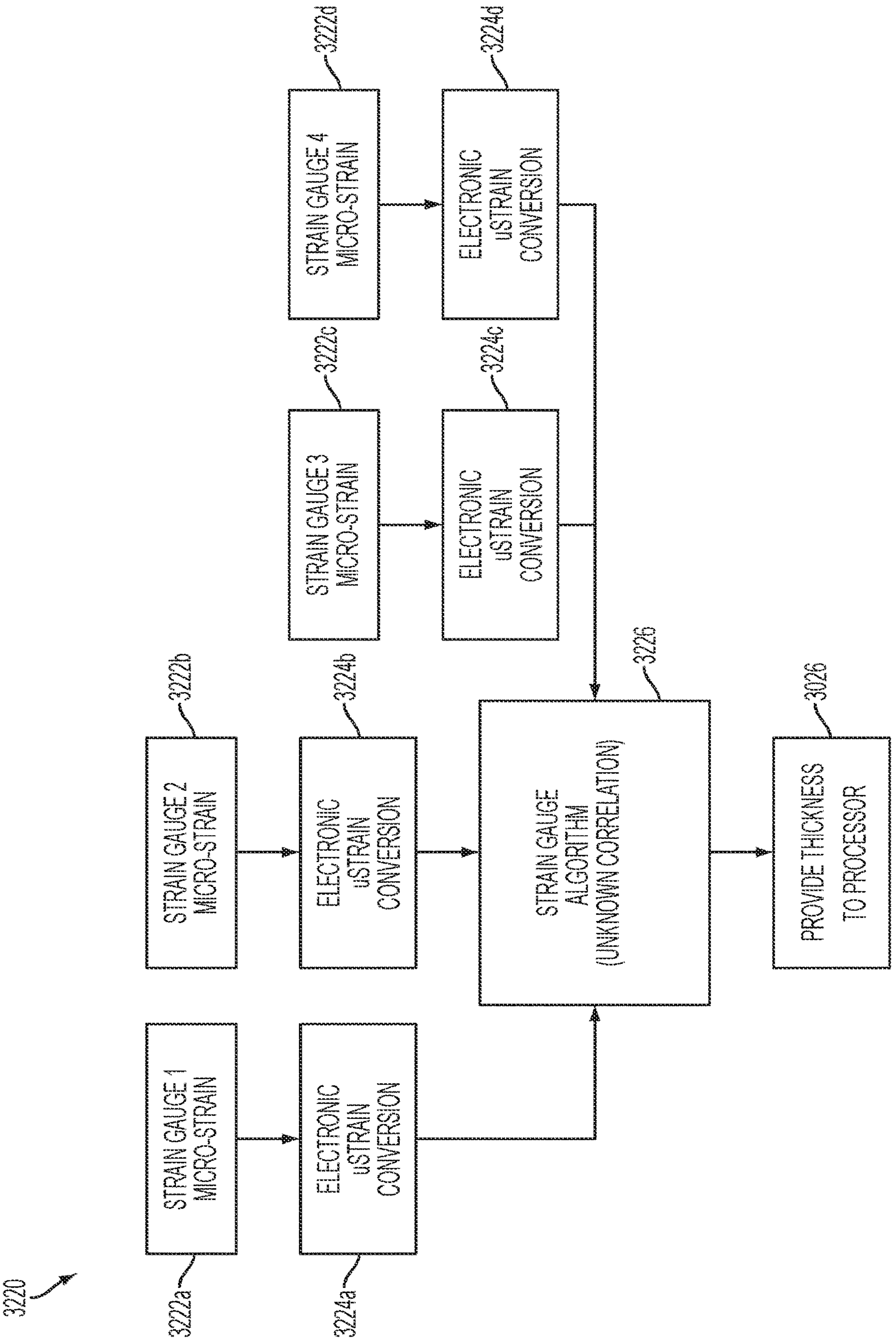

FIG. 63 is a logic diagram illustrating one aspect of a process for determining one or more tissue properties based on a plurality of sensors in accordance with one or more aspects of the present disclosure.

Figure 64:
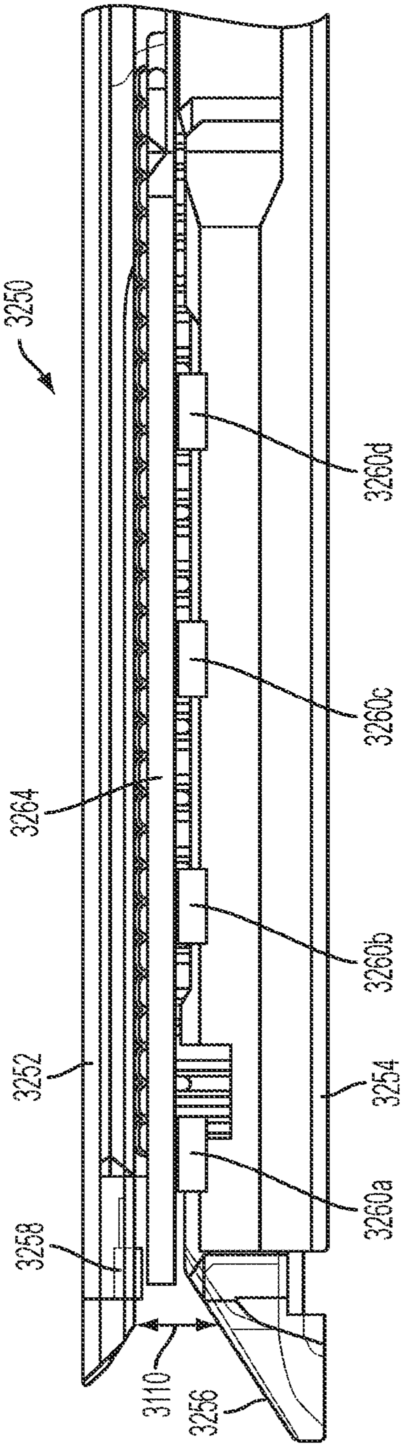

FIG. 64 illustrates one aspect of an end effector comprising a plurality of sensors coupled to a jaw member in accordance with one or more aspects of the present disclosure.

Figure 65:
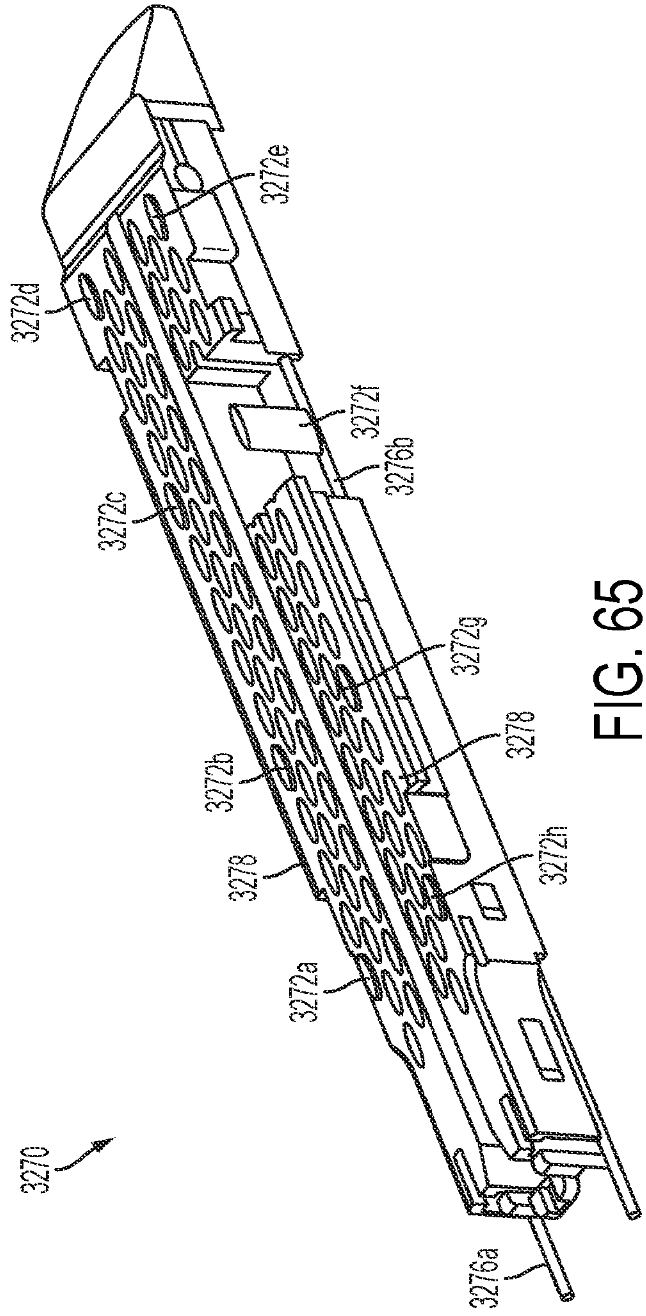

FIG. 65 illustrates one aspect of a staple cartridge comprising a plurality of sensors formed integrally therein in accordance with one or more aspects of the present disclosure.

Figure 66:
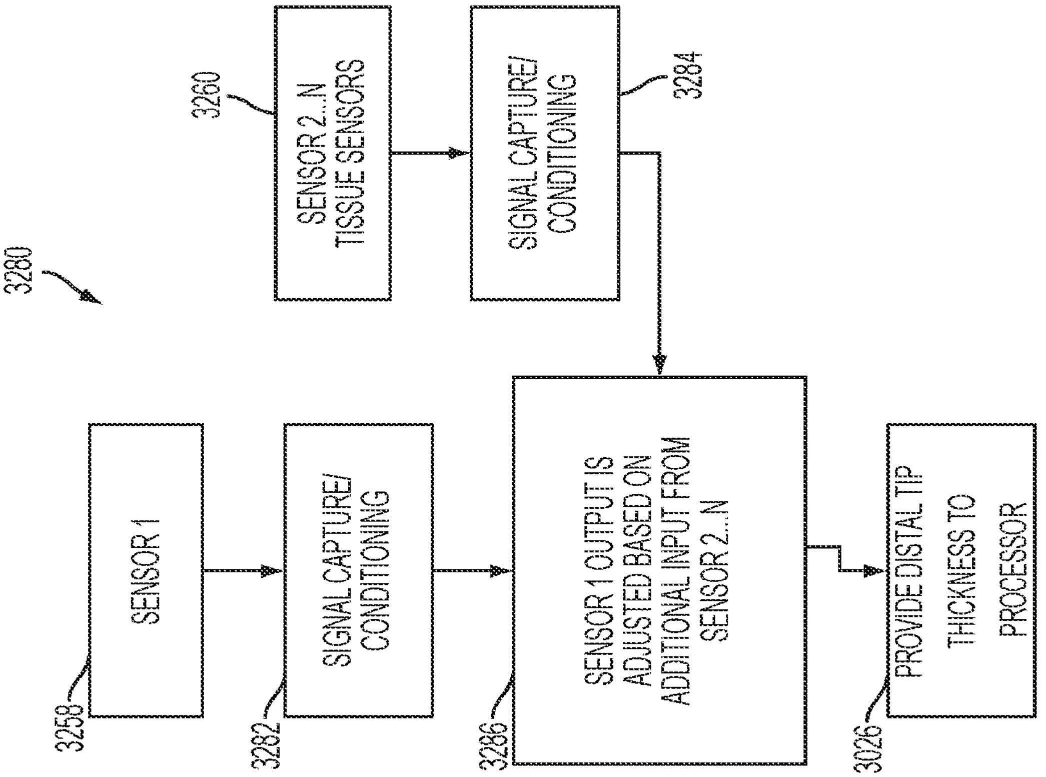

FIG. 66 is a logic diagram illustrating one aspect of a process for determining one or more parameters of a tissue section clamped within an end effector in accordance with one or more aspects of the present disclosure.

Figure 67:
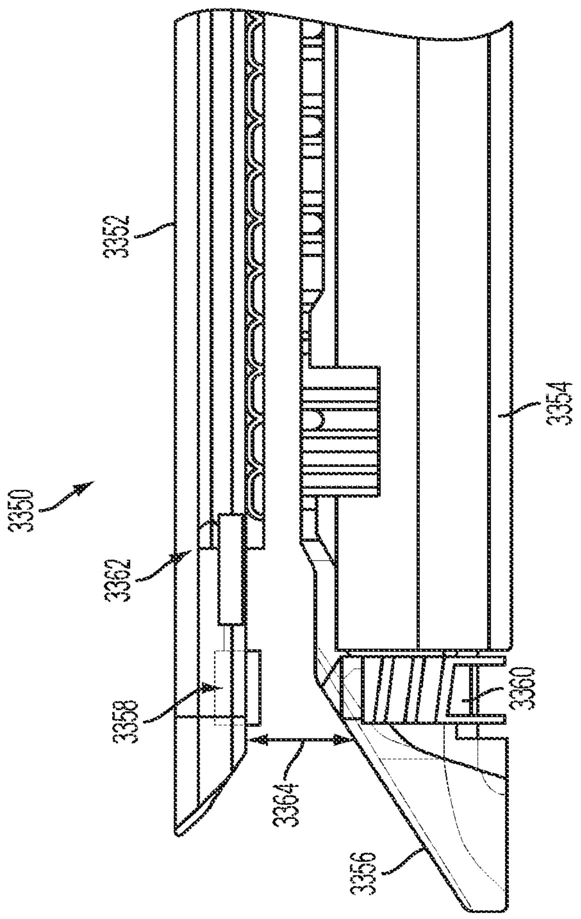

FIG. 67 illustrates one aspect of an end effector comprising a sensor comprising a specific sampling rate to limit or eliminate false signals in accordance with one or more aspects of the present disclosure.

Figure 68:
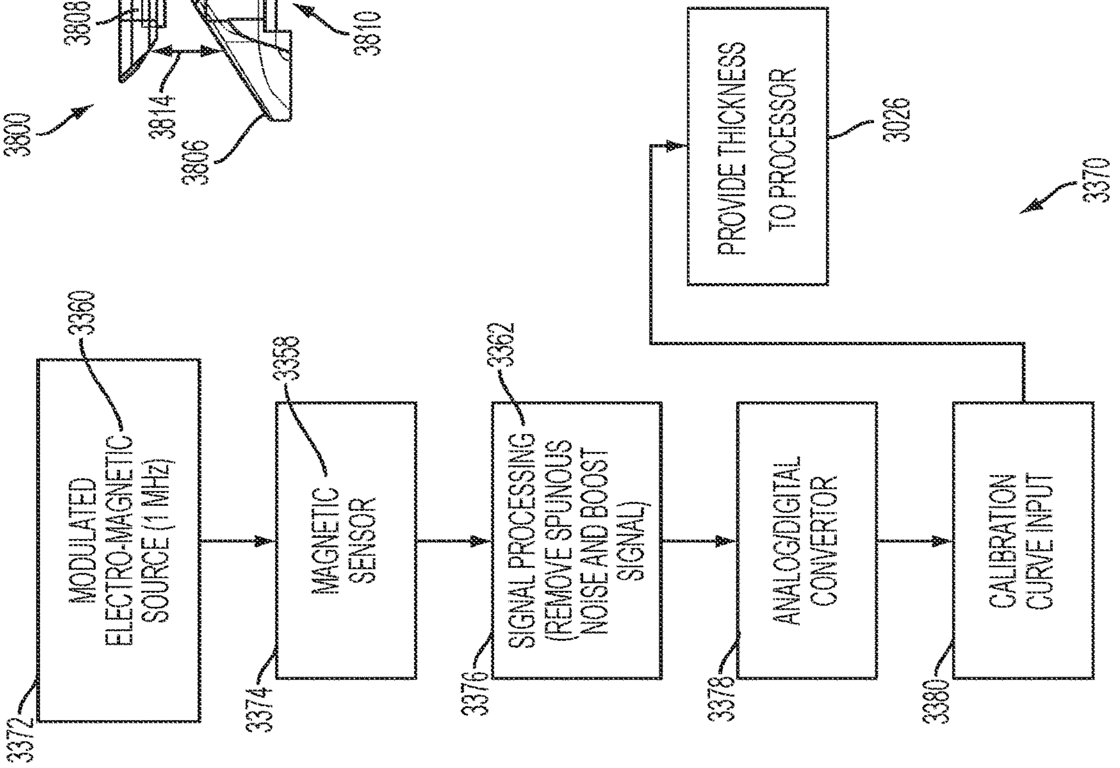

FIG. 68 is a logic diagram illustrating one aspect of a process for generating a thickness measurement for a tissue section located between an anvil and a staple cartridge of an end effector in accordance with one or more aspects of the present disclosure.

Figure 69A:
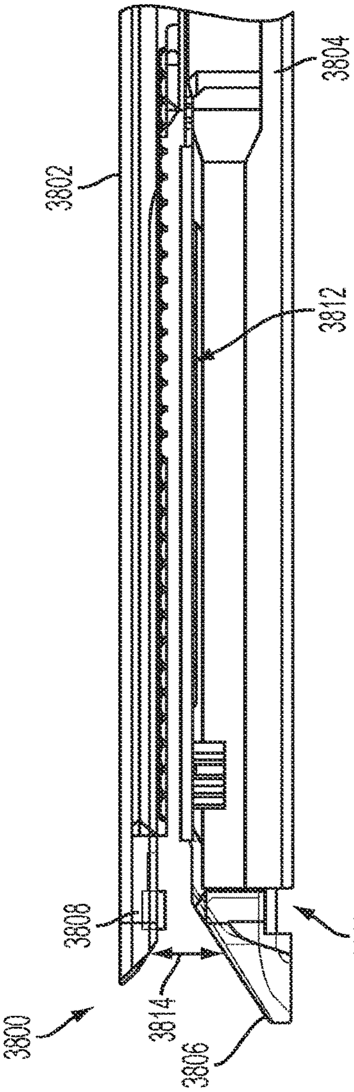
Figure 69B:
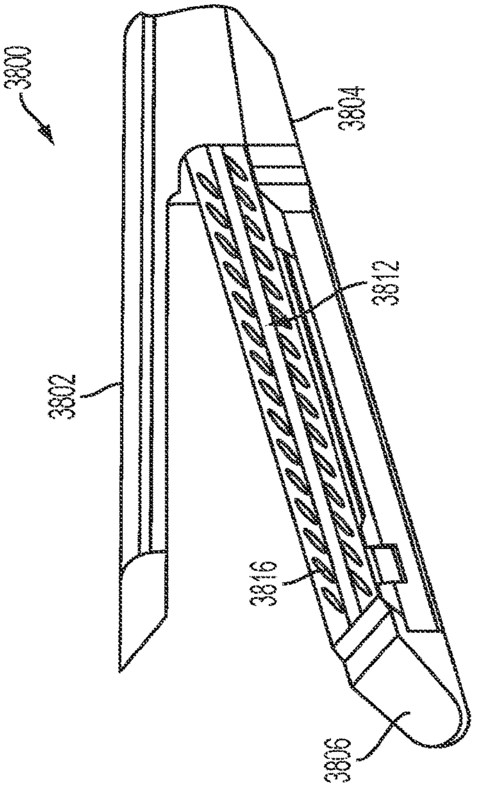

FIGS. 69A-69B illustrate one aspect of an end effector comprising a pressure sensor in accordance with one or more aspects of the present disclosure.

Figure 70:
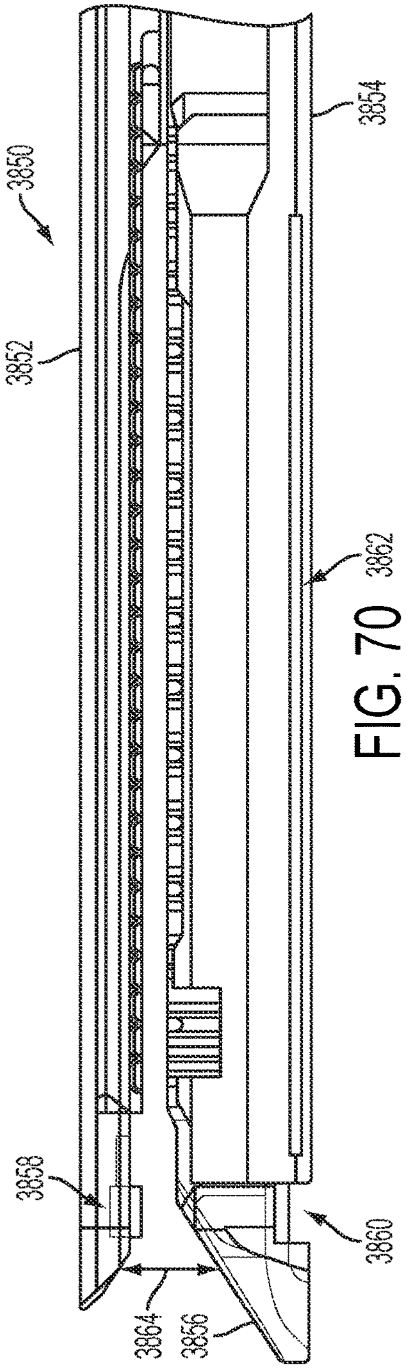

FIG. 70 illustrates one aspect of an end effector comprising a second sensor located between a staple cartridge and a jaw member in accordance with one or more aspects of the present disclosure.

Figure 71:
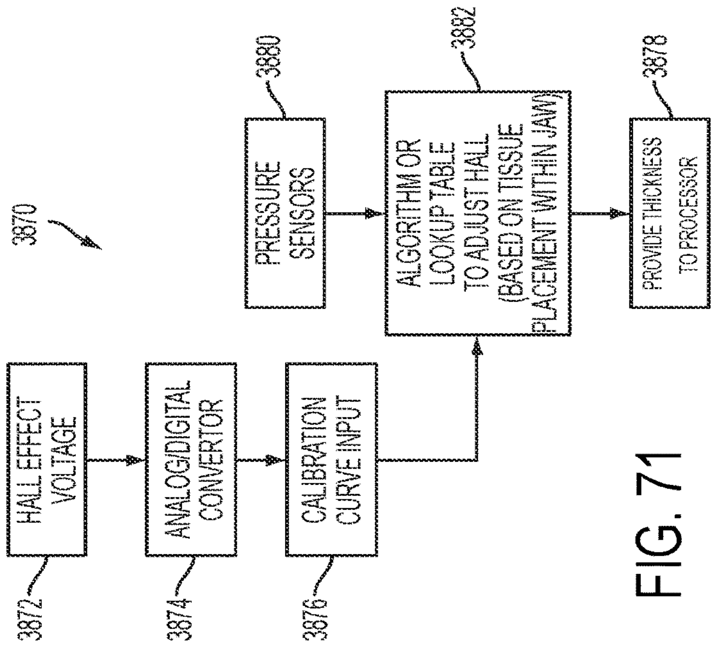

FIG. 71 is a logic diagram illustrating one aspect of a process for determining the thickness of a tissue section clamped in an end effector, according to FIGS. 69A-69B or FIG. 70 in accordance with one or more aspects of the present disclosure.

Figure 72:
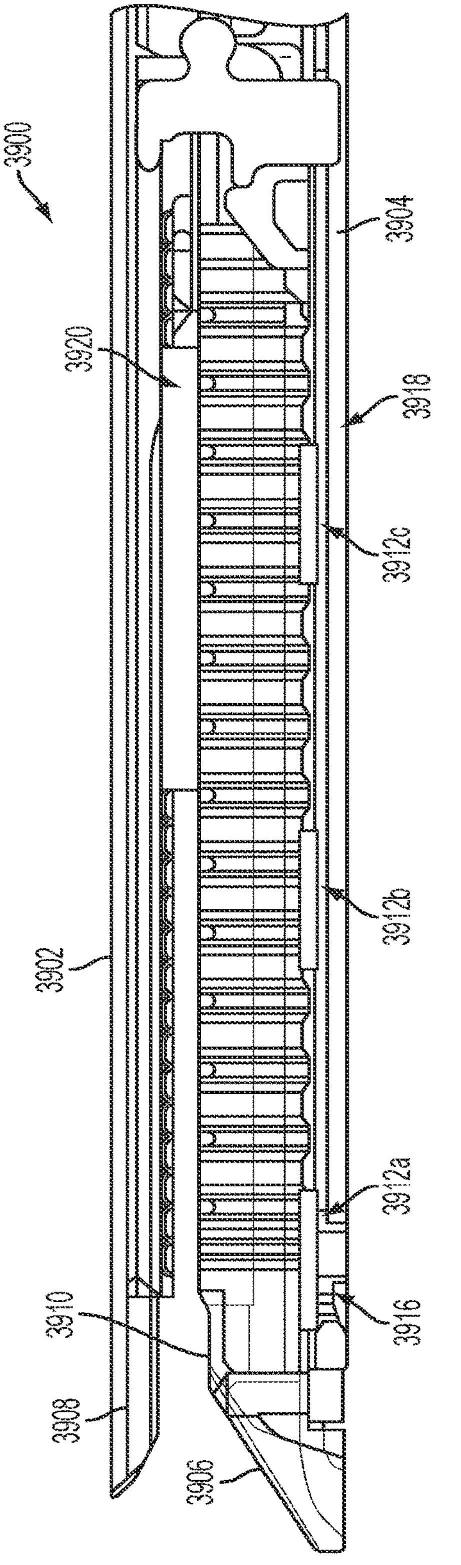

FIG. 72 illustrates one aspect of an end effector comprising a plurality of second sensors located between a staple cartridge and an elongated channel in accordance with one or more aspects of the present disclosure.

Figure 73B:
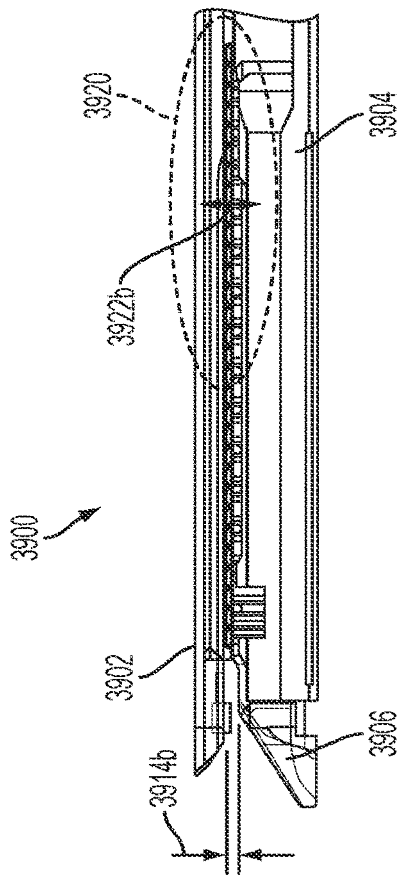
Figure 73A:
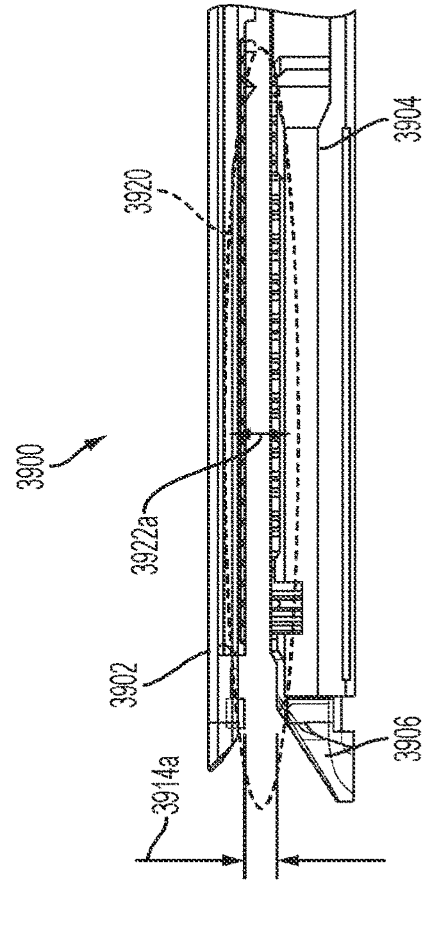

FIGS. 73A and 73B further illustrate the effect of a full versus partial bite of tissue in accordance with one or more aspects of the present disclosure.

Figure 74:
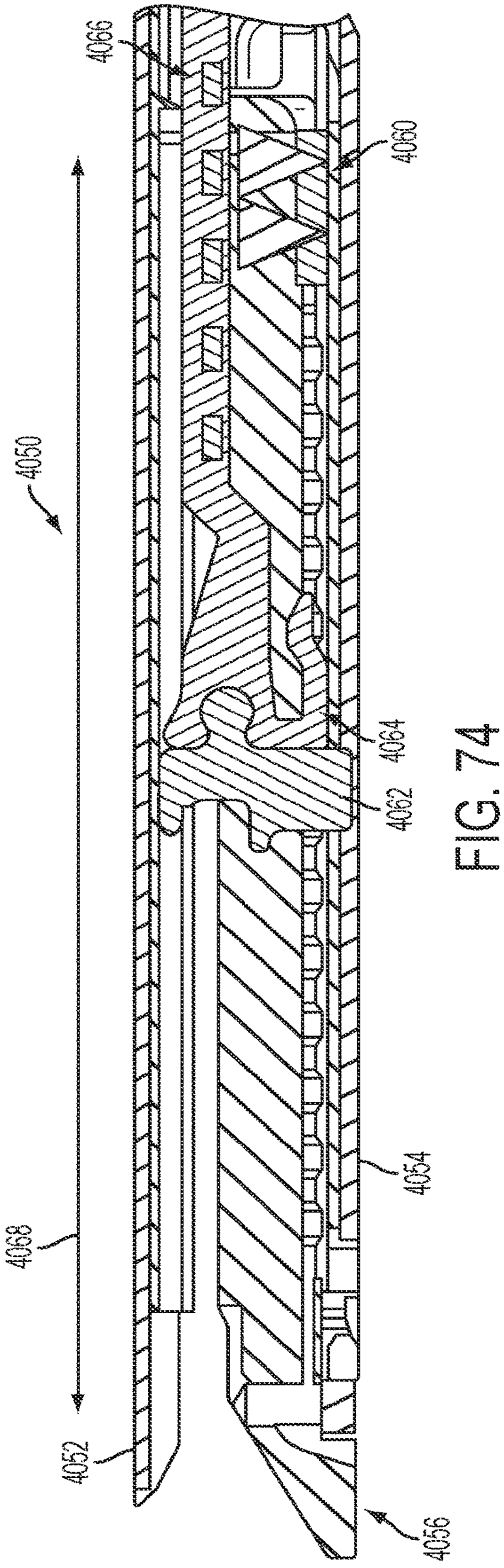

FIG. 74 illustrates an aspect of an end effector that is configured to determine the location of a cutting member or knife in accordance with one or more aspects of the present disclosure.

Figure 75:
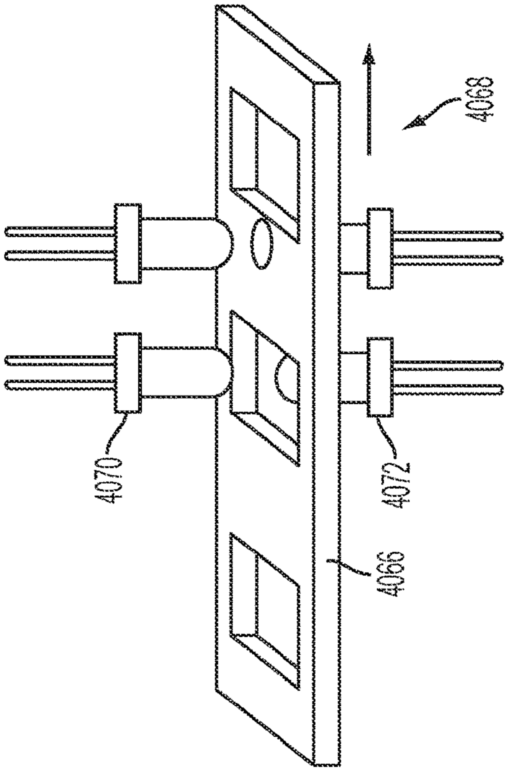

FIG. 75 illustrates an example of the code strip in operation with red LEDs and an infrared LED in accordance with one or more aspects of the present disclosure.

Figure 76:
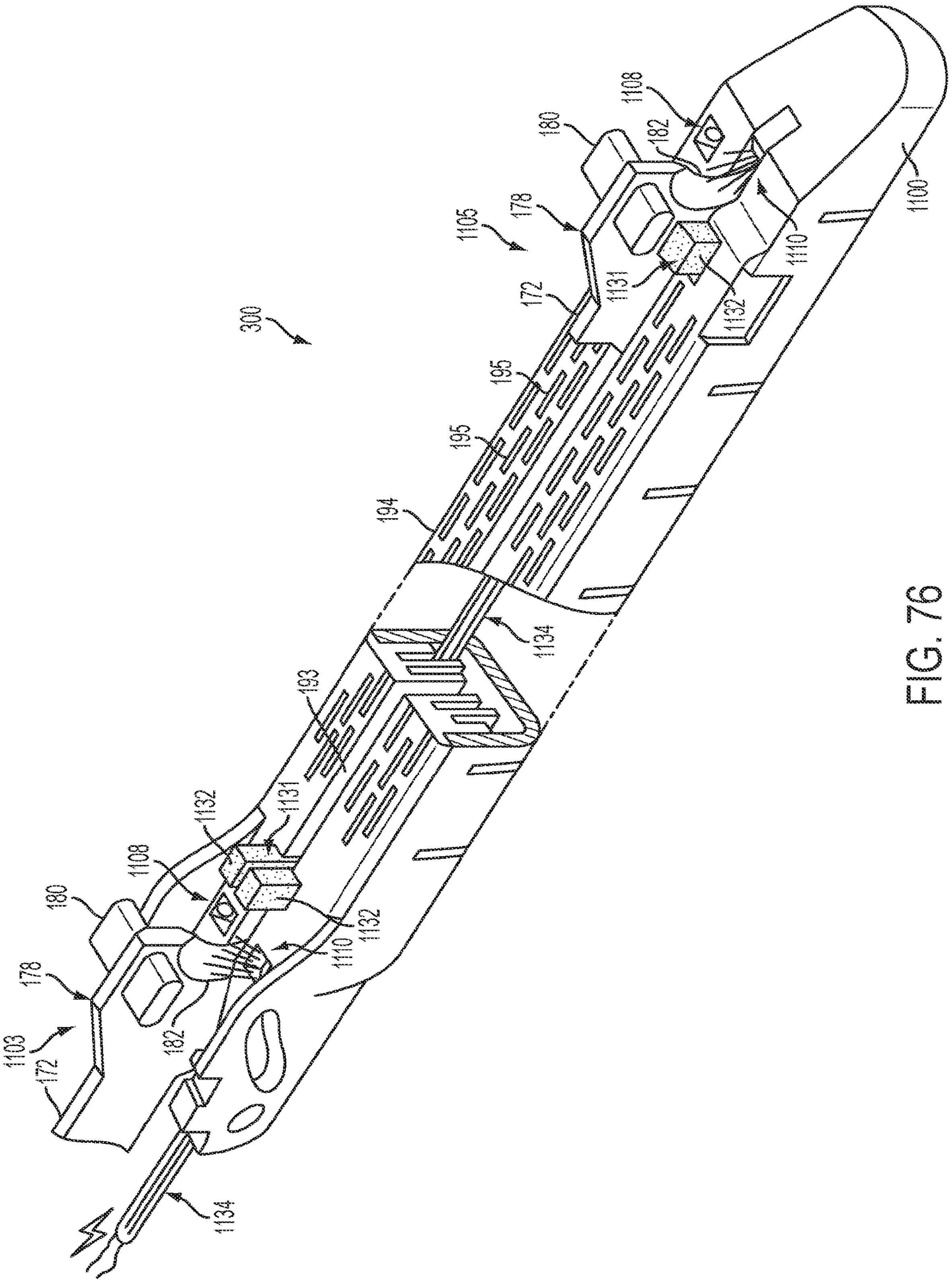

FIG. 76 illustrates a partial perspective view of an end effector of a surgical instrument comprising a staple cartridge in accordance with one or more aspects of the present disclosure.

Figure 77:
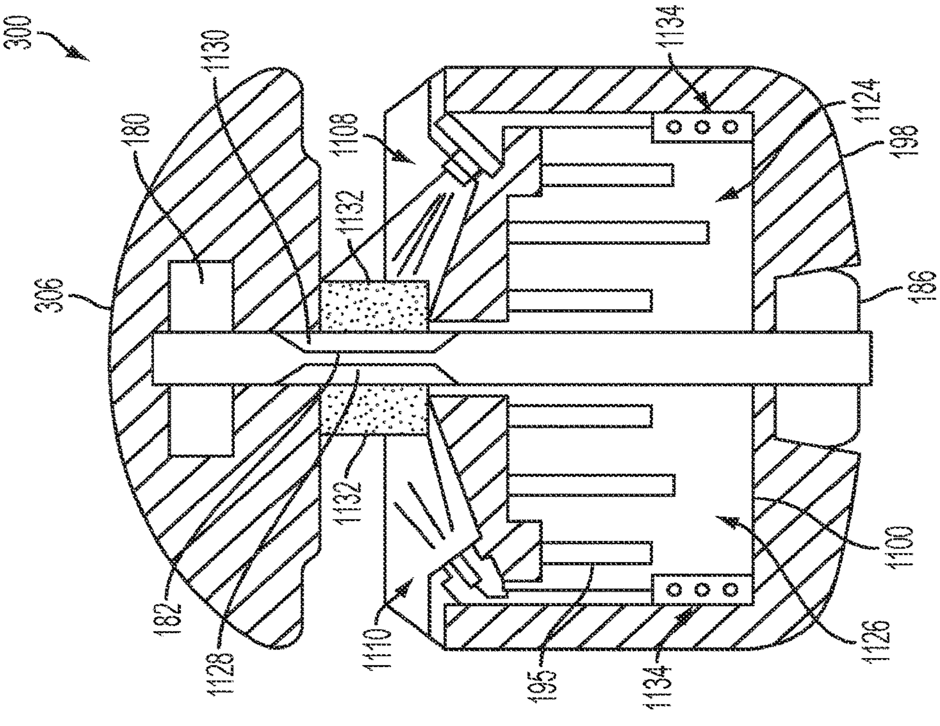

FIG. 77 illustrates an elevational view of a portion of the end effector of FIG. 76 in accordance with one or more aspects of the present disclosure.

Figure 78:
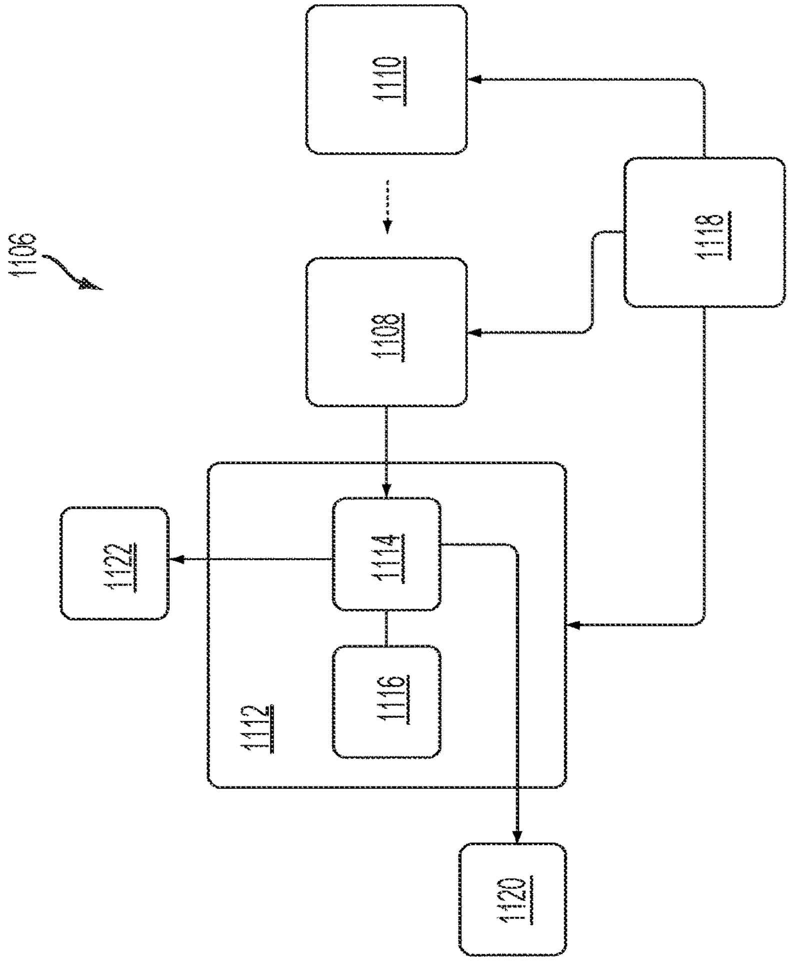

FIG. 78 illustrates a logic diagram of a module of the surgical instrument of FIG. 76 in accordance with one or more aspects of the present disclosure.

Figure 79:
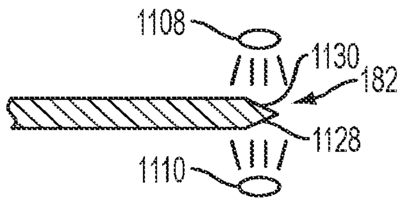

FIG. 79 illustrates a partial view of a cutting edge, an optical sensor, and a light source of the surgical instrument of FIG. 76 in accordance with one or more aspects of the present disclosure.

Figure 80:
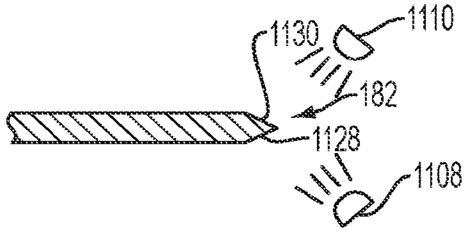

FIG. 80 illustrates a partial view of a cutting edge, an optical sensor, and a light source of the surgical instrument of FIG. 76 in accordance with one or more aspects of the present disclosure.

Figure 81:
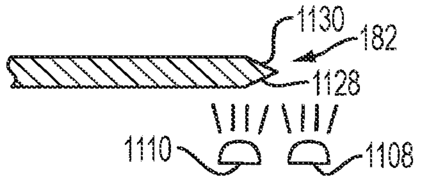

FIG. 81 illustrates a partial view of a cutting edge, an optical sensor, and a light source of the surgical instrument of FIG. 76 in accordance with one or more aspects of the present disclosure.

Figure 82:
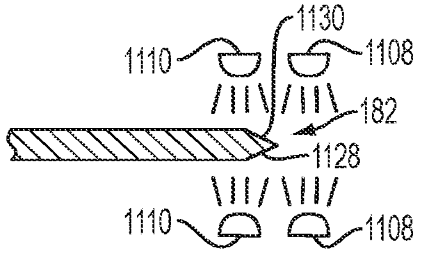

FIG. 82 illustrates a partial view of a cutting edge, optical sensors, and light sources of the surgical instrument of FIG. 76 in accordance with one or more aspects of the present disclosure.

Figure 83:
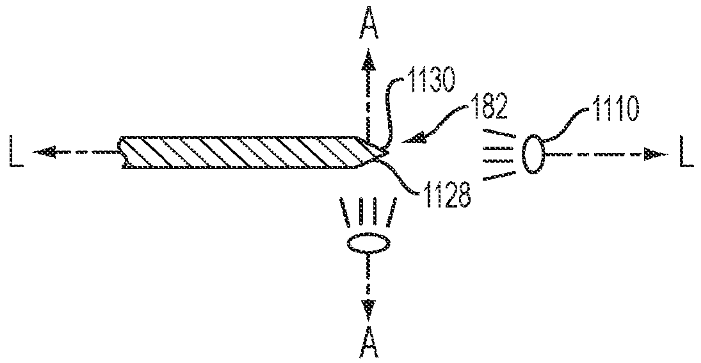

FIG. 83 illustrates a partial view of a cutting edge, an optical sensor, and a light source of the surgical instrument of FIG. 76 in accordance with one or more aspects of the present disclosure.

Figure 84:
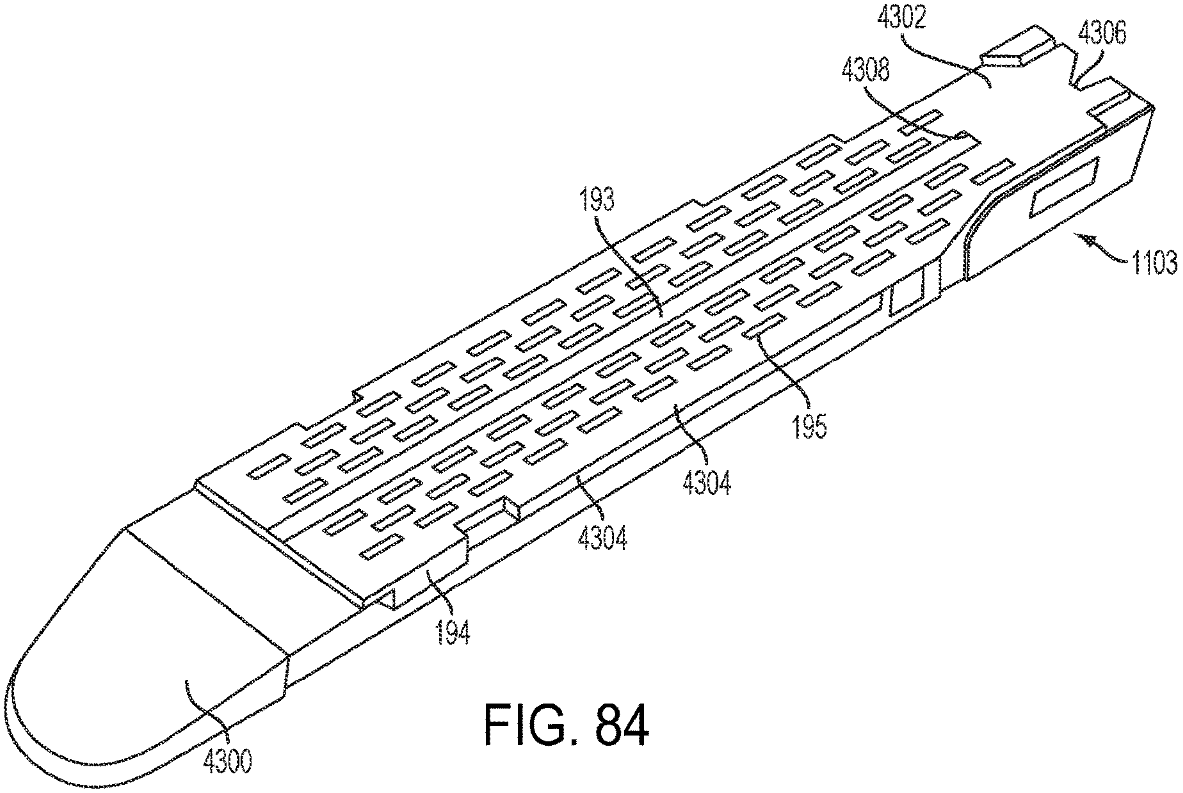

FIG. 84 illustrates a perspective view of a staple cartridge including a sharpness testing member in accordance with one or more aspects of the present disclosure.

Figure 85:
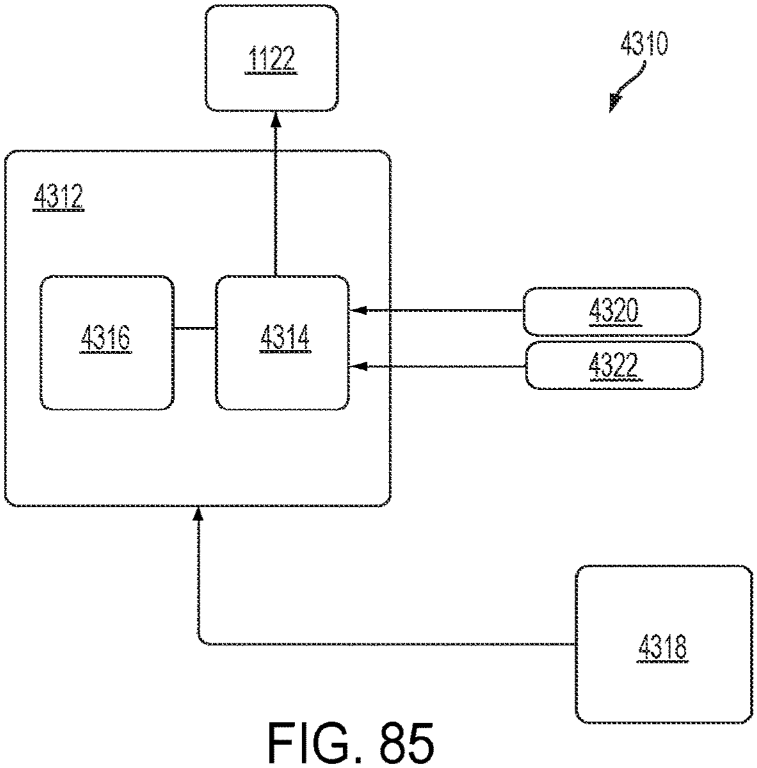

FIG. 85 illustrates a logic diagram of a module of a surgical instrument in accordance with one or more aspects of the present disclosure.

Figure 86:
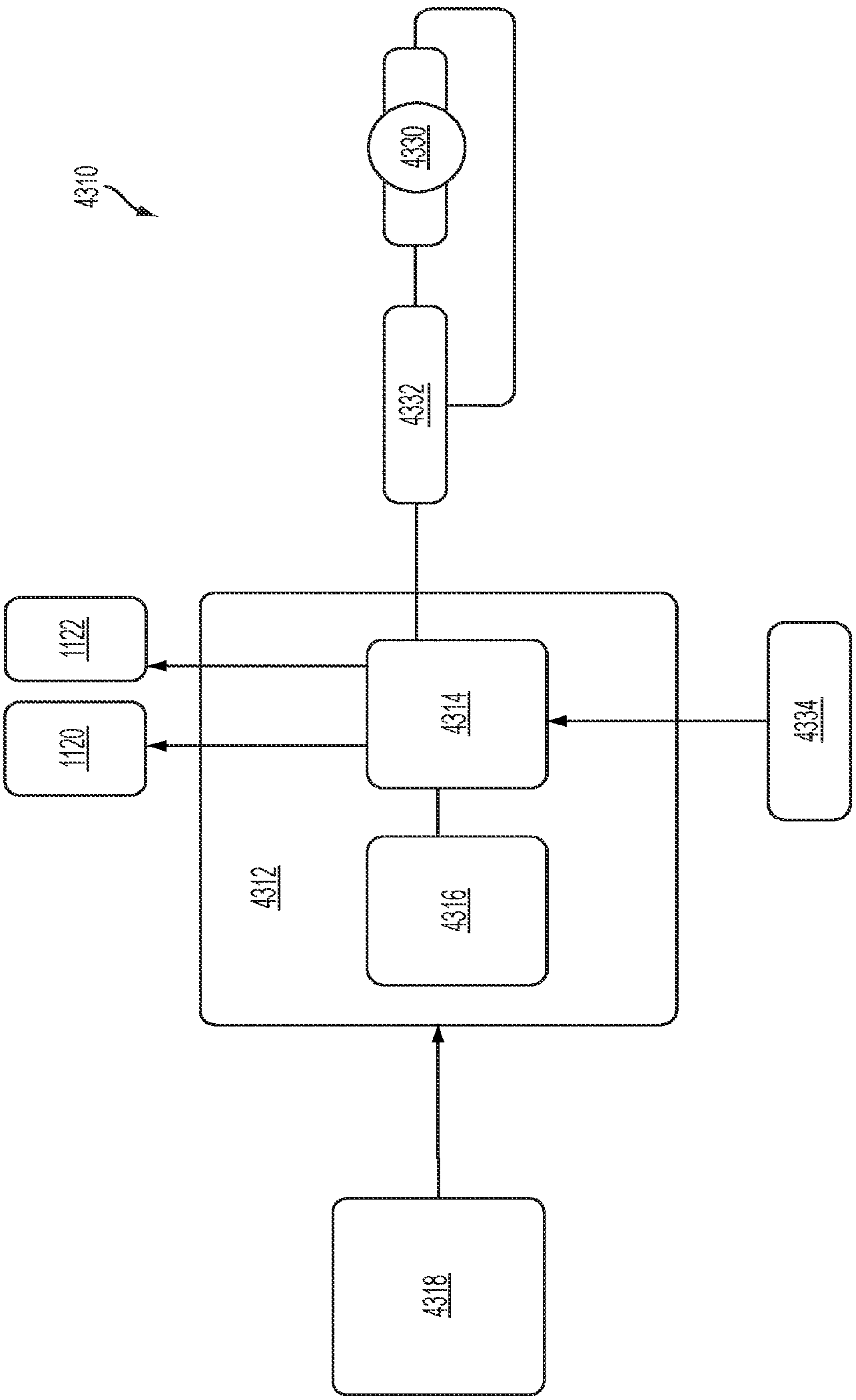

FIG. 86 illustrates a logic diagram of a module of a surgical instrument in accordance with one or more aspects of the present disclosure.

Figure 87:
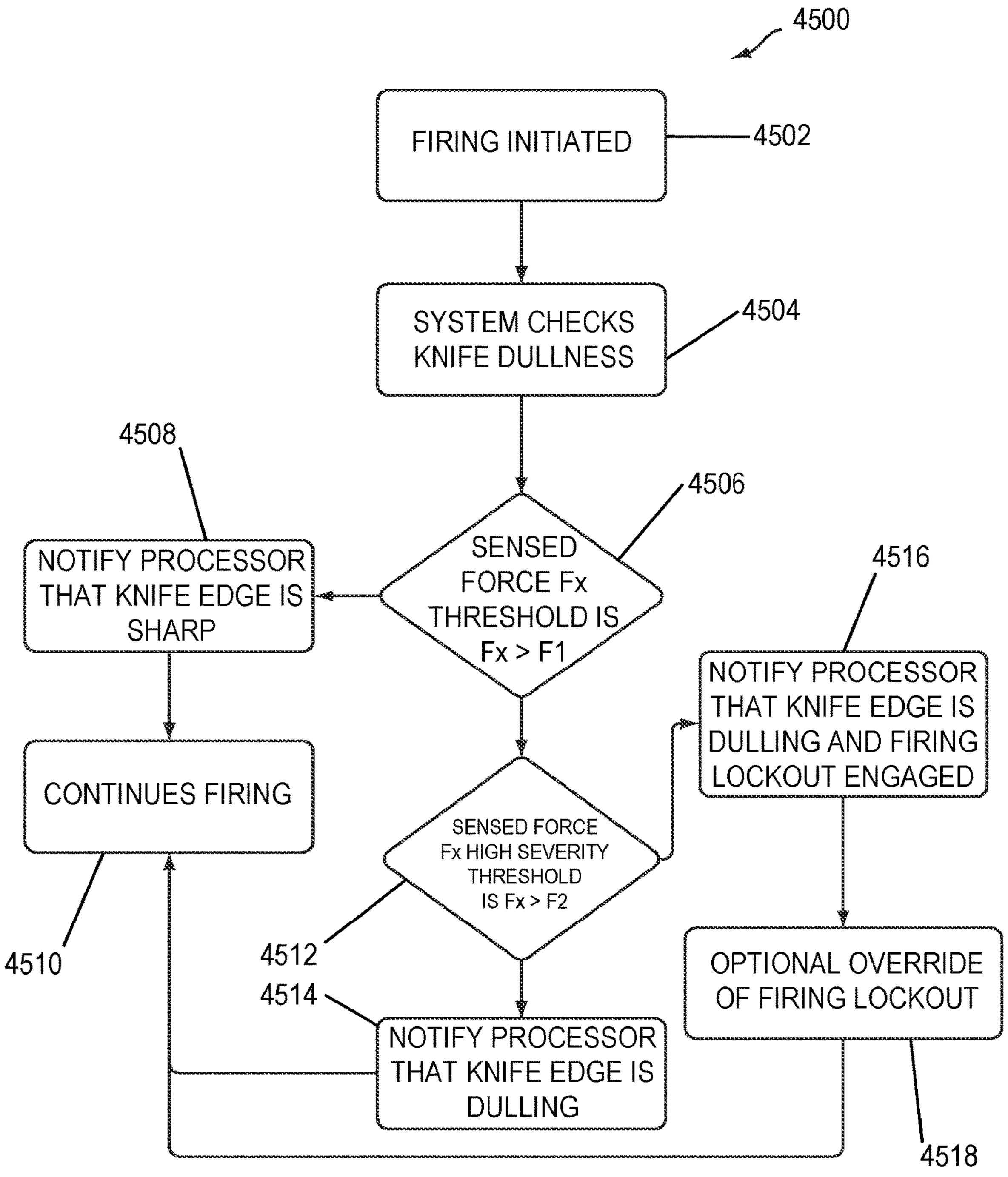

FIG. 87 illustrates a logic diagram outlining a method for evaluating sharpness of a cutting edge of a surgical instrument in accordance with one or more aspects of the present disclosure.

Figure 88:
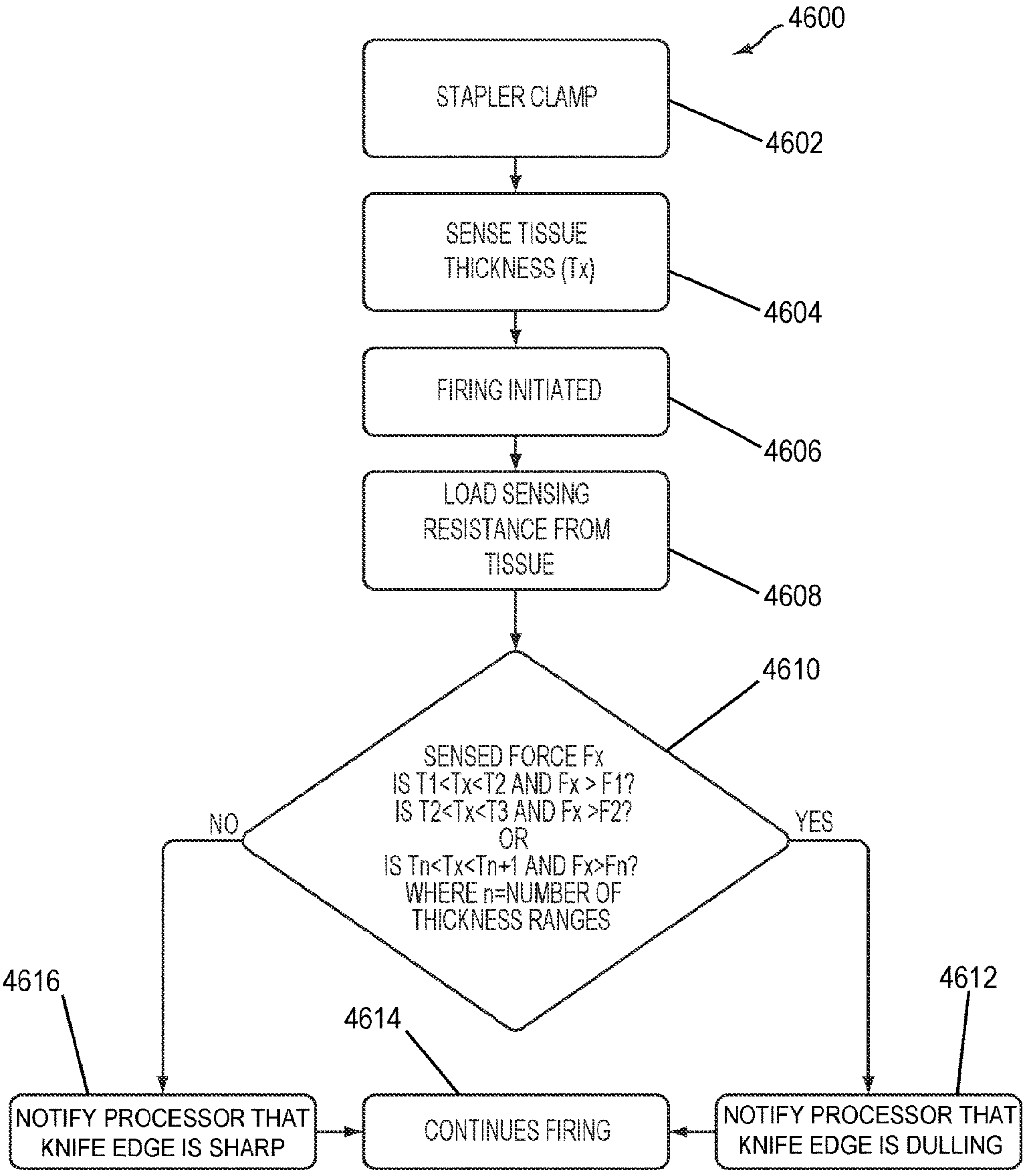

FIG. 88 illustrates a flow chart outlining a method for determining whether a cutting edge of a surgical instrument is sufficiently sharp to transect tissue captured by the surgical instrument in accordance with one or more aspects of the present disclosure.

Figures 89, 90:
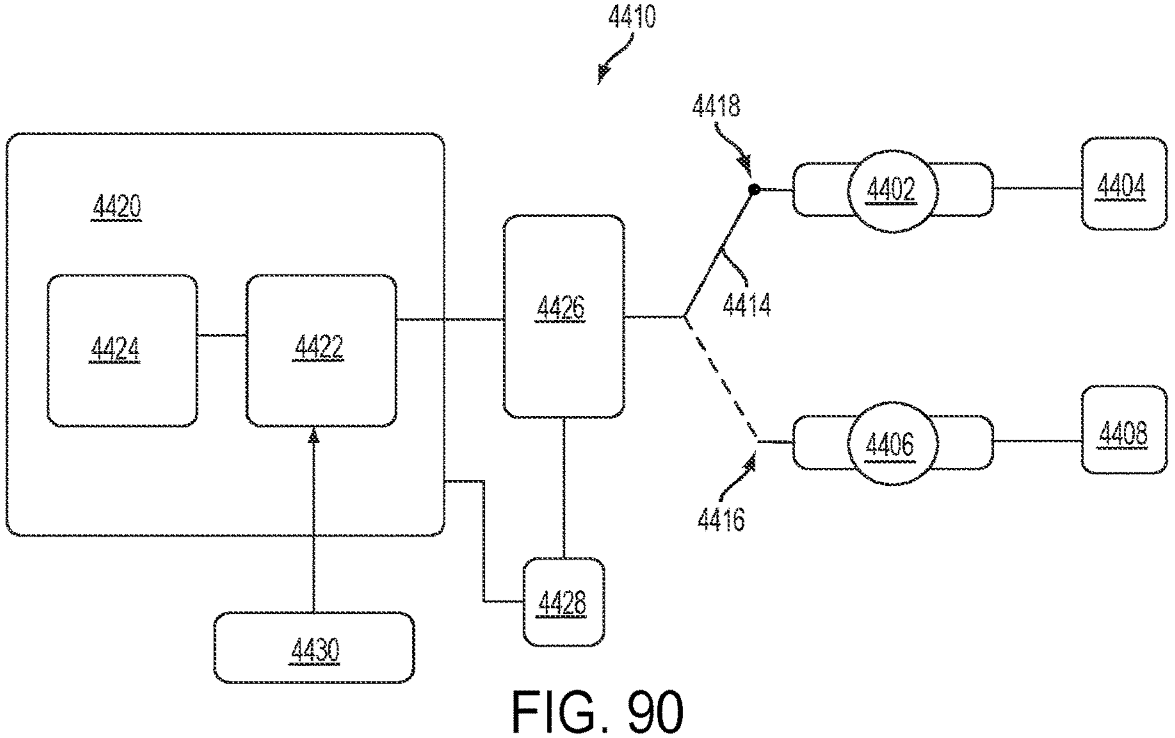

FIG. 89 illustrates a table showing predefined tissue thicknesses and corresponding predefined threshold forces in accordance with one or more aspects of the present disclosure.

FIG. 90 illustrates a logic diagram of a common controller for use with a plurality of motors of a surgical instrument in accordance with one or more aspects of the present disclosure.

Figure 91:
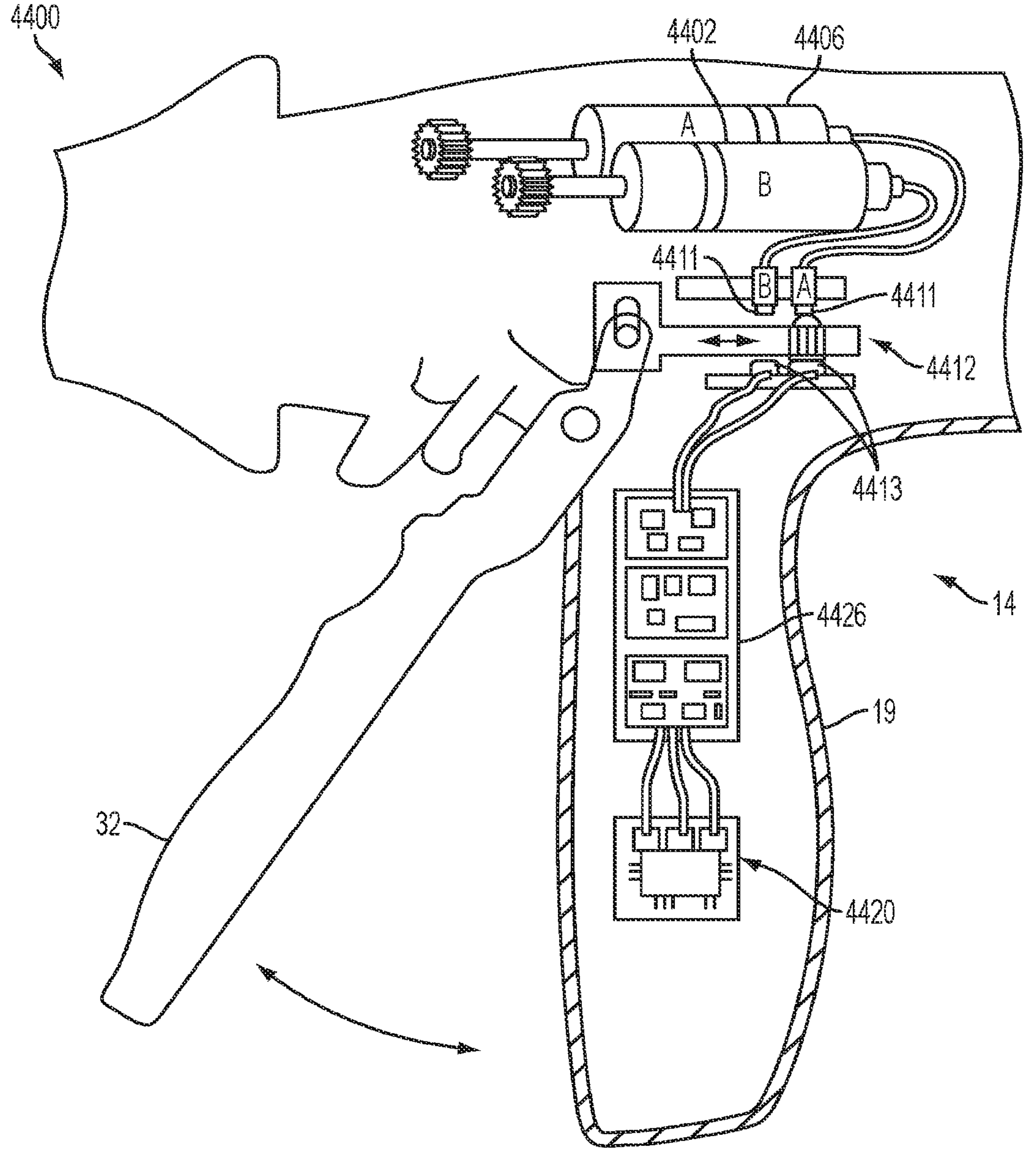

FIG. 91 illustrates a partial elevational view of the handle of the surgical instrument with a removed outer casing in accordance with one or more aspects of the present disclosure.

Figure 92:
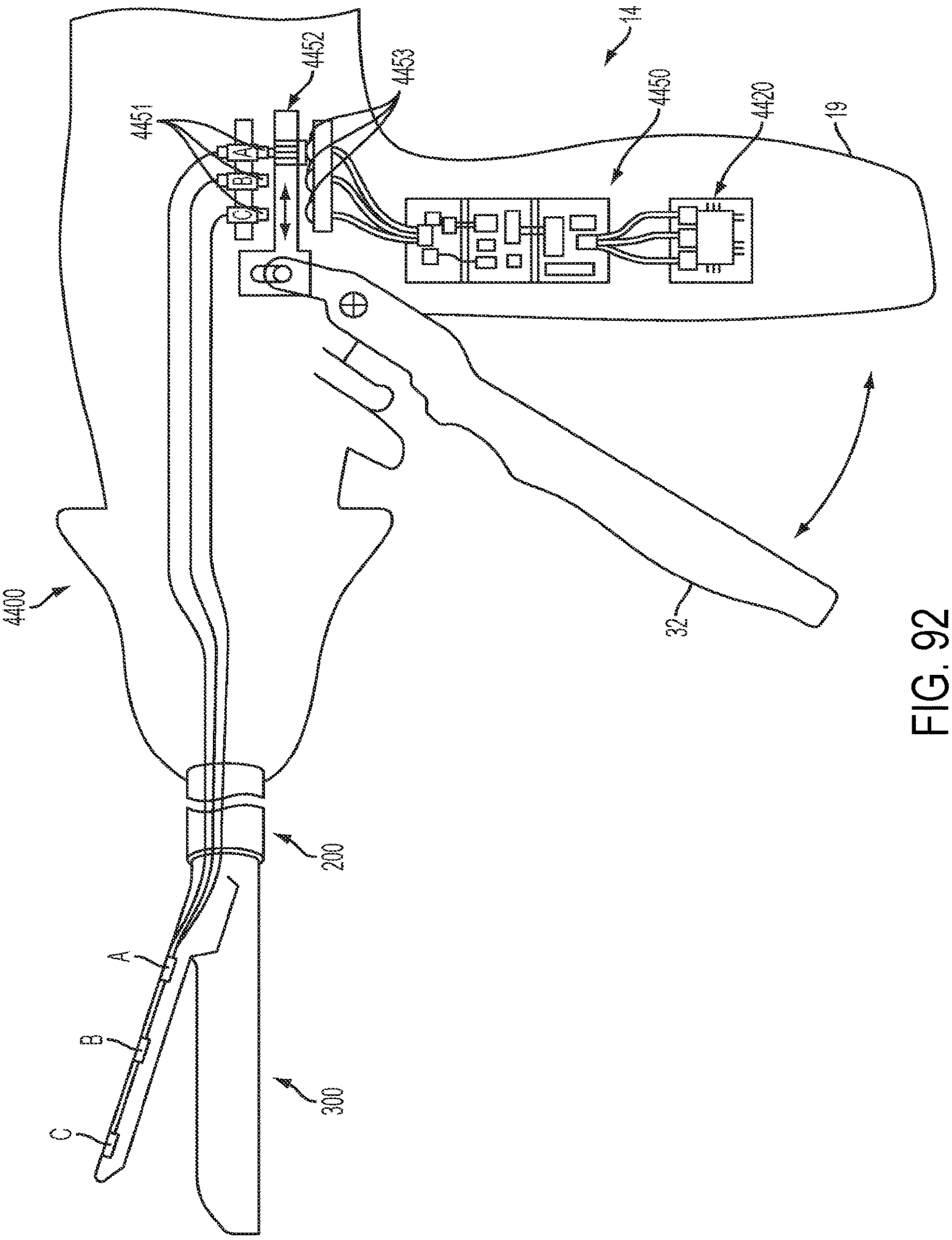

FIG. 92 illustrates a partial elevational view of the surgical instrument with a removed outer casing in accordance with one or more aspects of the present disclosure.

Figure 93A:
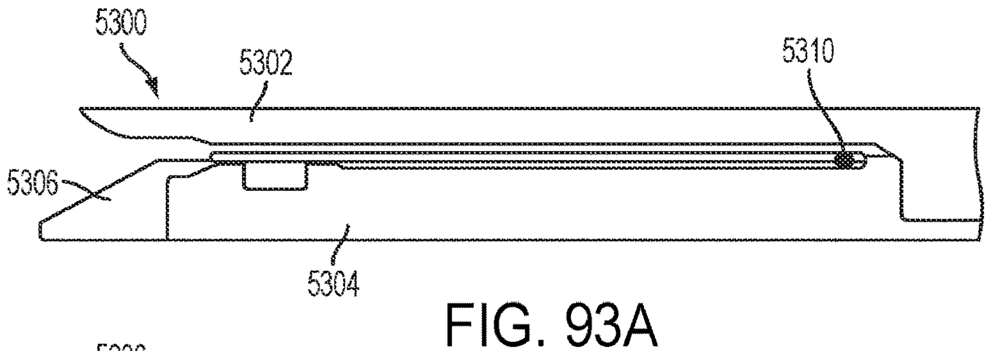

FIG. 93A illustrates a side angle view of an end effector with the anvil in a closed position, illustrating one located on either side of the cartridge deck in accordance with one or more aspects of the present disclosure.

Figure 93B:
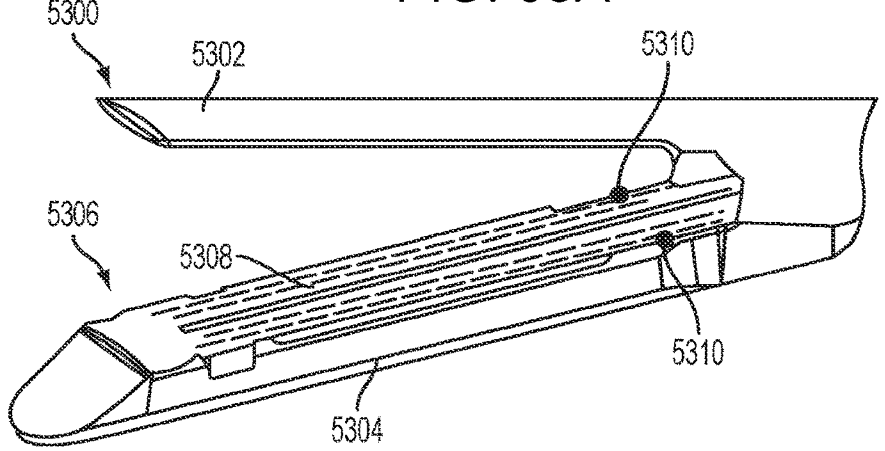

FIG. 93B illustrates a three-quarter angle view of the end effector with the anvil in an open position, and one LED located on either side of the cartridge deck in accordance with one or more aspects of the present disclosure.

Figure 94A:
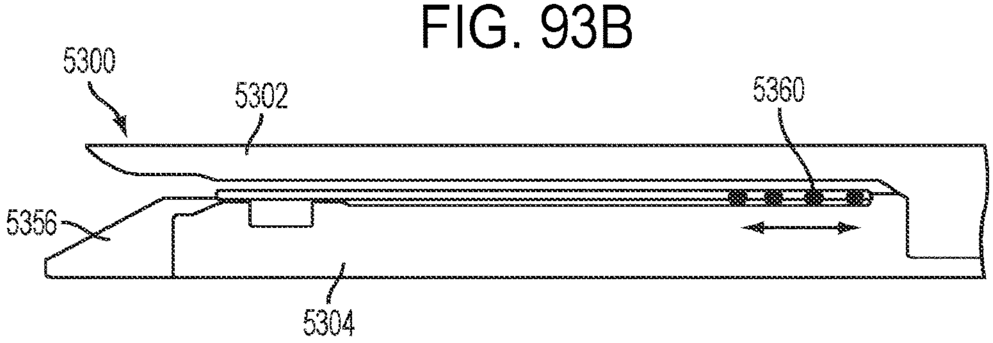

FIG. 94A illustrates a side angle view of an end effector with the anvil in a closed position and a plurality of LEDs located on either side of the cartridge deck in accordance with one or more aspects of the present disclosure.

Figure 94B:
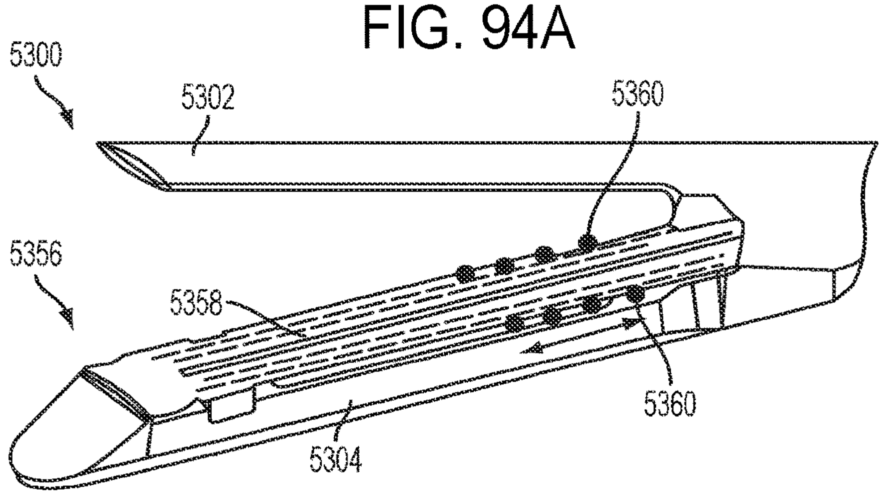

FIG. 94B illustrates a three-quarter angle view of the end effector with the anvil in an open position, and a plurality of LEDs located on either side of the cartridge deck in accordance with one or more aspects of the present disclosure.

Figure 95A:
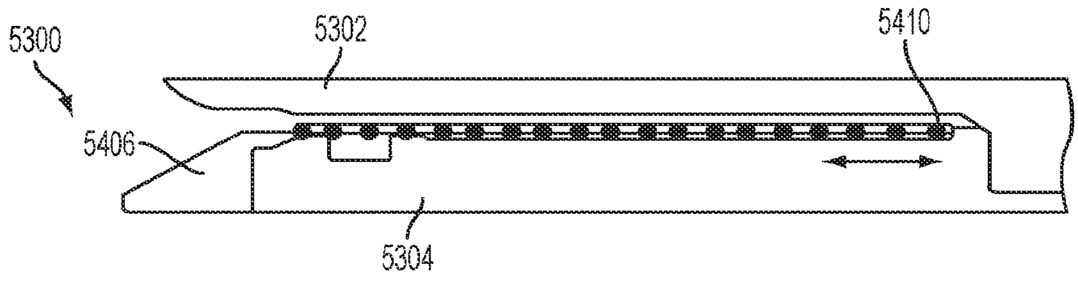

FIG. 95A illustrates a side angle view of an end effector with the anvil in a closed position, and a plurality of LEDs from the proximal to the distal end of the staple cartridge, on either side of the cartridge deck in accordance with one or more aspects of the present disclosure.

Figure 95B:
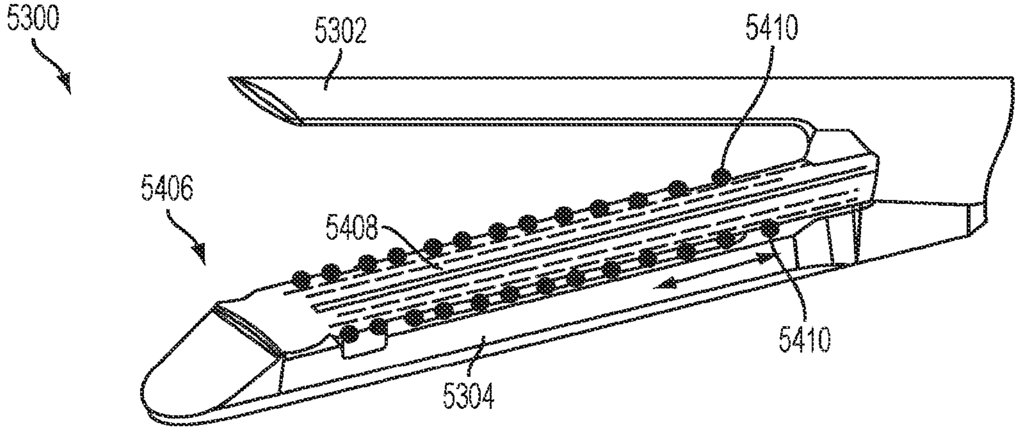

FIG. 95B illustrates a three-quarter angle view of the end effector with the anvil in an open position, illustrating a plurality of LEDs from the proximal to the distal end of the staple cartridge, and on either side of the cartridge deck in accordance with one or more aspects of the present disclosure.

Figure 96:
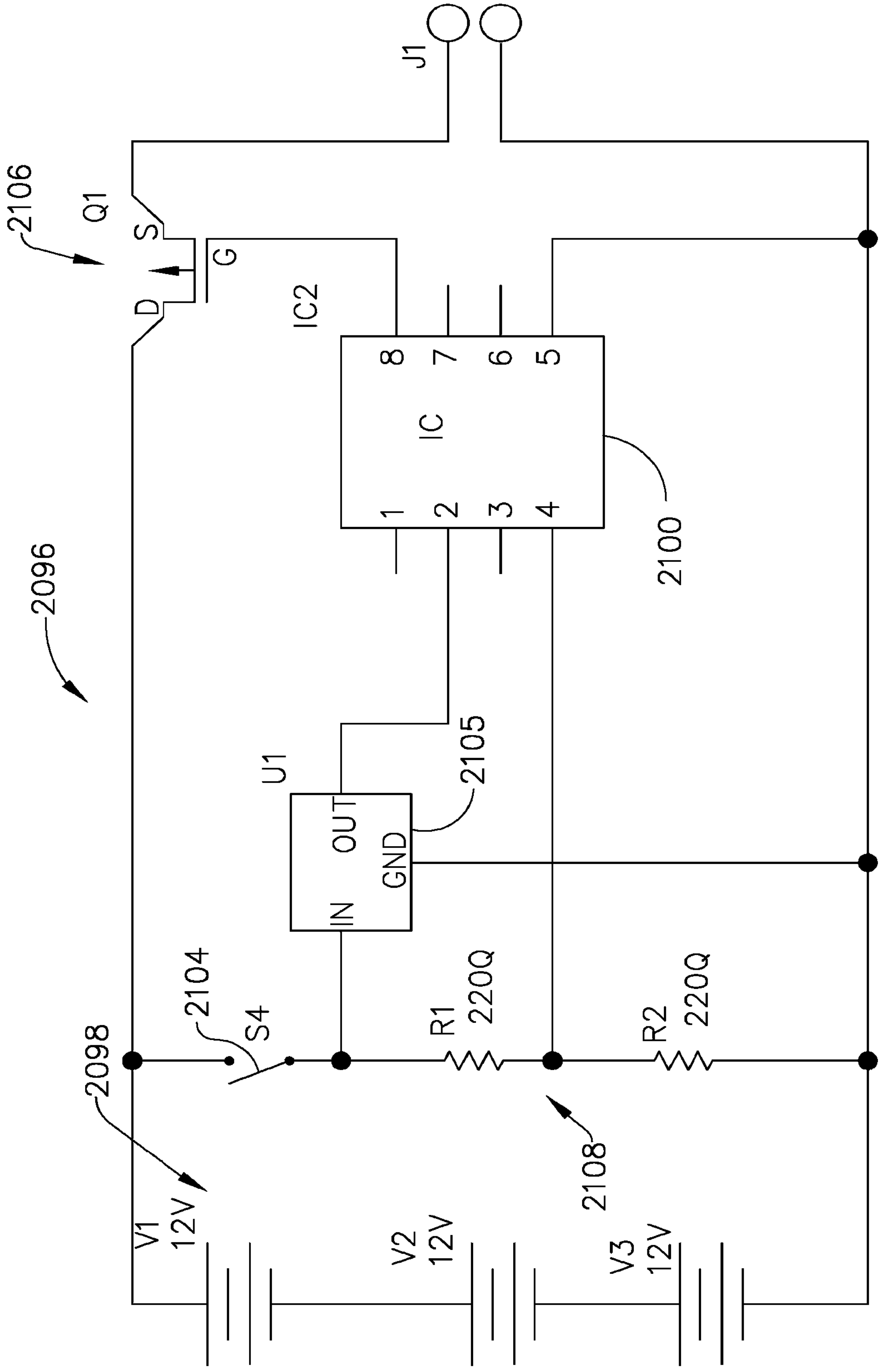

FIG. 96 is a circuit diagram of an example power assembly of a surgical instrument in accordance with one or more aspects of the present disclosure.

Figure 97:
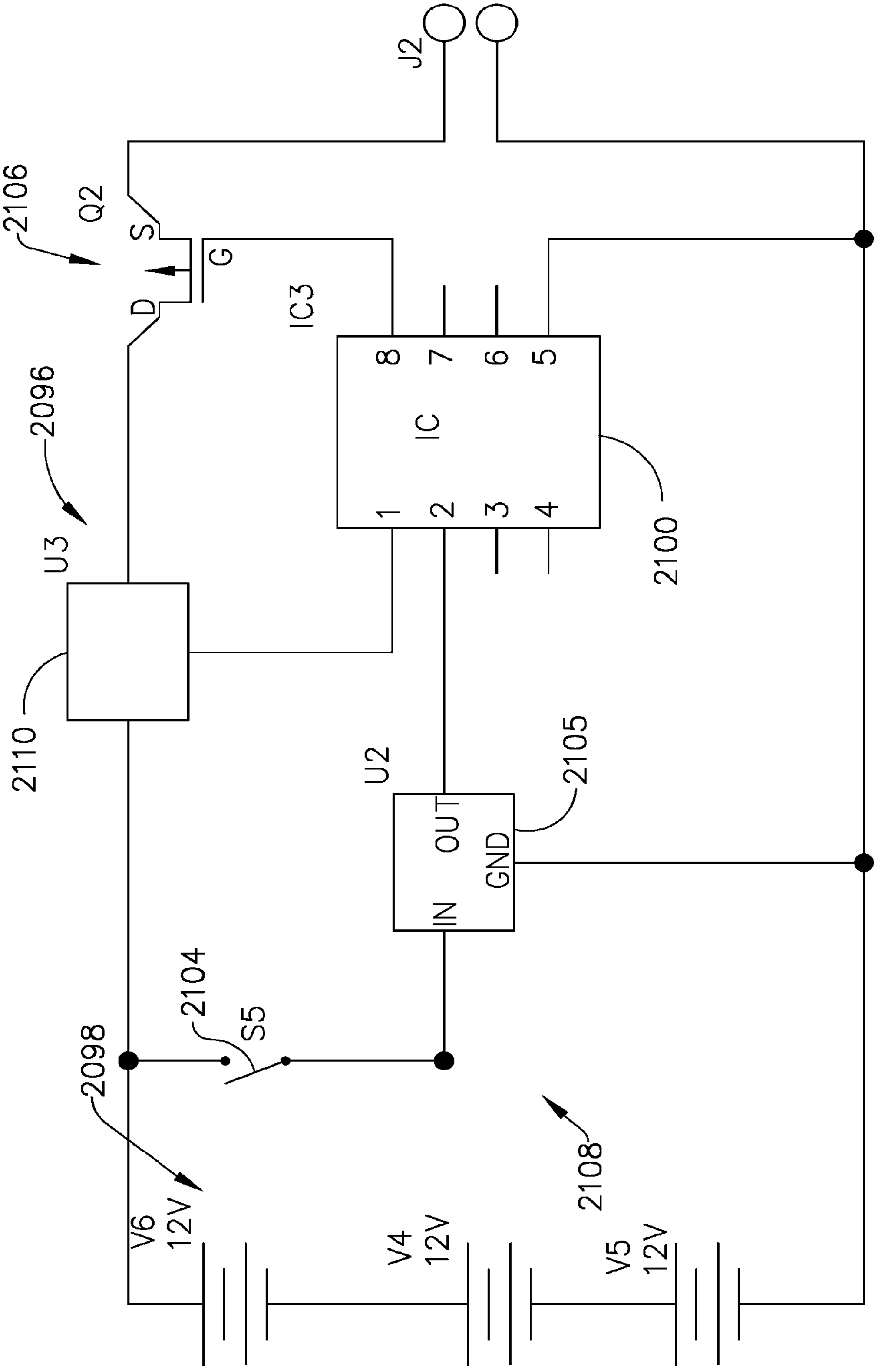

FIG. 97 is a circuit diagram of an example power assembly of a surgical instrument in accordance with one or more aspects of the present disclosure.

Figure 98:
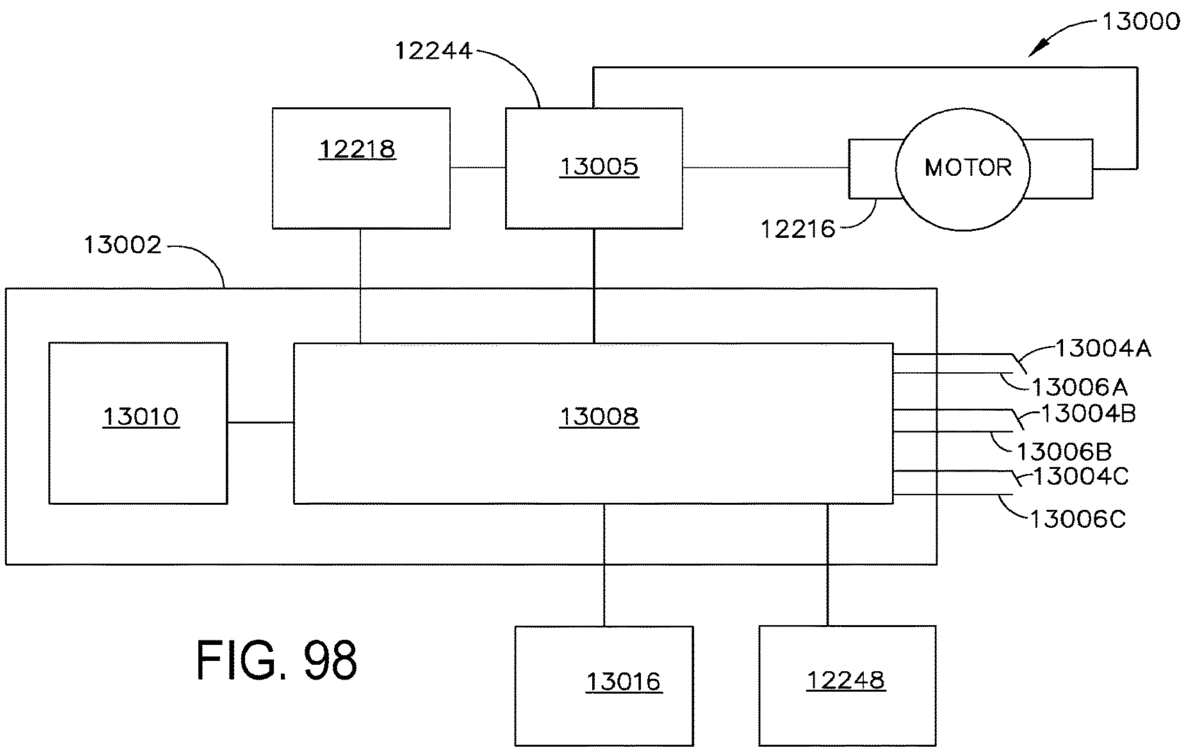

FIG. 98 is a schematic block diagram of a control system of a surgical instrument in accordance with one or more aspects of the present disclosure.

Figure 99:
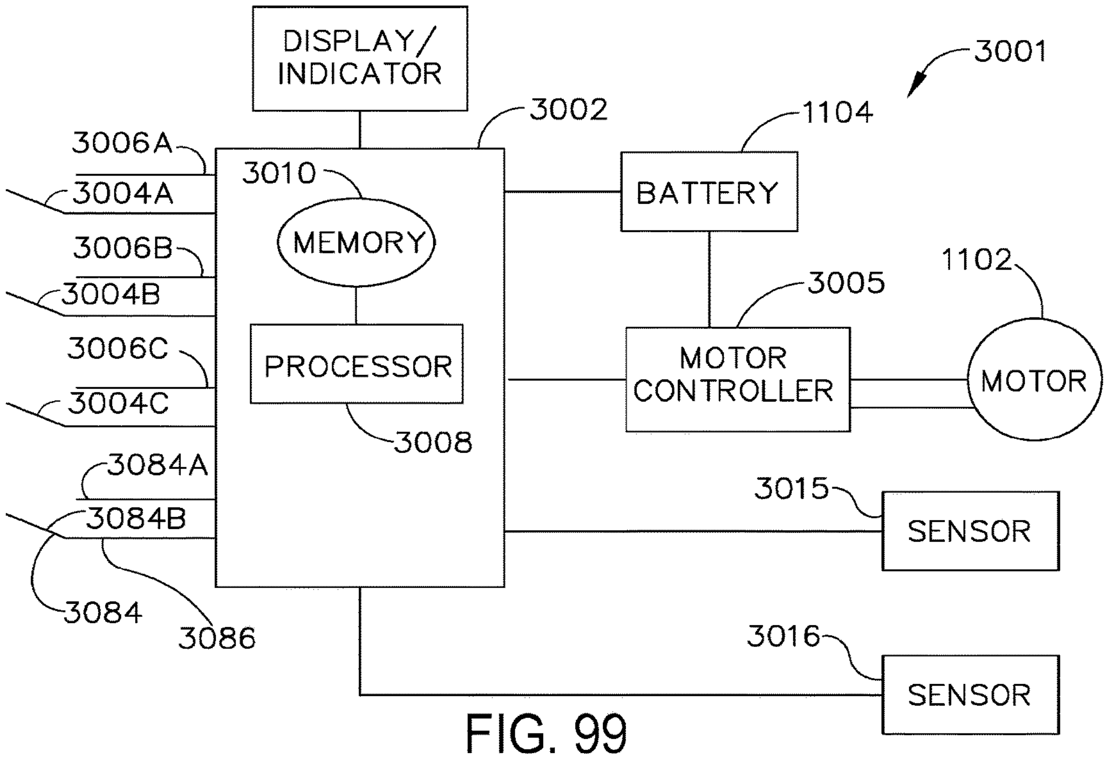

FIG. 99 is a schematic block diagram of a control system of a surgical instrument in accordance with one or more aspects of the present disclosure.

Figure 100:
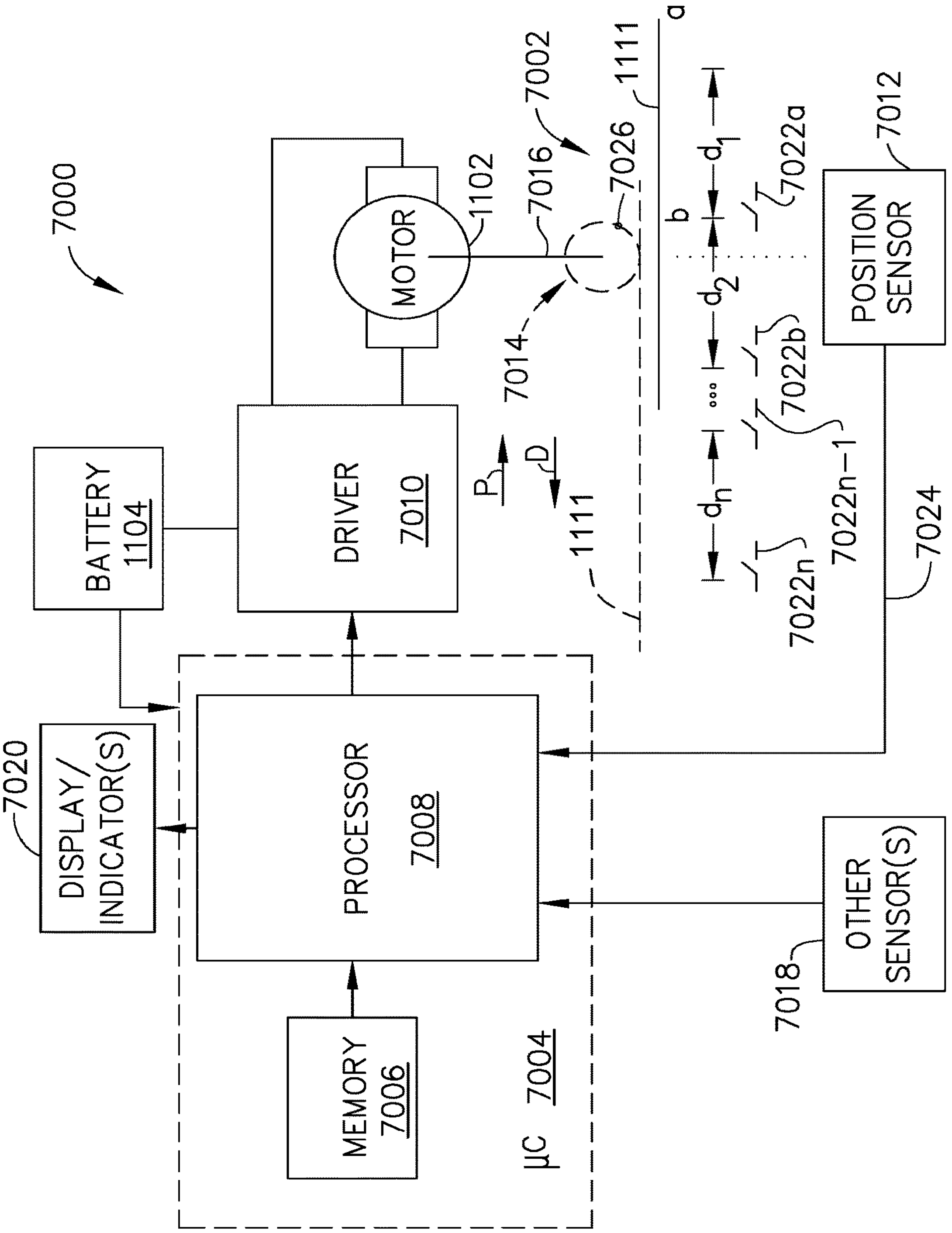

FIG. 100 is a schematic diagram of an absolute positioning system comprising a controlled motor drive circuit arrangement comprising a sensor arrangement in accordance with one or more aspects of the present disclosure.

Figure 101:
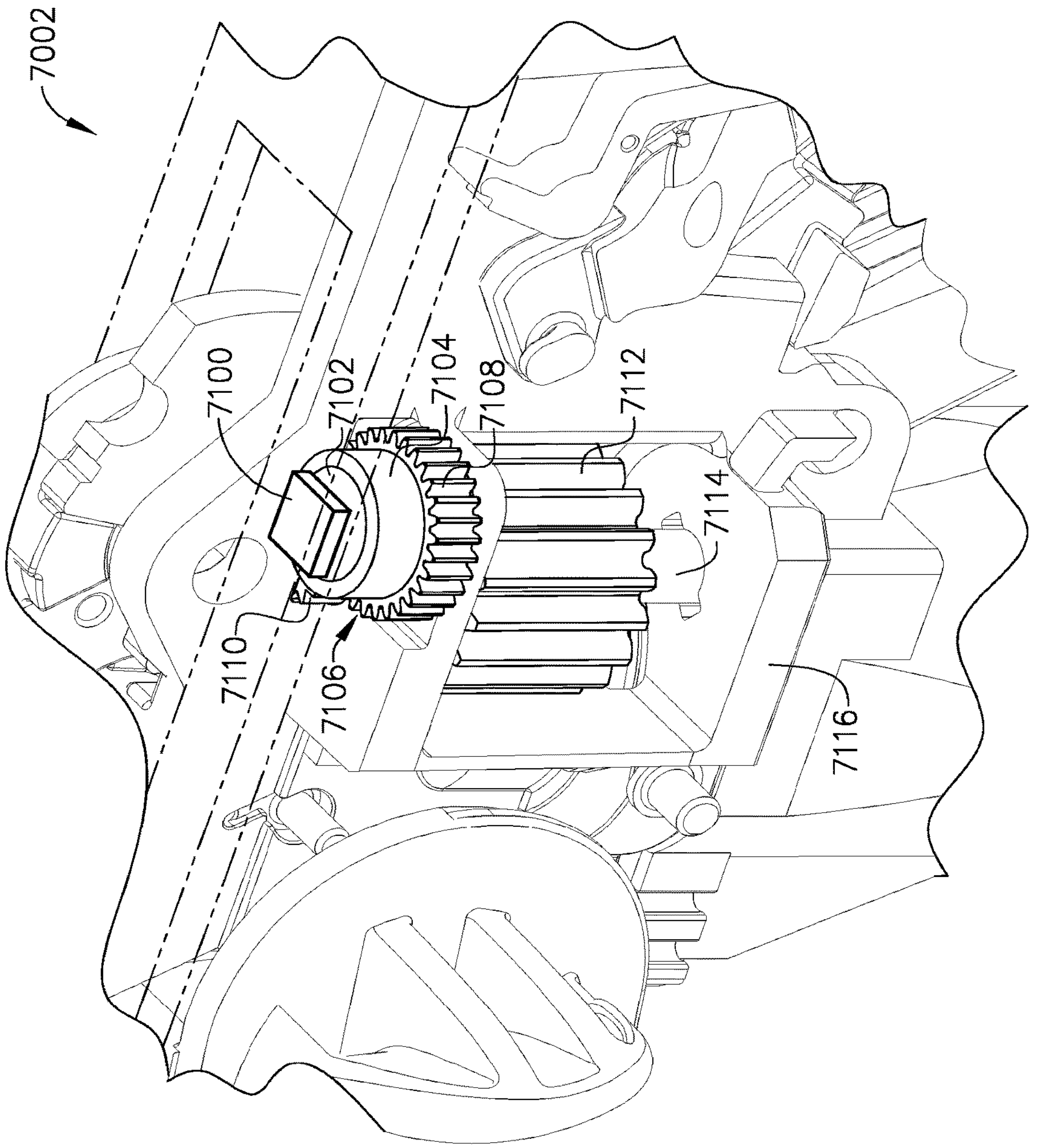

FIG. 101 is a detail perspective view of a sensor arrangement for an absolute positioning system in accordance with one or more aspects of the present disclosure.

Figure 102:
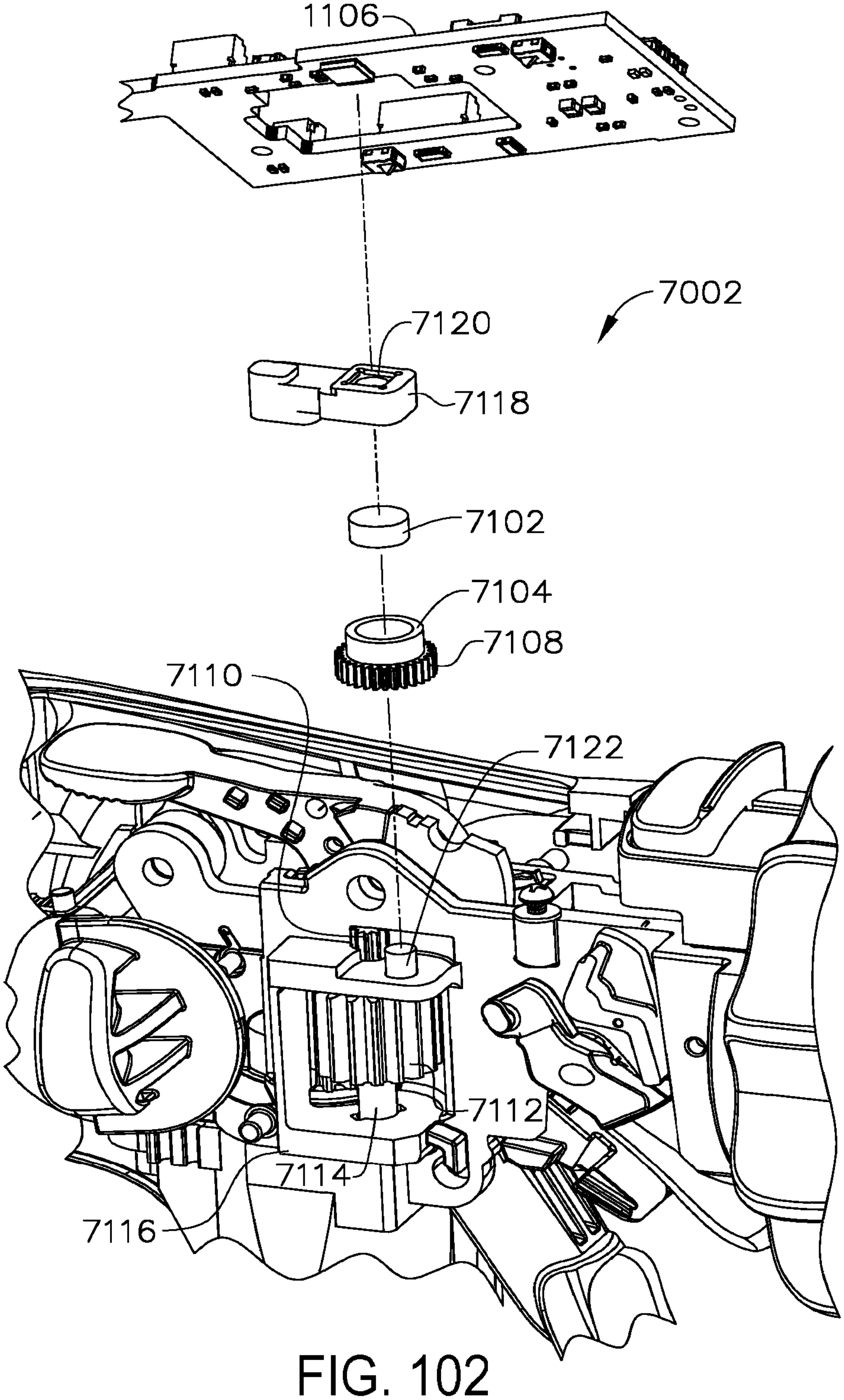

FIG. 102 is an exploded perspective view of the sensor arrangement for an absolute positioning system showing a control circuit board assembly and the relative alignment of the elements of the sensor arrangement in accordance with one or more aspects of the present disclosure.

Figure 103:
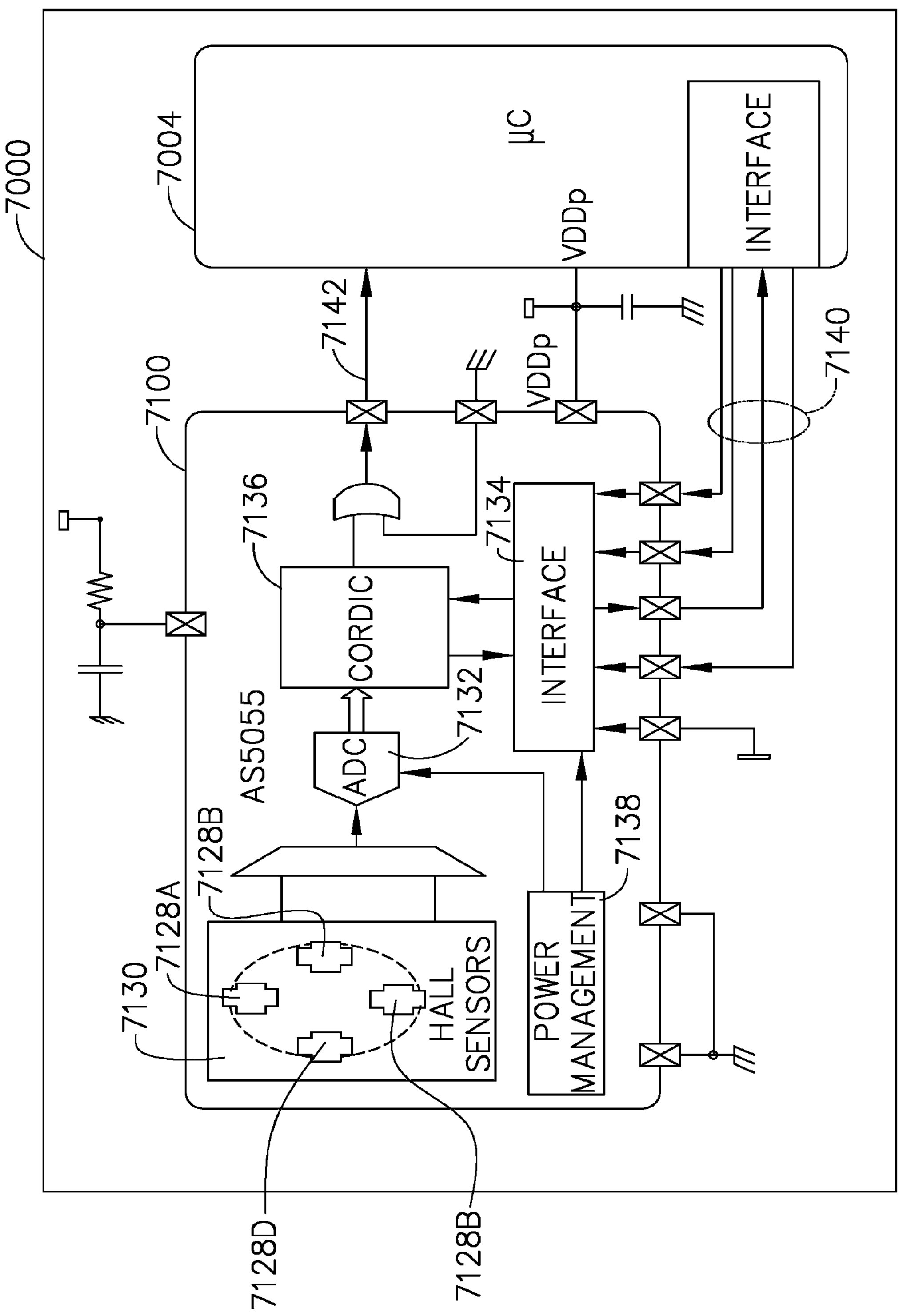

FIG. 103 is a schematic diagram of one aspect of a position sensor for an absolute positioning system comprising a magnetic rotary absolute positioning system in accordance with one or more aspects of the present disclosure.

Figure 104:
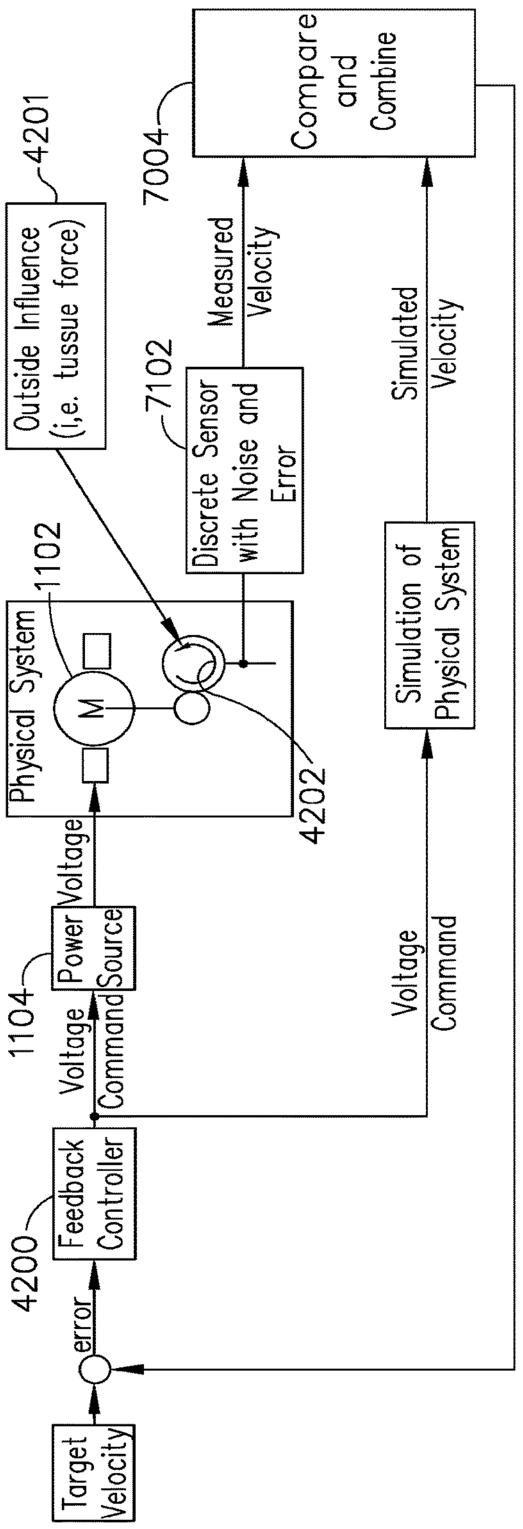

FIG. 104 is a schematic illustrating a system for controlling the speed of a motor and/or the speed of a drivable member of a surgical instrument in accordance with one or more aspects of the present disclosure.

Figure 105:
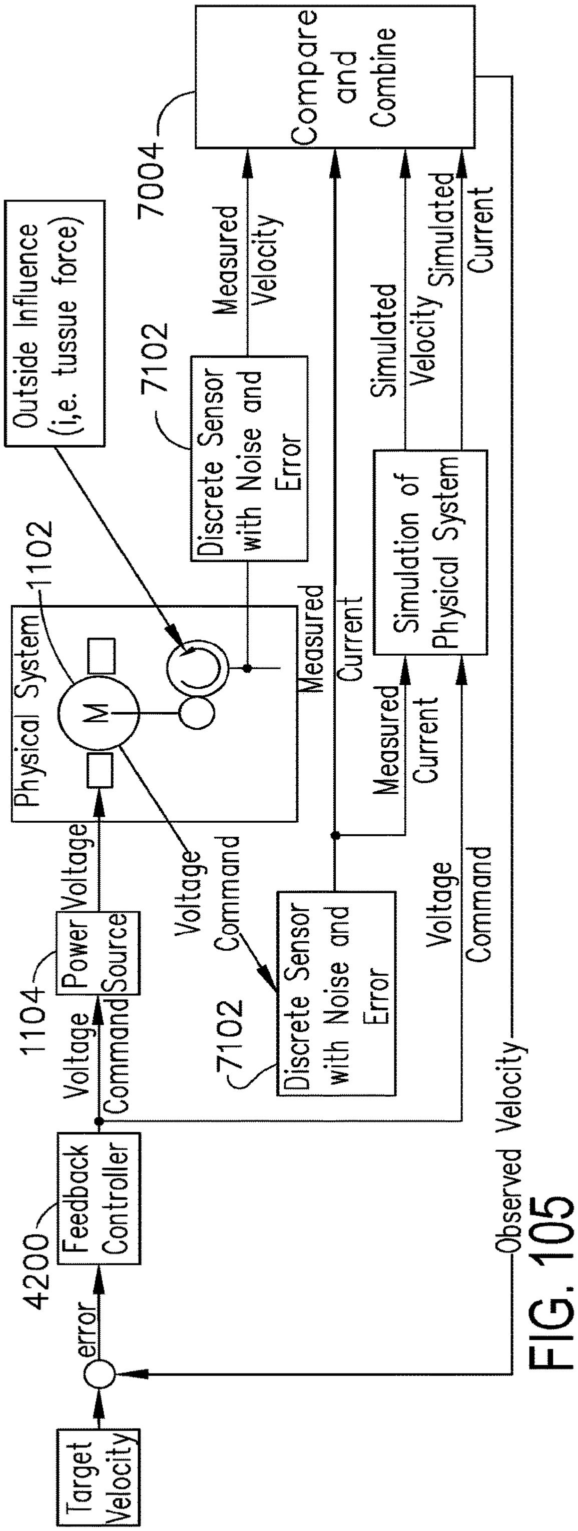

FIG. 105 is a schematic illustrating another system for controlling the speed of a motor and/or the speed of a drivable member of a surgical instrument in accordance with one or more aspects of the present disclosure.

Figure 106:
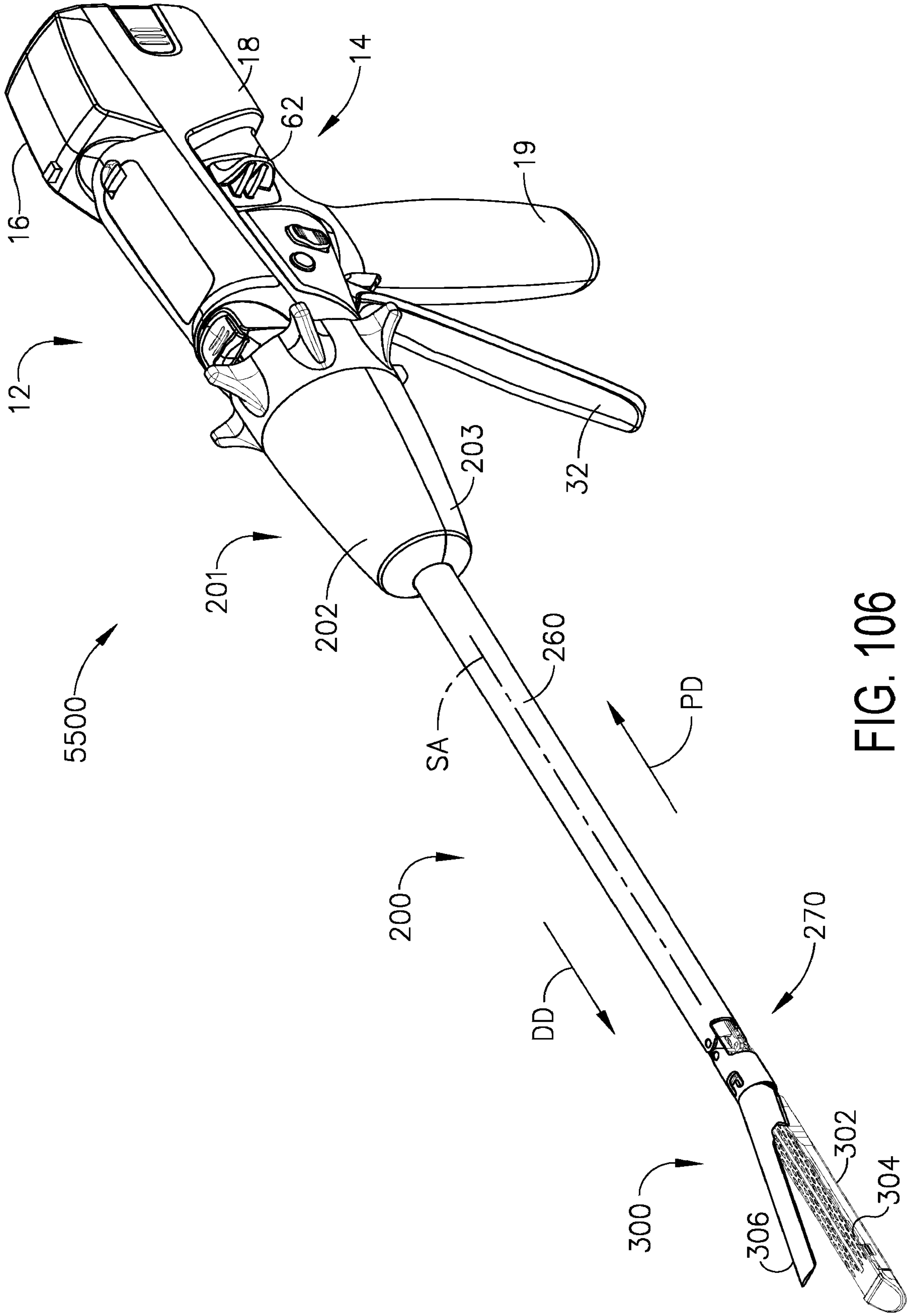

FIG. 106 illustrates a perspective view of a surgical instrument according to various aspects in accordance with one or more aspects of the present disclosure.

Figure 107:
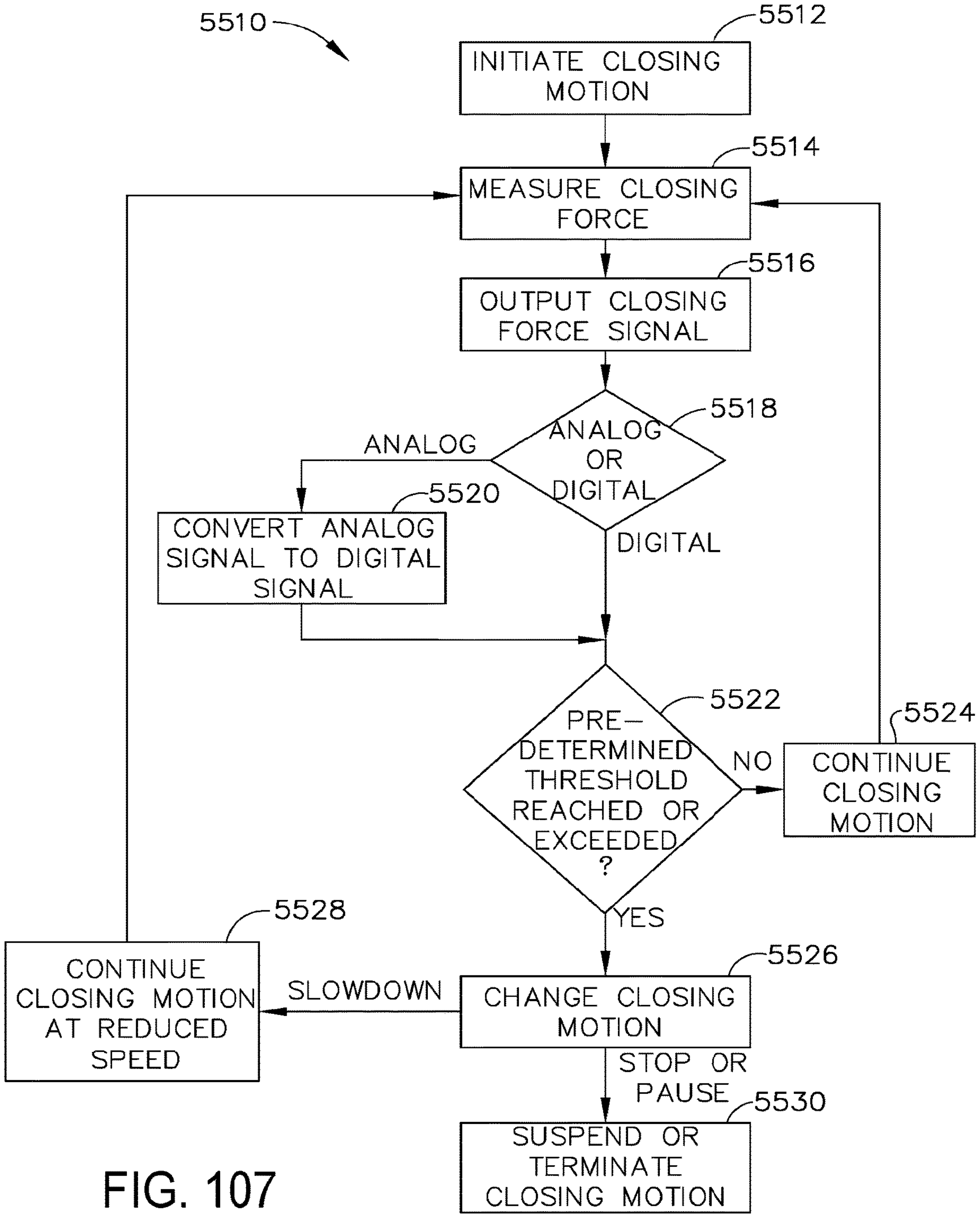

FIG. 107 illustrates a method of controlling a closing motion of the surgical instrument of FIG. 106 according to various aspects in accordance with one or more aspects of the present disclosure.

Figure 108:
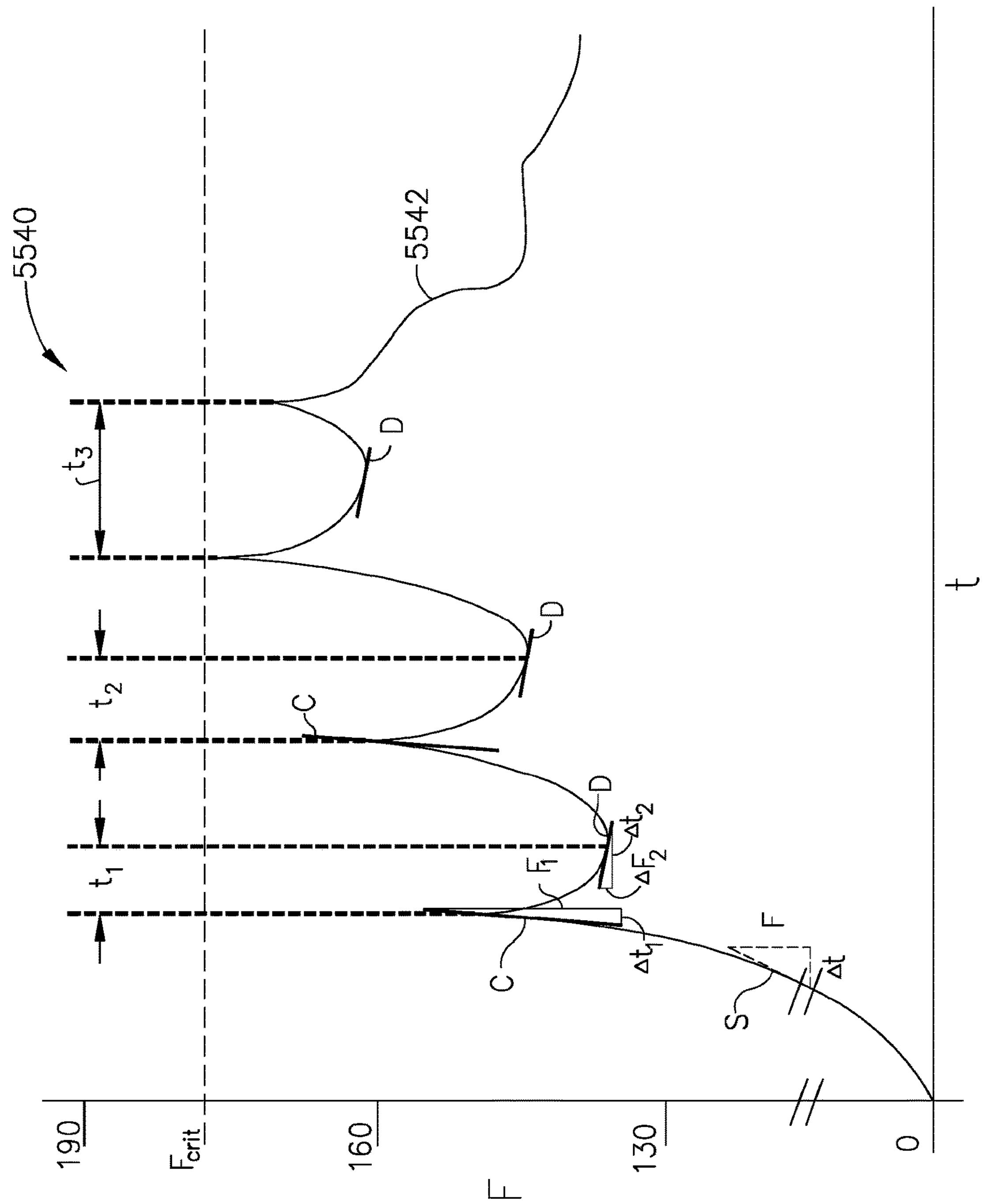

FIG. 108 illustrates an example graph showing a curve representative of a closing force signal over time for various aspects of the surgical instrument of FIG. 106 in accordance with one or more aspects of the present disclosure.

Figure 109:
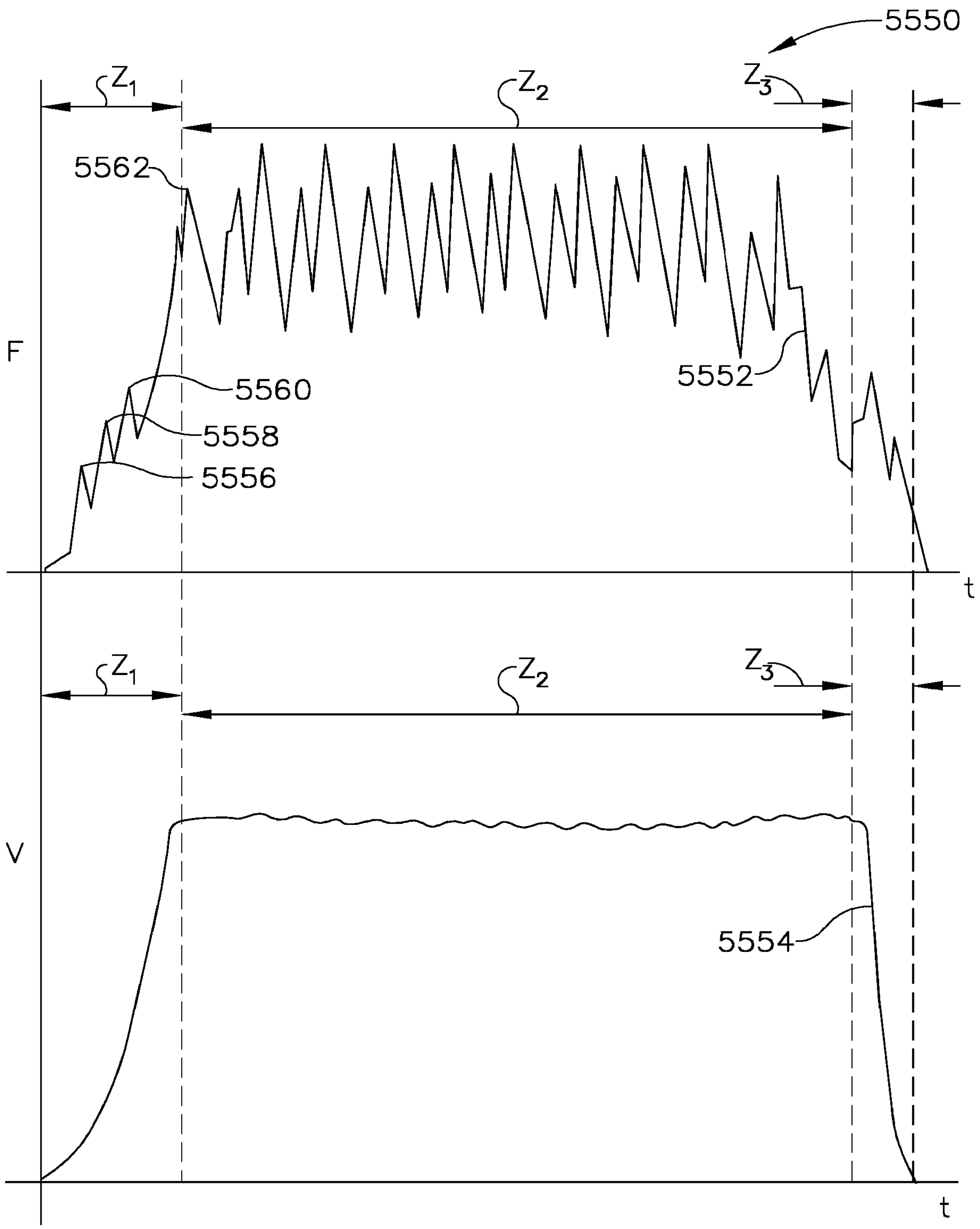

FIG. 109 illustrates an example graph showing a curve representative of a firing force signal over time and a curve representative of a knife velocity over time for various aspects of the surgical instrument of FIG. 106 in accordance with one or more aspects of the present disclosure.

Figure 110:
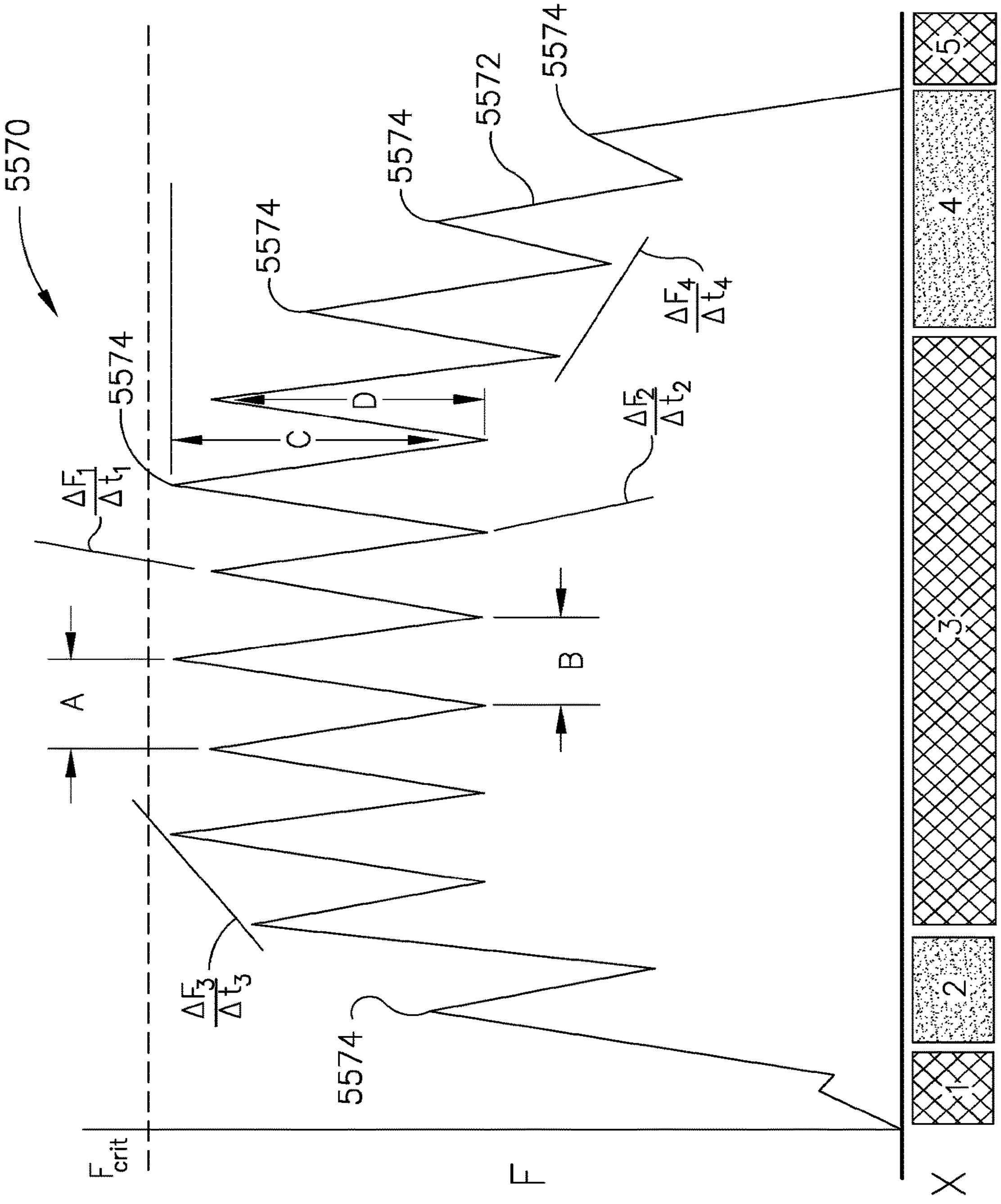

FIG. 110 illustrates an example graph showing a curve representative of a firing force signal and a knife position over time for various aspects of the surgical instrument of FIG. 106 in accordance with one or more aspects of the present disclosure.

Figure 111:
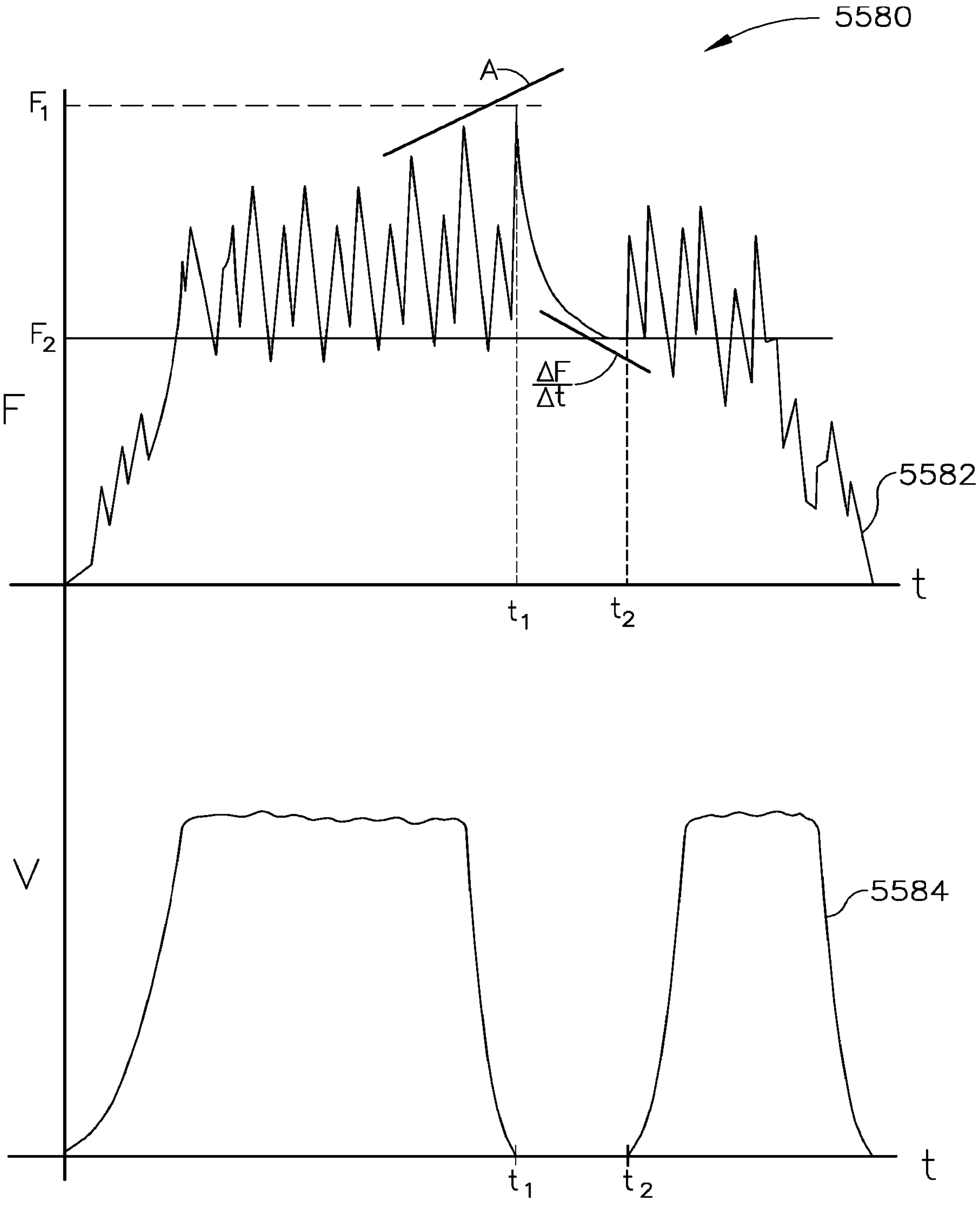

FIG. 111 illustrates an example graph showing a curve representative of a firing force signal and a curve representative of a knife velocity over time for various aspects of the surgical instrument of FIG. 106 in accordance with one or more aspects of the present disclosure.

Figure 112:
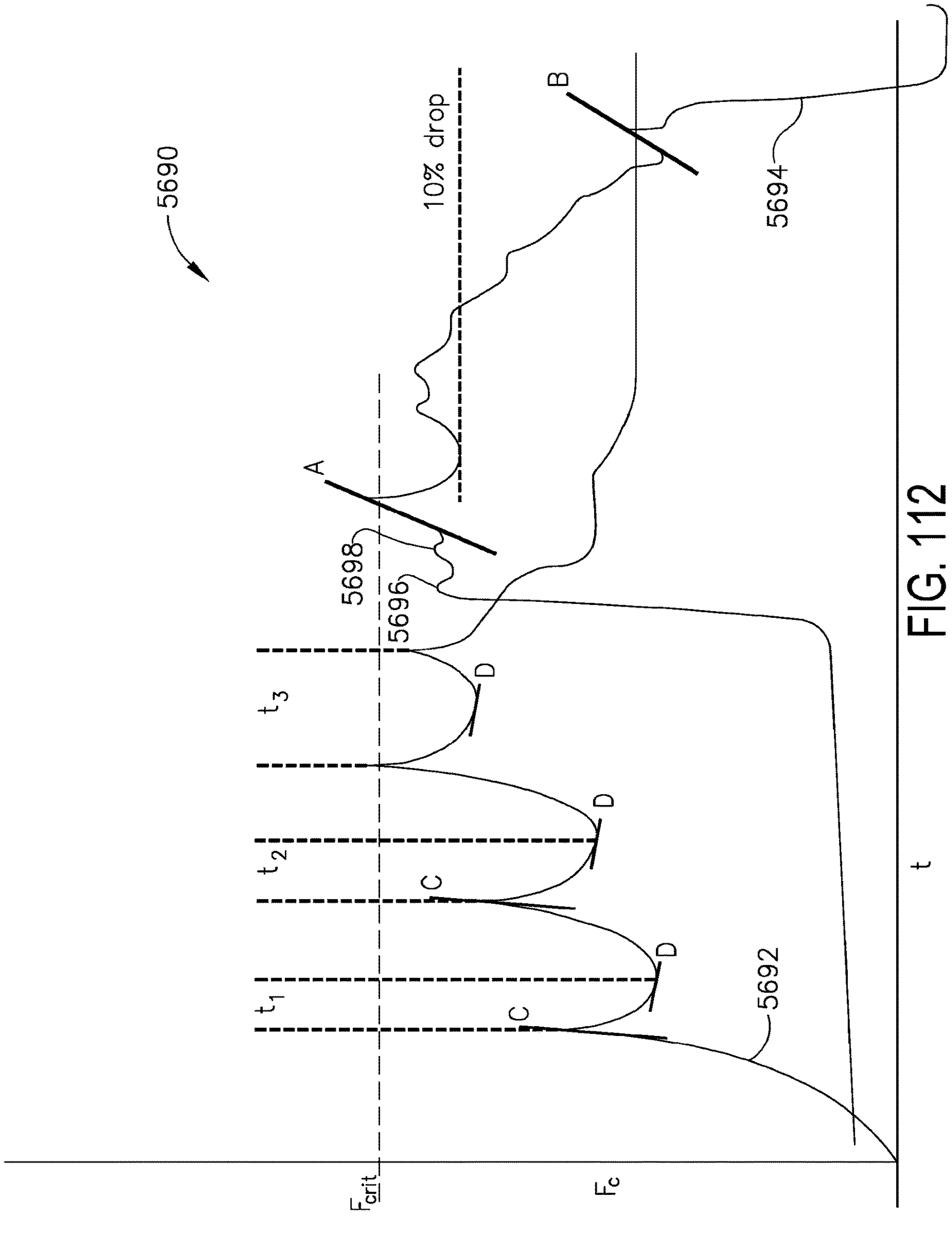

FIG. 112 illustrates an example graph showing a curve representative of a closing force FC over time t for various aspects of the surgical instrument of FIG. 106 and a curve representative of a firing force FF over time t of the surgical instrument of FIG. 106 in accordance with one or more aspects of the present disclosure.

Figure 113:
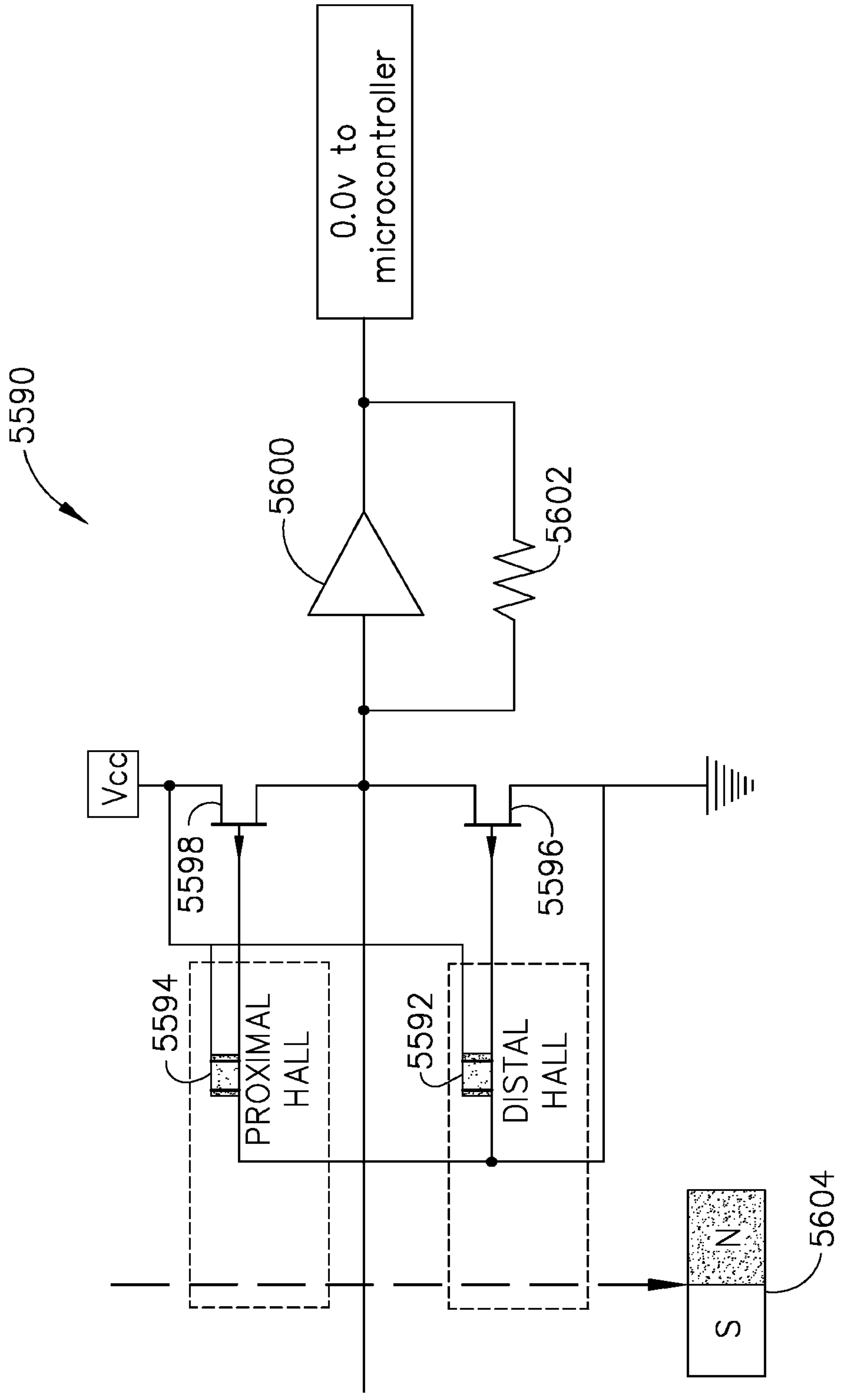

FIG. 113 illustrates various aspects of a direction sensor of the surgical instrument of FIG. 106 in accordance with one or more aspects of the present disclosure.

FIG. 114 illustrates various aspects of a direction sensor of the surgical instrument of FIG. 106 in accordance with one or more aspects of the present disclosure.

FIG. 115 illustrates a perspective view of another surgical instrument in accordance with one or more aspects of the present disclosure.

Figure 116:
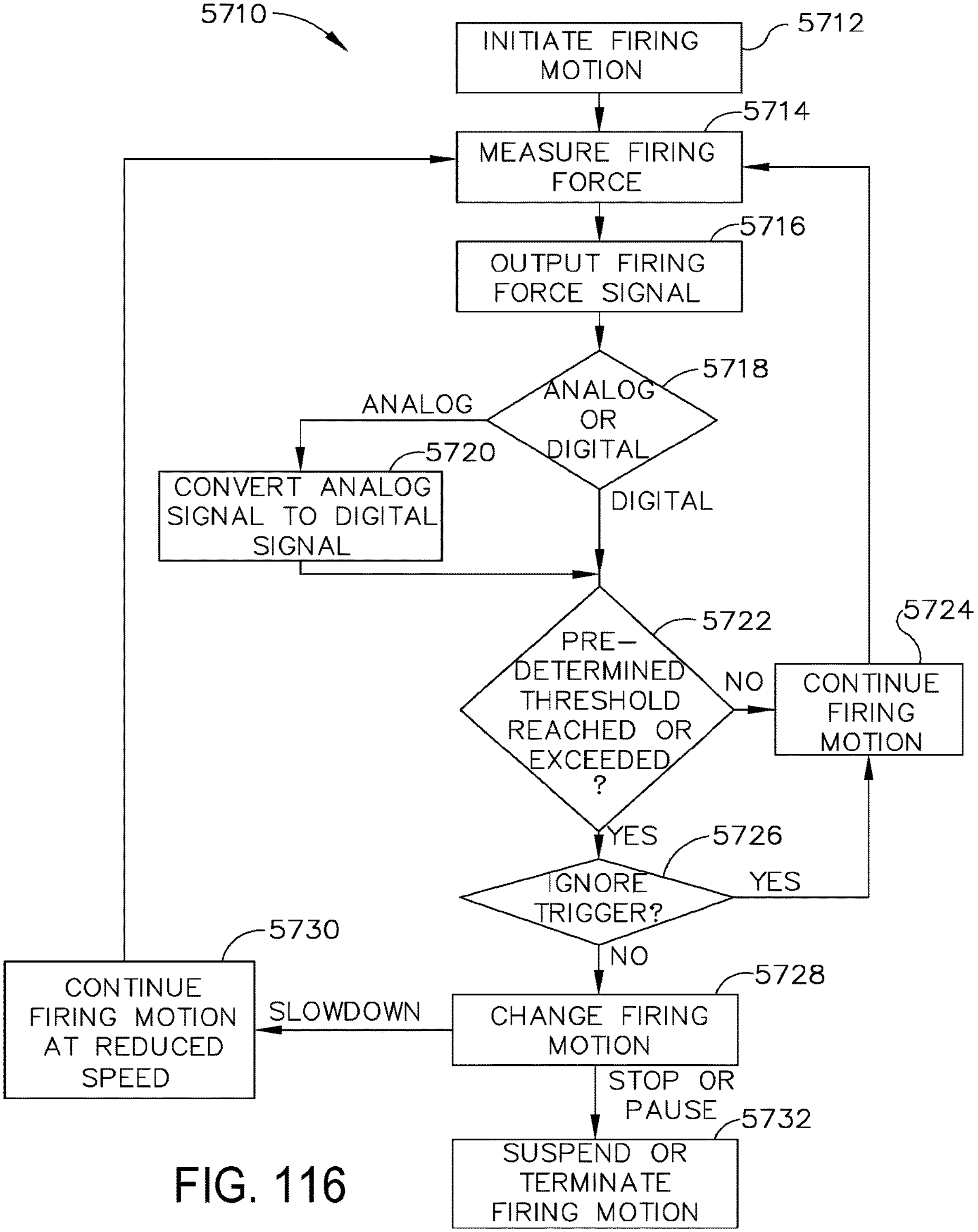

FIG. 116 illustrates a method of controlling a firing motion of the surgical instrument of FIG. 115 in accordance with one or more aspects of the present disclosure.

Figure 117:
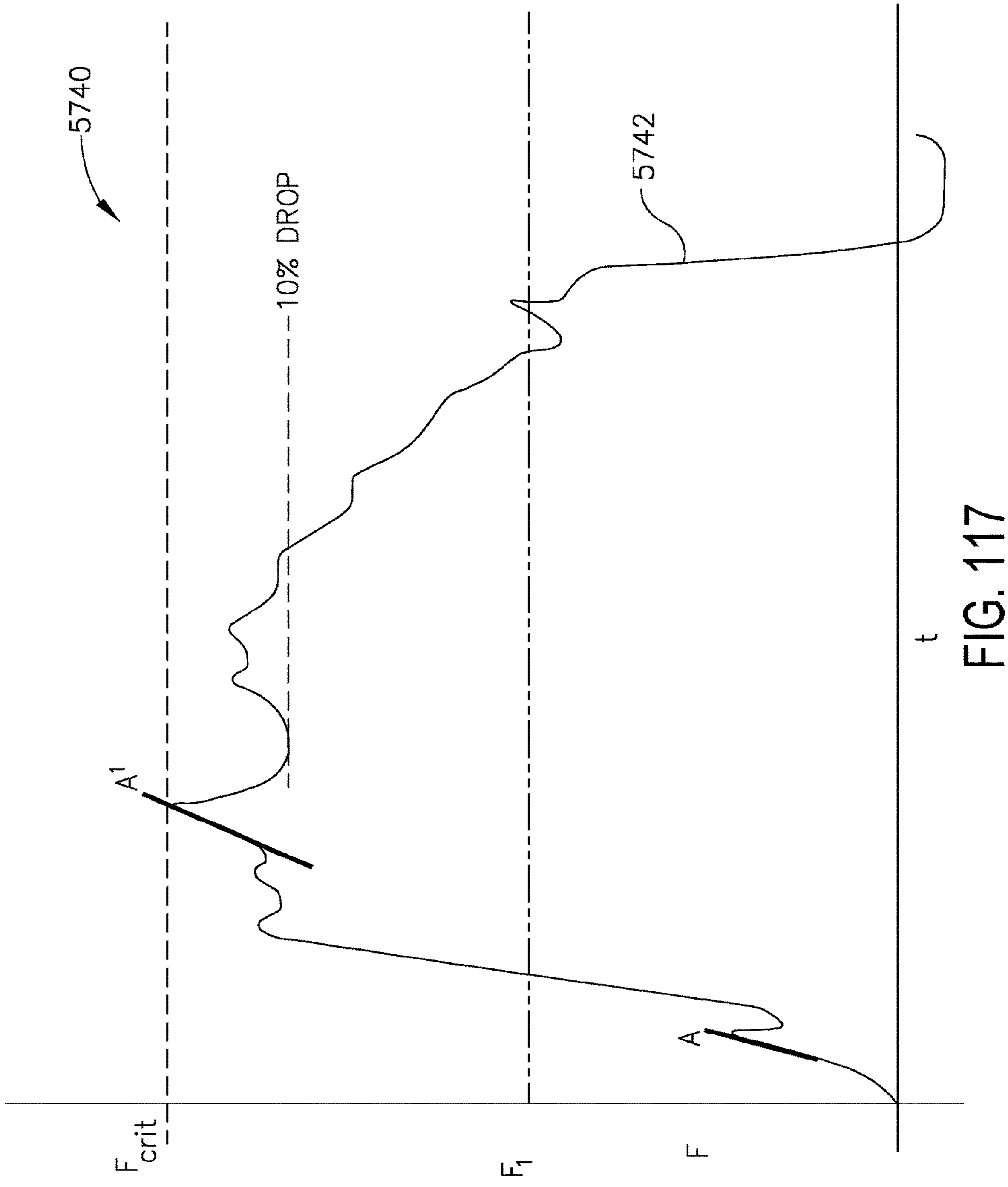

FIG. 117 illustrates an example graph showing a curve representative of a firing force signal over time for the surgical instrument of FIG. 115 in accordance with one or more aspects of the present disclosure.

Figure 118:
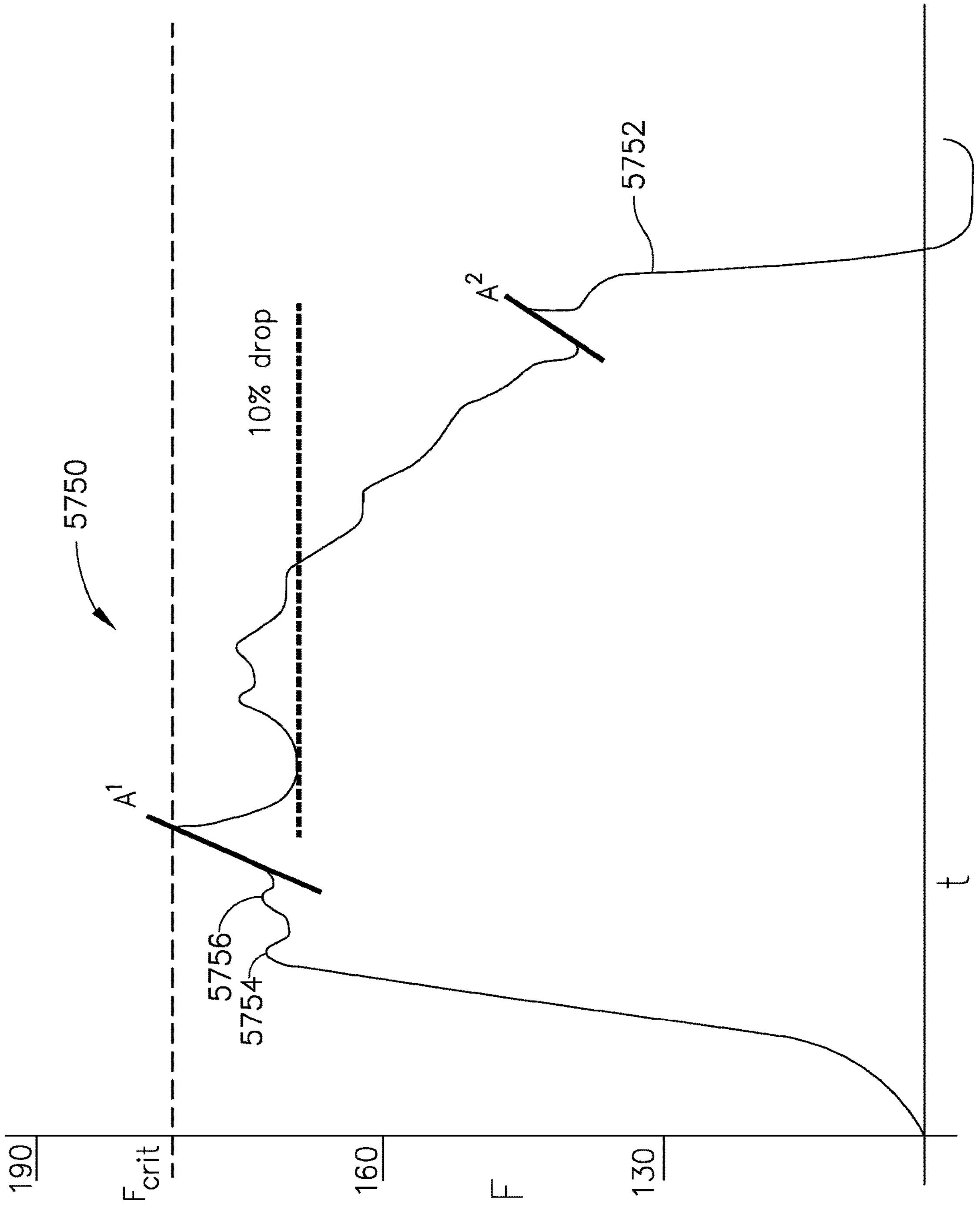

FIG. 118 illustrates another example graph showing a curve representative of a firing force signal over time for the surgical instrument of FIG. 115 in accordance with one or more aspects of the present disclosure.

Figure 119:
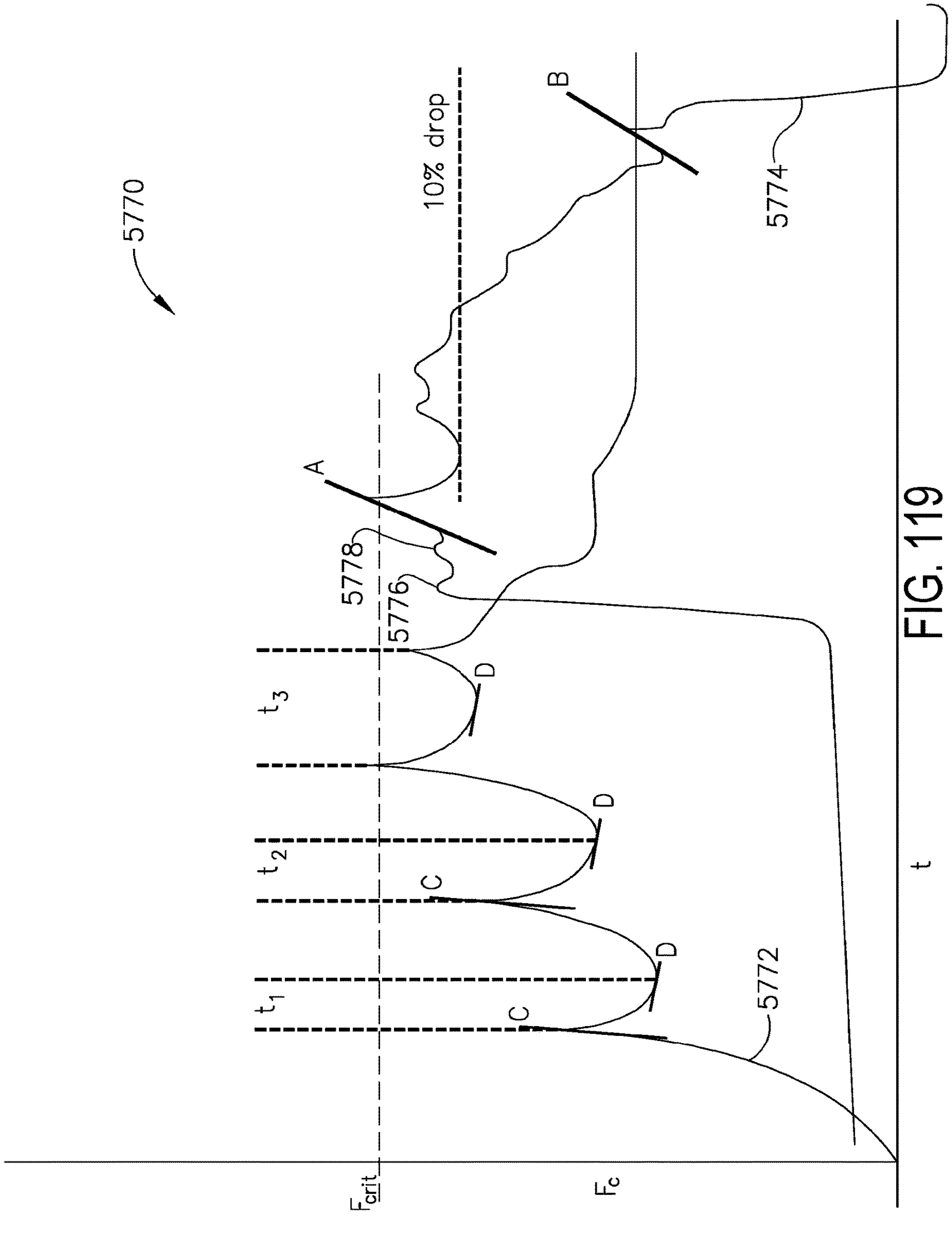

FIG. 119 illustrates an example graph showing a curve representative of a closing force FC over time t for various aspects of the surgical instrument and a curve representative of a firing force FF over time t for the surgical instrument of FIG. 115 in accordance with one or more aspects of the present disclosure.

Figure 120:
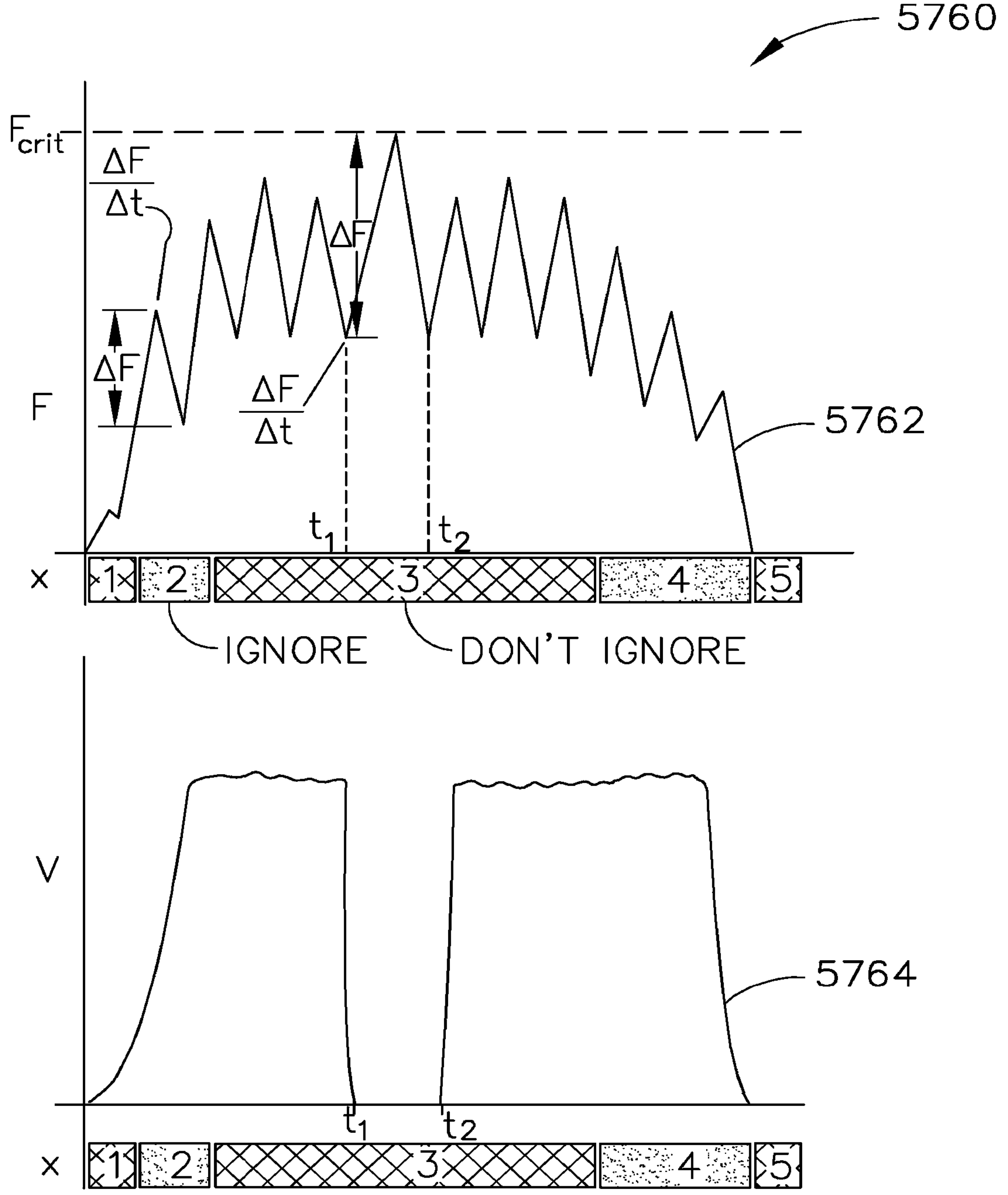

FIG. 120 illustrates an example graph showing a curve representative of a firing force signal and a knife position over time and a curve representative of a knife velocity over time for the surgical instrument of FIG. 115 in accordance with one or more aspects of the present disclosure.

Figure 121:
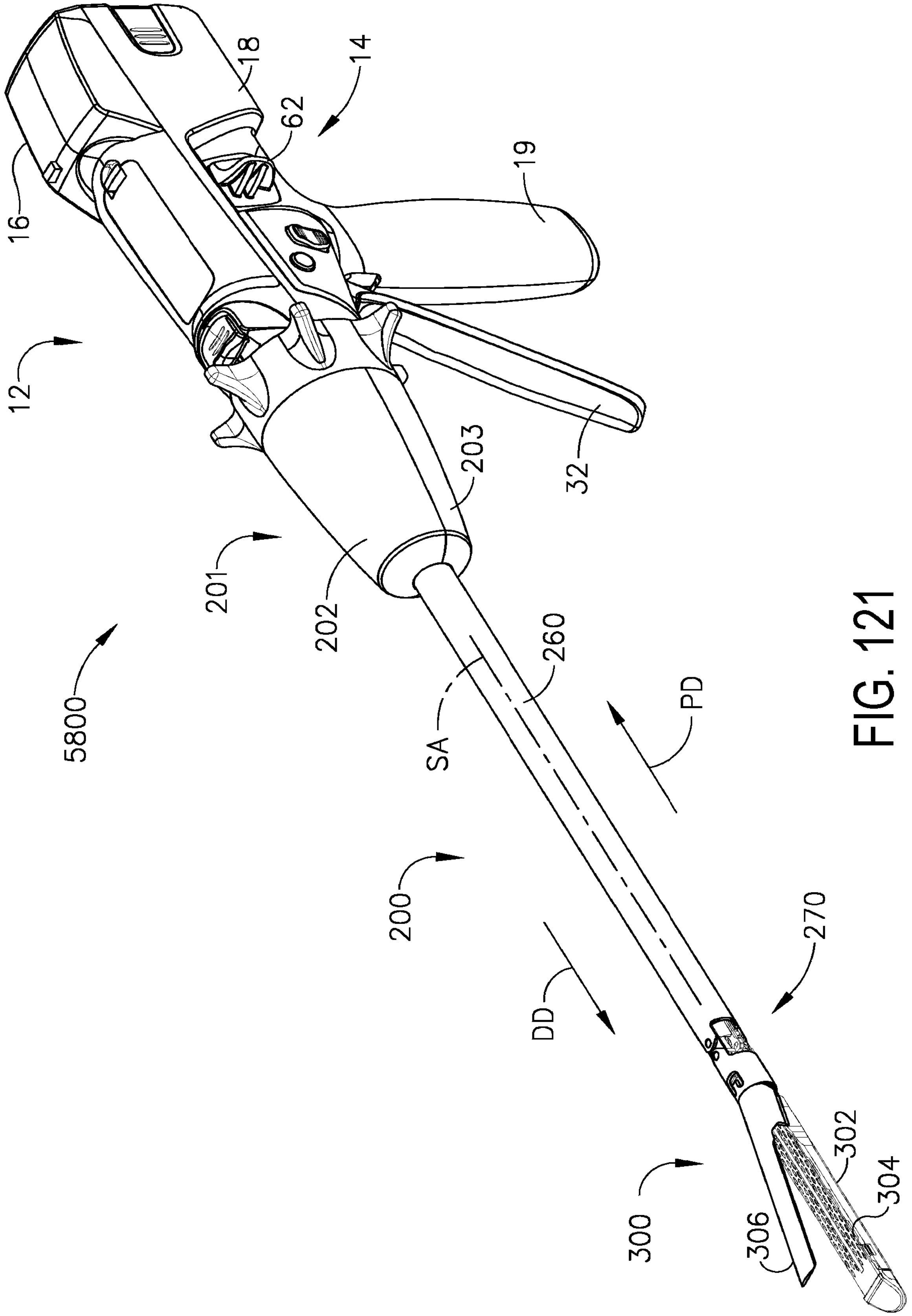

FIG. 121 illustrates a perspective view of another surgical instrument in accordance with one or more aspects of the present disclosure.

Figure 122:
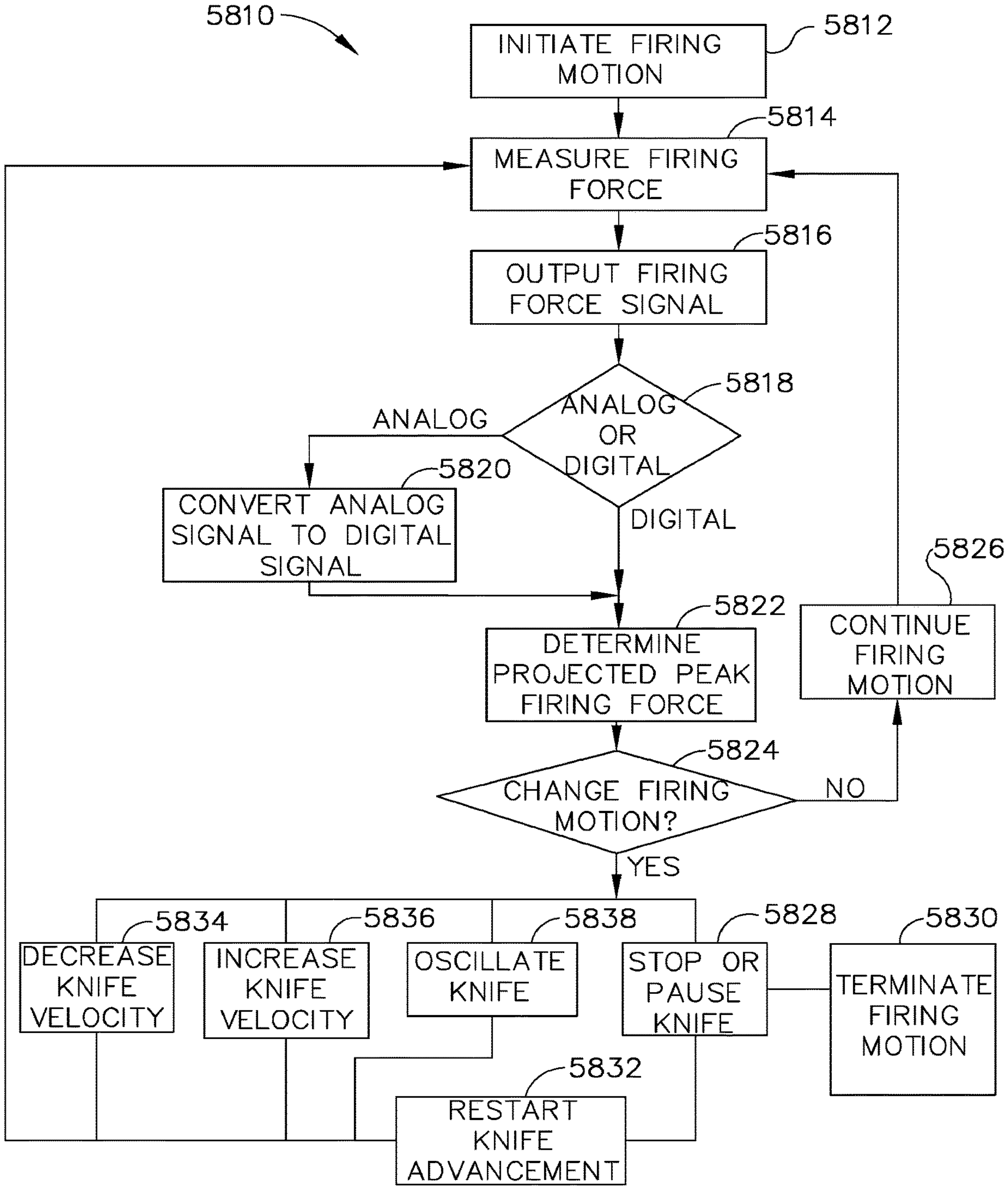

FIG. 122 illustrates a method of controlling a firing motion of the surgical instrument of FIG. 121 in accordance with one or more aspects of the present disclosure.

Figure 123:
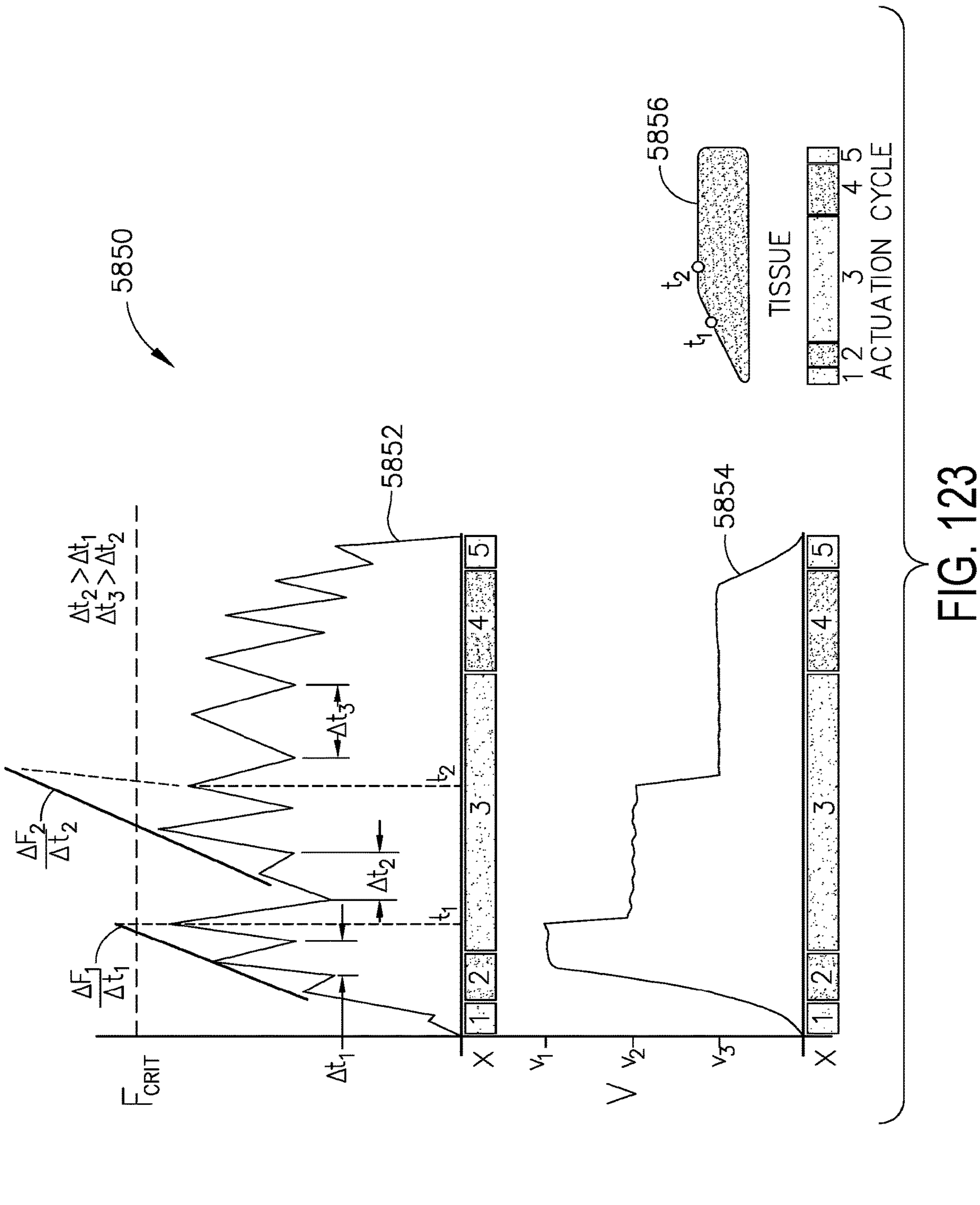

FIG. 123 illustrates an example graph showing a curve representative of a firing force signal over time and a knife position over time and a curve representative of a knife velocity over time for the surgical instrument of FIG. 121 in accordance with one or more aspects of the present disclosure.

Figure 124:
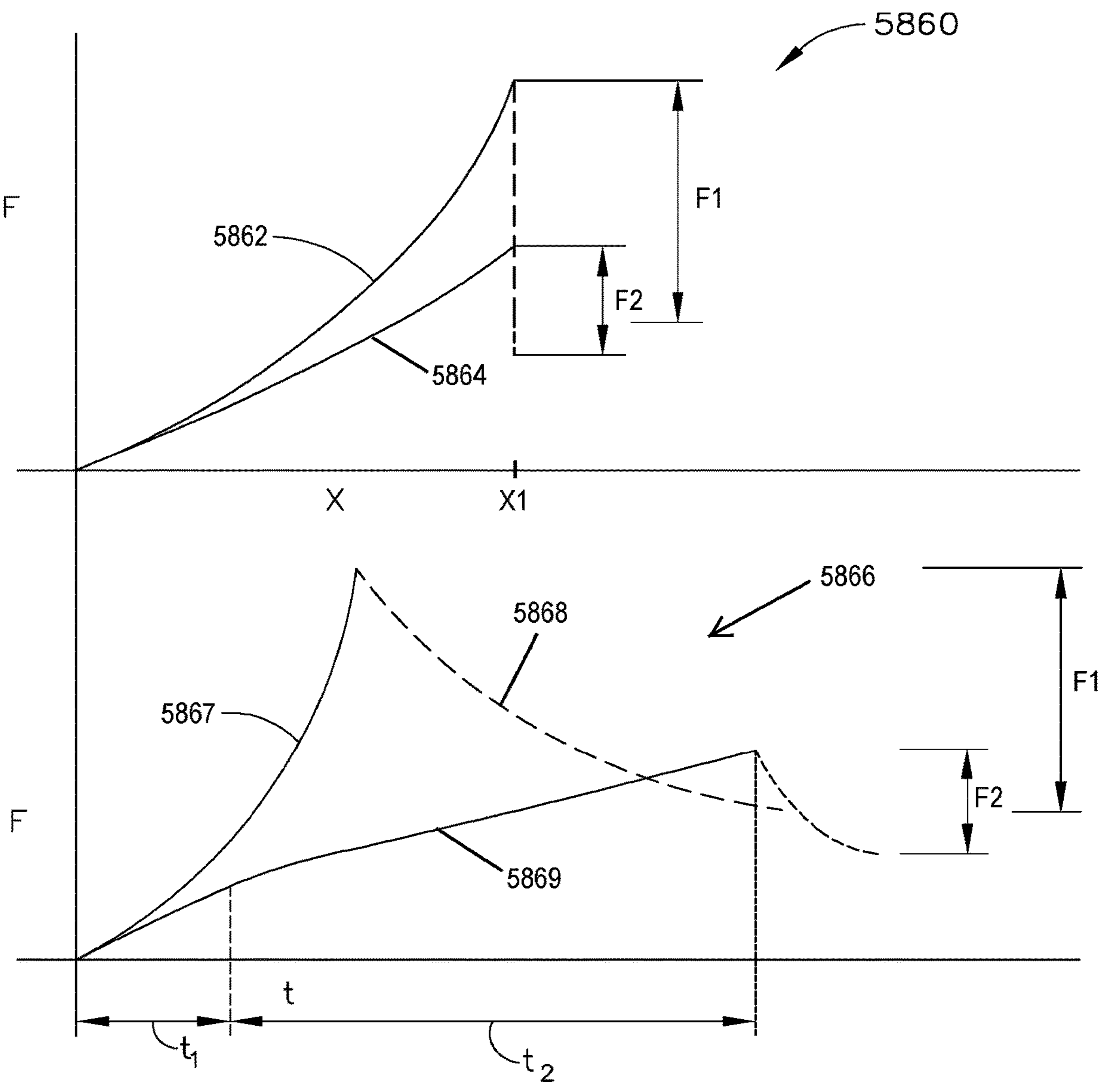

FIG. 124 illustrates an example graph showing the rate of closure of the jaws for the surgical instrument of FIG. 121 in accordance with one or more aspects of the present disclosure.

DETAILED DESCRIPTION

Applicant of the present application owns the following patent applications that were filed on Apr. 15, 2016 and which are each herein incorporated by reference in their respective entireties: U.S. patent application Ser. No. 15/130,575, entitled STAPLE FORMATION DETECTION MECHANISMS, now U.S. Pat. No. 10,456,137; U.S. patent application Ser. No. 15/130,582, entitled SURGICAL INSTRUMENT WITH DETECTION SENSORS, now U.S. Pat. No. 10,426,467; U.S. patent application Ser. No. 15/130,588, entitled SURGICAL INSTRUMENT WITH IMPROVED STOP/START CONTROL DURING A FIRING MOTION, now U.S. Pat. No. 10,492,783; U.S. patent application Ser. No. 15/130,595, entitled SURGICAL INSTRUMENT WITH ADJUSTABLE STOP/START CONTROL DURING A FIRING MOTION, now U.S. Pat. No. 10,405,859; U.S. patent application Ser. No. 15/130,571, entitled SURGICAL INSTRUMENT WITH MULTIPLE PROGRAM RESPONSES DURING A FIRING MOTION, now U.S. Pat. No. 10,357,247; U.S. patent application Ser. No. 15/130,581, entitled MODULAR SURGICAL INSTRUMENT WITH CONFIGURABLE OPERATING MODE, now U.S. Pat. No. 10,335,145; U.S. patent application Ser. No. 15/130,590, entitled SYSTEMS AND METHODS FOR CONTROLLING A SURGICAL STAPLING AND CUTTING INSTRUMENT, now U.S. Patent Application Publication No. 2017/0292613; and U.S. patent application Ser. No. 15/130,596, entitled SYSTEMS AND METHODS FOR CONTROLLING A SURGICAL STAPLING AND CUTTING INSTRUMENT, now U.S. Patent Application Publication No. 2017/0296169.

The present disclosure provides an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting examples. The features illustrated or described in connection with one example may be combined with the features of other examples. Such modifications and variations are intended to be included within the scope of the present disclosure.

Various example devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

In one aspect, the present disclosure provides a motorized surgical stapling and cutting instrument configured to provide different program responses/modifications based on rate of change while approaching a threshold. In one aspect, the present disclosure provides a motorized surgical stapling and cutting instrument configure to provide variable control program responses (pause, slow down, speed up, backup and re-advance, and stop) depending on how fast the load is increasing or decreasing (slope) as it approaches predefined staged thresholds (load, current, pressure, velocity). In one aspect, the motorized surgical instrument comprises a controller that provides variable functional response based on rate of change of load while approaching a predefined threshold. A rapid slope ramp causes the control program to stop advancing the cutting member and create an oscillating motion to move through obstruction. The control program vibrates the anvil to clamp and stabilize the tissue. The control program causes repetitive or oscillating advancement to improve compression on the tissue. The rate of slope change of load can be employed by the control program to determine the rate that the cutting member can to advance after the forced pause (tissue creep).

Before describing various aspects of a motorized stapling and cutting instrument (surgical instrument) as described in connection with FIGS. 106-124, the present disclosure first turns to FIGS. 1-105 for a general description of the mechanical and electrical platform upon which the present motorized surgical instrument may be implemented and provides the background necessary to appreciate the underlying operation and functionality of the motorized surgical instrument. Accordingly, FIGS. 1-14 provide an example of a general description of the underlying mechanical platform upon which the present motorized stapling and cutting instrument may be implemented. FIGS. 15-21 describe examples of the general underlying microcontroller, motor drive, and electrical interconnection platform upon which the present motorized surgical instrument may be implemented. FIGS. 22-34 describe example end effector channel frames and measuring forces applied to tissue located between the anvil and the staple cartridge of the end effector. FIGS. 35-37 described example circuits for controlling the functionality of the present motorized surgical instrument. FIGS. 38-95 describe example sensors and feedback systems to utilize the sensors outputs to implement the present motorized surgical instrument. FIGS. 97-97 describe example power assemblies for powering the present motorized surgical instrument. FIGS. 98-105 describe example control systems for controlling motor speed and drivable members of the present surgical instrument includes sensors and feedback elements therefor. Upon familiarization with the underlying mechanical and electrical platform upon which the present motorized surgical instrument may be implemented, the reader is directed to the description in connection with FIGS. 106-124 for a description of a motorized surgical stapling and cutting instrument configured to provide different program responses/modifications based on rate of change while approaching a threshold.

Accordingly, turning now to the figures, FIGS. 1-6 depict a motor-driven surgical instrument 10 for cutting and fastening that may or may not be reused. In the illustrated examples, the surgical instrument 10 includes a housing 12 that comprises a handle assembly 14 that is configured to be grasped, manipulated and actuated by the clinician. The housing 12 is configured for operable attachment to an interchangeable shaft assembly 200 that has an end effector 300 operably coupled thereto that is configured to perform one or more surgical tasks or procedures. As the present Detailed Description proceeds, it will be understood that the various unique and novel arrangements of the various forms of interchangeable shaft assemblies disclosed herein also may be effectively employed in connection with robotically-controlled surgical systems. Thus, the term "housing" also may encompass a housing or similar portion of a robotic system that houses or otherwise operably supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" also may represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

Figure 1:
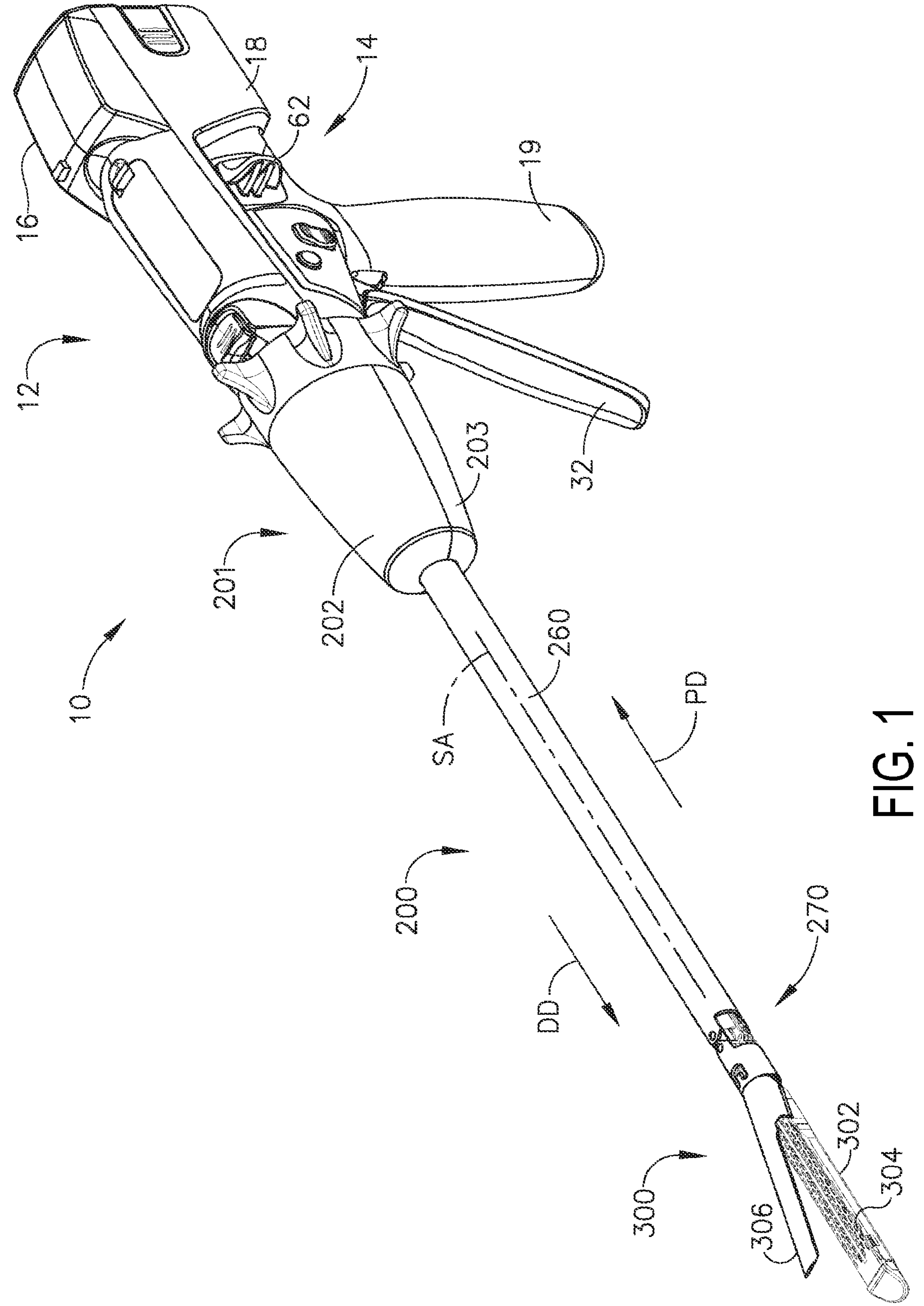
FIG. 1 is a perspective view of a surgical instrument that has an interchangeable shaft assembly operably coupled thereto in accordance with one or more aspects of the present disclosure.
Figure 2:
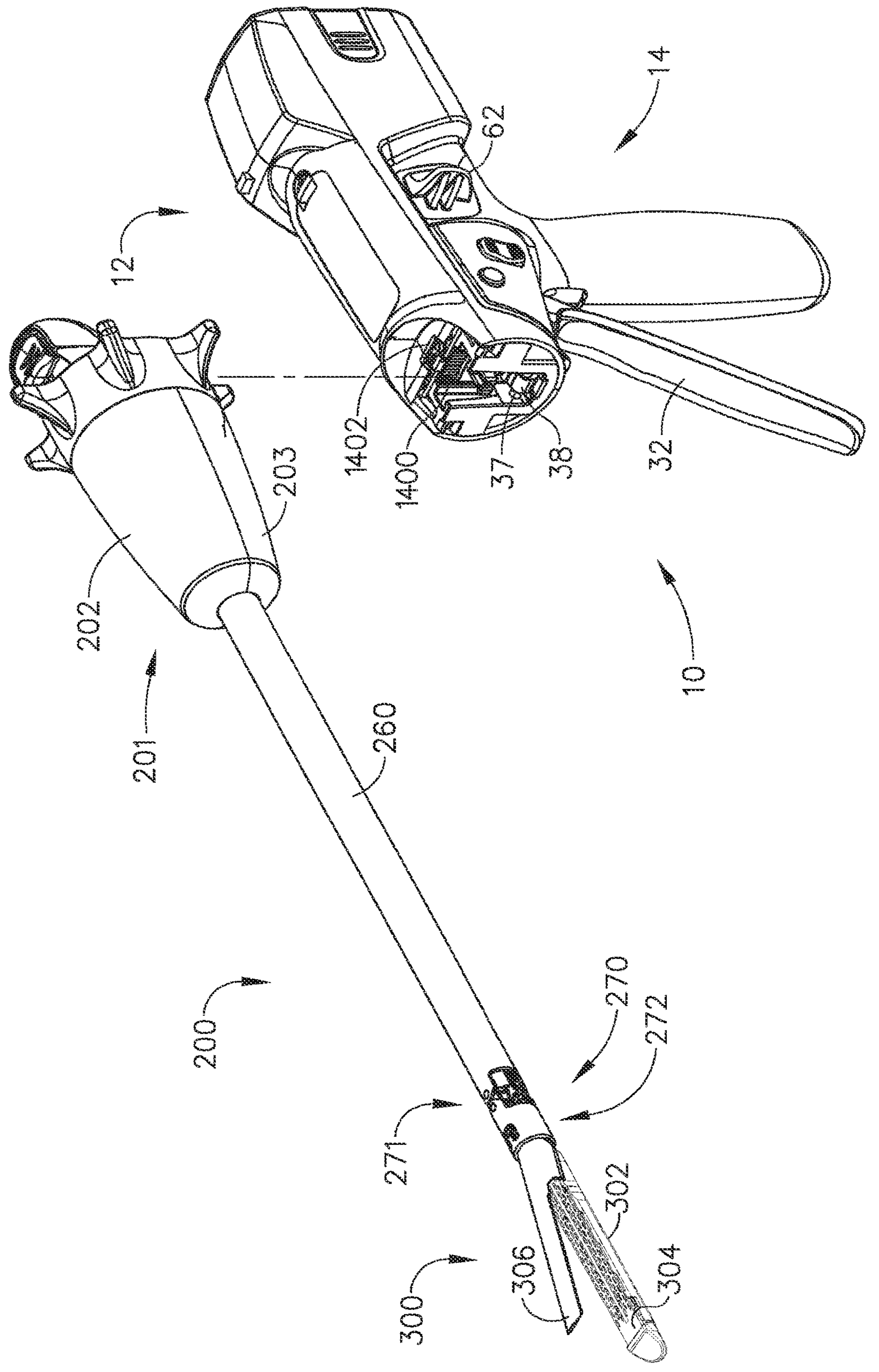
FIG. 2 is an exploded assembly view of the interchangeable shaft assembly and surgical instrument of FIG. 1 in accordance with one or more aspects of the present disclosure.

The housing 12 depicted in FIGS. 1-2 is shown in connection with an interchangeable shaft assembly 200 that includes an end effector 300 that comprises a surgical cutting and fastening device that is configured to operably support a surgical staple cartridge 304 therein. The housing 12 may be configured for use in connection with interchangeable shaft assemblies that include end effectors that are adapted to support different sizes and types of staple cartridges, have different shaft lengths, sizes, and types, etc. In addition, the housing 12 also may be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

Figure 4:
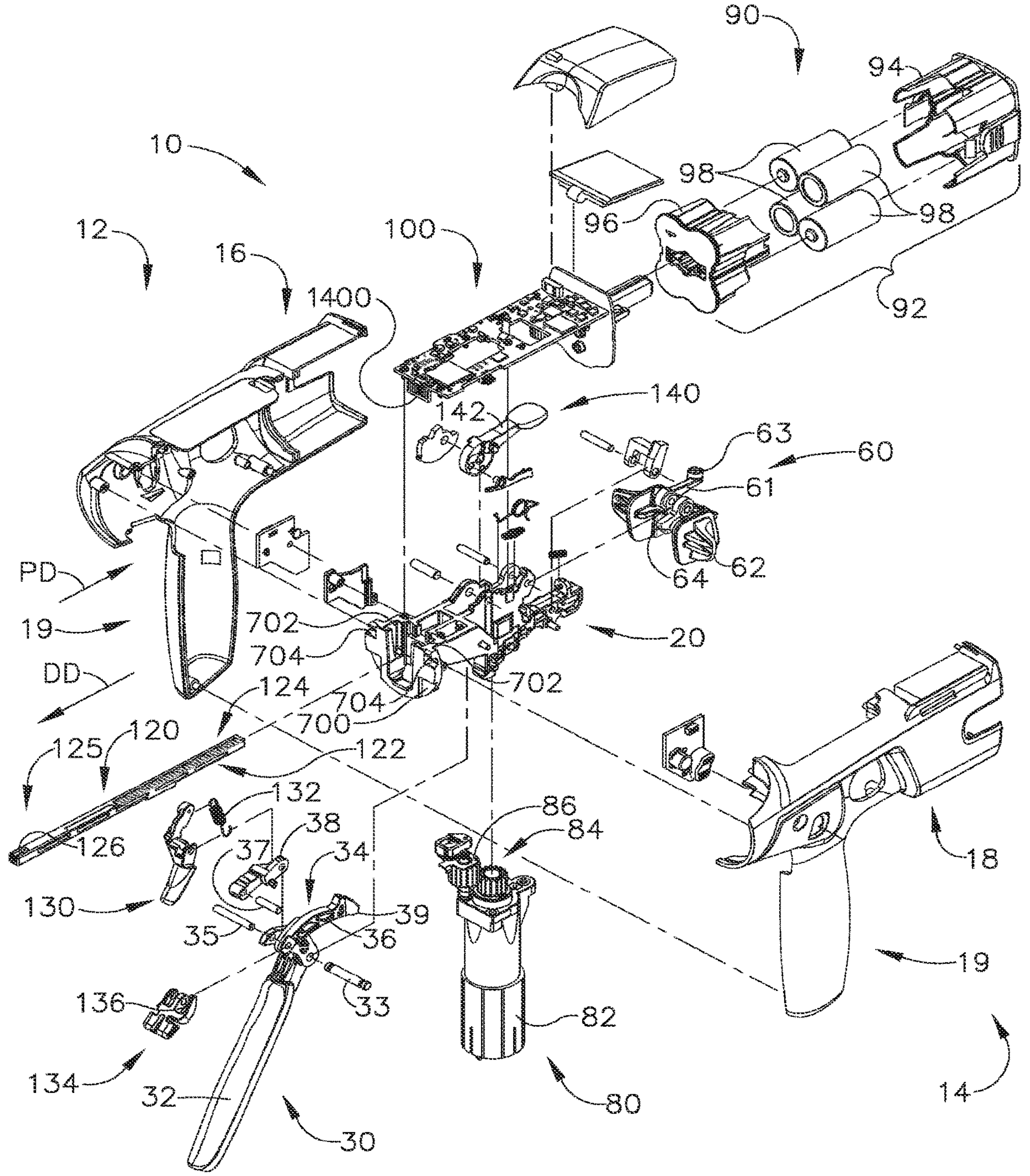
FIG. 4 is an exploded assembly view of a portion of the surgical instrument of FIGS. 1-3 in accordance with one or more aspects of the present disclosure.
Figure 5:
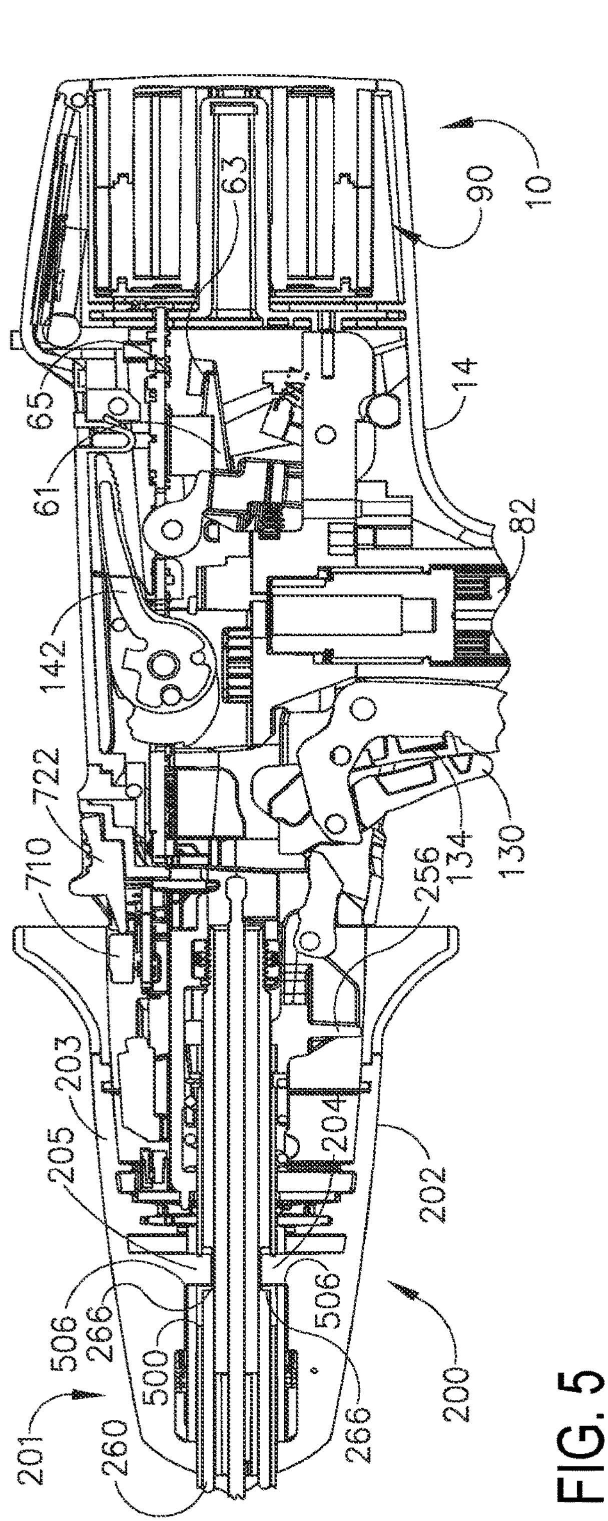
FIG. 5 is a cross-sectional side view of a portion of the surgical instrument of FIG. 4 with the firing trigger in a fully actuated position in accordance with one or more aspects of the present disclosure.

FIG. 1 illustrates the surgical instrument 10 with an interchangeable shaft assembly 200 operably coupled thereto. FIG. 2 illustrates attachment of the interchangeable shaft assembly 200 to the housing 12 or handle assembly 14. As shown in FIG. 4, the handle assembly 14 may comprise a pair of interconnectable handle housing segments 16 and 18 that may be interconnected by screws, snap features, adhesive, etc. In the illustrated arrangement, the handle housing segments 16, 18 cooperate to form a pistol grip portion 19 that can be gripped and manipulated by the clinician. As will be discussed in further detail below, the handle assembly 14 operably supports a plurality of drive systems therein that are configured to generate and apply various control motions to corresponding portions of the interchangeable shaft assembly that is operably attached thereto.

Referring now to FIG. 4, the handle assembly 14 may further include a frame 20 that operably supports a plurality of drive systems. For example, the frame 20 can operably support a "first" or closure drive system, generally designated as 30, which may be employed to apply closing and opening motions to the interchangeable shaft assembly 200 that is operably attached or coupled thereto. In at least one form, the closure drive system 30 may include an actuator in the form of a closure trigger 32 that is pivotally supported by the frame 20. More specifically, as illustrated in FIG. 4, the closure trigger 32 is pivotally coupled to the handle assembly 14 by a pivot pin 33. Such arrangement enables the closure trigger 32 to be manipulated by a clinician such that when the clinician grips the pistol grip portion 19 of the handle assembly 14, the closure trigger 32 may be easily pivoted from a starting or "unactuated" position to an "actuated" position and more particularly to a fully compressed or fully actuated position. The closure trigger 32 may be biased into the unactuated position by spring or other biasing arrangement (not shown). In various forms, the closure drive system 30 further includes a closure linkage assembly 34 that is pivotally coupled to the closure trigger 32. As shown in FIG. 4, the closure linkage assembly 34 may include a first closure link 36 and a second closure link 38 that are pivotally coupled to the closure trigger 32 by a pin 35. The second closure link 38 also may be referred to herein as an "attachment member" and include a transverse attachment pin 37.

Still referring to FIG. 4, it can be observed that the first closure link 36 may have a an end or locking wall 39 thereon that is configured to cooperate with a closure release assembly 60 that is pivotally coupled to the frame 20. In at least one form, the closure release assembly 60 may comprise a closure release button assembly 62 that has a distally protruding locking pawl 64 formed thereon. The closure release button assembly 62 may be pivoted in a counterclockwise direction by a release spring (not shown). As the clinician depresses the closure trigger 32 from its unactuated position towards the pistol grip portion 19 of the handle assembly 14, the first closure link 36 pivots upward to a point wherein the locking pawl 64 drops into retaining engagement with the locking wall 39 on the first closure link 36 thereby preventing the closure trigger 32 from returning to the unactuated position. Thus, the closure release assembly 60 serves to lock the closure trigger 32 in the fully actuated position. When the clinician desires to unlock the closure trigger 32 to permit it to be biased to the unactuated position, the clinician simply pivots the closure release button assembly 62 such that the locking pawl 64 is moved out of engagement with the locking wall 39 on the first closure link 36. When the locking pawl 64 has been moved out of engagement with the first closure link 36, the closure trigger 32 may pivot back to the unactuated position. Other closure trigger locking and release arrangements also may be employed.

Figure 10:
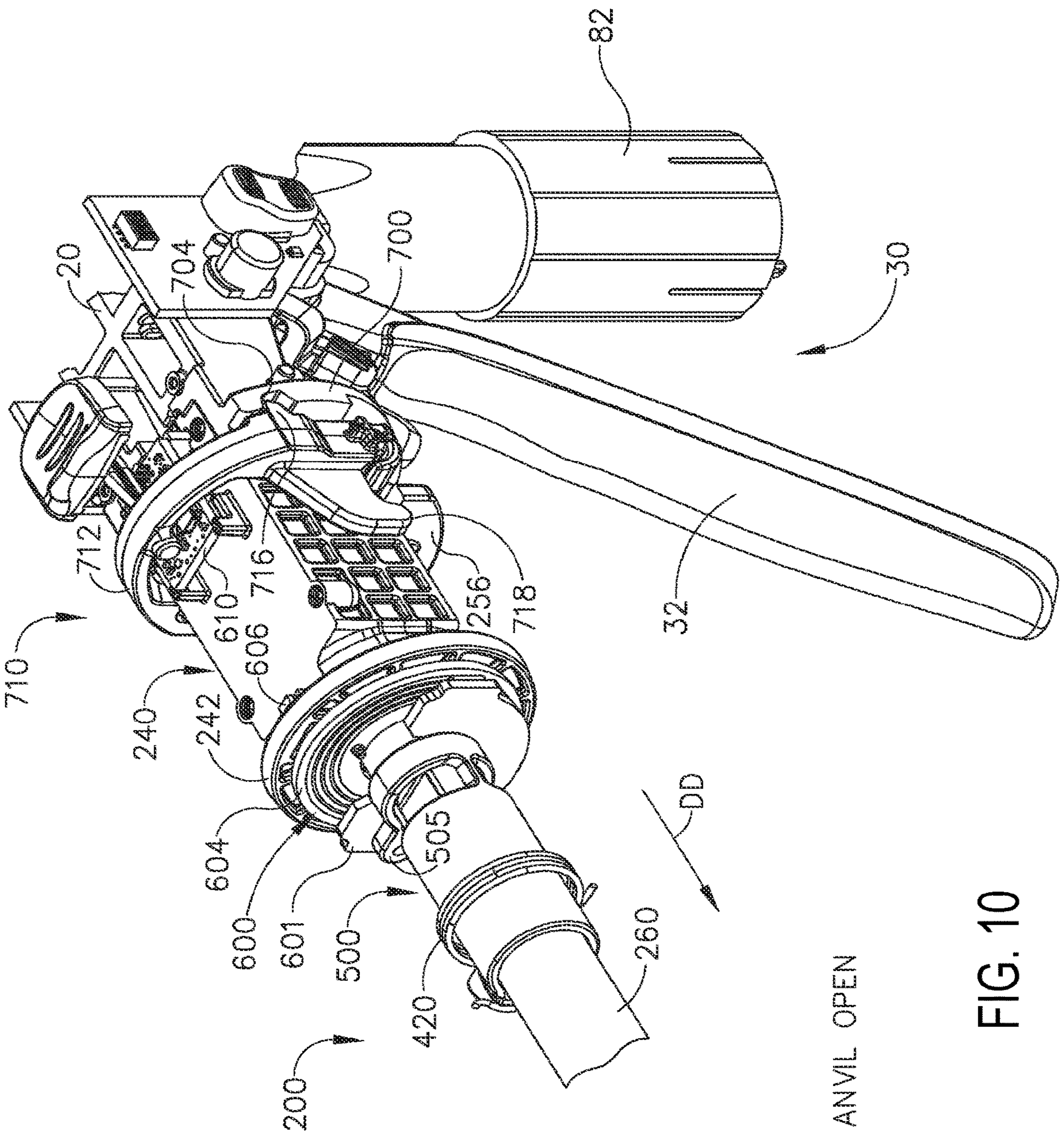
FIG. 10 is a perspective view of a portion of the interchangeable shaft assembly of FIG. 11 operably coupled to a portion of the surgical instrument of FIG. 1 illustrated with the closure trigger thereof in an unactuated position in accordance with one or more aspects of the present disclosure.
Figure 11:
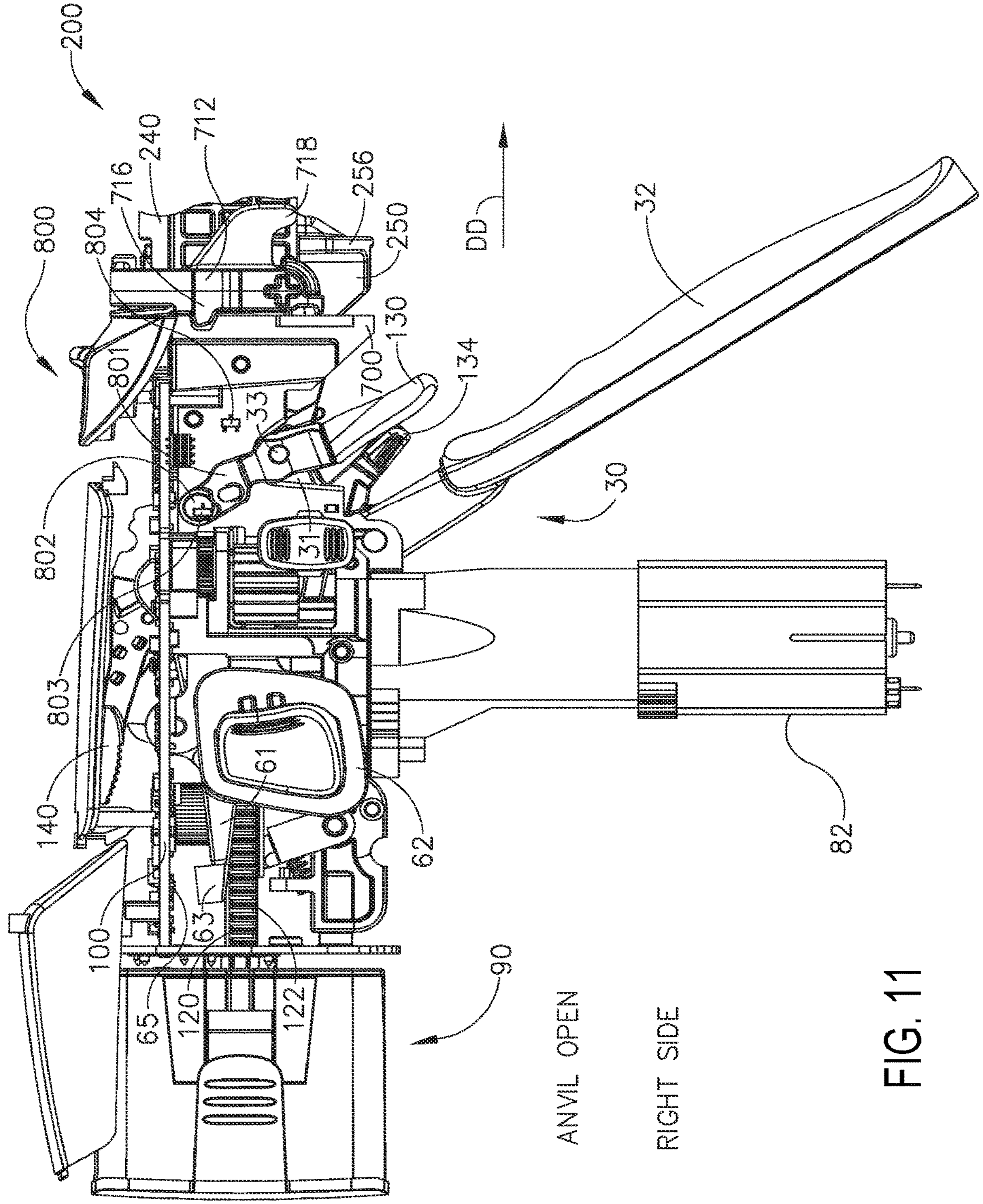
FIG. 11 is a right side elevational view of the interchangeable shaft assembly and surgical instrument of FIG. 10 in accordance with one or more aspects of the present disclosure.
Figure 12:
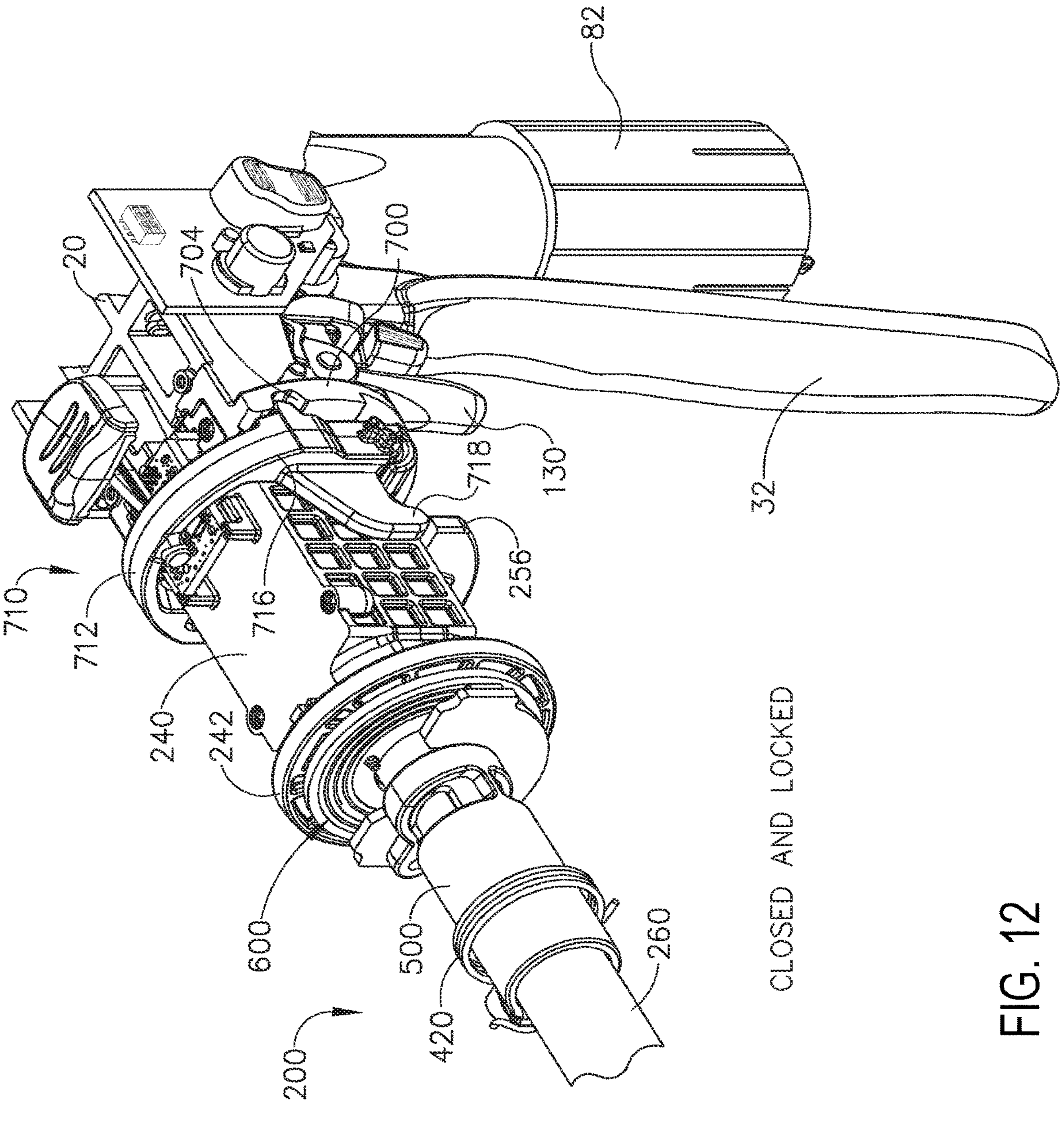
FIG. 12 is a perspective view of a portion of the interchangeable shaft assembly of FIG. 11 operably coupled to a portion of the surgical instrument of FIG. 1 illustrated with the closure trigger thereof in an actuated position and a firing trigger thereof in an unactuated position in accordance with one or more aspects of the present disclosure.
Figure 13:
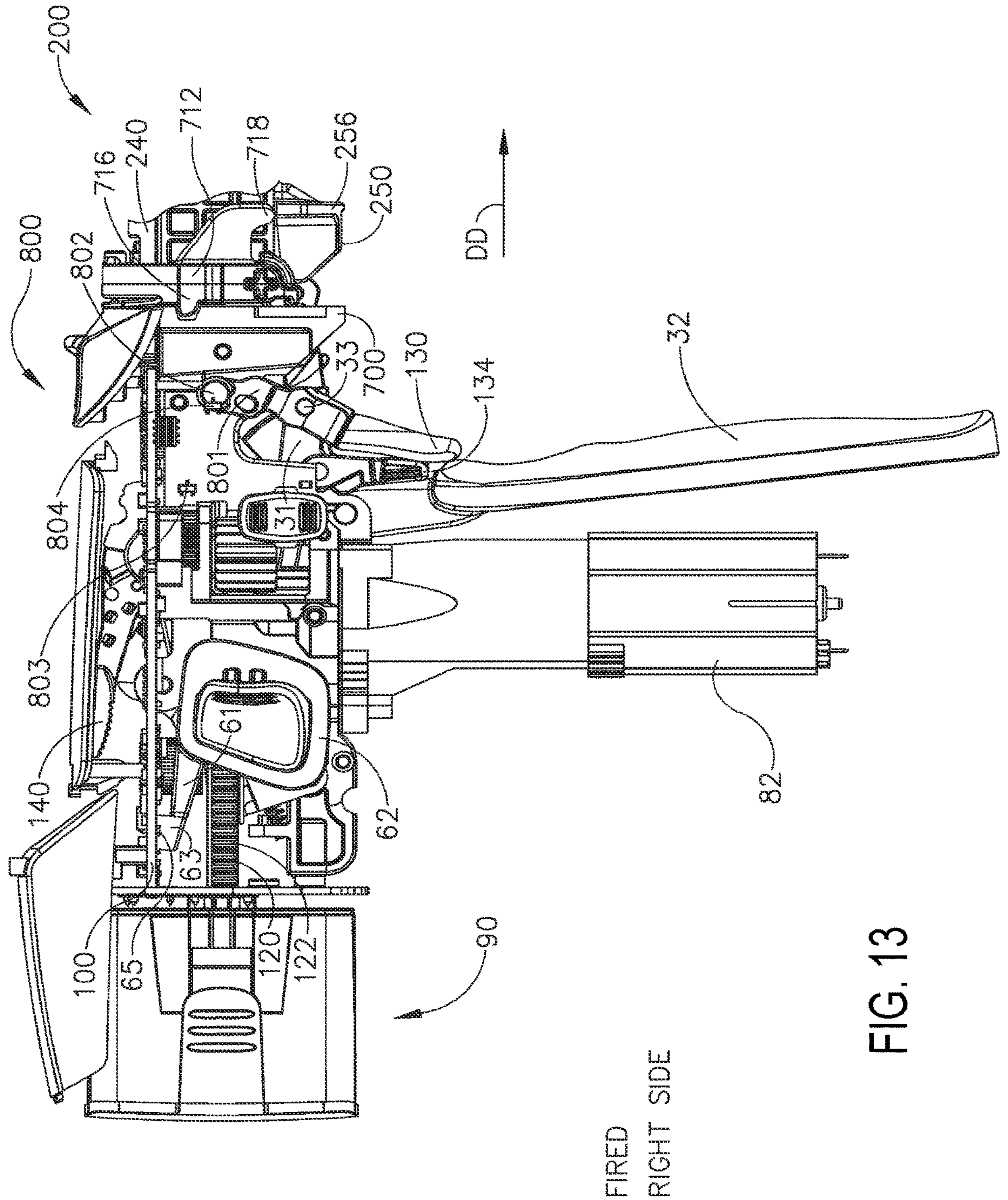
FIG. 13 is a right side elevational view of the interchangeable shaft assembly operably coupled to a portion of the surgical instrument of FIG. 1 illustrated with the closure trigger thereof in an actuated position and the firing trigger thereof in an actuated position in accordance with one or more aspects of the present disclosure.

Further to the above, FIGS. 10-11 illustrate the closure trigger 32 in its unactuated position which is associated with an open, or unclamped, configuration of the interchangeable shaft assembly 200 in which tissue can be positioned between the jaws of the interchangeable shaft assembly 200. FIG. 12 illustrates the closure trigger 32 in its actuated position which is associated with a closed, or clamped, configuration of the interchangeable shaft assembly 200 in which tissue is clamped between the jaws of the interchangeable shaft assembly 200. Upon comparing FIGS. 11 and 13, the reader will appreciate that, when the closure trigger 32 is moved from its unactuated position (FIG. 11) to its actuated position (FIG. 13), the closure release button assembly 62 is pivoted between a first position (FIG. 11) and a second position (FIG. 13). The rotation of the closure release button assembly 62 can be referred to as being an upward rotation; however, at least a portion of the closure release button assembly 62 is being rotated toward the circuit board 100. Referring to FIG. 4, the closure release button assembly 62 can include an arm 61 extending therefrom and a magnetic element 63, such as a permanent magnet, for example, mounted to the arm 61. When the closure release button assembly 62 is rotated from its first position to its second position, the magnetic element 63 can move toward the circuit board 100. The circuit board 100 can include at least one sensor configured to detect the movement of the magnetic element 63. In at least one aspect, a magnetic field sensor 65, for example, can be mounted to the bottom surface of the circuit board 100. The magnetic field sensor 65 can be configured to detect changes in a magnetic field surrounding the magnetic field sensor 65 caused by the movement of the magnetic element 63. The magnetic field sensor 65 can be in signal communication with a controller 1500, for example, which can determine whether the closure release button assembly 62 is in its first position, which is associated with the unactuated position of the closure trigger 32 and the open configuration of the end effector, its second position, which is associated with the actuated position of the closure trigger 32 and the closed configuration of the end effector, and/or any position between the first position and the second position.

As used throughout the present disclosure, a magnetic field sensor may be a Hall effect sensor, search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In at least one form, the handle assembly 14 and the frame 20 may operably support another drive system referred to herein as a firing drive system 80 that is configured to apply firing motions to corresponding portions of the interchangeable shaft assembly attached thereto. The firing drive system may 80 also be referred to herein as a "second drive system". The firing drive system 80 may employ an electric motor 82, located in the pistol grip portion 19 of the handle assembly 14. In various forms, the electric motor 82 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The electric motor 82 may be powered by a power source 90 that in one form may comprise a removable power pack 92. As shown in FIG. 4, for example, the removable power pack 92 may comprise a proximal housing portion 94 that is configured for attachment to a distal housing portion 96. The proximal housing portion 94 and the distal housing portion 96 are configured to operably support a plurality of batteries 98 therein. Batteries 98 may each comprise, for example, a Lithium Ion ("LI") or other suitable battery. The distal housing portion 96 is configured for removable operable attachment to a control circuit board 100 which is also operably coupled to the electric motor 82. A number of batteries 98 may be connected in series may be used as the power source for the surgical instrument 10. In addition, the power source 90 may be replaceable and/or rechargeable.

As outlined above with respect to other various forms, the electric motor 82 can include a rotatable shaft (not shown) that operably interfaces with a gear reducer assembly 84 that is mounted in meshing engagement with a with a set, or rack, of drive teeth 122 on a longitudinally movable drive member 120. In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the longitudinally movable drive member 120 will be axially driven in the distal direction "DD". When the electric motor 82 is driven in the opposite rotary direction, the longitudinally movable drive member 120 will be axially driven in a proximal direction "PD". The handle assembly 14 can include a switch which can be configured to reverse the polarity applied to the electric motor 82 by the power source 90. As with the other forms described herein, the handle assembly 14 can also include a sensor that is configured to detect the position of the longitudinally movable drive member 120 and/or the direction in which the longitudinally movable drive member 120 is being moved.

Actuation of the electric motor 82 can be controlled by a firing trigger 130 that is pivotally supported on the handle assembly 14. The firing trigger 130 may be pivoted between an unactuated position and an actuated position. The firing trigger 130 may be biased into the unactuated position by a spring 132 or other biasing arrangement such that when the clinician releases the firing trigger 130, it may be pivoted or otherwise returned to the unactuated position by the spring 132 or biasing arrangement. In at least one form, the firing trigger 130 can be positioned "outboard" of the closure trigger 32 as was discussed above. In at least one form, a firing trigger safety button 134 may be pivotally mounted to the closure trigger 32 by pin 35. The firing trigger safety button 134 may be positioned between the firing trigger 130 and the closure trigger 32 and have a pivot arm 136 protruding therefrom. See FIG. 4. When the closure trigger 32 is in the unactuated position, the firing trigger safety button 134 is contained in the handle assembly 14 where the clinician cannot readily access it and move it between a safety position preventing actuation of the firing trigger 130 and a firing position wherein the firing trigger 130 may be fired. As the clinician depresses the closure trigger 32, the firing trigger safety button 134 and the firing trigger 130 pivot down wherein they can then be manipulated by the clinician.

As discussed above, the handle assembly 14 can include a closure trigger 32 and a firing trigger 130. Referring to FIGS. 11-13, the firing trigger 130 can be pivotably mounted to the closure trigger 32. The closure trigger 32 can include an arm 31 extending therefrom and the firing trigger 130 can be pivotably mounted to the arm 31 about a pivot pin 33. When the closure trigger 32 is moved from its unactuated position (FIG. 11) to its actuated position (FIG. 13), the firing trigger 130 can descend downwardly, as outlined above. After the firing trigger safety button 134 has been moved to its firing position, referring primarily to FIG. 18A, the firing trigger 130 can be depressed to operate the motor of the surgical instrument firing system. In various instances, the handle assembly 14 can include a tracking system, such as system 800, for example, configured to determine the position of the closure trigger 32 and/or the position of the firing trigger 130. With primary reference to FIGS. 11 and 13, the tracking system 800 can include a magnetic element, such as magnet 802, for example, which is mounted to an arm 801 extending from the firing trigger 130. The tracking system 800 can comprise one or more sensors, such as a first magnetic field sensor 803 and a second magnetic field sensor 804, for example, which can be configured to track the position of the magnet 802.

Upon comparing FIGS. 11 and 13, the reader will appreciate that, when the closure trigger 32 is moved from its unactuated position to its actuated position, the magnet 802 can move between a first position adjacent the first magnetic field sensor 803 and a second position adjacent the second magnetic field sensor 804.

Upon comparing FIGS. 11 and 13, the reader will further appreciate that, when the firing trigger 130 is moved from an unfired position (FIG. 11) to a fired position (FIG. 13), the magnet 802 can move relative to the second magnetic field sensor 804. The first and second magnetic field sensors 803, 804 can track the movement of the magnet 802 and can be in signal communication with a controller on the circuit board 100. With data from the first magnetic field sensor 803 and/or the second magnetic field sensor 804, the controller can determine the position of the magnet 802 along a predefined path and, based on that position, the controller can determine whether the closure trigger 32 is in its unactuated position, its actuated position, or a position therebetween. Similarly, with data from the first magnetic field sensor 803 and/or the second magnetic field sensor 804, the controller can determine the position of the magnet 802 along a predefined path and, based on that position, the controller can determine whether the firing trigger 130 is in its unfired position, its fully fired position, or a position therebetween.

As indicated above, in at least one form, the longitudinally movable drive member 120 has a rack of drive teeth 122 formed thereon for meshing engagement with a corresponding drive gear 86 of the gear reducer assembly 84. At least one form also includes a manually-actuatable bailout assembly 140 that is configured to enable the clinician to manually retract the longitudinally movable drive member 120 should the electric motor 82 become disabled. The bailout assembly 140 may include a lever or handle assembly 14 that is configured to be manually pivoted into ratcheting engagement with teeth 124 also provided in the longitudinally movable drive member 120. Thus, the clinician can manually retract the longitudinally movable drive member 120 by using the handle assembly 14 to ratchet the longitudinally movable drive member 120 in the proximal direction "PD". U.S. Pat. No. 8,608,045, entitled POWERED SURGICAL CUTTING AND STAPLING APPARATUS WITH MANUALLY RETRACTABLE FIRING SYSTEM discloses bailout arrangements and other components, arrangements and systems that also may be employed with the various instruments disclosed herein. U.S. Pat. No. 8,608,045, is herein incorporated by reference in its entirety.

Figure 7:
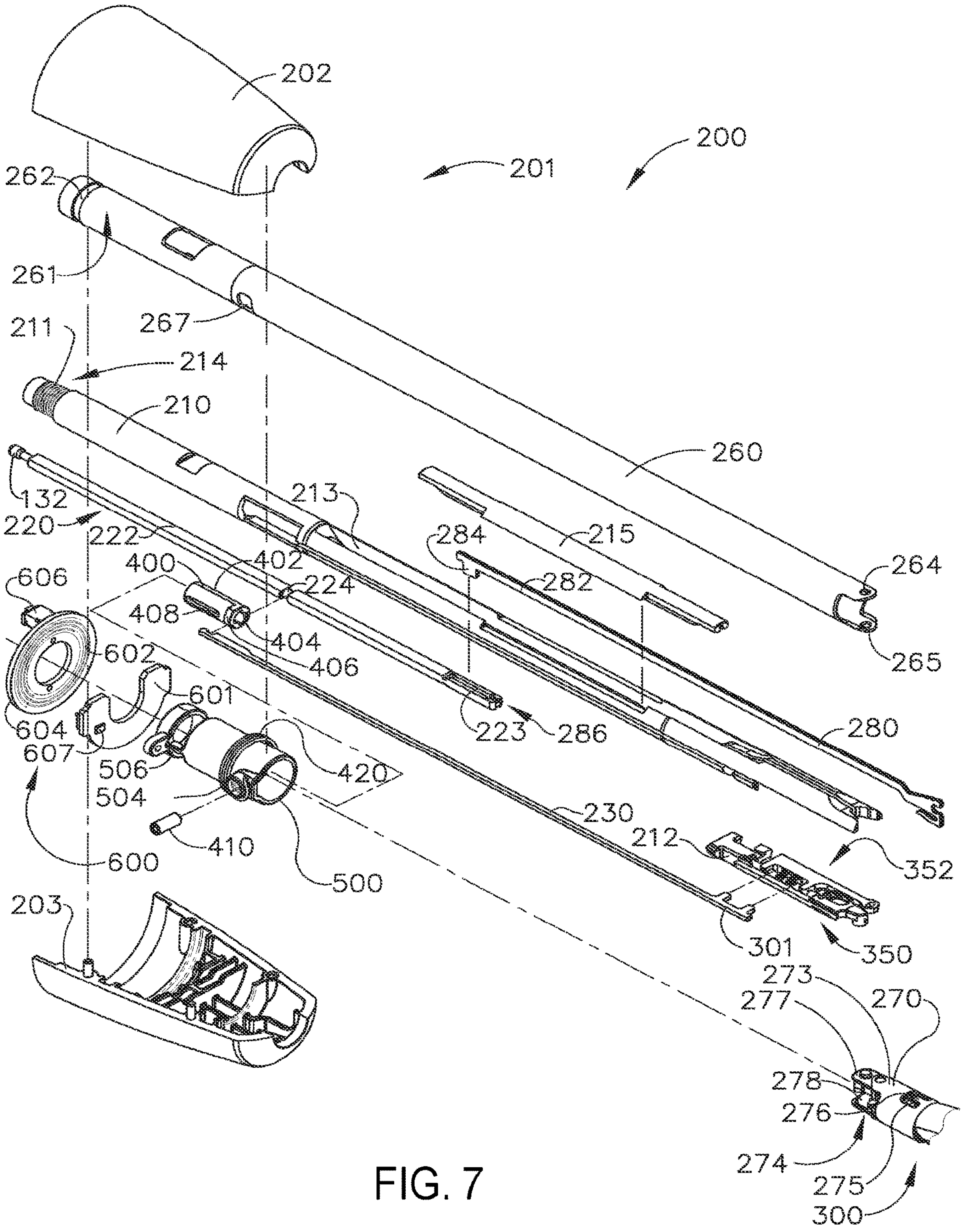
FIG. 7 is another exploded assembly view of portions of the interchangeable shaft assembly of FIG. 7 in accordance with one or more aspects of the present disclosure.

Turning now to FIG. 1, the interchangeable shaft assembly 200 includes an end effector 300 that comprises an elongated channel 302 that is configured to operably support a surgical staple cartridge 304 therein. The end effector 300 may further include an anvil 306 that is pivotally supported relative to the elongated channel 302. The interchangeable shaft assembly 200 may further include an articulation joint 270 and an articulation lock 350 (FIG. 7) which can be configured to releasably hold the end effector 300 in a desired position relative to a shaft axis SA-SA. Details regarding the construction and operation of the end effector 300, the articulation joint 270 and the articulation lock 350 are set forth in U.S. Patent Application Publication No. 2014/0263541, entitled ARTICULATABLE SURGICAL INSTRUMENT COMPRISING AN ARTICULATION LOCK, which is herein incorporated by reference in its entirety. As shown in FIG. 7, the interchangeable shaft assembly 200 can further include a proximal housing or nozzle 201 comprised of nozzle portions 202, 203. The interchangeable shaft assembly 200 can further include a closure tube 260 which can be utilized to close and/or open the anvil 306 of the end effector 300. Primarily referring now to FIG. 7, the interchangeable shaft assembly 200 can include a spine 210 which can be configured to fixably support a shaft frame 212 of the articulation lock 350. See FIG. 7. The spine 210 can be configured to, one, slidably support a firing member 220 therein and, two, slidably support the closure tube 260 which extends around the spine 210. The spine 210 can also be configured to slidably support an articulation driver 230. The articulation driver 230 has a distal end 231 that is configured to operably engage the articulation lock 350. The articulation lock 350 interfaces with an articulation frame 352 that is adapted to operably engage a drive pin (not shown) on the end effector frame (not shown). As indicated above, further details regarding the operation of the articulation lock 350 and the articulation frame may be found in U.S. Patent Application Publication No. 2014/0263541. In various circumstances, the spine 210 can comprise a proximal end 211 which is rotatably supported in a chassis 240. In one arrangement, for example, the proximal end 211 of the spine 210 has a thread 214 formed thereon for threaded attachment to a spine bearing 216 configured to be supported within the chassis 240. Such an arrangement facilitates rotatable attachment of the spine 210 to the chassis 240 such that the spine 210 may be selectively rotated about a shaft axis SA-SA relative to the chassis 240.

Figure 3:
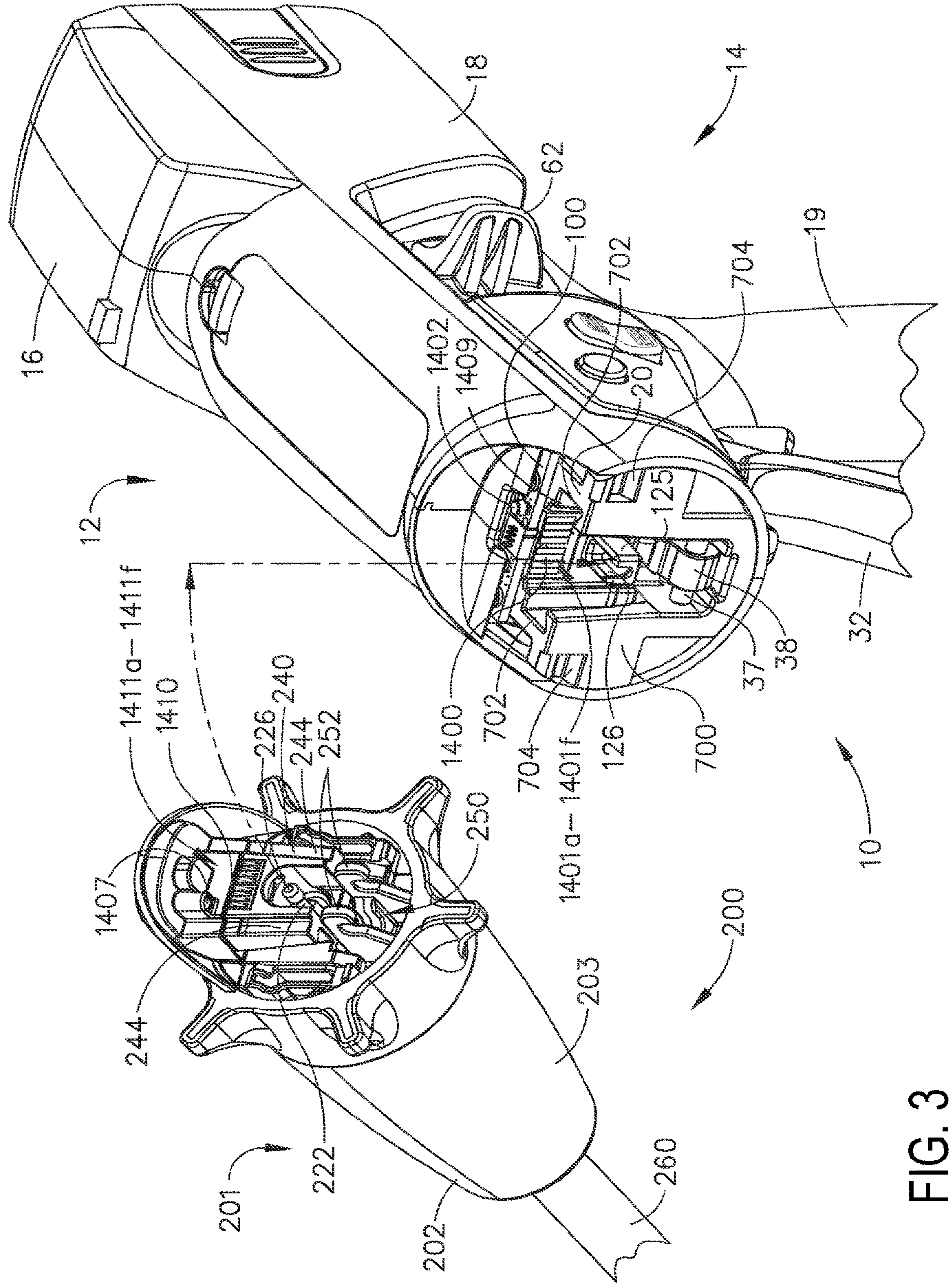
FIG. 3 is another exploded assembly view showing portions of the interchangeable shaft assembly and surgical instrument of FIGS. 1 and 2 in accordance with one or more aspects of the present disclosure.

The interchangeable shaft assembly 200 includes a closure shuttle 250 that is slidably supported within the chassis 240 such that it may be axially moved relative thereto. As shown in FIG. 3, the closure shuttle 250 includes a pair of proximally-protruding hooks 252 that are configured for attachment to the transverse attachment pin 37 that is attached to the second closure link 38 as will be discussed in further detail below. A proximal end 261 of the closure tube 260 is coupled to the closure shuttle 250 for relative rotation thereto. For example, a U shaped connector 263 is inserted into an annular slot 262 in the proximal end 261 of the closure tube 260 and is retained within vertical slots 253 in the closure shuttle 250. Such an arrangement serves to attach the closure tube 260 to the closure shuttle 250 for axial travel therewith while enabling the closure tube 260 to rotate relative to the closure shuttle 250 about the shaft axis SA-SA. A closure spring 268 is journaled on the closure tube 260 and serves to bias the closure tube 260 in the proximal direction "PD" which can serve to pivot the closure trigger into the unactuated position when the shaft assembly is operably coupled to the handle assembly 14.

In at least one form, the interchangeable shaft assembly 200 may further include an articulation joint 270. Other interchangeable shaft assemblies, however, may not be capable of articulation. According to various forms, the double pivot closure sleeve assembly 271 includes an end effector closure sleeve assembly 272 having upper and lower distally projecting tangs 273, 274. An end effector closure sleeve assembly 272 includes a horseshoe aperture 275 and a tab 276 for engaging an opening tab on the anvil 306 in the various manners described in U.S. Patent Application Publication No. 2014/0263541. As described in further detail therein, the horseshoe aperture 275 and tab 276 engage a tab on the anvil when the anvil 306 is opened. An upper double pivot link 277 includes upwardly projecting distal and proximal pivot pins that engage respectively an upper distal pin hole in the upper proximally projecting tang 273 and an upper proximal pin hole in an upper distally projecting tang 264 on the closure tube 260. A lower double pivot link 278 includes upwardly projecting distal and proximal pivot pins that engage respectively a lower distal pin hole in the lower proximally projecting tang 274 and a lower proximal pin hole in the lower distally projecting tang 265. See also FIG. 7.

In use, the closure tube 260 is translated distally (direction "DD") to close the anvil 306, for example, in response to the actuation of the closure trigger 32. The anvil 306 is closed by distally translating the closure tube 260 and thus the end effector closure sleeve assembly 272, causing it to strike a proximal surface on the anvil 306 in the manner described in the aforementioned reference U.S. Patent Application Publication No. 2014/0263541. As was also described in detail in that reference, the anvil 306 is opened by proximally translating the closure tube 260 and the end effector closure sleeve assembly 272, causing tab 276 and the horseshoe aperture 275 to contact and push against the anvil tab to lift the anvil 306. In the anvil-open position, the closure tube 260 is moved to its proximal position.

As indicated above, the surgical instrument 10 may further include an articulation lock 350 of the types and construction described in further detail in U.S. Patent Application Publication No. 2014/0263541, which can be configured and operated to selectively lock the end effector 300 in position. Such arrangement enables the end effector 300 to be rotated, or articulated, relative to the closure tube 260 when the articulation lock 350 is in its unlocked state. In such an unlocked state, the end effector 300 can be positioned and pushed against soft tissue and/or bone, for example, surrounding the surgical site within the patient in order to cause the end effector 300 to articulate relative to the closure tube 260. The end effector 300 also may be articulated relative to the closure tube 260 by an articulation driver 230.

As was also indicated above, the interchangeable shaft assembly 200 further includes a firing member 220 that is supported for axial travel within the spine 210. The firing member 220 includes an intermediate firing shaft 222 that is configured for attachment to a distal cutting portion or knife bar 280. The firing member 220 also may be referred to herein as a "second shaft" and/or a "second shaft assembly". As shown in FIG. 7, the intermediate firing shaft 222 may include a longitudinal slot 223 in the distal end thereof which can be configured to receive a tab 284 on the proximal end 282 of the knife bar 280. The longitudinal slot 223 and the proximal end 282 can be sized and configured to permit relative movement therebetween and can comprise a slip joint 286. The slip joint 286 can permit the intermediate firing shaft 222 of the firing member 220 to be moved to articulate the end effector 300 without moving, or at least substantially moving, the knife bar 280. Once the end effector 300 has been suitably oriented, the intermediate firing shaft 222 can be advanced distally until a proximal sidewall of the longitudinal slot 223 comes into contact with the tab 284 in order to advance the knife bar 280 and fire the staple cartridge positioned within the channel 302. As can be further seen in FIG. 7, the spine 210 has an elongated opening or window 213 therein to facilitate assembly and insertion of the intermediate firing shaft 222 into the spine 210. Once the intermediate firing shaft 222 has been inserted therein, a top frame segment 215 may be engaged with the shaft frame 212 to enclose the intermediate firing shaft 222 and knife bar 280 therein. Further description of the operation of the firing member 220 may be found in U.S. Patent Application Publication No. 2014/0263541.

Further to the above, the interchangeable shaft assembly 200 can include a clutch assembly 400 which can be configured to selectively and releasably couple the articulation driver 230 to the firing member 220. In one form, the clutch assembly 400 includes a lock collar, or lock sleeve 402, positioned around the firing member 220 wherein the lock sleeve 402 can be rotated between an engaged position in which the lock sleeve 402 couples the articulation driver 360 to the firing member 220 and a disengaged position in which the articulation driver 360 is not operably coupled to the firing member 220. When lock sleeve 402 is in its engaged position, distal movement of the firing member 220 can move the articulation driver 360 distally and, correspondingly, proximal movement of the firing member 220 can move the articulation driver 230 proximally. When lock sleeve 402 is in its disengaged position, movement of the firing member 220 is not transmitted to the articulation driver 230 and, as a result, the firing member 220 can move independently of the articulation driver 230. In various circumstances, the articulation driver 230 can be held in position by the articulation lock 350 when the articulation driver 230 is not being moved in the proximal or distal directions by the firing member 220.

Figure 8:
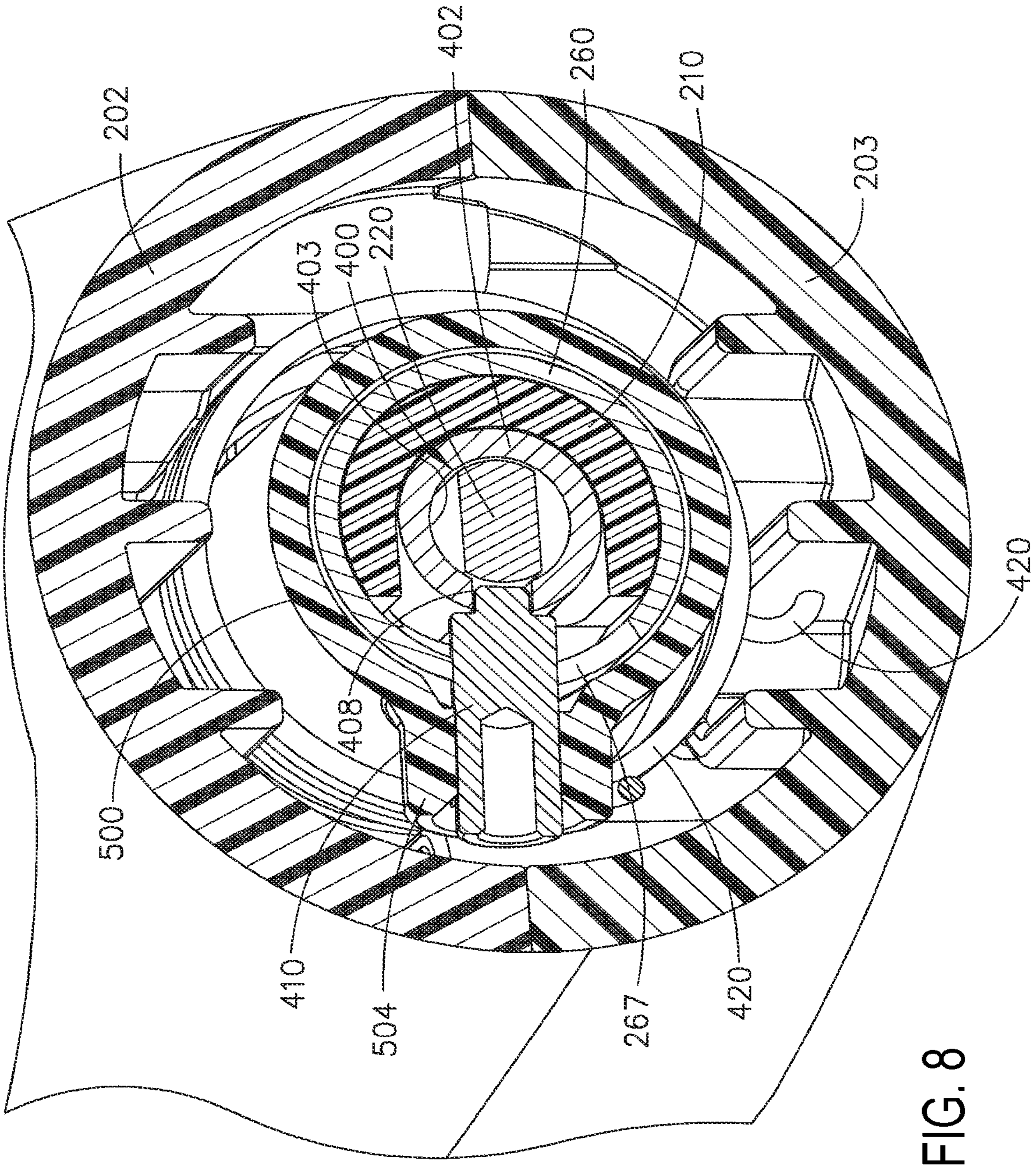
FIG. 8 is a cross-sectional view of a portion of the interchangeable shaft assembly of FIGS. 7-9, in accordance with one or more aspects of the present disclosure.
Figure 9:
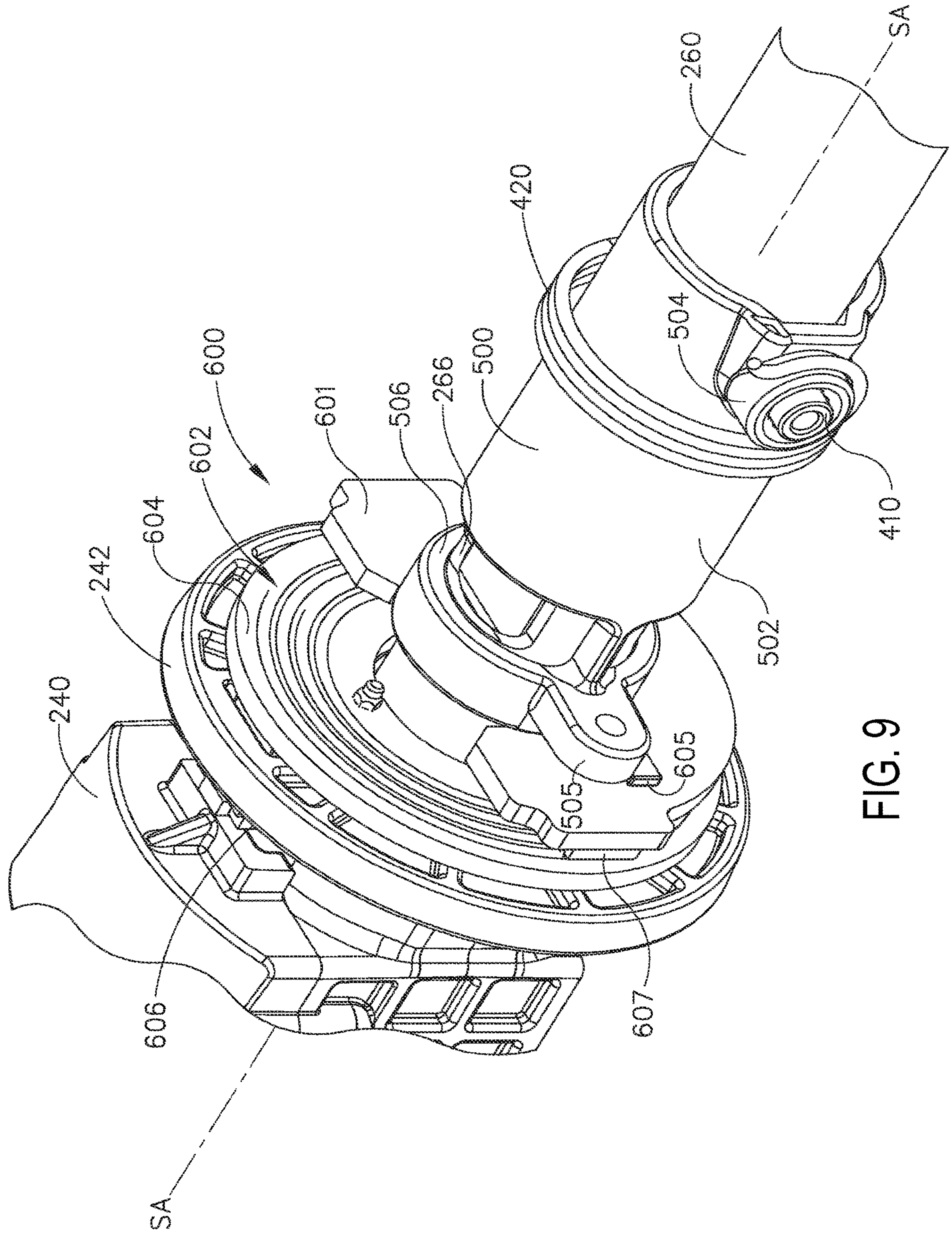
FIG. 9 is another perspective view of the portion of an interchangeable shaft assembly with the switch drum mounted thereon in accordance with one or more aspects of the present disclosure.

As shown in FIGS. 7-9, the interchangeable shaft assembly 200 further includes a switch drum 500 that is rotatably received on the closure tube 260. The switch drum 500 comprises a hollow shaft segment 502 that has a shaft boss 504 formed thereon for receive an outwardly protruding actuation pin 410 therein. In various circumstances, the actuation pin 410 extends through a slot 267 into a longitudinal slot 408 provided in the lock sleeve 402 to facilitate axial movement of the lock sleeve 402 when it is engaged with the articulation driver 230. A rotary torsion spring 420 is configured to engage the shaft boss 504 on the switch drum 500 and a portion of the nozzle portion 203 as shown in FIG. 8 to apply a biasing force to the switch drum 500. The switch drum 500 can further comprise at least partially circumferential openings 506 defined therein which, referring to FIGS. 5 and 6, can be configured to receive circumferential mounts 204, 205 extending from the nozzle portions 202, 203 and permit relative rotation, but not translation, between the switch drum 500 and the nozzle 201. As shown in those Figures, the circumferential mounts 204, 205 also extend through openings 266 in the closure tube 260 to be seated in recesses located in the spine 210. However, rotation of the nozzle 201 to a point where the circumferential mounts 204, 205 reach the end of their respective partially circumferential openings 506 in the switch drum 500 will result in rotation of the switch drum 500 about the shaft axis SA-SA. Rotation of the switch drum 500 will ultimately result in the rotation of the actuation pin 410 and the lock sleeve 402 between its engaged and disengaged positions. Thus, in essence, the nozzle 201 may be employed to operably engage and disengage the articulation drive system with the firing drive system in the various manners described in further detail in U.S. Patent Application Publication No. 2014/0263541.

As also illustrated in FIGS. 7-9, the interchangeable shaft assembly 200 can comprise a slip ring assembly 600 which can be configured to conduct electrical power to and/or from the end effector 300 and/or communicate signals to and/or from the end effector 300, for example. The slip ring assembly 600 can comprise a proximal connector flange 604 mounted to a chassis mounting flange 242 extending from the chassis 240 and a distal connector flange 601 positioned within a slot defined in the nozzle portions 202, 203. The proximal connector flange 604 can comprise a first face and the distal connector flange 601 can comprise a second face which is positioned adjacent to and movable relative to the first face. The distal connector flange 601 can rotate relative to the proximal connector flange 604 about the shaft axis SA-SA. The proximal connector flange 604 can comprise a plurality of concentric, or at least substantially concentric, conductors 602 defined in the first face thereof. A connector 607 can be mounted on the proximal side of the distal connector flange 601 and may have a plurality of contacts (not shown) wherein each contact corresponds to and is in electrical contact with one of the conductors 602. Such an arrangement permits relative rotation between the proximal connector flange 604 and the distal connector flange 601 while maintaining electrical contact therebetween. The proximal connector flange 604 can include an electrical connector 606 which can place the conductors 602 in signal communication with a shaft circuit board 610 mounted to the chassis 240, for example. In at least one instance, a wiring harness comprising a plurality of conductors can extend between the electrical connector 606 and the shaft circuit board 610. The electrical connector 606 may extend proximally through a connector opening 243 defined in the chassis mounting flange 242. U.S. Patent Application Publication No. 2014/0263551, entitled STAPLE CARTRIDGE TISSUE THICKNESS SENSOR SYSTEM, is incorporated herein by reference in its entirety. U.S. Patent Application Publication No. 2014/0263552, entitled STAPLE CARTRIDGE TISSUE THICKNESS SENSOR SYSTEM, is incorporated by reference in its entirety. Further details regarding slip ring assembly 600 may be found in U.S. Patent Application Publication No. 2014/0263541.

As discussed above, the interchangeable shaft assembly 200 can include a proximal portion which is fixably mounted to the handle assembly 14 and a distal portion which is rotatable about a longitudinal axis. The rotatable distal shaft portion can be rotated relative to the proximal portion about the slip ring assembly 600, as discussed above. The distal connector flange 601 of the slip ring assembly 600 can be positioned within the rotatable distal shaft portion. Moreover, further to the above, the switch drum 500 can also be positioned within the rotatable distal shaft portion. When the rotatable distal shaft portion is rotated, the distal connector flange 601 and the switch drum 500 can be rotated synchronously with one another. In addition, the switch drum 500 can be rotated between a first position and a second position relative to the distal connector flange 601. When the switch drum 500 is in its first position, the articulation drive system may be operably disengaged from the firing drive system and, thus, the operation of the firing drive system may not articulate the end effector 300 of the interchangeable shaft assembly 200. When the switch drum 500 is in its second position, the articulation drive system may be operably engaged with the firing drive system and, thus, the operation of the firing drive system may articulate the end effector 300 of the interchangeable shaft assembly 200. When the switch drum 500 is moved between its first position and its second position, the switch drum 500 is moved relative to distal connector flange 601. In various instances, the interchangeable shaft assembly 200 can comprise at least one sensor configured to detect the position of the switch drum 500. Turning now to FIGS. 9, the distal connector flange 601 can comprise a magnetic field sensor 605, for example, and the switch drum 500 can comprise a magnetic element, such as permanent magnet 505, for example. The magnetic field sensor 605 can be configured to detect the position of the permanent magnet 505. When the switch drum 500 is rotated between its first position and its second position, the permanent magnet 505 can move relative to the magnetic field sensor 605. In various instances, magnetic field sensor 605 can detect changes in a magnetic field created when the permanent magnet 505 is moved. The magnetic field sensor 605 can be in signal communication with the shaft circuit board 610 and/or the circuit board 100 located in the handle, for example. Based on the signal from the magnetic field sensor 605, a controller on the shaft circuit board 610 and/or the circuit board 100 located in the handle can determine whether the articulation drive system is engaged with or disengaged from the firing drive system.

Figure 6:
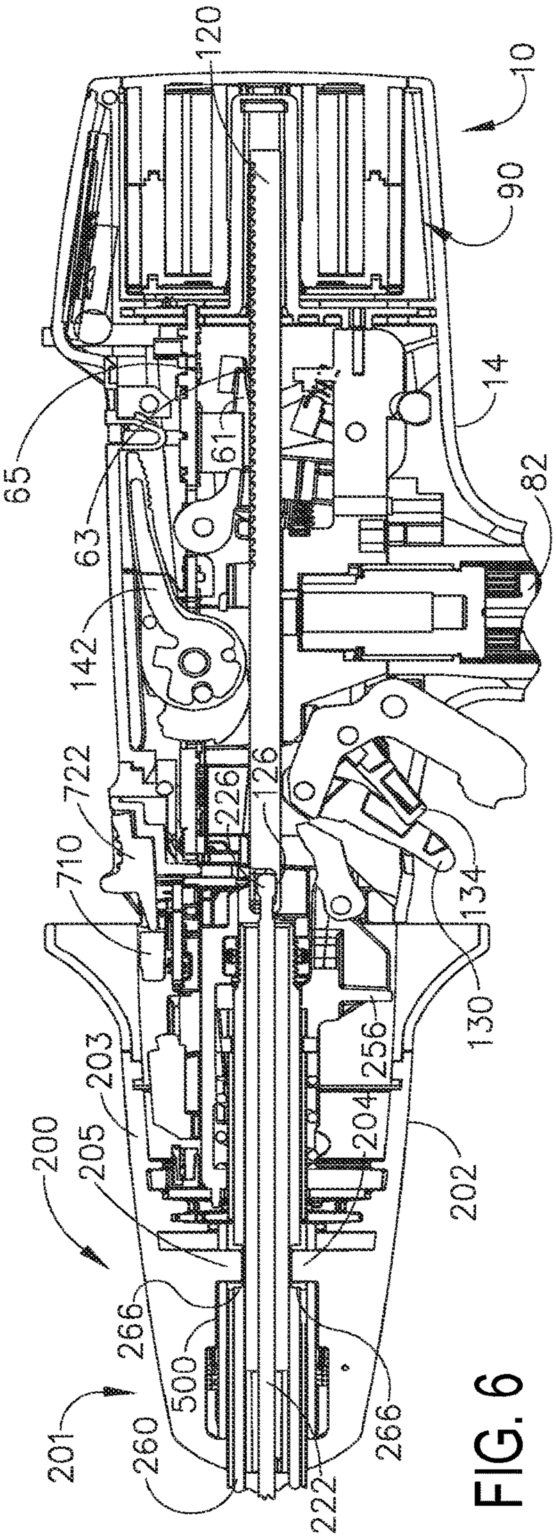
FIG. 6 is another cross-sectional view of a portion of the surgical instrument of FIG. 5 with the firing trigger in an unactuated position in accordance with one or more aspects of the present disclosure.

Referring again to FIG. 3, the chassis 240 includes at least one, and preferably two, tapered attachment portions 244 formed thereon that are adapted to be received within corresponding dovetail slots 702 formed within a distal attachment flange 700 of the frame 20. Each dovetail slot 702 may be tapered or, stated another way, be somewhat V-shaped to seatingly receive the tapered attachment portions 244 therein. As can be further seen in FIG. 3, a shaft attachment lug 226 is formed on the proximal end of the intermediate firing shaft 222. As will be discussed in further detail below, when the interchangeable shaft assembly 200 is coupled to the handle assembly 14, the shaft attachment lug 226 is received in a firing shaft attachment cradle 126 formed in the distal end 125 of the longitudinally movable drive member 120 as shown in FIGS. 3 and 6, for example.

Various shaft assemblies employ a latch system 710 for removably coupling the interchangeable shaft assembly 200 to the housing 12 and more specifically to the frame 20. The proximally protruding lock lugs 714 each have a pivot lock lugs 716 formed thereon that are adapted to be received in corresponding holes 245 formed in the chassis 240. Such arrangement facilitates pivotal attachment of the lock yoke 712 to the chassis 240. The lock yoke 712 may include two proximally protruding lock lugs 714 that are configured for releasable engagement with corresponding lock detents or grooves 704 in the distal attachment flange 700 of the frame 20. See FIG. 3. In various forms, the lock yoke 712 is biased in the proximal direction by spring or biasing member (not shown). Actuation of the lock yoke 712 may be accomplished by a latch button 722 that is slidably mounted on a latch actuator assembly 720 that is mounted to the chassis 240. The latch button 722 may be biased in a proximal direction relative to the lock yoke 712. As will be discussed in further detail below, the lock yoke 712 may be moved to an unlocked position by biasing the latch button the in distal direction which also causes the lock yoke 712 to pivot out of retaining engagement with the distal attachment flange 700 of the frame 20. When the lock yoke 712 is in "retaining engagement" with the distal attachment flange 700 of the frame 20, the pivot lock lugs 716 are retainingly seated within the corresponding lock detents or grooves 704 in the distal attachment flange 700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 32 to grasp and manipulate the target tissue into a desired position. Once the target tissue is positioned within the end effector 300 in a desired orientation, the clinician may then fully actuate the closure trigger 32 to close the anvil 306 and clamp the target tissue in position for cutting and stapling. In that instance, the first drive system 30 has been fully actuated. After the target tissue has been clamped in the end effector 300, it may be desirable to prevent the inadvertent detachment of the interchangeable shaft assembly 200 from the housing 12. One form of the latch system 710 is configured to prevent such inadvertent detachment.

The lock yoke 712 includes at least one, and preferably two, lock hooks 718 that are adapted to contact lock lugs 256 that are formed on the closure shuttle 250. Referring to FIGS. 10 and 11, when the closure shuttle 250 is in an unactuated position (i.e., the first closure drive system 30 is unactuated and the anvil 306 is open), the lock yoke 712 may be pivoted in a distal direction to unlock the interchangeable shaft assembly 200 from the housing 12. When in that position, the lock hooks 718 do not contact the lock lugs 256 on the closure shuttle 250. However, when the closure shuttle 250 is moved to an actuated position (i.e., the first closure drive system 30 is actuated and the anvil 306 is in the closed position), the lock yoke 712 is prevented from being pivoted to an unlocked position. See FIGS. 12 and 13. Stated another way, if the clinician were to attempt to pivot the lock yoke 712 to an unlocked position or, for example, the lock yoke 712 was in advertently bumped or contacted in a manner that might otherwise cause it to pivot distally, the lock hooks 718 on the lock yoke 712 will contact the lock lugs 256 on the closure shuttle 250 and prevent movement of the lock yoke 712 to an unlocked position.

Attachment of the interchangeable shaft assembly 200 to the handle assembly 14 will now be described with reference to FIG. 3. To commence the coupling process, the clinician may position the chassis 240 of the interchangeable shaft assembly 200 above or adjacent to the distal attachment flange 700 of the frame 20 such that the tapered attachment portions 244 formed on the chassis 240 are aligned with the dovetail slots 702 in the frame 20. The clinician may then move the interchangeable shaft assembly 200 along an installation axis IA that is perpendicular to the shaft axis SA-SA to seat the tapered attachment portions 244 in "operable engagement" with the corresponding dovetail receiving slots 702. In doing so, the shaft attachment lug 226 on the intermediate firing shaft 222 will also be seated in the firing shaft attachment cradle 126 in the longitudinally movable drive member 120 and the portions of the transverse attachment pin 37 on the second closure link 38 will be seated in the corresponding proximally-protruding hooks 252 in the closure shuttle 250. As used herein, the term "operable engagement" in the context of two components means that the two components are sufficiently engaged with each other so that upon application of an actuation motion thereto, the components may carry out their intended action, function and/or procedure.

As discussed above, at least five systems of the interchangeable shaft assembly 200 can be operably coupled with at least five corresponding systems of the handle assembly 14. A first system can comprise a frame system which couples and/or aligns the frame or spine of the interchangeable shaft assembly 200 with the frame 20 of the handle assembly 14. Another system can comprise a closure drive system 30 which can operably connect the closure trigger 32 of the handle assembly 14 and the closure tube 260 and the anvil 306 of the interchangeable shaft assembly 200. As outlined above, the closure shuttle 250 of the interchangeable shaft assembly 200 can be engaged with the transverse attachment pin 37 on the second closure link 38. Another system can comprise the firing drive system 80 which can operably connect the firing trigger 130 of the handle assembly 14 with the intermediate firing shaft 222 of the interchangeable shaft assembly 200.

As outlined above, the shaft attachment lug 226 can be operably connected with the firing shaft attachment cradle 126 of the longitudinally movable drive member 120. Another system can comprise an electrical system which can signal to a controller in the handle assembly 14, such as controller, for example, that a shaft assembly, such as the interchangeable shaft assembly 200, for example, has been operably engaged with the handle assembly 14 and/or, two, conduct power and/or communication signals between the interchangeable shaft assembly 200 and the handle assembly 14. For instance, the interchangeable shaft assembly 200 can include an electrical connector 1410 that is operably mounted to the shaft circuit board 610. The electrical connector 1410 located on the shaft is configured for mating engagement with an electrical connector 1400 on the circuit board 100 located in the handle. Further details regaining the circuitry and control systems may be found in U.S. Patent Application Publication No. 20140263541. The fifth system may consist of the latching system for releasably locking the interchangeable shaft assembly 200 to the handle assembly 14.

Figure 14:
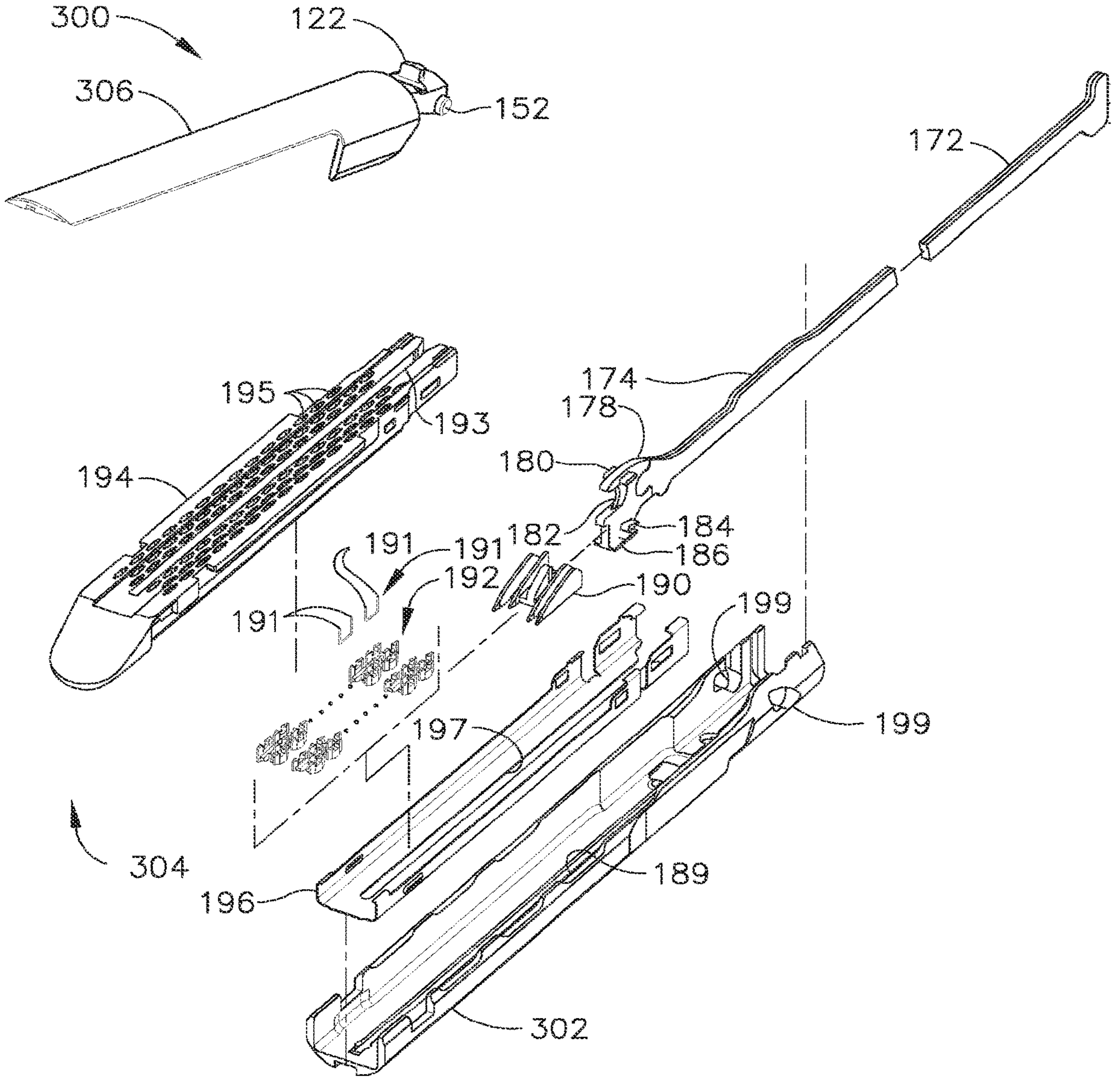
FIG. 14 is an exploded view of one aspect of an end effector of the surgical instrument of FIG. 1 in accordance with one or more aspects of the present disclosure.

Referring to FIG. 14, a non-limiting form of the end effector 300 is illustrated. As described above, the end effector 300 may include the anvil 306 and the surgical staple cartridge 304. In this non-limiting example, the anvil 306 is coupled to an elongated channel 198. For example, apertures 199 can be defined in the elongated channel 198 which can receive pins 152 extending from the anvil 306 and allow the anvil 306 to pivot from an open position to a closed position relative to the elongated channel 198 and surgical staple cartridge 304. In addition, FIG. 14 shows a firing bar 172, configured to longitudinally translate into the end effector 300. The firing bar 172 may be constructed from one solid section, or in various examples, may include a laminate material comprising, for example, a stack of steel plates. A distally projecting end of the firing bar 172 can be attached to an E-beam 178 that can, among other things, assist in spacing the anvil 306 from a surgical staple cartridge 304 positioned in the elongated channel 198 when the anvil 306 is in a closed position. The E-beam 178 can also include a sharpened cutting edge 182 which can be used to sever tissue as the E-beam 178 is advanced distally by the firing bar 172. In operation, the E-beam 178 can also actuate, or fire, the surgical staple cartridge 304. The surgical staple cartridge 304 can include a molded cartridge body 194 that holds a plurality of staples 191 resting upon staple drivers 192 within respective upwardly open staple cavities 195. A wedge sled 190 is driven distally by the E-beam 178, sliding upon a cartridge tray 196 that holds together the various components of the surgical staple cartridge 304. The wedge sled 190 upwardly cams the staple drivers 192 to force out the staples 191 into deforming contact with the anvil 306 while a cutting edge 182 of the E-beam 178 severs clamped tissue.

Further to the above, the E-beam 178 can include upper pins 180 which engage the anvil 306 during firing. The E-beam 178 can further include middle pins 184 and a bottom foot 186 which can engage various portions of the cartridge body 194, cartridge tray 196 and elongated channel 198. When a surgical staple cartridge 304 is positioned within the elongated channel 198, a slot 193 defined in the cartridge body 194 can be aligned with a longitudinal slot 197 defined in the cartridge tray 196 and a slot 189 defined in the elongated channel 198. In use, the E-beam 178 can slide through the aligned longitudinal slots 193, 197, and 189 wherein, as indicated in FIG. 14, the bottom foot 186 of the E-beam 178 can engage a groove running along the bottom surface of elongated channel 198 along the length of slot 189, the middle pins 184 can engage the top surfaces of cartridge tray 196 along the length of longitudinal slot 197, and the upper pins 180 can engage the anvil 306. In such circumstances, the E-beam 178 can space, or limit the relative movement between, the anvil 306 and the surgical staple cartridge 304 as the firing bar 172 is moved distally to fire the staples from the surgical staple cartridge 304 and/or incise the tissue captured between the anvil 306 and the surgical staple cartridge 304. Thereafter, the firing bar 172 and the E-beam 178 can be retracted proximally allowing the anvil 306 to be opened to release the two stapled and severed tissue portions (not shown).

Figure 15:
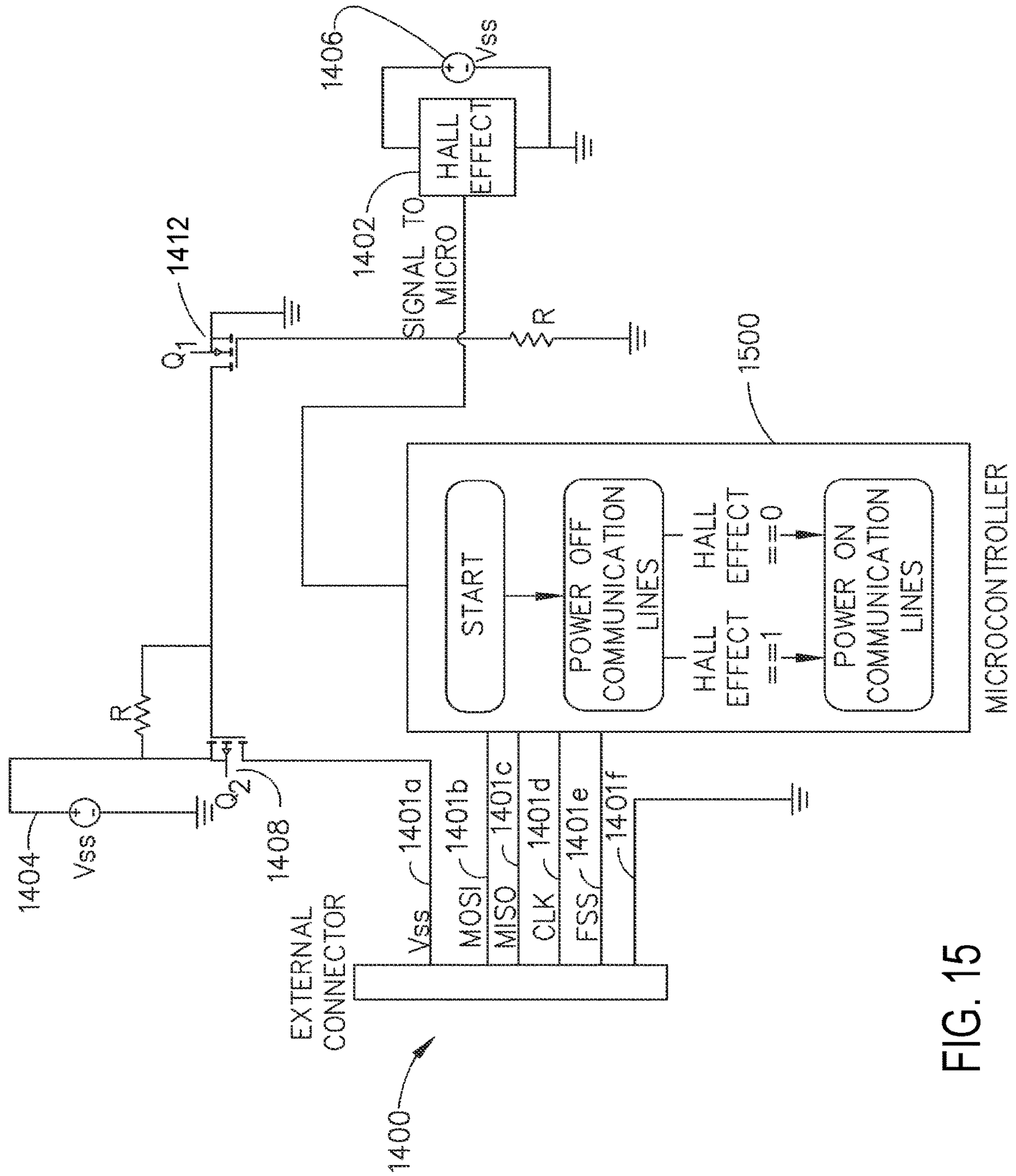
FIG. 15 is a schematic of a system for powering down an electrical connector of a surgical instrument handle when a shaft assembly is not coupled thereto in accordance with one or more aspects of the present disclosure.

Having described a surgical instrument 10 (FIGS. 1-14) in general terms, the description now turns to a detailed description of various electrical/electronic components of the surgical instrument 10. Referring again to FIGS. 2 and 3, the handle assembly 14 can include an electrical connector 1400 comprising a plurality of electrical contacts. Turning now to FIG. 15, the electrical connector 1400 can comprise a first electrical contact 1401*a*, a second electrical contact 1401*b*, a third electrical contact 1401*c*, a fourth electrical contact 1401*d*, a fifth electrical contact 1401*e*, and a sixth electrical contact 1401*f*, for example. While the illustrated example utilizes six contacts, other examples are envisioned which may utilize more than six contacts or less than six contacts.

As illustrated in FIG. 15, the first electrical contact 1401*a* can be in electrical communication with a transistor 1408, electrical contacts 1401*b*-1401*e* can be in electrical communication with a controller 1500, and the sixth electrical contact 1401*f* can be in electrical communication with a ground. In certain circumstances, one or more of the electrical contacts 1401*b*-1401*e* may be in electrical communication with one or more output channels of the controller 1500 and can be energized, or have a voltage potential applied thereto, when the handle 1042 is in a powered state. In some circumstances, one or more of the electrical contacts 1401*b*-1401*e* may be in electrical communication with one or more input channels of the controller 1500 and, when the handle assembly 14 is in a powered state, the controller 1500 can be configured to detect when a voltage potential is applied to such electrical contacts. When a shaft assembly, such as the interchangeable shaft assembly 200, for example, is assembled to the handle assembly 14, the electrical contacts 1401*a*-1401*f* may not communicate with each other. When a shaft assembly is not assembled to the handle assembly 14, however, the electrical contacts 1401*a*-1401*f* of the electrical connector 1400 may be exposed and, in some circumstances, one or more of the electrical contacts 1401*a*-1401*f* may be accidentally placed in electrical communication with each other. Such circumstances can arise when one or more of the electrical contacts 1401*a*-1401*f* come into contact with an electrically conductive material, for example. When this occurs, the controller 1500 can receive an erroneous input and/or the interchangeable shaft assembly 200 can receive an erroneous output, for example. To address this issue, in various circumstances, the handle assembly 14 may be unpowered when a shaft assembly, such as the interchangeable shaft assembly 200, for example, is not attached to the handle assembly 14.

In other circumstances, the handle 1042 can be powered when a shaft assembly, such as the interchangeable shaft assembly 200, for example, is not attached thereto. In such circumstances, the controller 1500 can be configured to ignore inputs, or voltage potentials, applied to the contacts in electrical communication with the controller 1500, i.e., electrical contacts 1401*b*-1401*e*, for example, until a shaft assembly is attached to the handle assembly 14. Even though the controller 1500 may be supplied with power to operate other functionalities of the handle assembly 14 in such circumstances, the handle assembly 14 may be in a powered-down state. In a way, the electrical connector 1400 may be in a powered-down state as voltage potentials applied to the electrical contacts 1401*b*-1401*e* may not affect the operation of the handle assembly 14. The reader will appreciate that, even though electrical contacts 1401*b*-1401*e* may be in a powered-down state, the electrical contacts 1401*a* and 1401*f*, which are not in electrical communication with the controller 1500, may or may not be in a powered-down state. For instance, sixth electrical contact 1401*f* may remain in electrical communication with a ground regardless of whether the handle assembly 14 is in a powered-up or a powered-down state.

Furthermore, the transistor 1408, and/or any other suitable arrangement of transistors, such as transistor 1412, for example, and/or switches may be configured to control the supply of power from a power source 1404, such as a battery, within the handle assembly 14, for example, to the first electrical contact 1401*a* regardless of whether the handle assembly 14 is in a powered-up or a powered-down state. In various circumstances, the interchangeable shaft assembly 200, for example, can be configured to change the state of the transistor 1408 when the interchangeable shaft assembly 200 is engaged with the handle assembly 14. In certain circumstances, further to the below, a magnetic field sensor 1402 can be configured to switch the state of transistor 1412 which, as a result, can switch the state of transistor 1408 and ultimately supply power from power source 1404 to first electrical contact 1401*a*. In this way, both the power circuits and the signal circuits to the electrical connector 1400 can be powered down when a shaft assembly is not installed to the handle assembly 14 and powered up when a shaft assembly is installed to the handle assembly 14.

In various circumstances, referring again to FIG. 15, the handle assembly 14 can include the magnetic field sensor 1402, for example, which can be configured to detect a detectable element, such as a magnetic element 1407 (FIG. 3), for example, on a shaft assembly, such as the interchangeable shaft assembly 200, for example, when the shaft assembly is coupled to the handle assembly 14. The magnetic field sensor 1402 can be powered by a power source 1406, such as a battery, for example, which can, in effect, amplify the detection signal of the magnetic field sensor 1402 and communicate with an input channel of the controller 1500 via the circuit illustrated in FIG. 15. Once the controller 1500 has a received an input indicating that a shaft assembly has been at least partially coupled to the handle assembly 14, and that, as a result, the electrical contacts 1401*a*-1401*f* are no longer exposed, the controller 1500 can enter into its normal, or powered-up, operating state. In such an operating state, the controller 1500 will evaluate the signals transmitted to one or more of the electrical contacts 1401*b*-1401*e* from the shaft assembly and/or transmit signals to the shaft assembly through one or more of the electrical contacts 1401*b*-1401*e* in normal use thereof. In various circumstances, the interchangeable shaft assembly 200 may have to be fully seated before the magnetic field sensor 1402 can detect the magnetic element 1407. While a magnetic field sensor 1402 can be utilized to detect the presence of the interchangeable shaft assembly 200, any suitable system of sensors and/or switches can be utilized to detect whether a shaft assembly has been assembled to the handle assembly 14, for example. In this way, further to the above, both the power circuits and the signal circuits to the electrical connector 1400 can be powered down when a shaft assembly is not installed to the handle assembly 14 and powered up when a shaft assembly is installed to the handle assembly 14.

In various examples, as may be used throughout the present disclosure, any suitable magnetic field sensor may be employed to detect whether a shaft assembly has been assembled to the handle assembly 14, for example. For example, the technologies used for magnetic field sensing include Hall effect sensor, search coil, fluxgate, optically pumped, nuclear precession, SQUID (superconducting quantum interference device—a very sensitive magnetometer used to measure extremely subtle magnetic fields, based on superconducting loops containing Josephson junctions), Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

Referring to FIG. 15, the controller 1500 may generally comprise a processor ("microprocessor") and one or more memory units operationally coupled to the processor. By executing instruction code stored in the memory, the processor may control various components of the surgical instrument, such as the motor, various drive systems, and/or a user display, for example. The controller 1500 may be implemented using integrated and/or discrete hardware elements, software elements, and/or a combination of both. Examples of integrated hardware elements may include processors, microprocessors, controllers, controllers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, controllers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the controller 1500 may include a hybrid circuit comprising discrete and integrated circuit elements or components on one or more substrates, for example.

Referring to FIG. 15, the controller 1500 may be an LM4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available from the product datasheet. Other controllers may be readily substituted for use with the present disclosure. Accordingly, the present disclosure should not be limited in this context.

As discussed above, the handle assembly 14 and/or the interchangeable shaft assembly 200 can include systems and configurations configured to prevent, or at least reduce the possibility of, the contacts of the electrical connector 1400 located on the handle and/or the contacts of the electrical connector 1410 located on the shaft from becoming shorted out when the interchangeable shaft assembly 200 is not assembled, or completely assembled, to the handle assembly 14. Referring to FIG. 3, the electrical connector 1400 located on the handle can be at least partially recessed within a cavity 1409 defined in the frame 20. The six electrical contacts 1401*a*-1401*f* of the electrical connector 1400 can be completely recessed within the cavity 1409. Such arrangements can reduce the possibility of an object accidentally contacting one or more of the electrical contacts 1401*a*-1401*f*. Similarly, the electrical connector 1410 located on the shaft can be positioned within a recess defined in the chassis 240 which can reduce the possibility of an object accidentally contacting one or more of the electrical contacts 1411*a*-1411*f* of the electrical connector 1410 located on the shaft. With regard to the particular example depicted in FIG. 3, the electrical contacts 1411*a*-1411*f* located on the shaft can comprise male contacts. In at least one example, each of the electrical contacts 1411*a*-1411*f* located in the shaft can comprise a flexible projection extending therefrom which can be configured to engage an electrical contact 1401*a*-1401*f* located on the handle, for example. The electrical contacts 1401*a*-1401*f* located on the handle can comprise female contacts. In at least one example, each electrical contact 1401*a*-1401*f* located on the handle can comprise a flat surface, for example, against which the male electrical contacts 1401*a*-1401*f* located on the shaft can wipe, or slide, against and maintain an electrically conductive interface therebetween. In various instances, the direction in which the interchangeable shaft assembly 200 is assembled to the handle assembly 14 can be parallel to, or at least substantially parallel to, the electrical contacts 1401*a*-1401*f* located on the handle such that the electrical contacts 1411*a*-1411*f* located on the shaft slide against the electrical contacts 1401*a*-1401*f* located on the handle when the interchangeable shaft assembly 200 is assembled to the handle assembly 14. In various alternative examples, the electrical contacts 1401*a*-1401*f* located in the handle can comprise male contacts and the electrical contacts 1411*a*-1411*f* located on the shaft can comprise female contacts. In certain alternative examples, the electrical contacts 1401*a*-1401*f* located on the handle and the electrical contacts 1411*a*-1411*f* located on the shaft can comprise any suitable arrangement of contacts.

In various instances, the handle assembly 14 can comprise a connector guard configured to at least partially cover the electrical connector 1400 located on the handle and/or a connector guard configured to at least partially cover the electrical connector 1410 located on the shaft. A connector guard can prevent, or at least reduce the possibility of, an object accidentally touching the contacts of an electrical connector when the shaft assembly is not assembled to, or only partially assembled to, the handle. A connector guard can be movable. For instance, the connector guard can be moved between a guarded position in which it at least partially guards a connector and an unguarded position in which it does not guard, or at least guards less of, the connector. In at least one example, a connector guard can be displaced as the shaft assembly is being assembled to the handle. For instance, if the handle comprises a handle connector guard, the shaft assembly can contact and displace the handle connector guard as the shaft assembly is being assembled to the handle. Similarly, if the shaft assembly comprises a shaft connector guard, the handle can contact and displace the shaft connector guard as the shaft assembly is being assembled to the handle. In various instances, a connector guard can comprise a door, for example. In at least one instance, the door can comprise a beveled surface which, when contacted by the handle or shaft, can facilitate the displacement of the door in a certain direction. In various instances, the connector guard can be translated and/or rotated, for example. In certain instances, a connector guard can comprise at least one film which covers the contacts of an electrical connector. When the shaft assembly is assembled to the handle, the film can become ruptured. In at least one instance, the male contacts of a connector can penetrate the film before engaging the corresponding contacts positioned underneath the film.

As described above, the surgical instrument can include a system which can selectively power-up, or activate, the contacts of an electrical connector, such as the electrical connector 1400, for example. In various instances, the contacts can be transitioned between an unactivated condition and an activated condition. In certain instances, the contacts can be transitioned between a monitored condition, a deactivated condition, and an activated condition. For instance, the controller 1500, for example, can monitor the electrical contacts 1401*a*-1401*f* when a shaft assembly has not been assembled to the handle assembly 14 to determine whether one or more of the electrical contacts 1401*a*-1401*f* may have been shorted. The controller 1500 can be configured to apply a low voltage potential to each of the electrical contacts 1401*a*-1401*f* and assess whether only a minimal resistance is present at each of the contacts. Such an operating state can comprise the monitored condition. In the event that the resistance detected at a contact is high, or above a threshold resistance, the controller 1500 can deactivate that contact, more than one contact, or, alternatively, all of the contacts. Such an operating state can comprise the deactivated condition. If a shaft assembly is assembled to the handle assembly 14 and it is detected by the controller 1500, as discussed above, the controller 1500 can increase the voltage potential to the electrical contacts 1401*a*-1401*f*. Such an operating state can comprise the activated condition.

The various shaft assemblies disclosed herein may employ sensors and various other components that require electrical communication with the controller in the housing. These shaft assemblies generally are configured to be able to rotate relative to the housing necessitating a connection that facilitates such electrical communication between two or more components that may rotate relative to each other. When employing end effectors of the types disclosed herein, the connector arrangements must be relatively robust in nature while also being somewhat compact to fit into the shaft assembly connector portion.

Figure 16A:
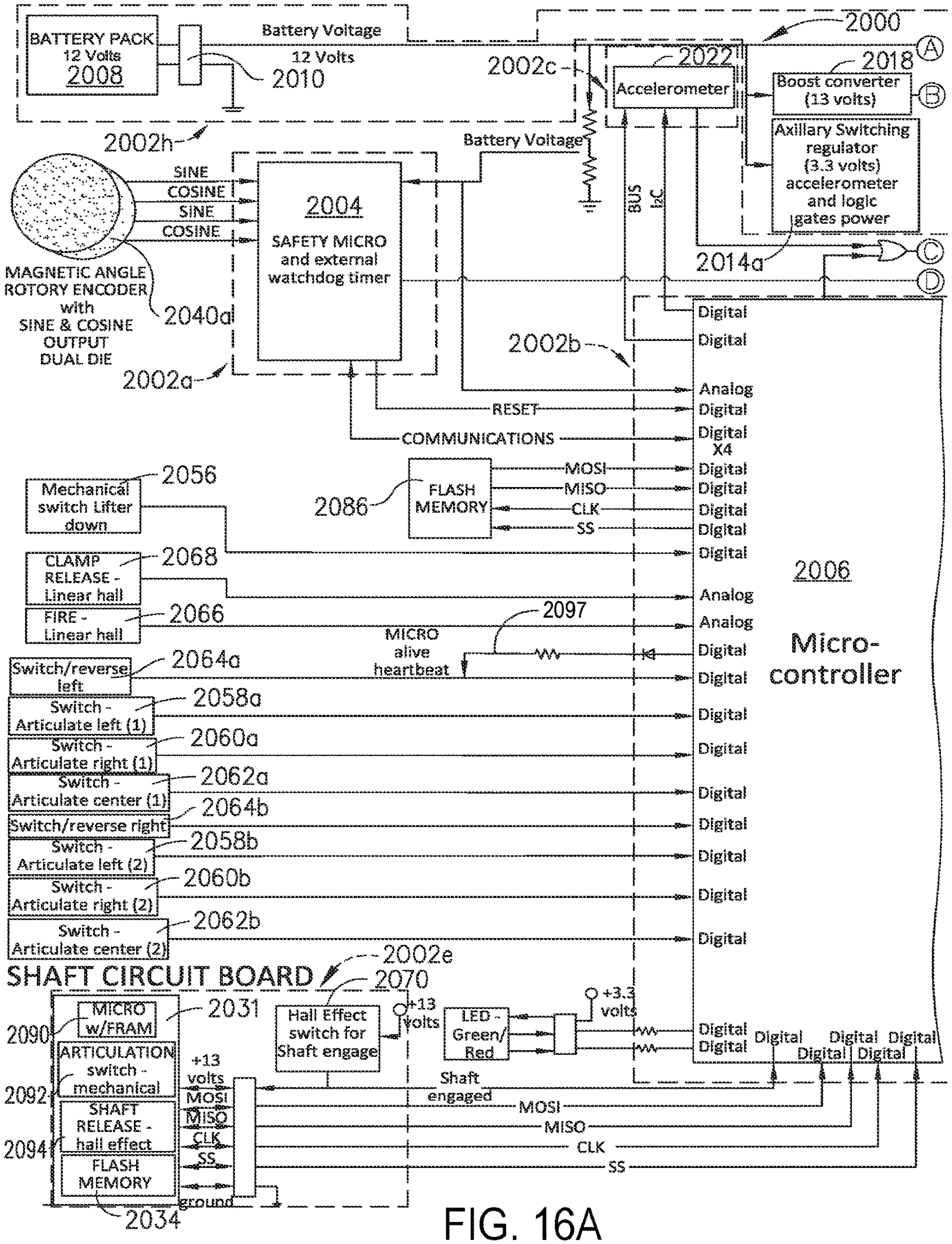
FIGS. 16A-16B is a circuit diagram of the surgical instrument of FIG. 1 spanning two drawings sheets in accordance with one or more aspects of the present disclosure
Figure 16B:
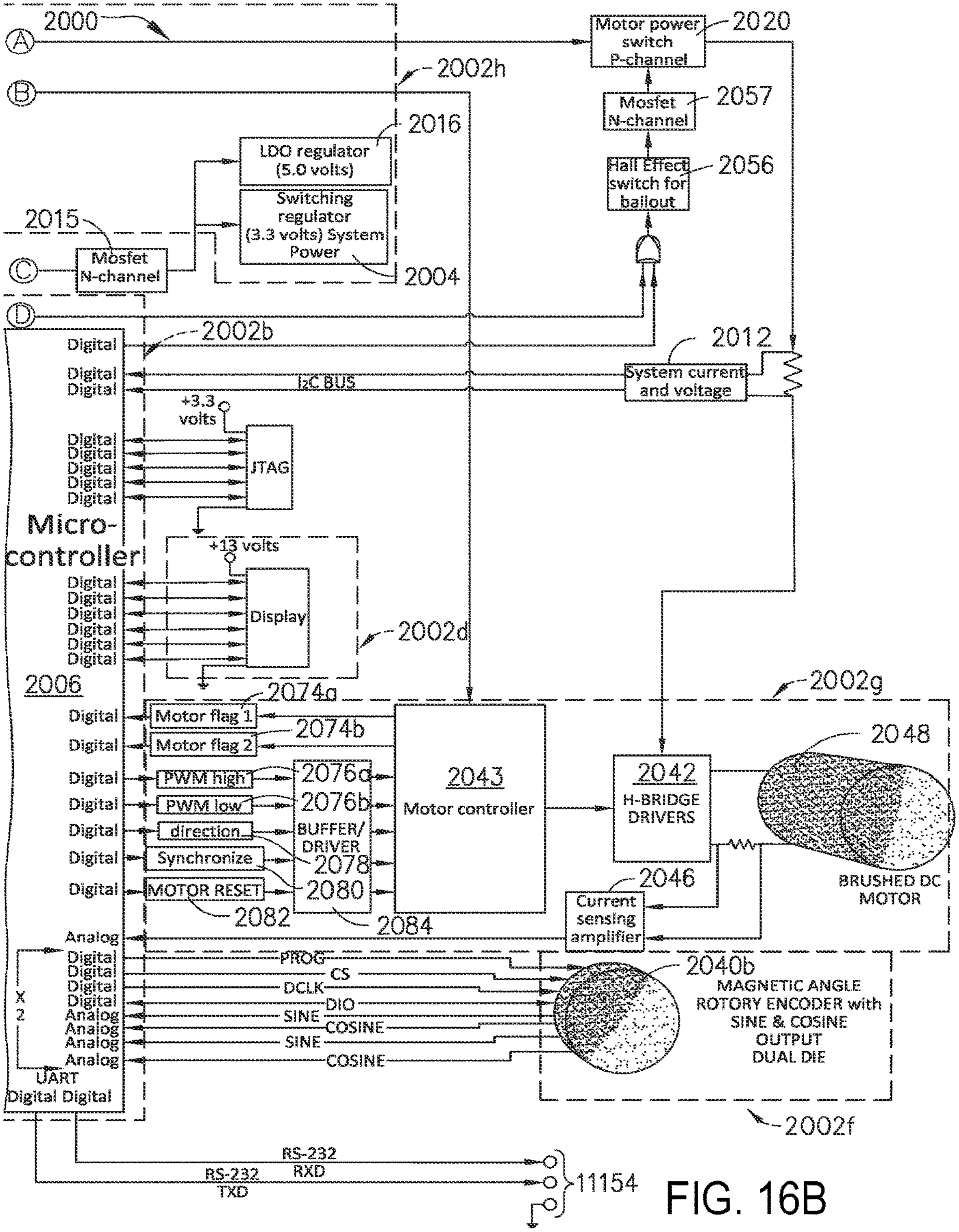

Turning now to FIGS. 16A and 16B, where one example of a segmented circuit 2000 comprising a plurality of circuit segments 2002*a*-2002*g* is illustrated. The segmented circuit 2000 comprising the plurality of circuit segments 2002*a*-2002*g* is configured to control a powered surgical instrument, such as, for example, the surgical instrument 10 illustrated in FIGS. 1-13, without limitation. The plurality of circuit segments 2002*a*-2002*g* is configured to control one or more operations of the powered surgical instrument 10. A safety processor segment 2002*a* (Segment 1) comprises a safety processor 2004. A primary processor segment 2002*b* (Segment 2) comprises a primary processor 2006. The safety processor 2004 and/or the primary processor 2006 are configured to interact with one or more additional circuit segments 2002*c*-2002*g* to control operation of the powered surgical instrument 10. The primary processor 2006 comprises a plurality of inputs coupled to, for example, one or more circuit segments 2002*c*-2002*g*, a battery 2008, and/or a plurality of switches 2058*a*-2070. The segmented circuit 2000 may be implemented by any suitable circuit, such as, for example, a printed circuit board assembly (PCBA) within the powered surgical instrument 10. It should be understood that the term processor as used herein includes any microprocessor, processors, controller, controllers, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one aspect, the primary processor 2006 may be any single core or multicore processor such as those known under the trade name ARM Cortex by Texas Instruments. In one example, the safety processor 2004 may be a safety controller platform comprising two controller-based families such as TMS570 and RM4x known under the trade name Hercules ARM Cortex R4, also by Texas Instruments. Nevertheless, other suitable substitutes for controllers and safety processor may be employed, without limitation. In one example, the safety processor 2004 may be configured specifically for IEC 61508 and ISO 26262 safety critical applications, among others, to provide advanced integrated safety features while delivering scalable performance, connectivity, and memory options. In certain instances, the primary processor 2006 may be a single core or multicore controller LM4F230H5QR as described in connection with FIGS. 14-17B.

In one aspect, the segmented circuit 2000 comprises an acceleration segment 2002*c* (Segment 3). The acceleration segment 2002*c* comprises an accelerometer 2022. The accelerometer 2022 is configured to detect movement or acceleration of the powered surgical instrument 10. In some examples, input from the accelerometer 2022 is used, for example, to transition to and from a sleep mode, identify an orientation of the powered surgical instrument, and/or identify when the surgical instrument has been dropped. In some examples, the acceleration segment 2002*c* is coupled to the safety processor 2004 and/or the primary processor 2006.

In one aspect, the segmented circuit 2000 comprises a display segment 2002*d* (Segment 4). The display segment 2002*d* comprises a display connector 2024 coupled to the primary processor 2006. The display connector 2024 couples the primary processor 2006 to a display 2028 through one or more integrated circuit drivers of the display 2026. The integrated circuit drivers of the display 2026 may be integrated with the display 2028 and/or may be located separately from the display 2028. The display 2028 may comprise any suitable display, such as, for example, an organic light-emitting diode (OLED) display, a liquid-crystal display (LCD), and/or any other suitable display. In some examples, the display segment 2002*d* is coupled to the safety processor 2004.

In some aspects, the segmented circuit 2000 comprises a shaft segment 2002*e* (Segment 5). The shaft segment 2002*e* comprises one or more controls for an interchangeable shaft assembly 200 (FIG. 1) coupled to the surgical instrument 10 and/or one or more controls for an end effector 300 coupled to the interchangeable shaft assembly 200 (FIG. 1). The shaft segment 2002*e* comprises a shaft connector 2030 configured to couple the primary processor 2006 to a shaft PCBA 2031. The shaft PCBA 2031 comprises a first articulation switch 2036, a second articulation switch 2032, and a shaft PCBA EEPROM 2034. In some examples, the shaft PCBA EEPROM 2034 comprises one or more parameters, routines, and/or programs specific to the interchangeable shaft assembly 200 and/or the shaft PCBA 2031. The shaft PCBA 2031 may be coupled to the interchangeable shaft assembly 200 and/or integral with the surgical instrument 10. In some examples, the shaft segment 2002*e* comprises a second shaft EEPROM 2038. The second shaft EEPROM 2038 comprises a plurality of algorithms, routines, parameters, and/or other data corresponding to one or more shaft assemblies 200 and/or end effectors 300 which may be interfaced with the powered surgical instrument 10.

In some aspects, the segmented circuit 2000 comprises a position encoder segment 2002*f* (Segment 6). The position encoder segment 2002*f* comprises one or more magnetic angle rotary position encoders 2040*a*-2040*b*. The one or more magnetic angle rotary position encoders 2040*a*-2040*b* are configured to identify the rotational position of a motor 2048, an interchangeable shaft assembly 200 (FIG. 1), and/or an end effector 300 of the surgical instrument 10. In some examples, the magnetic angle rotary position encoders 2040*a*-2040*b* may be coupled to the safety processor 2004 and/or the primary processor 2006.

In some aspects, the segmented circuit 2000 comprises a motor circuit segment 2002*g* (Segment 7). The motor circuit segment 2002*g* comprises a motor 2048 configured to control one or more movements of the powered surgical instrument 10. The motor 2048 is coupled to the primary processor 2006 by an H-Bridge driver 2042 and one or more H-bridge field-effect transistors 2044 (FETs). The H-bridge FETs 2044 are coupled to the safety processor 2004. A motor current sensor 2046 is coupled in series with the motor 2048 to measure the current draw of the motor 2048. The motor current sensor 2046 is in signal communication with the primary processor 2006 and/or the safety processor 2004. In some examples, the motor 2048 is coupled to a motor electromagnetic interference (EMI) filter 2050.

In some aspects, the segmented circuit 2000 comprises a power segment 2002*h* (Segment 8). A battery 2008 is coupled to the safety processor 2004, the primary processor 2006, and one or more of the additional circuit segments 2002*c*-2002*g*. The battery 2008 is coupled to the segmented circuit 2000 by a battery connector 2010 and a current sensor 2012. The current sensor 2012 is configured to measure the total current draw of the segmented circuit 2000. In some examples, one or more voltage converters 2014*a*, 2014*b*, 2016 are configured to provide predetermined voltage values to one or more circuit segments 2002*a*-2002*g*. For example, in some examples, the segmented circuit 2000 may comprise 3.3V voltage converters 2014*a*-2014*b* and/or 5V voltage converters 2016. A boost converter 2018 is configured to provide a boost voltage up to a predetermined amount, such as, for example, up to 13V. The boost converter 2018 is configured to provide additional voltage and/or current during power intensive operations and prevent brownout or low-power conditions.

In some aspects, the safety processor segment 2002*a* comprises a motor power switch 2020. The motor power switch 2020 is coupled between the power segment 2002*h* and the motor circuit segment 2002*g*. The safety processor segment 2002*a* is configured to interrupt power to the motor circuit segment 2002*g* when an error or fault condition is detected by the safety processor 2004 and/or the primary processor 2006 as discussed in more detail herein. Although the circuit segments 2002*a*-2002*g* are illustrated with all components of the circuit segments 2002*a*-2002*h* located in physical proximity, one skilled in the art will recognize that a circuit segment 2002*a*-2002*h* may comprise components physically and/or electrically separate from other components of the same circuit segment 2002*a*-2002*g*. In some examples, one or more components may be shared between two or more circuit segments 2002*a*-2002*g*.

In some aspects, a plurality of switches 2056-2070 are coupled to the safety processor 2004 and/or the primary processor 2006. The plurality of switches 2056-2070 may be configured to control one or more operations of the surgical instrument 10, control one or more operations of the segmented circuit 2000, and/or indicate a status of the surgical instrument 10. For example, a bail-out door switch 2056 is configured to indicate the status of a bail-out door. A plurality of articulation switches, such as, for example, a left side articulation left switch 2058*a*, a left side articulation right switch 2060*a*, a left side articulation center switch 2062*a*, a right side articulation left switch 2058*b*, a right side articulation right switch 2060*b*, and a right side articulation center switch 2062*b* are configured to control articulation of a shaft assembly 200 and/or an end effector 300. A left side reverse switch 2064*a* and a right side reverse switch 2064*b* are coupled to the primary processor 2006. In some examples, the left side switches comprising the left side articulation left switch 2058*a*, the left side articulation right switch 2060*a*, the left side articulation center switch 2062*a*, and the left side reverse switch 2064*a* are coupled to the primary processor 2006 by a left flex connector 2072*a*. The right side switches comprising the right side articulation left switch 2058*b*, the right side articulation right switch 2060*b*, the right side articulation center switch 2062*b*, and the right side reverse switch 2064*b* are coupled to the primary processor 2006 by a right flex connector 2072*b*. In some examples, a firing switch 2066, a clamp release switch 2068, and a shaft engaged switch 2070 are coupled to the primary processor 2006.

In some aspects, the plurality of switches 2056-2070 may comprise, for example, a plurality of handle controls mounted to a handle of the surgical instrument 10, a plurality of indicator switches, and/or any combination thereof. In various examples, the plurality of switches 2056-2070 allow a surgeon to manipulate the surgical instrument, provide feedback to the segmented circuit 2000 regarding the position and/or operation of the surgical instrument, and/or indicate unsafe operation of the surgical instrument 10. In some examples, additional or fewer switches may be coupled to the segmented circuit 2000, one or more of the switches 2056-2070 may be combined into a single switch, and/or expanded to multiple switches. For example, in one example, one or more of the left side and/or right side articulation switches 2058*a*-2064*b* may be combined into a single multi-position switch.

In one aspect, the safety processor 2004 is configured to implement a watchdog function, among other safety operations. The safety processor 2004 and the primary processor 2006 of the segmented circuit 2000 are in signal communication. A processor alive heartbeat signal is provided at output 2097. The acceleration segment 2002*c* comprises an accelerometer 2022 configured to monitor movement of the surgical instrument 10. In various examples, the accelerometer 2022 may be a single, double, or triple axis accelerometer. The accelerometer 2022 may be employed to measures proper acceleration that is not necessarily the coordinate acceleration (rate of change of velocity). Instead, the accelerometer sees the acceleration associated with the phenomenon of weight experienced by a test mass at rest in the frame of reference of the accelerometer 2022. For example, the accelerometer 2022 at rest on the surface of the earth will measure an acceleration $g=9.8\ m/s^2$ (gravity) straight upwards, due to its weight. Another type of acceleration that accelerometer 2022 can measure is g-force acceleration. In various other examples, the accelerometer 2022 may comprise a single, double, or triple axis accelerometer. Further, the acceleration segment 2002*c* may comprise one or more inertial sensors to detect and measure acceleration, tilt, shock, vibration, rotation, and multiple degrees-of-freedom (DoF). A suitable inertial sensor may comprise an accelerometer (single, double, or triple axis), a magnetometer to measure a magnetic field in space such as the earth's magnetic field, and/or a gyroscope to measure angular velocity.

In one aspect, the safety processor 2004 is configured to implement a watchdog function with respect to one or more circuit segments 2002*c*-2002*h*, such as, for example, the motor circuit segment 2002*g*. In this regards, the safety processor 2004 employs the watchdog function to detect and recover from malfunctions of the primary processor 2006. During normal operation, the safety processor 2004 monitors for hardware faults or program errors of the primary processor 2006 and to initiate corrective action or actions. The corrective actions may include placing the primary processor 2006 in a safe state and restoring normal system operation. In one example, the safety processor 2004 is coupled to at least a first sensor. The first sensor measures a first property of the surgical instrument 10 (FIGS. 1-4). In some examples, the safety processor 2004 is configured to compare the measured property of the surgical instrument 10 to a predetermined value. For example, in one example, a magnetic angle rotary position encoder 2040*a* is coupled to the safety processor 2004. The magnetic angle rotary position encoder 2040*a* provides motor speed and position information to the safety processor 2004. The safety processor 2004 monitors the magnetic angle rotary position encoder 2040*a* and compares the value to a maximum speed and/or position value and prevents operation of the motor 2048 above the predetermined values. In some examples, the predetermined values are calculated based on real-time speed and/or position of the motor 2048, calculated from values supplied by a second magnetic angle rotary position encoder 2040*b* in communication with the primary processor 2006, and/or provided to the safety processor 2004 from, for example, a memory module coupled to the safety processor 2004.

In some aspects, a second sensor is coupled to the primary processor 2006. The second sensor is configured to measure the first physical property. The safety processor 2004 and the primary processor 2006 are configured to provide a signal indicative of the value of the first sensor and the second sensor respectively. When either the safety processor 2004 or the primary processor 2006 indicates a value outside of an acceptable range, the segmented circuit 2000 prevents operation of at least one of the circuit segments 2002*c*-2002*h*, such as, for example, the motor circuit segment 2002*g*. For example, in the example illustrated in FIGS. 16A and 16B, the safety processor 2004 is coupled to a first magnetic angle rotary position encoder 2040*a* and the primary processor 2006 is coupled to a second magnetic angle rotary position encoder 2040*b*. The magnetic angle rotary position encoders 2040*a*, 2040*b* may comprise any suitable motor position sensor, such as, for example, a magnetic angle rotary input comprising a sine and cosine output. The magnetic angle rotary position encoders 2040*a*, 2040*b* provide respective signals to the safety processor 2004 and the primary processor 2006 indicative of the position of the motor 2048.

The safety processor 2004 and the primary processor 2006 generate an activation signal when the values of the first magnetic angle rotary position encoder 2040*a* and the second magnetic angle rotary position encoder 2040*b* are within a predetermined range. When either the primary processor 2006 or the safety processor 2004 to detect a value outside of the predetermined range, the activation signal is terminated and operation of at least one of the circuit segments 2002*c*-2002*h*, such as, for example, the motor circuit segment 2002*g*, is interrupted and/or prevented. For example, in some examples, the activation signal from the primary processor 2006 and the activation signal from the safety processor 2004 are coupled to an AND gate. The AND gate is coupled to a motor power switch 2020. The AND gate maintains the motor power switch 2020 in a closed, or on, position when the activation signal from both the safety processor 2004 and the primary processor 2006 are high, indicating a value of the magnetic angle rotary position encoders 2040*a*, 2040*b* within the predetermined range. When either of the magnetic angle rotary position encoders 2040*a*, 2040*b* detect a value outside of the predetermined range, the activation signal from that magnetic angle rotary position encoder 2040*a*, 2040*b* is set low, and the output of the AND gate is set low, opening the motor power switch 2020. In some examples, the value of the first magnetic angle rotary position encoder 2040*a* and the second magnetic angle rotary position encoder 2040*b* is compared, for example, by the safety processor 2004 and/or the primary processor 2006. When the values of the first sensor and the second sensor are different, the safety processor 2004 and/or the primary processor 2006 may prevent operation of the motor circuit segment 2002*g*.

In some aspects, the safety processor 2004 receives a signal indicative of the value of the second magnetic angle rotary position encoder 2040*b* and compares the second sensor value to the first sensor value. For example, in one aspect, the safety processor 2004 is coupled directly to a first magnetic angle rotary position encoder 2040*a*. A second magnetic angle rotary position encoder 2040*b* is coupled to a primary processor 2006, which provides the second magnetic angle rotary position encoder 2040*b* value to the safety processor 2004, and/or coupled directly to the safety processor 2004. The safety processor 2004 compares the value of the first magnetic angle rotary position encoder 2040 to the value of the second magnetic angle rotary position encoder 2040*b*. When the safety processor 2004 detects a mismatch between the first magnetic angle rotary position encoder 2040*a* and the second magnetic angle rotary position encoder 2040*b*, the safety processor 2004 may interrupt operation of the motor circuit segment 2002*g*, for example, by cutting power to the motor circuit segment 2002*g*.

In some aspects, the safety processor 2004 and/or the primary processor 2006 is coupled to a first magnetic angle rotary position encoder 2040*a* configured to measure a first property of a surgical instrument and a second magnetic angle rotary position encoder 2040*b* configured to measure a second property of the surgical instrument. The first property and the second property comprise a predetermined relationship when the surgical instrument is operating normally. The safety processor 2004 monitors the first property and the second property. When a value of the first property and/or the second property inconsistent with the predetermined relationship is detected, a fault occurs. When a fault occurs, the safety processor 2004 takes at least one action, such as, for example, preventing operation of at least one of the circuit segments, executing a predetermined operation, and/or resetting the primary processor 2006. For example, the safety processor 2004 may open the motor power switch 2020 to cut power to the motor circuit segment 2002*g* when a fault is detected.

In one aspect, the safety processor 2004 is configured to execute an independent control algorithm. In operation, the safety processor 2004 monitors the segmented circuit 2000 and is configured to control and/or override signals from other circuit components, such as, for example, the primary processor 2006, independently. The safety processor 2004 may execute a preprogrammed algorithm and/or may be updated or programmed on the fly during operation based on one or more actions and/or positions of the surgical instrument 10. For example, in one example, the safety processor 2004 is reprogrammed with new parameters and/or safety algorithms each time a new shaft and/or end effector is coupled to the surgical instrument 10. In some examples, one or more safety values stored by the safety processor 2004 are duplicated by the primary processor 2006. Two-way error detection is performed to ensure values and/or parameters stored by either of the safety processor 2004 or primary processor 2006 are correct.

In some aspects, the safety processor 2004 and the primary processor 2006 implement a redundant safety check. The safety processor 2004 and the primary processor 2006 provide periodic signals indicating normal operation. For example, during operation, the safety processor 2004 may indicate to the primary processor 2006 that the safety processor 2004 is executing code and operating normally. The primary processor 2006 may, likewise, indicate to the safety processor 2004 that the primary processor 2006 is executing code and operating normally. In some examples, communication between the safety processor 2004 and the primary processor 2006 occurs at a predetermined interval. The predetermined interval may be constant or may be variable based on the circuit state and/or operation of the surgical instrument 10.

Figure 17A:
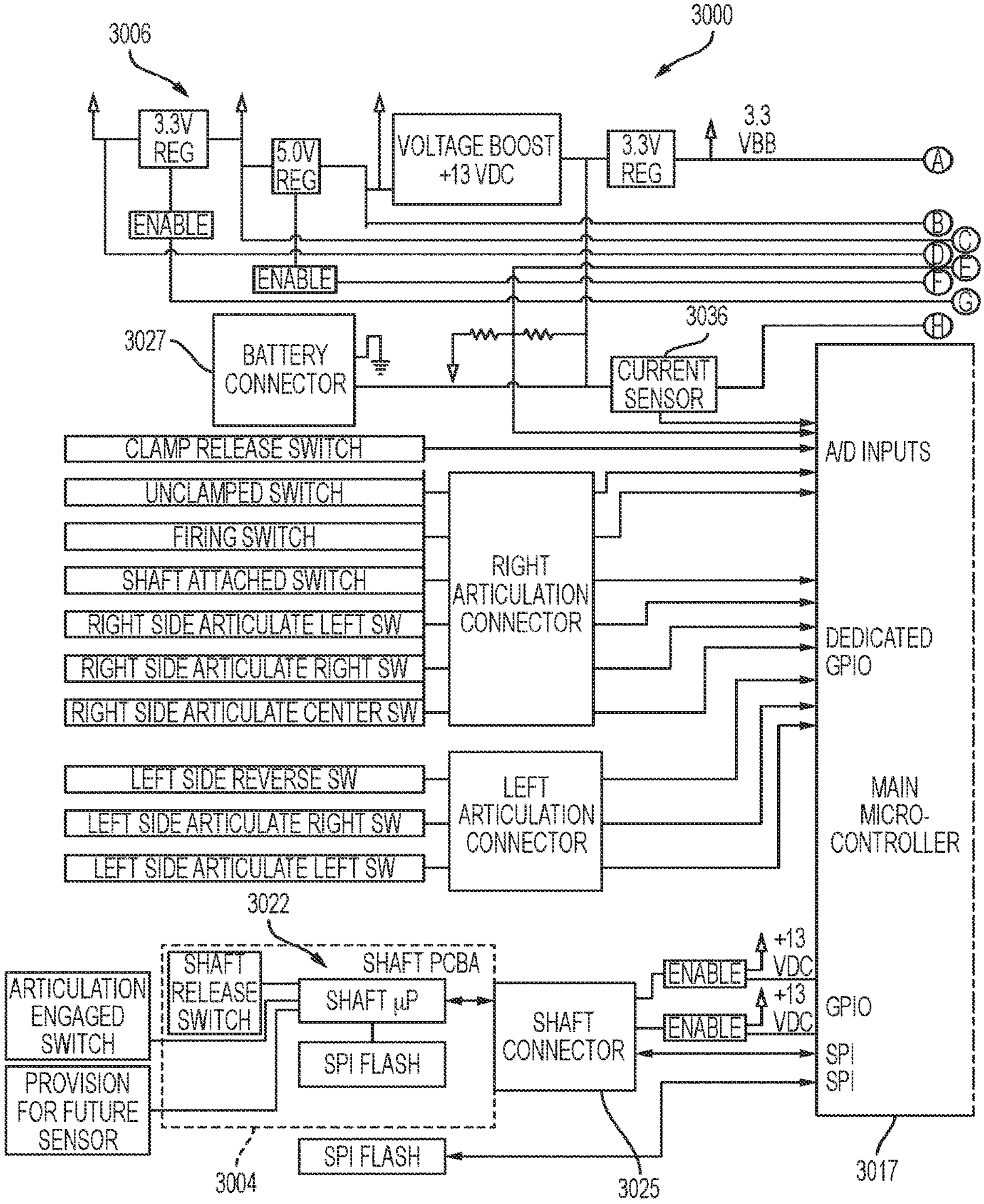
FIGS. 17A-17B is a circuit diagram of the surgical instrument of FIG. 1 in accordance with one or more aspects of the present disclosure.
Figure 17B:
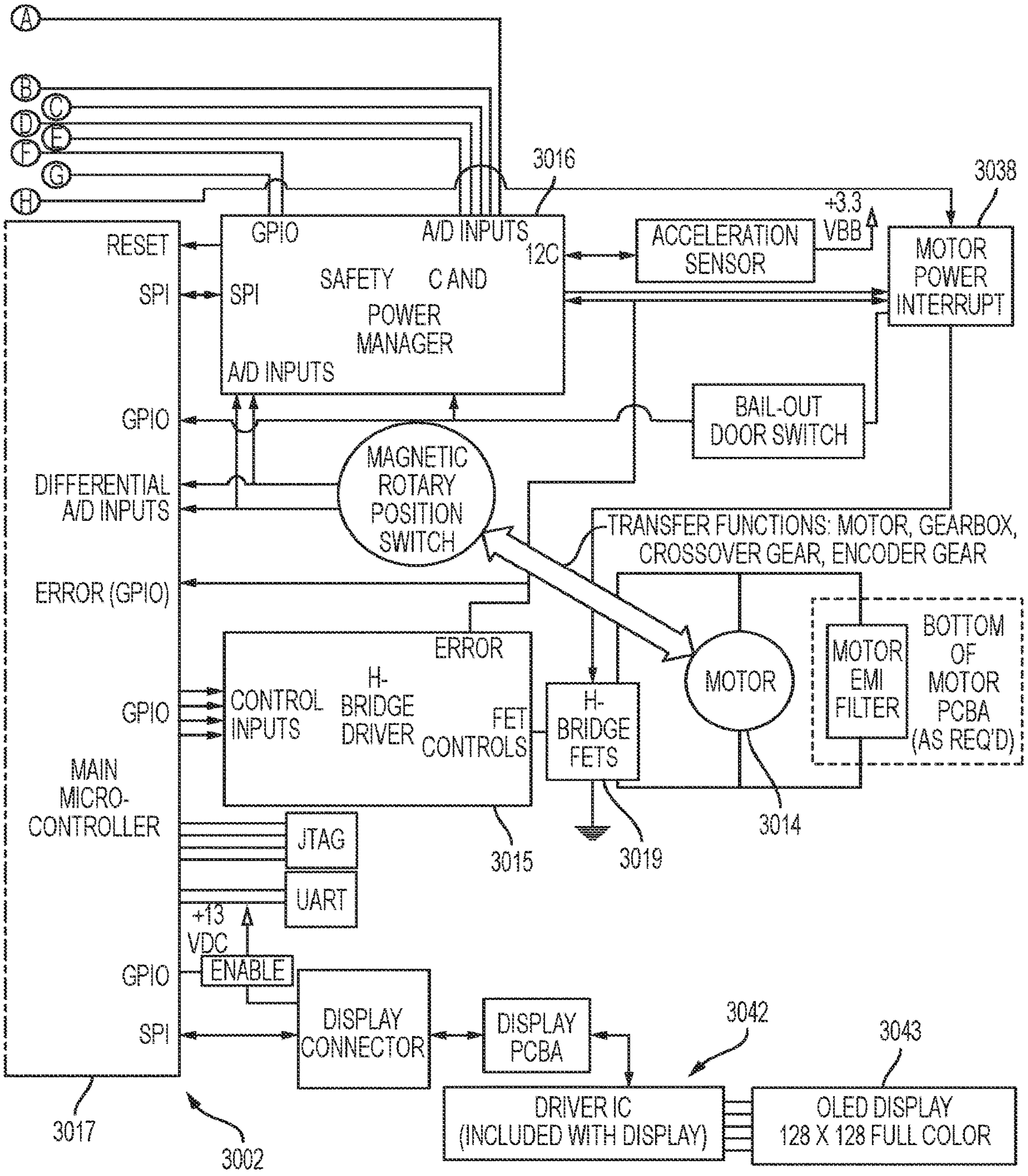

FIGS. 17A and 17B illustrate another aspect of a segmented circuit 3000 configured to control the powered surgical instrument 10, illustrated in FIGS. 1-14. As shown in FIGS. 14, 17B, the handle assembly 14 may include an electric motor 3014 which can be controlled by a motor driver 3015 and can be employed by the firing system of the surgical instrument 10. In various forms, the electric motor 3014 may be a DC brushed driving motor having a maximum rotation of, approximately, 25,000 RPM, for example. In other arrangements, the electric motor 3014 may include a brushless motor, a cordless motor, a synchronous motor, a stepper motor, or any other suitable electric motor. In certain circumstances, the motor driver 3015 may comprise an H-Bridge FETs 3019, as illustrated in FIGS. 17A and 17B, for example. The electric motor 3014 can be powered by a power assembly 3006, which can be releasably mounted to the handle assembly 14. The power assembly 3006 is configured to supply control power to the surgical instrument 10. The power assembly 3006 may comprise a battery which may include a number of battery cells connected in series that can be used as the power source to power the surgical instrument 10. In such configuration, the power assembly 3006 may be referred to as a battery pack. In certain circumstances, the battery cells of the power assembly 3006 may be replaceable and/or rechargeable. In at least one example, the battery cells can be Lithium-Ion batteries which can be separably couplable to the power assembly 3006.

Examples of drive systems and closure systems that are suitable for use with the surgical instrument 10 are disclosed in U.S. Patent Application Publication No. 2014/0263539, entitled CONTROL SYSTEMS FOR SURGICAL INSTRUMENTS, which is incorporated herein by reference herein in its entirety. For example, the electric motor 3014 can include a rotatable shaft (not shown) that may operably interface with a gear reducer assembly that can be mounted in meshing engagement with a set, or rack, of drive teeth on a longitudinally-movable drive member. In use, a voltage polarity provided by the battery can operate the electric motor 3014 to drive the longitudinally-movable drive member to effectuate the end effector 300. For example, the electric motor 3014 can be configured to drive the longitudinally-movable drive member to advance a firing mechanism to fire staples into tissue captured by the end effector 300 from a staple cartridge assembled with the end effector 300 and/or advance a cutting member to cut tissue captured by the end effector 300, for example.

As illustrated in FIGS. 17A and 17B and as described below in greater detail, the power assembly 3006 may include a power management controller which can be configured to modulate the power output of the power assembly 3006 to deliver a first power output to power the electric motor 3014 to advance the cutting member while the interchangeable shaft assembly 200 is coupled to the handle assembly 14 (FIG. 1) and to deliver a second power output to power the electric motor 3014 to advance the cutting member while the interchangeable shaft assembly 200 is coupled to the handle assembly 14, for example. Such modulation can be beneficial in avoiding transmission of excessive power to the electric motor 3014 beyond the requirements of an interchangeable shaft assembly that is coupled to the handle assembly 14.

In certain circumstances, the interface 3024 can facilitate transmission of the one or more communication signals between the power management controller 3016 and the shaft assembly controller 3022 by routing such communication signals through a main controller 3017 residing in the handle assembly 14 (FIG. 1), for example. In other circumstances, the interface 3024 can facilitate a direct line of communication between the power management controller 3016 and the shaft assembly controller 3022 through the handle assembly 14 while the interchangeable shaft assembly 200 (FIG. 1) and the power assembly 3006 are coupled to the handle assembly 14.

In one instance, the main controller 3017 may be any single core or multicore processor such as those known under the trade name ARM Cortex by Texas Instruments. In one instance, the surgical instrument 10 (FIGS. 1-4) may comprise a power management controller 3016 such as, for example, a safety controller platform comprising two controller-based families such as TMS570 and RM4x known under the trade name Hercules ARM Cortex R4, also by Texas Instruments. Nevertheless, other suitable substitutes for controllers and safety processor may be employed, without limitation. In one instance, the safety processor 2004 (FIG. 16*a*) may be configured specifically for IEC 61508 and ISO 26262 safety critical applications, among others, to provide advanced integrated safety features while delivering scalable performance, connectivity, and memory options.

In certain instances, the main controller 3017 may be a single core or multicore controller LM4F230H5QR as described in connection with FIGS. 15-17B.

Figure 18:
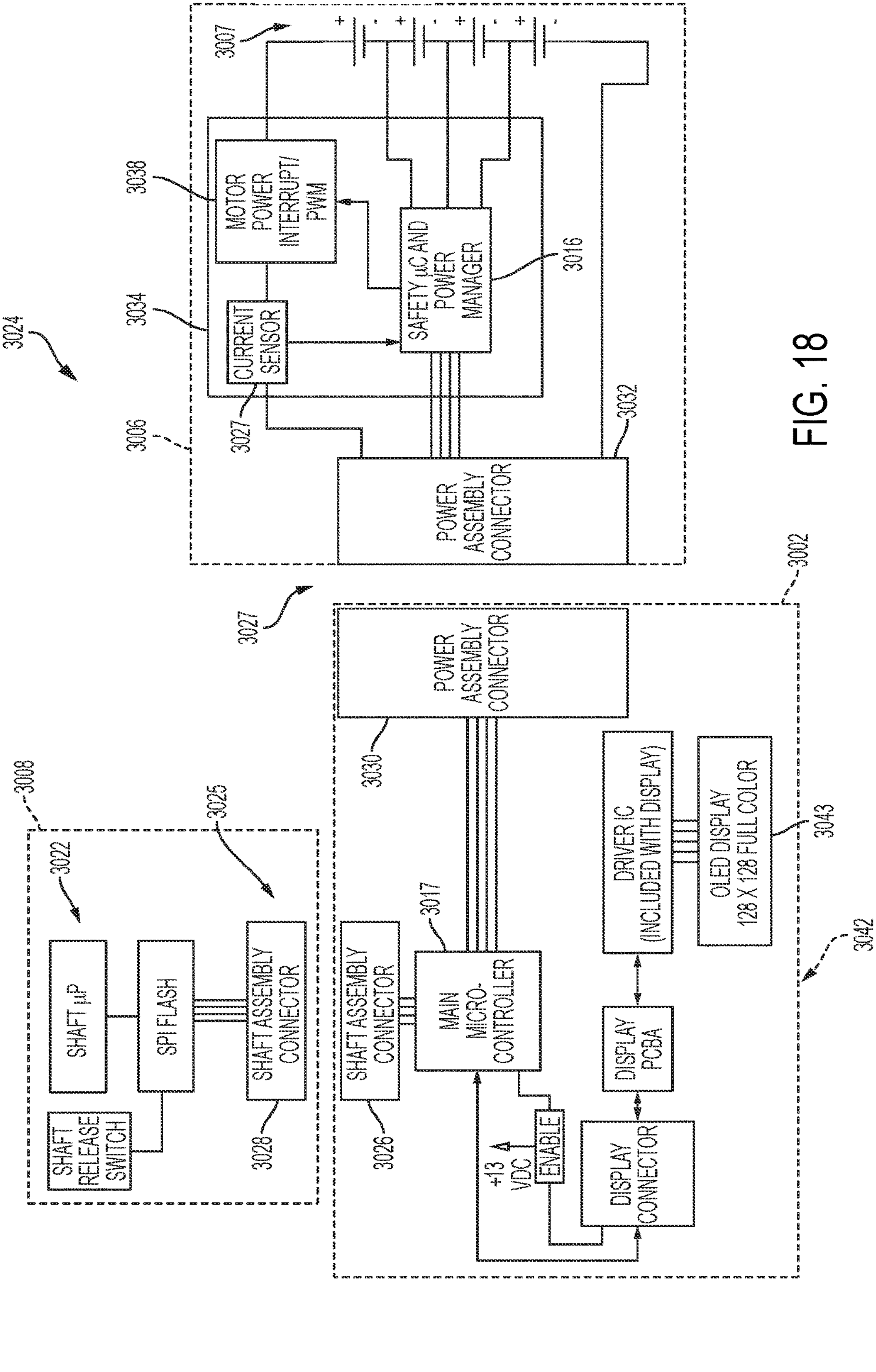
FIG. 18 is a block diagram the surgical instrument of FIG. 1 illustrating interfaces between the handle assembly and the power assembly and between the handle assembly and the interchangeable shaft assembly in accordance with one or more aspects of the present disclosure.

FIG. 18 is a block diagram the surgical instrument of FIG. 1 illustrating interfaces between the handle assembly 14 (FIG. 1) and the power assembly and between the handle assembly 14 and the interchangeable shaft assembly. As shown in FIG. 18, the power assembly 3006 may include a power management circuit 3034 which may comprise the power management controller 3016, a power modulator 3038, and a current sense circuit 3036. The power management circuit 3034 can be configured to modulate power output of the battery 3007 based on the power requirements of the interchangeable shaft assembly 200 (FIG. 1) while the interchangeable shaft assembly 200 and the power assembly 3006 are coupled to the handle assembly 14. For example, the power management controller 3016 can be programmed to control the power modulator 3038 of the power output of the power assembly 3006 and the current sense circuit 3036 can be employed to monitor power output of the power assembly 3006 to provide feedback to the power management controller 3016 about the power output of the battery 3007 so that the power management controller 3016 may adjust the power output of the power assembly 3006 to maintain a desired output.

It is noteworthy that the power management controller 3016 and/or the shaft assembly controller 3022 each may comprise one or more processors and/or memory units which may store a number of software modules. Although certain modules and/or blocks of the surgical instrument 10 (FIG. 1) may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In certain instances, the surgical instrument 10 (FIGS. 1-4) may comprise an output device 3042 which may include one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 3042 may comprise a display 3043 which may be included in the handle assembly 14 (FIG. 1). The shaft assembly controller 3022 and/or the power management controller 3016 can provide feedback to a user of the surgical instrument 10 through the output device 3042. The interface 3024 can be configured to connect the shaft assembly controller 3022 and/or the power management controller 3016 to the output device 3042. The reader will appreciate that the output device 3042 can instead be integrated with the power assembly 3006. In such circumstances, communication between the output device 3042 and the shaft assembly controller 3022 may be accomplished through the interface 3024 while the interchangeable shaft assembly 200 is coupled to the handle assembly 14.

Having described a surgical instrument 10 (FIGS. 1-4) and one or more segmented circuit 2000, 3000 for controlling the operation thereof, the disclosure now turns to various specific configurations of the surgical instrument 10 and a segmented circuit 2000 (or 3000).

In various aspects the present disclosure provides techniques for data storage and usage. In one aspect, data storage and usage is based on multiple levels of action thresholds. Such thresholds include upper and lower ultimate threshold limits, ultimate threshold that shuts down motor or activates return is current, pressure, firing load, torque is exceeded, and alternatively, while running within the limits the device automatically compensates for loading of the motor.

In one aspect, the surgical instrument 10 (described in connection with FIGS. 1-18) can be configured to monitor upper and lower ultimate threshold limits to maintain minimum and maximum closure clamp loads within acceptable limits. If a minimum is not achieved the surgical instrument 10 cannot start or if it drops below minimum a user action is required. If the clamp load is at a suitable level but drops under minimum during firing, the surgical instrument 10 can adjust the speed of the motor or warn the user. If the minimum limit is breached during operation the unit could give a warning that the firing may not be completely as anticipated. The surgical instrument 10 also can be configured to monitor when the battery voltage drops below the lower ultimate limit the remaining battery power is only direct able towards returning the device to the I-beam parked state. The opening force on the anvil can be employed to sense jams in the end effector. Alternatively, the surgical instrument 10 can be configured to monitor when the motor current goes up or the related speed goes down, then the motor control increases pulse width or frequency modulation to keep speed constant.

In another aspect, the surgical instrument 10 can (FIG. 1) be configured to detect an ultimate threshold of current draw, pressure, firing load, torque such that when any of these thresholds are exceeded, the surgical instrument 10 shuts down the motor or causes the motor to return the knife to a pre-fired position. A secondary threshold, which is less than the ultimate threshold, may be employed to alter the motor control program to accommodate changes in conditions by changing the motor control parameters. A marginal threshold can be configured as a step function or a ramp function based on a proportionate response to another counter or input. For example, in the case of sterilization, no changes between 0-200 sterilization cycles, slow motor 1% per use from 201-400 sterilization cycles, and prevent use over 400 sterilization cycles. The speed of the motor also can be varied based on tissue gap and current draw.

There are many parameters that could influence the ideal function of a powered reusable stapler device. Most of these parameters have an ultimate maximum and/or minimum threshold beyond which the device should not be operated. Nevertheless, there are also marginal limits that may influence the functional operation of the device. These multiple limits, from multiple parameters may provide an overlying and cumulative effect on the operations program of the device.

Accordingly, the present disclosure relates to surgical instruments and, in various circumstances, to surgical stapling and cutting instruments and staple cartridges therefor that are designed to staple and cut tissue.

Efficient performance of an electromechanical device depends on various factors. One is the operational envelope, i.e., range of parameters, conditions and events in which the device carries out its intended functions. For example, for a device powered by a motor driven by electrical current, there may be an operational region above a certain electrical current threshold where the device runs more inefficiently than desired. Put another way, there may be an upper "speed limit" above which there is decreasing efficiency. Such an upper threshold may have value in preventing substantial inefficiencies or even device degradation.

There may be thresholds within an operational envelope, however, that may form regions exploitable to enhance efficiency within operational states. In other words, there may be regions where the device can adjust and perform better within a defined operational envelope (or sub-envelope). Such a region can be one between a marginal threshold and an ultimate threshold. In addition, these regions may comprise "sweet spots" or a predetermined optional range or point. These regions also may comprise a large range within which performance is judged to be adequate.

An ultimate threshold can be defined, above which or below which an action or actions could be taken (or refrained from being taken) such as stopping the device. In addition, a marginal threshold or thresholds can be defined, above which or below which an action or actions could be taken (or refrained from being taken). By way of non-limiting example, a marginal threshold can be set to define where the current draw of the motor exceeds 75% of an ultimate threshold. Exceeding the marginal threshold can result, for example, in the device's beginning to slow motor speed at an increasing rate as it continues to climb toward the ultimate threshold.

Various mechanisms can be employed to carry out the adjustment(s) taken as a result of exceeding a threshold. For example, the adjustment can reflect a step function. It can also reflect a ramped function. Other functions can be utilized.

In various aspects, to enhance performance by additional mechanisms, an overlaying threshold can be defined. An overlaying threshold can comprise one or more thresholds defined by multiple parameters. An overlaying threshold can result in one or more thresholds being an input into the generation of another threshold or thresholds. An overlaying threshold can be predetermined or dynamically generated such as at runtime. The overlaying threshold may come into effect when you the threshold is defined by multiple inputs. For example, as the number of sterilization cycles exceeds 300 (the marginal threshold) but not 500 (the ultimate threshold) the device runs the motor slower. Then as the current draw exceeds its 75% marginal threshold it multiples the slow down going even slower.

Figure 19:
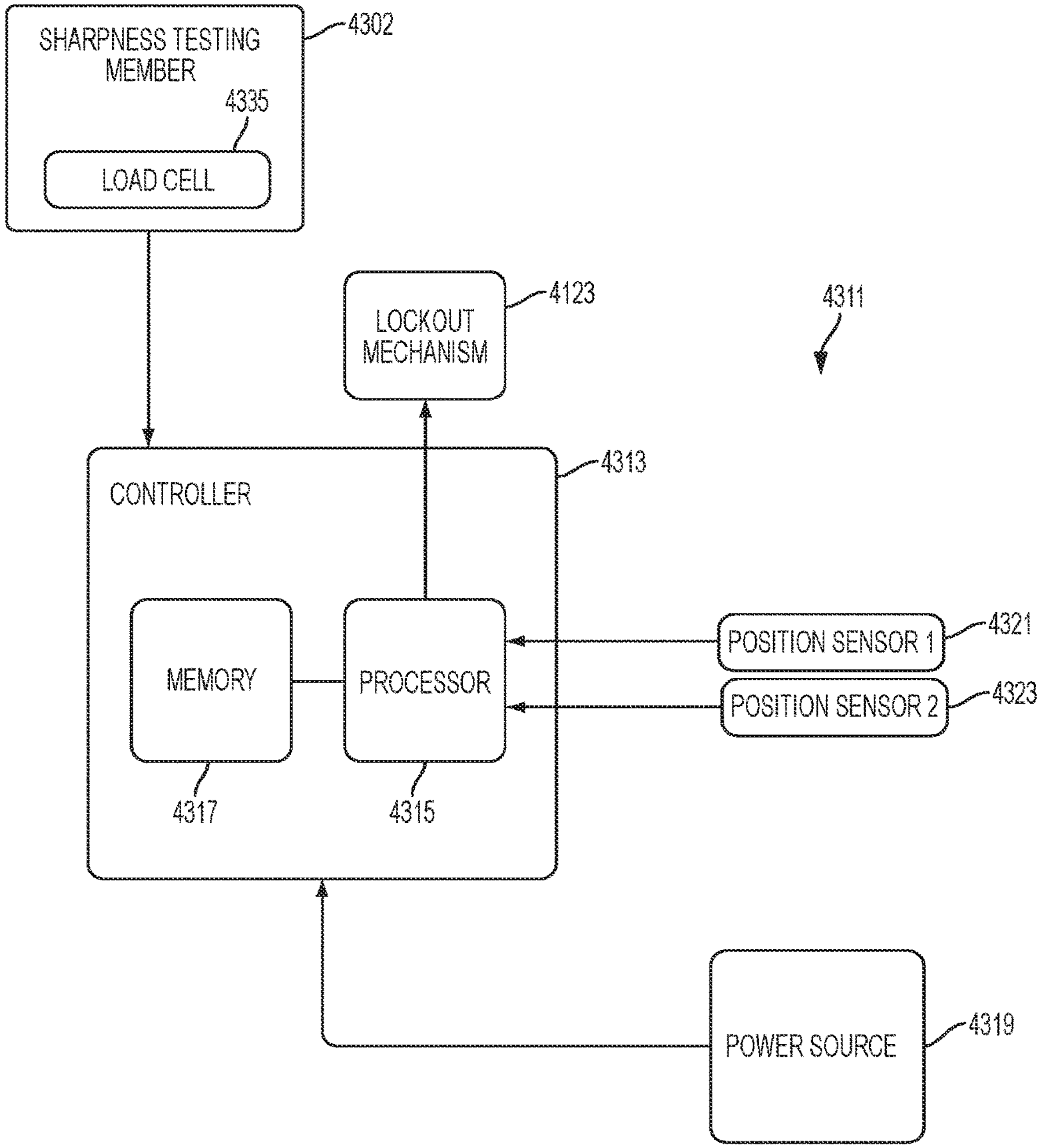
FIG. 19 illustrates a logic diagram of a system for evaluating sharpness of a cutting edge of a surgical instrument in accordance with one or more aspects of the present disclosure.

FIG. 19 illustrates a logic diagram of a system 4311 for evaluating sharpness of a cutting edge 182 (FIG. 14) of a surgical instrument 10 (FIGS. 1-4) according to various examples. In certain instances, the system 4311 can evaluate the sharpness of the cutting edge 182 by testing the ability of the cutting edge 182 to be advanced through a sharpness testing member 4302. For example, the system 4311 can be configured to observe the time period the cutting edge 182 takes to fully transect and/or completely pass through at least a predetermined portion of a sharpness testing member 4302. If the observed time period exceeds a predetermined threshold, the circuit 4310 may conclude that the sharpness of the cutting edge 182 has dropped below an acceptable level, for example.

In one aspect, the sharpness testing member 4302 can be employed to test the sharpness of the cutting edge 182 (FIG. 14). In certain instances, the sharpness testing member 4302 can be attached to and/or integrated with the cartridge body 194 (FIG. 14) of the surgical staple cartridge 304 (FIGS. 1, 2, and 15), for example. In certain instances, the sharpness testing member 4302 can be disposed in the proximal portion of the surgical staple cartridge 304, for example. In certain instances, the sharpness testing member 4302 can be disposed onto a cartridge deck or cartridge body 194 of the surgical staple cartridge 304, for example.

In certain instances, a load cell 4335 can be configured to monitor the force (Fx) applied to the cutting edge 182 (FIG. 14) while the cutting edge 182 is engaged and/or in contact with the sharpness testing member 4302, for example. The reader will appreciate that the force (Fx) applied by the sharpness testing member 4302 to the cutting edge 182 while the cutting edge 182 is engaged and/or in contact with the sharpness testing member 4302 may depend, at least in part, on the sharpness of the cutting edge 182. In certain instances, a decrease in the sharpness of the cutting edge 182 can result in an increase in the force (Fx) required for the cutting edge 182 to cut or pass through the sharpness testing member 4302. The load cell 4335 of the sharpness testing member 4302 may be employed to measure the force (Fx) applied to the cutting edge 182 while the cutting edge 182 travels a predefined distance (D) through the sharpness testing member 4302 may be employed to determine the sharpness of the cutting edge 182.

In certain instances, the system 4311 may include a controller 4313 ("microcontroller") which may include a processor 4315 ("microprocessor") and one or more computer readable mediums or memory 4317 units ("memory"). In certain instances, the memory 4317 may store various program instructions, which when executed may cause the processor 4315 to perform a plurality of functions and/or calculations described herein. In certain instances, the memory 4317 may be coupled to the processor 4315, for example. A power source 4319 can be configured to supply power to the controller 4313, for example. In certain instances, the power source 4319 may comprise a battery (or "battery pack" or "power pack"), such as a Li ion battery, for example. In certain instances, the battery pack may be configured to be releasably mounted to the handle assembly 14. A number of battery cells connected in series may be used as the power source 4319. In certain instances, the power source 4319 may be replaceable and/or rechargeable, for example.

In certain instances, the controller 4313 can be operably coupled to the feedback system and/or the lockout mechanism 4123, for example.

The system 4311 may comprise one or more position sensors. Example position sensors and positioning systems suitable for use with the present disclosure are described in U.S. Patent Application Publication No. 2014/0263538, entitled SENSOR ARRANGEMENTS FOR ABSOLUTE POSITIONING SYSTEM FOR SURGICAL INSTRUMENTS, which is herein incorporated by reference in its entirety. In certain instances, the system 4311 may include a first position sensor 4321 and a second position sensor 4323. In certain instances, the first position sensor 4321 can be employed to detect a first position of the cutting edge 182 (FIG. 14) at a proximal end of a sharpness testing member 4302, for example; and the second position sensor 4323 can be employed to detect a second position of the cutting edge 182 at a distal end of a sharpness testing member 4302, for example.

In certain instances, the first and second position sensors 4321, 4323 can be employed to provide first and second position signals, respectively, to the controller 4313. It will be appreciated that the position signals may be analog signals or digital values based on the interface between the controller 4313 and the first and second position sensors 4321, 4323. In one example, the interface between the controller 4313 and the first and second position sensors 4321, 4323 can be a standard serial peripheral interface (SPI), and the position signals can be digital values representing the first and second positions of the cutting edge 182, as described above.

Further to the above, the processor 4315 may determine the time period between receiving the first position signal and receiving the second position signal. The determined time period may correspond to the time it takes the cutting edge 182 (FIG. 14) to advance through a sharpness testing member 4302 from the first position at a proximal end of the sharpness testing member 4302, for example, to a second position at a distal end of the sharpness testing member 4302, for example. In at least one example, the controller 4313 may include a time element which can be activated by the processor 4315 upon receipt of the first position signal, and deactivated upon receipt of the second position signal. The time period between the activation and deactivation of the time element may correspond to the time it takes the cutting edge 182 to advance from the first position to the second position, for example. The time element may comprise a real time clock, a processor configured to implement a time function, or any other suitable timing circuit.

In various instances, the controller 4313 can compare the time period it takes the cutting edge 182 (FIG. 14) to advance from the first position to the second position to a predefined threshold value to assess whether the sharpness of the cutting edge 182 has dropped below an acceptable level, for example. In certain instances, the controller 4313 may conclude that the sharpness of the cutting edge 182 has dropped below an acceptable level if the measured time period exceeds the predefined threshold value by 1%, 5%, 10%, 25%, 50%, 100% and/or more than 100%, for example.

Figure 20:
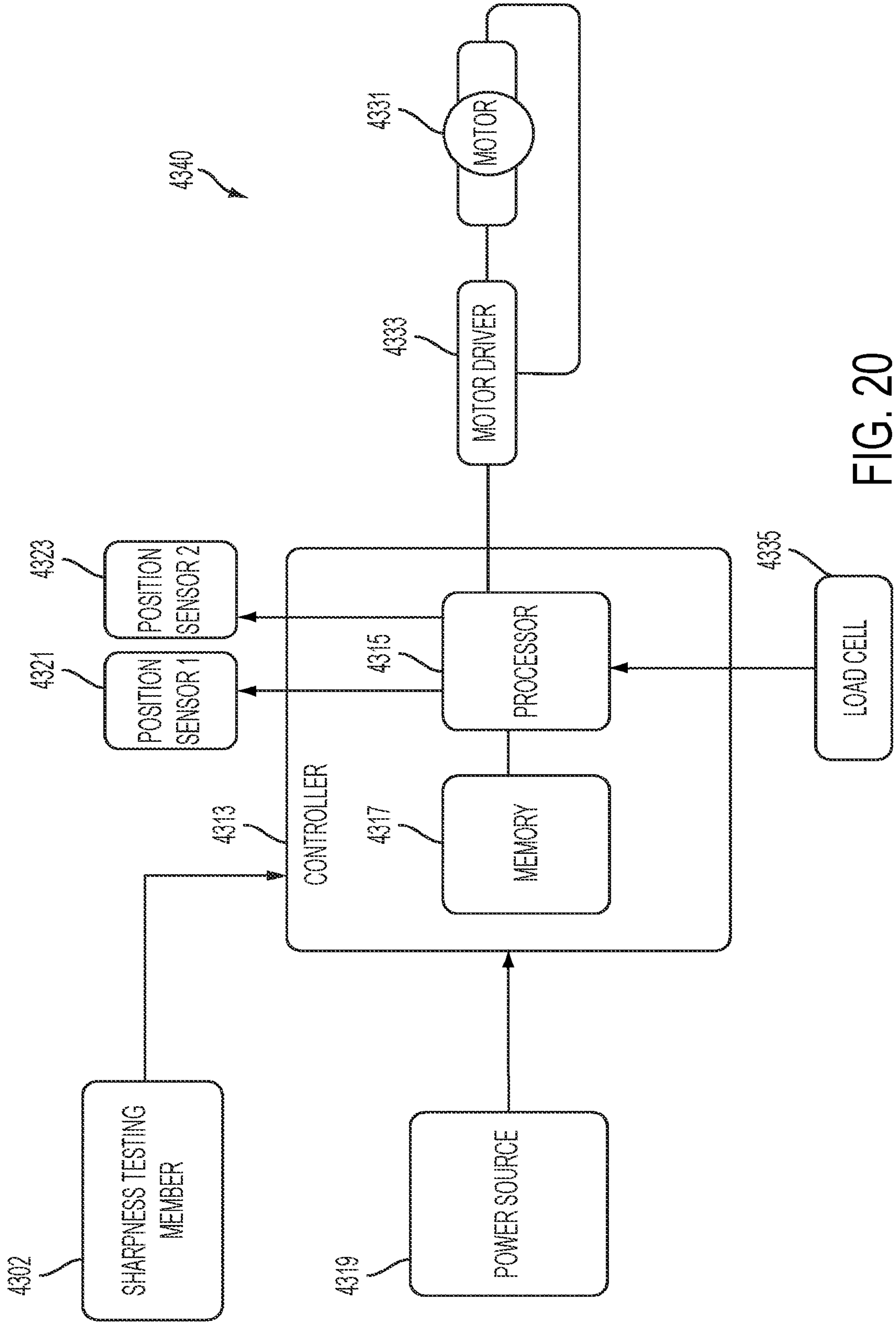
FIG. 20 illustrates a logic diagram of a system for determining the forces applied against a cutting edge of a surgical instrument by a sharpness testing member at various sharpness levels in accordance with one or more aspects of the present disclosure.

FIG. 20 illustrates a logic diagram of a system 4340 for determining the forces applied against a cutting edge of a surgical instrument 10 (FIGS. 1-4) by a sharpness testing member 4302 at various sharpness levels according to various aspects. Referring to FIG. 20, in various instances, an electric motor 4331 can drive the firing bar 172 (FIG. 20) to advance the cutting edge 182 (FIG. 14) during a firing stroke and/or to retract the cutting edge 182 during a return stroke, for example. A motor driver 4333 can control the electric motor 4331; and a controller such as, for example, the controller 4313 can be in signal communication with the motor driver 4333. As the electric motor 4331 advances the cutting edge 182, the controller 4313 can determine the current drawn by the electric motor 4331, for example. In such instances, the force required to advance the cutting edge 182 can correspond to the current drawn by the electric motor 4331, for example. Referring still to FIG. 20, the controller 4313 of the surgical instrument 10 can determine if the current drawn by the electric motor 4331 increases during advancement of the cutting edge 182 and, if so, can calculate the percentage increase of the current.

In certain instances, the current drawn by the electric motor 4331 may increase significantly while the cutting edge 182 (FIG. 14) is in contact with the sharpness testing member 4302 due to the resistance of the sharpness testing member 4302 to the cutting edge 182. For example, the current drawn by the electric motor 4331 may increase significantly as the cutting edge 182 engages, passes and/or cuts through the sharpness testing member 4302. The reader will appreciate that the resistance of the sharpness testing member 4302 to the cutting edge 182 depends, in part, on the sharpness of the cutting edge 182; and as the sharpness of the cutting edge 182 decreases from repetitive use, the resistance of the sharpness testing member 4302 to the cutting edge 182 will increase. Accordingly, the value of the percentage increase of the current drawn by the electric motor 4331 while the cutting edge is in contact with the sharpness testing member 4302 can increase as the sharpness of the cutting edge 182 decreases from repetitive use, for example.

In certain instances, the determined value of the percentage increase of the current drawn by the electric motor 4331 can be the maximum detected percentage increase of the current drawn by the electric motor 4331. In various instances, the controller 4313 can compare the determined value of the percentage increase of the current drawn by the electric motor 4331 to a predefined threshold value of the percentage increase of the current drawn by the electric motor 4331. If the determined value exceeds the predefined threshold value, the controller 4313 may conclude that the sharpness of the cutting edge 182 has dropped below an acceptable level, for example.

In certain instances, as illustrated in FIG. 20, the processor 4315 can be in communication with the feedback system and/or the lockout mechanism for example. In certain instances, the processor 4315 can employ the feedback system to alert a user if the determined value of the percentage increase of the current drawn by the electric motor 4331 exceeds the predefined threshold value, for example. In certain instances, the processor 4315 may employ the lockout mechanism to prevent advancement of the cutting edge 182 (FIG. 14) if the determined value of the percentage increase of the current drawn by the electric motor 4331 exceeds the predefined threshold value, for example. In certain instances, the system 4311 may include first and second position sensors 4321, 4323. The surgical instrument 10 (FIGS. 1-4) may include a load cell 4335.

In various instances, the controller 4313 can utilize an algorithm to determine the change in current drawn by the electric motor 4331. For example, a current sensor can detect the current drawn by the electric motor 4331 during the firing stroke. The current sensor can continually detect the current drawn by the electric motor and/or can intermittently detect the current draw by the electric motor. In various instances, the algorithm can compare the most recent current reading to the immediately proceeding current reading, for example. Additionally or alternatively, the algorithm can compare a sample reading within a time period X to a previous current reading. For example, the algorithm can compare the sample reading to a previous sample reading within a previous time period X, such as the immediately proceeding time period X, for example. In other instances, the algorithm can calculate the trending average of current drawn by the motor. The algorithm can calculate the average current draw during a time period X that includes the most recent current reading, for example, and can compare that average current draw to the average current draw during an immediately proceeding time period time X, for example.

In certain instances, the load cell 4335 (FIGS. 19, 20) can be configured to monitor the force (Fx) applied to the cutting edge 182 (FIG. 14) while the cutting edge 182 is engaged and/or in contact with the sharpness testing member 4302 (FIGS. 19, 20), for example. The reader will appreciate that the force (Fx) applied by the sharpness testing member 4302 to the cutting edge 182 while the cutting edge 182 is engaged and/or in contact with the sharpness testing member 4302 may depend, at least in part, on the sharpness of the cutting edge 182. In certain instances, a decrease in the sharpness of the cutting edge 182 can result in an increase in the force (Fx) required for the cutting edge 182 to cut or pass through the sharpness testing member 4302. In certain instances, the controller 4313 (FIGS. 19, 20) may compare a maximum value of the monitored force (Fx) applied to the cutting edge 182 (FIG. 14) to one or more predefined threshold values.

In certain instances, the cutting edge 182 (FIG. 14) may be sufficiently sharp for transecting a captured tissue comprising a first thickness but may not be sufficiently sharp for transecting a captured tissue comprising a second thickness greater than the first thickness, for example. In certain instances, a sharpness level of the cutting edge 182, as defined by the force required for the cutting edge 182 to transect a captured tissue, may be adequate for transecting the captured tissue if the captured tissue comprises a tissue thickness that is in a particular range of tissue thicknesses, for example. In certain instances, the memory 4317 (FIGS. 19, 20) can store one or more predefined ranges of tissue thicknesses of tissue captured by the end effector 300; and predefined threshold forces associated with the predefined ranges of tissue thicknesses. In certain instances, each predefined threshold force may represent a minimum sharpness level of the cutting edge 182 that is suitable for transecting a captured tissue comprising a tissue thickness (Tx) encompassed by the range of tissue thicknesses that is associated with the predefined threshold force. In certain instances, when the force (Fx) required for the cutting edge 182 to transect the captured tissue, comprising the tissue thickness (Tx), exceeds the predefined threshold force associated with the predefined range of tissue thicknesses that encompasses the tissue thickness (Tx), the cutting edge 182 may not be sufficiently sharp to transect the captured tissue, for example.

In various aspects, the present disclosure provides techniques for determining tissue compression and additional techniques to control the operation of the surgical instrument 10 (described in connection with FIGS. 1-18) in response to the tissue compression. In one example, the cartridges may be configured to define variable compression algorithm which drives the surgical instrument 10 to close differently based on intended tissue type and thickness. In another example, the surgical instrument 10 learns from surgeon use and original tissue compression profile to adapt closure based on load experienced during firing. When the surgical instrument 10 experiences tissue compression loads that are dramatically different that those experienced for this cartridge type the instrument highlights this to the user.

Active adjustment of a motor control algorithm over time as the instrument become acclimated to the hospital's usage can improve the life expectancy of a rechargeable battery as well as adjust to tissue/procedure requirements of minimizing tissue flow, thus improving staple formation in the tissue seal.

Accordingly, the present disclosure relates to surgical instruments and, in various circumstances, to surgical stapling and cutting instruments and staple cartridges therefor that are designed to staple and cut tissue. For example, in various aspects the present disclosure provides an endosurgical instrument configured to sense the cartridge type or tissue gap to enable the handle to adjust the closure and firing algorithms to adjust for intended tissue properties. This adaptive algorithm adjustment can "learn" from the user's operations allowing the device to react and benefit two different systems. The first benefit provided by the disclosed adaptive algorithm includes tissue flow and staple formation. As the device learns the users' basic habits and step timings, the device can adjust the closure speed and firing speed to provide a more consistent and reliable output. The second benefit provided by the disclosed adaptive algorithm is related to the battery pack. As the device learns how many firings and what conditions the instrument was used, the device can adjust motor current needs/speed in a predefined manner to prolong battery life. There is a substantially small likelihood that a device used in a hospital that performs predominantly bariatric procedures would be operated in a manner similar to a device used in a hospital that performs mostly colorectal or thoracic procedures. Thus, when the device is used to perform substantially similar procedure, over time, the device is configured to learn and adjust its operational algorithm to maintain within the "ideal" discharge and tissue flow envelopes.

Safe and effective surgery requires due knowledge of, and respect for, the tissue involved. Clinicians are mindful that adjustments made during surgery may be beneficial. These adjustments include mechanisms to detect and promote desirable staple formation.

Endosurgical instruments can generate, monitor and process a substantial amount of data during their use in connection with a surgical procedure. Such data can be obtained from the surgical instrument itself, including battery usage. Additionally, data can be obtained from the properties of the tissue with which the surgical instrument interacts, including properties such as tissue compression. Further, data can be obtained from the clinician's interaction with the surgical instrument itself. The repository of data so obtained can be processed and, where desired, the surgical instrument can be designed to adapt to circumstances so as to promote a safe and effective outcome to the current surgical procedure, as well as lay the foundation for more generalized productive use by multiple clinicians. Such adaptive adjustments—both during a surgical procedure, and wherein the instrument "learns" based on usage patterns drawn from multiple surgical procedures—can provide numerous mechanisms to enhance the overall patient-care environment.

Figure 21:
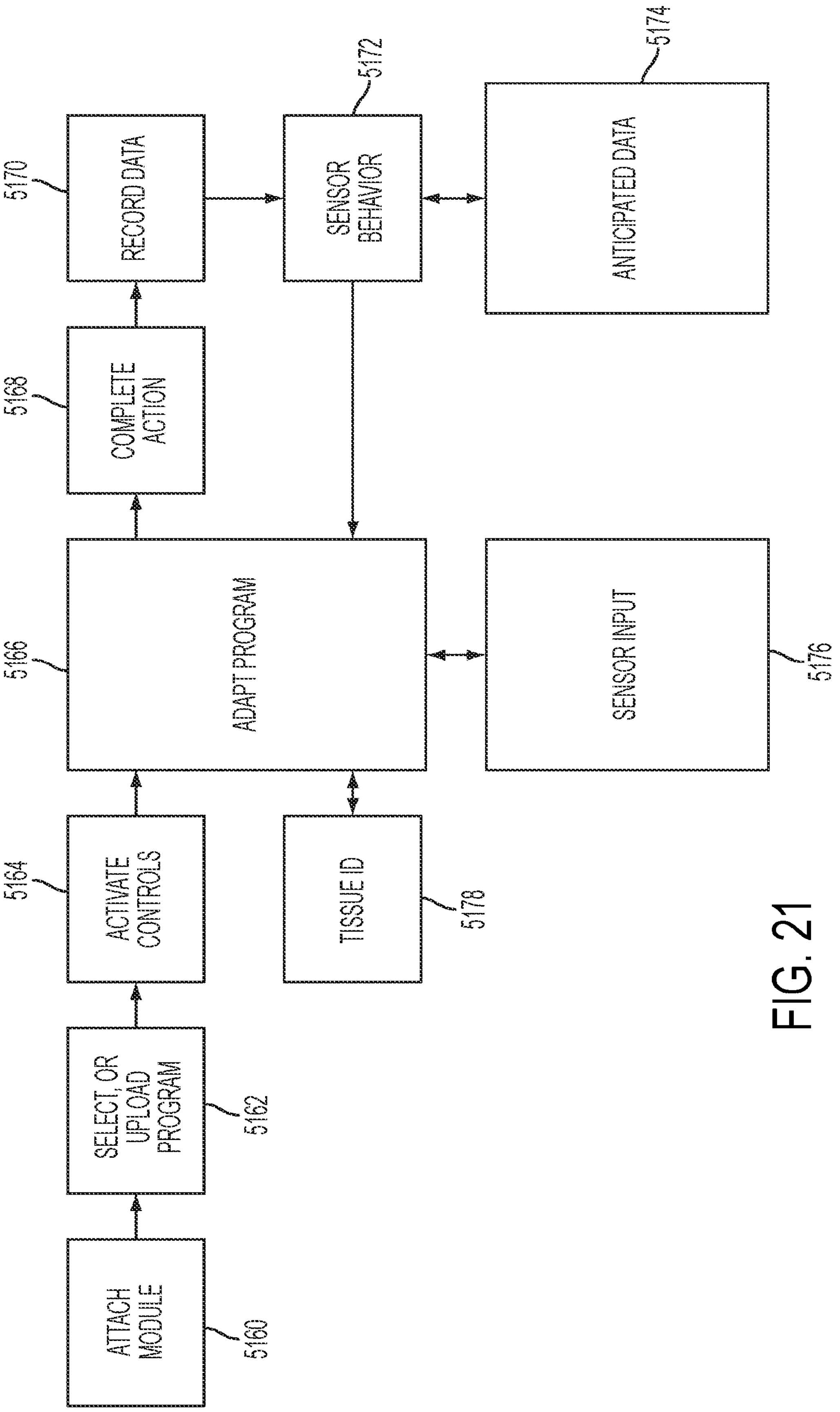
FIG. 21 illustrates one aspect of a process for adapting operations of a surgical instrument in accordance with one or more aspects of the present disclosure.
Figure 22A:
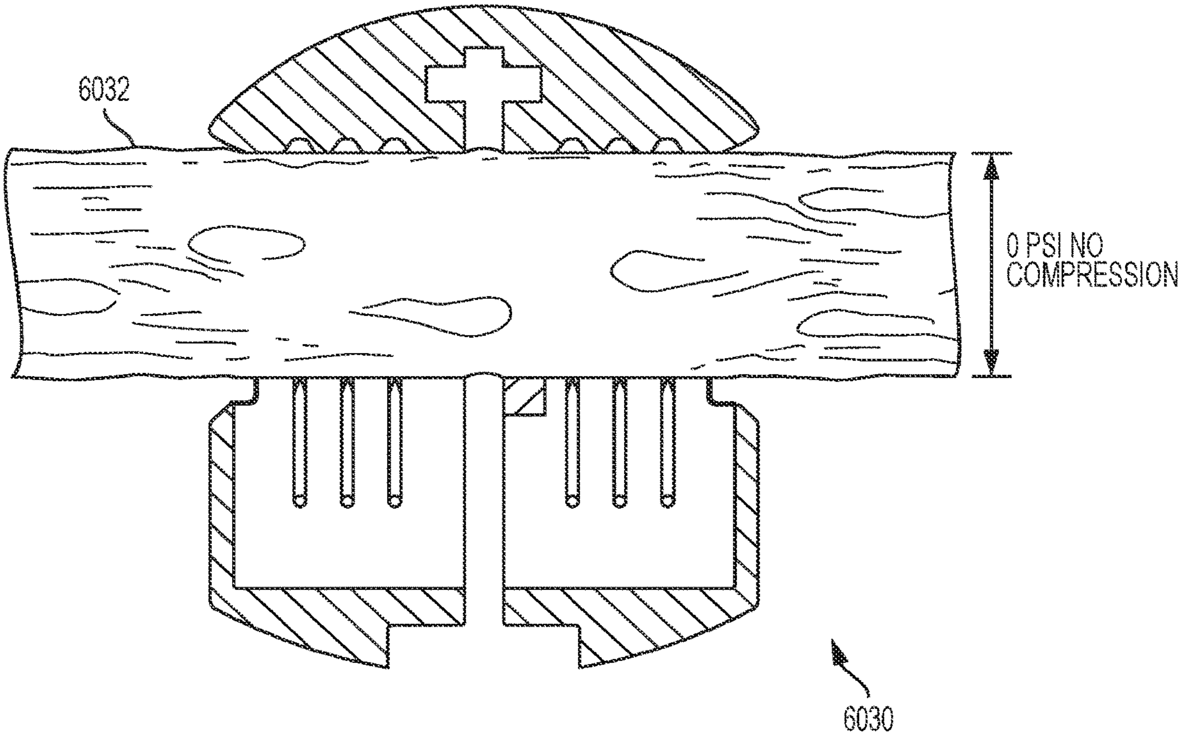
FIG. 22A depicts an example end-effector of a medical device surrounding tissue in accordance with one or more aspects of the present disclosure.
Figure 22B:
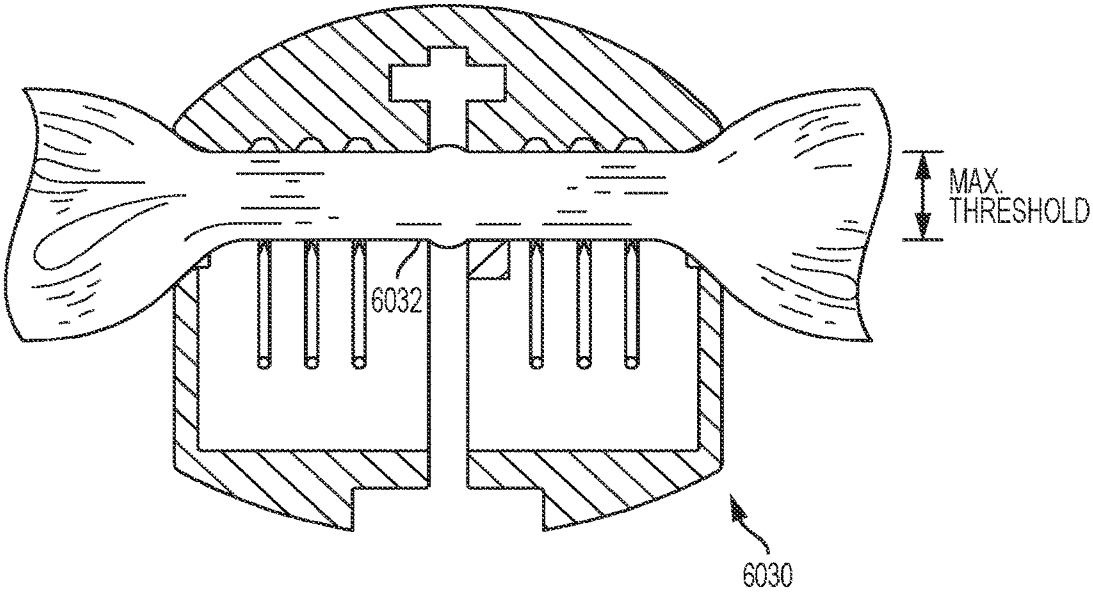
FIG. 22B depicts an example end-effector of a medical device compressing tissue in accordance with one or more aspects of the present disclosure.

FIG. 21 illustrates one aspect of a process for adapting operations of a surgical instrument. As depicted in FIG. 21, a module can be attached 5160 or otherwise loaded to the surgical instrument 10 (FIGS. 1-4). The module can contain a program that is selected or uploaded 5162. Controls can be activated 5164 such that they can be ready to operate the surgical instrument 10. During or after usage of the surgical instrument 10, control measures can be included to adapt 5166 a program. For example, this can include adjusting the data rate within the surgical instrument 10 or with respect to remote operation of the surgical instrument 10. This can include adjusting speed, such as speed by which anvil 306 (FIG. 1) and surgical staple cartridge 304 (FIG. 1) engage in a closure motion. This can also include a pulse from an emitter and sensor or to apply a pulse of electrical current to tissue, and the timing of such pulse. This can include adjusting a program to adapt to acceleration, such as acceleration of the surgical instrument 10 if dropped, or transition from a sleep mode. A program can be adapted to handle an actual and/or expected load based on clamping force.

The surgical instrument 10 (FIGS. 1-4) can be employed to complete an action 5168, for example to carry out a stapling procedure. Data can be recorded 5170 in appropriate memory locations of the surgical instrument 10. Sensor behavior 5172 can be assessed, such as to what extent a sensor accurately measured and/or measures a parameter. Anticipated data can be assessed 5174, including but not limited to tissue properties, wait period and firing speed. Foregoing mechanisms disclosed herein can provide an input to adapt 5166 a program further. In addition, a tissue identification 5178 can be performed, based on historical, actual or expected tissue properties, and this can provide an input to further adapt 5166 a program. In addition, tissue identification 5178 properties can be updated. Moreover, measured sensor input 5176 during a procedure can be used as an additional input to further adapt 5166 a program; such sensor measurements can include those of the gap between anvil 306 and surgical staple cartridge 304, obtaining a derivative measurement including a derivative of a function, current, or torque.

The end-effector 6006 may be used to compress, cut, or staple tissue. Referring now to FIG. 23A, an end-effector 6030 may be positioned by a physician to surround tissue 6032 prior to compression, cutting, or stapling. As shown in FIG. 23A, no compression may be applied to the tissue while preparing to use the end-effector. Referring now to FIG. 23B, by engaging the handle (e.g., handle 6002) of the endocutter, the physician may use the end-effector 6030 to compress the tissue 6032. In one aspect, the tissue 6032 may be compressed to its maximum threshold, as shown in FIG. 23B.

Referring to FIG. 23A, various forces may be applied to the tissue 6032 by the end-effector 6030. For example, vertical forces F1 and F2 may be applied by the anvil 6034 and the channel frame 6036 of the end-effector 6030 as tissue 6032 is compressed between the two. Referring now to FIG. 23B, various diagonal and/or lateral forces also may be applied to the tissue 6032 when compressed by the end-effector 6030. For example, force F3 may be applied. For the purposes of operating a medical device such as endocutter 6000, it may be desirable to sense or calculate the various forms of compression being applied to the tissue by the end-effector. For example, knowledge of vertical or lateral compression may allow the end-effector to more precisely or accurately apply a staple operation or may inform the operator of the endocutter such that the endocutter can be used more properly or safely.

The compression through tissue 6032 may be determined from an impedance of tissue 6032. At various levels of compression, the impedance Z of tissue 6032 may increase or decrease. By applying a voltage V and a current I to the tissue 6032, the impedance Z of the tissue 6032 may be determined at various levels of compression. For example, impedance Z may be calculated by dividing the applied voltage V by the current I.

Referring now to FIG. 24, in one aspect, an RF electrode 6038 may be positioned on the end-effector 6030 (e.g., on a staple cartridge, knife, or channel frame of the end-effector 6030). Further, an electrical contact 6040 may be positioned on the anvil 6034 of the end-effector 6030. In one aspect, the electrical contact may be positioned on the channel frame of the end-effector. As the tissue 6032 is compressed between the anvil 6034 and, for example, the channel frame 6036 of the end-effector 6030, an impedance Z of the tissue 6032 changes. The vertical tissue compression 6042 caused by the end-effector 6030 may be measured as a function of the impedance Z of the tissue 6032.

Referring now to FIG. 25, in one aspect, an electrical contact 6044 may be positioned on an opposite end of the anvil 6034 of the end-effector 6030 as the RF electrode 6038 is positioned. As the tissue 6032 is compressed between the anvil 6034 and, for example, the channel frame 6036 of the end-effector 6030, an impedance Z of the tissue 6032 changes. The lateral tissue compression 6046 caused by the end-effector 6030 may be measured as a function of the impedance Z of the tissue 6032.

Referring now to FIG. 26, in one aspect, electrical contact 6050 may be positioned on the anvil 6034 and electrical contact 6052 may be positioned on an opposite end of the end-effector 6030 at channel frame 6036. RF electrode 6048 may be positioned laterally to the central to the end-effector 6030. As the tissue 6032 is compressed between the anvil 6034 and, for example, the channel frame 6036 of the end-effector 6030, an impedance Z of the tissue 6032 changes. The lateral compression or angular compressions 6054 and 6056 on either side of the RF electrode 6048 may be caused by the end-effector 6030 and may be measured as a function of different impedances Z of the tissue 6032, based on the relative positioning of the RF electrode 6048 and electrical contacts 6050 and 6052.

In accordance with one or more of the techniques and features described in the present disclosure, and as discussed above, an RF electrode may be used as an RF sensor. Referring now to FIG. 27, in one aspect, an RF sensor 6062 may be positioned on a staple cartridge 6060 inserted into a channel frame 6066 an end-effector. The RF electrode may run from a power line 6064 which may be powered by a power source in a handle (e.g., handle 6002) of an endocutter.

Referring now to FIG. 28, in one aspect, RF electrodes 6074 and 6076 may be positioned on a staple cartridge 6072 inserted into a channel frame 6078 of end-effector 6070. As shown, RF electrode 6074 may be placed in a proximal position of the end-effector relative to an endocutter handle. Further, RF electrode 6076 may be placed in a distal position of the end-effector relative to the endocutter handle. RF electrodes 6074 and 6076 may be utilized to measure vertical, lateral, proximal, or distal compression at different points in a tissue based on the position of one or more electrical contacts on the end-effector.

Referring now to FIG. 29, in one aspect, RF electrodes 6084-6116 may be positioned on staple cartridge 6082 inserted into the channel frame 6080 (or other component of an end-effector) based on various points for which compression information is desired. Referring now to FIG. 30, in one aspect, RF electrodes 6122-6140 may be positioned on staple cartridge 6120 at discrete points for which compression information is desired. Referring now to FIG. 31, RF electrodes 6152-6172 may be positioned at different points in multiple zones of a staple cartridge based on how accurate or precise the compression measurements should be. For example, RF electrodes 6152-6156 may be positioned in zone 6158 of staple cartridge 6150 depending on how accurate or precise the compression measurements in zone 6158 should be. Further, RF electrodes 6160-6164 may be positioned in zone 6166 of staple cartridge 6150 depending on how accurate or precise the compression measurements in zone 6166 should be. Additionally, RF electrodes 6168-6172 may be positioned in zone 6174 of staple cartridge 6150 depending on how accurate or precise the compression measurements in zone 6174 should be.

The RF electrodes discussed herein may be wired through a staple cartridge inserted in the channel frame. Referring now to FIG. 32, in one aspect, an RF electrode may have a stamped "mushroom head" 6180 of about 1.0 mm in diameter. While the RF electrode may have the stamped "mushroom head" of about 1.0 mm in diameter, this is intended to be a non-limiting example and the RF electrode may be differently shaped and sized depending on each particular application or design. The RF electrode may be connected to, fastened to, or may form, a conductive wire 6182. The conductive wire 6182 may be about 0.5 mm in diameter, or may have a larger or smaller diameter based on a particular application or design. Further, the conductive wire may have an insulative coating 6184. In one example, the RF electrode may protrude through a staple cartridge, channel frame, knife, or other component of an end-effector.

Referring now to FIG. 33, the RF electrodes may be wired through a single wall or through multiple walls of a staple cartridge or channel frame of an end-effector. For example, RF electrodes 6190-6194 may be wired through wall 6196 of the staple cartridge or channel frame of an end-effector. One or more of wires 6198 may be connected to, fastened to, or be part of, RF electrodes 6190-6194 and may run through wall 6196 from a power source in, e.g., a handle of an endocutter.

Referring now to FIG. 34, the power source may be in communication with the RF electrodes or may provide power to the RF electrodes through a wire or cable. The wire or cable may join each individual wire and lead to the power source. For example, RF electrodes 6204-6212 may receive power from a power source through wire or cable 6202, which may run through staple cartridge 6200 or a channel frame of an end-effector. In one example, each of RF electrodes 6204-6212 may have its own wire that runs to or through wire or cable 6202. The staple cartridge 6200 or channel frame also may include a controller 6214, such as the primary processor 2006 shown in connection with FIGS. 16A and 16B, or the main controller 3017 shown in connection with FIGS. 17A, 17B, and 18, for example. It will be appreciated that the controller 6214 should be suitably sized to fit in the staple cartridge 6200 or channel frame form factor. Also, the controller In various aspects, the tissue compression sensor system described herein for use with medical devices may include a frequency generator. The frequency generator may be located on a circuit board of the medical device, such as an endocutter. For example the frequency generator may be located on a circuit board in a shaft or handle of the endocutter. Referring now to FIG. 35, an example circuit diagram 6220 in accordance with one example of the present disclosure is shown. As shown, frequency generator 6222 may receive power or current from a power source 6221 and may supply one or more RF signals to one or more RF electrodes 6224. As discussed above, the one or more RF electrodes may be positioned at various locations or components on an end-effector or endocutter, such as a staple cartridge or channel frame. One or more electrical contacts, such as electrical contacts 6226 or 6228 may be positioned on a channel frame or an anvil of an end-effector. Further, one or more filters, such as filters 6230 or 6232 may be communicatively coupled to the electrical contacts 6226 or 6228 as shown in FIG. 35. The filters 6230 and 6232 may filter one or more RF signals supplied by the frequency generator 6222 before joining a single return path 6234. A voltage V and a current I associated with the one or more RF signals may be used to calculate an impedance Z associated with a tissue that may be compressed and/or communicatively coupled between the one or more RF electrodes 6224 and the electrical contacts 6226 or 6228.

Referring now to FIG. 36, various components of the tissue compression sensor system described herein may be located in a handle 6236 of an endocutter. For example, as shown in circuit diagram 6220*a*, frequency generator 6222 may be located in the handle 6236 and receives power from power source 6221. Also, current I1 and current I2 may be measured on a return path corresponding to electrical contacts 6228 and 6226. Using a voltage V applied between the supply and return paths, impedances Z1 and Z2 may be calculated. Z1 may correspond to an impedance of a tissue compressed and/or communicatively coupled between one or more of RF electrodes 6224 and electrical contact 6228. Further, Z2 may correspond to an impedance of a tissue compressed and/or communicatively coupled between one or more of RF electrodes 6224 and electrical contact 6226. Applying the formulas Z1=V/I1 and Z2=V/I2, impedances Z1 and Z2 corresponding to different compression levels of a tissue compressed by an end-effector may be calculated.

Referring now to FIG. 37, one or more aspects of the present disclosure are described in circuit diagram 6250. In an implementation, a power source at a handle 6252 of an endocutter may provide power to a frequency generator 6254. The frequency generator 6254 may generate one or more RF signals. The one or more RF signals may be multiplexed or overlaid at a multiplexer 6256, which may be in a shaft 6258 of the endocutter. In this way, two or more RF signals may be overlaid (or, e.g., nested or modulated together) and transmitted to the end-effector. The one or more RF signals may energize one or more RF electrodes 6260 at an end-effector 6262 (e.g., positioned in a staple cartridge) of the endocutter. A tissue (not shown) may be compressed and/or communicatively coupled between the one or more of RF electrodes 6260 and one or more electrical contacts. For example, the tissue may be compressed and/or communicatively coupled between the one or more RF electrodes 6260 and the electrical contact 6264 positioned in a channel frame of the end-effector 6262 or the electrical contact 6266 positioned in an anvil of the end-effector 6262. A filter 6268 may be communicatively coupled to the electrical contact 6264 and a filter 6270 may be communicatively coupled to the electrical contact 6266.

A voltage V and a current I associated with the one or more RF signals may be used to calculate an impedance Z associated with a tissue that may be compressed between the staple cartridge (and communicatively coupled to one or more RF electrodes 6260) and the channel frame or anvil (and communicatively coupled to one or more of electrical contacts 6264 or 6266).

In one aspect, various components of the tissue compression sensor system described herein may be located in a shaft 6258 of the endocutter. For example, as shown in circuit diagram 6250 (and in addition to the frequency generator 6254), an impedance calculator 6272, a controller 6274, a non-volatile memory 6276, and a communication channel 6278 may be located in the shaft 6258. In one example, the frequency generator 6254, impedance calculator 6272, controller 6274, non-volatile memory 6276, and communication channel 6278 may be positioned on a circuit board in the shaft 6258.

The two or more RF signals may be returned on a common path via the electrical contacts. Further, the two or more RF signals may be filtered prior to the joining of the RF signals on the common path to differentiate separate tissue impedances represented by the two or more RF signals. Current I1 and current I2 may be measured on a return path corresponding to electrical contacts 6264 and 6266. Using a voltage V applied between the supply and return paths, impedances Z1 and Z2 may be calculated. Z1 may correspond to an impedance of a tissue compressed and/or communicatively coupled between one or more of RF electrodes 6260 and electrical contact 6264. Further, Z2 may correspond to an impedance of the tissue compressed and/or communicatively coupled between one or more of RF electrodes 6260 and electrical contact 6266. Applying the formulas Z1=V/I1 and Z2=V/I2, impedances Z1 and Z2 corresponding to different compressions of a tissue compressed by an end-effector 6262 may be calculated. In example, the impedances Z1 and Z2 may be calculated by the impedance calculator 6272. The impedances Z1 and Z2 may be used to calculate various compression levels of the tissue.

In one aspect, filters 6268 and 6270 may be High Q filters such that the filter range may be narrow (e.g., Q=10). Q may be defined by the Center frequency (Wo)/Bandwidth (BW) where Q=Wo/BW. In one example, Frequency 1 may be 150 kHz and Frequency 2 may be 300 kHz. A viable impedance measurement range may be 100 kHz-20 MHz. In various examples, other sophisticated techniques, such as correlation, quadrature detection, etc., may be used to separate the RF signals.

Using one or more of the techniques and features described herein, a single energized electrode on a staple cartridge or an isolated knife of an end-effector may be used to make multiple tissue compression measurements simultaneously. If two or more RF signals are overlaid or multiplexed (or nested or modulated), they may be transmitted down a single power side of the end-effector and may return on either the channel frame or the anvil of the end-effector. If a filter were built into the anvil and channel contacts before they join a common return path, the tissue impedance represented by both paths could be differentiated. This may provide a measure of vertical tissue vs lateral tissue compression. This approach also may provide proximal and distal tissue compression depending on placement of the filters and location of the metallic return paths. A frequency generator and signal processor may be located on one or more chips on a circuit board or a sub board (which may already exist in an endocutter).

In various aspects, the present disclosure provides techniques for monitoring the speed and precision incrementing of the drive motor in the surgical instrument 10 (described in connection with FIGS. 1-18). In one example, a magnet can be placed on a planet frame of one of the stages of gear reduction with an inductance sensor on the gear housing. In another example, placing the magnet and magnetic field sensor on the last stage would provide the most precise incremental movement monitoring.

Conventional motor control systems employ encoders to detect the location and speed of the motor in hand held battery powered endosurgical instruments such as powered endocutter/stapler devices. Precision operation of endocutter/stapler devices relies in part on the ability to verify the motor operation under load. Simple sensor implementations may be employed to achieve verify the motor operation under load.

Accordingly, the present disclosure includes a magnetic body on one of the planetary carriers of a gear reduction system or employ brushless motor technology. Both approaches involve the placement of an inductance sensor on the outside housing of the motor or planetary gear system. In the case of a brushless motor there are electromagnetic field coils (windings, inductors, etc.) arrayed radially around the center magnetic shaft of the motor. The coils are sequentially activated and deactivated to drive the central motor shaft. One or more inductance sensors can be placed outside of the motor and adjacent to at least some of the coils to sense the activation/deactivation cycles of the motor windings to determine the number times the shaft has been rotated. Alternatively, a permanent magnet can be placed on one of the planetary carriers and the inductance sensor can be placed adjacent to the radial path of the planetary carrier to measure the number of times that stage of the gear train is rotated. This implementation can be applied to any rotational components in the system with increasingly more resolution possible in regions with a relatively large number of rotations during function, or as the rotational components become closer (in terms of number of connections) to the end effector depending on the design. The gear train sensing method may be preferred since it actually measures rotation of one of the stages whereas the motor sensing method senses the number of times the motor has been commanded to energize, rather than the actual shaft rotation. For example, if the motor is stalled under high load, the motor sensing method would not be able to detect the lack of rotation because it senses only the energizing cycles not shaft rotation. Nevertheless, both techniques can be employed in a cost effective manner to sense motor rotation.

During stapling, for example, tissue is firmly clamped between opposing jaws before a staple is driven into the clamped tissue. Tissue compression during clamping can cause fluid to be displaced from the compressed tissue, and the rate or amount of displacement varies depending on tissue type, tissue thickness, the surgical operation (e.g., clamping pressure and clamping time). In various instances, fluid displacement between the opposing jaws of an end effector may contribute to malformation (e.g., bending) of staples between the opposing jaws. Accordingly, in various instances, it may be desirable to control the firing stroke, e.g., to control the firing speed, in relationship to the detected fluid flow, or lack thereof, intermediate opposing jaws of a surgical end effector.

Accordingly, also provided herein are methods, devices, and systems for monitoring speed and incremental movement of a surgical instrument drive train, which in turn provides information about the operational velocity of the device (e.g., jaw closure, stapling). In accordance with the present examples, the surgical instrument 10 (FIGS. 1-4) does not include a motor encoder. Rather, the surgical instrument 10 may be equipped with a motor comprising a speed sensor assembly for a power train of the motor, in accordance with an illustrative example. The speed sensor assembly can include a motor having an output shaft that is coupled directly or indirectly to a drive shaft. In some examples, the output shaft is connected to a gear reduction assembly, such as a planetary gear train comprising a sensor that detects the rotational speed of any suitable component of the system. For example, the sensor may be a proximity sensor, such as an induction sensor, which detects movement of one or more detectable elements affixed to any rotating part of the gear reduction assembly. The detectable element is affixed to the last stage annular gear and the sensor is positioned adjacent the radial path of the detectable element so as to detect movement of the detectable element. Rotating components may vary depending on design—and the sensor(s) can be affixed to any rotating component of the gear reduction assembly. For example, in another example, a detectable element is associated with the carrier gear of the final stage or even the drive gear. In some examples, a detectable element is located outside of the gear reduction assembly, such as on the driveshaft between gear reduction assembly and the end effector. In some example, a detectable element is located on a rotating component in the final gear reduction at the end effector.

Various functions may be implemented utilizing the circuitry previously described, For example, the motor may be controlled with a motor controller similar those described in connection with FIGS. 16A, 16B, 17A, 17B, and 18, where the encoder is replaced with the monitoring speed control and precision incrementing of motor systems for powered surgical instruments described herein.

In one aspect, the present disclosure provides a surgical instrument 10 (described in connection with FIGS. 1-18) configured with various sensing systems. Accordingly, for conciseness and clarity the details of operation and construction will not be repeated here. In one aspect, the sensing system includes a viscoelasticity/rate of change sensing system to monitor knife acceleration, rate of change of impedance, and rate of change of tissue contact. In one example, the rate of change of knife acceleration can be used as a measure of for tissue type. In another example, the rate of change of impedance can be measures with a pulse sensor ad can be employed as a measure for compressibility. Finally, the rate of change of tissue contact can be measured with a sensor based on knife firing rate to measure tissue flow.

The rate of change of a sensed parameter or stated otherwise, how much time is necessary for a tissue parameter to reach an asymptotic steady state value, is a separate measurement in itself and may be more valuable than the sensed parameter it was derived from. To enhance measurement of tissue parameters such as waiting a predetermined amount of time before making a measurement, the present disclosure provides a novel technique for employing the derivate of the measure such as the rate of change of the tissue parameter.

The derivative technique or rate of change measure becomes most useful with the understanding that there is no single measurement that can be employed alone to dramatically improve staple formation. It is the combination of multiple measurements that make the measurements valid. In the case of tissue gap it is helpful to know how much of the jaw is covered with tissue to make the gap measure relevant. Rate of change measures of impedance may be combined with strain measurements in the anvil to relate force and compression applied to the tissue grasped between the jaw members of the end effector such as the anvil and the staple cartridge. The rate of change measure can be employed by the endosurgical device to determine the tissue type and not merely the tissue compression. Although stomach and lung tissue sometimes have similar thicknesses, and even similar compressive properties when the lung tissue is calcified, an instrument may be able to distinguish these tissue types by employing a combination of measurements such as gap, compression, force applied, tissue contact area, and rate of change of compression or rate of change of gap. If any of these measurements were used alone, the endosurgical it may be difficult for the endosurgical device to distinguish one tissue type form another. Rate of change of compression also may be helpful to enable the device to determine if the tissue is "normal" or if some abnormality exists. Measuring not only how much time has passed but the variation of the sensor signals and determining the derivative of the signal would provide another measurement to enable the endosurgical device to measure the signal. Rate of change information also may be employed in determining when a steady state has been achieved to signal the next step in a process. For example, after clamping the tissue between the jaw members of the end effector such as the anvil and the staple cartridge, when tissue compression reaches a steady state (e.g., about 15 seconds), an indicator or trigger to start firing the device can be enabled.

Also provided herein are methods, devices, and systems for time dependent evaluation of sensor data to determine stability, creep, and viscoelastic characteristics of tissue during surgical instrument operation. A surgical instrument 10, such as the stapler illustrated in FIG. 1, can include a variety of sensors for measuring operational parameters, such as jaw gap size or distance, firing current, tissue compression, the amount of the jaw that is covered by tissue, anvil strain, and trigger force, to name a few. These sensed measurements are important for automatic control of the surgical instrument and for providing feedback to the clinician.

The examples shown in connection with FIGS. 22A-37 may be employed to measure the various derived parameters such as gap distance versus time, tissue compression versus time, and anvil strain versus time. Motor current may be monitored employing the current sensor 2312 in series with the battery 2308 as described herein, the current sensor 2412 in series with the battery 2408 or the current sensor 3027 in FIG. 18.

FIG. 38 illustrates a motor-driven surgical instrument 8010 for cutting and fastening that may or may not be reused. The surgical instrument 8010 is similarly constructed and equipped as the surgical instrument 10 for cutting and fastening described in connection with FIGS. 1-18. In the example illustrated in FIG. 38, the surgical instrument 8010 includes a housing 8012 that comprises a handle assembly 8014 that is configured to be grasped, manipulated and actuated by the clinician. The housing 8012 is configured for operable attachment to an interchangeable shaft assembly 8200 that has an end effector 8300 operably coupled thereto that is configured to perform one or more surgical tasks or procedures. Since the surgical instrument 8010 is similarly constructed and equipped as the surgical instrument 10 for cutting and fastening described in connection with FIGS. 1-18, for conciseness and clarity the details of operation and construction will not be repeated here.

The housing 8012 depicted in FIG. 38 is shown in connection with an interchangeable shaft assembly 8200 that includes an end effector 8300 that comprises a surgical cutting and fastening device that is configured to operably support a surgical staple cartridge 8304 therein. The housing 8012 may be configured for use in connection with interchangeable shaft assemblies that include end effectors that are adapted to support different sizes and types of staple cartridges, have different shaft lengths, sizes, and types, etc. In addition, the housing 8012 also may be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

Turning now to FIG. 38, the surgical instrument 8010 is depicted that may or may not be reused. The surgical instrument 8010 is similarly constructed and equipped as the surgical instrument 10 for cutting and fastening described herein. In the example illustrated in FIG. 38, the surgical instrument 8010 includes a housing 8012 that comprises a handle assembly 8014 that is configured to be grasped, manipulated and actuated by the clinician. The housing 8012 is configured for operable attachment to an interchangeable shaft assembly 8200 that has an end effector 8300 operably coupled thereto that is configured to perform one or more surgical tasks or procedures. Since the surgical instrument 8010 is similarly constructed and equipped as the surgical instrument 10 for cutting and fastening described herein in connection with FIGS. 1-18, for conciseness and clarity the details of operation and construction will not be repeated here.

The housing 8012 depicted in FIG. 38 is shown in connection with an interchangeable shaft assembly 8200 that includes an end effector 8300 that comprises a surgical cutting and fastening device that is configured to operably support a surgical staple cartridge 8304 therein. The housing 8012 may be configured for use in connection with interchangeable shaft assemblies that include end effectors that are adapted to support different sizes and types of staple cartridges, have different shaft lengths, sizes, and types, etc. In addition, the housing 8012 also may be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

FIG. 38 illustrates the surgical instrument 8010 with an interchangeable shaft assembly 8200 operably coupled thereto. In the illustrated arrangement, the handle housing forms a pistol grip portion 8019 that can be gripped and manipulated by the clinician. The handle assembly 8014 operably supports a plurality of drive systems therein that are configured to generate and apply various control motions to corresponding portions of the interchangeable shaft assembly that is operably attached thereto. Trigger 8032 is operably associated with the pistol grip for controlling various of these control motions.

With continued reference to FIG. 38, the interchangeable shaft assembly 8200 includes an end effector 8300 that comprises an elongated channel 8302 that is configured to operably support a surgical staple cartridge 8304 therein. The end effector 8300 may further include an anvil 8306 that is pivotally supported relative to the elongated channel 8302.

The inventors have discovered that derived parameters can be even more useful for controlling a surgical instrument, such as the instrument illustrated in FIG. 38, than the sensed parameter(s) upon which the derived parameter is based. Non-limiting examples of derived parameters include the rate of change of a sensed parameter (e.g., jaw gap distance) and how much time elapses before a tissue parameter reaches an asymptotic steady state value (e.g., 15 seconds). Derived parameters, such as rate of change, are particularly useful because they dramatically improve measurement accuracy and also provide information not otherwise evident directly from sensed parameters. For example, impedance (i.e., tissue compression) rate of change can be combined with strain in the anvil to relate compression and force, which enables the controller to determine the tissue type and not merely the amount of tissue compression. This example is illustrative only, and any derived parameters can be combined with one or more sensed parameters to provide more accurate information about tissue types (e.g., stomach vs. lung), tissue health (calcified vs. normal), and operational status of the surgical device (e.g., clamping complete). Different tissues have unique viscoelastic properties and unique rates of change, making these and other parameters discussed herein useful indicia for monitoring and automatically adjusting a surgical procedure.

Specifically, referring to FIGS. 38 and 39, the gap 8040 is the distance between the anvil 8306 and the elongated channel 8302 of the end effector 8300. In the open jaw position, at time zero, the gap 8040 between the anvil 8306 and the elongated member is at its maximum distance. The width of the gap 8040 decreases as the anvil 8306 closes, such as during tissue clamping. The gap distance rate of change can vary because tissue has non-uniform resiliency. For example, certain tissue types may initially show rapid compression, resulting in a faster rate of change. However, as tissue is continually compressed, the viscoelastic properties of the tissue can cause the rate of change to decrease until the tissue cannot be compressed further, at which point the gap distance will remain substantially constant. The gap decreases over time as the tissue is squeezed between the anvil 8306 and the surgical staple cartridge 8304 of the end effector 8300. The one or more sensors described in connection with FIGS. 22A-37 and FIG. 40 may be adapted and configured to measure the gap distance "d" between the anvil 8306 and the surgical staple cartridge 8304 over time t and the rate of change of the gap distance "d" over time t is the Slope of the curve, where Slope=$\Delta d/\Delta t$. In addition, the rate of change of firing current is can be used as an indicator that the tissue is transitioning from one state to another state. Accordingly, firing current and, in particular, the rate of change of firing current can be used to monitor device operation. The firing current decreases over time as the knife cuts through the tissue. The rate of change of firing current can vary if the tissue being cut provides more or less resistance due to tissue properties or sharpness of the knife 8305 (FIG. 39). For example, the motor current may be monitored employing the current sensor 2312 in series with the battery 2308 as described herein, the current sensor 2412 in series with the battery 2408 shown herein, or the current sensor 3027 shown in FIG. 18. The current sensors 2312, 2314, 3027 may be adapted and configured to measure the motor firing current "i" over time t and the rate of change of the firing current "i" over time t is the Slope of the curve, where Slope=$\Delta i/\Delta t$. The sensors described in connection with FIGS. 22A-37 and 40 may be adapted and configured to measure tissue compression/impedance. The sensors may be adapted and configured to measure tissue impedance "Z" over time t and the rate of change of the tissue impedance "Z" over time t is the Slope, where Slope=$\Delta Z/\Delta t$. The rate of change of anvil 8306 strain can be measured by a pressure sensor or strain gauge positioned on either or both the anvil 8306 and the surgical staple cartridge 8304 (FIGS. 38, 39) to measure the pressure or strain applied to the tissue grasped between the anvil 8306 and the surgical staple cartridge 8304. Thus, at time zero, trigger 8020 (FIG. 38) pressure may be at its lowest and trigger pressure may increase until completion of an operation (e.g., clamping, cutting, or stapling). The rate of change trigger force can be measured by a pressure sensor or strain gauge positioned on the trigger 8032 of the pistol grip portion 8019 of the handle of the surgical instrument 8010 (FIG. 38) to measure the force required to drive the knife 8305 (FIG. 39) through the tissue grasped between the anvil 8306 and the surgical staple cartridge 8304.

Turning briefly to FIG. 40, the end effector 9012 is one aspect of the end effector 8300 (FIG. 38) that may be adapted to operate with surgical instrument 8010 (FIG. 38) to measure the various derived parameters such as gap distance versus time, tissue compression versus time, and anvil strain versus time. Accordingly, the end effector 9012 shown in FIG. 40 may include one or more sensors configured to measure one or more parameters or characteristics associated with the end effector 9012 and/or a tissue section captured by the end effector 9012. In the example illustrated in FIG. 40, the end effector 9012 comprises a first sensor 9020 and a second sensor 9026. In various examples, the first sensor 9020 and/or the second sensor 9026 may comprise, for example, a magnetic sensor such as, for example, a magnetic field sensor, a strain gauge, a pressure sensor, a force sensor, an inductive sensor such as, for example, an eddy current sensor, a resistive sensor, a capacitive sensor, an optical sensor, and/or any other suitable sensor for measuring one or more parameters of the end effector 9012.

In certain instances, the first sensor 9020 and/or the second sensor 9026 may comprise, for example, a magnetic field sensor embedded in an anvil 9014 and configured to detect a magnetic field generated by a magnet 9024 embedded in a jaw member 9016 and/or the staple cartridge 9018. The anvil 9014 is pivotally rotatable between open and closed positions. The strength of the detected magnetic field may correspond to, for example, the thickness and/or fullness of a bite of tissue located between the anvil 9014 and the jaw member 9016. In certain instances, the first sensor 9020 and/or the second sensor 9026 may comprise a strain gauge, such as, for example, a micro-strain gauge, configured to measure the magnitude of the strain in the anvil 9014 during a clamped condition. The strain gauge provides an electrical signal whose amplitude varies with the magnitude of the strain.

In some aspects, one or more sensors of the end effector 9012 such as, for example, the first sensor 9020 and/or the second sensor 9026 may comprise a pressure sensor configured to detect a pressure generated by the presence of compressed tissue between the anvil 9014 and the jaw member 9016. In some examples, one or more sensors of the end effector 9012 such as, for example, the first sensor 9020 and/or the second sensor 9026 are configured to detect the impedance of a tissue section located between the anvil 9014 and the jaw member 9016. The detected impedance may be indicative of the thickness and/or fullness of tissue located between the anvil 9014 and the jaw member 9016.

In one aspect, one or more of the sensors of the end effector 9012 such as, for example, the first sensor 9020 is configured to measure the gap 9022 between the anvil 9014 and the jaw member 9016. In certain instances, the gap 9022 can be representative of the thickness and/or compressibility of a tissue section clamped between the anvil 9014 and the jaw member 9016. In at least one example, the gap 9022 can be equal, or substantially equal, to the thickness of the tissue section clamped between the anvil 9014 and the jaw member 9016. In one example, one or more of the sensors of the end effector 9012 such as, for example, the first sensor 9020 is configured to measure one or more forces exerted on the anvil 9014 by the jaw member 9016 and/or tissue clamped between the anvil 9014 and the jaw member 9016. The forces exerted on the anvil 9014 can be representative of the tissue compression experienced by the tissue section captured between the anvil 9014 and the jaw member 9016. In one aspect, the gap 9022 between the anvil 9014 and the jaw member 9016 can be measured by positioning a magnetic field sensor on the anvil 9014 and positioning a magnet on the jaw member 9016 such that the gap 9022 is proportional to the signal detected by the magnetic field sensor and the signal is proportional to the distance between the magnet and the magnetic field sensor. It will be appreciated that the location of the magnetic field sensor and the magnet may be swapped such that the magnetic field sensor is positioned on the jaw member 9016 and the magnet is placed on the anvil 9014.

One or more of the sensors such as, for example, the first sensor 9020 and/or the second sensor 9026 may be measured in real-time during a clamping operation. Real-time measurement allows time based information to be analyzed, for example, by a processor, and used to select one or more algorithms and/or look-up tables for the purpose of assessing, in real-time, a manual input of an operator of the surgical instrument 9010. Furthermore, real-time feedback can be provided to the operator to assist the operator in calibrating the manual input to yield a desired output.

FIG. 41 is a logic diagram illustrating one aspect of a real-time feedback system 9060 for assessing, in real-time, a manual input 9064 of an operator of the surgical instrument 9010 and providing to the operator real-time feedback as to the adequacy of the manual input 9064. With reference to FIGS. 40 and 41, in the example illustrated in FIG. 41, the real-time feedback system 9060 is comprised of a circuit. The circuit includes a controller 9061 comprising a processor 9062. A sensor such as, for example, the first sensor 9020 is employed by the processor 9062 to measure a parameter of the end effector 9012. In addition, the processor 9062 can be configured to determine or receive a value representative of a manual input 9064 of an operator of the surgical instrument 9010. The manual input 9064 can be continuously assessed by the processor 9062 for as long as the manual input 9064 is being provided by the operator. The processor 9062 can be configured to monitor a value representative of the manual input 9064. Furthermore, the processor 9062 is configured to assign, select, or determine a position, rank, and/or status for the determined value with respect to a desired zone or range. The measurement of the parameter of the end effector 9012 and the determined value can be employed by the processor 9062 to select or determine the position, rank, and/or status associated with the determined value, as described in greater detail below. A change in the manual input 9064 yields a change in the determined value which, in turn, yields a change in the position, rank, and/or status assigned to the determined value with respect to the desired zone or range.

As illustrated in FIG. 41, the real-time feedback system 9060 may further include a feedback indicator 9066 which can be adjusted between a plurality of positions, ranks, and/or statuses inside and outside a desired zone or range. In one example, the processor 9062 may select a first position (P1), rank, and/or status that characterizes the manual input 9064 based on a measurement (M1) of a parameter of the end effector 9012 and a first determined value (V1) representing a first manual input (I1). In certain instances, the first position (P1), rank, and/or status may fall outside the desired zone or range. In such instances, the operator may change the manual input 9064 from the first manual input (I1) to a second manual input (I2) by increasing or decreasing the manual input 9064, for example. In response, the processor 9062 may adjust the feedback indicator 9066 from the first position (P1), rank, and/or status to a second position (P2), rank, and/or status, which characterizes the change to the manual input 9064. The processor 9062 may select the second position (P2), rank, and/or status based on the measurement (M1) of the parameter of the end effector 9012 and a second determined value (V2) representing a second manual input (I2). In certain instances, the second position (P2), rank, and/or status may fall inside the desired zone or range. In such instances, the operator may maintain the second manual input (I2) for a remainder of a treatment cycle or procedure, for example.

In the aspect illustrated in FIG. 41, the controller 9061 includes a storage medium such as, for example, a memory 9068. The memory 9068 may be configured to store correlations between measurements of one or more parameters of the end effector 9012, values representing manual inputs, and corresponding positions, ranks, and/or statuses characterizing the manual input 9064 with respect to a desired zone or range. In one example, the memory 9068 may store the correlation between the measurement (M1), the first determined value (V1), and the first manual input (I1), and the correlation between the measurement (M1), the second determined value (V2), and the second manual input (I2). In one example, the memory 9068 may store an algorism, an equation, or a look-up table for determining correlations between measurements of one or more parameters of the end effector 9012, values representing manual inputs, and corresponding positions, ranks, or statuses with respect to a desired zone or range. The processor 9062 may employ such algorism, equation, and/or look-up table to characterize a manual input 9064 provided by an operator of the surgical instrument 9010 and provide feedback to the operator as to the adequacy of the manual input 9064.

FIG. 42 is a logic diagram illustrating one aspect of a real-time feedback system 9070. The real-time feedback system 9070 is similar in many respects to the real-time feedback system 9060. For example, like the real-time feedback system 9060, the real-time feedback system 9070 is configured for assessing, in real-time, a manual input of an operator of the surgical instrument 9010 and providing to the operator real-time feedback as to the adequacy of the manual input. Furthermore, like the real-time feedback system 9060, the real-time feedback system 9070 is comprised of a circuit that may include the controller 9061.

In the aspect illustrated in FIG. 42, a sensor 9072, such as, for example, a strain gauge or a micro-strain gauge, is configured to measure one or more parameters of the end effector 9012, such as, for example, the amplitude of the strain exerted on the anvil 9014 during a clamping operation, which can be indicative of the tissue compression. The measured strain is converted to a digital signal and provided to the processor 9062. A sensor 9074, such as, for example, a load sensor, can measure the force to advance the cutting member 9040 to cut tissue captured between the anvil 9014 and the staple cartridge 9018. Alternatively, a current sensor (not shown) can be employed to measure the current drawn by the motor 9082. The force required to advance the firing bar 9036 can correspond to the current drawn by the motor 9082, for example. The measured force is converted to a digital signal and provided to the processor 9062. A sensor 9076, such as, for example, a magnetic field sensor, can be employed to measure the thickness of the captured tissue, as described above. The measurement of the magnetic field sensor 9076 is also converted to a digital signal and provided to the processor 9062.

In the aspect illustrated in FIG. 42, the real-time feedback system 9070 further includes the tracking system 9080 which can be configured to determine the position of the firing trigger. As described above, the firing trigger 9094 can be depressed or actuated by moving the firing trigger 9094 between a plurality of positions, each corresponding to one of a plurality of values of a characteristic of motion of the firing bar 9036 and/or the cutting member 9040 during a firing stroke. As describe above, a characteristic of motion can be a speed of advancement of the firing bar 9036 and/or the cutting member 9040 during the firing stroke. In certain instances, a motor driver 9092 can be in communication with the controller 9061, and can be configured to drive the motor 9082 in accordance with an operator's manual input as detected by the tracking system 9080.

Further to the above, the real-time feedback system 9070 may include a feedback indicator 9066. In one aspect, the feedback indicator 9066 can be disposed in the handle 9030. Alternatively, the feedback indicator can be disposed in the shaft assembly 9032, for example. In any event, the controller 9061 may employ the feedback indicator 9066 to provide feedback to an operator of the surgical instrument 9010 with regard to the adequacy of a manual input such as, for example, a selected position of the firing trigger 9094. To do so, the controller 9061 may assess the selected position of the firing trigger 9094 and/or the corresponding value of the speed of the firing bar 9036 and/or the cutting member 9040. The measurements of the tissue compression, the tissue thickness, and/or the force required to advance the firing bar 9036, as respectively measured by the sensors 9072, 9074, and 9076, can be used by the controller 9061 to characterize the selected position of the firing trigger 9094 and/or the corresponding value of the speed of the firing bar 9036 and/or the cutting member 9040. In one instance, the memory 9068 may store an algorism, an equation, and/or a look-up table which can be employed by the controller 9061 in the assessment. In one example, the measurements of the sensors 9072, 9074, and/or 9076 can be used to select or determine a position, rank, and/or a status that characterizes the selected position of the firing trigger 9094 and/or the corresponding value of the speed of the firing bar 9036 and/or the cutting member 9040. The determined position, rank, and/or status can be communicated to the operator via the feedback indicator 9066.

The reader will appreciate that an optimal speed of the firing bar 9036 and/or the cutting member 9040 during a firing stroke can depend on several parameters of the end effector 9012 such as, for example, the thickness of the tissue captured by the end effector 9012, the tissue compression, and/or the force required to advance the firing bar 9036 and, in turn, the cutting member 9040. As such, measurements of these parameters can be leveraged by the controller 9061 in assessing whether a current speed of advancement of the cutting member 9040 through the captured tissue is within an optimal zone or range.

In one aspect, a plurality of smart sensors may be positioned on a power line of an end-effector and may be communicatively coupled to a handle of an endocutter. The smart sensors may be positioned in series or parallel with respect to the power line. Referring now to FIG. 43, smart sensors 12060 and 12062 may be in communication with a signal processing component or a processor 12064 which may be local to the smart sensors. Both the smart sensors 12060 and 12062 and the processor 12064 may be located at the end-effector (represented by dashed-box 12066). For example, smart sensor 12060 may output signals or data to an operational amplifier 12068 and an ADC converter 12070, which may condition the signals or data for input into processor 12064. Similarly, smart sensor 12062 may output signals or data to an operational amplifier 12072 and an ADC converter 12074, which may condition the signals or data for input into processor 12064.

Smart sensors 12060 and/or 12062 may be different types of sensors or the same type of sensor, which may be, for example, magnetic field sensors, magnetic sensors, inductive sensors, capacitive sensors, or other types of sensors used in medical devices or endocutters. Component 12064, previously referred to as a processor, also may be a computational core, FPGA (field programmable gate array), logic unit (e.g., logic processor or logic controller), signal processing unit, or other type of processor. The processor 12064 may be in communication with a memory, such as non-volatile memory 12076, which may store calculation data, equipment information such as a type of cartridge inserted in the end-effector 12066, tabular data, or other reference data that may enable the processor 12064 to process signals or data received from one or more of the smart sensors 12060 or 12062 for use in operating the end-effector 12066 or an endocutter.

Further, a shaft 12078 may include a return path through which at least one of the plurality of smart sensors (e.g., smart sensors 12060 or 12062) and the handle 12080 are communicatively coupled. The shaft may include one or more wires which may transfer information from the processor 12064 to the handle 12080 for operation of the end-effector 12066 or endocutter. In one example, the information from the processor 12064 may be communicated to the handle 12080 (by way of shaft 12078 or directly without use of shaft 12078) over one or more of: a wired-line, a single-wired line, a multi-wired line, a wireless communication protocol such as Bluetooth, an optical line, or an acoustic line.

In one aspect, at least one of a plurality of smart sensors positioned at an end-effector may include a signal processing component. For example, the signal processing component may be built into the smart sensor or may be locally coupled to the smart sensor as a single module. The signal processing component may be configured to process data received from a sensor component (e.g., sensor component 12020) of at least one of the plurality of smart sensors. A controller 12024 (e.g., a controller) at the handle may be communicatively coupled to at least one of the plurality of smart sensors.

In one aspect, a smart sensor may be configured for local signal processing in a medical device. The smart sensor may include at least one sensor component (e.g., sensor component 12020) and at least one processing component (e.g., processing component 12022). The processing component may be configured to receive data from the at least one sensor component and to process the data into information for use by the medical device. The medical device may be, for example, an endocutter, however this is not intended to be a limitation of the present disclosure. It should be understood that the techniques and features discussed herein for smart sensors with local signal processing may be used in any medical device where processing of sensor signals or data is used for operation of the medical device.

Further, a controller (e.g., controller 12024, controller) in the medical device may be configured to receive the information (i.e., processed signals or data) from the at least one processing component (e.g., processing component 12022). As discussed above, the medical device may be a surgical instrument such as an endocutter and the smart sensor may be configured for local signal processing in the surgical instrument. Local signal processing may refer to, for example, processing signals or data from a sensor component at a processing component coupled to the sensor, where the resulting processed information may be used by a separate component. For example, the controller 12024 may be positioned in the handle 12012 of the surgical instrument (i.e., the endocutter 12010) and the smart sensor may be configured to be positioned in a separate component (i.e., the end-effector 12016) of the surgical instrument (i.e., the endocutter 12010), separate from the handle 12012. Thus, the controller 12024 may be positioned at the handle 12012 of the surgical instrument and the signal processing component 12022 and the sensor 12020 may be located in a component separate from the handle 12012 (e.g., end-effector 12016).

In this way, the handle or controller 12024 need not have information about the smart sensor, knowledge of what the smart sensor is doing, or capability to interpret data feed back from the smart sensor. This is because the processing component 12022 may transform or condition the data from the smart sensor and generate information from the data directly usable by the handle or controller 12024. The information generated by the processing component may be used directly, without the data from the smart sensor needing to be processed in another part of the medical device (e.g., near the handle 12012 or controller 12024). Thus, the surgical instrument may be controlled based on the (processed) information from the signal processing component local to the sensor.

In one aspect, a current draw on a power line communicatively coupled to the signal processing component 12022 (i.e., local to the sensor 12020) may be monitored. The current draw may be monitored by a processor, controller, or other monitoring device at the shaft 12014 or the handle 12012, or at another processor, controller or other monitoring device separate from the signal processing component 12022. For example, the monitoring may be a standard Morse Code type monitoring of the current draw on the power line. An issue with the surgical instrument based on the current draw and a particular sensor may be determined by the separate processor at, e.g., the handle 12012. In this way, the monitoring may allow the handle (or a processor or controller therein) to be informed of various issues related to signals or data received by one or more sensor and which particular sensor identified the issue, without a further communication requirement (e.g., pairing, or other coupled communication).

FIG. 44 illustrates one aspect of a circuit 13190 configured to convert signals from the first sensor 13158 and the plurality of secondary sensors 13160*a*, 13160*b* into digital signals receivable by a processor, such as, for example, the primary processor 2006 (FIGS. 16A-16B). The circuit 13190 comprises an analog-to-digital convertor 13194. In some examples, the analog-to-digital convertor 13194 comprises a 4-channel, 18-bit analog to digital convertor. Those skilled in the art will recognize that the analog-to-digital convertor 13194 may comprise any suitable number of channels and/or bits to convert one or more inputs from analog to digital signals. The circuit 13190 comprises one or more level shifting resistors 13196 configured to receive an input from the first sensor 13158, such as, for example, a magnetic field sensor. The level shifting resistors 13196 adjust the input from the first sensor, shifting the value to a higher or lower voltage depending on the input. The level shifting resistors 13196 provide the level-shifted input from the first sensor 13158 to the analog-to-digital convertor.

In some aspects, a plurality of secondary sensors 13160*a*, 13160*b* are coupled to a plurality of bridges 13192*a*, 13192*b* within the circuit 13190. The plurality of bridges 13192*a*, 13192*b* may provide filtering of the input from the plurality of secondary sensors 13160*a*, 13160*b*. After filtering the input signals, the plurality of bridges 13192*a*, 13192*b* provide the inputs from the plurality of secondary sensors 13160*a*, 13160*b* to the analog-to-digital convertor 13194. In some examples, a switch 13198 coupled to one or more level shifting resistors may be coupled to the analog-to-digital convertor 13194. The switch 13198 is configured to calibrate one or more of the input signals, such as, for example, an input from a magnetic field sensor. The switch 13198 may be engaged to provide one or more level shifting signals to adjust the input of one or more of the sensors, such as, for example, to calibrate the input of a magnetic field sensor. In some examples, the adjustment is not necessary, and the switch 13198 is left in the open position to decouple the level shifting resistors. The switch 13198 is coupled to the analog-to-digital convertor 13194. The analog-to-digital convertor 13194 provides an output to one or more processors, such as, for example, the primary processor 2006 (FIGS. 16A-16B). The primary processor 2006 calculates one or more parameters of the end effector 13150 based on the input from the analog-to-digital convertor 13194. For example, in one example, the primary processor 2006 calculates a thickness of tissue located between the anvil 13152 and the staple cartridge 13156 based on inputs from the first sensor 13158 and the plurality of secondary sensors 13160*a*, 13160*b*.

FIG. 45 illustrates one aspect of a staple cartridge 13606 that comprises a flex cable 13630 connected to a magnetic field sensor 13610 and processor 13612. The staple cartridge 13606 is similar to the staple cartridge 13606 is similar to the surgical staple cartridge 304 (FIG. 1) described above in connection with surgical instrument 10 (FIGS. 1-6). FIG. 112 is an exploded view of the staple cartridge 13606. The staple cartridge comprises 13606 a cartridge body 13620, a wedge sled 13618, a cartridge tray 13622, and a flex cable 13630. The flex cable 13630 further comprises electrical contacts 13632 at the proximal end of the staple cartridge 13606, placed to make an electrical connection when the staple cartridge 13606 is operatively coupled with an end effector, such as end effector 13800 described below. The electrical contacts 13632 are integrated with cable traces 13634, which extend along some of the length of the staple cartridge 13606. The cable traces 13634 connect 13636 near the distal end of the staple cartridge 13606 and this connection 13636 joins with a conductive coupling 13614. A magnetic field sensor 13610 and a processor 13612 are operatively coupled to the conductive coupling 13614 such that the magnetic field sensor 13610 and the processor 13612 are able to communicate.

FIG. 46 illustrates one aspect of an end effector 13800 with a flex cable 13830 operable to provide power to a staple cartridge 13806 that comprises a distal sensor plug 13816. The end effector 13800 is similar to the end effector 300 (FIG. 1) described above in connection with surgical instrument 10 (FIGS. 1-6). The end effector 13800 comprises an anvil 13802, a jaw member or elongated channel 13804, and a staple cartridge 13806 operatively coupled to the elongated channel 13804. The end effector 13800 is operatively coupled to a shaft assembly. The shaft assembly is similar to interchangeable shaft assembly 200 (FIG. 1) described above in connection with surgical instrument 10 (FIGS. 1-6). The shaft assembly further comprises a closure tube that encloses the exterior of the shaft assembly. In some examples the shaft assembly further comprises an articulation joint 13904, which includes a double pivot closure sleeve assembly. The double pivot closure sleeve assembly includes an end effector closure sleeve assembly that is operable to couple with the end effector 13800.

FIGS. 47 and 48 illustrate the elongated channel 13804 portion of the end effector 13800 without the anvil 13802 or the staple cartridge, to illustrate how the flex cable 13830 can be seated within the elongated channel 13804. In some examples, the elongated channel 13804 further comprises a third aperture 13824 for receiving the flex cable 13830. Within the body of the elongated channel 13804 the flex cable splits 13834 to form extensions 13836 on either side of the elongated channel 13804. FIG. 48 further illustrates that connectors 13838 can be operatively coupled to the flex cable extensions 13836.

FIG. 49 illustrates the flex cable 13830 alone. As illustrated, the flex cable 13830 comprises a single coil 13832 operative to wrap around the articulation joint 13904 (FIG. 46), and a split 13834 that attaches to extensions 13836. The extensions can be coupled to connectors 13838 that have on their distal facing surfaces prongs 13840 for coupling to the staple cartridge 13806, as described below.

FIG. 50 illustrates a close up view of the elongated channel 13804 shown in FIGS. 47 and 48 with a staple cartridge 13804 coupled thereto. The staple cartridge 13804 comprises a cartridge body 13822 and a cartridge tray 13820. In some examples the staple cartridge 13806 further comprises electrical traces 13828 that are coupled to proximal contacts 13856 at the proximal end of the staple cartridge 13806. The proximal contacts 13856 can be positioned to form a conductive connection with the prongs 13840 of the connectors 13838 that are coupled to the flex cable extensions 13836. Thus, when the staple cartridge 13806 is operatively coupled with the elongated channel 13804, the flex cable 13830, through the connectors 13838 and the connector prongs 13840, can provide power to the staple cartridge 13806.

FIGS. 51 and 52 illustrate one aspect of a distal sensor plug 13816. FIG. 51 illustrates a cutaway view of the distal sensor plug 13816. As illustrated, the distal sensor plug 13816 comprises a magnetic field sensor 13810 and a processor 13812. The distal sensor plug 13816 further comprises a flex board 13814. As further illustrated in FIG. 52, the magnetic field sensor 13810 and the processor 13812 are operatively coupled to the flex board 13814 such that they are capable of communicating.

FIG. 53 illustrates one aspect of an end effector 13950 with a flex cable 13980 operable to provide power to sensors and electronics in the distal tip 13952 of the anvil 13961 portion. The end effector 13950 comprises an anvil 13961, a jaw member or elongated channel 13954, and a staple cartridge 13956 operatively coupled to the elongated channel. The end effector 13950 is operatively coupled to a shaft assembly 13960. The shaft assembly 13960 further comprises a closure tube 13962 that encloses the shaft assembly 13960. In some examples the shaft assembly 13960 further comprises an articulation joint 13964, which includes a double pivot closure sleeve assembly 13966.

In various aspects, the end effector 13950 further comprises a flex cable 13980 that is configured to not interfere with the function of the articulation joint 13964. In some examples, the closure tube 13962 comprises a first aperture 13968 through which the flex cable 13980 can extend. In some examples, flex cable 13980 further comprises a loop or coil 13982 that wraps around the articulation joint 13964 such that the flex cable 13980 does not interfere with the operation of the articulation joint 13964, as further described below. In some examples, the flex cable 13980 extends along the length of the anvil 13961 to a second aperture 13970 in the distal tip of the anvil 13961.

A portion of a surgical stapling instrument 16000 is illustrated in FIGS. 54-56. The stapling instrument 16000 is usable with a manually-operated system and/or a robotically-controlled system, for example. The stapling instrument 16000 comprises a shaft 16010 and an end effector 16020 extending from the shaft 16010. The end effector 16020 comprises a cartridge channel 16030 and a staple cartridge 16050 positioned in the cartridge channel 16030. The staple cartridge 16050 comprises a cartridge body 16051 and a retainer 16057 attached to the cartridge body 16051. The cartridge body 16051 is comprised of a plastic material, for example, and the retainer 16057 is comprised of metal, for example; however, the cartridge body 16051 and the retainer 16057 can be comprised of any suitable material. The cartridge body 16051 comprises a deck 16052 configured to support tissue, a longitudinal slot 16056, and a plurality of staple cavities 16053 defined in the deck 16052.

Referring primarily to FIGS. 55 and 56, staples 16055 are removably positioned in the staple cavities 16053 and are supported by staple drivers 16054 which are also movably positioned in the staple cavities 16053. The retainer 16057 extends around the bottom of the cartridge body 16051 to keep the staple drivers 16054 and/or the staples 16055 from falling out of the bottom of the staple cavities 16053. The staple drivers 16054 and the staples 16055 are movable between an unfired position (FIG. 55) and a fired position by a sled 16060. The sled 16060 is movable between a proximal, unfired position (FIG. 55) toward a distal, fired position to eject the staples 16055 from the staple cartridge 16050, as illustrated in FIG. 56. The sled 16060 comprises one or more ramped surfaces 16064 which are configured to slide under the staple drivers 16054. The end effector 16020 further comprises an anvil 16040 configured to deform the staples 16055 when the staples 16055 are ejected from the staple cartridge 16050. In various instances, the anvil 16040 can comprise forming pockets 16045 defined therein which are configured to deform the staples 16055.

The shaft 16010 comprises a frame 16012 and an outer sleeve 16014 which is movable relative to the frame 16012. The cartridge channel 16030 is mounted to and extends from the shaft frame 16012. The outer sleeve 16014 is operably engaged with the anvil 16040 and is configured to move the anvil 16040 between an open position (FIG. 54) and a closed position (FIG. 55). In use, the anvil 16040 is movable toward a staple cartridge 16050 positioned in the cartridge channel 16030 to clamp tissue against the deck 16052 of the staple cartridge 16050. In various alternative aspects, the cartridge channel 16030 and the staple cartridge 16050 are movable relative to the anvil 16040 to clamp tissue therebetween. In either event, the shaft 16010 further comprises a firing member 16070 configured to push the sled 16060 distally. The firing member 16070 comprises a knife edge 16076 which is movable within the longitudinal slot 16056 and is configured to incise the tissue positioned intermediate the anvil 16040 and the staple cartridge 16050 as the firing member 16070 is advanced distally to eject the staples 16055 from the staple cartridge 16050. The firing member 16070 further comprises a first cam 16071 configured to engage the cartridge channel 16030 and a second cam 16079 configured to engage the anvil 16040 and hold the anvil 16040 in position relative to the staple cartridge 16050. The first cam 16071 is configured to slide under the cartridge channel 16030 and the second cam 16079 is configured to slide within an elongated slot 16049 defined in the anvil 16040.

FIG. 57 illustrates one aspect of an end effector 3011 comprising a first sensor 3008*a* and a second sensor 3008*b*. The end effector 3011 is similar to the end effector 300 described above. The end effector 3011 comprises an anvil 3013 pivotally coupled to a jaw member 3004. The jaw member 3004 is configured to receive a staple cartridge 3021 therein. The staple cartridge 3021 comprises a plurality of staples (not shown). The plurality of staples is deployable from the staple cartridge 3021 during a surgical operation. The end effector 3011 comprises a first sensor 3008*a* configured to measure one or more parameters of the end effector 3011. For example, in one aspect, the first sensor 3008*a* is configured to measure the gap 3023 between the anvil 3013 and the jaw member 3004. The first sensor 3008*a* may comprise, for example, a Hall effect sensor configured to detect a magnetic field generated by a magnet 3012 embedded in the second jaw member 3004 and/or the staple cartridge 3021. As another example, in one aspect, the first sensor 3008*a* is configured to measure one or more forces exerted on the anvil 3013 by the second jaw member 3004 and/or tissue clamped between the anvil 3013 and the second jaw member 3004.

The end effector 3011 comprises a second sensor 3008*b*. The second sensor 3008*b* is configured to measure one or more parameters of the end effector 3011. For example, in various aspects, the second sensor 3008*b* may comprise a strain gauge configured to measure the magnitude of the strain in the anvil 3013 during a clamped condition. The strain gauge provides an electrical signal whose amplitude varies with the magnitude of the strain. In various aspects, the first sensor 3008*a* and/or the second sensor 3008*b* may comprise, for example, a magnetic sensor such as, for example, a Hall effect sensor, a strain gauge, a pressure sensor, a force sensor, an inductive sensor such as, for example, an eddy current sensor, a resistive sensor, a capacitive sensor, an optical sensor, and/or any other suitable sensor for measuring one or more parameters of the end effector 3011. The first sensor 3008*a* and the second sensor 3008*b* may be arranged in a series configuration and/or a parallel configuration. In a series configuration, the second sensor 3008*b* may be configured to directly affect the output of the first sensor 3008*a*. In a parallel configuration, the second sensor 3008*b* may be configured to indirectly affect the output of the first sensor 3008*a*.

In one aspect, the one or more parameters measured by the first sensor 3008*a* are related to the one or more parameters measured by the second sensor 3008*b*. For example, in one aspect, the first sensor 3008*a* is configured to measure the gap 3023 between the anvil 3013 and the jaw member 3004. The gap 3023 is representative of the thickness and/or compressibility of a tissue section clamped between the anvil 3013 and the staple cartridge 3021 located in the jaw member 3004. The first sensor 3008*a* may comprise, for example, a Hall effect sensor configured to detect a magnetic field generated by a magnet 3012 coupled to the second jaw member 3004 and/or the staple cartridge 3021. Measuring at a single location accurately describes the compressed tissue thickness for a calibrated full bit of tissue, but may provide inaccurate results when a partial bite of tissue is placed between the anvil 3013 and the second jaw member 3004. A partial bite of tissue, either a proximal partial bite or a distal partial bite, changes the clamping geometry of the anvil 3013.

In some aspects, the second sensor 3008*b* is configured to detect one or more parameters indicative of a type of tissue bite, for example, a full bite, a partial proximal bite, and/or a partial distal bite. The measurement of the second sensor 3008*b* may be used to adjust the measurement of the first sensor 3008*a* to accurately represent a proximal or distal positioned partial bite's true compressed tissue thickness. For example, in one aspect, the second sensor 3008*b* comprises a strain gauge, such as, for example, a micro-strain gauge, configured to monitor the amplitude of the strain in the anvil during a clamped condition. The amplitude of the strain of the anvil 3013 is used to modify the output of the first sensor 3008*a*, for example, a Hall effect sensor, to accurately represent a proximal or distal positioned partial bite's true compressed tissue thickness. The first sensor 3008*a* and the second sensor 3008*b* may be measured in real-time during a clamping operation. Real-time measurement allows time based information to be analyzed, for example, by the primary processor 2006, and used to select one or more algorithms and/or look-up tables to recognize tissue characteristics and clamping positioning to dynamically adjust tissue thickness measurements.

In some aspects, the thickness measurement of the first sensor 3008*a* may be provided to an output device of a surgical instrument 10 coupled to the end effector 3011. For example, in one aspect, the end effector 3011 is coupled to the surgical instrument 10 comprising a display 2028. The measurement of the first sensor 3008*a* is provided to a processor, for example, the primary processor 2006. The primary processor 2006 adjusts the measurement of the first sensor 3008*a* based on the measurement of the second sensor 3008*b* to reflect the true tissue thickness of a tissue section clamped between the anvil 3013 and the staple cartridge 3021. The primary processor 2006 outputs the adjusted tissue thickness measurement and an indication of full or partial bite to the display 2028. An operator may determine whether or not to deploy the staples in the staple cartridge 3021 based on the displayed values.

In some aspects, the first sensor 3008*a* and the second sensor 3008*b* may be located in different environments, such as, for example, the first sensor 3008*a* being located within a patient at a treatment site and the second sensor 3008*b* being located externally to the patient. The second sensor 3008*b* may be configured to calibrate and/or modify the output of the first sensor 3008*a*. The first sensor 3008*a* and/or the second sensor 3008*b* may comprise, for example, an environmental sensor. Environmental sensors may comprise, for example, temperature sensors, humidity sensors, pressure sensors, and/or any other suitable environmental sensor.

FIG. 58 is a logic diagram illustrating one aspect of a process 3050 for determining and displaying the thickness of a tissue section clamped between the anvil 3013 and the staple cartridge 3021 of the end effector 3011. The process 3050 comprises obtaining a Hall effect voltage 3052, for example, through a Hall effect sensor located at the distal tip of the anvil 3013. The Hall effect voltage 3052 is provided to an analog to digital convertor 3054 and converted into a digital signal. The digital signal is provided to a processor, such as, for example, the primary processor 2006. The primary processor 2006 calibrates 3056 the curve input of the Hall effect voltage 3052 signal. A strain gauge 3058, such as, for example, a micro-strain gauge, is configured to measure one or more parameters of the end effector 3011, such as, for example, the amplitude of the strain exerted on the anvil 3013 during a clamping operation. The measured strain is converted 3060 to a digital signal and provided to the processor, such as, for example, the primary processor 2006. The primary processor 2006 uses one or more algorithms and/or lookup tables to adjust the Hall effect voltage 3052 in response to the strain measured by the strain gauge 3058 to reflect the true thickness and fullness of the bite of tissue clamped by the anvil 3013 and the staple cartridge 3021. The adjusted thickness is displayed 3026 to an operator by, for example, a display 2026 embedded in the surgical instrument 10.

In some aspects, the surgical instrument can further comprise a load sensor 3082 or load cell. The load sensor 3082 can be located, for instance, in the interchangeable shaft assembly 200, described above, or in the housing 12, also described above.

FIG. 59 is a logic diagram illustrating one aspect of a process 3070 for determining and displaying the thickness of a tissue section clamped between the anvil 3013 and the staple cartridge 3021 of the end effector 3011. The process comprises obtaining a Hall effect voltage 3072, for example, through a Hall effect sensor located at the distal tip of the anvil 3013. The Hall effect voltage 3072 is provided to an analog to digital convertor 3074 and converted into a digital signal. The digital signal is provided to a processor, such as, for example, the primary processor 2006. The primary processor 2006 applies calibrates 3076 the curve input of the Hall effect voltage 3072 signal. A strain gauge 3078, such as, for example, a micro-strain gauge, is configured to measure one or more parameters of the end effector 3011, such as, for example, the amplitude of the strain exerted on the anvil 3013 during a clamping operation. The measured strain is converted 3080 to a digital signal and provided to the processor, such as, for example, the primary processor 2006. The load sensor 3082 measures the clamping force of the anvil 3013 against the staple cartridge 3021. The measured clamping force is converted 3084 to a digital signal and provided to the processor, such as for example, the primary processor 2006. The primary processor 2006 uses one or more algorithms and/or lookup tables to adjust the Hall effect voltage 3072 in response to the strain measured by the strain gauge 3078 and the clamping force measured by the load sensor 3082 to reflect the true thickness and fullness of the bite of tissue clamped by the anvil 3013 and the staple cartridge 3021. The adjusted thickness is displayed 3026 to an operator by, for example, a display 2026 embedded in the surgical instrument 10.

FIG. 60 illustrates one aspect of an end effector 3100 comprising a first sensor 3108*a* and a second sensor 3108*b*. The end effector 3100 is similar to the end effector 3011. The end effector 3100 comprises an anvil, or anvil, 3102 pivotally coupled to a jaw member 3104. The jaw member 3104 is configured to receive a staple cartridge 3106 therein. The end effector 3100 comprises a first sensor 3108*a* coupled to the anvil 3102. The first sensor 3108*a* is configured to measure one or more parameters of the end effector 3100, such as, for example, the gap 3110 between the anvil 3102 and the staple cartridge 3106. The gap 3110 may correspond to, for example, a thickness of tissue clamped between the anvil 3102 and the staple cartridge 3106. The first sensor 3108*a* may comprise any suitable sensor for measuring one or more parameters of the end effector. For example, in various aspects, the first sensor 3108*a* may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In some aspects, the end effector 3100 comprises a second sensor 3108*b*. The second sensor 3108*b* is coupled to jaw member 3104 and/or the staple cartridge 3106. The second sensor 3108*b* is configured to detect one or more parameters of the end effector 3100. For example, in some aspects, the second sensor 3108*b* is configured to detect one or more instrument conditions such as, for example, a color of the staple cartridge 3106 coupled to the jaw member 3104, a length of the staple cartridge 3106, a clamping condition of the end effector 3100, the number of uses/number of remaining uses of the end effector 3100 and/or the staple cartridge 3106, and/or any other suitable instrument condition. The second sensor 3108*b* may comprise any suitable sensor for detecting one or more instrument conditions, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In one aspect, input from the second sensor **3108*b* may be used to calibrate the input of the first sensor 3108*a*. The second sensor 3108*b* may be configured to detect one or more parameters of the staple cartridge 3106, such as, for example, the color and/or length of the staple cartridge 3106. The detected parameters, such as the color and/or the length of the staple cartridge 3106, may correspond to one or more properties of the cartridge, such as, for example, the height of the cartridge deck, the thickness of tissue useable/optimal for the staple cartridge, and/or the pattern of the staples in the staple cartridge 3106. The known parameters of the staple cartridge 3106 may be used to adjust the thickness measurement provided by the first sensor 3108*a*. For example, if the staple cartridge 3106 has a higher deck height, the thickness measurement provided by the first sensor 3108*a* may be reduced to compensate for the added deck height. The adjusted thickness may be displayed to an operator, for example, through a display 2026 coupled to the surgical instrument 10**.

FIG. 61 illustrates one aspect of an end effector 3150 comprising a first sensor 3158 and a plurality of secondary sensors **3160*a*, 3160*b*. The end effector 3150 comprises an anvil, or anvil, 3152 and a jaw member 3154. The jaw member 3154 is configured to receive a staple cartridge 3156. The anvil 3152 is pivotally moveable with respect to the jaw member 3154 to clamp tissue between the anvil 3152 and the staple cartridge 3156. The anvil comprises a first sensor 3158. The first sensor 3158 is configured to detect one or more parameters of the end effector 3150, such as, for example, the gap 3110 between the anvil 3152 and the staple cartridge 3156. The gap 3110 may correspond to, for example, a thickness of tissue clamped between the anvil 3152 and the staple cartridge 3156. The first sensor 3158 may comprise any suitable sensor for measuring one or more parameters of the end effector. For example, in various aspects, the first sensor 3158** may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In some aspects, the end effector 3150 comprises a plurality of secondary sensors **3160*a*, 3160*b*. The secondary sensors 3160*a*, 3160*b* are configured to detect one or more parameters of the end effector 3150. For example, in some aspects, the secondary sensors 3160*a*, 3160*b* are configured to measure an amplitude of strain exerted on the anvil 3152 during a clamping procedure. In various aspects, the secondary sensors 3160*a*, 3160*b* may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor. The secondary sensors 3160*a*, 3160*b* may be configured to measure one or more identical parameters at different locations of the anvil 3152, different parameters at identical locations on the anvil 3152, and/or different parameters at different locations on the anvil 3152**.

FIG. 62 illustrates one aspect of an end effector 3200 comprising a plurality of sensors **3208*a*-3208*d*. The end effector 3200 comprises an anvil 3202 pivotally coupled to a jaw member 3204. The jaw member 3204 is configured to receive a staple cartridge 3206 therein. The anvil 3202 comprises a plurality of sensors 3208*a*-3208*d* thereon. The plurality of sensors 3208*a*-3208*d* is configured to detect one or more parameters of the end effector 3200, such as, for example, the anvil 3202. The plurality of sensors 3208*a*-3208*d* may comprise one or more identical sensors and/or different sensors. The plurality of sensors 3208*a*-3208*d* may comprise, for example, magnetic sensors, such as a Hall effect sensor, strain gauges, pressure sensors, inductive sensors, such as an eddy current sensor, resistive sensors, capacitive sensors, optical sensors, and/or any other suitable sensors or combination thereof. For example, in one aspect, the plurality of sensors 3208*a*-3208*d*** may comprise a plurality of strain gauges.

In one aspect, the plurality of sensors **3208*a*-3208*d* allows a robust tissue thickness sensing process to be implemented. By detecting various parameters along the length of the anvil 3202, the plurality of sensors 3208*a*-3208*d* allow a surgical instrument, such as, for example, the surgical instrument 10, to calculate the tissue thickness in the jaws regardless of the bite, for example, a partial or full bite. In some aspects, the plurality of sensors 3208*a*-3208*d* comprises a plurality of strain gauges. The plurality of strain gauges is configured to measure the strain at various points on the anvil 3202. The amplitude and/or the slope of the strain at each of the various points on the anvil 3202 can be used to determine the thickness of tissue in between the anvil 3202 and the staple cartridge 3206. The plurality of strain gauges may be configured to optimize maximum amplitude and/or slope differences based on clamping dynamics to determine thickness, tissue placement, and/or material properties of the tissue. Time based monitoring of the plurality of sensors 3208*a*-3208*d* during clamping allows a processor, such as, for example, the primary processor 2006, to utilize algorithms and look-up tables to recognize tissue characteristics and clamping positions and dynamically adjust the end effector 3200 and/or tissue clamped between the anvil 3202 and the staple cartridge 3206**.

FIG. 63 is a logic diagram illustrating one aspect of a process 3220 for determining one or more tissue properties based on a plurality of sensors **3208*a*-3208*d*. In one aspect, a plurality of sensors 3208*a*-3208*d* generate 3222*a*-3222*d* a plurality of signals indicative of one or more parameters of the end effector 3200. The plurality of generated signals is converted 3224*a*-3224*d* to digital signals and provided to a processor. For example, in one aspect comprising a plurality of strain gauges, a plurality of electronic μStrain (micro-strain) conversion circuits convert 3224*a*-3224*d* the strain gauge signals to digital signals. The digital signals are provided to a processor, such as, for example, the primary processor 2006. The primary processor 2006 determines 3226 one or more tissue characteristics based on the plurality of signals. The primary processor 2006 may determine the one or more tissue characteristics by applying an algorithm and/or a look-up table. The one or more tissue characteristics are displayed 3026 to an operator, for example, by a display 2026 embedded in the surgical instrument 10**.

FIG. 64 illustrates one aspect of an end effector 3250 comprising a plurality of secondary sensors **3260*a*-3260*d* coupled to a jaw member 3254. The end effector 3250 comprises an anvil 3252 pivotally coupled to a jaw member 3254. The anvil 3252 is moveable relative to the jaw member 3254 to clamp one or more materials, such as, for example, a tissue section 3264, therebetween. The jaw member 3254 is configured to receive a staple cartridge 3256. A first sensor 3258 is coupled to the anvil 3252. The first sensor is configured to detect one or more parameters of the end effector 3150, such as, for example, the gap 3110 between the anvil 3252 and the staple cartridge 3256. The gap 3110 may correspond to, for example, a thickness of tissue clamped between the anvil 3252 and the staple cartridge 3256. The first sensor 3258 may comprise any suitable sensor for measuring one or more parameters of the end effector. For example, in various aspects, the first sensor 3258** may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

A plurality of secondary sensors 3260*a*-3260*d* is coupled to the jaw member 3254. The plurality of secondary sensors 3260*a*-3260*d* may be formed integrally with the jaw member 3254 and/or the staple cartridge 3256. For example, in one aspect, the plurality of secondary sensors 3260*a*-3260*d* is disposed on an outer row of the staple cartridge 3256 (see FIG. 63). The plurality of secondary sensors 3260*a*-3260*d* are configured to detect one or more parameters of the end effector 3250 and/or a tissue section 3264 clamped between the anvil 3252 and the staple cartridge 3256. The plurality of secondary sensors 3260*a*-3260*d* may comprise any suitable sensors for detecting one or more parameters of the end effector 3250 and/or the tissue section 3264, such as, for example, magnetic sensors, such as a Hall effect sensor, strain gauges, pressure sensors, inductive sensors, such as an eddy current sensor, resistive sensors, capacitive sensors, optical sensors, and/or any other suitable sensors or combination thereof. The plurality of secondary sensors 3260*a*-3260*d* may comprise identical sensors and/or different sensors.

In some aspects, the plurality of secondary sensors 3260*a*-3260*d* comprises dual purpose sensors and tissue stabilizing elements. The plurality of secondary sensors 3260*a*-3260*d* comprise electrodes and/or sensing geometries configured to create a stabilized tissue condition when the plurality of secondary sensors 3260*a*-3260*d* are engaged with a tissue section 3264, such as, for example, during a clamping operation. In some aspects, one or more of the plurality of secondary sensors 3260*a*-3260*d* may be replaced with non-sensing tissue stabilizing elements. The secondary sensors 3260*a*-3260*d* create a stabilized tissue condition by controlling tissue flow, staple formation, and/or other tissue conditions during a clamping, stapling, and/or other treatment process.

FIG. 65 illustrates one aspect of a staple cartridge 3270 comprising a plurality of sensors 3272*a*-3272*h* formed integrally therein. The staple cartridge 3270 comprises a plurality of rows containing a plurality of holes for storing staples therein. One or more of the holes in the outer row 3278 are replaced with one of the plurality of sensors 3272*a*-3272*h*. A cut-away section 3274 is shown to illustrate a sensor 3272*f* coupled to a sensor wire 3276*b*. The sensor wires 3276*a*, 3276*b* may comprise a plurality of wires for coupling the plurality of sensors 3272*a*-3272*h* to one or more circuits of a surgical instrument, such as, for example, the surgical instrument 10. In some aspects, one or more of the plurality of sensors 3272*a*-3272*h* comprise dual purpose sensor and tissue stabilizing elements having electrodes and/or sensing geometries configured to provide tissue stabilization. In some aspects, the plurality of sensors 3272*a*-3272*h* may be replaced with and/or co-populated with a plurality of tissue stabilizing elements. Tissue stabilization may be provided by, for example, controlling tissue flow and/or staple formation during a clamping and/or stapling process. The plurality of sensors 3272*a*-3272*h* provide signals to one or more circuits of the surgical instrument 10 to enhance feedback of stapling performance and/or tissue thickness sensing.

FIG. 66 is a logic diagram illustrating one aspect of a process 3280 for determining one or more parameters of a tissue section 3264 clamped within an end effector, such as, for example, the end effector 3250 illustrated in FIG. 64. In one aspect, a first sensor 3258 is configured to detect one or more parameters of the end effector 3250 and/or a tissue section 3264 located between the anvil 3252 and the staple cartridge 3256. A first signal is generated 3282 by the first sensors 3258. The first signal is indicative of the one or more parameters detected by the first sensor 3258. One or more secondary sensors 3260 are configured to detect one or more parameters of the end effector 3250 and/or the tissue section 3264. The secondary sensors 3260 may be configured to detect the same parameters, additional parameters, or different parameters as the first sensor 3258. Secondary signals 3284 are generated by the secondary sensors 3260. The secondary signals 3284 are indicative of the one or more parameters detected by the secondary sensors 3260. The first signal and the secondary signals are provided to a processor, such as, for example, a primary processor 2006. The primary processor 2006 adjusts 3286 the first signal generated by the first sensor 3258 based on input generated by the secondary sensors 3260. The adjusted signal may be indicative of, for example, the true thickness of a tissue section 3264 and the fullness of the bite. The adjusted signal is displayed 3026 to an operator by, for example, a display 2026 embedded in the surgical instrument 10.

FIG. 67 illustrates one aspect of an end effector 3350 comprising a magnetic sensor 3358 comprising a specific sampling rate to limit or eliminate false signals. The end effector 3350 comprises an anvil, or anvil, 3352 pivotably coupled to a jaw member 3354. The jaw member 3354 is configured to receive a staple cartridge 3356 therein. The staple cartridge 3356 contains a plurality of staples that may be delivered to a tissue section located between the anvil 3352 and the staple cartridge 3356. A magnetic sensor 3358 is coupled to the anvil 3352. The magnetic sensor 3358 is configured to detect one or more parameters of the end effector 3350, such as, for example, the gap 3364 between the anvil 3352 and the staple cartridge 3356. The gap 3364 may correspond to the thickness of a material, such as, for example, a tissue section, and/or the fullness of a bite of material located between the anvil 3352 and the staple cartridge 3356. The magnetic sensor 3358 may comprise any suitable sensor for detecting one or more parameters of the end effector 3350, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In one aspect, the magnetic sensor 3358 comprises a magnetic sensor configured to detect a magnetic field generated by an electromagnetic source 3360 coupled to the jaw member 3354 and/or the staple cartridge 3356. The electromagnetic source 3360 generates a magnetic field detected by the magnetic sensor 3358. The strength of the detected magnetic field may correspond to, for example, the thickness and/or fullness of a bite of tissue located between the anvil 3352 and the staple cartridge 3356. In some aspects, the electromagnetic source 3360 generates a signal at a known frequency, such as, for example, 1 MHz. In other aspects, the signal generated by the electromagnetic source 3360 may be adjustable based on, for example, the type of staple cartridge 3356 installed in the jaw member 3354, one or more additional sensor, an algorithm, and/or one or more parameters.

In one aspect, a signal processor 3362 is coupled to the end effector 3350, such as, for example, the anvil 3352. The signal processor 3362 is configured to process the signal generated by the magnetic sensor 3358 to eliminate false signals and to boost the input from the magnetic sensor 3358. In some aspects, the signal processor 3362 may be located separately from the end effector 3350, such as, for example, in the handle assembly 14 of a surgical instrument 10. In some aspects, the signal processor 3362 is formed integrally with and/or comprises an algorithm executed by a general processor, such as, for example, the primary processor 2006. The signal processor 3362 is configured to process the signal from the magnetic sensor 3358 at a frequency substantially equal to the frequency of the signal generated by the electromagnetic source 3360. For example, in one aspect, the electromagnetic source 3360 generates a signal at a frequency of 1 MHz. The signal is detected by the magnetic sensor 3358. The magnetic sensor 3358 generates a signal indicative of the detected magnetic field which is provided to the signal processor 3362. The signal is processed by the signal processor 3362 at a frequency of 1 MHz to eliminate false signals. The processed signal is provided to a processor, such as, for example, the primary processor 2006. The primary processor 2006 correlates the received signal to one or more parameters of the end effector 3350, such as, for example, the gap 3364 between the anvil 3352 and the staple cartridge 3356.

FIG. 68 is a logic diagram illustrating one aspect of a process 3370 for generating a thickness measurement for a tissue section located between an anvil and a staple cartridge of an end effector, such as, for example, the end effector 3350 illustrated in FIG. 45. In one aspect of the process 3370, a signal is generated 3372 by a modulated electromagnetic source 3360. The generated signal may comprise, for example, a 1 MHz signal. A magnetic sensor 3358 is configured to detect 3374 the signal generated by the electromagnetic source 3360. The magnetic sensor 3358 generates a signal indicative of the detected magnetic field and provides the signal to a signal processor 3362. The signal processor 3362 processes 3376 the signal to remove noise, false signals, and/or to boost the signal. The processed signal is provided to an analog-to-digital convertor for conversion 3378 to a digital signal. Calibration 3380 of the digital signal may be performed, for example, by application of a calibration curve input algorithm and/or look-up table. The processes 3376, conversion 3378, and calibration 3380 may be performed by one or more circuits. The calibrated signal is displayed 3026 to a user by, for example, a display 2026 formed integrally with the surgical instrument 10.

FIGS. 69A and 69B illustrate one aspect of an end effector 3800 comprising a pressure sensor. The end effector 3800 comprises an anvil, or anvil, 3802 pivotally coupled to a jaw member 3804. The jaw member 3804 is configured to receive a staple cartridge 3806 therein. The staple cartridge 3806 comprises a plurality of staples. A first sensor 3808 is coupled to the anvil 3802 at a distal tip. The first sensor 3808 is configured to detect one or more parameters of the end effector, such as, for example, the distance, or gap 3814, between the anvil 3802 and the staple cartridge 3806. The first sensor 3808 may comprise any suitable sensor, such as, for example, a magnetic sensor. A magnet 3810 may be coupled to the jaw member 3804 and/or the staple cartridge 3806 to provide a magnetic signal to the magnetic sensor.

In some aspects, the end effector 3800 comprises a second sensor 3812. The second sensor 3812 is configured to detect one or more parameters of the end effector 3800 and/or a tissue section located therebetween. The second sensor 3812 may comprise any suitable sensor, such as, for example, one or more pressure sensors. The second sensor 3812 may be coupled to the anvil 3802, the jaw member 3804, and/or the staple cartridge 3806. A signal from the second sensor 3812 may be used to adjust the measurement of the first sensor 3808 to adjust the reading of the first sensor to accurately represent proximal and/or distal positioned partial bites true compressed tissue thickness. In some aspects, the second sensor 3812 may be surrogate with respect to the first sensor 3808.

In some aspects, the second sensor 3812 may comprise, for example, a single continuous pressure sensing film and/or an array of pressure sensing films. The second sensor 3812 is coupled to the deck of the staple cartridge 3806 along the central axis covering, for example, a slot 3816 configured to receive a cutting and/or staple deployment member. The second sensor 3812 provides signals indicate of the amplitude of pressure applied by the tissue during a clamping procedure. During firing of the cutting and/or deployment member, the signal from the second sensor 3812 may be severed, for example, by cutting electrical connections between the second sensor 3812 and one or more circuits. In some aspects, a severed circuit of the second sensor 3812 may be indicative of a spent staple cartridge 3806. In other aspects, the second sensor 3812 may be positioned such that deployment of a cutting and/or deployment member does not sever the connection to the second sensor 3812.

FIG. 70 illustrates one aspect of an end effector 3850 comprising a second sensor 3862 located between a staple cartridge 3806 and a jaw member 3804. The end effector 3850 comprises an anvil, or anvil, 3852 pivotally coupled to a jaw member 3854. The jaw member 3854 is configured to receive a staple cartridge 3856 therein. A first sensor 3858 is coupled to the anvil 3852 at a distal tip. The first sensor 3858 is configured to detect one or more parameters of the end effector 3850, such as, for example, the distance, or gap 3864, between the anvil 3852 and the staple cartridge 3856. The first sensor 3858 may comprise any suitable sensor, such as, for example, a magnetic sensor. A magnet 3860 may be coupled to the jaw member 3854 and/or the staple cartridge 3856 to provide a magnetic signal to the magnetic sensor. In some aspects, the end effector 3850 comprises a second sensor 3862 similar in all respect to the second sensor 3812 of FIGS. 69A-69B, except that it is located between the staple cartridge 3856 and the jaw member 3854.

FIG. 71 is a logic diagram illustrating one aspect of a process 3870 for determining and displaying the thickness of a tissue section clamped in an end effector 3800 or 3850, according to FIGS. 69A-69B or FIG. 70. The process comprises obtaining a Hall effect voltage 3872, for example, through a Hall effect sensor located at the distal tip of the anvil 3802. The Hall effect voltage 3872 is proved to an analog to digital converter 3876 and converted into a digital signal. The digital signal is provided to a process, such as for example the primary processor 2006. The primary processor 2006 calibrates 3874 the curve input of the Hall effect voltage 3872 signal. Pressure sensors, such as for example, second sensor 3812, is configured to measure 3880 one or more parameters of, for example, the end effector 3800, such as for example the amount of pressure being exerted by the anvil 3802 on the tissue clamped in the end effector 3800. In some aspects the pressure sensors may comprise a single continuous pressure sensing film and/or array of pressure sensing films. The pressure sensors may thus be operable determine variations in the measure pressure at different locations between the proximal and distal ends of the end effector 3800. The measured pressure is provided to the processor, such as for example the primary processor 2006. The primary processor 2006 uses one or more algorithms and/or lookup tables to adjust 3882 the Hall effect voltage 3872 in response to the pressure measured 3880 by the pressure sensors to more accurately reflect the thickness of the tissue clamped between, for example, the anvil 3802 and the staple cartridge 3806. The adjusted thickness is displayed 3878 to an operator by, for example, a display 2026 embedded in the surgical instrument 10.

FIG. 72 illustrates one aspect of an end effector 3900 comprising a plurality of second sensors 3192*a*-3192*b* located between a staple cartridge 3906 and an elongated channel 3904. The end effector 3900 comprises an anvil 3902 pivotally coupled to a jaw member or elongated channel 3904. The elongated channel 3904 is configured to receive a staple cartridge 3906 therein. The anvil 3902 further comprises a first sensor 3908 located in the distal tip. The first sensor 3908 is configured to detect one or more parameters of the end effector 3900, such as, for example, the distance, or gap, between the anvil 3902 and the staple cartridge 3906. The first sensor 3908 may comprise any suitable sensor, such as, for example, a magnetic sensor. A magnet 3910 may be coupled to the elongated channel 3904 and/or the staple cartridge 3906 to provide a magnetic signal to the first sensor 3908. In some aspects, the end effector 3900 comprises a plurality of second sensors 3912*a*-3912*c* located between the staple cartridge 3906 and the elongated channel 3904. The second sensors 3912*a*-3912*c* may comprise any suitable sensors, such as for instance piezoresistive pressure film strips. In some aspects, the second sensors 3912*a*-3912*c* may be uniformly distributed between the distal and proximal ends of the end effector 3900.

In some aspects, signals from the second sensors 3912*a*-3912*c* may be used to adjust the measurement of the first sensor 3908. For instance, the signals from the second sensors 3912*a*-3912*c* may be used to adjust the reading of the first sensor 3908 to accurately represent the gap between the anvil 3902 and the staple cartridge 3906, which may vary between the distal and proximal ends of the end effector 3900, depending on the location and/or density of tissue 3920 between the anvil 3902 and the staple cartridge 3906. FIG. 11 illustrates an example of a partial bite of tissue 3920. As illustrated for purposes of this example, the tissue is located only in the proximal area of the end effector 3900, creating a high pressure 3918 area near the proximal area of the end effector 3900 and a corresponding low pressure 3916 area near the distal end of the end effector.

FIGS. 73A and 73B further illustrate the effect of a full versus partial bite of tissue 3920. FIG. 73A illustrates the end effector 3900 with a full bite of tissue 3920, where the tissue 3920 is of uniform density. With a full bite of tissue 3920 of uniform density, the measured first gap 3914*a* at the distal tip of the end effector 3900 may be approximately the same as the measured second gap 3922*a* in the middle or proximal end of the end effector 3900. For example, the first gap 3914*a* may measure 2.4 mm, and the second gap may measure 2.3 mm. FIG. 73B illustrates an end effector 3900 with a partial bite of tissue 3920, or alternatively a full bit of tissue 3920 of non-uniform density. In this case, the first gap 3914*b* will measure less than the second gap 3922*b* measured at the thickest or densest portion of the tissue 3920. For example, the first gap may measure 1.0 mm, while the second gap may measure 1.9 mm. In the conditions illustrated in FIGS. 73A-73B, signals from the second sensors 3912*a*-3912*c*, such as for instance measured pressure at different points along the length of the end effector 3900, may be employed by the instrument to determine tissue 3920 placement and/or material properties of the tissue 3920. The instrument may further be operable to use measured pressure over time to recognize tissue characteristics and tissue position, and dynamically adjust tissue thickness measurements.

FIG. 74 illustrates an aspect of an end effector 4050 that is configured to determine the location of a cutting member or knife 4062. The end effector 4050 comprises an anvil 4052 pivotally coupled to a jaw member or elongated channel 4054. The elongated channel 4054 is configured to receive a staple cartridge 4056 therein. The staple cartridge 4056 further comprises a slot (not shown) and a cutting member or knife 4062 located therein. The knife 4062 is operably coupled to a knife bar 4064. The knife bar 4064 is operable to move the knife 4062 from the proximal end of the slot to the distal end. The end effector 4050 may further comprise an optical sensor 4060 located near the proximal end of the slot. The optical sensor may be coupled to a processor, such as for instance the primary processor 2006. The optical sensor 4060 may be operable to emit an optical signal towards the knife bar 4064. The knife bar 4064 may further comprise a code strip 4066 along its length. The code strip 4066 may comprise cut-outs, notches, reflective pieces, or any other configuration that is optically readable. The code strip 4066 is placed such that the optical signal from the optical sensor 4060 will reflect off or through the code strip 4066. As the knife 4062 moves and knife bar 4064 moves 4068 along the slot 4058, the optical sensor 4060 will detect the reflection of the emitted optical signal coupled to the code strip 4066. The optical sensor 4060 may be operable to communicate the detected signal to the primary processor 2006. The primary processor 2006 may be configured to use the detected signal to determine the position of the knife 4062. The position of the knife 4062 may be sensed more precisely by designing the code strip 4066 such that the detected optical signal has a gradual rise and fall.

FIG. 75 illustrates an example of the code strip 4066 in operation with red LEDs 4070 and infrared LEDs 4072. For purposes of this example only, the code strip 4066 comprises cut-outs. As the code strip 4066 moves 4068, the light emitted by the red LEDs 4070 will be interrupted as the cut-outs passed before it. The infrared LEDs 4072 will therefore detect the motion of the code strip 4066, and therefore, by extension, the motion of the knife 4062.

FIG. 76 depicts a partial view of the end effector 300 of the surgical instrument 10. In the example form depicted in FIG. 76, the end effector 300 comprises a staple cartridge 1100 which is similar in many respects to the surgical staple cartridge 304 (FIG. 15). Several parts of the end effector 300 are omitted to enable a clearer understanding of the present disclosure. In certain instances, the end effector 300 may include a first jaw such as, for example, the anvil 306 (FIG. 20) and a second jaw such as, for example, the elongated channel 198 (FIG. 14). In certain instances, as described above, the elongated channel 198 may accommodate a staple cartridge such as, for example, the surgical staple cartridge 304 or the staple cartridge 1100, for example. At least one of the elongated channel 198 and the anvil 306 may be movable relative to the other one of the elongated channel 198 and the anvil 306 to capture tissue between the staple cartridge 1100 and the anvil 306. Various actuation assemblies are described herein to facilitation motion of the elongated channel 198 and/or the anvil 306 between an open configuration (FIG. 1) and a closed configuration (FIG. 77), for example.

In certain instances, as described above, the E-beam 178 can be advanced distally to deploy the staples 191 into the captured tissue and/or advance the cutting edge 182 between a plurality of positions to engage and cut the captured tissue. As illustrated in FIG. 76, the cutting edge 182 can be advanced distally along a path defined by the slot 193, for example. In certain instances, the cutting edge 182 can be advanced from a proximal portion 1103 of the staple cartridge 1100 to a distal portion 1105 of the staple cartridge 1100 to cut the captured tissue. In certain instances, the cutting edge 182 can be retracted proximally from the distal portion 1105 to the proximal portion 1103 by retraction of the E-beam 178 proximally, for example.

In certain instances, the cutting edge 182 can be employed to cut tissue captured by the end effector 300 in multiple procedures. The reader will appreciate that repetitive use of the cutting edge 182 may affect the sharpness of the cutting edge 182. The reader will also appreciate that as the sharpness of the cutting edge 182 decreases, the force required to cut the captured tissue with the cutting edge 182 may increase. Referring to FIGS. 78-83, in certain instances, the surgical instrument 10 may comprise a circuit 1106 (FIG. 78) for monitoring the sharpness of the cutting edge 182 during, before, and/or after operation of the surgical instrument 10 in a surgical procedure, for example. In certain instances, the circuit 1106 can be employed to test the sharpness of the cutting edge 182 prior to utilizing the cutting edge 182 to cut the captured tissue. In certain instances, the circuit 1106 can be employed to test the sharpness of the cutting edge 182 after the cutting edge 182 has been used to cut the captured tissue. In certain instances, the circuit 1106 can be employed to test the sharpness of the cutting edge 182 prior to and after the cutting edge 182 is used to cut the captured tissue. In certain instances, the circuit 1106 can be employed to test the sharpness of the cutting edge 182 at the proximal portion 1103 and/or at the distal portion 1105.

Referring to FIGS. 78-83, the circuit 1106 may include one or more sensors such as, for example, an optical sensor 1108; the optical sensor 1108 of the circuit 1106 can be employed to test the reflective ability of the cutting edge 182, for example. In certain instances, the ability of the cutting edge 182 to reflect light may correlate with the sharpness of the cutting edge 182. In other words, a decrease in the sharpness of the cutting edge 182 may result in a decrease in the ability of the cutting edge 182 to reflect the light. Accordingly, in certain instances, the dullness of the cutting edge 182 can be evaluated by monitoring the intensity of the light reflected from the cutting edge 182, for example. In certain instances, the optical sensor 1108 may define a light sensing region. The optical sensor 1108 can be oriented such that the optical sensing region is disposed in the path of the cutting edge 182, for example. The optical sensor 1108 may be employed to sense the light reflected from the cutting edge 182 while the cutting edge 182 is in the optical sensing region, for example. A decrease in intensity of the reflected light beyond a threshold can indicate that the sharpness of the cutting edge 182 has decreased beyond an acceptable level.

Referring again to FIGS. 78-83, the circuit 1106 may include one or more lights sources such as, for example, a light source 1110. In certain instances, the circuit 1106 may include a controller 1112 ("microcontroller") which may be operably coupled to the optical sensor 1108, as illustrated in FIGS. 78-83. In certain instances, the controller 1112 may include a processor 1114 ("microprocessor") and one or more computer readable mediums or memory 1116 ("memory units"). In certain instances, the memory 1116 may store various program instructions, which when executed may cause the processor 1114 to perform a plurality of functions and/or calculations described herein. In certain instances, the memory 1116 may be coupled to the processor 1114, for example. A power source 1118 can be configured to supply power to the controller 1112, the optical sensors 1108, and/or the light sources 1110, for example. In certain instances, the power source 1118 may comprise a battery (or "battery pack" or "power pack"), such as a Li ion battery, for example. In certain instances, the battery pack may be configured to be releasably mounted to the handle assembly 14 for supplying power to the surgical instrument 10. A number of battery cells connected in series may be used as the power source 4428. In certain instances, the power source 1118 may be replaceable and/or rechargeable, for example.

The controller 1112 and/or other controllers of the present disclosure may be implemented using integrated and/or discrete hardware elements, software elements, and/or a combination of both. Examples of integrated hardware elements may include processors, microprocessors, controllers, integrated circuits, ASICs, PLDs, DSPs, FPGAs, logic gates, registers, semiconductor devices, chips, microchips, chip sets, controllers, SoC, and/or SIP. Examples of discrete hardware elements may include circuits and/or circuit elements such as logic gates, field effect transistors, bipolar transistors, resistors, capacitors, inductors, and/or relays. In certain instances, the controller 1112 may include a hybrid circuit comprising discrete and integrated circuit elements or components on one or more substrates, for example. In certain instances, the controller 1112 and/or other controllers of the present disclosure may be a single core or multicore controller LM4F230H5QR as described in connection with FIGS. 14-17B.

In certain instances, the light source 1110 can be employed to emit light which can be directed at the cutting edge 182 in the optical sensing region, for example. The optical sensor 1108 may be employed to measure the intensity of the light reflected from the cutting edge 182 while in the optical sensing region in response to exposure to the light emitted by the light source 1110. In certain instances, the processor 1114 may receive one or more values of the measured intensity of the reflected light and may store the one or more values of the measured intensity of the reflected light on the memory 1116, for example. The stored values can be detected and/or recorded before, after, and/or during a plurality of surgical procedures performed by the surgical instrument 10, for example.

In certain instances, the processor 1114 may compare the measured intensity of the reflected light to a predefined threshold values that may be stored on the memory 1116, for example. In certain instances, the controller 1112 may conclude that the sharpness of the cutting edge 182 has dropped below an acceptable level if the measured light intensity exceeds the predefined threshold value by 1%, 5%, 10%, 25%, 50%, 100% and/or more than 100%, for example. In certain instances, the processor 1114 can be employed to detect a decreasing trend in the stored values of the measured intensity of the light reflected from the cutting edge 182 while in the optical sensing region.

In certain instances, the surgical instrument 10 may include one or more feedback systems such as, for example, the feedback system 1120. In certain instances, the processor 1114 can employ the feedback system 1120 to alert a user if the measured light intensity of the light reflected from cutting edge 182 while in the optical sensing region is beyond the stored threshold value, for example. In certain instances, the feedback system 1120 may comprise one or more visual feedback systems such as display screens, backlights, and/or LEDs, for example. In certain instances, the feedback system 1120 may comprise one or more audio feedback systems such as speakers and/or buzzers, for example. In certain instances, the feedback system 1120 may comprise one or more haptic feedback systems, for example. In certain instances, the feedback system 1120 may comprise combinations of visual, audio, and/or tactile feedback systems, for example.

In certain instances, the surgical instrument 10 may comprise a firing lockout mechanism 1122 which can be employed to prevent advancement of the cutting edge 182. Various suitable firing lockout mechanisms are described in greater detail in U.S. Patent Application Publication No. 2014/0001231, entitled FIRING SYSTEM LOCKOUT ARRANGEMENTS FOR SURGICAL INSTRUMENTS, which is herein incorporated by reference in its entirety. In certain instances, as illustrated in FIG. 78, the processor 1114 can be operably coupled to the firing lockout mechanism 1122; the processor 1114 may employ the firing lockout mechanism 1122 to prevent advancement of the cutting edge 182 in the event it is determined that the measured intensity of the light reflected from the cutting edge 182 is beyond the stored threshold, for example. In other words, the processor 1114 may activate the firing lockout mechanism 1122 if the cutting edge is not sufficiently sharp to cut the tissue captured by the end effector 300.

In certain instances, the optical sensor 1108 and the light source 1110 can be housed at a distal portion of the interchangeable shaft assembly 200. In certain instances, the sharpness of cutting edge 182 can be evaluated by the optical sensor 1108, as described above, prior to transitioning the cutting edge 182 into the end effector 300. The firing bar 172 (FIG. 14) may advance the cutting edge 182 through the optical sensing region defined by the optical sensor 1108 while the cutting edge 182 is in the interchangeable shaft assembly 200 and prior to entering the end effector 300, for example. In certain instances, the sharpness of cutting edge 182 can be evaluated by the optical sensor 1108 after retracting the cutting edge 182 proximally from the end effector 300. The firing bar 172 (FIG. 14) may retract the cutting edge 182 through the optical sensing region defined by the optical sensor 1108 after retracting the cutting edge 182 from the end effector 300 into the interchangeable shaft assembly 200, for example.

In certain instances, the optical sensor 1108 and the light source 1110 can be housed at a proximal portion of the end effector 300 which can be proximal to the staple cartridge 1100, for example. The sharpness of cutting edge 182 can be evaluated by the optical sensor 1108 after transitioning the cutting edge 182 into the end effector 300 but prior to engaging the staple cartridge 1100, for example. In certain instances, the firing bar 172 (FIG. 14) may advance the cutting edge 182 through the optical sensing region defined by the optical sensor 1108 while the cutting edge 182 is in the end effector 300 but prior to engaging the staple cartridge 1100, for example.

In various instances, the sharpness of cutting edge 182 can be evaluated by the optical sensor 1108 as the cutting edge 182 is advanced by the firing bar 172 through the slot 193. As illustrated in FIGS. 78-83, the optical sensor 1108 and the light source 1110 can be housed at the proximal portion 1103 of the staple cartridge 1100, for example; and the sharpness of cutting edge 182 can be evaluated by the optical sensor 1108 at the proximal portion 1103, for example. The firing bar 172 (FIG. 14) may advance the cutting edge 182 through the optical sensing region defined by the optical sensor 1108 at the proximal portion 1103 before the cutting edge 182 engages tissue captured between the staple cartridge 1100 and the anvil 306, for example. In certain instances, as illustrated in FIGS. 78-83, the optical sensor 1108 and the light source 1110 can be housed at the distal portion 1105 of the staple cartridge 1100, for example. The sharpness of cutting edge 182 can be evaluated by the optical sensor 1108 at the distal portion 1105. In certain instances, the firing bar 172 (FIG. 14) may advance the cutting edge 182 through the optical sensing region defined by the optical sensor 1108 at the distal portion 1105 after the cutting edge 182 has passed through the tissue captured between the staple cartridge 1100 and the anvil 306, for example.

Referring again to FIG. 76, the staple cartridge 1100 may comprise a plurality of optical sensors 1108 and a plurality of corresponding light sources 1110, for example. In certain instances, a pair of the optical sensor 1108 and the light source 1110 can be housed at the proximal portion 1103 of the staple cartridge 1100, for example; and a pair of the optical sensor 1108 and the light source 1110 can be housed at the distal portion 1105 of the staple cartridge 1100, for example. In such instances, the sharpness of the cutting edge 182 can be evaluated a first time at the proximal portion 1103 prior to engaging the tissue, for example, and a second time at the distal portion 1105 after passing through the captured tissue, for example.

The reader will appreciate that an optical sensor 1108 may evaluate the sharpness of the cutting edge 182 a plurality of times during a surgical procedure. For example, the sharpness of the cutting edge can be evaluated a first time during advancement of the cutting edge 182 through the slot 193 in a firing stroke, and a second time during retraction of the cutting edge 182 through the slot 193 in a return stroke, for example. In other words, the light reflected from the cutting edge 182 can be measured by the optical sensor 1108 once as the cutting edge is advanced through the optical sensing region, and once as the cutting edge 182 is retracted through the optical sensing region, for example.

The reader will appreciate that the processor 1114 may receive a plurality of readings of the intensity of the light reflected from the cutting edge 182 from one or more of the optical sensors 1108. In certain instances, the processor 1114 may be configured to discard outliers and calculate an average reading from the plurality of readings, for example. In certain instances, the average reading can be compared to a threshold stored in the memory 1116, for example. In certain instances, the processor 1114 may be configured to alert a user through the feedback system 1120 and/or activate the firing lockout mechanism 1122 if it is determined that the calculated average reading is beyond the threshold stored in the memory 1116, for example.

In certain instances, as illustrated in FIGS. 77, 79, and 80, a pair of the optical sensor 1108 and the light source 1110 can be positioned on opposite sides of the staple cartridge 1100. In other words, the optical sensor 1108 can be positioned on a first side 1124 of the slot 193, for example, and the light source 1110 can be positioned on a second side 1126, opposite the first side 1124, of the slot 193, for example. In certain instances, the pair of the optical sensor 1108 and the light source 1110 can be substantially disposed in a plane transecting the staple cartridge 1100, as illustrated in FIG. 77. The pair of the optical sensor 1108 and the light source 1110 can be oriented to define an optical sensing region that is positioned, or at least substantially positioned, on the plane transecting the staple cartridge 1100, for example. Alternatively, the pair of the optical sensor 1108 and the light source 1110 can be oriented to define an optical sensing region that is positioned proximal to the plane transecting the staple cartridge 1100, for example, as illustrated in FIG. 80.

In certain instances, a pair of the optical sensor 1108 and the light source 1110 can be positioned on a same side of the staple cartridge 1100. In other words, as illustrated in FIG. 81, the pair of the optical sensor 1108 and the light source 1110 can be positioned on a first side of the cutting edge 182, e.g. the side 1128, as the cutting edge 182 is advanced through the slot 193. In such instances, the light source 1110 can be oriented to direct light at the side 1128 of the cutting edge 182; and the intensity of the light reflected from the side 1128, as measured by the optical sensor 1108, may represent the sharpness of the side 1128.

In certain instances, as illustrated in FIG. 82, a second pair of the optical sensor 1108 and the light source 1110 can be positioned on a second side of the cutting edge 182, e.g. the side 1130, for example. The second pair can be employed to evaluate the sharpness of the side 1130. For example, the light source 1110 of the second pair can be oriented to direct light at the side 1130 of the cutting edge 182; and the intensity of the light reflected from the side 1130, as measured by the optical sensor 1108 of the second pair, may represent the sharpness of the side 1130. In certain instances, the processor can be configured to assess the sharpness of the cutting edge 182 based upon the measured intensities of the light reflected from the sides 1128 and 1130 of the cutting edge 182, for example.

In certain instances, as illustrated in FIG. 77, a pair of the optical sensor 1108 and the light source 1110 can be housed at the distal portion 1105 of the staple cartridge 1100. As illustrated in FIG. 81, the optical sensor 1108 can be positioned, or at least substantially positioned, on an axis LL which extends longitudinally along the path of the cutting edge 182 through the slot 193, for example. In addition, the light source 1110 can be positioned distal to the cutting edge 182 and oriented to direct light at the cutting edge 182 as the cutting edge is advanced toward the light source 1110, for example. Furthermore, the optical sensor 1108 can be positioned, or at least substantially positioned, along an axis AA that intersects the axis LL, as illustrated in FIG. 81. In certain instances, the axis AA may be perpendicular to the axis LL, for example. In any event, the optical sensor 1108 can be oriented to define an optical sensing region at the intersection of the axis LL and the axis AA, for example.

The reader will appreciate that the position, orientation and/or number of optical sensors and corresponding light sources described herein in connection with the surgical instrument 10 are example aspects intended for illustration purposes. Various other arrangements of optical sensors and light sources can be employed by the present disclosure to evaluate the sharpness of the cutting edge 182.

The reader will appreciate that advancement of the cutting edge 182 through the tissue captured by the end effector 300 may cause the cutting edge to collect tissue debris and/or bodily fluids during each firing of the surgical instrument 10. Such debris may interfere with the ability of the circuit 1106 to accurately evaluate the sharpness of the cutting edge 182. In certain instances, the surgical instrument 10 can be equipped with one or more cleaning mechanisms which can be employed to clean the cutting edge 182 prior to evaluating the sharpness of the cutting edge 182, for example.

Referring to FIG. 76, in certain instances, the staple cartridge 1100 may include a first pair of the optical sensor 1108 and the light source 1110, which can be housed in the proximal portion 1103 of the staple cartridge 1100, for example. Furthermore, as illustrated in FIG. 76, the staple cartridge 1100 may include a first pair of the cleaning members 1132, which can be housed in the proximal portion 1103 on opposite sides of the slot 193. The first pair of the cleaning members 1132 can be positioned distal to the first pair of the optical sensor 1108 and the light source 1110, for example. As illustrated in FIG. 76, the staple cartridge 1100 may include a second pair of the optical sensor 1108 and the light source 1110, which can be housed in the distal portion 1105 of the staple cartridge 1100, for example. As illustrated in FIG. 76, the staple cartridge 1100 may include a second pair of the cleaning members 1132, which can be housed in the distal portion 1105 on opposite sides of the slot 193. The second pair of the cleaning members 1132 can be positioned proximal to the second pair of the optical sensor 1108 and the light source 1110.

Further to the above, as illustrated in FIG. 76, the cutting edge 182 may be advanced distally in a firing stroke to cut tissue captured by the end effector 300. As the cutting edge is advanced, a first evaluation of the sharpness of the cutting edge 182 can be performed by the first pair of the optical sensor 1108 and the light source 1110 prior to tissue engagement by the cutting edge 182, for example. A second evaluation of the sharpness of the cutting edge 182 can be performed by the second pair of the optical sensor 1108 and the light source 1110 after the cutting edge 182 has transected the captured tissue, for example. The cutting edge 182 may be advanced through the second pair of the cleaning members 1132 prior to the second evaluation of the sharpness of the cutting edge 182 to remove any debris collected by the cutting edge 182 during the transection of the captured tissue.

Further to the above, as illustrated in FIG. 76, the cutting edge 182 may be retracted proximally in a return stroke. As the cutting edge is retracted, a third evaluation of the sharpness of the cutting edge 182 can be performed by the first pair of the optical sensor 1108 and the light source 1110 during the return stroke. The cutting edge 182 may be retracted through the first pair of the cleaning members 1132 prior to the third evaluation of the sharpness of the cutting edge 182 to remove any debris collected by the cutting edge 182 during the transection of the captured tissue, for example.

In certain instances, one or more of the lights sources 1110 may comprise one or more optical fiber cables. In certain instances, one or more flex circuits 1134 can be employed to transmit energy from the power source 1118 to the optical sensors 1108 and/or the light sources 1110. In certain instances, the flex circuits 1134 may be configured to transmit one or more of the readings of the optical sensors 1108 to the controller 1112, for example.

Referring now to FIG. 84, a staple cartridge 4300 is depicted; the staple cartridge 4300 is similar in many respects to the surgical staple cartridge 304 (FIG. 14). For example, the staple cartridge 4300 can be employed with the end effector 300. In certain instances, as illustrated in FIG. 84, the staple cartridge 4300 may comprise a sharpness testing member 4302 which can be employed to test the sharpness of the cutting edge 182. In certain instances, the sharpness testing member 4302 can be attached to and/or integrated with the cartridge body 194 of the staple cartridge

4300, for example. In certain instances, the sharpness testing member 4302 can be disposed in the proximal portion 1103 of the staple cartridge 4300, for example. In certain instances, as illustrated in FIG. 84, the sharpness testing member 4302 can be disposed onto a cartridge deck 4304 of the staple cartridge 4300, for example.

In certain instances, as illustrated in FIG. 84, the sharpness testing member 4302 can extend across the slot 193 of the staple cartridge 4300 to bridge, or at least partially bridge, the gap defined by the slot 193, for example. In certain instances, the sharpness testing member 4302 may interrupt, or at least partially interrupt, the path of the cutting edge 182. The cutting edge 182 may engage, cut, and/or pass through the sharpness testing member 4302 as the cutting edge 182 is advanced during a firing stroke, for example. In certain instances, the cutting edge 182 may be configured to engage, cut, and/or pass through the sharpness testing member 4302 prior to engaging tissue captured by the end effector 300 in a firing stroke, for example. In certain instances, the cutting edge 182 may be configured to engage the sharpness testing member 4302 at a proximal end 4306 of the sharpness testing member 4302, and exit and/or disengage the sharpness testing member 4302 at a distal end 4308 of the sharpness testing member 4302, for example. In certain instances, the cutting edge 182 can travel and/or cut through the sharpness testing member 4302 a distance (D) between the proximal end 4306 and the distal end 4308, for example, as the cutting edge 182 is advanced during a firing stroke.

Referring primarily to FIGS. 84 and 85, the surgical instrument 10 may comprise a circuit 4310 for testing the sharpness of the cutting edge 182, for example. In certain instances, the circuit 4310 can evaluate the sharpness of the cutting edge 182 by testing the ability of the cutting edge 182 to be advanced through the sharpness testing member 4302. For example, the circuit 4310 can be configured to observe the time period the cutting edge 182 takes to fully transect and/or completely pass through at least a predetermined portion of the sharpness testing member 4302. If the observed time period exceeds a predetermined threshold, the circuit 4310 may conclude that the sharpness of the cutting edge 182 has dropped below an acceptable level, for example.

In certain instances, the circuit 4310 may include a controller 4312 ("microcontroller") which may include a processor 4314 ("microprocessor") and one or more computer readable mediums or memory 4316 units ("memory"). In certain instances, the memory 4316 may store various program instructions, which when executed may cause the processor 4314 to perform a plurality of functions and/or calculations described herein. In certain instances, the memory 4316 may be coupled to the processor 4314, for example. A power source 4318 can be configured to supply power to the controller 4312, for example. In certain instances, the power source 4138 may comprise a battery (or "battery pack" or "power pack"), such as a Li ion battery, for example. In certain instances, the battery pack may be configured to be releasably mounted to the handle assembly 14. A number of battery cells connected in series may be used as the power source 4318. In certain instances, the power source 4318 may be replaceable and/or rechargeable, for example.

In certain instances, the controller 4313 can be operably coupled to the feedback system 1120 and/or the firing lockout mechanism 1122, for example.

Referring to FIGS. 84 and 85, the circuit 4310 may comprise one or more position sensors. Example position sensors and positioning systems suitable for use with the present disclosure are described in U.S. Patent Application Publication No. 2014/0263538, entitled SENSOR ARRANGEMENTS FOR ABSOLUTE POSITIONING SYSTEM FOR SURGICAL INSTRUMENTS, which is herein incorporated by reference in its entirety. In certain instances, the circuit 4310 may include a first position sensor 4320 and a second position sensor 4322. In certain instances, the first position sensor 4320 can be employed to detect a first position of the cutting edge 182 at the proximal end 4306 of the sharpness testing member 4302, for example; and the second position sensor 4322 can be employed to detect a second position of the cutting edge 182 at the distal end 4308 of the sharpness testing member 4302, for example.

In certain instances, the first and second position sensors 4320, 4322 can be employed to provide first and second position signals, respectively, to the controller 4312. It will be appreciated that the position signals may be analog signals or digital values based on the interface between the controller 4312 and the first and second position sensors 4320, 4322. In one aspect, the interface between the controller 4312 and the first and second position sensors 4320, 4322 can be a standard serial peripheral interface (SPI), and the position signals can be digital values representing the first and second positions of the cutting edge 182, as described above.

Further to the above, the processor 4314 may determine the time period between receiving the first position signal and receiving the second position signal. The determined time period may correspond to the time it takes the cutting edge 182 to advance through the sharpness testing member 4302 from the first position at the proximal end 4306 of the sharpness testing member 4302, for example, to the second position at the distal end 4308 of the sharpness testing member 4302, for example. In at least one example, the controller 4312 may include a time element which can be activated by the processor 4314 upon receipt of the first position signal, and deactivated upon receipt of the second position signal. The time period between the activation and deactivation of the time element may correspond to the time it takes the cutting edge 182 to advance from the first position to the second position, for example. The time element may comprise a real time clock, a processor configured to implement a time function, or any other suitable timing circuit.

In various instances, the controller 4312 can compare the time period it takes the cutting edge 182 to advance from the first position to the second position to a predefined threshold value to assess whether the sharpness of the cutting edge 182 has dropped below an acceptable level, for example. In certain instances, the controller 4312 may conclude that the sharpness of the cutting edge 182 has dropped below an acceptable level if the measured time period exceeds the predefined threshold value by 1%, 5%, 10%, 25%, 50%, 100% and/or more than 100%, for example.

Referring to FIG. 86, in various instances, an electric motor 4330 can drive the firing bar 172 (FIG. 14) to advance the cutting edge 182 during a firing stroke and/or to retract the cutting edge 182 during a return stroke, for example. A motor driver 4332 can control the electric motor 4330; and a controller such as, for example, the controller 4312 can be in signal communication with the motor driver 4332. As the electric motor 4330 advances the cutting edge 182, the controller 4312 can determine the current drawn by the electric motor 4330, for example. In such instances, the force required to advance the cutting edge 182 can correspond to the current drawn by the electric motor 4330, for example. Referring still to FIG. 86, the controller 4312 of the surgical instrument 10 can determine if the current drawn by the electric motor 4330 increases during advancement of the cutting edge 182 and, if so, can calculate the percentage increase of the current.

In certain instances, the current drawn by the electric motor 4330 may increase significantly while the cutting edge 182 is in contact with the sharpness testing member 4302 due to the resistance of the sharpness testing member 4302 to the cutting edge 182. For example, the current drawn by the electric motor 4330 may increase significantly as the cutting edge 182 engages, passes and/or cuts through the sharpness testing member 4302. The reader will appreciate that the resistance of the sharpness testing member 4302 to the cutting edge 182 depends, in part, on the sharpness of the cutting edge 182; and as the sharpness of the cutting edge 182 decreases from repetitive use, the resistance of the sharpness testing member 4302 to the cutting edge 182 will increase. Accordingly, the value of the percentage increase of the current drawn by the electric motor 4330 while the cutting edge is in contact with the sharpness testing member 4302 can increase as the sharpness of the cutting edge 182 decreases from repetitive use, for example.

In certain instances, the determined value of the percentage increase of the current drawn by the electric motor 4330 can be the maximum detected percentage increase of the current drawn by the electric motor 4330. In various instances, the controller 4312 can compare the determined value of the percentage increase of the current drawn by the electric motor 4330 to a predefined threshold value of the percentage increase of the current drawn by the electric motor 4330. If the determined value exceeds the predefined threshold value, the controller 4312 may conclude that the sharpness of the cutting edge 182 has dropped below an acceptable level, for example.

In certain instances, as illustrated in FIG. 86, the processor 4314 can be in communication with the feedback system 1120 and/or the firing lockout mechanism 1122, for example. In certain instances, the processor 4314 can employ the feedback system 1120 to alert a user if the determined value of the percentage increase of the current drawn by the electric motor 4330 exceeds the predefined threshold value, for example. In certain instances, the processor 4314 may employ the firing lockout mechanism 1122 to prevent advancement of the cutting edge 182 if the determined value of the percentage increase of the current drawn by the electric motor 4330 exceeds the predefined threshold value, for example.

In various instances, the controller 4312 can utilize an algorithm to determine the change in current drawn by the electric motor 4330. For example, a current sensor can detect the current drawn by the electric motor 4330 during the firing stroke. The current sensor can continually detect the current drawn by the electric motor and/or can intermittently detect the current draw by the electric motor. In various instances, the algorithm can compare the most recent current reading to the immediately proceeding current reading, for example. Additionally or alternatively, the algorithm can compare a sample reading within a time period X to a previous current reading. For example, the algorithm can compare the sample reading to a previous sample reading within a previous time period X, such as the immediately proceeding time period X, for example. In other instances, the algorithm can calculate the trending average of current drawn by the motor. The algorithm can calculate the average current draw during a time period X that includes the most recent current reading, for example, and can compare that average current draw to the average current draw during an immediately proceeding time period time X, for example.

Referring to FIG. 87, a method 4500 is depicted for evaluating the sharpness of the cutting edge 182 of the surgical instrument 10; and various responses are outlined in the event the sharpness of the cutting edge 182 drops to and/or below an alert threshold and/or a high severity threshold, for example. In various instances, a controller such as, for example, the controller 4312 can be configured to implement the method depicted in FIG. 85. In certain instances, the surgical instrument 10 may include a load cell 4334 (FIG. 86); as illustrated in FIG. 84, the controller 4312 may be in communication with the load cell 4334. In certain instances, the load cell 4334 may include a force sensor such as, for example, a strain gauge, which can be operably coupled to the firing bar 172, for example. In certain instances, the controller 4312 may employ the load cell 4334 to monitor the force (Fx) applied to the cutting edge 182 as the cutting edge 182 is advanced during a firing stroke.

Accordingly, when the knife firing is initiated 4502 the system checks 4504 the dullness of the cutting edge 182 of the knife by sensing a force Fx. The sensed force Fx is compared to a threshold force F1 and determines 4506 whether the sensed force Fx is greater than the threshold force F1. When the sensed force Fx is less than or equal to the threshold force F1, the process proceeds along NO branch and displays 4508 nothing and continues 4510 the knife firing process. When the sensed force Fx is greater than the threshold force F1, the process proceeds along YES branch and determines 4512 whether the sensed force Fx exceeds a high severity threshold force F2. When the sensed force Fx is less than or equal to the threshold F2, the process proceeds along NO branch and notifies 4514 the processor that the cutting edge 182 of the knife is dulling and the continues 4510 the knife firing process. When the sensed force Fx is greater than the threshold F2, the process proceeds along YES branch and notifies 4516 the processor that the cutting edge 182 of the knife is dulled and the knife firing lockout is engaged. Subsequently, optionally, the processor may override 4518 the knife firing lockout and continues 4510 the knife firing process if the lockout is overridden.

Referring to FIG. 88, a method 4600 is depicted for determining whether a cutting edge such as, for example, the cutting edge 182 is sufficiently sharp to be employed in transecting a tissue of a particular tissue thickness that is captured by the end effector 300, for example. As described above, repetitive use of the cutting edge 182 may dull or reduce the sharpness of the cutting edge 182 which may increase the force required for the cutting edge 182 to transect the captured tissue. In other words, the sharpness level of the cutting edge 182 can be defined by the force required for the cutting edge 182 to transect the captured tissue, for example. The reader will appreciate that the force required for the cutting edge 182 to transect a captured tissue may also depend on the thickness of the captured tissue. In certain instances, the greater the thickness of the captured tissue, the greater the force required for the cutting edge 182 to transect the captured tissue at the same sharpness level, for example.

Accordingly, initially, the stapler clamps 4602 the tissue between the anvil and the jaw member. The system senses 4604 the tissue thickness Tx and initiates 4606 the knife firing process. Upon initiating the knife firing process, the system senses 4608 the load resistance from the clamped tissue and compares the sensed force Fx and senses thickness Tx against various thresholds and determines 4610 several outcomes based on the evaluation. In one aspect, when the process determines 4610 whether the sensed tissue thickness Tx is within a first tissue thickness range defined between a first tissue thickness threshold T1 and a second tissue thickness threshold T2 AND the sensed force Fx is greater than a first force threshold F1 AND the process determines 4610 whether the sensed tissue thickness Tx is within a second tissue thickness range defined between the second tissue thickness threshold T2 and a third tissue thickness threshold T3 AND the sensed force Fx is greater than a second force threshold F2, the process proceeds along the YES branch and notifies 4612 or alerts the processor that the knife is dulling and then continues 4614 the knife firing process. Otherwise, the process proceeds along the NO branch and the does not notify 4616 the processor and continues the knife firing process. Generally, the process determines whether the sensed tissue thickness Tx is within a tissue thickness range defined between tissue thickness thresholds Tn and Tn+1 AND the sensed force Fx is greater than a force threshold Tn, where n indicates a tissue thickness range. When the process determines 4610 that the sensed tissue thickness Tx is within a first tissue thickness range defined between a first tissue thickness threshold T1 and a second tissue thickness threshold T2 AND the sensed force Fx is greater than a first force threshold F1 AND when the process determines 4610 that the sensed tissue thickness Tx is within a second tissue thickness range defined between the second tissue thickness threshold T2 and a third tissue thickness threshold T3 AND the sensed force Fx is greater than a second force threshold F2, the process continues.

In certain instances, the cutting edge 182 may be sufficiently sharp for transecting a captured tissue comprising a first thickness but may not be sufficiently sharp for transecting a captured tissue comprising a second thickness greater than the first thickness, for example. In certain instances, a sharpness level of the cutting edge 182, as defined by the force required for the cutting edge 182 to transect a captured tissue, may be adequate for transecting the captured tissue if the captured tissue comprises a tissue thickness that is in a particular range of tissue thicknesses, for example.

In certain instances, as illustrated in FIG. 89, the memory 4316 can store one or more predefined ranges of tissue thicknesses of tissue captured by the end effector 300; and predefined threshold forces associated with the predefined ranges of tissue thicknesses. In certain instances, each predefined threshold force may represent a minimum sharpness level of the cutting edge 182 that is suitable for transecting a captured tissue comprising a tissue thickness (Tx) encompassed by the range of tissue thicknesses that is associated with the predefined threshold force. In certain instances, if the force (Fx) required for the cutting edge 182 to transect the captured tissue, comprising the tissue thickness (Tx), exceeds the predefined threshold force associated with the predefined range of tissue thicknesses that encompasses the tissue thickness (Tx), the cutting edge 182 may not be sufficiently sharp to transect the captured tissue, for example.

In certain instances, the predefined threshold forces and their corresponding predefined ranges of tissue thicknesses can be stored in a database and/or a table on the memory 4316 such as, for example, a table 4342, as illustrated in FIG. 89. In certain instances, the processor 4314 can be configured to receive a measured value of the force (Fx) required for the cutting edge 182 to transect a captured tissue and a measured value of the tissue thickness (Tx) of the captured tissue. The processor 4314 may access the table 4342 to determine the predefined range of tissue thicknesses that encompasses the measured tissue thickness (Tx). In addition, the processor 4314 may compare the measured force (Fx) to the predefined threshold force associated with the predefined range of tissue thicknesses that encompasses the tissue thickness (Tx). In certain instances, if the measured force (Fx) exceeds the predefined threshold force, the processor 4314 may conclude that the cutting edge 182 may not be sufficiently sharp to transect the captured tissue, for example.

Further to the above, the processor 4314 (FIGS. 85, 86) may employ one or more tissue thickness sensing modules such as, for example, a tissue thickness sensing module 4336 to determine the thickness of the captured tissue. Various suitable tissue thickness sensing modules are described in the present disclosure. In addition, various tissue thickness sensing devices and methods, which are suitable for use with the present disclosure, are disclosed in U.S. Patent Application Publication No. 2011/0155781, entitled SURGICAL CUTTING INSTRUMENT THAT ANALYZES TISSUE THICKNESS, which is herein incorporated by reference in its entirety.

In certain instances, the processor 4314 may employ the load cell 4334 to measure the force (Fx) required for the cutting edge 182 to transect a captured tissue comprising a tissue thickness (Tx). The reader will appreciate that that the force applied to the cutting edge 182 by the captured tissue, while the cutting edge 182 is engaged and/or in contact with the captured tissue, may increase as the cutting edge 182 is advanced against the captured tissue up to the force (Fx) at which the cutting edge 182 may transect the captured tissue. In certain instances, the processor 4314 may employ the load cell 4334 to continually monitor the force applied by the captured tissue against the cutting edge 182 as the cutting edge 182 is advanced against the captured tissue. The processor 4314 may continually compare the monitored force to the predefined threshold force associated with the predefined tissue thickness range encompassing the tissue thickness (Tx) of the captured tissue. In certain instances, if the monitored force exceeds the predefined threshold force, the processor 4314 may conclude that the cutting edge is not sufficiently sharp to safely transect the captured tissue, for example.

The method 4600 described in FIG. 88 outline various example actions that can be taken by the controller 4313 in the event it is determined that the cutting edge 182 is not be sufficiently sharp to safely transect the captured tissue, for example. In certain instances, the controller 4312 may warn the user that the cutting edge 182 is too dull for safe use, for example, through the feedback system 1120, for example. In certain instances, the controller 4312 may employ the firing lockout mechanism 1122 to prevent advancement of the cutting edge 182 upon concluding that the cutting edge 182 is not sufficiently sharp to safely transect the captured tissue, for example. In certain instances, the controller 4312 may employ the feedback system 1120 to provide instructions to the user for overriding the firing lockout mechanism 1122, for example.

FIGS. 90, 91 illustrate various aspects of an apparatus, system, and method for employing a common controller with a plurality of motors in connection with a surgical instrument such as, for example, a motor-driven surgical instrument 4400. The surgical instrument 4400 is similar in many respects to other surgical instruments described by the present disclosure such as, for example, the surgical instrument 10 of FIG. 1 which is described in greater detail above.

The surgical instrument 4400 includes the housing 12, the handle assembly 14, the closure trigger 32, the interchangeable shaft assembly 200, and the end effector 300. Accordingly, for conciseness and clarity of disclosure, a detailed description of certain features of the surgical instrument 4400, which are common with the surgical instrument 10, will not be repeated here.

Referring still to FIGS. 90, 91, the surgical instrument 4400 may include a plurality of motors which can be activated to perform various functions in connection with the operation of the surgical instrument 4400. In certain instances, a first motor can be activated to perform a first function; a second motor can be activated to perform a second function; and a third motor can be activated to perform a third function. In certain instances, the plurality of motors of the surgical instrument 4400 can be individually activated to cause articulation, closure, and/or firing motions in the end effector 300 (FIGS. 1, 15). The articulation, closure, and/or firing motions can be transmitted to the end effector 300 through the interchangeable shaft assembly 200 (FIG. 1), for example.

In certain instances, as illustrated in FIG. 91, the surgical instrument 4400 may include a firing motor 4402. The firing motor 4402 may be operably coupled to a firing drive assembly 4404 which can be configured to transmit firing motions generated by the firing motor 4402 to the end effector 300 (FIGS. 1, 14). In certain instances, the firing motions generated by the firing motor 4402 may cause the staples 191 to be deployed from the surgical staple cartridge 304 into tissue captured by the end effector 300 and/or the cutting edge 182 to be advanced to cut the captured tissue, for example.

In certain instances, as illustrated in FIG. 91, the surgical instrument 4400 may include an articulation motor 4406, for example. The articulation motor 4406 may be operably coupled to an articulation drive assembly 4408 which can be configured to transmit articulation motions generated by the articulation motor 4406 to the end effector 300 (FIGS. 1, 14). In certain instances, the articulation motions may cause the end effector 300 to articulate relative to the interchangeable shaft assembly 200 (FIG. 1), for example. In certain instances, the surgical instrument 4400 may include a closure motor, for example. The closure motor may be operably coupled to a closure drive assembly which can be configured to transmit closure motions to the end effector 300. In certain instances, the closure motions may cause the end effector 300 to transition from an open configuration to an approximated configuration to capture tissue, for example. The reader will appreciate that the motors described herein and their corresponding drive assemblies are intended as examples of the types of motors and/or driving assemblies that can be employed in connection with the present disclosure. The surgical instrument 4400 may include various other motors which can be utilized to perform various other functions in connection with the operation of the surgical instrument 4400.

As described above, the surgical instrument 4400 may include a plurality of motors which may be configured to perform various independent functions. In certain instances, the plurality of motors of the surgical instrument 4400 can be individually or separately activated to perform one or more functions while the other motors remain inactive. For example, the articulation motor 4406 can be activated to cause the end effector 300 (FIGS. 1, 14) to be articulated while the firing motor 4402 remains inactive. Alternatively, the firing motor 4402 can be activated to fire the plurality of staples 191 (FIG. 14) and/or advance the cutting edge 182 while the articulation motor 4406 remains inactive.

With reference to FIGS. 90, 91, in certain instances, the surgical instrument 4400 may include a common controller 4410 which can be employed with a plurality of motors 4402, 4406 of the surgical instrument 4400. In certain instances, the common controller 4410 may accommodate one of the plurality of motors at a time. For example, the common controller 4410 can be separably couplable to the plurality of motors of the surgical instrument 4400 individually. In certain instances, a plurality of the motors of the surgical instrument 4400 may share one or more common controllers such as the common controller 4410. In certain instances, a plurality of motors of the surgical instrument 4400 can be individually and selectively engaged the common controller 4410. In certain instances, the common controller 4410 can be selectively switched from interfacing with one of a plurality of motors of the surgical instrument 4400 to interfacing with another one of the plurality of motors of the surgical instrument 4400.

In at least one example, the common controller 4410 can be selectively switched between operable engagement with the articulation motor 4406 and operable engagement with the firing motor 4402. In at least one example, as illustrated in FIG. 90, a switch 4414 can be moved or transitioned between a plurality of positions and/or states such as a first position 4416 and a second position 4418, for example. In the first position 4416, the switch 4414 may electrically couple the common controller 4410 to the articulation motor 4406; and in the second position 4418, the switch 4414 may electrically couple the common controller 4410 to the firing motor 4402, for example. In certain instances, the common controller 4410 can be electrically coupled to the articulation motor 4406, while the switch 4414 is in the first position 4416, to control the operation of the articulation motor 4406 to articulate the end effector 300 (FIGS. 1, 15) to a desired position. In certain instances, the common controller 4410 can be electrically coupled to the firing motor 4402, while the switch 4414 is in the second position 4418, to control the operation of the firing motor 4402 to fire the plurality of staples 191 (FIG. 14) and/or advance the cutting edge 182 (FIG. 14), for example. In certain instances, the switch 4414 may be a mechanical switch, an electromechanical switch, a solid state switch, or any suitable switching mechanism.

Referring now to FIG. 91, an outer casing of the handle assembly 14 of the surgical instrument 4400 is removed and several features and elements of the surgical instrument 4400 are also removed for clarity of disclosure. In certain instances, as illustrated in FIG. 91, the surgical instrument 4400 may include an interface 4412 which can be selectively transitioned between a plurality of positions and/or states. In a first position and/or state, the interface 4412 may couple the common controller 4410 (FIG. 90) to a first motor such as, for example, the articulation motor 4406; and in a second position and/or state, the interface 4412 may couple the common controller 4410 to a second motor such as, for example, the firing motor 4402. Additional positions and/or states of the interface 4412 are contemplated by the present disclosure.

In certain instances, the interface 4412 is movable between a first position and a second position, wherein the common controller 4410 (FIG. 90) is coupled to a first motor in the first position and a second motor in the second position. In certain instances, the common controller 4410 is decoupled from first motor as the interface 4412 is moved from the first position; and the common controller 4410 is decoupled from second motor as the interface 4412 is moved from the second position. In certain instances, a switch or a trigger can be configured to transition the interface 4412 between the plurality of positions and/or states. In certain instances, a trigger can be movable to simultaneously effectuate the end effector and transition the common controller 4410 from operable engagement with one of the motors of the surgical instrument 4400 to operable engagement with another one of the motors of the surgical instrument 4400.

In at least one example, as illustrated in FIG. 91, the closure trigger 32 can be operably coupled to the interface 4412 and can be configured to transition the interface 4412 between a plurality of positions and/or states. As illustrated in FIG. 91, the closure trigger 32 can be movable, for example during a closure stroke, to transition the interface 4412 from a first position and/or state to a second position and/or state while transitioning the end effector 300 to an approximated configuration to capture tissue by the end effector, for example.

In certain instances, in the first position and/or state, the common controller 4410 can be electrically coupled to a first motor such as, for example, the articulation motor 4406, and in the second position and/or state, the common controller 4410 can be electrically coupled to a second motor such as, for example, the firing motor 4402. In the first position and/or state, the common controller 4410 may be engaged with the articulation motor 4406 to allow the user to articulate the end effector 300 (FIGS. 1, 15) to a desired position; and the common controller 4410 may remain engaged with the articulation motor 4406 until the closure trigger 32 is actuated. As the user actuates the closure trigger 32 to capture tissue by the end effector 300 at the desired position, the interface 4412 can be transitioned or shifted to transition the common controller 4410 from operable engagement with the articulation motor 4406, for example, to operable engagement with the firing motor 4402, for example. Once operable engagement with the firing motor 4402 is established, the common controller 4410 may take control of the firing motor 4402; and the common controller 4410 may activate the firing motor 4402, in response to user input, to fire the plurality of staples 191 (FIG. 14) and/or advance the cutting edge 182 (FIG. 14), for example.

In certain instances, as illustrated in FIG. 91, the common controller 4410 may include a plurality of electrical and/or mechanical contacts 4411 adapted for coupling engagement with the interface 4412. The plurality of motors of the surgical instrument 4400, which share the common controller 4410, may each comprise one or more corresponding electrical and/or mechanical contacts 4413 adapted for coupling engagement with the interface 4412, for example.

In various instances, the motors of the surgical instrument 4400 can be electrical motors. In certain instances, one or more of the motors of the surgical instrument 4400 can be a DC brushed driving motor having a maximum rotation of, approximately, 25,000 RPM, for example. In other arrangements, the motors of the surgical instrument 4400 may include one or more motors selected from a group of motors comprising a brushless motor, a cordless motor, a synchronous motor, a stepper motor, or any other suitable electric motor.

In various instances, as illustrated in FIG. 90, the common controller 4410 may comprise a motor driver 4426 which may comprise one or more H-Bridge field-effect transistors (FETs). The motor driver 4426 may modulate the power transmitted from a power source 4428 to a motor coupled to the common controller 4410 based on input from a controller 4420 ("microcontroller"), for example. In certain instances, the controller 4420 can be employed to determine the current drawn by the motor, for example, while the motor is coupled to the common controller 4410, as described above.

In certain instances, the controller 4420 may include a processor 4422 ("microprocessor") and one or more computer readable mediums or memory 4424 units ("memory"). In certain instances, the memory 4424 may store various program instructions, which when executed may cause the processor 4422 to perform a plurality of functions and/or calculations described herein. In certain instances, one or more of the memory 4424 may be coupled to the processor 4422, for example.

In certain instances, the power source 4428 can be employed to supply power to the controller 4420, for example. In certain instances, the power source 4428 may comprise a battery (or "battery pack" or "power pack"), such as a Li ion battery, for example. In certain instances, the battery pack may be configured to be releasably mounted to the handle assembly 14 for supplying power to the surgical instrument 4400. A number of battery cells connected in series may be used as the power source 4428. In certain instances, the power source 4428 may be replaceable and/or rechargeable, for example.

In various instances, the processor 4422 may control the motor driver 4426 to control the position, direction of rotation, and/or velocity of a motor that is coupled to the common controller 4410. In certain instances, the processor 4422 can signal the motor driver 4426 to stop and/or disable a motor that is coupled to the common controller 4410. It should be understood that the term processor as used herein includes any suitable processor, controller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system. In one instance, the processor 4422 may be a single core or multicore controller LM4F230H5QR as described in connection with FIGS. 15-17B.

In certain instances, the memory 4424 may include program instructions for controlling each of the motors of the surgical instrument 4400 that are couplable to the common controller 4410. For example, the memory 4424 may include program instructions for controlling the articulation motor 4406. Such program instructions may cause the processor 4422 to control the articulation motor 4406 to articulate the end effector 300 in accordance with user input while the articulation motor 4406 is coupled to the common controller 4410. In another example, the memory 4424 may include program instructions for controlling the firing motor 4402. Such program instructions may cause the processor 4422 to control the firing motor 4402 to fire the plurality of staples 191 and/or advance the cutting edge 182 in accordance with user input while the firing motor 4402 is coupled to the common controller 4410.

In certain instances, one or more mechanisms and/or sensors such as, for example, sensors 4430 can be employed to alert the processor 4422 to the program instructions that should be used in a particular setting. For example, the sensors 4430 may alert the processor 4422 to use the program instructions associated with articulation of the end effector 300 (FIGS. 1, 14) while the common controller 4410 is coupled to the articulation motor 4406; and the sensors 4430 may alert the processor 4422 to use the program instructions associated with firing the surgical instrument 4400 while the common controller 4410 is coupled to the firing motor 4402. In certain instances, the sensors 4430 may comprise position sensors which can be employed to sense the position of the switch 4414, for example. Accordingly, the processor 4422 may use the program instructions associated with articulation of the end effector 300 upon detecting, through the sensors 4430 for example, that the switch 4414 is in the first position 4416; and the processor 4422 may use the program instructions associated with firing the surgical instrument 4400 upon detecting, through the sensors 4430 for example, that the switch 4414 is in the second position 4418.

Referring now to FIG. 92, an outer casing of the surgical instrument 4400 is removed and several features and elements of the surgical instrument 4400 are also removed for clarity of disclosure. As illustrated in FIG. 92, the surgical instrument 4400 may include a plurality of sensors which can be employed to perform various functions in connection with the operation of the surgical instrument 4400. For example, as illustrated in FIG. 92, the surgical instrument 4400 may include sensors A, B, and/or C. In certain instances, the sensor A can be employed to perform a first function, for example; the sensor B can be employed to perform a second function, for example; and the sensor C can be employed to perform a third function, for example. In certain instances, the sensor A can be employed to sense a thickness of the tissue captured by the end effector 300 (FIGS. 1, 14) during a first segment of a closure stroke; the sensor B can be employed to sense the tissue thickness during a second segment of the closure stroke following the first segment; and the sensor C can be employed to sense the tissue thickness during a third segment of the closure stroke following the second segment, for example. In certain instances, the sensors A, B, and C can be disposed along the end effector 300, for example.

In certain instances, the sensors A, B, and C can be arranged, as illustrated in FIG. 94, such that the sensor A is disposed proximal to the sensor B, and the sensor C is disposed proximal to the sensor B, for example. In certain instances, as illustrated in FIG. 92, the sensor A can sense the tissue thickness of the tissue captured by the end effector 300 at a first position; the sensor B can sense the tissue thickness of the tissue captured by the end effector 300 at a second position distal to the first position; and the sensor C can sense the tissue thickness of the tissue captured by the end effector 300 at a third position distal to the second position, for example. The reader will appreciate that the sensors described herein are intended as examples of the types of sensors which can be employed in connection with the present disclosure. Other suitable sensors and sensing arrangements can be employed by the present disclosure.

In certain instances, the surgical instrument 4400 may include a controller 4450 which can be similar in many respects to the common controller 4410. For example, the controller 4450, like the common controller 4410, may comprise the controller 4420, the processor 4422, and/or the memory 4424. In certain instances, the power source 4428 can supply power to the controller 4450, for example. In certain instances, the surgical instrument 4400 may include a plurality of sensors such as the sensors A, B, and C, for example, which can activated to perform various functions in connection with the operation of the surgical instrument 4400. In certain instances, one of the sensors A, B, and C, for example, can be individually or separately activated to perform one or more functions while the other sensors remain inactive. In certain instances, a plurality of sensors of the surgical instrument 4400 such as, for example, the sensors A, B, and C may share the controller 4450. In certain instances, only one of the sensors A, B, and C can be coupled to the controller 4450 at a time. In certain instances, the plurality of sensors of the surgical instrument 4400 can be individually and separately couplable to the controller 4450, for example. In at least one example, the controller 4450 can be selectively switched between operable engagement with sensor A, Sensor B, and/or Sensor C.

In certain instances, as illustrated in FIG. 92, the controller 4450 can be disposed in the handle assembly 14, for example, and the sensors that share the controller 4450 can be disposed in the end effector 300 (FIGS. 1, 14), for example. The reader will appreciate that the controller 4450 and/or the sensors that share the controller 4450 are not limited to the above identified positions. In certain instances, the controller 4450 and the sensors that share the controller 4450 can be disposed in the end effector 300, for example. Other arrangements for the positions of the controller 4450 and/or the sensors that share the controller 4450 are contemplated by the present disclosure.

In certain instances, as illustrated in FIG. 92, an interface 4452 can be employed to manage the coupling and/or decoupling of the sensors of the surgical instrument 4400 to the controller 4450. In certain instances, the interface 4452 can be selectively transitioned between a plurality of positions and/or states. In a first position and/or state, the interface 4452 may couple the controller 4450 to the sensor A, for example; in a second position and/or state, the interface 4452 may couple the controller 4450 to the sensor B, for example; and in a third position and/or state, the interface 4452 may couple the controller 4450 to the sensor C, for example. Additional positions and/or states of the interface 4452 are contemplated by the present disclosure.

In certain instances, the interface 4452 is movable between a first position, a second position, and/or a third position, for example, wherein the controller 4450 is coupled to a first sensor in the first position, a second sensor in the second position, and a third sensor in the third position. In certain instances, the controller 4450 is decoupled from first sensor as the interface 4452 is moved from the first position; the controller 4450 is decoupled from second sensor as the interface 4452 is moved from the second position; and the controller 4450 is decoupled from third sensor as the interface 4452 is moved from the third position. In certain instances, a switch or a trigger can be configured to transition the interface 4452 between the plurality of positions and/or states. In certain instances, a trigger can be movable to simultaneously effectuate the end effector and transition the controller 4450 from operable engagement with one of the sensors that share the controller 4450 to operable engagement with another one of the sensors that share the controller 4450, for example.

In at least one example, as illustrated in FIG. 92, the closure trigger 32 can be operably coupled to the interface 4452 and can be configured to transition the interface 4452 between a plurality of positions and/or states. As illustrated in FIG. 92, the closure trigger 32 can be moveable between a plurality of positions, for example during a closure stroke, to transition the interface 4452 between a first position and/or state wherein the controller 4450 is electrically coupled to the sensor A, for example, a second position and/or state wherein the controller 4450 is electrically coupled to the sensor B, for example, and/or a third position and/or state wherein the controller 4450 is electrically coupled to the sensor C, for example.

In certain instances, a user may actuate the closure trigger 32 to capture tissue by the end effector 300. Actuation of the closure trigger may cause the interface 4452 to be transitioned or shifted to transition the controller 4450 from operable engagement with the sensor A, for example, to operable engagement with the sensor B, for example, and/or from operable engagement with sensor B, for example, to operable engagement with sensor C, for example.

In certain instances, the controller 4450 may be coupled to the sensor A while the closure trigger 32 is in a first actuated position. As the closure trigger 32 is actuated past the first actuated position and toward a second actuated position, the controller 4450 may be decoupled from the sensor A. Alternatively, the controller 4450 may be coupled to the sensor A while the closure trigger 32 is in an unactuated position. As the closure trigger 32 is actuated past the unactuated position and toward a second actuated position, the controller 4450 may be decoupled from the sensor A. In certain instances, the controller 4450 may be coupled to the sensor B while the closure trigger 32 is in the second actuated position. As the closure trigger 32 is actuated past the second actuated position and toward a third actuated position, the controller 4450 may be decoupled from the sensor B. In certain instances, the controller 4450 may be coupled to the sensor C while the closure trigger 32 is in the third actuated position.

In certain instances, as illustrated in FIG. 92, the controller 4450 may include a plurality of electrical and/or mechanical contacts 4451 adapted for coupling engagement with the interface 4452. The plurality of sensors of the surgical instrument 4400, which share the controller 4450, may each comprise one or more corresponding electrical and/or mechanical contacts 4453 adapted for coupling engagement with the interface 4452, for example.

In certain instances, the processor 4422 may receive input from the plurality of sensors that share the controller 4450 while the sensors are coupled to the interface 4452. For example, the processor 4422 may receive input from the sensor A while the sensor A is coupled to the controller 4450; the processor 4422 may receive input from the sensor B while the sensor B is coupled to the controller 4450; and the processor 4422 may receive input from the sensor C while the sensor C is coupled to the controller 4450. In certain instances, the input can be a measurement value such as, for example, a measurement value of a tissue thickness of tissue captured by the end effector 300 (FIGS. 1, 15). In certain instances, the processor 4422 may store the input from one or more of the sensors A, B, and C on the memory 4424. In certain instances, the processor 4422 may perform various calculations based on the input provided by the sensors A, B, and C, for example.

FIGS. 93A and 93B illustrate one aspect of an end effector 5300 comprising a staple cartridge 5306 that further comprises two light-emitting diodes 5310 (LEDs). FIG. 93A illustrates an end effector 5300 comprising one LED 5310 located on either side of the cartridge deck 5308. FIG. 91B illustrates a three-quarter angle view of the end effector 5300 with the anvil 5302 in an open position, and one LED 5310 located on either side of the cartridge deck 5308. The end effector 5300 is similar to the end effector 300 (FIGS. 1, 15) described above. The end effector comprises an anvil 5302, pivotally coupled to a jaw member or elongated channel 5304. The elongated channel 5304 is configured to receive the staple cartridge 5306 therein. The staple cartridge 5306 comprises a plurality of staples (not shown). The plurality of staples are deployable from the staple cartridge 5306 during a surgical operation. The staple cartridge 5306 further comprises two LEDs 5310 mounted on the upper surface, or cartridge deck 5308 of the staple cartridge 5306. The LEDs 5310 are mounted such that they will be visible when the anvil 5302 is in a closed position. Furthermore, the LEDs 5310 can be sufficiently bright to be visible through any tissue that may be obscuring a direct view of the LEDs 5310. Additionally, one LED 5310 can be mounted on either side of the staple cartridge 5306 such that at least one LED 5310 is visible from either side of the end effector 5300. The LED 5310 can be mounted near the proximal end of the staple cartridge 530, as illustrated, or may be mounted at the distal end of the staple cartridge 5306.

The LEDs 5310 may be in communication with a processor or controller, such as, for instance, controller 1500 (FIG. 19). The controller 1500 can be configured to detect a property of tissue compressed by the anvil 5302 against the cartridge deck 5308. Tissue that is enclosed by the end effector 5300 may change height as fluid within the tissue is exuded from the tissue's layers. Stapling the tissue before it has sufficiently stabilized may affect the effectiveness of the staples. Tissue stabilization is typically communicates as a rate of change, where the rate of change indicates how rapidly the tissue enclosed by the end effector is changing height.

The LEDs 5310 mounted to the staple cartridge 5306, in the view of the operator of the instrument, can be used to indicate rate at which the enclosed tissue is stabilizing and/or whether the tissue has reached a stable state. The LEDs 5310 can, for example, be configured to flash at a rate that directly correlates to the rate of stabilization of the tissue, that is, can flash quickly initially, flash slower as the tissue stabilizes, and remain steady when the tissue is stable. Alternatively, the LEDs 5310 can flash slowly initially, flash more quickly as the tissue stabilizes, and turn off when the tissue is stable.

The LEDs 5310 mounted on the staple cartridge 5306 can be used additionally or optionally to indicate other information. Examples of other information include, but are not limited to: whether the end effector 5300 is enclosing a sufficient amount of tissue, whether the staple cartridge 5306 is appropriate for the enclosed tissue, whether there is more tissue enclosed than is appropriate for the staple cartridge 5306, whether the staple cartridge 5306 is not compatible with the surgical instrument, or any other indicator that would be useful to the operator of the instrument. The LEDs 5310 can indicate information by either flashing at a particular rate, turning on or off at a particular instance, lighting in different colors for different information. The LEDs 5310 can alternatively or additionally be used to illuminate the area of operation. In some aspects the LEDs 5310 can be selected to emit ultraviolet or infrared light to illuminate information not visible under normal light, where that information is printed on the staple cartridge located in the end effector 5300 or on a tissue compensator (not illustrated). Alternatively or additionally, the staples can be coated with a fluorescing dye and the wavelength of the LEDs 5310 chosen so that the LEDs 5310 cause the fluorescing dye to glow. By illuminating the staples with the LEDs 5310 allows the operator of the instrument to see the staples after they have been driven.

FIGS. 94A and 94B illustrate one aspect of the end effector 5300 comprising a staple cartridge 5356 that further comprises a plurality of LEDs 5360. FIG. 92A illustrates a side angle view of the end effector 5300 with the anvil 5302 in a closed position. The illustrated aspect comprises, by way of example, a plurality of LEDs 5360 located on either side of the cartridge deck 5358. FIG. 92B illustrates a three-quarter angle view of the end effector 5300 with the anvil 5302 in an open position, illustrating a plurality of LEDs 5360 located on either side of the cartridge deck 5358. The staple cartridge 5356 comprises a plurality of LEDs 5360 mounted on the cartridge deck 5358 of the staple cartridge 5356. The LEDs 5360 are mounted such that they will be visible when the anvil 5302 is in a closed position. Furthermore, the LEDs6 530 can be sufficiently bright to be visible through any tissue that may be obscuring a direct view of the LEDs 5360. Additionally, the same number of LEDs 5360 can be mounted on either side of the staple cartridge 5356 such that the same number of LEDs 5360 is visible from either side of the end effector 5300. The LEDs 5360 can be mounted near the proximal end of the staple cartridge 5356, as illustrated, or may be mounted at the distal end of the staple cartridge 5356.

The LEDs 5360 may be in communication with a processor or controller, such as, for instance, controller 1500 of FIG. 15. The controller 1500 can be configured to detect a property of tissue compressed by the anvil 5302 against the cartridge deck 5358, such as the rate of stabilization of the tissue, as described above. The LEDs 5360 can be used to indicate the rate at which the enclose tissue is stabilizing and/or whether the tissue has reached a stable state. The LEDs 5360 can be configured, for instance, to light in sequence starting at the proximal end of the staple cartridge 5356 with each subsequent LED 5360 lighting at the rate at which the enclosed tissue is stabilizing; when the tissue is stable, all the LEDs 5360 can be lit. Alternatively, the LEDs 5360 can light in sequence beginning at the distal end of the staple cartridge 5356. Yet another alternative is for the LEDs 5360 to light in a sequential, repeating sequence, with the sequence starting at either the proximal or distal end of the LEDs 5360. The rate at which the LEDs 5360 light and/or the speed of the repeat can indicate the rate at which the enclosed tissue is stabilizing. It is understood that these are only examples of how the LEDs 5360 can indicate information about the tissue, and that other combinations of the sequence in which the LEDs 5360 light, the rate at which they light, and or their on or off state are possible. It is also understood that the LEDs 5360 can be used to communicate some other information to the operator of the surgical instrument, or to light the work area, as described above.

FIGS. 95A and 95B illustrate one aspect of the end effector 5300 comprising a staple cartridge 5406 that further comprises a plurality of LEDs 5410. FIG. 93A illustrates a side angle view of the end effector 5300 with the anvil 5302 in a closed position. The illustrated aspect comprises, by way of example, a plurality of LEDs 5410 from the proximal to the distal end of the staple cartridge 5406, on either side of the cartridge deck 5408. FIG. 93B illustrates a three-quarter angle view of the end effector 5300 with the anvil 5302 in an open position, illustrating a plurality of LEDs 5410 from the proximal to the distal end of the staple cartridge 5406, and on either side of the cartridge deck 5408. The staple cartridge 5406 comprises a plurality of LEDs 5410 mounted on the cartridge deck 5408 of the staple cartridge 5406, with the LEDs 5410 placed continuously from the proximal to the distal end of the staple cartridge 5406. The LEDs 5410 are mounted such that they will be visible when the anvil 5302 is in a closed position. The same number of LEDs 5410 can be mounted on either side of the staple cartridge 5406 such that the same number of LEDs 5410 is visible from either side of the end effector 5300.

The LEDs 5410 can be in communication with a processor or controller, such as, for instance, controller 1500 of FIG. 15. The controller 1500 can be configured to detect a property of tissue compressed by the anvil 5302 against the cartridge deck 5408, such as the rate of stabilization of the tissue, as described above. The LEDs 5410 can be configured to be turned on or off in sequences or groups as desired to indicate the rate of stabilization of the tissue and/or that the tissue is stable. The LEDs 5410 can further be configured communicate some other information to the operator of the surgical instrument, or to light the work area, as described above. Additionally or alternatively, the LEDs 5410 can be configured to indicate which areas of the end effector 5300 contain stable tissue, and or what areas of the end effector 5300 are enclosing tissue, and/or if those areas are enclosing sufficient tissue. The LEDs 5410 can further be configured to indicate if any portion of the enclosed tissue is unsuitable for the staple cartridge 5406.

Referring now primarily to FIGS. 96 and 97, the power assembly 2096 may include a power modulator control 2106 which may comprise, for example, one or more field-effect transistors (FETs), a Darlington array, an adjustable amplifier, and/or any other power modulator. The power assembly controller 2100 may actuate the power modulator control 2106 to set the power output of the battery 2098 to the power requirement of the interchangeable working assembly 2094 in response to the signal generated by working assembly controller 2102 while the interchangeable working assembly 2094 is coupled to the power assembly 2096.

Still referring primarily to FIGS. 96 and 97, the power assembly controller 2100 can be configured to monitor power transmission from the power assembly 2096 to the interchangeable working assembly 2094 for the one or more signals generated by the working assembly controller 2102 of the interchangeable working assembly 2094 while he interchangeable working assembly 2094 is coupled to the power assembly 2096. As illustrated in FIG. 96, the power assembly controller 2100 may utilize a voltage monitoring mechanism for monitoring the voltage across the battery 2098 to detect the one or more signals generated by the working assembly controller 2102, for example. In certain instances, a voltage conditioner can be utilized to scale the voltage of the battery 2098 to be readable by an Analog to Digital Converter (ADC) of the power assembly controller 2100. As illustrated in FIG. 96, the voltage conditioner may comprise a voltage divider 2108 which can create a reference voltage or a low voltage signal proportional to the voltage of the battery 2098 which can be measured and reported to the power assembly controller 2100 through the ADC, for example.

In other circumstances, as illustrated in FIG. 97, the power assembly 2096 may comprise a current monitoring mechanism for monitoring current transmitted to the interchangeable working assembly 2094 to detect the one or more signals generated by the working assembly controller 2102, for example. In certain instances, the power assembly 2096 may comprise a current sensor 2110 which can be utilized to monitor current transmitted to the interchangeable working assembly 2094. The monitored current can be reported to the power assembly controller 2100 through an ADC, for example. In other circumstances, the power assembly controller 2100 may be configured to simultaneously monitor both of the current transmitted to the interchangeable working assembly 2094 and the corresponding voltage across the battery 2098 to detect the one or more signals generated by the working assembly controller 2102. The reader will appreciate that various other mechanisms for monitoring current and/or voltage can be utilized by the power assembly controller 2100 to detect the one or more signals generated by the working assembly controller 2102; all such mechanisms are contemplated by the present disclosure.

Referring to FIG. 98, the controller 13002 may generally comprise a processor 13008 ("microprocessor") and one or more memory units 13010 operationally coupled to the processor 13008. By executing instruction code stored in the memory 13010, the processor 13008 may control various components of the surgical instrument 12200, such as the motor 12216, various drive systems, and/or a user display, for example. The controller 13002 may be implemented using integrated and/or discrete hardware elements, software elements, and/or a combination of both. Examples of integrated hardware elements may include processors, microprocessors, controllers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, controllers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the controller 13002 may include a hybrid circuit comprising discrete and integrated circuit elements or components on one or more substrates, for example. In certain instances, the controller 13002 may be a single core or multicore controller LM4F230H5QR as described in connection with FIGS. 15-17B.

In various forms, the motor 12216 may be a DC brushed driving motor having a maximum rotation of, approximately, 25,000 RPM, for example. In other arrangements, the motor 12216 may include a brushless motor, a cordless motor, a synchronous motor, a stepper motor, or any other suitable electric motor. A battery 12218 (or "power source" or "power pack"), such as a Li ion battery, for example, may be coupled to the housing 12212 to supply power to the motor 12216, for example.

Referring again to FIG. 98, the surgical instrument 12200 may include a motor controller 13005 in operable communication with the controller 13002. The motor controller 13005 can be configured to control a direction of rotation of the motor 12216. In certain instances, the motor controller 13005 may be configured to determine the voltage polarity applied to the motor 12216 by the battery 12218 and, in turn, determine the direction of rotation of the motor 12216 based on input from the controller 13002. For example, the motor 12216 may reverse the direction of its rotation from a clockwise direction to a counterclockwise direction when the voltage polarity applied to the motor 12216 by the battery 12218 is reversed by the motor controller 13005 based on input from the controller 13002. In addition, the motor 12216 can be operably coupled to an articulation drive which can be driven by the motor 12216 distally or proximally depending on the direction in which the motor 12216 rotates, for example. Furthermore, the articulation drive can be operably coupled to the end effector 12208 such that, for example, the axial translation of the articulation drive proximally may cause the end effector 12208 to be articulated in the counterclockwise direction, for example, and/or the axial translation of the articulation drive distally may cause the end effector 12208 to be articulated in the clockwise direction, for example.

In the aspect illustrated in FIG. 99, an interface 3001 comprises multiple switches 3004A-C, 3084B wherein each of the switches 3004A-C is coupled to the controller 3002 via one of three electrical circuits 3006A-C, respectively, and switch 3084B is coupled to the controller 3002 via circuit 3084A. The reader will appreciate that other combinations of switches and circuits can be utilized with the interface 3001.

Further to the above, the controller 3002 may comprise a processor 3008 and/or one or more memory 3010 units. By executing instruction code stored in the memory 3010, the processor 3008 may control various components of the surgical instrument, such as the electric motor 1102 and/or a user display. The controller 3002 may be implemented using integrated and/or discrete hardware elements, software elements, and/or a combination of both. Examples of integrated hardware elements may include processors, microprocessors, controllers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, controller, system-on-chip (SoC), and/or system-in-package (SIP). Examples of discrete hardware elements may include circuits and/or circuit elements (e.g., logic gates, field effect transistors, bipolar transistors, resistors, capacitors, inductors, relay and so forth). In other aspects, the controller 3002 may include a hybrid circuit comprising discrete and integrated circuit elements or components on one or more substrates, for example.

Referring again to FIG. 99, the surgical instrument 1010 may include a motor controller 3005 in operable communication with the controller 3002. The motor controller 3005 can be configured to control a direction of rotation of the electric motor 1102. For example, the electric motor 1102 can be powered by a battery such as, for example, the battery 1104 and the controller 3002 may be configured to determine the voltage polarity applied to the electric motor 1102 by the battery 1104 and, in turn, the direction of rotation of the electric motor 1102 based on input from the controller 3002. For example, the electric motor 1102 may reverse the direction of its rotation from a clockwise direction to a counterclockwise direction when the voltage polarity applied to the electric motor 1102 by the battery 1104 is reversed by the motor controller 3005 based on input from the controller 3002. Examples of suitable motor controllers are described elsewhere in this document and include but are not limited to the driver 7010 (FIG. 100).

In addition, as described elsewhere in this document in greater detail, the electric motor 1102 can be operably coupled to an articulation drive. In use, the electric motor 1102 can drive the proximal articulation drive distally or proximally depending on the direction in which the electric motor 1102 rotates. Furthermore, the proximal articulation drive can be operably coupled to the end effector 1300 such that, for example, the axial translation of the proximal articulation drive 10030 proximally may cause the end effector 1300 to be articulated in the counterclockwise direction, for example, and/or the axial translation of the proximal articulation drive 10030 distally may cause the end effector 1300 to be articulated in the clockwise direction, for example.

Further to the above, referring again to FIG. 99, the interface 3001 can be configured such that the switch 3004A can be dedicated to clockwise articulation of the end effector 1300 and the switch 3004B can be dedicated to counterclockwise articulation of the end effector 1300. For example, the operator may articulate the end effector 1300 in the clockwise direction by closing the switch 3004A which may signal the controller 3002 to cause the electric motor 1102 to rotate in the clockwise direction thereby, as a result, causing the proximal articulation drive 10030 to be advanced distally and causing the end effector 1300 to be articulated in the clockwise direction. In another example, the operator may articulate the end effector 1300 in the counterclockwise direction by closing the switch 3004B which may signal the controller 3002 to cause the electric motor 1102 to rotate in the counterclockwise direction, for example, and retracting the proximal articulation drive 10030 proximally to articulate the end effector 1300 to in the counterclockwise direction.

As shown in FIG. 100, a sensor arrangement 7002 provides a unique position signal corresponding to the location of the longitudinally-movable drive member 1111. The electric motor 1102 can include a rotatable shaft 7016 that operably interfaces with a gear assembly 7014 that is mounted in meshing engagement with a with a set, or rack, of drive teeth on the longitudinally-movable drive member 1111. With reference also to FIG. 101, the sensor element 7026 may be operably coupled to the gear assembly 7106 such that a single revolution of the sensor element 7026 corresponds to some linear longitudinal translation of the longitudinally-movable drive member 1111, as described in more detail hereinbelow. In one aspect, an arrangement of gearing and sensors can be connected to the linear actuator via a rack and pinion arrangement, or a rotary actuator via a spur gear or other connection. For aspects comprising a rotary screw-drive configuration where a larger number of turns would be required, a high reduction gearing arrangement between the drive member and the sensor, like a worm and wheel, may be employed.

In accordance one aspect of the present disclosure, the sensor arrangement 7002 for the absolute positioning system 7000 provides a position sensor 7012 that is more robust for use with surgical devices. By providing a unique position signal or value for each possible actuator position, such arrangement eliminates the need for a zeroing or calibration step and reduces the possibility of negative design impact in the cases where noise or power brown-out conditions may create position sense errors as in conventional rotary encoder configurations.

In one aspect, the sensor arrangement 7002 for the absolute positioning system 7000 replaces conventional rotary encoders typically attached to the motor rotor and replaces it with a position sensor 7012 which generates a unique position signal for each rotational position in a single revolution of a sensor element associated with the position sensor 7012. Thus, a single revolution of a sensor element associated with the position sensor 7012 is equivalent to a longitudinal linear displacement d1 of the of the longitudinally-movable drive member 1111. In other words, d1 is the longitudinal linear distance that the longitudinally-movable drive member 1111 moves from point “a” to point “b” after a single revolution of a sensor element coupled to the longitudinally-movable drive member 1111. The sensor arrangement 7002 may be connected via a gear reduction that results in the position sensor 7012 completing only a single turn for the full stroke of the longitudinally-movable drive member 1111. With a suitable gear ratio, the full stroke of the longitudinally-movable drive member 1111 can be represented in one revolution of the position sensor 7012.

A series of switches 7022*a* to 7022*n*, where n is an integer greater than one, may be employed alone or in combination with gear reduction to provide a unique position signal for more than one revolution of the position sensor 7012. The state of the switches 7022*a*-7022*n* are fed back to a controller 7004 which applies logic to determine a unique position signal corresponding to the longitudinal linear displacement d1+d2+ . . . dn of the longitudinally-movable drive member 1111.

Accordingly, the absolute positioning system 7000 provides an absolute position of the longitudinally-movable drive member 1111 upon power up of the instrument without retracting or advancing the longitudinally-movable drive member 1111 to a reset (zero or home) position as may be required with conventional rotary encoders that merely count the number of steps forwards or backwards that motor has taken to infer the position of a device actuator, drive bar, knife, and the like.

In various aspects, the position sensor 7012 of the sensor arrangement 7002 may comprise one or more magnetic sensor, analog rotary sensor like a potentiometer, array of analog Hall-effect elements, which output a unique combination of position signals or values, among others, for example.

In various aspects, the controller 7004 may be programmed to perform various functions such as precise control over the speed and position of the knife and articulation systems. Using the known physical properties, the controller 7004 can be designed to simulate the response of the actual system in the software of the controller 7004. The simulated response is compared to (noisy and discrete) measured response of the actual system to obtain an “observed” response, which is used for actual feedback decisions. The observed response is a favorable, tuned, value that balances the smooth, continuous nature of the simulated response with the measured response, which can detect outside influences on the system.

In various aspects, the absolute positioning system 7000 may further comprise and/or be programmed to implement the following functionalities. A feedback controller, which can be one of any feedback controllers, including, but not limited to: PID, state feedback and adaptive. A power source converts the signal from the feedback controller into a physical input to the system, in this case voltage. Other examples include, but are not limited to pulse width modulated (PWMed) voltage, current and force. The electric motor 1102 may be a brushed DC motor with a gearbox and mechanical links to an articulation or knife system. Other sensor(s) 7018 may be provided to measure physical parameters of the physical system in addition to position measured by the position sensor 7012. Since it is a digital signal (or connected to a digital data acquisition system) its output will have finite resolution and sampling frequency. A compare and combine circuit may be provided to combine the simulated response with the measured response using algorithms such as, without limitation, weighted average and theoretical control loop that drives the simulated response towards the measured response. Simulation of the physical system takes in account of properties like mass, inertial, viscous friction, inductance resistance, etc. to predict what the states and outputs of the physical system will be by knowing the input. In one aspect, the controller 7004 may be a single core or multicore controller LM4F230H5QR as described in connection with FIGS. 15-17B.

In one aspect, the driver 7010 may be a A3941 available from Allegro Microsystems, Inc. The A3941 driver 7010 is a full-bridge controller for use with external N-channel power metal oxide semiconductor field effect transistors (MOSFETs) specifically designed for inductive loads, such as brush DC motors. The driver 7010 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted for use in the absolute positioning system 7000. Accordingly, the present disclosure should not be limited in this context.

Having described a general architecture for implementing various aspects of an absolute positioning system 7000 for a sensor arrangement 7002, the disclosure now turns to FIGS. 101-103 for a description of one aspect of a sensor arrangement for the absolute positioning system 7000. In the aspect illustrated in FIG. 101, the sensor arrangement 7002 comprises a position sensor 7100, a magnet 7102 sensor element, a magnet holder 7104 that turns once every full stroke of the longitudinally-movable drive member 1111 (FIG. 100), and a gear assembly 7106 to provide a gear reduction. A structural element such as bracket 7116 is provided to support the gear assembly 7106, the magnet holder 7104, and the magnet 7102. The position sensor 7100 comprises one or more than one magnetic sensing elements such as Hall elements and is placed in proximity to the magnet 7102. Accordingly, as the magnet 7102 rotates, the magnetic sensing elements of the position sensor 7100 determine the absolute angular position of the magnet 7102 over one revolution.

In various aspects, any number of magnetic sensing elements may be employed on the absolute positioning system 7000, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In the illustrated aspect, the gear assembly 7106 comprises a first gear 7108 and a second gear 7110 in meshing engagement to provide a 3:1 gear ratio connection. A third gear 7112 rotates about shaft 7114. The third gear is in meshing engagement with the longitudinally-movable drive member 1111 and rotates in a first direction as the longitudinally-movable drive member 1111 advances in a distal direction D and rotates in a second direction as the longitudinally-movable drive member 1111 retracts in a proximal direction P. The second gear 7110 also rotates about the shaft 7114 and therefore, rotation of the second gear 7110 about the shaft 7114 corresponds to the longitudinal translation of the longitudinally-movable drive member 1111. Thus, one full stroke of the longitudinally-movable drive member 1111 in either the distal or proximal directions D, P corresponds to three rotations of the second gear 7110 and a single rotation of the first gear 7108. Since the magnet holder 7104 is coupled to the first gear 7108, the magnet holder 7104 makes one full rotation with each full stroke of the longitudinally-movable drive member 1111.

FIG. 102 is an exploded perspective view of the sensor arrangement 7002 for the absolute positioning system 7000 showing a circuit 1106 and the relative alignment of the elements of the sensor arrangement 7002, according to one aspect. The position sensor 7100 (not shown in this view) is supported by a position sensor holder 7118 defining an aperture 7120 suitable to contain the position sensor 7100 in precise alignment with a magnet 7102 rotating below. The fixture is coupled to the bracket 7116 and to the circuit 1106 and remains stationary while the magnet 7102 rotates with the magnet holder 7104. A hub 7122 is provided to mate with the first gear 7108 and the magnet holder 7104.

FIG. 103 is a schematic diagram of one aspect of a position sensor 7100 sensor for an absolute positioning system 7000 comprising a magnetic rotary absolute positioning system, according to one aspect. In one aspect, the position sensor 7100 may be implemented as an AS5055EQFT single-chip magnetic rotary position sensor available from Austria Microsystems, AG. The position sensor 7100 is interfaced with the controller 7004 to provide an absolute positioning system 7000. The position sensor 7100 is a low voltage and low power component and includes four Hall-effect elements 7128A, 7128B, 7128C, 7128D in an area 7130 of the position sensor 7100 that is located above the magnet 7102 (FIGS. 99, 100). A high resolution ADC 7132 and a smart power management controller 7138 are also provided on the chip. A CORDIC processor 7136 (for COordinate Rotation DIgital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits and magnetic field information are transmitted over a standard serial communication interface such as an SPI interface 7134 to the controller 7004. The position sensor 7100 provides 12 or 14 bits of resolution. The position sensor 7100 may be an AS5055 chip provided in a small QFN 16-pin 4×4×0.85 mm package.

The Hall-effect elements 7128A, 7128B, 7128C, 7128D are located directly above the rotating magnet. The Hall-effect is a well known effect and will not be described in detail herein for the sake of conciseness and clarity of disclosure. Generally, the Hall-effect is the production of a voltage difference (the Hall voltage) across an electrical conductor, transverse to an electric current in the conductor and a magnetic field perpendicular to the current. It was discovered by Edwin Hall in 1879. The Hall coefficient is defined as the ratio of the induced electric field to the product of the current density and the applied magnetic field. It is a characteristic of the material from which the conductor is made, since its value depends on the type, number, and properties of the charge carriers that constitute the current. In the AS5055 position sensor 7100, the Hall-effect elements 7128A, 7128B, 7128C, 7128D are capable producing a voltage signal that is indicative of the absolute position of the magnet 7102 (FIGS. 186, 187) in terms of the angle over a single revolution of the magnet 7102. This value of the angle, which is unique position signal, is calculated by the CORDIC processor 7136 is stored onboard the AS5055 position sensor 7100 in a register or memory. The value of the angle that is indicative of the position of the magnet 7102 over one revolution is provided to the controller 7004 in a variety of techniques, e.g., upon power up or upon request by the controller 7004.

The AS5055 position sensor 7100 requires only a few external components to operate when connected to the controller 7004. Six wires are needed for a simple application using a single power supply: two wires for power and four wires 7140 for the SPI interface 7134 with the controller 7004. A seventh connection can be added in order to send an interrupt to the controller 7004 to inform that a new valid angle can be read.

Upon power-up, the AS5055 position sensor 7100 performs a full power-up sequence including one angle measurement. The completion of this cycle is indicated as an INT output 7142 and the angle value is stored in an internal register. Once this output is set, the AS5055 position sensor 7100 suspends to sleep mode. The controller 7004 can respond to the INT request at the INT output 7142 by reading the angle value from the AS5055 position sensor 7100 over the SPI interface 7134. Once the angle value is read by the controller 7004, the INT output 7142 is cleared again. Sending a "read angle" command by the SPI interface 7134 by the controller 7004 to the position sensor 7100 also automatically powers up the chip and starts another angle measurement. As soon as the controller 7004 has completed reading of the angle value, the INT output 7142 is cleared and a new result is stored in the angle register. The completion of the angle measurement is again indicated by setting the INT output 7142 and a corresponding flag in the status register.

Due to the measurement principle of the AS5055 position sensor 7100, only a single angle measurement is performed in very short time (~600 μs) after each power-up sequence. As soon as the measurement of one angle is completed, the AS5055 position sensor 7100 suspends to power-down state. An on-chip filtering of the angle value by digital averaging is not implemented, as this would require more than one angle measurement and consequently, a longer power-up time which is not desired in low power applications. The angle jitter can be reduced by averaging of several angle samples in the controller 7004. For example, an averaging of 4 samples reduces the jitter by 6 dB (50%).

As discussed above, the electric motor 1102 positioned within the handle 1042 of surgical instrument system 1000 can be utilized to advance and/or retract the firing system of the shaft assembly 1200, including firing members 1272 and 1280, for example, relative to the end effector 1300 of the shaft assembly 1200 in order to staple and/or incise tissue captured within the end effector 1300. In various circumstances, it may be desirable to advance the firing members 1272 and 1280 at a desired speed, or within a range of desired speeds. Likewise, it may be desirable to retract the firing members 1272 and 1280 at a desired speed, or within a range of desired speeds. In various circumstances, the controller 7004 of the handle 1042, for example, and/or any other suitable controller, can be configured to control the speed of the firing members 1272 and 1280. In some circumstances, the controller can be configured to predict the speed of the firing members 1272 and 1280 based on various parameters of the power supplied to the electric motor 1102, such as voltage and/or current, for example, and/or other operating parameters of the electric motor 1102. The controller can also be configured to predict the current speed of the firing members 1272 and 1280 based on the previous values of the current and/or voltage supplied to the electric motor 1102, and/or previous states of the system like velocity, acceleration, and/or position. Furthermore, the controller can also be configured to sense the speed of the firing members 1272 and 1280 utilizing the absolute positioning sensor system described above, for example. In various circumstances, the controller can be configured to compare the predicted speed of the firing members 1272 and 1280 and the sensed speed of the firing members 1272 and 1280 to determine whether the power to the electric motor 1102 should be increased in order to increase the speed of the firing members 1272 and 1280 and/or decreased in order to decrease the speed of the firing members 1272 and 1280. U.S. Pat. No. 8,210,411, entitled MOTOR-DRIVEN SURGICAL CUTTING INSTRUMENT, which is incorporated herein by reference in its entirety. U.S. Pat. No. 7,845,537, entitled SURGICAL INSTRUMENT HAVING RECORDING CAPABILITIES, which is incorporated herein by reference in its entirety.

Using the physical properties of the instruments disclosed herein, turning now to FIGS. 104 and 105, a controller, such as controller 7004, for example, can be designed to simulate the response of the actual system of the instrument in the software of the controller. The simulated response is compared to a (noisy and discrete) measured response of the actual system to obtain an "observed" response, which is used for actual feedback decisions. The observed response is a favorable, tuned, value that balances the smooth, continuous nature of the simulated response with the measured response, which can detect outside influences on the system. With regard to FIGS. 104 and 105, a firing element, or cutting element, in the end effector 1300 of the shaft assembly 1200 can be moved at or near a target velocity, or speed. The systems disclosed in FIGS. 102 and 103 can be utilized to move the cutting element at a target velocity. The systems can include a feedback controller 4200, which can be one of any feedback controllers, including, but not limited to a PID, a State Feedback, LQR, and/or an Adaptive controller, for example. The systems can further include a power source. The power source can convert the signal from the feedback controller 4200 into a physical input to the system, in this case voltage, for example. Other examples include, but are not limited to, pulse width modulated (PWM) voltage, frequency modulated voltage, current, torque, and/or force, for example.

With continued reference to FIGS. 104 and 105, the physical system referred to therein is the actual drive system of the instrument configured to drive the firing member, or cutting member. One example is a brushed DC motor with gearbox and mechanical links to an articulation and/or knife system. Another example is the electric motor 1102 disclosed herein that operates the firing member 10060 and the articulation driver 10030, for example, of an interchangeable shaft assembly. The outside influence 4201 referred to in FIGS. 104 and 105 is the unmeasured, unpredictable influence of things like tissue, surrounding bodies and friction on the physical system, for example. Such outside influence can be referred to as drag and can be represented by a motor 4202 which acts in opposition to the electric motor 1102, for example. In various circumstances, outside influence, such as drag, is the primary cause for deviation of the simulation of the physical system from the actual physical system. The systems depicted in FIGS. 104 and 105 and further discussed below can address the differences between the predicted behavior of the firing member, or cutting member, and the actual behavior of the firing member, or cutting member.

With continued reference to FIGS. 104 and 105, the discrete sensor referred to therein measures physical parameters of the actual physical system. One aspect of such a discrete sensor can include an absolute positioning sensor and system described herein, such as the magnet 7102. As the output of such a discrete sensor can be a digital signal (or connected to a digital data acquisition system) its output may have finite resolution and sampling frequency. The output of the discrete sensor can be supplied to a controller, such as controller 7004, for example. In various circumstances, the controller can combine the simulated, or estimated, response with the measured response. In certain circumstances, it may be useful to use enough measured response to ensure that the outside influence is accounted for without making the observed response unusably noisy. Examples for algorithms that do so include a weighted average and/or a theoretical control loop that drives the simulated response towards the measured response, for example. Ultimately, further to the above, the simulation of the physical system takes in account of properties like mass, inertial, viscous friction, and/or inductance resistance, for example, to predict what the states and outputs of the physical system will be by knowing the input. FIG. 103 shows an addition of evaluating and measuring the current supplied to operate the actual system, which is yet another parameter that can be evaluated for controlling the speed of the cutting member, or firing member, of the shaft assembly 1200, for example. By measuring current in addition to or in lieu of measuring the voltage, in certain circumstances, the physical system can be made more accurate. Nonetheless, the ideas disclosed herein can be extended to the measurement of other state parameters of other physical systems.

FIG. 106 illustrates a perspective view of a surgical instrument 5500 according to various aspects described herein. The surgical instrument 5500 is similar to those described hereinabove in that the surgical instrument 5500 includes an elongated channel configured to support a staple cartridge, an anvil pivotably connected to the elongated channel, a closure member mechanically coupled to the anvil, a knife mechanically coupled to the staple cartridge, an electric motor mechanically coupled to the closure member and/or the knife, a motor controller electrically coupled to the motor, and a control circuit electrically coupled to the motor controller. The surgical instrument 5500 is also similar to those described hereinabove in that the surgical instrument 5500 also includes sensors which are collectively configured to sense or measure a closing force, a firing force, a current drawn by the electric motor, an impedance of tissue positioned between the elongated channel and the anvil, a position of the anvil relative to the elongated channel, a position of the knife, or any combination thereof. The surgical instrument 5500 is also similar to those described hereinabove in that the surgical instrument 5500 also includes algorithms such as closing algorithms, firing algorithms, motor control algorithms, or any combination thereof, which operate to dynamically adjust the operation of the surgical instrument 5500. However, the surgical instrument 5500 is different from those described hereinabove in that the surgical instrument 5500 further includes one or more additional algorithms (in addition to those described hereinabove) which provide additional control functionality for the surgical instrument 5500, as described hereinbelow.

In general, the surgical instrument 5500 may utilize one or more closing algorithms to control a closing motion which clamps the jaws to tissue positioned therebetween and/or one or more firing algorithms to control a firing motion which staples and severs the tissue clamped between the jaws. In operation, a given sensor senses or measures a given parameter (e.g., a closing force, a firing force, and/or any combination thereof) and outputs a signal indicative of the sensed/measured parameter. The output signal can be an analog signal or a digital signal. For instances where the signal output by the sensor is an analog signal, the analog signal is input to an analog-to-digital (A/D) converter which outputs a digital signal indicative of the analog signal. The digital signal is then input to a controller resident in the surgical instrument 5500. For instances where the signal output by the sensor is a digital signal, there is no need for an A/D conversion and the digital signal output by the sensor can be input to the controller. Upon the occurrence of a trigger, a threshold and/or an event, the controller may modify or adjust a closing algorithm, or initiate a different closing algorithm, thereby automatically changing the operation of the surgical instrument 5500 during a closing motion. Similarly, upon the occurrence of a trigger, a threshold and/or an event, the controller may modify or adjust a firing algorithm, or initiate a different firing algorithm, thereby automatically changing the operation of the surgical instrument 5500 during a firing motion.

According to various aspects, the trigger, threshold or event is defined by the sensed/measured closing force. According to other aspects, the trigger, threshold or event is defined by a parameter related to the sensed/measured closing force. Similarly, according to various aspects, the trigger, threshold or event is defined by the sensed/measured firing force. According to other aspects, the trigger, threshold or event is defined by a parameter related to the sensed/measured firing force.

FIG. 107 illustrates a method 1010 of controlling a closing motion of the surgical instrument 5500 according to various aspects. The process starts when a closing motion is initiated 5512. The closing motion may be initiated, for example, by pulling a closing trigger toward a handle. A sensor resident with the surgical instrument 5500 senses/measures 5514 a closing force. The closing force may be, for example, a force experienced by tissue clamped between the jaws of the surgical instrument 5500, a force experienced by the jaws of the surgical instrument 5500 (e.g., by the anvil and/or the elongated channel), a force experienced by the closure tube of the surgical instrument 5500, and/or any combinations thereof.

In response to the closing force, the sensor outputs 5516 a closing force signal, which is indicative of the closing force sensed/measured 5514 by the sensor. Depending on the configuration of the sensor, the closing force signal can be an analog signal or a digital signal. Upon determining 5518 whether the closing force signal is either an analog signal or a digital signal, the process proceeds along the corresponding branch. When the determination 5518 is that the closing force signal is an analog signal, the process proceeds along the analog branch, where the analog signal is received by an A/D converter, converted 5520 to a digital signal representative of the analog signal by the A/D converter and the digital signal is output by the A/D converter. When the determination 5518 is that the closing force signal is a digital signal, the process proceeds along the digital branch because there is no need for an A/D conversion 5520 when the closing force signal is a digital signal.

The closing force signal which is a digital signal representative of the closing force sensed/measured 5514 by the sensor is received by a controller. The controller utilizes the digital signal and determines 5522 whether the closing force sensed/measured 5514 by the sensor reaches or exceeds a predetermined threshold. The controller may make this determination 5522 based on a comparison of a magnitude of the closing force sensed/measured 5514 by the sensor and the predetermined threshold, based on a comparison of an amplitude of the closing force signal output 5516 by the sensor and a predetermined threshold, or any combination thereof.

When the controller determines 5522 that the closing force sensed/measured 5514 by the sensor has not reached or exceeded the predetermined threshold, the closing motion originally initiated 5512 is continued 5524 along with interim processes 5514-5522. When the controller determines 5522 that the closing force sensed/measured 5514 by the sensor has reached or exceeded the predetermined threshold, the controller changes 5526 the closing motion. According to some aspects, the controller may change the closing motion by modifying or adjusting a closing algorithm being executed by the controller to cause the closing motion to be slowed down, paused or stopped to prevent the surgical instrument 5500 from experiencing excessive forces. According to other aspects, the controller may change the closing motion by executing a different closing algorithm which causes the closing motion to be slowed down, paused or stopped to prevent the surgical instrument 5500 from experiencing excessive forces. In either case, the closing motion may be slowed down, stopped or paused by having the controller communicate a slow down signal, a stop signal or a pause signal to the motor controller to slow down, stop or pause the rotation of the motor(s) which drive the closing of the jaws of the surgical instrument 5500.

Upon changing the closing motion 5526, when the change of the closing motion 5526 is a slowing down of the closing motion (a slowing down of the rotation of the motor(s) which drive the closing of the jaws), the process continues 5528 the closing motion originally initiated 5512 but at a reduced speed and the interim process 5514-5522 is continued but the closing of the jaws occurs at a reduced speed. When the change of the closing motion 5526 is a stopping or pausing of the closing motion (a stopping or pausing of the rotation of the motor(s) which drive the closing of the jaws), the process suspends or terminates 5530 the closing motion.

FIG. 108 illustrates an example graph 5540 showing a curve 5542 representative of a closing force F over time t for various aspects of the surgical instrument 5500. The closing force F is shown along the vertical axis and the time t is shown along the horizontal axis. Stated differently, the curve 5542 is a graphical representation of the closing force signal at various times during a closing motion. The curve 5542 may be generated mathematically by the controller based on the closing force signal(s) received by the controller. The closing force F represented on the vertical axis may be a force experienced by tissue clamped between the jaws of the surgical instrument 5500, a force experienced by the jaws of the surgical instrument 5500 (e.g., by the anvil and/or the elongated channel), a force experienced by the closure tube of the surgical instrument 5500, and/or any combinations thereof. The closing force F can be measured in any suitable manner, either directly or indirectly. For example, according to various aspects, the closing force F can be measured directly by a sensor (e.g., a strain gauge) positioned on the anvil, on the elongated channel, on the closure tube, or indirectly by an impedance of the tissue, a current draw of the motor, and/or any combinations thereof.

According to various aspects, the operation of the surgical instrument 5500 may be controlled by monitoring the amplitude of the closing force signal and changing the closing motion when the amplitude of the closing force signal reaches or exceeds a predetermined threshold. With reference to FIG. 107, for example, the closing force amplitude Fcrit may be determined to be an excessive amount of the closing force F experienced by the surgical instrument 5500. Upon the occurrence of the amplitude of the closing force signal reaching or exceeding the closing force amplitude Fcrit, an algorithm, such as the method 1010 of controlling a closing motion of the surgical instrument 5500 according to various aspects illustrated in FIG. 106, may operate to change the closing motion by slowing down, pausing or stopping the motor(s) of the surgical instrument 5500 to prevent the surgical instrument 5500 from experiencing excessive forces.

The curve 5542 provides a useful representation of how the closing force F varies over time t. The change in the closing force F over time t (i.e., the rate of change of the closing force F) may provide useful feedback to the control circuit to control the jaw closing mechanism of the surgical instrument 5500. The change in the closing force F over time t may be represented as a derivative of the curve 5542 and may be approximated over short periods of time by the equation Slope $S=\Delta F/\Delta t$, where $\Delta F$ is the change of the closing force F and $\Delta t$ is the change of the time t. The curve 5542 is representative of an analog signal over time which is sampled and converted to a digital value by an A/D converter as the jaws are closed/opened. Once the analog signal is digitized, the control circuit may thereafter determine the slope of the closing force signal represented by the curve 5542 at any point during the closing motion.

According to various aspects, the operation of the surgical instrument 5500 may be controlled by monitoring the slope of the curve 5542 (the slope of the closing force signal) and changing the closing motion based on the value of the slope. In general, with reference to FIG. 108, the slope of the curve 5542 may be approximated by the equation $S=\Delta F/\Delta t$, where $\Delta F$ is the change of the closing force F and $\Delta t$ is the change of the time t. Those skilled in the art will appreciate that the instantaneous slope may be calculated by taking the derivative of the curve 5542. Over time t, the slope S may be monitored by the control circuit and utilized by the control circuit to control the operation of the surgical instrument 5500. For example, an algorithm of the surgical instrument 5500 may be configured to monitor the change of the closing force F over the time t, stop or pause the closing motion when the slope of the curve 5542 reaches or exceeds a first predetermined threshold, then restart the closing motion when the slope of the curve 5542 reaches or falls below a second predetermined threshold. The value of the slope $C=\Delta F1/\Delta t1$ (a positive value) shown in FIG. 108 may be determined by the controller and may represent the first predetermined threshold. Similarly, the value of the slope $D=\Delta F2/\Delta t2$ (a negative value) shown in FIG. 108 may be determined by the controller and may represent the second predetermined threshold. Thus, according to various aspects, the algorithm can control the operation of the control circuit based on the determined slope, whether instantaneous or approximated.

For the example graph 5540 shown in FIG. 108, at time t=0 the jaws are in the open position and there is no closing force F experienced by the jaws. Once tissue is positioned between the jaws, as the jaws are moved toward a closed position, the jaws come in contact with tissue and begin to compress the tissue. Thus, as the time moves from the time t=0, the closing force F experienced by the jaws begins to increase. An algorithm of the surgical instrument 5500 may automatically stop or pause a further closing of the jaws based on a trigger, a threshold and/or an event. For example, when the change of the closing force F over time t reaches or exceeds a predetermined threshold (e.g., the slope C is greater than the predetermined threshold), the algorithm may automatically stop or pause further closing of the jaws. Alternatively, when the closing force F reaches or exceeds another predetermined threshold (e.g., the closing force F is greater than Fcrit), the algorithm may automatically stop or pause further closing of the jaws.

After the closing of the jaws is stopped or paused, fluid may continue to be displaced from the tissue over time thereby causing the pressure experienced by the jaws to decrease. The control algorithm may automatically re-enable a further closing of the jaws based on a trigger, a threshold or and/or an event. For example, when the change of the closing force F over time t reaches or falls below a predetermined threshold (e.g., the slope D is more negative than the predetermined threshold), the algorithm may automatically restart a further closing of the jaws. A portion of the curve 5542 having the slope D may be indicative of a stabilized tissue condition. Alternatively, when a predetermined period of time has passed since the closing of the jaws was stopped or paused (e.g., the time period t1 in FIG. 108), the algorithm may automatically restart a further closing of the jaws. The predetermined period of time may be considered an adequate amount of time for an adequate amount of tissue creep to occur and/or for the tissue to reach a stabilized condition.

The above-described automatic stopping or pausing and automatic restarting may be repeated any number of times. As more pressure is applied to the tissue (i.e., the jaws experience more force), the amount of time which occurs between an automatic stopping or pausing and an automatic restarting tends to increase (e.g., the time period t3 is greater than the time period t2 which is greater than the time period t1). Once the tissue is deemed to be sufficiently compressed, the jaws of the surgical instrument 5500 can be locked into a closed or clamped position, the closing force F remains essentially constant and the firing motion can be initiated.

Although the example graph 5540 of FIG. 108 was described in the context of various aspects of the surgical instrument 5500, it will be appreciated that the respective illustrations and descriptions of the closing force F can vary for other aspects. For example, in various aspects of the surgical instrument 5500, fewer than or more than three automatic stops or pauses may be required before the tissue is deemed to be sufficiently compressed. Similarly, fewer than or more than three automatic restarts may occur before the tissue is deemed to be sufficiently compressed. Also, although FIG. 108 was described in the context of the closing force F over time t, it will be appreciated that in various aspects, a firing force (not shown) may also be measured/sampled over time. As described in more detail hereinbelow, the firing force measurements and parameters related thereto may be utilized by the control circuit to automatically change a firing motion based on a trigger, a threshold and/or an event.

FIG. 109 illustrates an example graph 5550 showing a curve 5552 representative of a firing force F over time t for various aspects of the surgical instrument 5500 and a curve 5554 representative of a knife velocity V over time t for various aspects of the surgical instrument 5500. The firing force F is shown along an upper portion of the vertical axis, the knife velocity V is shown along a lower portion of the vertical axis and the time t is shown along the upper horizontal axis as well as along the lower horizontal axis. Stated differently, the curve 5552 is a representation of the firing force signal at various times during a firing motion and the curve 5554 is a representation of the knife velocity signal at various times during a firing motion. As shown in FIG. 109, the knife transitions over three distinct zones Z1, Z2, Z3. In zone Z1, the knife velocity V and force F are ramping up from a zero initial value. In zone Z2, the knife is traveling at a relatively constant velocity V and spikes in the measured force F are due to the staple driving force. In zone Z3, the knife velocity V and the force F are ramping down to zero.

The curves 5552, 5554 may be generated mathematically by the controller based on the firing force signal(s) and the knife velocity signal(s) received by the controller. The firing force F and the knife velocity V shown in the example graph 5550 of FIG. 109 may be representative of a condition where the thickness and composition of the tissue along the cut line is uniform. The firing force F represented on the upper portion of the vertical axis may be a force experienced by the drive system of the surgical instrument (e.g., by the sled, the knife and/or the firing bar), and/or any combination thereof. The firing force F can be measured in any suitable manner, either directly or indirectly. For example, according to various aspects, the firing force F can be measured directly by a sensor (e.g. a strain gauge) positioned on the sled, on the knife, or indirectly by a current draw of the motor, and/or any combination thereof. The knife velocity V represented on the lower portion of the vertical axis may be a velocity of the knife, a velocity of the sled, a velocity of another component of the drive system (e.g., the firing bar), and/or any combination thereof. The knife velocity V can be measured in any suitable manner, either directly or indirectly. For example, according to various aspects, the knife velocity V can be measured directly by a combination of a magnet positioned on the firing bar and a Hall-effect sensor or indirectly by a current draw of the motor, an encoder coupled to the shaft of the motor, and/or any combination thereof.

As explained in more detail hereinbelow (See, e.g., FIG. 110), in various aspects the surgical instrument 5500 can measure and/or determine the following: an instantaneous firing force F, one or more peak values of the firing force F, one or more valley values of the firing force F, an average of the firing force F, a change of the firing force F over time t (i.e., a rate of change of the firing force F), a slope of a line connecting successive peak values of the firing force F, a slope of a line connecting successive valley values of the firing force F, a time between successive peak values of the firing force F, a time between successive valley values of the firing force F, a decrease of the firing force F from a peak value of the firing force F to a following valley value of the firing force F, an increase of the firing force F from a valley value of the firing force F to a following peak value of the firing force F, an instantaneous knife velocity V, one or more peak values of the knife velocity V, one or more valley values of knife velocity V, an average of the knife velocity V, a change of the knife velocity V over time t (i.e., a rate of change of the knife velocity V), and/or any combinations thereof.

For the example graph 5550 shown in FIG. 109, at time t=0 the firing force F is essentially zero, the knife is in the fully retracted position and the knife is stationary (the knife velocity V is zero). Once the firing motion is actuated, the knife begins to advance and initially advances at an increasing velocity. As the knife advances, the sled advances and the staples are driven from the staple cartridge, through the tissue and against the anvil. As the knife and sled advance and the knife velocity V increases, the firing force F increases and reaches a first peak value when a first row of staples is driven from the staple cartridge. At this point in time, the knife is not yet in contact with the tissue. For the example graph 5550 shown in FIG. 109, the first peak 5556 of the firing force F is indicative of the first row of staples being driven from the staple cartridge. According to various aspects, the first row of staples is not driven through the tissue and is thus not driven against the anvil. According to other aspects, the first row of staples is driven through a portion of the tissue which is thinner than the thickest portion of the tissue and against the anvil. According to yet other aspects, the first row of staples is driven through a portion of the tissue which was previously stapled (with staples from another staple cartridge), thereby resulting in that portion of the tissue being double stapled.

After the first row of staples is driven as described hereinabove, the firing force F decreases until a second row of staples is driven, which causes the firing force F to reach a second peak 5558. At this point in time, the knife is not yet in contact with the tissue. For the example graph 5550 shown in FIG. 109, the second peak 5558 is indicative of the second row of staples being driven from the staple cartridge. According to various aspects, the second row of staples is not driven through the tissue and is thus not driven against the anvil. According to other aspects, the second row of staples is driven through a portion of the tissue which is thicker than the portion of tissue through which the first row staples was driven (but thinner than the thickest portion of the tissue) and against the anvil. According to yet other aspects, the second row of staples is driven through a portion of the tissue which was already stapled (with staples from another staple cartridge), thereby resulting in that portion of the tissue being double stapled.

After the second row of staples is driven as described hereinabove, the firing force F decreases until a third row of staples is driven, which causes the firing force F to reach a third peak 5560. At this point in time, the knife is not yet in contact with the tissue. For the example graph 5550 shown in FIG. 109, the third peak 5560 is indicative of the third row of staples being driven from the staple cartridge. According to various aspects, the third row of staples is not driven through the tissue and is thus not driven against the anvil. According to other aspects, the third row of staples is driven through a portion of the tissue which is thicker than the portion of tissue through which the second row staples was driven (but thinner than the thickest portion of the tissue) and against the anvil. According to yet other aspects, the third row of staples is driven through a portion of the tissue which was already stapled (with staples from another staple cartridge), thereby resulting in that portion of the tissue being double stapled.

After the third row of staples is driven as described hereinabove, the firing force F decreases until a fourth row of staples is driven, which causes the firing force F to reach a fourth peak 5562. At some point after the third row of staples is driven, the knife comes into contact with the tissue, begins severing the tissue and advances at a substantially constant velocity. For the example graph 5550 shown in FIG. 109, the fourth peak 5562 is indicative of the knife severing the tissue and the fourth row of staples being driven from the staple cartridge through the tissue and against the anvil.

After the fourth row of staples is driven as described hereinabove, the firing force F continues the cycle of decreasing and increasing as the knife advances through the tissue at a substantially constant velocity and additional rows of staples are driven through the tissue and against the anvil. For the aspects shown in FIG. 109, the knife velocity V is substantially constant from the time the knife comes in contact with the tissue (shortly before the fourth peak value of the firing force is reached) to a time shortly after the knife has severed through the tissue (the last peak value before the last three rows of staples are driven). Shortly after the knife has severed through the tissue, the knife velocity V begins to decrease from the substantially constant velocity to zero. The decrease in the knife velocity V and the lower forces required to drive the last three rows of staples produces lower and lower peak values of the firing force F. There are a number of different reasons why lower forces are required to drive the last three rows of staples. For example, according to various aspects, the last three rows of staples may extend past the tissue (and thus are not driven through the tissue and against the anvil), the last three rows of staples may be driven through a less compressed portion of the tissue (due to the geometry of the anvil and the elongated channel), the last three rows of staples may be driven through a thinner portion of the tissue, and/or any combination thereof. Once all of the staples have been driven and the knife velocity V has reached zero (the knife has stopped advancing), the firing force F is zero.

Although the example graph 5550 of FIG. 109 was described in the context of various aspects of the surgical instrument 5500, it will be appreciated that the respective illustrations and descriptions of the firing force F and the knife velocity V can vary for other aspects. For example, in various aspects of the surgical instrument 5500, the knife may come into contact with the tissue after fewer than or more than three rows of staples have been driven from the staple cartridge. Similarly, fewer than or more than three rows of staples may be driven after the knife has severed through the tissue.

FIG. 110 illustrates an example graph 5570 showing a curve 5572 representative of a firing force F and a knife position X over time t for various aspects of the surgical instrument 5500. The firing force F is shown along the vertical axis and the knife position X and the time t are shown along the horizontal axis. As shown along the horizontal axis, the knife position X travels over five Zones 1-5 along the knife channel in the cartridge 304 located in the lower jaw 302 of the end effector 300 of the surgical instrument 5500, as described in more detail hereinbelow. In summary, Zone 1 is a tissue free zone where the knife moves without contacting tissue until it initially contacts tissue in Zone 2. The knife then transects the tissue as it travels along Zone 3. The knife transitions out of the tissue in Zone 4 and in stops in Zone 5, where the knife reaches the end of its travel span in a tissue free region. The spikes 5574 in the various sections 1-5 are due the additional force required to drive staples through the tissue located in the jaws 306, 302 of the end effector 300 portion of the surgical instrument 5500.

Accordingly, the curve 5572 is a representation of the firing force signal at various times during a firing motion in combination with the staple driving force, collectively referred to herein a the driving force F. The curve 5572 may be generated mathematically by the controller based on the firing force signal(s) received by the controller. The firing force F and the knife position X force shown in the example graph 5570 may be representative of a condition where the thickness and composition of the tissue along the cut line is uniform. The firing force F represented on the vertical axis may be a force experienced by the drive system of the surgical instrument 5500 (e.g., by the sled, the knife, and/or the firing bar), and/or any combination thereof. The firing force F can be measured in any suitable manner, either directly or indirectly. For example, according to various aspects, the firing force F can be measured directly by a sensor (e.g., a strain gauge) positioned on the sled, on the knife, or indirectly by a current draw of the motor, and/or any combination thereof.

According to various aspects, the operation of the surgical instrument 5500 may be controlled by monitoring the amplitude of the firing force signal and the knife position X, and changing the firing motion when the amplitude of the firing force signal reaches or exceeds a predetermined threshold. As previously described, this process may be controlled with an algorithm such as the method 1010 of controlling a closing motion of the surgical instrument 5500 according to various aspects illustrated in FIG. 107. According to some aspects, the changing of the firing motion only proceeds when the knife position is within a predetermined range of positions. With reference to FIG. 110, for example, firing force amplitude Fcrit may be determined to be an excessive amount of the firing force F experienced by the surgical instrument 5500. Upon the occurrence of the amplitude of the firing force signal reaching or exceeding the firing force amplitude Fcrit, an algorithm may operate to change the firing motion by slowing down, pausing or stopping the rotation of the motor(s) which drive the knife of the surgical instrument 5500 to prevent the surgical instrument 5500 from experiencing excessive forces.

The curve 5572 provides a useful representation of how the firing force F and the knife position X vary over time t. The change in the firing force F over time t (i.e., the rate of change of the closing force F) may provide useful feedback to the control circuit to control the firing mechanism of the surgical instrument 5500. The change in the firing force F over time t may be represented as a derivative of the curve 5572 and may be approximated over short periods of time by the equation Slope $S=\Delta F/\Delta t$, where $\Delta F$ is the change of the firing force F and $\Delta t$ is the change of the time t. The slope can have a positive value or a negative value. The slope represented by $\Delta F\mathbf{1}/\Delta t\mathbf{1}$ of the curve 5572 has a positive value and the slope represented by $\Delta F\mathbf{2}/\Delta t\mathbf{2}$ of the curve 5572 has a negative value. The curve 5572 is representative of an analog signal over time which is sampled and converted to a digital value by an A/D converter as the firing mechanism is advanced/retracted. Once the analog signal is digitized, the control circuit may thereafter determine the slope of the firing force signal represented by the curve 5542 at any point during the firing motion.

According to various aspects, the operation of the surgical instrument 5500 may be controlled by monitoring the slope of the curve 5572 (the slope of the firing force signal) and the knife position X, and changing the firing motion based on the value of the slope. According to some aspects, the changing of the firing motion only proceeds when the knife position is within a predetermined range of positions. In general, with reference to FIG. 110, the slope of the curve 5572 may be approximated by the equation $S=\Delta F/\Delta t$, where $\Delta F$ is the change of the firing force F and $\Delta t$ is the change of the time t. Those skilled in the art will appreciate that the instantaneous slope may be calculated by taking the derivative of the curve 5572. Over time t, the slope S may be monitored by the control circuit and utilized by the control circuit to control the operation of the surgical instrument 5500. For example, an algorithm of the surgical instrument 5500 may be configured to monitor the change of the firing force F over the time t, stop or pause the firing motion when the slope of the curve 5572 reaches or exceeds a first predetermined threshold, then restart the firing motion when the slope of the curve 5572 reaches or falls below a second predetermined threshold. The value of the slope represented by $\Delta F\mathbf{1}/\Delta t\mathbf{1}$ (a positive value) shown in FIG. 110 may be determined by the controller and may represent the first predetermined threshold. Similarly, the value of the slope represented by $\Delta F\mathbf{2}/\Delta t\mathbf{2}$ (a negative value) shown in FIG. 110 may be determined by the controller and may represent the second predetermined threshold. Thus, according to various aspects, the algorithm can control the operation of the control circuit based on the determined slope, whether instantaneous or approximated.

According to various aspects, the operation of the surgical instrument 5500 may be controlled by monitoring a parameter related to the firing force signal and the knife position X, and changing the firing motion based on the value of the parameter. According to some aspects, the changing of the firing motion only proceeds when the knife position is within a predetermined range of positions. With reference to FIG. 110, for example, an algorithm of the surgical instrument 5500 may be configured to monitor first and second parameters (e.g., the slope of a line connecting successive peak values of the firing force signal represented by $\Delta F\mathbf{3}/\Delta t\mathbf{3}$ and the slope of a line connecting successive valley values of the firing force signal represented by $\Delta F\mathbf{4}/\Delta t\mathbf{4}$ in FIG. 110), stop or pause the firing motion when the value of the first parameter reaches or exceeds a first predetermined threshold, then restart the firing motion when the value of the second parameter reaches or falls below a second predetermined threshold. The value of the slope represented by $\Delta F\mathbf{3}/\Delta t\mathbf{3}$ (a positive value) shown in FIG. 110 may be determined by the controller and may represent the first predetermined threshold. Similarly, the value of the slope represented by $\Delta F\mathbf{4}/\Delta t\mathbf{4}$ (a negative value) shown in FIG. 110 may be determined by the controller and may represent the second predetermined threshold. Thus, according to various aspects, the algorithm, such as the method 1010 of controlling a closing motion of the surgical instrument 5500 according to various aspects shown in FIG. 107, can control the operation of the control circuit based on the determined slopes, whether instantaneous or approximated.

Alternatively, the controller may determine values for other parameters related to the firing force signal and utilize the values of the parameters to change the firing motion. According to some aspects, the changing of the firing motion only proceeds when the knife position is within a predetermined range of positions. With regard to FIG. 110, the other parameters may include, for example, a duration between successive peak values of the firing force signal represented by the time period A shown in FIG. 110, a duration between successive valley values of the firing force signal represented by the time period B shown in FIG. 110, a decrease in the amplitude of the firing force signal from a peak value to a following valley value as represented by the magnitude C shown in FIG. 110 and an increase in the firing force signal from a valley value to a following peak value represented by the magnitude D shown in FIG. 110. The above-described parameters/values determined by the control circuit can be utilized with or without the knife position X to automatically control the firing motion of the surgical instrument 5500. Additionally, the above-described parameters/values determined by the control circuit can be utilized within a limited time/rate window in combination with surgeon variable rate actuation control and feedback.

For the example graph 5570 shown in FIG. 110, at time t=0 the knife is in a fully retracted position near the proximal end of the end effector and over time advances to a fully advanced position near the distal end of the end effector. The overall distance the knife moves from the fully retracted position to the fully advanced position during a firing motion can be divided into predefined zones, with each predefined zone representative of a different operating condition of the surgical instrument 5500. For example, according to various aspects, the overall distance the knife moves from the fully retracted position to the fully advanced position during a firing motion can be divided into five predefined zones and the five zones may be representative of the following: Zone 1 is representative of the knife advancing from a fully retracted position at an increasing velocity but not yet being in contact with tissue positioned between the jaws of the surgical instrument; Zone 2 is representative of the knife advancing at a more rapidly increasing velocity and staples being driven into the tissue (but not into the thickest portion of the tissue); Zone 3 is representative of the knife reaching a maximum or peak velocity, then continuing to advance at a substantially constant velocity and staples being driven into the thickest portion of the tissue; Zone 4 is representative of the knife continuing to advance at a substantial constant velocity, then decreasing in velocity after the tissue has been severed and staples still being driven into the thickest portion of the tissue; and Zone 5 is representative of the knife having reached its fully advanced position (the knife has stopped) and all of the staples have been fired.

Although five zones are shown in FIG. 110, it will be appreciated that the overall distance the knife moves from the fully retracted position to the fully advanced position during a firing motion can be divided into more than or less than five zones, and the respective zones can be representative of operating conditions different from those described hereinabove.

In practice, the thickness and composition of the tissue can vary along the cut line. Thus, it will be appreciated that there are many conditions which can cause the firing force F, the knife velocity V and/or the knife position X to deviate from the firing force F, the knife velocity V and/or the knife position X shown in FIGS. 103 and 104.

FIG. 111 illustrates an example graph 5580 showing a curve 5582 representative of a firing force F over time t for various aspects of the surgical instrument 5500 and a curve 5584 representative of a knife velocity V over time t for various aspects of the surgical instrument 5500. Stated differently, the curve 5582 is a representation of the firing force signal at various times during a firing motion and the curve 5584 is a representation of the knife velocity signal at various times during a firing motion. The curves 5582, 5584 may be generated mathematically by the controller based on the firing force signal(s) and the knife velocity signal(s) received by the controller. The firing force F is shown along an upper portion of the vertical axis, the knife velocity V is shown along a lower portion of the vertical axis and the time t is shown along the upper horizontal axis as well as along the lower horizontal axis. The firing force F represented on the upper portion of the vertical axis may be a force experienced by the drive system of the surgical instrument 5500 (e.g., by the sled, the knife and/or the firing bar), and/or any combination thereof. The firing force F can be measured in any suitable manner, either directly or indirectly. For example, according to various aspects, the firing force F can be measured directly by a sensor (e.g., a strain gauge) positioned on the sled, on the knife, or indirectly by a current draw of the motor, and/or any combination thereof.

The knife velocity V represented on the lower portion of the vertical axis may be a velocity of the knife, a velocity of the sled, a velocity of another component of the drive system (e.g., the firing bar), and/or any combination thereof. The knife velocity V can be measured in any suitable manner, either directly or indirectly. For example, according to various aspects, the knife velocity V can be measured directly by a combination of a magnet positioned on the firing bar and a Hall-effect sensor or indirectly by a current draw of the motor, an encoder coupled to the shaft of the motor, and/or any combination thereof.

In addition to the firing force F and the knife velocity V being measured, the firing force measurements (including the parameters/values derived therefrom) and the knife velocity measurements can be stored by a memory of the surgical instrument 5500. An algorithm of the control circuit of the surgical instrument 5500 can utilize the stored measurements to provide automated control of the surgical instrument 5500. For example, according to various aspects, the algorithm can automatically stop or pause a further advancement of the knife based on a trigger, a threshold and/or an event. For example, when a slope of a line connecting successive peak values of the firing force signal (e.g., the slope of the line A shown in FIG. 111) reaches or exceeds a predetermined threshold (e.g., the slope of the line A is greater than the predetermined threshold), the algorithm can automatically stop or pause a further advancement of the knife.

According to other aspects, the algorithm can automatically stop or pause a further advancement of the knife when a slope of a line connecting successive peak values of the firing force signal and the amplitude of the firing force signal reaches or exceeds a second predetermined threshold (e.g., the amplitude is greater than the firing force amplitude F1). According to yet other aspects, the algorithm can automatically stop or pause a further advancement of the knife when the a slope of a line connecting successive peak values of the firing force signal reaches or exceeds a predetermined threshold, the amplitude of the firing force signal reaches or exceeds a second predetermined threshold and the position of the knife is within a predefined zone of operation (e.g., a position where the knife is advancing at a substantially constant velocity). For these aspects, when the combinations are met, the controller signals the motor controller to change the firing motion by slowing down, pausing or stopping the rotation of the motor(s) which drive the knife of the surgical instrument 5500 to prevent the surgical instrument 5500 from experiencing excessive forces. For the example graph 5580 shown in FIG. 111, when the combinations are met, the controller communicates a pause signal or a stop signal to the motor controller to change the firing motion by pausing or stopping the rotation of the motor(s) which drive the knife velocity and the knife velocity is reduced from the substantially constant velocity to zero.

After the advancement of the knife has been stopped or paused, the algorithm may automatically restart the advancement of the knife based on a trigger, a threshold and/or an event. For example, according to various aspects, the algorithm can automatically restart the advancement of the knife when a slope of the curve 5582 (e.g., the slope ΔF/Δt shown in FIG. 111) reaches or falls below a predetermined threshold. The predetermined threshold may be indicative of a stabilized tissue condition. According to other aspects, when a predetermined period of time has passed since the advancement of the knife was stopped or paused (e.g., the period of time between t1 and t2 in FIG. 111), the algorithm may automatically restart a further advancement of the knife. The predetermined period of time may be considered an adequate amount of time for an adequate amount of tissue creep to occur and/or for the tissue to reach a stabilized condition.

According to yet other aspects, when the amplitude of the firing force signal drops a predetermined amount from what the amplitude of the firing force signal was at the time of the initiation of the stop or pause, the algorithm may automatically restart a further advancement of the knife. The predetermined amount of the drop in the amplitude of the firing force signal may be a quantitative amount (e.g., the difference between the firing force amplitude F1 and the firing force amplitude F2 in FIG. 111) or a percentage (e.g., a 10% drop). The predetermined amount of the drop in firing force signal may be considered sufficient enough for an adequate amount of tissue creep to have occurred and/or for the tissue to have reached a stabilized condition.

According to yet other aspects, when the amplitude of the firing force signal drops to a predetermined value (e.g., the firing force amplitude F2 shown in FIG. 111), the algorithm may automatically restart a further advancement of the knife. The predetermined value of the firing force F may be considered low enough for an adequate amount of tissue creep to have occurred and/or for the tissue to have reached a stabilized condition. Regardless of what the restarting of the knife is based on, when the trigger, threshold and/or event occurs, the controller communicates a start signal to the motor controller to restart the firing motion by restarting the rotation of the motor(s) which drive the knife of the surgical instrument 5500, and the restarting of the rotation of the motor(s) causes the knife velocity V to increase from zero to a substantially constant velocity.

After the knife has severed through the tissue, the knife velocity V begins to decrease from the substantially constant velocity to zero. The decrease in the knife velocity V and the lower firing force F required to drive the last few rows of staples produces lower and lower peak values of the firing force signal. Once all of the staples have been driven and the knife velocity V has reached zero (the knife has stopped advancing), the firing force F is zero.

Although the knife position X is not shown in FIG. 111, it will be appreciated that according to some aspects the changing of the firing motion only proceeds when the knife position is within a predetermined range of positions.

FIG. 112 illustrates an example graph 5690 showing a curve 5692 representative of a closing force FC over time t for various aspects of the surgical instrument 5500 and a curve 5694 representative of a firing force FF over time t for various aspects of the surgical instrument 5500. The closing force FC is shown along the "left" vertical axis, the firing force FF is shown along the "right" vertical axis and the time t is shown along the horizontal axis. When viewed together the curves 5692, 5694 reflect the timing of the closing motion and the firing motion relative to one another, where the closing motion is initiated prior to the initiation of the firing motion. Although the example graph 5690 shows a threshold force Fcrit as being the same amplitude for both the closing force FC and the firing force FF, it will be appreciated that the amplitude of the threshold force Fcrit for the closing force FC may be different from the amplitude of the threshold force Fcrit for the firing force FF. Stated differently, the scale of the "left" vertical axis can be different from the scale of the "right" vertical axis.

The curve 5692 is a graphical representation of the closing force signal at various times during a closing motion and may be similar or identical to the curve 5542 of FOG. 108. Thus, as set forth hereinabove, the curve 5692 may be generated mathematically by the controller based on the closing force signal(s) received by the controller. The closing force FC represented on the "left" vertical axis may be a force experienced by tissue clamped between the jaws of the surgical instrument 5500, a force experienced by the jaws of the surgical instrument 5500 (e.g., by the anvil and/or the elongated channel), a force experienced by the closure tube of the surgical instrument 5500, and/or any combinations thereof. The closing force FC can be measured in any suitable manner, either directly or indirectly. For example, according to various aspects, the closing force FC can be measured directly by a sensor (e.g., a strain gauge) positioned on the anvil, on the elongated channel, on the closure tube, or indirectly by an impedance of the tissue, a current draw of the motor, and/or any combinations thereof.

The curve 5694 is a graphical representation of the firing force signal at various times during a firing motion. The curve 5694 may be generated mathematically by the controller based on the firing force signal(s) received by the controller. The firing force FF represented on the "right" vertical axis may be a force experienced by the drive system of the surgical instrument 5500 (e.g., by the sled, the knife, and/or the firing bar), and/or any combination thereof. The firing force FF can be measured in any suitable manner, either directly or indirectly. For example, according to various aspects, the firing force FF can be measured directly by a sensor (e.g., a strain gauge) positioned on the sled, on the knife, or indirectly by a current draw of the motor, and/or any combination thereof. Although not shown for purposes of simplicity, the respective zones of the firing cycle (e.g., zones 1-5 as described hereinabove) could also be shown along the horizontal axis.

For the example graph 5690 in FIG. 112, at some time after the closing motion has commenced, the knife is still in the fully-retracted position and the firing force FF is approximately zero. As the knife and sled advance and the velocity of the knife increases, the firing force FF increases and reaches a first peak value 5696 when a first row of staples is driven from the staple cartridge. After the first row of staples is driven as described hereinabove, the firing force FF decreases until a second row of staples is driven, which causes the firing force FF to reach a second peak value 5698.

At a later point in the firing motion, the slope of the firing force signal reaches or exceeds a predetermined threshold (this condition is shown as the slope A of the firing force signal in FIG. 112) and the amplitude of the firing force FF reaches or exceeds a predetermined amplitude threshold (e.g., the amplitude Fcrit shown in FIG. 112). In response, the control algorithm acts to slow down, stop or pause the further advancement of the knife and the firing force FF begins to decrease.

For the example graph 5690, the slowing down, stopping or pausing of the knife continues until the firing force FF reaches a value which is 10% less than the predetermined amplitude threshold (e.g., Fcrit), at which point the further advancement of the knife is commenced. Of course, according to various aspects, the further advancement of the knife can be commenced when the firing force FF reaches a value which is less than or more than the 10% example shown in FIG. 112. The above-described automatic stopping or pausing and automatic restarting may be repeated any number of times. For the example graph 5690, once the further advancement of the knife is commenced, the knife advances towards its fully advanced position and the firing force FF eventually decreases to zero as indicated at the far right side.

FIGS. 113, 114 illustrate various aspects of a direction sensor 5590 of the surgical instrument 5500. According to various aspects, the control circuit of the surgical instrument 5500 may be configured to stop an advancement of the knife when a staple cartridge is not positioned or properly positioned in the elongated channel. For such aspects, the control circuit may include the direction sensor 5590, a main processor and a safety processor, each positioned in the shaft assembly, as described above in connection with FIGS. 16A-17B. The direction sensor 5590 is electrically connected to the main processor and/or the safety processor of the shaft assembly. The main processor and/or the safety processor of the shaft assembly may be electrically connected to the main processor and/or the safety processor of the handle assembly. The direction sensor 5590 is positioned at a location relative to a starting point of the tissue transection, and is configured to sense movement of the firing bar and output a signal (e.g., a voltage) related to the sensed position of the firing bar to the main processor and/or safety processor of the shaft assembly. Based on the sensed movement of the firing bar, the main processor and/or the safety processor of the shaft assembly can determine and track a status of the movement and the direction of the movement of the firing bar as the firing bar moves distally and proximally of the starting point of the tissue transection. The main processor and/or the safety processor of the shaft assembly can signal the motor controller to power, cycle and/or reboot the electric motor to control the movement and the direction of the movement of the firing bar, and thus the movement and the direction of the movement of the knife, all while continuing to determine the relevant position of the firing bar based on the output signal of the direction sensor 5590.

As shown in FIGS. 113, 114, the direction sensor 5590 includes first and second sensors 5592, 5594, first and second transistors 5596, 5598, an operational amplifier 5600 and a resistive element 5602. The first and second sensors 5592, 5594 may be Hall-effect sensors, with each of the first and second Hall-effect sensors being positioned a set distance from the tissue transection or cut line. Collectively, the first and second transistors 5596, 5598, the operational amplifier 5600 and the resistive element 5602 comprise a latching circuit, where the latching circuit outputs only the voltage related to the last Hall-effect sensor that was activated.

FIG. 113 indicates a firing stroke in which the magnet 5604 moves from an initial proximal position to a distal position. In FIG. 113, the magnet 5604 is shown in the final distal position and the output of the operational amplifier 5600 indicates the distal position of the magnet 5604. In operation, as the firing bar moves distally from a proximal starting point of the tissue transection as shown in FIG. 113, a magnet 5604 positioned on the firing bar moves past the first Hall-effect sensor 5594 then past the second Hall-effect sensor 5592. As the magnet 5604 moves past the first Hall-effect sensor 5594, the first Hall-effect sensor 5594 outputs a signal which is indicative of the movement of the firing bar to a gate of the first transistor 5598 to drive the latching circuit to a first stable state Vcc. As the magnet 5604 moves past the second Hall-effect sensor 5592, the second Hall-effect sensor 5592 outputs a signal which is indicative of the movement of the firing bar to a gate of the second transistor 5596 to drive the latching circuit to a second stable state 0.0 V. The latching circuit outputs a signal (e.g., a voltage 0.0 V) indicative of the second stable state to the main processor and/or the safety processor of the shaft assembly indicating that the firing bar is in the distal fired position.

FIG. 114 indicates a retracting stroke in which the magnet 5604 moves from an initial distal position to a final proximal position. In FIG. 114, the magnet 5604 is shown in the final proximal position and the output of the operational amplifier 5600 indicates the proximal position of the magnet 5604. In operation, as the firing bar moves proximally toward the starting point of the tissue transection as shown in FIG. 114, the magnet 5604 positioned on the firing bar moves past the second Hall-effect sensor 5592 then past the first Hall-effect sensor 5594. As the magnet 5604 moves past the second Hall-effect sensor 5592, the second Hall-effect sensor 5592 outputs a signal which is indicative of the movement of the firing bar to the gate of the second transistor 5596 to drive the latching circuit to the second stable state of 0.0 V. As the magnet 5604 moves past the first Hall-effect sensor 5594, the first Hall-effect sensor 5594 outputs a signal which is indicative of the movement of the firing bar to the gate of the first transistor 5598 to drive the latching circuit to the first stable state Vcc. The latching circuit outputs a signal (e.g., a voltage of Vcc) indicative of the first stable state to the main processor and/or the safety processor of the shaft assembly indicating that the firing bar is in the proximal retracted position.

FIG. 115 illustrates a perspective view of a surgical instrument 5700 in accordance with one or more aspects described herein. The surgical instrument 5700 is similar to the surgical instrument 5500 and includes an elongated channel configured to support a staple cartridge, an anvil pivotably connected to the elongated channel, a closure member mechanically coupled to the anvil, a knife mechanically coupled to the staple cartridge, an electric motor mechanically coupled to the closure member and/or the knife, a motor controller electrically coupled to the motor, and a control circuit electrically coupled to the motor controller. The surgical instrument 5700 is also similar to the surgical instrument 5500 in that the surgical instrument 5700 also includes sensors which are collectively configured to sense or measure a closing force, a firing force, a current drawn by the electric motor, an impedance of tissue positioned between the elongated channel and the anvil, a position of the anvil relative to the elongated channel, a position of the knife, or any combination thereof. The surgical instrument 5700 is also similar to the surgical instrument 5500 in that the surgical instrument 5700 also includes algorithms such as closing algorithms, firing algorithms, motor control algorithms, or any combination thereof, which operate to dynamically adjust the operation of the surgical instrument 5700. However, the surgical instrument 5700 is different from the surgical instrument 5500 in that the surgical instrument 5700 further includes one or more additional algorithms (in addition to those described hereinabove) which provide additional control functionality for the surgical instrument 5700, as described hereinbelow.

In certain situations, it may be desirable for the surgical instrument 5700 to ignore the occurrence of one or more of the above-described triggers, thresholds and/or events associated with the firing force. In accordance with one or more aspects, the surgical instrument 5700 includes one or more control algorithms which are configured to ignore certain triggers, thresholds and/or events if the triggers, thresholds and/or events occur before an amplitude of the firing force has reached or exceeded a predetermined threshold, if the triggers, thresholds and/or events occur within certain zones of the firing motion, and combinations thereof. As described hereinabove, the zones of the firing motion are related to the position of the knife. In other words, the control algorithms can vary the firing force triggers, thresholds and/or events (e.g., values of the thresholds) based on the position of the knife within the firing motion.

FIG. 116 illustrates a method 5710 of controlling a firing motion of the surgical instrument 5700 in accordance with one or more aspects. The process starts when a firing motion is initiated 5712. The closing motion may be initiated, for example, by pulling a firing trigger toward a handle. A sensor resident with the surgical instrument 5700 senses/measures 5714 a firing force. The firing force may be, for example, a force experienced by the drive system of the surgical instrument (e.g., by the sled, the knife and/or the firing bar), and/or any combination thereof. The firing force F can be measured in any suitable manner, either directly or indirectly. For example, in accordance with one or more aspects, the firing force F can be measured directly by a sensor (e.g. a strain gauge) positioned on the sled, on the knife, or indirectly by a current draw of the motor.

In response to the firing force, the sensor outputs 5716 a firing force signal, which is indicative of the firing force sensed/measured 5714 by the sensor. Depending on the configuration of the sensor, the firing force signal can be an analog signal or a digital signal. Upon determining 5718 whether the firing force signal is either an analog signal or a digital signal, the process proceeds along the corresponding branch. When the determination 5718 is that the firing force signal is an analog signal, the process proceeds along the analog branch, where the analog signal is received by an A/D converter, converted 5720 to a digital signal representative of the analog signal by the A/D converter and the digital signal is output by the A/D converter. When the determination 5718 is that the firing force signal is a digital signal, the process proceeds along the digital branch because there is no need for an A/D conversion 5720 when the firing force signal is a digital signal.

The firing force signal which is a digital signal representative of the firing force sensed/measured 5714 by the sensor is received by a controller. The controller utilizes the digital signal and determines 5722 whether the firing force sensed/measured 5714 by the sensor reaches or exceeds a predetermined threshold. The controller may make this determination 5722 based on a comparison of a magnitude of the firing force sensed/measured 5714 by the sensor and the predetermined threshold, based on a comparison of an amplitude of the firing force signal output 5716 by the sensor and a predetermined threshold, or any combination thereof.

When the controller determines 5722 that the firing force sensed/measured 5714 by the sensor has not reached or exceeded the predetermined threshold, the firing motion originally initiated 5712 is continued 5724 along with interim processes 5714-5722. When the controller determines 5722 that the firing force sensed/measured 5714 by the sensor has reached or exceeded the predetermined threshold, the controller then determines 5726 whether or not to ignore the fact that the firing force has reached or exceeded the predetermined threshold. This determination 5726 can be based, for example, on whether or not the amplitude of the firing force signal has reached or exceeded a predetermined threshold, based on the position of the sled, the knife and/or the firing bar, or any combinations thereof. For example, as described in more detail hereinbelow, in certain aspects the controller may determine 5726 to ignore the fact that the slope of the firing force signal has reached or exceeded a predetermined slope threshold if the amplitude of the firing force signal has not yet reached or exceeded a predetermined amplitude threshold. In other aspects, the controller may determine 5726 to ignore the fact that the slope of the firing force signal has reached or exceeded a predetermined slope threshold based on the position of the sled, the knife, the firing bar, or any combination thereof when the knife is in a certain zone (e.g., Zone 1 or Zone 5) of the firing motion. For instances when the controller determines 5726 to ignore the fact that a parameter of the firing force signal has reached or exceeded a predetermined threshold, the firing motion originally initiated 5712 is continued 5724 along with interim processes 5714-5722.

In other aspects, the controller may determine 5726 not to ignore the fact that a parameter of the firing force signal has reached or exceeded a predetermined threshold. The determination 5726 not to ignore the fact that a parameter of the firing force signal has reached or exceeded the predetermined threshold can be based, for example, on whether or not the amplitude of the firing force signal has reached or exceeded a predetermined threshold, based on the position of the sled, the knife and/or the firing bar, or any combinations thereof. For instances when the controller determines 5726 not to ignore the fact that a parameter of the firing force signal has reached or exceeded the predetermined threshold the controller changes 5730 the firing motion. According to some aspects, the controller may change the firing motion by modifying or adjusting a firing algorithm being executed by the controller to cause the firing motion to be slowed down, paused or stopped to prevent the surgical instrument 5700 from experiencing excessive forces. According to other aspects, the controller may change the firing motion by executing a different firing algorithm which causes the firing motion to be slowed down, paused or stopped to prevent the surgical instrument 5700 from experiencing excessive forces. In either case, the firing motion may be slowed down, stopped or paused by having the controller communicate a slow down signal, a stop signal or a pause signal to the motor controller to slow down, stop or pause the rotation of the motor(s) which drive the sled, knife, firing bar or any combination thereof of the surgical instrument 5700.

Upon changing the firing motion 5728, when the change of the firing motion 5728 is a slowing down of the firing motion (a slowing down of the rotation of the motor(s) which drive the sled, knife and/or firing bar), the process continues 5730 the closing motion originally initiated 5712 but at a reduced speed and the interim process 5714-5726 is continued but the firing of the sled, knife and/or firing bar occurs at a reduced speed. When the change of the firing motion 5728 is a stopping or pausing of the firing motion (a stopping or pausing of the rotation of the motor(s) which drive the sled, knife and/or firing bar), the process suspends or terminates 5732 the firing motion.

In accordance with one or more aspects, the operation of the surgical instrument 5700 may be controlled by monitoring parameters of the firing force signal (e.g., the amplitude, the slope, etc.) and in cases where a predetermined threshold is reached or exceeded, deciding whether change the firing motion based on the monitored parameters or to ignore the reaching or exceeding of the predetermined threshold. For example, in accordance with one or more aspects, if the change of the firing force F over time t (e.g., the slope of the firing force signal) reaches or exceeds a predetermined threshold before the firing force F reaches or exceeds a first firing force threshold, the control algorithm may ignore the fact that the slope of the firing force signal reached or exceeded the predetermined threshold and allow the operation of the surgical instrument 5700 to proceed as if the slope of the firing force signal had never reached or exceed the predetermined threshold.

FIG. 117 illustrates an example graph 5740 showing a curve 5742 representative of a firing force F over time t for various aspects of the surgical instrument 5700. The firing force F is shown along the vertical axis and the time t is shown along the horizontal axis. Stated differently, the curve 5742 is a graphical representation of the firing force signal at various times during a firing motion. The curve 5742 may be generated mathematically by the controller based on the firing force signal(s) received by the controller. The firing force F shown in the example graph 5740 may be representative of a condition where the thickness and composition of the tissue along the cut line is uniform. The firing force F represented on the vertical axis may be a force experienced by the drive system of the surgical instrument 1000 (e.g., by the sled, the knife, and/or the firing bar), and/or any combination thereof. The firing force F can be measured in any suitable manner, either directly or indirectly. For example, in accordance with one or more aspects, the firing force F can be measured directly by a sensor (e.g., a strain gauge) positioned on the sled, on the knife, or indirectly by a current draw of the motor, and/or any combination thereof.

For the example graph 5740 shown in FIG. 117, at time t=0, the knife is in a fully retracted position near the proximal end of the end effector and over time advances to a fully advanced position near the distal end of the end effector. As described hereinabove, the overall distance the knife moves from the fully retracted position to the fully advanced position during a firing motion can be divided into predefined zones, with each zone being representative of a different operating condition of the surgical instrument 5700. Although not shown in FIG. 117 for purposes of simplicity, the respective zones of the firing motion (e.g., zones 1-5 as described hereinabove) could also be shown along the horizontal axis of FIG. 117.

Shortly after the knife moves from its fully retracted position towards its fully advanced position, the change of the firing force F over time t reaches or exceeds a predetermined slope threshold (this condition is shown as the slope A of the firing force signal in FIG. 117). As the slope A occurs in this example prior to the firing force F reaching or exceeding a first firing force threshold (shown as F1 in FIG. 117), the control algorithm may ignore the fact that the slope A reached or exceeded the predetermined threshold and allow the operation of the surgical instrument 5700 to proceed as if the slope A had never reached or exceed the predetermined threshold. Similarly, the control algorithm could also ignore the Slope A trigger, threshold or event based on the position of the knife (e.g., if the knife was in zone 2 of the firing motion when the predetermined slope threshold was reached or exceeded).

Due to the slope A trigger, threshold and/or event effectively being ignored, the knife continues to advance toward the fully advanced position and the firing force F continues to rise over time t. As shown in FIG. 117, the slope of the firing force signal again reaches or exceeds the predetermined slope threshold (this instance is shown as the slope A1 of the firing force signal in FIG. 117). In accordance with one or more aspects, the reaching or exceeding of the predetermined slope threshold alone is sufficient for the control algorithm to change the firing motion to slow down, stop or pause the further advancement of the knife. According to other aspects, the reaching or exceeding of the predetermined amplitude threshold (e.g., the amplitude Fcrit shown in FIG. 117) alone is sufficient for the control algorithm to change the firing motion to slow down, stop or pause the further advancement of the knife. According to yet other aspects, the combination of the reaching or exceeding of the predetermined slope threshold and the reaching or exceeding of the predetermined amplitude threshold causes the control algorithm to change the firing motion to slow down, stop or pause the further advancement of the knife. As shown in FIG. 117, when the slope A1 of the firing force signal reaches or exceeds the predetermined slope threshold and the amplitude of the firing force signal reaches or exceeds the predetermined amplitude threshold (e.g., Fcrit), the control algorithm changes the firing motion to slow down, stop or pause the further advancement of the knife and the firing force F begins to decrease.

The slowing down, stopping or pausing of the knife continues until the firing force F reaches a value which is 10% less than the predetermined amplitude threshold (e.g., Fcrit), at which point the further advancement of the knife is commenced. Of course, in accordance with one or more aspects, the further advancement of the knife can be commenced when the firing force reaches a value which is less than or more than the 10% example shown in FIG. 117. For the example graph 5742, once the further advancement of the knife is commenced, the knife advances to its fully advanced position and the firing force decreases to zero as indicated at the far right side of FIG. 117.

According to other aspects, the decision to change the firing motion or to ignore the reaching or exceeding of the predetermined threshold may be further based on the position of the sled, knife, firing bar or combinations thereof. For example, in accordance with one or more aspects, if the change of the firing force over time t reaches or exceeds a predetermined threshold while the knife is within a certain zone of the firing motion (e.g., zone 2 or zone 4), the control algorithm may ignore the fact that the slope of the firing force signal reached or exceeded the predetermined threshold and allow the operation of the surgical instrument 5700 to proceed as if the slope of the firing force signal had never reached or exceed the predetermined threshold.

FIG. 118 illustrates an example graph 5750 showing a curve 5752 representative of a firing force F over time t for various aspects of the surgical instrument 5700. The curve 5752 may be generated mathematically by the controller based on the firing force signal(s) received by the controller. The firing force F shown in the example graph 5750 may be representative of a condition where the thickness and composition of the tissue along the cut line is uniform. The firing force F represented on the vertical axis may be a force experienced by the drive system of the surgical instrument 5700 (e.g., by the sled, the knife, and/or the firing bar), and/or any combination thereof. Although not shown for purposes of simplicity, the respective zones of the firing cycle (e.g., zones 1-5 as described hereinabove) could also be shown along the horizontal axis.

The firing force F can be measured in any suitable manner, either directly or indirectly. For example, in accordance with one or more aspects, the firing force F can be measured directly by a sensor (e.g., a strain gauge) positioned on the sled, on the knife, or indirectly by a current draw of the motor, and/or any combination thereof.

For the example graph 5750 in FIG. 118, at time t=0 the knife is in the fully-retracted position and the firing force F is zero. As the knife and sled advance and the velocity of the knife increases, the firing force F increases and reaches a first peak value 5754 when a first row of staples is driven from the staple cartridge. After the first row of staples is driven as described hereinabove, the firing force F decreases until a second row of staples is driven, which causes the firing force F to reach a second peak value 5756.

At a later point in the firing motion, the slope of the firing force signal reaches or exceeds a predetermined threshold (this condition is shown as the slope A1 of the firing force signal in FIG. 118) and the amplitude of the firing force F reaches or exceeds a predetermined amplitude threshold (e.g., the amplitude Fcrit shown in FIG. 118). In response, the control algorithm acts to slow down, stop or pause the further advancement of the knife and the firing force F begins to decrease.

For the example graph 5752, the slowing down, stopping or pausing of the knife continues until the firing force F reaches a value which is 10% less than the predetermined amplitude threshold (e.g., Fcrit), at which point the further advancement of the knife is commenced. Of course, in accordance with one or more aspects, the further advancement of the knife can be commenced when the firing force reaches a value which is less than or more than the 10% example shown in FIG. 118. The above-described automatic stopping or pausing and automatic restarting may be repeated any number of times.

For the example graph 5752, once the further advancement of the knife is commenced, as the knife advances towards its fully advanced position the slope of the firing force signal once again reaches or exceeds the predetermined slope threshold (this condition is shown as the slope A2 of the firing force signal in FIG. 118). However, because the predetermined slope threshold was reached or exceeded while the knife was in zone 4 of the firing motion, the control algorithm ignores this "slope" trigger and continues advancing the knife to its fully advanced position, resulting in the firing force decreasing to zero as indicated at the far right side of FIG. 118.

In addition to ignoring triggers, thresholds and/or events based on where the triggers, thresholds and/or events occur within the firing motion, the control algorithms may also vary or modify the triggers, thresholds and/or events based on where the triggers, thresholds and/or events occur within the firing motion. For example, in accordance with one or more aspects, the control algorithms may set the value for a predetermined slope threshold at a first value for zone 1 of the firing motion, at a second value for zone 2 of the firing motion, at a third value for zone 3 of the firing motion, etc.

FIG. 119 illustrates an example graph 5770 showing a curve representative of a closing force FC over time t for various aspects of the surgical instrument and a curve representative of a firing force FF over time t for the surgical instrument 5700 of FIG. 115. FIG. 119 illustrates an example graph 5770 showing a curve 5772 representative of a closing force FC over time t for various aspects of the surgical instrument 5700 and a curve 5774 representative of a firing force FF over time t for various aspects of the surgical instrument 5700. The closing force FC is shown along the "left" vertical axis, the firing force FF is shown along the "right" vertical axis and the time t is shown along the horizontal axis. When viewed together the curves 5772, 5774 reflect the timing of the closing motion and the firing motion relative to one another, where the closing motion is initiated prior to the initiation of the firing motion. Although the example graph 5770 shows a threshold force Fcrit as being the same amplitude for both the closing force FC and the firing force FF, it will be appreciated that the amplitude of the threshold force Fcrit for the closing force FC may be different from the amplitude of the threshold force Fcrit for the firing force FF. Stated differently, the scale of the "left" vertical axis can be different from the scale of the "right" vertical axis.

The curve 5772 is a graphical representation of the closing force signal at various times during a closing motion. Thus, as set forth hereinabove, the curve 5772 may be generated mathematically by the controller based on the closing force signal(s) received by the controller. The closing force FC represented on the "left" vertical axis may be a force experienced by tissue clamped between the jaws of the surgical instrument 5700, a force experienced by the jaws of the surgical instrument 5700 (e.g., by the anvil and/or the elongated channel), a force experienced by the closure tube of the surgical instrument 5700, and/or any combinations thereof. The closing force FC can be measured in any suitable manner, either directly or indirectly. For example, according to various aspects, the closing force FC can be measured directly by a sensor (e.g., a strain gauge) positioned on the anvil, on the elongated channel, on the closure tube, or indirectly by an impedance of the tissue, a current draw of the motor, and/or any combinations thereof.

The curve 5774 is a graphical representation of the firing force signal at various times during a firing motion and may be similar or identical to the curve 5752 of FIG. 109. Thus, as set forth hereinabove, the curve 5774 may be generated mathematically by the controller based on the firing force signal(s) received by the controller. The firing force FF represented on the "right" vertical axis may be a force experienced by the drive system of the surgical instrument 5700 (e.g., by the sled, the knife, and/or the firing bar), and/or any combination thereof. The firing force FF can be measured in any suitable manner, either directly or indirectly. For example, according to various aspects, the firing force FF can be measured directly by a sensor (e.g., a strain gauge) positioned on the sled, on the knife, or indirectly by a current draw of the motor, and/or any combination thereof. Although not shown for purposes of simplicity, the respective zones of the firing cycle (e.g., zones 1-5 as described hereinabove) could also be shown along the horizontal axis.

For the example graph 5770 in FIG. 110, at some time after the closing motion has commenced, the knife is still in the fully-retracted position and the firing force FF is approximately zero. As the knife and sled advance and the velocity of the knife increases, the firing force FF increases and reaches a first peak value 5776 when a first row of staples is driven from the staple cartridge. After the first row of staples is driven as described hereinabove, the firing force FF decreases until a second row of staples is driven, which causes the firing force FF to reach a second peak value 5778.

At a later point in the firing motion, the slope of the firing force signal reaches or exceeds a predetermined threshold (this condition is shown as the slope A of the firing force signal in FIG. 117) and the amplitude of the firing force FF reaches or exceeds a predetermined amplitude threshold (e.g., the amplitude Fcrit shown in FIG. 117). In response, the control algorithm acts to slow down, stop or pause the further advancement of the knife and the firing force FF begins to decrease.

For the example graph 5770, the slowing down, stopping or pausing of the knife continues until the firing force FF reaches a value which is 10% less than the predetermined amplitude threshold (e.g., Fcrit), at which point the further advancement of the knife is commenced. Of course, according to various aspects, the further advancement of the knife can be commenced when the firing force FF reaches a value which is less than or more than the 10% example shown in FIG. 117. The above-described automatic stopping or pausing and automatic restarting may be repeated any number of times.

For the example graph 5770, once the further advancement of the knife is commenced, as the knife advances towards its fully advanced position the slope of the firing force signal once again reaches or exceeds the predetermined slope threshold (this condition is shown as the slope B of the firing force signal in FIG. 117). However, because the predetermined slope threshold was reached or exceeded while the knife was in zone 4 (not shown) of the firing motion, the control algorithm ignores this "slope" trigger and continues advancing the knife to its fully advanced position, resulting in the firing force decreasing to zero as indicated at the far right side of FIG. 117.

FIG. 120 illustrates an example graph 5760 showing a first curve 5762 representative of a firing force F over time t for various aspects of the surgical instrument 5700, a knife position X over time t for various aspects of the surgical instrument 5700 and a second curve 5764 representative of knife velocity V over time t for various aspects of the surgical instrument 5700. The firing force F is shown along the top vertical axis, the knife velocity V is shown along the bottom vertical axis, the knife position X is shown along the top horizontal axis and the time t are shown along both the top and bottom the horizontal axes. As shown along the top horizontal axis, the knife position X travels over five Zones 1-5 along the knife channel in the cartridge 304 located in the lower jaw 302 of the end effector 300 of the surgical instrument 5700. The knife velocity V and the firing force F shown in FIG. 120 may be based on the assumption that the thickness and composition of the tissue along the cut line is uniform.

Accordingly, the curve 5762 is a representation of the firing force signal at various times during a firing motion and the curve 5764 is a representation of the knife velocity signal at various times during a firing motion. The curves 5762, 5764 may be generated mathematically by the controller based on the firing force signal(s) and the knife velocity signal(s) received by the controller. The firing force F represented on the top vertical axis may be a force experienced by the drive system of the surgical instrument 5500 (e.g., by the sled, the knife and/or the firing bar), and/or any combination thereof. The firing force F can be measured in any suitable manner, either directly or indirectly. For example, in accordance with one or more aspects, the firing force F can be measured directly by a sensor (e.g., a strain gauge) positioned on the sled, on the knife, or indirectly by a current draw of the motor, and/or any combination thereof.

The knife velocity V represented on the bottom vertical axis may be a velocity of the knife, a velocity of the sled, a velocity of another component of the drive system (e.g., the firing bar), and/or any combination thereof. The knife velocity V can be measured in any suitable manner, either directly or indirectly. For example, in accordance with one or more aspects, the knife velocity V can be measured directly by a combination of a magnet positioned on the firing bar and a Hall-effect sensor or indirectly by a current draw of the motor, an encoder coupled to the shaft of the motor, and/or any combination thereof.

For the example graph 5764, the knife velocity V is shown as increasing from zero to a substantially maximum velocity while the knife advances from its fully retracted position through zone 1 and into zone 2 of the firing motion. Even if the change of the firing force F over time (e.g., the slope $\Delta F/\Delta t$ shown occurring in zone 1 and/or zone 2) reaches or exceeds a predetermined threshold, the control algorithm may ignore this trigger, threshold and/or event and allow the knife to continue advancing as shown by the knife velocity V in FIG. 120. Once the substantially maximum velocity is reached in zone 2, the knife continues to advance in zone 2 and zone 3 until another trigger, threshold and/or event prompts the control algorithm to automatically stop the advancement of the knife. For the example graph 5762, this occurs in zone 3 when the firing force F exceeds the predetermined threshold Fcrit. According to other aspects, the trigger, threshold and/or event could be a change of firing force F over time t reaching or exceeding a certain value, a combination of the change of firing force F over time t reaching or exceeding a certain value and the firing force F reaching or exceeding a certain value, a change of a peak-to-peak firing force over time t reaching or exceeding a certain value, a combination of a change of a peak-to-peak firing force over time t reaching or exceeding a certain value and the firing force F reaching or exceeding a certain value, etc.

Once the firing force F reaches or exceeds the predetermined threshold Fcrit and the knife is in a position associated with zone 3 of the firing motion, the control algorithm automatically stops or pauses the further advancement of the knife and the knife velocity V falls from a substantially constant velocity to zero at time t1. In other words, instead of ignoring the trigger, the control algorithm acts on the trigger and changes the firing motion. After a predefined period of time (e.g., the time period t2–t1) as shown in FIG. 120 or a predefined drop in the amplitude of the firing force F, the control algorithm automatically restarts the advancement of the knife and the knife velocity V increases from zero at time t2 to a substantially maximum velocity, then continues in zone 3 and zone 4 at a substantially constant velocity. At some point in zone 4, the knife velocity drops from a substantially constant velocity to zero and the firing force also drops to zero.

Although FIG. 120 depicts the control algorithm as not acting on a firing force trigger, threshold and/or event which occurs in zone 2 of the firing motion and acting on a firing force trigger, threshold and/or event which occurs in zone 3 of the firing motion, it will be appreciated that the control algorithm can be configured to act or not act on firing force triggers, thresholds and/or events which occur in other zones of the firing motion. For example, as described hereinabove with respect to FIG. 118, the control algorithm can be configured to not act (ignore) a firing force trigger, threshold and/or event which occurs in zone 4 of the firing motion.

Furthermore, although the functionality of the control algorithms described in connection with FIGS. 115-120 were described in the context of ignoring or varying triggers, thresholds and/or events during the firing motion, it will be appreciated that the control algorithms of the surgical instrument 5700 may also be configured to ignore or vary triggers, thresholds and/or events during the closing cycle (i.e., the closing of the jaws).

FIG. 121 illustrates a perspective view of a surgical instrument 5800 according to various aspects described herein. The surgical instrument 5800 is similar to the surgical instrument 5500 and includes an elongated channel configured to support a staple cartridge, an anvil pivotably connected to the elongated channel, a closure member mechanically coupled to the anvil, a knife mechanically coupled to the staple cartridge, an electric motor mechanically coupled to the closure member and/or the knife, a motor controller electrically coupled to the motor, and a control circuit electrically coupled to the motor controller. The surgical instrument 5800 is also similar to the surgical instrument 5500 in that the surgical instrument 5800 also includes sensors which are collectively configured to sense or measure a closing force, a firing force, a current drawn by the electric motor, an impedance of tissue positioned between the elongated channel and the anvil, a position of the anvil relative to the elongated channel, a position of the knife, or any combination thereof. The surgical instrument 5500 is also similar to the surgical instrument 5800 in that the surgical instrument 5800 also includes algorithms such as closing algorithms, firing algorithms, motor control algorithms, or any combination thereof, which operate to dynamically adjust the operation of the surgical instrument 5800. However, the surgical instrument 5800 is different from the surgical instrument 5500 in that the surgical instrument 5800 further includes one or more additional algorithms (in addition to those described hereinabove) which provide additional control functionality for the surgical instrument 5800, as described herein below.

In certain aspects, for different circumstances, the control algorithms are configured to automatically invoke different adjustments to the closing motion and/or the firing motion. For example, in certain aspects, a control algorithm is configured to adjust the firing motion based on how fast the load is increasing or decreasing as it approaches a predefined staged threshold. For such aspects, a first adjustment to the firing motion may be invoked when the load is increasing at a first rate as it approaches a predefined threshold, and a second adjustment to the firing motion may be invoked when the load is increasing at a second rate as it approaches a predefined threshold. In other aspects, the control algorithms are configured to adjust the closure algorithm and/or the firing algorithm based on how fast aspects of the closing force, the closure tube velocity, the firing force, the knife velocity, the motor current and combinations thereof are increasing or decreasing as they approaches respective predefined staged thresholds.

FIG. 122 illustrates a method 5810 of controlling a firing motion of the surgical instrument 5800 according to various aspects. The process starts when a firing motion is initiated 5812. The firing motion may be initiated, for example, by pulling a firing trigger toward a handle. A sensor resident with the surgical instrument 5800 senses/measures 5814 a firing force. The firing force may be, for example, a force experienced by the drive system of the surgical instrument (e.g., by the sled, the knife and/or the firing bar), and/or any combination thereof. The firing force F can be measured in any suitable manner, either directly or indirectly. For example, according to various aspects, the firing force F can be measured directly by a sensor (e.g. a strain gauge) positioned on the sled, on the knife, or indirectly by a current draw of the motor.

In response to the firing force, the sensor outputs 5816 a firing force signal, which is indicative of the firing force sensed/measured 5814 by the sensor. Depending on the configuration of the sensor, the firing force signal can be an analog signal or a digital signal. Upon determining 5818 whether the firing force signal is either an analog signal or a digital signal, the process proceeds along the corresponding branch. When the determination 5818 is that the firing force signal is an analog signal, the process proceeds along the analog branch, where the analog signal is received by an A/D converter, converted 5820 to a digital signal representative of the analog signal by the A/D converter and the digital signal is output by the A/D converter. When the determination 5818 is that the firing force signal is a digital signal, the process proceeds along the digital branch because there is no need for an A/D conversion 5820 when the firing force signal is a digital signal.

The firing force signal which is a digital signal representative of the firing force sensed/measured 5814 by the sensor is received by a controller. The controller utilizes the digital signal and determines 5822 a projected peak firing force. According to various aspects, the projected peak firing force is determined by constructing a straight line which passes through the two most recent peak values of the firing force signal, projecting when the next peak firing force will occur and determining the value of the firing force on the straight line at that time. The straight line is representative of a change of peak firing force values over time and may thus be considered a slope of the peak firing force values. The controller may project when the next peak firing force will occur in any suitable manner. For example, according to various aspects, the controller may utilize the time lapse between the last two peak firing forces, the average of the time lapses between each of the peak firing forces which have occurred in a given firing motion, the pattern or trend of the time lapses between each of the peak firing forces which have occurred in a given firing motion and combinations thereof.

After the controller determines 5822 that the projected peak firing force, the controller then determines 5824 whether or not the firing motion should be changed. The determination 5824 may be based, for example, on how fast or slow the projected peak firing force is approaching a predetermined threshold, on the amplitude of the firing force and how fast or slow the projected peak firing force is approaching a predetermined threshold, and combinations thereof. In other words, the determination 5824 may be based on the amplitude of the firing force and the value of the slope of the peak firing force values as the slope is approaching a predetermined threshold. The predetermined threshold may be any suitable threshold such as, for example, a predetermined firing force threshold. When the controller determines 5824 that the firing motion should not be changed, the firing motion originally initiated 5812 is continued 5826 along with interim processes 5814-5824. When the controller determines 5824 that the motion should be changed, the firing motion may be changed in a multitude of different ways, with the particular way determined based on how fast or slow the projected peak firing force is approaching a predetermined threshold.

According to various aspects, when the projected peak firing force is approaching a predetermined threshold at a first rate, the controller may stop or pause 5828 the firing motion by communicating a stop signal or a pause signal to the motor controller to stop or pause the rotation of the motor(s) which drive the sled, knife, firing bar or any combination thereof of the surgical instrument 5800. After the firing motion is stopped or paused, the firing motion may be subsequently terminated 5830 or the controller may restart 5832 the firing motion by communicating a restart signal to the motor controller to restart the rotation of the motor(s) which drive the sled, knife, firing bar or any combination thereof of the surgical instrument 5800. The firing motion may be restarted 5832 based on, for example, a period of time, a predetermined drop in the firing force and combinations thereof. After the firing motion is restarted 5832, interim processes 5814-5824 of the firing motion originally initiated 5812 are continued.

According to various aspects, when the projected peak firing force is approaching a predetermined threshold at a second rate, the controller may change the firing motion to decrease the knife velocity 5834 by communicating a slow down signal to the motor controller to slow down the rotation of the motor(s) which drive the sled, knife, firing bar or any combination thereof of the surgical instrument 5800. Similarly, according to various aspects, when the projected peak firing force is approaching a predetermined threshold at a third rate, the controller may change the firing motion to increase the knife velocity 5836 by communicating a speed up signal to the motor controller to speed up the rotation of the motor(s) which drive the sled, knife, firing bar or any combination thereof of the surgical instrument 5800.

According to various aspects, when the projected peak firing force is approaching a predetermined threshold at a fourth rate, the controller may change the firing motion to oscillate the knife 5838 by communicating an oscillation signal to the motor controller to alternate the rotation of the motor(s) which drive the sled, knife, firing bar or any combination thereof of the surgical instrument 5800 in a clockwise direction and a counterclockwise direction, thereby producing a back and forth motion of the sled, knife, firing bar or any combination thereof.

FIG. 123 illustrates an example graph 5850 showing a first curve 5852 representative of a firing force F over time t for various aspects of the surgical instrument 5800, a knife position X over time t for various aspects of the surgical instrument 5800 and a second curve 5854 representative of knife velocity V over time t for various aspects of the surgical instrument 5800. The firing force F is shown along the top vertical axis, the knife velocity V is shown along the bottom vertical axis, the knife position X is shown along both the top and bottom horizontal axes and the time t is shown along both the top and bottom the horizontal axes. As shown along the top an bottom horizontal axes, the knife position X travels over five zones (zones 1-5) along the knife channel in the cartridge 304 located in the lower jaw 302 of the end effector 300 of the surgical instrument 5800. The knife velocity V and the firing force F shown in FIG. 123 may be based on the assumption that the thickness and composition of the tissue 5856 along the cut line is non-uniform as shown on the far right side of FIG. 123.

Accordingly, the curve 5852 is a representation of the firing force signal at various times during a firing motion and the curve 5854 is a representation of the knife velocity signal at various times during a firing motion. The curves 5852, 5854 may be generated mathematically by the controller based on the firing force signal(s) and the knife velocity signal(s) received by the controller. The firing force F represented on the top vertical axis may be a force experienced by the drive system of the surgical instrument 5800 (e.g., by the sled, the knife and/or the firing bar), and/or any combination thereof. The firing force F can be measured in any suitable manner, either directly or indirectly. For example, according to various aspects, the firing force F can be measured directly by a sensor (e.g., a strain gauge) positioned on the sled, on the knife, or indirectly by a current draw of the motor, and/or any combination thereof.

The knife velocity V represented on the bottom vertical axis may be a velocity of the knife, a velocity of the sled, a velocity of another component of the drive system (e.g., the firing bar), and/or any combination thereof. The knife velocity V can be measured in any suitable manner, either directly or indirectly. For example, according to various aspects, the knife velocity V can be measured directly by a combination of a magnet positioned on the firing bar and a Hall-effect sensor or indirectly by a current draw of the motor, an encoder coupled to the shaft of the motor, and/or any combination thereof.

For the example graph 5840, the curve 5854 shows the knife velocity V increasing from zero at time t=0 to a substantially maximum velocity V1 while the knife advances from its fully retracted position through zone 1 and into zone 2 of the firing motion. Once the substantially maximum velocity V1 is reached in zone 2, the knife continues to advance in zone 2 and zone 3 until a trigger, threshold and/or event prompts the control algorithm to automatically change the firing motion, in this case decreasing the knife velocity V. Such a trigger, threshold or event is shown in the curve 5852, where the projected peak firing force on the slope (ΔF1/Δt1) reaches or exceeds a predetermined threshold (e.g., the firing force value Fcrit) at the time t1. As shown in FIG. 123, the time t1 may correspond to the knife cutting through a portion of tissue 5856 which is less than a full thickness of the tissue 5856.

Once the projected peak firing force on the slope (ΔF1/Δt1) reaches or exceeds the predetermined threshold Fcrit and the knife is in a position associated with zone 3 of the firing motion at time t1, the control algorithm changes the firing motion to decrease the knife velocity from the substantially maximum velocity V1 to the reduced velocity V2. Although the velocity V2 is shown as being approximately ⅔ of the velocity V1, it will be appreciated that the decrease in the knife velocity V can be more or less than ⅓ of the maximum velocity V1. According to various aspects, the amount of the decrease is based on the value of the slope (ΔF1/Δt1), essentially how quickly the peak firing forces are approaching the predetermined threshold. The knife then advances at the reduced velocity V2 in zone 3 until another trigger, threshold and/or event prompts the control algorithm to automatically change the firing motion, in this case further decreasing the knife velocity V. Such a trigger, threshold or event is shown in the curve 5852, where the projected peak firing force on the slope (ΔF2/Δt2) reaches or exceeds a predetermined threshold (e.g., the firing force value Fcrit) at the time t2. As shown in FIG. 123, the time t2 may correspond to the knife cutting through a portion of tissue 5856 which is the full thickness of the tissue 5856.

Once the projected peak firing force on the slope (ΔF2/Δt2) reaches or exceeds the predetermined threshold Fcrit and the knife is in a position associated with zone 3 of the firing motion at time t2, the control algorithm again changes the firing motion to further decrease the knife velocity from the reduced V2 to the further reduced velocity V3. Although the velocity V3 is shown as being approximately ⅓ of the velocity V1 and ½ of the velocity V2, it will be appreciated that the further decrease in the knife velocity V can be more or less than ⅓ of the maximum velocity V1 or more or less than ½ of the previous velocity V2. According to various aspects, the amount of the decrease is based on the value of the slope (ΔF2/Δt2), essentially how quickly the peak firing forces are approaching the predetermined threshold.

After the time t2, the knife continues advancing through zones 3 and 4 of the firing motion at the velocity V2, then begins dropping in zone 4 and reaches zero in zone 5 of the firing motion. As shown in the curve 5852, the firing force F also drops to zero in zone 5. Due to the differences in the knife velocity V brought about by the controller, it will be appreciated that the time period Δt1, the time between successive valley firing force values when the knife is in zone 2 of the firing motion and advancing at the velocity V1, is less than the time period Δt2, the time between successive valley firing force values when the knife is in zone 3 of the firing motion and advancing at the velocity V2, which is less than the time period Δt3, the time between successive valley firing force values when the knife is in zone 3 of the firing motion and advancing at the velocity V3.

Although FIG. 123 depicts the control algorithm as acting to reduce the knife velocity V based on triggers, thresholds and/or events which occur in zones 2 and/or 3 of the firing motion, it will be appreciated that the control algorithm can be configured to act to increase the knife velocity, oscillate the knife and combinations thereof in zones 2 and 3 of the firing motion and/or in other zones of the firing motion. For example, when the peak firing forces are rapidly approaching a predetermined threshold (i.e., the slope is steep), the firing algorithm may interpret this as an obstruction to the knife and change the firing motion to stop the advancement of the knife then create an oscillating motion. The stop, backup, re-advance, stop, backup, re-advance pattern assists the knife in moving through the obstruction.

Furthermore, although the functionality of the control algorithms described in connection with FIG. 123 were described in the context of adjusting the knife velocity V, it will be appreciated that the control algorithms of the surgical instrument 5800 may also be configured to adjust the closure tube velocity during the closing motion (i.e., the closing of the jaws). Similarly, the control algorithms may operate to change the closing motion such that the anvil vibrates/ oscillates toward a fully closed position to improve compression of the tissue 5856.

FIG. 124 illustrates the rate of closure of the jaws (jaws closure speed) for the surgical instrument of FIG. 121 in accordance with one or more aspects of the present disclosure. In other words, the rate of closure of the anvil 306 closing onto the staple cartridge 304 with tissue located therebetween. The top graph 5860 represents the jaws closing at a constant speed where the jaw closing force (F) is represented along the vertical axis as the knife advances over a longitudinal distance (X) in the cartridge 304, as represented along the horizontal axis, until the stop trigger is actuated by the control program at X1. The stop trigger stops the jaws from closing for a period of time prior to initiating the firing stroke. As previously described herein, this enables the jaws to squeeze excess moisture from the tissue prior to initiating the firing stroke after a brief delay period of 5 to 20 seconds and preferably about 15 seconds. At X1, the jaws closing force reaches a peak amplitude and the gap between the jaws is set to a predetermined distance. Still with reference to the top graph 5860, the first curve 5862 represents the force over distance as the jaws close at a first constant speed until the stop trigger stops the jaws from closing at X1. At this point, the force F reaches a peak force of F1 and the gap between the jaws is set to a first distance. The second curve 5864 represents the force over distance as the jaws close at a second speed, which is less than the first speed, until the stop trigger stops the jaws from closing at X1. The first jaw closing speed is adjusted to the second closing speed by the control circuit when the control circuit predicts that the closing force will be too high. At X1, the force F reaches a peak force of F2, which is less than F1, and the gap between the jaws is set to a second distance which is less than the first distance.

With reference still to FIG. 124, the bottom graph 5866 represents the jaws closing force (F) along the vertical axis and time (t) along the horizontal axis. The first curve 5867 represents the jaws closing force over time as the jaws close at a constant speed. As shown by the first curve 5867, when the jaws closing speed is constant, the jaws can experience a force that reaches a maximum F1 that is too high and reaches this peak force F1 before the stop trigger is activated. Accordingly, when the control circuit predicts that the jaws closing force will be high, the control circuit slows down the jaws closure speed after a period of t1. At the lower jaw closing speed the second curve 5869 can lead to a lower force (and a lower gap) and ultimately a lower peak force F2 (and gap) after a period t2 prior to initiating a firing stroke. As shown, the stop trigger actually changes speed the keep the jaws closing force F below the slope threshold 5868.

In various aspects, the control algorithms operate to effectively take control of the surgical instrument during the closing and/or firing motions. In certain aspects, a control algorithm automatically operates the surgical instrument in a cutting mode which optimizes staple form. For example, an exemplary control algorithm advances the knife in three incremental stages to optimize staple form. In the first stage, the knife is advanced distally a small increment (e.g., 3 mm) and is then stopped. Pressure applied to the tissue near the knife operates to force fluid out of the tissue. The knife remains stopped until a predetermined time passes, a sensor (pressure, distance, etc.) in the distal shaft indicates an asymptote, and combinations thereof. In the second stage, the knife is retracted proximally a smaller distance (e.g., 1 mm) from the first stage stopping point and is then stopped. The distance between the first stage stopping point and the second stage stopping point allows for the knife acceleration which occurs in the third stage. In the third stage, the knife is driven distally at a rapid speed until sufficient knife advancement is made to drive/form one staple (or one row of staples). The high speed move forms the staple quickly, reducing the chances of staple buckling and improving form quality. High speed forming is a technique used in nail guns, particularly in finishing nails that are extremely prone to buckling. The three stages are repeated for each row of staples for the length of the cut, effectively ratcheting through the tissue.

According to certain aspects, the surgical instrument includes a button which can be utilized by an operator to selectively enable or disable the above-described cutting mode. The button may be positioned on the shaft. Although the cutting mode was described as a cutting mode which optimizes staple form, it will be appreciated that according to other aspects the control algorithm may operate the surgical instrument in a cutting mode which is different than that described hereinabove.

While various details have been set forth in the foregoing description, it will be appreciated that the various aspects of the motorized surgical instruments may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a “step” refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

In a general sense, those skilled in the art will recognize that the various aspects described herein which can be implemented, individually and/or collectively, by a wide range of hardware, software, firmware, or any combination thereof can be viewed as being composed of various types of “electrical circuitry.” Consequently, as used herein “electrical circuitry” includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a processor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various aspects of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), or other integrated formats. Those skilled in the art will recognize, however, that some aspects of the aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

In addition, those skilled in the art will appreciate that the mechanisms of the subject matter described herein are capable of being distributed as a program product in a variety of forms, and that an illustrative aspect of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.).

In summary, numerous benefits have been described which result from employing the concepts described herein. The foregoing description of the one or more aspects has been presented for purposes of illustration and description. It is not intended to be exhaustive or limiting to the precise form disclosed. Modifications or variations are possible in light of the above teachings. The one or more aspects were chosen and described in order to illustrate principles and practical application to thereby enable one of ordinary skill in the art to utilize the various aspects and with various modifications as are suited to the particular use contemplated. It is intended that the claims submitted herewith define the overall scope.

The invention claimed is:

1. A surgical instrument, comprising:
- an elongated channel configured to support a staple cartridge;
- an anvil pivotably connected to the elongated channel;
- a closure tube mechanically coupled to the anvil;
- an electric motor; and
- a control circuit electrically connected to the electric motor, wherein the control circuit is configured to:
  - determine a firing force of the surgical instrument during a firing motion of the surgical instrument;
  - determine a projected peak firing force based on the determined firing force;
  - determine, based on the projected peak firing force, whether to change the firing motion of the surgical instrument;
  - determine, in response to a determination to change the firing motion of the surgical instrument, a rate of at which the projected peak firing force is approaching a predetermined threshold firing force; and
  - change the firing motion of the surgical instrument to (i) a first firing motion in response to the rate being equal to a first rate and (ii) a second firing motion, different from the first firing motion, in response to the rate being equal to a second rate different from the first rate.

2. The surgical instrument of claim 1, wherein to determine whether to change the firing motion of the surgical instrument comprises to determine whether to change the firing motion of the surgical instrument based on the projected peak firing force and an amplitude of the determined firing force.

3. The surgical instrument of claim 1, wherein to change the firing motion of the surgical instrument to the first firing motion comprises to pause the firing motion of the surgical instrument.

4. The surgical instrument of claim 3, wherein to pause the firing motion of the surgical instrument comprises to pause movement of the closure tube.

5. The surgical instrument of claim 4, wherein the control circuit is further configured to:
- determine whether to restart the firing motion of the surgical instrument based on a criteria; and
- restart, subsequent to the pause of the firing motion, the firing motion in response to a determination to restart the firing motion.

6. The surgical instrument of claim 1, wherein to change the firing motion of the surgical instrument to the first firing motion comprises to reduce a speed of movement of the closure tube.

7. The surgical instrument of claim 1, wherein to change the firing motion of the surgical instrument to the first firing motion comprises to increase a speed of movement of the closure tube.

8. The surgical instrument of claim 1, wherein to change the firing motion of the surgical instrument to the first firing motion comprises to oscillate the closure tube.

9. The surgical instrument of claim 1, wherein to change the firing motion of the surgical instrument to the first firing motion comprises to perform one of: (i) pause the firing motion of the surgical instrument, (ii) reduce a speed of movement of the closure tube, (iii) increase a speed of movement of the closure tube, or (iv) oscillate the closure tube, and
- wherein to change the firing motion of the surgical instrument to the second firing motion comprises to perform a different one of: (i) pause the firing motion of the surgical instrument, (ii) reduce a speed of movement of the closure tube, (iii) increase a speed of movement of the closure tube, or (iv) oscillate the closure tube.

10. The surgical instrument of claim 9, wherein to change the firing motion of the surgical instrument to the first firing motion comprises to reduce a speed of movement of the closure tube, and wherein to change the firing motion of the surgical instrument to the second firing motion comprises to increase a speed of movement of the closure tube.

11. The surgical instrument of claim 9, wherein the second rate is greater than the first rate.

12. The surgical instrument of claim 1, wherein the control circuit is configured to change the firing motion of the surgical instrument to (i) a third firing motion, different from the first and second firing motions, in response to the rate being equal to a third rate different from the first and second rates and (ii) a fourth firing motion, different from the first, second, and third firing motions, in response to the rate being equal to a fourth rate different from the first rate, second, and third rates.

13. The surgical instrument of claim 12, wherein the first rate is greater than the second rate, the second rate is greater than the third rate, and the third rate is greater than the first rate.

14. The surgical instrument of claim 12, wherein to:

change the firing motion to the first motion comprises to pause the firing motion of the surgical instrument, change the firing motion to the second motion comprises to reduce a speed of movement of the closure tube, change the firing motion to the third motion comprises to increase a speed of movement of the closure tube, and change the firing motion to the fourth motion comprises to oscillate the closure tube.

15. The surgical instrument of claim 1, wherein to change the firing motion of the surgical instrument to the first firing motion comprises to oscillate the knife.

16. A surgical instrument comprising:

an end effector configured to receive a staple cartridge, the end effector comprising:

a first jaw, a second jaw movable relative to the first jaw, and a knife;

a drive system configured to effect a firing motion of the surgical instrument; and a control circuit electrically coupled to the drive system, wherein the control circuit is configured to:

determine a firing force of the surgical instrument during the firing motion of the surgical instrument;

determine a projected peak firing force based on the determined firing force;

determine, based on the projected peak firing force, whether to change the firing motion of the surgical instrument;

determine, in response to a determination to change the firing motion of the surgical instrument, a rate of at which the projected peak firing force is approaching a predetermined threshold firing force; and change the firing motion of the surgical instrument to (i) a first firing motion in response to the rate being equal to a first rate and (ii) a second firing motion, different from the first firing motion, in response to the rate being equal to a second rate different from the first rate.

17. The surgical instrument of claim 16, wherein to determine whether to change the firing motion of the surgical instrument comprises to determine whether to change the firing motion of the surgical instrument based on the projected peak firing force and an amplitude of the determined firing force.

18. The surgical instrument of claim 16, wherein to change the firing motion of the surgical instrument to the first firing motion comprises to pause an advancement of the knife.

19. The surgical instrument of claim 16, wherein to change the firing motion of the surgical instrument to the first firing motion comprises to reduce a velocity of movement of the knife.

20. The surgical instrument of claim 16, wherein to change the firing motion of the surgical instrument to the first firing motion comprises to increase a velocity of movement of the knife.

* * * * *